(12) United States Patent
Bird et al.

(10) Patent No.: US 8,105,787 B2
(45) Date of Patent: Jan. 31, 2012

(54) APPLICATIONS OF NUCLEIC ACID FRAGMENTS

(75) Inventors: Adrian Peter Bird, Edinburgh (GB); Robert Scott Illingworth, Edinburgh (GB); Helle Faerk Jorgensen, London (GB)

(73) Assignee: The University Court of the University of Edinburgh, Old College, South Bridge, Edinburgh (GB)

( * ) Notice: Subject to any disclaimer, the term of this patent is extended or adjusted under 35 U.S.C. 154(b) by 790 days.

(21) Appl. No.: 11/666,558

(22) PCT Filed: Oct. 31, 2005

(86) PCT No.: PCT/GB2005/004202
§ 371 (c)(1),
(2), (4) Date: Jul. 12, 2007

(87) PCT Pub. No.: WO2006/046076
PCT Pub. Date: May 4, 2006

(65) Prior Publication Data
US 2008/0076671 A1 Mar. 27, 2008

(30) Foreign Application Priority Data
Oct. 29, 2004 (GB) .................................. 0423991.9

(51) Int. Cl.
*G01N 31/00* (2006.01)
*G01N 33/53* (2006.01)
(52) U.S. Cl. .......... 435/7.1; 435/4; 435/287.9; 436/501; 436/518; 436/525; 436/529; 436/535; 436/809; 422/50; 530/300; 530/350
(58) Field of Classification Search .................. None
See application file for complete search history.

(56) References Cited

U.S. PATENT DOCUMENTS
2003/0129602 A1   7/2003   Huang

OTHER PUBLICATIONS

Nakao et al., Brain Development. vol. 23: S174-176; 2001.*
Shiraishi et al., Analytical Biochemistry. vol. 329: 1-10; Apr. 30, 2004.*
Huang, Tim Hui-Ming, et al., "Methylation profiling of CpG islands in human breast cancer cells", Human Molecular Genetics, 1999, vol. 8(3), pp. 459-470.
Yan, Pearlly, S., et al., "Dissecting Complex Epigenetic Alterations in Breast Cancer Using CpG Island Microarrays", Cancer Research, 2001, pp. 8375-8380.
Cross, Sally H., et al., "CpG island libraries from human Chromosomes 18 and 22: landmarks for novel genes", Mammalian Genome, 2000, vol. 11(5), pp. 373-383.
Purification of CpG islands using a methylated DNA binding column, Nature Genetics, 1994, vol. 6(3), pp. 236-244.
Weinmann, Amy S., et al., "Isolating human transcription factor targets by coupling chromatin immunoprecipitation and CpG island microarray analysis", Genes & Development, 2002, vol. 16(2), pp. 235-244.
Jorgensen, Helle, F., et al., "Mbd1 is Recruited to both Methylated and Nonmethylated CpGs Distinct DNA Binding Domains", Molecular and Cellular Biology, 2004, vol. 24(8), page.
Lee, Jeong-Heon, et al., "Identification and Characterization of the DNA Binding Domain of CpG-binding Protein", The Journal of Biological Chemistry, 2001, vol. 276(48), pp. 44669-44676.
Cross, Sally H., et al., "CpG islands and genes", Current Opinion in Genetics and Development, Current Biology Ltd., 1995, vol. 5(3), pp. 309-314.

* cited by examiner

*Primary Examiner* — Lisa Cook
(74) *Attorney, Agent, or Firm* — Hoxie & Associates LLC

(57) ABSTRACT

The present invention relates to a method of isolating fragments of nucleic acid according to the density of CpG dinucleotides and subsequent procedures for producing a library and/or an array or microarray of these fragments, as well as uses thereof.

10 Claims, 4 Drawing Sheets

Figure 4:
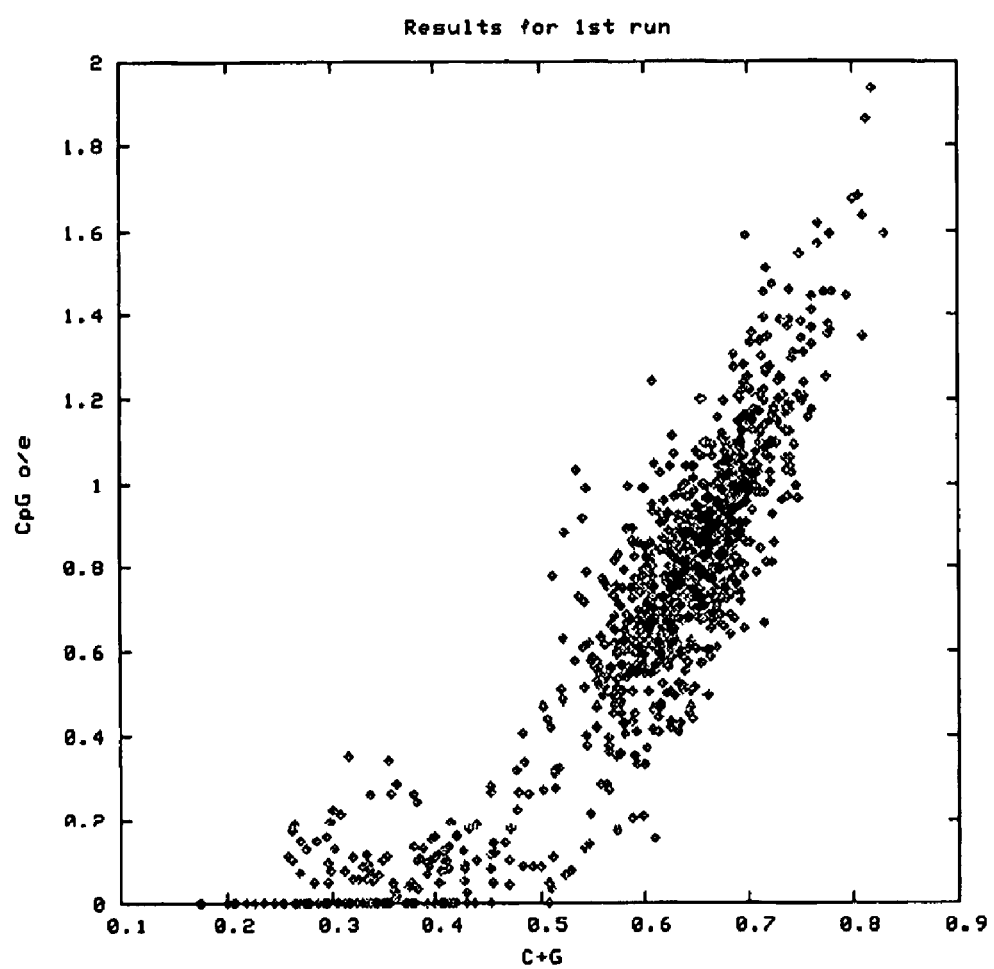

Figure 1 a.

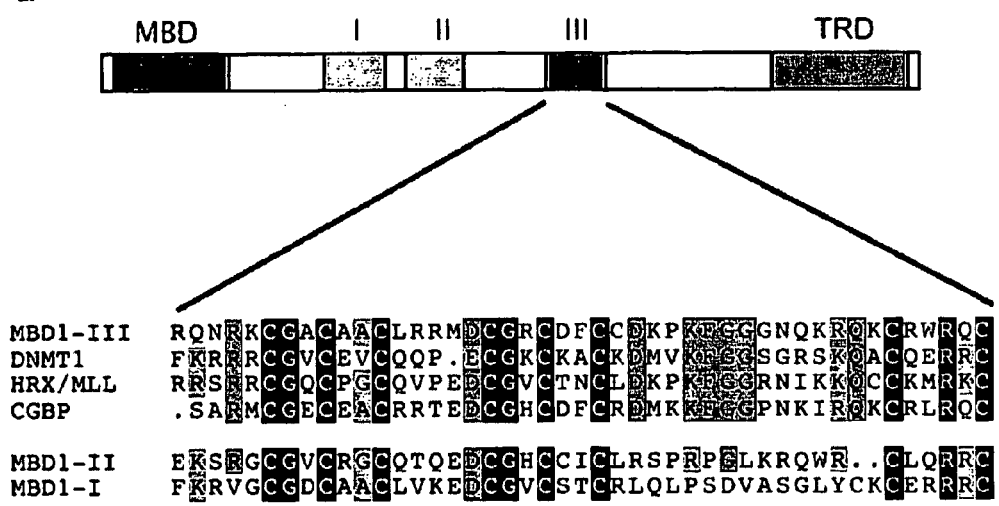

```
MBD1-III  RQNRKCGACAACLRRMDCGRCDFCCDKPKFGGGNQKRQKCRWRQC
DNMT1     FKRRRCGVCEVCQQP.ECGKCKACKDMVKFEGSGRSKQACQERRC
HRX/MLL   RRSRRCGQCPGCQVPEDCGVCTNCLDKPKEGGRNIKKQCCKMRKC
CGBP      .SARMCGECEACRRTEDCGHCDFCRDMKKFEGPNKIRQKCRLRQC

MBD1-II   EKSRGCGVCRGCQTQEDCGHCCICLRSPRPGLKRQWR..CLQRRC
MBD1-I    FKRVGCGDCAACLVKEDCGVCSTCRLQLPSDVASGLYCKCERRRC
``` b.

```
MHHHHHHSSG LVPRGSGMKE TAAAKFERQH MDSPDLGTDD DDKAMAISDP
NSLQPYTNQR QNRKCGACAA CLRRMDCGRC DFCCDKPKFG GGNQKRQKCR
WRQCLQFAMK RLLPSAGSGS GEGAGLRPYQ THQTHQKRPA SARQLQLS.
``` c.

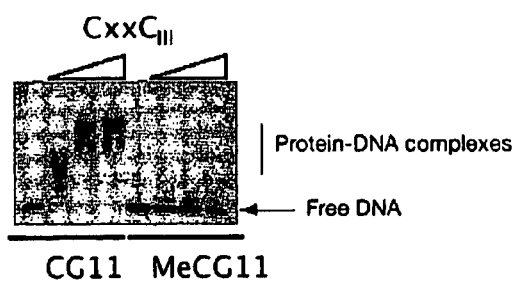

Figure 2
a.
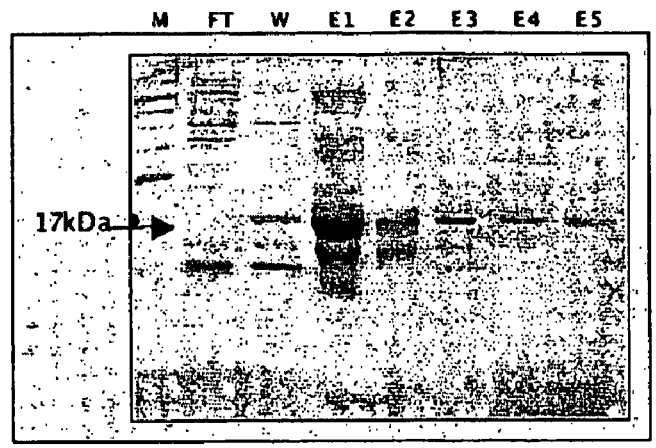
b.
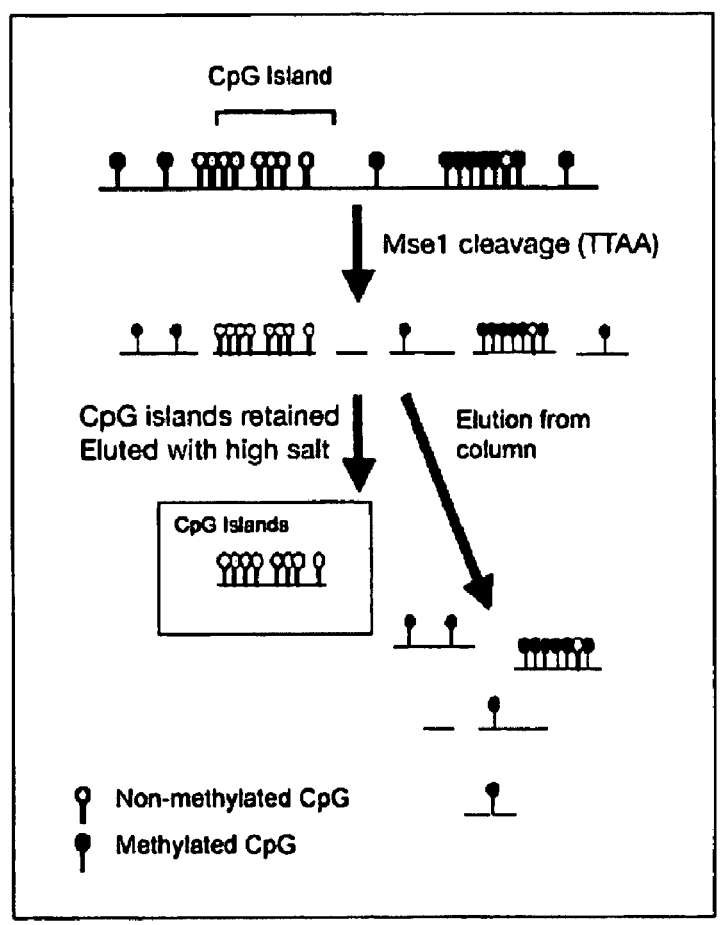

Figure 3
a.
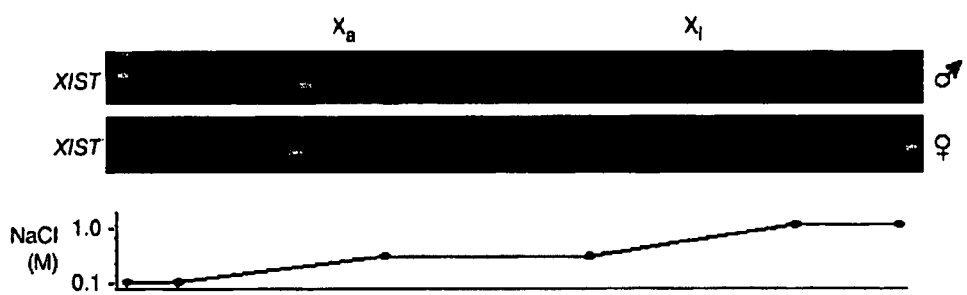
b.
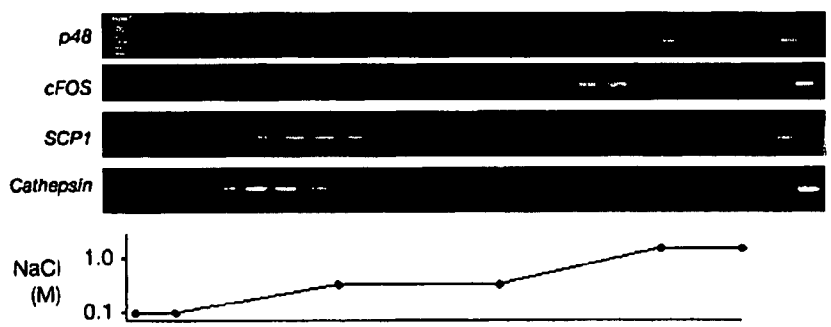

SEQUENCE LISTING

<160> NUMBER OF SEQ ID NOS: 7

<210> SEQ ID NO 1
<211> LENGTH: 45
<212> TYPE: PRT
<213> ORGANISM: Mouse

<400> SEQUENCE: 1

Arg Gln Asn Arg Lys Cys Gly Ala Cys Ala Ala Cys Leu Arg Arg Met
1               5                   10                  15

Asp Cys Gly Arg Cys Asp Phe Cys Asp Lys Pro Lys Phe Gly Gly
            20                  25                  30

Gly Asn Gln Lys Arg Gln Lys Cys Arg Trp Arg Gln Cys
        35                  40                  45

<210> SEQ ID NO 2
<211> LENGTH: 44
<212> TYPE: PRT
<213> ORGANISM: Mouse

<400> SEQUENCE: 2

Phe Lys Arg Arg Arg Cys Gly Val Cys Glu Val Cys Gln Gln Pro Glu
1               5                   10                  15

Cys Gly Lys Cys Lys Ala Cys Lys Asp Met Val Lys Phe Gly Gly Ser
            20                  25                  30

Gly Arg Ser Lys Gln Ala Cys Gln Glu Arg Arg Cys
        35                  40

<210> SEQ ID NO 3
<211> LENGTH: 45
<212> TYPE: PRT
<213> ORGANISM: Mouse

<400> SEQUENCE: 3

Arg Arg Ser Arg Arg Cys Gly Gln Cys Pro Gly Cys Gln Val Pro Glu
1               5                   10                  15

Asp Cys Gly Val Cys Thr Asn Cys Leu Asp Lys Pro Lys Phe Gly Gly
            20                  25                  30

Arg Asn Ile Lys Lys Gln Cys Cys Lys Met Arg Lys Cys
        35                  40                  45

<210> SEQ ID NO 4
<211> LENGTH: 44
<212> TYPE: PRT
<213> ORGANISM: Mouse

<400> SEQUENCE: 4

Ser Ala Arg Met Cys Gly Glu Cys Glu Ala Cys Arg Arg Thr Glu Asp
1               5                   10                  15

Cys Gly His Cys Asp Phe Cys Arg Asp Met Lys Lys Phe Gly Gly Pro
            20                  25                  30

Asn Lys Ile Arg Gln Lys Cys Arg Leu Arg Gln Cys
        35                  40

<210> SEQ ID NO 5
<211> LENGTH: 43
<212> TYPE: PRT
<213> ORGANISM: Mouse

<400> SEQUENCE: 5

```
Glu Lys Ser Arg Gly Cys Gly Val Cys Arg Gly Cys Gln Thr Gln Glu
1               5                   10                  15

Asp Cys Gly His Cys Cys Ile Cys Leu Arg Ser Pro Arg Pro Gly Leu
                20              25              30

Lys Arg Gln Trp Arg Cys Leu Gln Arg Arg Cys
            35                  40

<210> SEQ ID NO 6
<211> LENGTH: 45
<212> TYPE: PRT
<213> ORGANISM: Mouse

<400> SEQUENCE: 6

Phe Lys Arg Val Gly Cys Gly Asp Cys Ala Ala Cys Leu Val Lys Glu
1               5                   10                  15

Asp Cys Gly Val Cys Ser Thr Cys Arg Leu Gln Leu Pro Ser Asp Val
                20              25              30

Ala Ser Gly Leu Tyr Cys Lys Cys Glu Arg Arg Cys
            35              40              45

<210> SEQ ID NO 7
<211> LENGTH: 148
<212> TYPE: PRT
<213> ORGANISM: Mouse

<400> SEQUENCE: 7

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
                20                  25                  30

Ser Pro Asp Leu Gly Thr Asp Asp Asp Lys Ala Met Ala Ile Ser
            35                  40              45

Asp Pro Asn Ser Leu Gln Pro Tyr Thr Asn Gln Arg Gln Asn Arg Lys
        50              55                  60

Cys Gly Ala Cys Ala Ala Cys Leu Arg Arg Met Asp Cys Gly Arg Cys
65                  70                  75                  80

Asp Phe Cys Cys Asp Lys Pro Lys Phe Gly Gly Asn Gln Lys Arg
                85              90              95

Gln Lys Cys Arg Trp Arg Gln Cys Leu Gln Phe Ala Met Lys Arg Leu
            100                 105                 110

Leu Pro Ser Ala Gly Ser Gly Ser Gly Glu Gly Ala Gly Leu Arg Pro
            115                 120                 125

Tyr Gln Thr His Gln Thr His Gln Lys Arg Pro Ala Ser Ala Arg Gln
            130                 135                 140

Leu Gln Leu Ser
145
```

APPLICATIONS OF NUCLEIC ACID FRAGMENTS

CROSS REFERENCE TO RELATED APPLICATIONS

This application is the National Phase of International Application Number PCT/GB2005/004202, filed on Oct. 31, 2005, which claims priority to GB0423991.9, filed on Oct. 29, 2004, the contents of which applications are incorporated herein by reference.

FIELD OF THE INVENTION

The present invention relates to a method of isolating fragments of nucleic acid according to the density of CpG dinucleotides and subsequent procedures for producing a library and/or an array or microarray of these fragments, as well as uses thereof.

BACKGROUND OF THE INVENTION

Genomes of mammals and other vertebrates display a pattern of post-synthetic chemical modification. Only one kind of modification is known in these organisms, namely the methylation of cytosine to give 5-methylcytosine. The target DNA sequence of this methylation modification is the dinucleotide 5'CpG3', also referred to as the CpG dinucleotide, which is self-complementary and occurs in symmetrical pairs.

In the human genome, approximately 70% of CpG dinucleotides are methylated in most cell types. In particular clusters of non-methylated CpG dinucleotides called CpG islands occur at the transcriptional start sites of 56% of human genes. These CpG islands are generally between 1 and 2 Kbp in length. Altogether these CpG island clusters account for about 2% of the genome. CpG moieties in the remaining 98% of the genome are sparsely distributed and approximately 80% of the CpG pairs located therein are methylated. Because of the high cytosine-guanine frequency of CpG islands, it is possible to identify them without knowledge of the methylation pattern of the DNA. Using this bioinformatic criterion, the human genome project has estimated that there are about 30,000 CpG islands per genome.

Promoters and transcription start sites of most mammalian genes comprise CpG islands. Normally CpG dinucleotide pairs within a CpG island are non-methylated and as a result, the gene associated with the CpG island is transcribable, though not necessarily transcribed. Almost all of the CpG islands within the inactive X-chromosome of cells derived from female humans are heavily methylated and condensed, with the exception of the Xist gene which remains unmethylated at its 5' CpG island. This corresponds to the activity of the Xist gene which is required for the initial propagation of the inactive state.

As a result of the fact that the methylation status of these CpG islands is copied during the replication of DNA, a gene silenced by heavy methylation of CpG dinucleotide pairs, may be propagated indefinitely.

The relative association with increased CpG dinucleotide density and non-methylation has been explained by the occurrence of spontaneous deamination over time. Un-methylated CpG dinucleotides may spontaneously deaminate to the nucleotide uracil, which is recognised by DNA repair mechanisms within the cell, and converted back to cytosine. However, deamination of methylated cytosine results in conversion to thymine, which is not recognised by the same DNA repair mechanisms and consequently persists as a 5'TG3' dinucleotide. This is highlighted by pseudogenes in which sequences homologous to expressed genes (for example α-globulin pseudogene) are methylated at the cytosine nucleotides and are seen to loose a large proportion of the CpG dinucleotides over time but gain 5'TG3' dinucleotides.

The mechanism by which CpG islands are maintained in an unmethylated state is poorly understood. It is thought that the maintenance of the methyltransferase DNMT1 may play a role in the propagation of these epigenetic landmarks. The expression of certain genes within the human genome at least, would appear to be very tightly regulated by CpG island methylation.

Under normal circumstances, CpG island methylation occurs when genes are shut down irrevocably during development as may occur with, for example, certain genes on the inactive X-chromosome, for example phosphoglycerate kinase 1, and at imprinted genes for example insulin-like growth factor 2 receptor gene (Igf2r), H19. Unscheduled CpG island methylation may also occur as a result of disease and has been extensively documented in conditions such as cancer: for example, shut down of the RB genes causes Retinoblastoma, and silencing of the MLH1 gene causes increased mutability that promotes several tumour types. Although genes of this kind are usually lost through the occurrence of inactivating mutations, it is apparent that they can also be silenced by DNA methylation. Another example of aberrant CpG island methylation is the silencing of the FMRI gene in fragile X syndrome, which is the most common genetic form of mental retardation affecting males. In addition to these documented cases of CpG island methylation in disease, there have been suggestions that other common conditions (schizophrenia, arthritis, autoimmune diseases) might also have a similar basis.

The formation of a CpG island library may significantly facilitate research into the methylation patterns of these CpG islands in diseases such as those detailed above.

Previous attempts at generating such libraries have involved the use of a peptide derived from MeCP2 of *Rattus rattus* that is capable of binding methylated CpG dinucleotide pairs (Cross et al, 1994). Due to the fact that in most CpG islands a proportion of the CpG dinucleotides are not methylated, the use of these peptides was limited to the purification of methylated CpG dinucleotides or to the purification of CpG islands which had been artificially methylated prior to purification. These techniques lack sensitivity, accuracy and above all fail to generate a library of fragments that represent substantially all the CpG islands within, for example, the human genome.

It is among the objects of the present invention to obviate and/or mitigate at least one of the aforementioned disadvantages.

The present invention is based in part on the applicants' discovery that CpG island nucleic acid fragments may be isolated using a peptide which is capable of binding exclusively to non-methylated CpG dinucleotides.

SUMMARY OF THE INVENTION

In a first aspect of the present invention there is provided a method of isolating CpG island nucleic acid fragments said method comprising the steps of;
 a) obtaining a sample of nucleic acid from an organism;
 b) fragmenting the nucleic acid sample;
 c) contacting said nucleic acid fragments with a peptide which is capable of binding CpG dinucleotide pairs;

d) separating unbound nucleic acid fragments from bound nucleic acid fragments; and
e) detaching bound nucleic acid fragments from said peptide;

Typically the peptide capable of binding CpG dinucleotide pairs is complexed to (coupled/otherwise associated with) an appropriate support, for example a solid support. Advantageously the peptide may be coupled to/associated with said solid support by, for example, covalent, ionic or hydrophobic interactions.

The solid support may, for example, be agarose, sepharose, polyacrylamide, agarose/polyacrylamide co-polymers, dextran, cellulose, polypropylene, polycarbonate, nitrocellulose, glass paper or any other suitable substance capable of providing a suitable solid support.

Advantageously the solid support may be in the form of granules, a powder or a gel suitable for use in chromatography such as those available from Amersham Biosciences.

Preferably the peptide capable of binding CpG dinucleotide pairs comprises at least a portion of the CpG Binding Domain protein 1 (MBD1) which retains the ability to bind CpG dinucleotide pairs.

Preferably the peptide capable of binding CpG dinucleotide pairs comprises the cysteine rich CxxC-3 domain of the MBD1 transcriptional repressor (Jorgensen, 2004).

In one embodiment of the present invention, the peptide capable of binding CpG dinucleotide pairs comprises the MBD1 transcriptional repressor.

Additionally or alternatively the peptide capable of binding CpG dinucleotide pairs may be provided by a peptide or fragment thereof, homologous to the MBD1 transcriptional repressor. (Lee et al., 2001 and Birke et al., 2002).

It is to be understood that the term "homologous" refers to a polypeptide, or fragment thereof that retains the means of binding CpG dinucleotide pairs and shares a degree of sequence identity/similarity with the naturally occurring MBD1 transcriptional repressor and in particular the CxxC-3 domain. It is well known to one of skill in the art that the quaternary and tertiary structure of a polypeptide is usually highly conserved such that the specific function of that polypeptide is also retained. It is also well known that the primary structure of a peptide may exhibit considerable variation in its sequence without resulting in a significant decrease in the activity of the mature peptide. Consequently an homologous peptide useful in the present invention may share only, for example, 25% amino acid sequence identity with the MBD1 polypeptide when the conserved residues of the two peptides are aligned. Accordingly, the polypeptide of the present invention, capable of binding CpG dinucleotide pairs may include polypeptides or fragments thereof which show 25%, preferably 40%, more preferably 60% even more preferably 75% and most preferably 90% or 95% sequence identity with the MBD1 transcriptional repressor.

It is also to be understood that there are potentially a number of "conservative substitutions" which may occur within the primary sequence of the peptide which is capable of binding CpG dinucleotide pairs. By "conservative substitution" it is meant the replacement of an amino acid residue and/or residues with an amino acid residue and/or residues which do not substantially differ in terms of physical and chemical properties from the naturally occurring amino acid residue and or residues. These "conservative substitutions" will have substantially no effect on the function of the peptide.

Advantageously the peptide capable of binding CpG dinucleotide pairs preferentially binds those CpG dinucleotide pairs which are unmethylated. It is to be understood that the term "unmethylated" refers to CpG dinucleotide pairs that lack modification by way of the addition of a methyl group to the 5' cytosine nucleotide which would otherwise yield 5-methylcytosine.

Conveniently the peptide capable of binding CpG dinucleotide pairs is coupled to the solid support.

In one embodiment of the present invention the peptide capable of binding CpG dinucleotide pairs further comprises a binding moiety providing a means of coupling said peptide to the solid support. Such a binding moiety could be for example a peptide or other small chemical moiety, for example biotin/streptavidin Preferably the binding moiety is a peptide fused to the peptide capable of binding CpG dinucleotide pairs. Advantageously the resultant peptide fusion may be produced by recombinant means. Alternatively the binding moiety may be conjugated to the peptide capable of binding CpG dinucleotide pairs.

In one embodiment of the present invention the binding moiety may comprise any of the oligopeptides $His_n$ where n is 4-20, preferably n is 5-10 and more preferably n is 6. Such oligopeptides have a high affinity for divalent nickel (Ni), enabling the polypeptide to be coupled to the nickel chelating resin $Ni^{2+}$-NTA-agarose.

Exemplary vectors suitable for expressing a peptide capable of binding CpG dinucleotides::binding moiety fusion, for example peptide capable of binding CpG dinucleotides::$His_n$, are generally available from Merck Biosciences (Novagen®) and include, for example pET14b, pET15b, pET16b, pET19b and pET30b. [REFERENCE]

Alternatively in a further embodiment of the present invention the binding moiety may comprise a glutathione S-transferase (GST). GST has a high affinity for glutathione which may be coupled to a solid support such as, for example, sepharose 4B.

Exemplary vectors suitable for expressing a peptide capable of binding CpG nucleotide pairs::binding moiety fusion, for example peptide capable of binding CpG dinucleotides::GST, are generally available from Amersham Biosciences and include pGEX-4T-2, pGEX-6P-1 and pGEX-4T-3.

It is to be understood that any small molecule capable of being immobilised on a solid support such as those substantially described above may be suitable for immobilising a peptide capable of binding CpG nucleotide pairs. By "small molecule" it is to be understood that molecules with a $M_r$ of less than 2000 are envisaged useful.

For example, a peptide capable of binding CpG nucleotide pairs may be labelled with, for example, biotin and contacted to a suitable solid support, for example agarose, to which a molecule such as streptavidin is coupled. In this way the formation of a biotin/streptavidin complex facilitates the association of said peptide to said support media.

Alternatively, and in a further embodiment of the present invention, the peptide capable of binding CpG dinucleotide pairs may be chemically cross-linked to the solid support.

Advantageously the peptides capable of binding CpG dinucleotide pairs may be chemically cross-linked to the solid support by means of, for example, activation of the solid support by the addition of cyanogen bromide (CNBr) as disclosed by Axen et al (1967). Briefly upon addition of CNBr the solid support reacts rapidly at pH 8-9 with free amino acid groups in the polypeptide to be cross-linked to the solid support. Preferably the solid support for use in this way is agarose, for example CNBr-activated agarose.

Advantageously the peptide which is capable of binding CpG dinucleotide pairs may be coupled to the solid support by means of an antibody or fragment thereof which specifically reacts with a portion of said peptide. Preferably the antibody is coupled to the suitable solid support.

Advantageously the antibody or fragments thereof useful in this way may be monoclonal antibodies or fragments which have an affinity for the peptide which is capable of binding CpG dinucleotide pairs. The techniques of monoclonal antibody production are well known to one of ordinary skill in the art.

It may also be desirable to isolate CpG island nucleic acid fragments from a variety of organisms. Samples of nucleic acid, for example DNA, may be obtained from animals such as rodents, for example rats and mice, humans, fish, horses, cattle, sheep, pigs, chicken's etc. In addition it is also envisaged that the methods of the present invention may also be applicable to samples isolated from plant material. Plant genomes are heavily methylated at CpG, but it has been shown that plant genes can be greatly enriched from genomic DNA by selecting non-methylated DNA that is equivalent to the CpG islands of animals (Whitelaw et al, 2003; Palmer et al, 2003). The present invention may therefore be used for gene isolation from genomes of many plant species.

It is understood that a sample of a nucleic acid may be obtained from, for example cells grown in vitro, or in vivo or a tissue biopsy or where appropriate, may include blood, saliva or any other suitable sample from which nucleic acid may be obtained. Preferably the sample obtained should yield nucleic acid which accurately reflects the methylation status of the patient's 5'CP3' islands, said methylation status arising as a result of a subject's disease state i.e. healthy, having a particular disease or predisposed to/developing a disease. For example, in the case of a cancer, the sample may, if possible, comprise a tissue biopsy obtained directly from the tumour or from cells neighbouring the tumour. Advantageously the sample may at least comprise cells derived from the same tissue affected by the disease. Techniques of DNA extraction from cells are well known and may comprise, for example, the use of lipid membrane solubilising agents, e.g. detergents and protesase enzymes. Substances which cause nucleic acid to precipitate, for example ethanol, may then be used to isolate the nucleic acid (see for example Sambrook et al).

Preferably the nucleic acid obtained from the sample may be fragmented using restriction endonuclease enzymes, for example HindIII, EcoR1, BamH1 and Pst1. The restriction endonuclease enzymes may be used individually to fragment the nucleic acid sample, or alternatively a number of restriction endonuclease enzymes could be used in combination.

It should also be understood that other methods of nucleic acid fragmentation fall within the scope of this patent and may include, sonic disruption of the nucleic acid or the use of shearing forces.

Generally unbound material, for example fragmented nucleic acid, preferably absent of any CpG islands or possessing solely methylated CpG islands, remain unbound to the solid support media. Typically the solid substrate may be washed, for example, and an osmotically balanced and neutral solution such as e.g. phosphate buffered saline (PBS), may be applied to the solid support media such that unbound material is removed. Typically such a procedure is repeated a number of times to maximise the amount of unbound material removed from the solid support media.

Techniques used to separate bound material, for example nucleic acid fragments, from solid supports such as those described above, are well known in the art and such techniques are applicable here. For example a sodium chloride gradient may be established within a resin, such as a nickel chelating resin, for example NTA-agarose, packed within an affinity chromatography column, such that particular fragments of nucleic acid are caused to be separated from the column upon contact with a particular concentration of sodium chloride. Other means of separation include the use of reduced glutathione solutions in the case of GST affinity chromatography, alterations in pH or enzymatic cleavage.

In a preferred embodiment steps c) and d) of the method according to the first aspect of the present invention may be repeated. In this way substantially all the nucleic acid fragments containing CpG islands may be isolated while ensuring that contamination with nucleic acid fragments not containing CpG islands or methylated CpG islands is significantly reduced.

In a second aspect of the present invention there is provided a use of a peptide/support complex comprising a solid support and a peptide which is capable of binding CpG nucleotide pairs, for isolating CpG island nucleic acid fragments.

In a third aspect of the present invention there is provided a method of producing a CpG island library, said method comprising the steps of;
  a) isolating CpG island nucleic acid fragments in accordance with the first and/or second aspect of the present invention; and
  b) cloning the isolated fragments into a suitable vector;

The fragments may be cloned into suitable vectors by many methods, all of which are known to a person of ordinary skill in the art. For example, the nucleic acid fragments dissociated from the solid support may be added to a suitable vector in the presence of a DNA ligating enzyme, such as, for example T4 ligase and left to incubate for a period of time, for example 16° C. for approximately 10 hours. Alternatively commercial cloning and sequencing vectors such as TOPO pCR4, available form Invitrogen lifesciences, or other such ligase free systems, may be used to clone fragments of nucleic acid in preparation for subsequent amplification by PCR and/or sequencing.

Conveniently the cloned fragments of the CpG island library of the present invention may be sequenced. The techniques of nucleic acid sequencing are well known in the art and may include Sanger's method of dideoxynucleotide sequencing. By sequencing the cloned fragments of nucleic acid obtained by the above described method it is possible to obtain a library of fragments which represent substantially all the CpG islands within the genome of the organism from which the sample is derived (Molecular Cloning: A Laboratory Manual, Sambrook & Russell).

In a fourth aspect of the present invention there is provided a method of producing a CpG island library array comprising the steps of;
  a) amplifying the nucleic acid fragments of the CpG library produced in accordance with the third aspect of the present invention;
  b) denaturing the amplified nucleic acid fragments; and
  c) coupling, in an array, the denatured nucleic acid fragments to a suitable library array substrate.

Typically the cloned CpG island nucleic acid fragments of the CpG island library are amplified by use of the polymerase chain reaction (PCR). Again, such techniques are well know and described for example in Sambrook et al. Alternatively the cloned CpG island nucleic acid fragments of the CpG island nucleic acid library may be excised from the suitable vector into which they have been cloned, by use of a restriction endonuclease, additionally or alternatively a combination of restriction endonuclease enzymes may be used. Typically the restriction endonuclease or combination of restriction endonuclease enzymes, fragment the vector at a point either side of the cloned CpG island nucleic acid fragment.

Preferably the amplified nucleic acid fragments may be denatured so as create fragments of single stranded nucleic acid. Advantageously the amplified nucleic acid fragments are subjected to heat treatment, for example incubated for a period of time in a boiling water bath or heating block, such that the fragments of double stranded DNA are caused to dissociate to single stranded fragments.

Alternatively, the CpG island array may be produced by synthesising oligonucleotides which are specific to the nucleic acid fragments of the CpG island produced in accordance with the present invention and coupling, in an array, the oligonucleotides to a suitable library array substrate.

The skilled addressee will appreciate that arrays need not be produced covering the entire genome. It is possible using the present method to prepare arrays based on portions of the genome including, for example, one or more chromosomes (including mitochondrial DNA as being representative of a chromosome).

Following the procedures described herein, the present inventors have obtained library of CpG island fragments and cloned and sequenced them (see Table 1). This shows that a library produced according to the present methods is much more representative than libraries obtained following prior art methods, such as described in Cross et al (1994). Thus, in further aspects the present invention provides libraries comprising CpG island specific nucleic acid sequences derived from the clones identified in Table 1.

There is provided a method of making a CpG island array, comprising the steps of: preparing one or more CpG island specific sequence(s) using the information derived from Table 1; and binding in an array said one or more sequences to a substrate.

The library may comprise sequence from one or more clones, e.g. more than 1,000, 2,000, 3,000, 4,000, 5,000, 6,000, 7,000, 8,000, 9,000, 10,000 or from substantially all clones identified or sequence from one or more clones from a particular genome, typically greater than 25%, 50%, 60%, 70%, 80%, 90% or 95%, including substantially all clones identified from a particular genome.

The present invention also provides use of the information derived from Table 1 in the preparation of a CpG island library and/or array.

The sequences may be obtained, for example, by recombinant or synthetic means.

Preferably the library of CpG islands is arranged in an array, preferably a microarray. Advantageously the array or microarray is prepared on any suitable, preferably non-porous substrate. Typically the suitable substrate may include glass or a plastics materials. Information regarding suitable substrates and the protocols used to generate arrays or microarrays may be obtained from the National Human Genome Research Institute, Bethesda USA.

Generally the surface of the suitable microarray substrate is treated in someway so that the fragmented nucleic acid may be coupled to it. For example the surface of the suitable substrate may be made hydrophobic so as to prevent spread of individual nucleic acid samples applied to the microarray substrate and positively charged so as to facilitate the coupling of the fragmented nucleic acid to the microarray substrates. Such a hydrophobic/positively charged surface may be obtained by use of a substance such as poly-L-lysine.

After such preparation of the microarray substrate, the amplified nucleic acid fragments may be spotted on to the surface as an array. Preferably automated printing procedures known in the art may be utilised to apply the amplified nucleic acid fragments as an array.

The methods of producing a CpG library and an array or microarray as substantially described herein, result in a library of CpG island fragments which accurately represent substantially all of the CpG islands in the genome of the organism being investigated. In this way the resultant library and/or array or microarray may provide a means of probing the entire complement of CpG islands for modifications which may result in aberrant gene expression. Alternatively arrays may be provided which accurately represent substantially all of the CcpG islands from a specific portion or portions of a genome, such as a chromosome or chromosomes.

Modifications include, for example, the methylation of CpG dinucleotide pairs resulting in the silencing of genes associated with the CpG island. Other modifications may include the removal of methyl groups from CpG islands such that genes silenced by methylation may suddenly, through removal of the methyl modification, become active.

In a fifth aspect of the present invention there is provided a CpG island library array, preferably a microarray obtainable by the method according to the fourth aspect.

The CpG island library microarray may provide a means of determining the methylation status of nucleic acid isolated from e.g. a subject possessing a specific disease. In this way it may be possible to obtain an accurate profile of those genes that have been modulated by addition or removal of methyl groups.

Thus in a yet further aspect of the present invention there is provided a method of determining methylation patterns of CpG islands in a nucleic acid sample said method comprising the steps of;
  a) obtaining a sample of nucleic acid from a subject;
  b) subjecting the sample to the method of CpG island fragment isolation as described in the first and/or second aspect of the present invention;
  d) amplifying the isolated fragmented CpG island nucleic acid fragments optionally in the presence of a label (e.g. according to Cross et al., 2000);
  e) contacting the labelled amplified fragmented nucleic acid with a CpG island library microarray of the present invention and detecting bound, optionally labelled, amplified fragmented nucleic acid; and
  f) comparing the results with those obtained from a control sample.

The sample may be from any suitable human or non human subject, for example plants, horses, pigs or chickens (see above) and in the form of a tissue biopsy or, for example, a fluid sample, for example blood, saliva or the like. Advantageously the sample may comprise cells. Additionally or alternatively a sample may be obtained using sterile swabs, scalpels or the like to scrape or wipe across a particular tissue surface, for example the skin or the cheek or palate inside the buccal cavity.

Cross et al., 2000 disclose the use of short oligonucleotide catch-linker molecules to facilitate the amplification of small amounts of nucleic acid. CpG island nucleic acid fragments isolated in accordance with the first and/or second aspect of the present invention may be ligated to catch-linker oligonucleotides. Ligation of isolated CpG nucleotide fragments to catch-linker oligonucleotides permits the amplification of said fragments by PCR. Additionally or alternatively, random oligonucleotide primers may be used to amplify the isolated CpG island fragments.

Alternatively radiolabelled nucleotides may be used in a PCR reaction to obtain amplified DNA fragments which are capable of being detected. Additionally or alternatively fluorescent, colourmetric or chemilluminescent tagged nucleotides may also be used. Typically fluorochromes such as Cy3 and Cy5 may be used to label the amplified DNA fragments.

Generally the DNA fragments may be contacted with the array or microarray of the present invention by means of a hybridisation procedure. The optionally labelled nucleic acid fragments may be hybridised to the suitable microarray surface using conditions suitable to cause hybridisation of the DNA fragments to the suitable microarray substrate. The hybridisation conditions under which DNA fragments bind to microarray substrates, are well known in the art. Briefly, various combinations of temperature, salt concentration and incubation time are used dependant upon the length and AT:: GC content of the DNA fragments being hybridised. (McCarthy & Church, 1970; McKeon et al., 1982; McKim & Hawley, 1995; McKnight & Kingsbury, 1982 and McNally et al., 2000)

Detection of bound fragmented DNA fragments may be achieved by any suitable means. If, for example, fluorochromes such as Cy3 and Cy5 are used the microarray, these may be subjected to light generated by a laser typically of wavelengths about 525 nm and 650 nm which have the effect of causing the Cy3 and Cy5 fluorochromes used to label the amplified fragmented DNA to fluoresce. Under these circumstances the microarray may be viewed under a microscope and wherever hybridisation between a DNA fragment obtained from a sample of diseased tissue hybridises with a DNA fragment within the CpG library microarray, a fluorescing spot will be visible.

By "control sample" it is meant a sample of nucleic acid, derived from tissue, blood, saliva or any other suitable source, from a patient possessing a normal CpG island methylation pattern. By "normal" it is meant a methylation patter typical of that possessed by a healthy individual Using this technique it may be possible to compare the methylation pattern of CpG islands in diseased tissue with that from normal healthy tissue.

In a further aspect of the present invention there is provided a further way of determining methylation patterns of CpG islands in a nucleic acid sample said method comprising the steps of;
 a) isolating CpG island nucleic acid fragments using a material capable of binding methyl CpG, such as according to the method of Cross et al, 1994;
 b) amplifying the isolated fragmented CpG island nucleic acid fragments optionally in the presence of a label (e.g. according to Cross et al., 2000);
 c) contacting the, optionally labelled, amplified fragmented nucleic acid with the microarray of the present invention and detecting bound amplified fragmented nucleic acid; and
 d) comparing the results with those obtained from a control sample.

Cross et al, 1994 disclose the use of an affinity matrix that contains the methyl-CpG binding domain from the rat chromosomal protein MeCP2, attached to a solid support. A column containing this matrix fractionates DNA according to its degree of CpG methylation, strongly retaining those sequences that are highly methylated.

In a further aspect of the present invention there is provided a method of determining whether or not an agent is capable of modulating the methylation pattern of CpG islands comprising the steps of;
 a) contacting a cell or cells with an agent;
 b) obtaining a nucleic acid sample from said cell or cells;
 c) isolating the CpG island nucleic acid fragments from the nucleic acid sample in accordance with a first and/or second aspect of the present invention;
 d) applying the nucleic acid fragments obtained to the array or microarray of the present invention;
 e) detecting the bound fragments; and
 f) comparing the results with those obtained from a control sample not treated with the agent.

In this way it may be possible to identify agents which are capable of modulating the methylation status of CpG islands. For example, it may be desirable to remove a methyl group from a CpG island in order that a gene may become reactivated, alternatively it may be desirable to identify an agent capable of silencing a gene by methylation of the associated CpG island. Agents identified by this method may be potentially beneficial in the treatment of diseases such as, for example, cancer, schizophrenia, arthritis, Alzheimer's disease and auto immune diseases.

In a yet further aspect of the present invention there is provided an alternative method of determining the methylation pattern of CpG islands in diseased tissue, said method comprising the steps of;
 a) obtaining a sample of nucleic acid from a subject
 b)
  (i) isolating CpG island nucleic acid fragments from a portion of said sample in accordance with the first aspect of the present invention;
  (ii) isolating methylated CpG island nucleic acid fragments as described by Cross et al, 1994 from a further portion of said sample;
 c) amplifying the isolated fragmented CpG island nucleic acid fragments obtained from b) (i) and (ii) optionally in the presence of a label (Cross et al., 2000);
 d) contacting, optionally the labelled, amplified fragmented nucleic acid with the microarray of the present invention and detecting bound amplified fragmented nucleic acid; and
 e) comparing the results obtained with those exhibited by a control sample.

In this way, the simultaneous extraction of methylated CpG islands using the method of Cross et al, 1994 and the method of obtaining unmethylated CpG islands as described herein followed by the subsequent labelling and simultaneous hybridisation of the resultant fragments to the array or microarray of the present invention may facilitate the determination of the methylation status of CpG islands in certain diseases.

The methods and apparatus of the present invention may also be used analytically to identify the CpG methylation status of any DNA fragment. Genomic DNA from any source may be applied, for example, to two separate small volume columns (for example spun columns known in the art) that contain, respectively, an immobilised peptide of the present invention, preferably the peptide comprising the CxxC-3 domain of MBD1, which is capable of binding non-methylated DNA and an immobilised peptide capable of binding methylated CpG islands, such as the methyl-CpG binding domain taught by Cross et al 1994. After washing of the columns to remove weakly bound DNA, the "methylated" column will have retained densely methylated DNA (for example CpG islands), whereas the column of the present invention will have retained CpG-rich non-methylated DNA (for example non-methylated CpG islands). PCR amplification of the retained DNA (after elution from the column) using primers for a specific DNA sequence will identify if that sequence is methylated (retained by "methylated" prior art column but not by column of the present invention) or nonmethylated (retained by the column of the present invention but not by the prior art column capable of binding methylated DNA). The use of both complementary columns together provides a robust assay that provides a reliable readout of CpG methylation status of a particular DNA sequence.

In a further aspect of the present invention there is provided a method of identifying transcription factor gene targets, said method comprising the steps of;
a) obtaining a sample from a subject;
b) subjecting the sample to the method of Weinmann, A. S. et al., 2002;
c) contacting the labelled nucleic acid with the microarray of the present invention.

Briefly, Weinmann, A. S. et al., 2002, disclose a method for identifying the gene targets of transcription factors. In the first instance nucleic acid is caused to crosslink with proteins capable of binding nucleic acid, for example chromatin, by the addition of, for example, a chemical such as formaldehyde. The nucleic acid/protein fragments are then isolated by cellular disruption by means of, for example, sonication or the use of a French Press. Antibodies specifically reactive to a nucleic acid binding protein, or transcription factor of interest are then contacted with the nucleic acid/protein complexes. Techniques such as affinity chromatography may be used to recover the antibody/nucleic acid/protein complexes. Affinity chromatography may involve the use of compounds capable of binding antibodies for example protein A and/or antibodies. The nucleic acid of the antibody/nucleic acid/protein complex is then removed from the complex by means of reversing the crosslinks formed by the addition of formaldehyde. The removed nucleic acid is then applied to the microarray of the present invention. In this way the target genes that are likely to be regulated by the protein capable of binding nucleic acid, for example a transcription factor, may be identified.

The present invention will now be further described by way of example and with reference to the figures, which show:

FIG. 1. a): A linear diagram of the methyl-CpG binding protein MBD1. The methyl-CpG binding domain (MBD), the three CxxC domains (I, II and III) and the transcriptional repression domain (TRD) are indicated. Below the diagram is a blow-up of the CxxC-III domain of MBD1 showing its amino acid sequence (top line). The aligned sequences of related domains in other proteins are shown immediately below. The CxxC-I and -II domains of MBD1 are shown at the bottom; unlike CxxC-III, these two domains show no binding specificity for 5'CG3'. Black shading denotes completely identical amino acid residues. Grey shading indicates amino acids that are shared by some but not all members of the group;

b) Amino acid sequence of the CxxC protein used for construction of the MBD1 matrix. The region derived from mouse Mbd1 is shaded green and the portion shown in a) is underlined. The poly-histidine tag is shaded yellow. Electromobility shift assays demonstrate that the CxxC domain forms protein DNA complexes with DNA methylated at 27 CpG sites (MeCG11), but not to the same DNA sequence in the non-methylated state (CG11);

FIG. 2. a) Purification of the bacterially expressed CxxC domain on a nickel agarose affinity column. The 17 kDa protein fragment predominantly elutes in the first elution wash (E1) and less so in the later washes (E2-5). The protein binds quantitatively to the nickel affinity column as it is absent in the flowthrough (FT) and first column wash (W1);

b) Schematic diagram of the strategy used to prepare a CpG island fraction from genomic DNA. Genomic DNA containing a non-methylated (grey lollipops) CpG island and surrounding methylated (black lollipops) bulk genomic DNA is cleaved with Mse1 at TTAA sites. The resulting fragments are passed over or incubated with the CxxC matrix so that DNA rich in non-methylated CpGs binds. Unbound DNA is washed away, after which bound CpG island fragments are washed off the matrix;

FIG. 3: Test of the CxxC column on human genomic DNA.
a) Separation of methylated and non-methylated XIST CpG islands on the active $(X_a)$ and inactive $(X_i)$ X chromosomes. The gradient of increasing salt elutes methylated XIST at relatively low salt (male and female) and non-methylated XIST (female only) at high salt. Primers within the XIST CpG island were used to detect XIST sequences in each column fraction by PCR.

b) A gene with a methylated CpG island (SCP1) and a non-CpG island gene (CATHEPSIN) are weakly bound to the CxxC matrix and elute at low salt concentrations. CpG island sequences from the p48 gene and the c-FOS gene bind tightly to the column; and FIG. 4: DNA sequence analysis of a putative CpG island library made according to the strategy in FIG. 2. A total of 1,119 sequences were obtained by the Sanger Centre (collaboration with Dr Jane Rogers and colleagues) and analysed (Dr Alastair Kerr, Wellcome Trust Centre, Edinburgh) with respect to base composition and CpG frequency. The data indicate that the great majority of sequence inserts cluster around an average base composition of 65% G+C and a CpG [observed/expected] frequency of ~0.8. The bulk genome has an average base composition of 40% G+C and an [observed/expected] frequency of ~0.25 (marked by the green square).

MATERIALS AND METHODS

Transformation and Inoculation of Competent Cells

Both X1L Blue and BL21 pre-prepared competent cells and pet30b and c3581 plasmids were thawed on ice. Pet30b was pre-diluted, c3581 was diluted in TE (Tris/EDTA) by 100× to 10-100 ng/μl. Two μl aliquots of each plasmid were pipetted into 2×2 round based snap top, 15 ml tubes, with the subsequent addition of 70 μl of competent cells (such that each strain was added to each plasmid). A fifth control tube contained 70 μl of BL21 alone, was prepared to test the viability of the kanomycin plates. The tubes were returned to ice for 30 minutes, after which they were transferred to a 42° C. water bath for 45 seconds (heat shock activation) and returned to ice for 5 minutes. 0.5 mls of LB broth was added to each tube and then they were transferred to 37° C. for 1 hour in an agitating incubator (to express kanomycin resistance prior to plating). Using a glass spreader, each strain was inoculated onto five pre-dried kanomycin/agar plates, and placed in a 37° C. incubator overnight (spreading was carried using sterile technique).

Two separate colonies were inoculated using sterile plastic loops from each overnight plate into 3 mls of kan/LB (3 μl–1000×/50 mg/ml stock), and thoroughly mixed. X1L Blue cultures were then transferred to a 37° C. incubator overnight, whereas BL21 cultures were incubated for five hours (prior to IPTG induction for lac promoter mediated expression). Large scale BL21 inoculation, for bulk CxxC-3 production, was carried out with a 40 ml overnight culture (inoculated as before), which was subsequently diluted into 4 liters of LB/kan (8×0.51 per 2½ liter conical flask) and grown in an agitating incubator until the OD$^{600}$ was between 0.4-0.7 (see later section).

Mini-Prep of Plasmid DNA 1.5 ml of each of the four X1L Blue overnight cultures were transferred to eppendorf tubes and centrifuged in a microfuge at 16k rpm for 30 seconds. The plasmid DNA present in the pellet was subsequently extracted via the QIA prep, Miniprep kit (Qiagen) following the standard protocol.

IPTG Induction of His-CxxC-3

3 µl of (1000×/1M) IPTG was added to the 3 ml analytical BL21 culture (grown for five hours at 37° C.). Once mixed, the culture was returned to the incubator for a further three hours to induce. 250 µl samples were taken just prior to addition of IPTG and after 1, 2 and 3 hours for induction analysis. Once these samples had been analysed by SDS-PAGE (see later section), the large scale BL21 induction was carried out. The 4 liters of diluted overnight cultures were analysed for growth state by $OD^{600}$. 1 ml samples of each culture were removed at various time courses, and their absorbance at 600 nm was determined using a photospectrophotometer and 1 ml cuvettes (kan/LB was used as a zero). Once the cultures reached an $OD^{600}$ of 0.4-0.7 (optimal IPTG induction density), IPTG was added, as for the analytical sample and induced for 2 hours (as determined by SDS-PAGE analysis of analytical samples). Induced cultures were then transferred to ice for protein extraction. 250 µl samples of un-induced and induced culture were stored for SDS-PAGE analysis.

Protein Extraction from Culture

The two-hour IPTG induced BL21 cultures were transferred to 4 pre-cooled, 1 liter centrifugation tubes, and centrifuged at 4° C. for 20 minutes at 4200 rpm. Supernatants were carefully decanted and the pellets resuspended in 50 mls of pre-cooled (1×) PBS. The cells were transferred to four 50 ml, pre-cooled centrifuge tubes and, centrifuged again, this time for ten minutes. Supernatants were disregarded and the pellets were resuspended, each in 30 mls of lysis buffer (precooled) using disposable pasteur pipettes. Once the pellets were fully resuspended (important), 30 mg of lysozyme was added (to a final concentration of 1 mg/ml) and the samples left on ice for 30 minutes. The suspensions were then sonicated (30%, setting 4) for five minutes and then centrifuged at 4° C., for ten minutes at 17,000 g (in a JA25.50 Rotor). Supernatants were subsequently decanted into 4×50 ml falcon tubes and frozen at −80° C. for purification. A 250 µl sample was taken of the supernatant, and a small sample of the pellet (as soluble & insoluble protein fractions respectively), for SDS-PAGE analysis.

Nickel Protein Purification

Frozen lysates were thawed on ice and subsequently centrifuged for 15 minutes at 17,000 g (4° C.) and the supernatant then kept on ice. Stock Ni-NTA superflow (Qiagen) was gently inverted to re-suspend the beads into a slurry (slurry volume is ca 2× bed volume). Three 2 ml aliquots of slurry were transferred to three 50 ml falcon tubes and sedimented at 500 g for 5 minutes. The Supernatant (ethanol), was carefully decanted and the beads resuspended in 10 mls of pre-cooled, wash buffer (10× bed volume). This was centrifuged again, as before, and the supernatant disregarded. This wash was repeated a further twice prior to addition of lysate. The lysate was split equally into 3×40 ml aliquots and added to the three tubes of washed beads. The beads were resuspended in the lysate and place on rollers at 4° C. for two hours (for His tag binding to the Ni-NTA beads). The beads were then centrifuged as for the washes, the supernatant removed and stored and the beads resuspended in 5 mls of wash buffer. All three tubes were transferred to a single 20 ml Bio-Rad poly-prep column and the tubes rinsed with wash buffer on to the column. The flow through was stored and the column washed with three 10 ml volumes of wash buffer, after which the column was capped.

The His-CxxC-3 was eluted from the column over seven 2 ml fractions, in a 250 mM Imidazole wash buffer. A 1 ml aliquot of the elution buffer was added to the column and allowed to equilibrate for 10 minutes, after which it was allowed to flow through and was collected. This process was repeated a further six times (until the Ni-NTA had become blue rather than brown). The un-bound sample, washes and fractions were analysed by SDS-PAGE to assess both purity and which fractions to pool and dialyze (to remove the bulk of the Imidazole from the protein).

Pooled fractions were transferred into 25 mm-3500 Da Spectrapor dialysis tubing, and the ends thoroughly sealed (both tied and clipped). The dialysis tubing was then transferred to 2 liters of pre-cooled dialysis buffer on a magnetic stirrer for four hours, after which it was transferred to fresh dialysis buffer and left overnight at 4° C. Once dialyzed, the His-CxxC-3 was centrifuged at 14,000 rpm for ten minutes at and the supernatant transferred to a 15 ml Falcon tube and stored at 4° C.

Ion (Cation) Exchange Protein Purification

Further His-CxxC-3 purification involved Fractogel (Merck) EMD $SO_3^-$ cation exchange and elution with a HEPES based elution buffer (according to the Fractogel handbook). In brief; stock EMD $SO_3^-$ gel was gently inverted until the slurry was fully equilibrated. 5 mls was pipetted onto a 20 ml Biorad poly-prep column (ca 4 ml bed volume) and the ethanol was allowed to drain from the column. The column was then washed with 4×20 ml of 1× binding buffer. The 4 ml pooled fractions from the Nickel purification were made up to 8 mls in 2× binding buffer and transferred onto the column. The sample was allowed to flow through the column and was washed with 20 mls of 1× binding buffer. Elution's were then carried out using elution buffers ranging 200-1000 mM NaCl in 100 mM steps (prepared using 2× master mix, 5M NaCl and $dH_2O$). 2 mls of the first elution buffer was passed through the column and stored on ice, followed by the second, etc. Once all the fractions had been collected, the column was disregarded and the un-bound fractions, washes and fractions were SDS-PAGE analysed for both, purity and determination of the fractions to be pooled (those containing the His-CxxC-3). Once these fractions had been pooled they were dialyzed as for the Nickel purification and stored at 4° C.

Protein Concentration Determination

Protein concentrations of the purified His-CxxC-3 was determined using the protein dye (Bio-Rad 500-0002) Bradford assay of (Bradford, 1976).

Bandshift Assays

Bandshift assays were carried out on 100 ml 1.3% w/v agarose gels, consisting of 1.3 gs of agarose in 0.5×TBE set with 15 wells. Bandshifts were probed with the radiolabeled probe CG11 constructed as reported by (Meehan et al., 1989) in both methylated and non-methylated form. CG11 was diluted in bromophenol blue dye at a ratio of 1:1 to give a concentration of 15-25 pmol/µl, prior to loading the gel. Non-specific competitor DNA was already prepared from E. coli.

20 µl reactions were prepared, containing 4 µl of (5×) Binding buffer, 1 µl E. coli competitor DNA, 2 µl of CG11 (methylated or non-methylated depending on requirement), a range of His-CxxC-3 (200-1000 ng) and $dH_2O$ as required to make reaction up to 20 µl. Controls were duplicated for both CG11 forms, one containing 3 µls of His-CxxC-3 (activity proven by previous bandshifts) and another with no protein factor.

Samples were prepared as above without probe and His-CxxC-3 added last, then allowed to incubate at room temperature for ten minutes. 2 µl of the diluted probe was the added (with careful pipette mixing) and then a further 25 minutes of incubation at room temperature. The 20 µl reactions were loaded onto the pre-cooled (4° C.) gel in 0.5×TBE and run at 120 v at this temperature for 2 hours. The gel was subsequently placed on two sheets of DE81 and two sheets of 3 mm Whatman paper, covered in Saran wrap and vacuum dried at 80° C. for between 2-3 hours. The gel was transferred to a phosphorimager screen and left overnight, and imaged on the phosphorimager the following morning.

Preparation and Packing of Column

His-CxxC-3 was bound to 1 ml of Ni-NTA superflow beads and packed onto a Pharmacia HR5/5 liquid chromatography column according to the method of (3) with the following adjustments. Buffer washes were 2×3 mls and a total of six fractions were collected. Bradford assay was carried out on all fractions to assess non-specific binding to the column. An additional SDS-PAGE analysis of a sample of protein bound Ni-NTA was compared against BSA standards to determine the CxxC-3 content of the column. The HR5/5 column was fully disassembled and equilibrated in column buffer 1 prior to packing. Beads were re-suspended in 3×3 ml of column buffer 1, and packed onto the column (1 ml/min continuous flow rate from the bottom) until all beads were fully sedimented. The column was assembled using the drop to drop method (ensuring no air traps), and the flow direction reversed for 20 mls of column buffer 1 to thoroughly pack the Ni-NTA (see Pharmacia instructions sheet on assembly).

Preparation of pABS DNA for Column Calibration

Restriction:

2×5 µl (6 µg) of the plasmid pABS, was digested using EcoRI and BamHI (1 and 2 restriction sites respectively), producing three different sized fragments of 2:7, 2.1 and 1.4 kb (for restriction digestion see later section). The completion of the digest was analysed by agarose gel electrophoresis. Restriction samples were subsequently NaCl/Ethanol precipitated according to standard procedures with the addition of tRNA (2 µl of 10 mg/ml) stock as a carrier, to reduce DNA loss. Samples were then resuspended in 30 µl TE (Tris/EDTA).

SssI Methylation:

300 µl SssI methylation reaction mixture was prepared, sufficient to methylate 6 µg of DNA: (222 µl dH$_2$O, 9 µl SAM (S-adenosylmethionine), 30 µl NEBuffer 2 (10×), 30 µl DNA and finally 9 µl of SssI methylase). The reaction was then incubated at 37° C. overnight, after which, an additional 6 µl of SAM and SssI was added to the reaction and incubated for a further six hours. Methylation efficiency was analysed by HpaII restriction and agarose gel electrophoresis (methylation sensitive endonuclease which does not cut methylated DNA).

Both methylated and un-methylated samples were run on an agarose gel with an EcoRI/HindIII restricted sample to determine approximate relative DNA contents of the reactions.

Klenow Labeling:

EcoRI and HindIII overhangs of the DNA fragments (both methyl/non-methyl) were labeled with $^{32P}$dCTP, using the klenow fragment of DNA polymerase I. The reaction mixture was prepared with 3 µl of DNA, 4 µl NEBuffer H, 1 µl each of A/T/G dNTP's, 2 µl of $^{32P}$dCTP and 1 µl Klenow, and then incubated at room temperature for one hour.

Labeling of the AATT overhang of EcoRI was possible due to the slight exonuclease activity of the Klenow fragment.

Precipitation and Re-Suspension of Labeled DNA:

Labelled samples were precipitated differently from previous samples to avoid the need for maintenance at cold temperatures (more difficult in the radioactive lab). 2☐l of stock tRNA (carrier) and 1/10 the sample volume of 5M NaOAC was added to the sample and inverted several times to mix. 2½ volumes (of total mixture) of −20° C. Ethanol was added to the sample then vortexed thoroughly and allowed to precipitate for 20 minutes at room temperature. The samples were the centrifuged in microfuge for 20 minutes at 14k rpm, and the supernatant carefully pipetted off. 1 ml of −20° C., 70% Ethanol was then added to the samples which was then vortexed and centrifuged for a further 10 minutes. The ethanol was removed using a p1000 pipette and then carefully with p20 pipette to avoid dislodging the pelleted DNA, and then air-dried for 5-10 minutes. Samples were the resuspended in the desired amount of TE, using a p1000 pipette and stored in a Perspex holder at −20° C.

Mounting and Running the Column

Samples:

3×1 ml samples were prepared for loading, such that the DNA was contained within a 0.1M NaCl running buffer. Both the methylated and non-methylated samples contained 500 ng of DNA and the methylated/non-methylated sample contained 500 ng of each. These samples were prepared in 0.1M NaCl running buffer just prior to loading onto the column.

Mounting the CxxC-3 affinity column to the Pharmacia FPLC system (Fast Protein Liquid Chromatography):

The FPLC pumps were set to 1 ml/min, valve position 1.3 and WASH A.B to position 1.1 and washed through, (first with dH$_2$O/Azide and then with a sample of 0.1M NaCl running buffer). Pump A and B were run from column buffers 1 and 2 respectively, and the FPLC set to wash the system through with a 0.1M NaCl Buffer (10 mls at 1 ml/min), the CxxC-3 column was then attached by the drop to drop method ensuring that the outlet was higher than the inlet during attachment (0.1M NaCl buffer being pumped at 0.2 ml/min during attachment).

Washing and Running the Column:

This was carried out using the method of (3) with several adjustments. Briefly, the FPLC was set to run two separate methods files, first a wash and then a column run. The wash cycle ran 5 mls of 0.1M NaCl buffer through the column, followed by 5 mls of 1M NaCl buffer and then another 5 mls of 0.1M NaCl buffer. Once complete the run cycle introduced a pre-loaded 1 ml DNA sample (from the sample loop) on to the column, then ran 0.1M NaCl buffer through the column for 4.8 mls. At this point the concentration was increased to 1M NaCl buffer (to produce a concentration gradient over 30 1 ml fractions). This concentration was maintained for 5 mls before returning to 0.1M NaCl buffer for the final 5 mls. All running was carried out at 1 ml/min, with 1 ml fractions collected from 0-41 mls and the UV chart reader measuring over the entire program. Fractions were stored in Perspex container until their analysis.

Analysis of Primary Calibration:

Scintillation Analysis:

The 41 fractions were transferred into liquid scintillation viles containing the protocol 4 flag (for $^{32}$P counting). The counter was started and measured the CPM (counts per minute) of the 41 samples over 2½ hours. The values were subsequently plotted with Microsoft EXCEL to determine the elution profile of labeled DNA.

Electrophoretic Analysis:

300 µl aliquots of the methylated and non-methylated fractions were precipitated (as for the products of the klenow labeling) and resuspended in TE/6× loading buffer. 400 µl of the methylated/non-methylated run fractions were precipitated as above, but were resuspended in 30 µl of TE and then divided into 3×10 µl aliquots. Two sets were then digested with restriction endonucleases (one with HpaII and the other with MspI, methylation sensitive and resistant respectively)

and then all three sets were prepared with 6× loading buffer. All samples were run on an agarose gel (see later section) and imaged under UV and phosphorimager.

Restriction Digests:

Restriction digestion was carried out using the New England Biolabs restriction endonucleases and supplied buffers/BSA as directed. In brief; reactions were generally made to 20 µl, such as to contain the desired amount of DNA (e.g. 1-10 µl), 0.5 µl of each restriction enzyme, 2 µl of (10×) BSA (if required), 2 µl of (10×) NEBuffer (whichever gives the optimum activity for the endonucleases being used) and then made up to 20 µl in $dH_2O$. Reactions were then transferred to 37° C. for 3-4 hours prior to analysis of cleavage. Restriction endonucleases were always added to the reaction mixture last to ensure that they were correctly buffered. It is important that the volume of enzyme added never exceeds 10% of the total reaction volume as the resultant elevated glycerol content may lead to inhibition of the endonuclease activity.

Restriction reactions that were seen not to go to completion, were pushed harder by digestion overnight, and then addition of more NEBuffer, enzyme and $dH_2O$ (to maintain the correct concentrations) and digested for a further four hours whilst ensuring that 10% enzyme volume was not exceeded.

Agarose Gel Electrophoresis:

All agarose gel electrophoresis carried out, was on plasmid and restricted-plasmid DNA, ranging in size from 100-6000 bp. As such, agarose gels were made 1.3% (w/v) in TAE buffer (1×) containing ethidium bromide (50,000×) according to standard techniques (1). For plasmid analysis (restriction/methylation), 100 ml gels with 15 well combs were made and run in 1 liter tanks, flooded with (1×) TAE (to ca 3 mm above the surface of the gel) and run at 120 v until the loading buffer was 0.5 cm from the foot of the gel. Gels were subsequently removed from their frames and visualized under UV (visualizes DNA via Ethidium Bromide intercalation) and photographed. For $^{32}P$ labeled DNA (column fraction analysis) large 400 ml gels with 26 lane wells were set and run (in 2.6 liters of TAE) as before, but after UV imaging were then dried and imaged as for the Bandshifts.

Samples were prepared in (6×) loading buffer (e.g. 20 µl DNA with 4 µl loading buffer/or made to volume in water). For precipitated samples (fraction analysis), the dried DNA was resuspended in 15 µl of (TE:loading buffer/6:1) and loaded. Every gel was imaged with a 10 µl load of 1 kb+DNA ladder in lane 1. UV images of the fraction gels were taken with a UV ruler such that the size markers could be superimposed onto the $^{32}P$ Phosphor images.

SDS-PAGE (Sodium Dodecyl Sulfate-Polyacrylemide Gel Electrophoresis):

All CxxC-3 SDS-PAGE analysis was carried out in 3 ml, 10 well, 15% SDS-PAGE gels made and loaded according to standard procedures (1). When the comb was removed all wells were syringe flushed with buffer to ensure both detached gel and air bubbles were removed to allow efficient sample loading. Gels were loaded and run for 45-60 minutes or until the loading buffer (dye) was at the base of the gel.

Samples were prepared depending on the specific procedure used, but generally large sample (250 µl), were centrifuged for 1 minute at 16k rpm and the pellet resuspended in a desired amount of 1×DTT loading buffer (pellet samples such as the lysate were prepared in the same way). Small fraction sample such as those from the purification stages were made to the desired concentration in 2×DTT loading buffer. Each SDS-PAGE gel was calibrated using a 10 µl load of the 2-212 kDa broad range size markers (New England Biolabs). All samples and size markers were boiled for 3 minutes, at 100° C. and returned to ice briefly before loading.

Once run gels was stained for 20 minutes in coomasie brilliant blue on a shaker table. Gels were then removed, bathed in fresh $dH_2O$, heated for 5 minutes in the microwave and then the gel transferred to clean $dH_2O$. This process was repeated several times until distinct protein banding could be identified.

Following the procedures described above, the present inventors have generated a library and sequenced the CpG island sequences. These sequences have been correlated with the human genome sequence and the sequences, clone identifiers and their positions are described in Table 1. Using the CxxC column of the present invention, a far more representative library of fragments has been generated from the human genome in comparison to the library obtained using, for example, the Cross et al (1994) method (12,000 uniquely mapped sequences versus 6,000 uniquely mapped sequences). The present method and resulting library is therefore about twice as representative than those libraries obtained using prior art methods and therefore has potentially much greater utility.

REFERENCES

Birke, M., Schreiner, S., Garcia-Cuellar, M. P., Mahr, K., Titgemeyer, F., and Slany, R. K. (2002). The MT domain of the proto-oncoprotein MLL binds to CpG-containing DNA and discriminates against methylation. Nucleic Acids Res 30, 958-965.

Cross S. H., Charlton J. A., Nan X. and Bird A. P. (1994). Purification of CpG islands using a methylated DNA binding column. Nature Genetics 6, 236-243

Cross, S. H., Clark, V. H., Simmen, M. W., Bickmore, W. A., Maroon, H., Langford, C. F., Carter, N. P., and Bird, A. P. (2000). CpG island libraries from human chromosomes 18 and 22: landmarks for novel genes. Mammalian Genome 11, 373-383.

Jørgensen H. F., Ben-Porath I. and Bird A. P. (2004) Mbd1 is recruited to both methylated and nonmethylated CpGs via distinct DNA binding domains. Molecular and Cellular Biology 24, 3387-3395

Lee, J. H., Voo, K. S., and Skalnik, D. G. (2001). Identification and characterization of the DNA binding domain of CpG-binding protein. J Biol Chem 276, 44669-44676.

McCarthy, B. J., and Church, R. B. (1970). The specificity of molecular hybridization reactions. Annu Rev Biochem 39, 131-150.

McKeon, C., Pastan, I., and de Crombrugghe, B. (1982). DNaseI sensitivity of the alpha 2(I) collagen gene varies with gene expression but not with its methylation pattern. Nuc Acids Res 12, 3491-3502.

McKim, K. S., and Hawley, R. S. (1995). Chromosomal control of meiotic cell division. Science 270, 1595-1601.

McKnight, S. L., and Kingsbury, R. (1982). Transcriptional control signals of a eukaryotic protein-coding gene. Science 217, 316-324.

McNally, J. G., Muller, W. G., Walker, D., Wolford, R., and Hager, G. L. (2000). The glucocorticoid receptor: rapid exchange with regulatory sites in living cells. Science 287, 1262-1265.

Palmer, L. E., Rabinowicz, P. D., O'Shaughnessy, A. L., Balija, V. S., Nascimento, L. U., Dike, S., de la Bastide, M., Martienssen, R. A. & McCombie, W. R. (2003) Maize genome sequencing by methylation filtration. Science 302, 2115-7.

Sambrook, J & Russel, D; "Molecular Cloning: A laboratory manual", Cold Spring Harbor Press, 2001.

Weinmann, A. S., Yan, P. S., Oberley, M. J., Huang, T. H., and Farnham, P. J. (2002). Isolating human transcription factor targets by coupling chromatin immunbprecipitation and CpG island microarray analysis. Genes Dev 16, 235-244.

Whitelaw, C. A., Barbazuk, W. B., Pertea, G., Chan, A. P., Cheung, F., Lee, Y., Zheng, L., van Heeringen, S., Karamycheva, S., Bennetzen, J. L., SanMiguel, P., Lakey, N., Bedell, J., Yuan, Y., Budiman, M. A., Resnick, A., Van Aken, S., Utterback, T., Riedmuller, S., Williams, M., Feldblyum, T., Schubert, K., Beachy, R., Fraser, C. M. & Quackenbush, J. (2003) Enrichment of gene-coding sequences in maize by genome filtration. Science 302, 2118-20.

TABLE 1

| Chr | Start | Stop | Clone Identifier |
|---|---|---|---|
| MT | 11341 | 11466 | H_c139m24 |
| MT | 13699 | 13869 | H_c133b08_M |
| MT | 16300 | 16544 | H_c_261a19 |
| X | 100121443 | 100121629 | H_c_167b01_M |
| X | 100158993 | 100159395 | H_c_256i22_M |
| X | 100409006 | 100410412 | H_c_107g20 |
| X | 100451997 | 100452218 | H_c131n21 |
| X | 10047252 | 10047374 | H_c_257i07_M |
| X | 100477682 | 100480148 | H_c_219p09_M |
| X | 100546082 | 100547375 | H_c143p07_M |
| X | 101729806 | 101731586 | H_c_26p03 |
| X | 102006153 | 102006242 | H_c_168n07 |
| X | 102437043 | 102438384 | H_c_248d10_M |
| X | 102748440 | 102748695 | H_c_266a01_M |
| X | 103344543 | 103344644 | H_c140m06 |
| X | 103617575 | 103618673 | H_c_11b12 |
| X | 104540780 | 104540908 | H_c_81f10_M |
| X | 104705744 | 104705863 | H_c_123p19 |
| X | 104877696 | 104877787 | H_c_124h09 |
| X | 105310321 | 105310399 | H_c_85d04 |
| X | 105775973 | 105776522 | H_c_169m08_M |
| X | 106048851 | 106049659 | H_c_261m19 |
| X | 106255151 | 106255814 | H_c_44f02 |
| X | 106321263 | 106323057 | H_c_252m18 |
| X | 106372406 | 106375251 | H_c_152i02 |
| X | 106677516 | 106678760 | H_c_174g18 |
| X | 106764762 | 106766542 | H_c_269a10_M |
| X | 106824055 | 106825778 | H_c_186f01_M |
| X | 106875533 | 106876300 | H_c_21f14 |
| X | 107744995 | 107745184 | H_c_119d12 |
| X | 108781728 | 108783124 | H_c_272l14_M |
| X | 109366404 | 109367899 | H_c_99b21_M |
| X | 109806337 | 109806533 | H_c_130j09 |
| X | 110730327 | 110731415 | H_c_213i10 |
| X | 111854004 | 111854470 | H_c_184l20 |
| X | 111890688 | 111891071 | H_c_212e03 |
| X | 11205738 | 11205849 | H_c_261m18 |
| X | 112173671 | 112173753 | H_c_113l05 |
| X | 113641354 | 113642555 | H_c133g16 |
| X | 114284586 | 114284836 | H_c_67i10 |
| X | 114290989 | 114291548 | H_c_66g16_M |
| X | 11441947 | 11443864 | H_c_203f04_M |
| X | 114496143 | 114497005 | H_c_231c23 |
| X | 114619504 | 114619663 | H_c_209o07_M |
| X | 114998768 | 114998986 | H_c_239a14 |
| X | 11535316 | 11536439 | H_c_117b14_M |
| X | 115691725 | 115691796 | H_c_82j03 |
| X | 117031858 | 117033236 | H_c_205h05 |
| X | 117083245 | 117083396 | H_c_64d09 |
| X | 117129333 | 117129530 | H_c_171c22 |
| X | 117261173 | 117262195 | H_c_240i01_M |
| X | 117419302 | 117419474 | H_c_56n04 |
| X | 117642848 | 117644226 | H_c_248d11_M |
| X | 117755000 | 117755691 | H_c_4e09 |
| X | 117889030 | 117891434 | H_c_266a14_M |
| X | 118188707 | 118190226 | H_c_108j09 |
| X | 118314466 | 118315934 | H_c_72g04 |
| X | 118383877 | 118385306 | H_c_90h22 |
| X | 118490269 | 118491186 | H_c_231a14 |
| X | 118521065 | 118522511 | H_c_151b09_M |
| X | 118607943 | 118609171 | H_c_234h23 |
| X | 118673535 | 118675676 | H_c_248l14 |
| X | 118786409 | 118788901 | H_c_169d23_M |
| X | 118858930 | 118859777 | H_c_80h14 |
| X | 11915448 | 11916899 | H_c_69j16_M |
| X | 119166034 | 119166611 | H_c_239e24 |
| X | 119640157 | 119640257 | H_c_17j13_M |
| X | 119906789 | 119906973 | H_c_34f15_M |
| X | 122454377 | 122454599 | H_c_90c15 |
| X | 122819352 | 122822679 | H_c_58l12_M |
| X | 12302001 | 12302097 | H_c_20a02 |
| X | 124064120 | 124065281 | H_c_73a09 |
| X | 124819549 | 124819638 | H_c_9e18 |
| X | 124984963 | 124985085 | H_c_70n23 |
| X | 125024763 | 125026047 | H_c_233l23_M |
| X | 125045743 | 125045881 | H_c_148o08 |
| X | 125410651 | 125412617 | H_c_257b18_M |
| X | 128399637 | 128400655 | H_c_77f08_M |
| X | 128702355 | 128703591 | H_c_159e05 |
| X | 128790667 | 128791410 | H_c_175e16 |
| X | 128816531 | 128816656 | H_c_69h22 |
| X | 128838540 | 128840996 | H_c_234l03_M |
| X | 128919448 | 128920574 | H_c_110k13 |
| X | 129030980 | 129032325 | H_c_202c18 |
| X | 129762058 | 129763103 | H_c_98j08 |
| X | 129926927 | 129928224 | H_c_184d06 |
| X | 129940989 | 129943484 | H_c_211a24_M |
| X | 130344129 | 130344201 | H_c_49i01 |
| X | 130882277 | 130883545 | H_c_81e17_M |
| X | 131076582 | 131078296 | H_c_72m04 |
| X | 131348343 | 131348588 | H_c_22jl16_M |
| X | 131699150 | 131699250 | H_c_176j10 |
| X | 131970623 | 131970684 | H_c_107j05 |
| X | 132762359 | 132762483 | H_c_253e24_M |
| X | 132844175 | 132845905 | H_c_3a13_M |
| X | 133032238 | 133032530 | H_c_2j24 |
| X | 133262686 | 133262793 | H_c_81e07 |
| X | 133319342 | 133320603 | H_c_90n23 |
| X | 133404078 | 133404813 | H_c_41a16 |
| X | 13347183 | 13347848 | H_c_76o16 |
| X | 133655583 | 133657061 | H_c144i11 |
| X | 133804478 | 133804657 | H_c_33g13_M |
| X | 133863465 | 133863724 | H_c_228d01 |
| X | 13430600 | 13431314 | H_c_264g07 |
| X | 134379889 | 134381728 | H_c_43g12 |
| X | 134781180 | 134782370 | H_c_76o09 |
| X | 134848234 | 134848466 | H_c_223a10 |
| X | 134954512 | 134956327 | H_c_236h09_M |
| X | 135028316 | 135028511 | H_c_81c01 |
| X | 135304231 | 135305738 | H_c_175b17_M |
| X | 135574498 | 135575945 | H_c_61b02_M |
| X | 135687791 | 135688684 | H_c_162p23_M |
| X | 135840785 | 135841701 | H_c_202f06 |
| X | 135859972 | 135860874 | H_c_102f04 |
| X | 136236080 | 136237325 | H_c_204p09 |
| X | 136353699 | 136359014 | H_c_45j15_M_M |
| X | 136374092 | 136375881 | H_c_244e02 |
| X | 136381298 | 136382513 | H_c_160b11_M |
| X | 136824944 | 136825076 | H_c_93b24 |
| X | 136845 | 138831 | H_c_98g23 |
| X | 13715945 | 13716876 | H_c_48e12_M |
| X | 13790563 | 13790715 | H_c_208m11 |
| X | 137921392 | 137921646 | H_c_161p17 |
| X | 138002423 | 138002999 | H_c_111m07_M |
| X | 138010056 | 138012342 | H_c_199g11 |
| X | 13807425 | 13807979 | H_c_22e14_M |
| X | 138738830 | 138741143 | H_c_150h04_M |
| X | 138898554 | 138900326 | H_c_207k18 |
| X | 139175704 | 139175824 | H_c_214e04_M |
| X | 139247027 | 139248189 | H_c142e19 |
| X | 139314588 | 139316983 | H_c_249j13_M |
| X | 139726245 | 139726436 | H_c_201b02 |
| X | 13996921 | 13997034 | H_c_89o12 |
| X | 1403506 | 1406009 | H_c_16g09 |
| X | 141483228 | 141483538 | H_c_211c18 |
| X | 141665745 | 141665897 | H_c_79j22 |
| X | 142446748 | 142449229 | H_c_173k19_M |
| X | 143487510 | 143487631 | H_c_38o17 |

TABLE 1-continued

| | | | |
|---|---|---|---|
| X | 144169133 | 144169289 | H_c_123j18 |
| X | 144310686 | 144310884 | H_c_85b08 |
| X | 145367250 | 145367457 | H_c_202g13 |
| X | 145409941 | 145410081 | H_c_4g23 |
| X | 145412156 | 145412255 | H_c_68j15 |
| X | 146185591 | 146185724 | H_c_221b20 |
| X | 14650607 | 14651557 | H_c_6f21_M |
| X | 146640877 | 146640999 | H_c_23n23 |
| X | 146698376 | 146700012 | H_c_11f07_M |
| X | 14683587 | 14683695 | H_c_190o08 |
| X | 147436091 | 147436258 | H_c_228c01 |
| X | 148544357 | 148547067 | H_c_21e24 |
| X | 149199884 | 149205017 | H_c_209l06_M |
| X | 149307432 | 149307553 | H_c_108o20 |
| X | 149385901 | 149387269 | H_c_231d12_M |
| X | 149406581 | 149408334 | H_c_21p15_M |
| X | 149531879 | 149533131 | H_c_19l11 |
| X | 149736770 | 149738491 | H_c_19k19_M |
| X | 149814542 | 149817187 | H_c_52c11 |
| X | 150016390 | 150017292 | H_c_206f19_M |
| X | 150591989 | 150593188 | H_c_198a23 |
| X | 150813116 | 150815303 | H_c_129m20_M |
| X | 15112784 | 15113455 | H_c_66n08_M |
| X | 151669419 | 151670829 | H_c_195o07 |
| X | 151736786 | 151737631 | H_c_108b04 |
| X | 152082659 | 152084498 | H_c137c17 |
| X | 152256124 | 152261780 | H_c_19n15_M |
| X | 152280693 | 152282058 | H_c137c06 |
| X | 152395754 | 152397583 | H_c_168b23 |
| X | 152430155 | 152432071 | H_c_122n17 |
| X | 152604781 | 152606350 | H_c_219j08 |
| X | 152615002 | 152616780 | H_c_208i06 |
| X | 152714291 | 152714721 | H_c_168n19 |
| X | 152720183 | 152721950 | H_c_61d10_M |
| X | 152756615 | 152758544 | H_c_60e03_M |
| X | 153120598 | 153122003 | H_c_2n01_M |
| X | 153147273 | 153148179 | H_c_68k21 |
| X | 153235986 | 153237401 | H_c_259o22_M |
| X | 153249596 | 153250293 | H_c_59g03 |
| X | 153270472 | 153271925 | H_c_96c04_M |
| X | 153281912 | 153283504 | H_c_81i06 |
| X | 153307635 | 153309884 | H_c_204k07_M |
| X | 153338587 | 153338789 | H_c_152f16_M |
| X | 153542380 | 153543633 | H_c_71h09_M |
| X | 153542988 | 153543636 | H_c_268k05 |
| X | 153554363 | 153555095 | H_c_157p15_M |
| X | 153596985 | 153597601 | H_c_68e24 |
| X | 153640806 | 153640978 | H_c142p11_M |
| X | 153700330 | 153700424 | H_c_168c18 |
| X | 154274036 | 154274082 | H_c_73o21 |
| X | 15452349 | 15453849 | H_c_105g15 |
| X | 15524223 | 15524423 | H_c_207b07 |
| X | 1553854 | 1556456 | H_c_48p20_M |
| X | 15723378 | 15723667 | H_c_82i04 |
| X | 16497145 | 16498175 | H_c_28n12_M |
| X | 16563278 | 16565190 | H_c_205i07 |
| X | 16647029 | 16648855 | H_c_86b12_M |
| X | 16723144 | 16725216 | H_c_243n11_M |
| X | 17152310 | 17154332 | H_c_185d24 |
| X | 17638059 | 17640380 | H_c_121k12_M |
| X | 18131435 | 18133216 | H_c_66k21_M |
| X | 18202395 | 18204294 | H_c_77b18 |
| X | 18679572 | 18680692 | H_c_59h10 |
| X | 18877190 | 18877260 | H_c_237h17 |
| X | 18899470 | 18901249 | H_c_75j20_M |
| X | 18938069 | 18938152 | H_c_101j18 |
| X | 19507673 | 19507916 | H_c_268c23 |
| X | 19893654 | 19895693 | H_c_81o14_M |
| X | 19954934 | 19955531 | H_c_168d23 |
| X | 20043691 | 20046169 | H_c_149d20_M |
| X | 21151404 | 21153414 | H_c133m21_M |
| X | 21433509 | 21435702 | H_c_64h15_M |
| X | 21617155 | 21617948 | H_c_174a15 |
| X | 23282805 | 23283745 | H_c_195o01_M |
| X | 23831980 | 23832239 | H_c_217j24 |
| X | 23926883 | 23928484 | H_c_128i02 |
| X | 2411632 | 2414245 | H_c_20n14 |
| X | 24242493 | 24243637 | H_c_184o15 |
| X | 24782112 | 24785476 | H_c_249g11_M |
| X | 24800123 | 24801140 | H_c_106l10 |
| X | 2494572 | 2496873 | H_c_271n15_M |
| X | 25150915 | 25151079 | H_c_257c13 |
| X | 2520400 | 2521254 | H_c_115g10 |
| X | 2602326 | 2603564 | H_c_274e18_M |
| X | 26068626 | 26068727 | H_c_111e03 |
| X | 26142592 | 26142691 | H_c_213k04 |
| X | 26166941 | 26167053 | H_c_70c08 |
| X | 26638221 | 26638327 | H_c_79o12 |
| X | 27200657 | 27200737 | H_c_70a08 |
| X | 28123403 | 28123498 | H_c_26f15 |
| X | 30085976 | 30087334 | H_c_71f07_M |
| X | 303896 | 305282 | H_c_214p12 |
| X | 30430533 | 30431984 | H_c_181f12 |
| X | 30666534 | 30667519 | H_c_74h14_M |
| X | 31018390 | 31018695 | H_c_6k23 |
| X | 31043778 | 31044921 | H_c_211l23 |
| X | 31152845 | 31152973 | H_c_106p20 |
| X | 3150024 | 3150118 | H_c_118c02 |
| X | 31766766 | 31766856 | H_c_29i11 |
| X | 32089612 | 32089693 | H_c_199i22 |
| X | 32308359 | 32308578 | H_c_113p15_M |
| X | 32378123 | 32378293 | H_c_78b12 |
| X | 33774192 | 33774257 | H_c_15n05 |
| X | 34046407 | 34046480 | H_c_232i13 |
| X | 34764307 | 34764517 | H_c137b08 |
| X | 35542176 | 35542316 | H_c_193a15 |
| X | 357696 | 359520 | H_c_98h14_M |
| X | 36740685 | 36741862 | H_c_224m14 |
| X | 37300823 | 37301948 | H_c_251c13 |
| X | 37462332 | 37463371 | H_c_246e20 |
| X | 38176241 | 38177214 | H_c_37l24_M |
| X | 38201609 | 38201890 | H_c_170o13 |
| X | 38419028 | 38421593 | H_c144c11_M |
| X | 38837243 | 38837377 | H_c132i15 |
| X | 3886938 | 3887273 | H_c_247i15 |
| X | 39436455 | 39437655 | H_c_85a05_M |
| X | 39627937 | 39628501 | H_c139j16 |
| X | 39710141 | 39712507 | H_c_50j08_M |
| X | 39722617 | 39725532 | H_c_94a08_M |
| X | 39761636 | 39761793 | H_c_176m06 |
| X | 39766466 | 39770571 | H_c_74a17_M_M |
| X | 39772915 | 39774037 | H_c_11p06_M |
| X | 39787276 | 39790170 | H_c_20b13_M_M |
| X | 39853242 | 39853641 | H_c_49p04_M |
| X | 40196321 | 40197121 | H_c_82h13 |
| X | 40350496 | 40351799 | H_c_39e07_M |
| X | 40699651 | 40700337 | H_c_11k07_M |
| X | 40868278 | 40869738 | H_c_117k20 |
| X | 43270248 | 43272137 | H_c_12g18 |
| X | 43270603 | 43272139 | H_c_124f10 |
| X | 44488559 | 44489393 | H_c133p15_M |
| X | 45069448 | 45069783 | H_c_37c04 |
| X | 45466438 | 45467697 | H_c_50d06_M |
| X | 45810628 | 45810795 | H_c_193n08 |
| X | 4594014 | 4594239 | H_c_200o18_M |
| X | 46134268 | 46135349 | H_c_21m21 |
| X | 46188710 | 46189982 | H_c_41h15_M |
| X | 46374220 | 46375222 | H_c_118a05 |
| X | 46528272 | 46529183 | H_c_164f09_M |
| X | 46809216 | 46810057 | H_c_228p10 |
| X | 46848167 | 46849583 | H_c_232j06_M |
| X | 47098125 | 47098903 | H_c_81a06_M |
| X | 47138934 | 47139367 | H_c_190n07 |
| X | 47176625 | 47177209 | H_c_39g10 |
| X | 47234880 | 47236828 | H_c_186h07_M |
| X | 47451817 | 47452661 | H_c_105e22 |
| X | 47686286 | 47687738 | H_c_23p16 |
| X | 48090363 | 48091444 | H_c_23o09 |
| X | 48189208 | 48189520 | H_c_69i06_M |
| X | 48311041 | 48311381 | H_c_127j16_M |
| X | 48326502 | 48326651 | H_c_49b16 |
| X | 48415934 | 48416822 | H_c_228e23_M |
| X | 48440568 | 48441915 | H_c_92n02_M |
| X | 48444942 | 48447177 | H_c_272k11 |
| X | 48478924 | 48479205 | H_c_54g22 |
| X | 48511140 | 48512241 | H_c_152k05_M |
| X | 48551773 | 48553312 | H_c_32d21 |
| X | 48687905 | 48688355 | H_c_129c11_M |
| X | 48691851 | 48694631 | H_c_200h01 |
| X | 48784323 | 48785377 | H_c_183f04_M |

TABLE 1-continued

| | | | |
|---|---|---|---|
| X | 48803663 | 48804535 | H_c_139h02_M |
| X | 48812416 | 48813316 | H_c_76m06 |
| X | 48821903 | 48824453 | H_c_242k20 |
| X | 48881452 | 48883869 | H_c_4h12_M |
| X | 49346897 | 49347690 | H_c_45d07 |
| X | 49390084 | 49390937 | H_c_82l19_M |
| X | 49599014 | 49599105 | H_c_33o05 |
| X | 49665620 | 49665751 | H_c_94j22 |
| X | 50045073 | 50047039 | H_c_125g02 |
| X | 50389981 | 50390640 | H_c_102n05 |
| X | 50971474 | 50972652 | H_c_115c01 |
| X | 51071791 | 51072713 | H_c_34a13 |
| X | 51319395 | 51320788 | H_c_84g13_M |
| X | 52846639 | 52847676 | H_c_51i15 |
| X | 52912718 | 52913377 | H_c_99f23 |
| X | 52994106 | 52995783 | H_c_27e08 |
| X | 53237606 | 53237706 | H_c_110e18 |
| X | 53593465 | 53593690 | H_c_150i11_M |
| X | 53953225 | 53954041 | H_c_29p09_M |
| X | 54091936 | 54093350 | H_c_29c14 |
| X | 54266680 | 54268389 | H_c_89b16_M |
| X | 54404064 | 54405792 | H_c_240d21_M |
| X | 54548748 | 54549123 | H_c_245h01 |
| X | 548253 | 550541 | H_c_184b13_M |
| X | 55068585 | 55068683 | H_c_92g20 |
| X | 55397793 | 55398733 | H_c_115b04 |
| X | 55445109 | 55446300 | H_c_198i13 |
| X | 55782996 | 55783166 | H_c_261h13 |
| X | 564545 | 565030 | H_c_247b17 |
| X | 57548108 | 57548284 | H_c_63a16 |
| X | 57957506 | 57958503 | H_c_142g02 |
| X | 6003811 | 6005082 | H_c_151m16 |
| X | 61944191 | 61944344 | H_c_101f06 |
| X | 62238898 | 62238998 | H_c_156e05 |
| X | 62353770 | 62354541 | H_c_272n14 |
| X | 6286290 | 6286366 | H_c_168d21 |
| X | 64037428 | 64038334 | H_c_209b20 |
| X | 64097465 | 64097589 | H_c_272j20 |
| X | 64537532 | 64537811 | H_c_156l13_M |
| X | 64669985 | 64671423 | H_c_27c06 |
| X | 67339263 | 67339473 | H_c_50k09 |
| X | 67501696 | 67502725 | H_c_85m18 |
| X | 67696209 | 67697138 | H_c_44p15 |
| X | 67830564 | 67834175 | H_c_235b03_M |
| X | 68161037 | 68161325 | H_c_90l22 |
| X | 68287976 | 68290492 | H_c_218a07 |
| X | 68618689 | 68620041 | H_c_202i19 |
| X | 68950970 | 68951144 | H_c136b16 |
| X | 69190742 | 69190849 | H_c_157e16 |
| X | 6925184 | 6926694 | H_c_94g16_M |
| X | 69292556 | 69292956 | H_c_5g22 |
| X | 69436561 | 69438122 | H_c_183g02 |
| X | 69934592 | 69934659 | H_c_65c19 |
| X | 70099099 | 70100531 | H_c_151b12 |
| X | 70285928 | 70286990 | H_c_127b07_M |
| X | 70535722 | 70537143 | H_c_192i12_M |
| X | 70913573 | 70914742 | H_c_168d22 |
| X | 71021241 | 71023102 | H_c_64a16 |
| X | 71134348 | 71135216 | H_c_194a13_M |
| X | 71164420 | 71164557 | H_c_213d04 |
| X | 71193527 | 71194483 | H_c_268k24_M |
| X | 73424073 | 73425235 | H_c_35c07 |
| X | 73539012 | 73540292 | H_c_272e10_M |
| X | 73616554 | 73617861 | H_c_251c18 |
| X | 73926849 | 73927202 | H_c_39n08 |
| X | 74664538 | 74664685 | H_c139g19 |
| X | 74754286 | 74754380 | H_c_79m03 |
| X | 75151762 | 75152837 | H_c_19e21_M |
| X | 75834242 | 75834476 | H_c_92e16 |
| X | 759114 | 759249 | H_c134h21 |
| X | 76956903 | 76957612 | H_c_45h13 |
| X | 7705104 | 7705280 | H_c_264g11_M |
| X | 77062835 | 77062900 | H_c_112m08 |
| X | 77165362 | 77166012 | H_c_84d18 |
| X | 77773149 | 77773220 | H_c_79n09 |
| X | 77912371 | 77912717 | H_c_65n18 |
| X | 78890279 | 78890529 | H_c_156g23 |
| X | 78957538 | 78957667 | H_c_233d18 |
| X | 79870765 | 79871841 | H_c_6g01 |
| X | 80183390 | 80183706 | H_c_69h15 |
| X | 81539788 | 81540807 | H_c_23m23 |
| X | 82569097 | 82570953 | H_c_100i08 |
| X | 83248093 | 83249954 | H_c_252f10 |
| X | 83531616 | 83531768 | H_c_111i19 |
| X | 84171738 | 84171817 | H_c_108h09 |
| X | 84304804 | 84306096 | H_c144m08_M |
| X | 84851608 | 84852979 | H_c_175b08 |
| X | 8508409 | 8510718 | H_c_169j21 |
| X | 85209915 | 85210356 | H_c_236e09 |
| X | 85514750 | 85514924 | H_c_239a20_M |
| X | 87400 | 90282 | H_c_232m20 |
| X | 8970544 | 8970690 | H_c_223l20_M |
| X | 9030947 | 9031087 | H_c_31b08 |
| X | 91290238 | 91290429 | H_c_74g15 |
| X | 92224317 | 92224543 | H_c_13d02 |
| X | 92734430 | 92734788 | H_c135a12_M |
| X | 92949760 | 92949873 | H_c_222n08 |
| X | 93501255 | 93501328 | H_c_30k18 |
| X | 93900068 | 93900183 | H_c_229m10 |
| X | 95871256 | 95871295 | H_c_102h24 |
| X | 96012208 | 96012420 | H_c_116f19 |
| X | 97712070 | 97712182 | H_c_264n18 |
| X | 9791928 | 9794425 | H_c_57f09 |
| X | 98070657 | 98070818 | H_c_265g22 |
| X | 99468179 | 99469672 | H_c_4h07 |
| X | 99469674 | 99470631 | H_c_27m22 |
| X | 99697479 | 99698274 | H_c_243p08 |
| X | 9976074 | 9976149 | H_c_118a09 |
| Y | 10611811 | 10613246 | H_c143g16 |
| Y | 13160819 | 13160992 | H_c_98p17 |
| Y | 13454605 | 13455444 | H_c_33o02_M |
| Y | 14253222 | 14253990 | H_c_252b22 |
| Y | 15074268 | 15075548 | H_c_19p03 |
| Y | 15547960 | 15548118 | H_c_74a05 |
| Y | 17006034 | 17006115 | H_c_13b08 |
| Y | 19542652 | 19543182 | H_c_192d13 |
| Y | 19625963 | 19627475 | H_c_43d17 |
| Y | 20117345 | 20118144 | H_c_94h02 |
| Y | 21453019 | 21453809 | H_c_245j01 |
| Y | 21609130 | 21609302 | H_c_149l06 |
| Y | 2752775 | 2753586 | H_c_178k08 |
| Y | 6671351 | 6671420 | H_c_192d20 |
| Y | 7184770 | 7186521 | H_c_26k07_M |
| Y | 7246339 | 7246415 | H_c_221b13_M |
| 1 | 100027493 | 100028311 | H_c_29m08 |
| 1 | 100215880 | 100216547 | H_c_46c23_M |
| 1 | 10026657 | 10027717 | H_c144e13_M |
| 1 | 100443723 | 100444455 | H_c_9g12_M |
| 1 | 100529951 | 100530529 | H_c_267n09_M |
| 1 | 100631387 | 100631548 | H_c_262n21 |
| 1 | 100684417 | 100684568 | H_c_164f05 |
| 1 | 100974469 | 100974687 | H_c_233j23 |
| 1 | 101203306 | 101203613 | H_c_187d06 |
| 1 | 101294447 | 101294530 | H_c_34h01 |
| 1 | 101413451 | 101414642 | H_c_21k16_M |
| 1 | 10204173 | 10206516 | H_c_217l21_M |
| 1 | 1032772 | 1036265 | H_c_208d23_M |
| 1 | 103760584 | 103760744 | H_c_247l16 |
| 1 | 103780109 | 103780423 | H_c_215d02_M |
| 1 | 103833841 | 103833931 | H_c_204h18 |
| 1 | 10392751 | 10393972 | H_c_134l14_M |
| 1 | 10424231 | 10425556 | H_c_137f02_M |
| 1 | 104621695 | 104621793 | H_c_209g09 |
| 1 | 10466485 | 10466992 | H_c_177m01_M |
| 1 | 10469149 | 10470139 | H_c_227o08 |
| 1 | 104724328 | 104724409 | H_c_36m16 |
| 1 | 105579814 | 105580055 | H_c_62i18 |
| 1 | 105904819 | 105905011 | H_c_233l15_M |
| 1 | 106602401 | 106602562 | H_c_57a10 |
| 1 | 10687674 | 10688650 | H_c_43h22 |
| 1 | 107298242 | 107298332 | H_c_207h03 |
| 1 | 107311075 | 107312699 | H_c_39j08_M |
| 1 | 107395810 | 107396633 | H_c_199d22_M |
| 1 | 107799148 | 107800265 | H_c_165n08 |
| 1 | 10789081 | 10791527 | H_c_136c18_M |
| 1 | 108219392 | 108220164 | H_c_173a23_M |
| 1 | 108454355 | 108455270 | H_c_46d17_M |
| 1 | 10860548 | 10862092 | H_c_208c09_M |
| 1 | 108814568 | 108815110 | H_c_96c17_M |
| 1 | 10882025 | 10883783 | H_c132i05 |

TABLE 1-continued

| | | | |
|---|---|---|---|
| 1 | 108915296 | 108916303 | H_c__77g18_M |
| 1 | 108946618 | 108947526 | H_c__9n18_M |
| 1 | 109008047 | 109008154 | H_c__3g18_M |
| 1 | 1090536 | 1092241 | 1_23113 |
| 1 | 109131206 | 109132157 | H_c__268e11_M |
| 1 | 109175474 | 109175594 | H_c__90k04 |
| 1 | 109217686 | 109218357 | H_c__78h10_M |
| 1 | 109295931 | 109297202 | H_c__259h11 |
| 1 | 109354829 | 109356413 | H_c__213e22_M |
| 1 | 109368183 | 109369322 | H_c__238j03_M |
| 1 | 109468175 | 109469363 | H_c__30o15_M |
| 1 | 10948623 | 10948731 | H_c__94f14 |
| 1 | 109503935 | 109505104 | H_c__16g23_M |
| 1 | 109536979 | 109538279 | H_c__168h13_M |
| 1 | 109652009 | 109653430 | H_c__82b20_M |
| 1 | 109657713 | 109657786 | H_c__273f04 |
| 1 | 109680590 | 109681678 | H_c__121e11_M |
| 1 | 109720857 | 109721140 | H_c__198o21_M |
| 1 | 109737623 | 109739608 | H_c__210m06_M |
| 1 | 109761901 | 109764657 | H_c__165o04_M |
| 1 | 109803200 | 109804235 | H_c__190n20_M |
| 1 | 109874294 | 109875878 | H_c__189c04_M |
| 1 | 109910517 | 109911645 | H_c137o20_M |
| 1 | 109994333 | 109995240 | H_c__66p01_M |
| 1 | 11006054 | 11007686 | H_c__84i05_M |
| 1 | 110165536 | 110167136 | H_c__68i04 |
| 1 | 110289278 | 110290058 | H_c__168d09 |
| 1 | 110322134 | 110325451 | H_c__106e23_M |
| 1 | 110338541 | 110339707 | H_c__205e18 |
| 1 | 110384210 | 110385722 | H_c__17m24 |
| 1 | 110404943 | 110406058 | H_c__89a02 |
| 1 | 11052585 | 11055198 | H_c__7j17_M |
| 1 | 110592841 | 110593383 | H_c__65c24_M |
| 1 | 110662066 | 110662623 | H_c__14m23 |
| 1 | 110795157 | 110795356 | H_c__162a17 |
| 1 | 110861447 | 110862119 | H_c__83g07_M |
| 1 | 110927747 | 110930183 | H_c__84a11_M |
| 1 | 11093606 | 11094618 | H_c__230m03 |
| 1 | 111218132 | 111219032 | H_c__156h08_M |
| 1 | 111394263 | 111395638 | H_c__99i14_M |
| 1 | 111515075 | 111515190 | H_c__209f11 |
| 1 | 111600755 | 111601886 | H_c__49h05 |
| 1 | 11168186 | 11168347 | H_c__191k05 |
| 1 | 111703400 | 111704060 | H_c__130i17_M |
| 1 | 111874325 | 111875256 | H_c__69c21_M |
| 1 | 1119730 | 1121806 | H_c__3e23 |
| 1 | 112010560 | 112011042 | H_c__117e05 |
| 1 | 112243400 | 112246233 | H_c__91b20 |
| 1 | 112281680 | 112281854 | H_c__275h22 |
| 1 | 112325589 | 112325775 | H_c__208g15_M |
| 1 | 11256282 | 11257341 | H_c135a07_M |
| 1 | 11267079 | 11267843 | H_c__68k01 |
| 1 | 112763166 | 112764626 | H_c__62p14_M |
| 1 | 112873367 | 112874993 | H_c__194h10_M |
| 1 | 112929353 | 112930502 | H_c133k19 |
| 1 | 112960971 | 112962095 | H_c__43m23_M |
| 1 | 112969307 | 112970413 | H_c__27l08_M |
| 1 | 112998999 | 112999328 | H_c__89n11 |
| 1 | 113148904 | 113149165 | H_c__108f04 |
| 1 | 113210011 | 113211592 | H_c__244d04_M |
| 1 | 1132459 | 1134249 | H_c__222h13_M |
| 1 | 113644348 | 113646721 | H_c__121p04_M |
| 1 | 113845004 | 113845388 | H_c__71j20 |
| 1 | 11385767 | 11386733 | H_c__265k13_M |
| 1 | 113904508 | 113904679 | H_c__160p04 |
| 1 | 114013155 | 114014358 | H_c__241n21_M |
| 1 | 114065854 | 114067513 | H_c__33c13_M |
| 1 | 114158510 | 114160573 | H_c__158j07_M |
| 1 | 114184030 | 114184884 | H_c__246a22_M |
| 1 | 114463104 | 114463421 | H_c__109o24 |
| 1 | 11472390 | 11475679 | H_c__214n07_M |
| 1 | 114766070 | 114766421 | H_c__122k18_M |
| 1 | 114924185 | 114924614 | H_c__8a23_M |
| 1 | 114978117 | 114978207 | H_c__180m13 |
| 1 | 115096653 | 115096978 | H_c__187n17 |
| 1 | 115109837 | 115110027 | H_c__11i15 |
| 1 | 115343096 | 115344429 | H_c__102d22 |
| 1 | 115424306 | 115424445 | H_c__81g23 |
| 1 | 115591899 | 115593554 | H_c__232m22_M |
| 1 | 115896029 | 115897561 | H_c__63i21_M |
| 1 | 116092317 | 116093737 | H_c__30g11_M |
| 1 | 116093740 | 116094489 | H_c__213k16_M |
| 1 | 116192604 | 116192677 | H_c__165m15 |
| 1 | 116230979 | 116231678 | H_c144l19_M |
| 1 | 116274252 | 116274457 | H_c__2h22 |
| 1 | 11648781 | 11649502 | H_c__93p14_M |
| 1 | 11657968 | 11660239 | H_c__232f16 |
| 1 | 116626831 | 116629534 | H_c__86o19_M |
| 1 | 116672901 | 116673528 | H_c__129b19_M |
| 1 | 11674631 | 11675926 | H_c__205p20_M |
| 1 | 116805654 | 116805757 | H_c__23d01 |
| 1 | 116823867 | 116825931 | H_c__264d12_M |
| 1 | 116921380 | 116922622 | H_c__66n15 |
| 1 | 11723733 | 11725053 | H_c__250e04_M |
| 1 | 117313967 | 117315351 | H_c__83o04_M |
| 1 | 117375934 | 117377367 | H_c__80f08_M |
| 1 | 117621193 | 117622393 | H_c__73f08 |
| 1 | 117840188 | 117840304 | H_c__196m21 |
| 1 | 117859868 | 117861432 | H_c__264c18_M |
| 1 | 11799334 | 11801689 | H_c134b12_M |
| 1 | 118183572 | 118184498 | H_c__33g21_M |
| 1 | 118194483 | 118194739 | H_c__19h07 |
| 1 | 118783122 | 118783214 | H_c__192f19 |
| 1 | 118829333 | 118829524 | H_c__62d04 |
| 1 | 11919676 | 11920918 | H_c__64b22 |
| 1 | 119234115 | 119234876 | H_c__2m01 |
| 1 | 119241556 | 119248627 | H_c__251k08_M_M |
| 1 | 119261183 | 119262231 | H_c__235e23_M |
| 1 | 11928657 | 11929311 | H_c__120e01_M |
| 1 | 119394603 | 119395626 | H_c__93i06 |
| 1 | 11974145 | 11975265 | H_c__192o14_M |
| 1 | 11980397 | 11981999 | H_c__144h06 |
| 1 | 119901643 | 119903308 | H_c__45c05_M |
| 1 | 120126925 | 120127085 | H_c__264e23_M |
| 1 | 120547987 | 120551444 | H_c__272k05_M_M |
| 1 | 121096332 | 121097343 | H_c__10f13_M |
| 1 | 12224020 | 12224951 | H_c__97e17_M |
| 1 | 12391670 | 12392675 | H_c__222a19 |
| 1 | 1248339 | 1251061 | H_c__86f20 |
| 1 | 12612237 | 12614415 | H_c__156c08_M |
| 1 | 12655483 | 12655732 | H_c__66n03 |
| 1 | 1282651 | 1285230 | H_c__31b18_M |
| 1 | 1299203 | 1300807 | H_c__74e21 |
| 1 | 1323298 | 1324215 | H_c__210a14_M |
| 1 | 1324221 | 1324682 | H_c__11e13_M |
| 1 | 13584235 | 13585652 | H_c__194f15_M |
| 1 | 13820880 | 13821974 | H_c__100k10_M |
| 1 | 13964042 | 13965700 | H_c__38m21 |
| 1 | 1418823 | 1422159 | H_c__48n10_M |
| 1 | 142170887 | 142171008 | H_c__200k11 |
| 1 | 142419869 | 142421824 | H_c__78j22_M |
| 1 | 142441798 | 142441923 | H_c__25a01 |
| 1 | 142501494 | 142501615 | H_c__31j18 |
| 1 | 142528427 | 142529435 | H_c__230c20_M |
| 1 | 142564453 | 142565570 | H_c__180k11 |
| 1 | 142585345 | 142585855 | H_c__228m09 |
| 1 | 142628279 | 142629033 | H_c__97d22_M |
| 1 | 142903588 | 142905171 | H_c__91b05 |
| 1 | 142959170 | 142966589 | H_c__81p17_M_M |
| 1 | 143064647 | 143065140 | H_c138e17 |
| 1 | 143099488 | 143100559 | H_c__124h14_M |
| 1 | 143478877 | 143480153 | H_c137l11 |
| 1 | 143552030 | 143552214 | H_c__196c18 |
| 1 | 143868270 | 143869384 | H_c__198c20_M |
| 1 | 143938849 | 143939757 | H_c__102c13 |
| 1 | 14407387 | 14408738 | H_c__186o06 |
| 1 | 144295204 | 144296266 | H_c133k20_M |
| 1 | 144591164 | 144591432 | H_c__191k24 |
| 1 | 144625176 | 144626266 | H_c__36l14_M |
| 1 | 145726868 | 145726978 | H_c__185i13 |
| 1 | 1459130 | 1461385 | H_c__246j21_M |
| 1 | 146636720 | 146637523 | H_c__48o17 |
| 1 | 14665970 | 14666383 | H_c__222k01_M |
| 1 | 14670463 | 14671611 | H_c__266l05_M |
| 1 | 146859964 | 146860035 | H_c__182l11 |
| 1 | 146998948 | 146999438 | H_c__79e13 |
| 1 | 147079196 | 147079695 | H_c__226e21 |
| 1 | 47106519 | 147107751 | H_c__244b10_M |
| 1 | 147204718 | 147204885 | H_c__113i05 |
| 1 | 147301074 | 147301493 | H_c__112b24_M |

TABLE 1-continued

| | | | |
|---|---|---|---|
| 1 | 147333641 | 147336875 | H_c__62f13_M |
| 1 | 147346463 | 147347449 | H_c__18f03 |
| 1 | 147364378 | 147365224 | H_c__226i05 |
| 1 | 147661767 | 147662513 | H_c__69n10_M |
| 1 | 147677507 | 147677640 | H_c__187c12_M |
| 1 | 147711793 | 147712294 | H_c__253e17 |
| 1 | 147759667 | 147761064 | H_c__97c16 |
| 1 | 147793690 | 147794715 | H_c139g08_M |
| 1 | 147833133 | 147833695 | H_c__201g05_M |
| 1 | 147844750 | 147845611 | H_c__77k16_M |
| 1 | 147855977 | 147856119 | H_c__53g06_M |
| 1 | 147916878 | 147917065 | H_c__148d02_M |
| 1 | 147930578 | 147933412 | H_c__169o16_M |
| 1 | 147974848 | 147976386 | H_c__115f24 |
| 1 | 147983806 | 147984148 | H_c141f02 |
| 1 | 148112659 | 148113337 | H_c__215n08 |
| 1 | 148132394 | 148133050 | H_c__234k17 |
| 1 | 148184850 | 148185565 | H_c__91i08 |
| 1 | 148243111 | 148244754 | H_c__92i07 |
| 1 | 148296341 | 148297229 | H_c__80j08 |
| 1 | 148325651 | 148326966 | H_c__253f21_M |
| 1 | 148397280 | 148399118 | H_c__192d01_M |
| 1 | 148439167 | 148440142 | H_c__21o01 |
| 1 | 148506887 | 148507503 | H_c__233g17_M |
| 1 | 148548355 | 148549320 | H_c__118e17_M |
| 1 | 148575591 | 148576276 | H_c__120d24_M |
| 1 | 148694685 | 148695652 | H_c__2g23_M |
| 1 | 148778604 | 148780078 | H_c__117h21_M |
| 1 | 148892935 | 148898801 | H_c__225n20_M_M |
| 1 | 148974261 | 148974902 | H_c__239m18 |
| 1 | 149184557 | 149185116 | H_c__63g10_M |
| 1 | 149300746 | 149301622 | H_c__189j02 |
| 1 | 149309176 | 149309462 | H_c__151c21 |
| 1 | 149600727 | 149600925 | H_c__67b17 |
| 1 | 150046281 | 150047545 | H_c__111h23_M |
| 1 | 150321236 | 150322119 | H_c__154l20_M |
| 1 | 150419358 | 150420172 | H_c__86n09_M |
| 1 | 150560578 | 150562793 | H_c__24m07_M |
| 1 | 150568207 | 150569511 | H_c__236c08_M |
| 1 | 150707839 | 150708701 | H_c__45i08_M |
| 1 | 150731229 | 150732783 | H_c__218h19_M |
| 1 | 150742981 | 150744554 | H_c__43i05_M |
| 1 | 150752778 | 150753634 | H_c__68i11_M |
| 1 | 150762727 | 150763427 | H_c__66l20_M |
| 1 | 150967694 | 150969369 | H_c__227g13 |
| 1 | 151005745 | 151006608 | H_c__36b13 |
| 1 | 151110971 | 151114971 | H_c__275g08_M |
| 1 | 151286999 | 151288746 | H_c__29m11_M |
| 1 | 151317076 | 151318304 | H_c__89l17 |
| 1 | 151352931 | 151354847 | H_c135e24 |
| 1 | 151393216 | 151394450 | H_c__38i24 |
| 1 | 151545848 | 151546645 | H_c__187o15_M |
| 1 | 151721893 | 151722929 | H_c__106n17_M |
| 1 | 151746769 | 151747833 | H_c__28l17_M |
| 1 | 151759119 | 151760660 | H_c__75p06 |
| 1 | 151784298 | 151787847 | H_c__38c15_M |
| 1 | 151849183 | 151850327 | H_c__191n13 |
| 1 | 151862641 | 151865602 | H_c__214c14_M |
| 1 | 151921052 | 151923051 | H_c__205k14_M |
| 1 | 151951845 | 151952734 | H_c133j08_M |
| 1 | 151958194 | 151961190 | H_c__227i09_M |
| 1 | 151976433 | 151977835 | H_c__222e13_M |
| 1 | 151985869 | 151986273 | H_c__72h01 |
| 1 | 151990536 | 151992330 | H_c__70k14_M |
| 1 | 152055413 | 152056636 | H_c__106f19_M |
| 1 | 152102458 | 152108871 | H_c__272k17_M |
| 1 | 15224140 | 15227711 | H_c__164b13_M |
| 1 | 152392025 | 152394180 | H_c__165k17 |
| 1 | 152643213 | 152644040 | H_c__164k14 |
| 1 | 152693694 | 152694424 | H_c__247d02 |
| 1 | 152717208 | 152717385 | H_c139f12 |
| 1 | 152760087 | 152761787 | H_c__99m13 |
| 1 | 152800569 | 152800790 | H_c__117a19 |
| 1 | 152802850 | 152804680 | H_c__61g05 |
| 1 | 152835848 | 152838251 | H_c__90g05_M |
| 1 | 152863562 | 152866179 | H_c__210i22_M |
| 1 | 152897508 | 152898119 | H_c__247g17_M |
| 1 | 152976757 | 152977916 | H_c__95c24 |
| 1 | 152995639 | 152996504 | H_c__18g04_M |
| 1 | 153064993 | 153065872 | H_c__113e15_M |
| 1 | 153120858 | 153121432 | H_c__99l20_M |
| 1 | 153151723 | 153152437 | H_c__49l16_M |
| 1 | 153169603 | 153171785 | H_c__16j10_M |
| 1 | 15318481 | 15319603 | H_c132i23 |
| 1 | 153218026 | 153219463 | H_c__104e14_M |
| 1 | 153273512 | 153275348 | H_c__191c01 |
| 1 | 153282960 | 153284166 | H_c__231n15_M |
| 1 | 153374195 | 153375000 | H_c__56o20_M |
| 1 | 153408734 | 153408972 | H_c__8o21 |
| 1 | 153424375 | 153426292 | H_c__207p21 |
| 1 | 153429652 | 153430241 | H_c__157c04 |
| 1 | 153458585 | 153460347 | H_c__156f10_M |
| 1 | 153533815 | 153534917 | H_c__268j19_M |
| 1 | 153550440 | 153551245 | H_c__120o21 |
| 1 | 153596510 | 153598240 | H_c__29m06 |
| 1 | 153614050 | 153614998 | H_c__4n22 |
| 1 | 153631551 | 153633387 | H_c__151k02 |
| 1 | 153643452 | 153643700 | H_c__225l05 |
| 1 | 153706352 | 153710947 | H_c__234d13_M |
| 1 | 153828071 | 153829380 | H_c__19n04_M |
| 1 | 153920951 | 153921847 | H_c__28e15_M |
| 1 | 153935831 | 153935959 | H_c__126f15 |
| 1 | 15398035 | 15398178 | H_c__216f08_M |
| 1 | 15401620 | 15401754 | H_c__25i22 |
| 1 | 154776293 | 154778287 | H_c__254f02 |
| 1 | 15481265 | 15482622 | H_c__189k23_M |
| 1 | 154841231 | 154842593 | H_c__264f07 |
| 1 | 154895855 | 154896721 | H_c__9f19_M |
| 1 | 154960479 | 154960621 | H_c__147c21 |
| 1 | 154963493 | 154964856 | H_c__30f10 |
| 1 | 15531663 | 15531806 | H_c__268b24_M |
| 1 | 15595471 | 15597523 | H_c__19a04_M |
| 1 | 1559594 | 1562482 | H_c144b02_M |
| 1 | 155970942 | 155971693 | H_c__155f24_M |
| 1 | 15655623 | 15657212 | H_c__112g18_M |
| 1 | 156563449 | 156564319 | H_c__70k08_M |
| 1 | 156636711 | 156638336 | H_c__215m13 |
| 1 | 156727860 | 156729551 | H_c__191p16 |
| 1 | 15674875 | 15676057 | H_c__46h04 |
| 1 | 156814203 | 156815259 | H_c__88p13_M |
| 1 | 156824029 | 156824133 | H_c__101b15 |
| 1 | 156853485 | 156853890 | H_c138k14 |
| 1 | 156866778 | 156868090 | H_c__200f19_M |
| 1 | 15688985 | 15690016 | H_c__224i02_M |
| 1 | 156988015 | 156988908 | H_c__118m11_M |
| 1 | 157044459 | 157045429 | H_c__82n07 |
| 1 | 157077039 | 157077613 | H_c__49p23 |
| 1 | 157136351 | 157136600 | H_c__234h15 |
| 1 | 157182958 | 157184035 | H_c139p13 |
| 1 | 157361292 | 157361494 | H_c__179o17 |
| 1 | 15754707 | 15756529 | H_c135b09 |
| 1 | 157820600 | 157821933 | H_c__53m08 |
| 1 | 157827131 | 157829123 | H_c139j08 |
| 1 | 157900339 | 157901410 | H_c__124c04_M |
| 1 | 157942195 | 157942797 | H_c__90b19 |
| 1 | 157949071 | 157949831 | H_c__30e16_M |
| 1 | 158041225 | 158042502 | H_c__33j13_M |
| 1 | 158150532 | 158150674 | H_c__262c08 |
| 1 | 158172451 | 158173659 | H_c__194f13_M |
| 1 | 158210980 | 158211271 | H_c__187g04 |
| 1 | 158228904 | 158230238 | H_c__203f23 |
| 1 | 15829936 | 15831307 | H_c__51c01_M |
| 1 | 158313507 | 158313858 | H_c__105k11_M |
| 1 | 158367627 | 158367746 | H_c__117a18 |
| 1 | 158427178 | 158428999 | H_c142k20_M |
| 1 | 158724554 | 158725711 | H_c__162h11_M |
| 1 | 158770919 | 158772086 | H_c__41i21_M |
| 1 | 15906283 | 15909518 | H_c__1h19_M_M |
| 1 | 15918920 | 15920706 | H_c__172f20_M |
| 1 | 159199142 | 159199434 | H_c__268n05 |
| 1 | 159204977 | 159205178 | H_c__212p08 |
| 1 | 1594719 | 1595915 | H_c__191k18_M |
| 1 | 159921190 | 159921579 | H_c__54a09 |
| 1 | 159942761 | 159943068 | H_c__196c08 |
| 1 | 160022970 | 160023841 | H_c__8h02_M |
| 1 | 16084607 | 16085699 | H_c144h20 |
| 1 | 160901660 | 160901812 | H_c__130c10 |
| 1 | 161022081 | 161022587 | H_c__90p16 |
| 1 | 16144728 | 16145681 | H_c__274b19_M |
| 1 | 161748408 | 161748528 | H_c__229e10 |

TABLE 1-continued

| | | | |
|---|---|---|---|
| 1 | 161818330 | 161818509 | H_c_93k14 |
| 1 | 161936441 | 161936601 | H_c_41m12_M |
| 1 | 162053160 | 162058083 | H_c_37g05_M |
| 1 | 16225844 | 16227864 | H_c_21n07 |
| 1 | 162298872 | 162299346 | H_c_185j15 |
| 1 | 162331215 | 162332748 | H_c_6p23_M |
| 1 | 162398977 | 162399693 | H_c_146h20 |
| 1 | 162469282 | 162470262 | H_c_272n16 |
| 1 | 162528329 | 162529066 | H_c_205c05_M |
| 1 | 16276806 | 16279100 | H_c_215i07_M |
| 1 | 162832814 | 162832959 | H_c_212k16_M |
| 1 | 162865711 | 162867961 | H_c_59e15_M |
| 1 | 16298187 | 16299934 | H_c_204i16_M |
| 1 | 163042503 | 163044544 | H_c_184f01 |
| 1 | 163145962 | 163146061 | H_c_10g20 |
| 1 | 163235678 | 163235910 | H_c_107c14 |
| 1 | 163540096 | 163541277 | H_c_68m08 |
| 1 | 163576490 | 163577083 | H_c132e12 |
| 1 | 163621312 | 163622784 | H_c_91h06 |
| 1 | 163648217 | 163648840 | H_c_31i13_M |
| 1 | 163676017 | 163676845 | H_c_54n08 |
| 1 | 163767540 | 163767838 | H_c_189m20 |
| 1 | 163822224 | 163823017 | H_c_230o11_M |
| 1 | 163921071 | 163923303 | H_c_52l12_M |
| 1 | 164140102 | 164140943 | H_c_42g08 |
| 1 | 164156117 | 164157304 | H_c_34p12 |
| 1 | 164253980 | 164254838 | H_c_93c08_M |
| 1 | 164331041 | 164331608 | H_c_199i08_M |
| 1 | 16438854 | 16439269 | H_c_181o03 |
| 1 | 164414340 | 164415722 | H_c_203n17_M |
| 1 | 164422485 | 164423611 | H_c_111e13_M |
| 1 | 164554126 | 164554213 | H_c_128g16 |
| 1 | 164838958 | 164838354 | H_c_69g02 |
| 1 | 164860412 | 164860499 | H_c_208a21 |
| 1 | 164926520 | 164928205 | H_c_4g14_M |
| 1 | 16511957 | 16512692 | H_c_103k17_M |
| 1 | 1656943 | 1657934 | H_c_34n13 |
| 1 | 16570327 | 16572339 | H_c_273g15_M |
| 1 | 165996976 | 165997102 | H_c_124h02 |
| 1 | 166068277 | 166068521 | H_c_104g19 |
| 1 | 166098485 | 166098593 | H_c137b15 |
| 1 | 166161112 | 166161714 | H_c_13k03 |
| 1 | 166185956 | 166187315 | H_c_91f17_M |
| 1 | 166593949 | 166594816 | H_c_118k20 |
| 1 | 1666014 | 1666179 | H_c_39l20 |
| 1 | 167364711 | 167365615 | H_c133b04_M |
| 1 | 16757578 | 16758121 | H_c_67j09_M |
| 1 | 168442415 | 168443342 | H_c_170h04 |
| 1 | 168525664 | 168525901 | H_c_158n19 |
| 1 | 168541786 | 168543544 | H_c_60b08_M |
| 1 | 1687448 | 1688398 | H_c_14b14_M |
| 1 | 169233190 | 169234694 | H_c_89o06_M |
| 1 | 169712963 | 169713045 | H_c_113n11 |
| 1 | 16985562 | 16986544 | H_c_28e01_M |
| 1 | 170018071 | 170018228 | H_c_275h21 |
| 1 | 170177321 | 170178639 | H_c_257k24 |
| 1 | 170370276 | 170370845 | H_c_185j09 |
| 1 | 170525306 | 170525738 | H_c_114d16 |
| 1 | 170568926 | 170569876 | H_c_224g20 |
| 1 | 170722297 | 170723775 | H_c_153l21_M |
| 1 | 17083197 | 17085182 | H_c_88f06 |
| 1 | 17125850 | 17126952 | H_c_81a18 |
| 1 | 171893403 | 171894461 | H_c_149e02_M |
| 1 | 17190198 | 17192679 | H_c_179o16_M |
| 1 | 17204163 | 17205431 | H_c_105c04 |
| 1 | 172299787 | 172300328 | H_c_14a24 |
| 1 | 172851680 | 172851757 | H_c_264a15 |
| 1 | 172907105 | 172908239 | H_c_184g19_M |
| 1 | 173302460 | 173302621 | H_c_120f10 |
| 1 | 173372190 | 173372380 | H_c139p16 |
| 1 | 173762797 | 173762948 | H_c_21p09_M |
| 1 | 17378915 | 17380793 | H_c_80g03 |
| 1 | 173871730 | 173872808 | H_c_107d03_M |
| 1 | 1741302 | 1743670 | H_c_16c11_M |
| 1 | 174181087 | 174181264 | H_c_103m19 |
| 1 | 174303307 | 174303475 | H_c_222d03_M |
| 1 | 174529087 | 174529719 | H_c_167f01 |
| 1 | 174738187 | 174739034 | H_c_254n17_M |
| 1 | 174794304 | 174795707 | H_c_117o13_M |
| 1 | 174825930 | 174826088 | H_c_99j22 |
| 1 | 175072818 | 175072935 | H_c_7i18 |
| 1 | 17509472 | 17510682 | H_c_100b01 |
| 1 | 17510817 | 17511007 | H_c_92e21_M |
| 1 | 175186748 | 175188754 | H_c_152n07 |
| 1 | 175425611 | 175427242 | H_c_173f07_M |
| 1 | 175477457 | 175477525 | H_c_58k01 |
| 1 | 175601750 | 175601928 | H_c_151e08 |
| 1 | 175726543 | 175727487 | H_c_57g17_M |
| 1 | 175782867 | 175783969 | H_c_195i08_M |
| 1 | 175928478 | 175930460 | H_c_192d18 |
| 1 | 175994017 | 175994938 | H_c_179i07 |
| 1 | 176066581 | 176066841 | H_c_68o14 |
| 1 | 17610731 | 17612492 | H_c_98k10_M |
| 1 | 176276043 | 176277206 | H_c_200d09_M |
| 1 | 176287011 | 176287770 | H_c_21p12_M |
| 1 | 176321769 | 176322047 | H_c_218c24 |
| 1 | 176443463 | 176446347 | H_c_197i24_M |
| 1 | 176582977 | 176584163 | H_c142n13_M |
| 1 | 176655380 | 176656432 | H_c_216j03 |
| 1 | 176719218 | 176719384 | H_c_163l22 |
| 1 | 176854837 | 176856643 | H_c137c03 |
| 1 | 176929576 | 176934829 | H_c_55h02_M_M |
| 1 | 177203558 | 177204051 | H_c_19j16_M |
| 1 | 177255668 | 177255794 | H_c_7l11 |
| 1 | 177389826 | 177389934 | H_c_159b24 |
| 1 | 177612384 | 177614375 | H_c_236a06_M |
| 1 | 177619010 | 177619982 | H_c_4j16 |
| 1 | 177654155 | 177655493 | H_c_238j19_M |
| 1 | 177722678 | 177724149 | H_c_34h21 |
| 1 | 177789321 | 177790887 | H_c_210p16_M |
| 1 | 177805921 | 177807202 | H_c_210e10_M |
| 1 | 177920852 | 177921107 | H_c_236m04 |
| 1 | 17796424 | 17797672 | H_c_166h24 |
| 1 | 178018910 | 178020043 | H_c_178h21_M |
| 1 | 178182644 | 178184021 | H_c_254o07 |
| 1 | 178246077 | 178247715 | H_c_26l22_M |
| 1 | 178377364 | 178377577 | H_c_208a02 |
| 1 | 178756264 | 178758909 | H_c_181l11_M |
| 1 | 178840380 | 178840645 | H_c_97i06 |
| 1 | 17905993 | 17906283 | H_c_41k06 |
| 1 | 179091493 | 179093457 | H_c_246k15_M |
| 1 | 179315816 | 179316334 | H_c_17b06_M |
| 1 | 179323689 | 179324642 | H_c_226b09 |
| 1 | 179336835 | 179338364 | H_c_246d06 |
| 1 | 179490191 | 179490904 | H_c_188d06_M |
| 1 | 179539176 | 179540826 | H_c_198e20_M |
| 1 | 179653324 | 179654543 | H_c_22c07 |
| 1 | 179723485 | 179725026 | H_c_151o21_M |
| 1 | 179916641 | 179916855 | H_c_162n05 |
| 1 | 180171947 | 180174154 | H_c_85c23_M |
| 1 | 180335813 | 180337401 | H_c_60f04_M |
| 1 | 180505572 | 180506427 | H_c_247g19 |
| 1 | 180737549 | 180738746 | H_c_45h21_M |
| 1 | 180746309 | 180746436 | H_c_59l13 |
| 1 | 180752307 | 180752854 | H_c_237l17 |
| 1 | 180770271 | 180770341 | H_c_47l22 |
| 1 | 180841042 | 180841192 | H_c_159h13 |
| 1 | 181042109 | 181042226 | H_c_162f16 |
| 1 | 181087202 | 181088871 | H_c_76p01_M |
| 1 | 181364701 | 181365878 | H_c_129l12 |
| 1 | 181454865 | 181456381 | H_c_68o22_M |
| 1 | 181473523 | 181473703 | H_c_205c15 |
| 1 | 181674213 | 181675200 | H_c_15e05 |
| 1 | 18179458 | 18183006 | H_c_100h17_M |
| 1 | 181857008 | 181858581 | H_c_10k06_M |
| 1 | 181918032 | 181918108 | H_c_226k01 |
| 1 | 181944716 | 181944877 | H_c_95j24 |
| 1 | 182016904 | 182018566 | H_c134j24 |
| 1 | 182434511 | 182435932 | H_c_270b13 |
| 1 | 183072305 | 183072425 | H_c_71h20_M |
| 1 | 183075679 | 183076908 | H_c_28b12_M |
| 1 | 183380816 | 183381331 | H_c_28p13_M |
| 1 | 183517765 | 183518084 | H_c_35m15_M |
| 1 | 183697076 | 183697262 | H_c_42l23 |
| 1 | 184039960 | 184040128 | H_c_108c05_M |
| 1 | 184405865 | 184406075 | H_c_266g15 |
| 1 | 184512863 | 184512979 | H_c_257c19 |
| 1 | 184535898 | 184535999 | H_c_114p18 |
| 1 | 1853420 | 1854824 | H_c_69i07_M |
| 1 | 185442581 | 185442739 | H_c_109c22 |

TABLE 1-continued

| | | |
|---|---|---|
| 1 | 1854830 | 1856602 | H_c_242i11_M |
| 1 | 185921592 | 185921832 | H_c_209a04 |
| 1 | 186934828 | 186934944 | H_c_85e14 |
| 1 | 18701132 | 18703290 | H_c_21d19 |
| 1 | 18703295 | 18704905 | H_c_162b03_M |
| 1 | 18712369 | 18715600 | H_c_69f24_M |
| 1 | 187178820 | 187179796 | H_c_108e11 |
| 1 | 18718034 | 18720560 | H_c_241i08 |
| 1 | 187570736 | 187570840 | H_c_49p20 |
| 1 | 18763837 | 18765967 | H_c_161f13 |
| 1 | 187832793 | 187832944 | H_c_61j04 |
| 1 | 18787368 | 18789813 | H_c_145d09_M |
| 1 | 188223894 | 188224064 | H_c_232n04 |
| 1 | 188243347 | 188243469 | H_c_29f03_M |
| 1 | 189068891 | 189068975 | H_c_185b03 |
| 1 | 189200562 | 189200636 | H_c_5j04 |
| 1 | 189379230 | 189379377 | H_c_195c08 |
| 1 | 189509189 | 189510109 | H_c_33g04_M |
| 1 | 18973726 | 18975047 | H_c134l16_M |
| 1 | 189759983 | 189761093 | H_c_261h12 |
| 1 | 18978980 | 18979663 | H_c_123f08 |
| 1 | 189805278 | 189806710 | H_c_28h10_M |
| 1 | 189822463 | 189823187 | H_c_56k16_M |
| 1 | 189858017 | 189858232 | H_c_205g17 |
| 1 | 190223437 | 190223519 | H_c_200i01 |
| 1 | 19027182 | 19028819 | H_c_176o13_M |
| 1 | 19034054 | 19034305 | H_c_14f22 |
| 1 | 190648735 | 190648873 | H_c_213f21 |
| 1 | 191209858 | 191210081 | H_c_223h03 |
| 1 | 191216592 | 191216737 | H_c_4d03 |
| 1 | 191396990 | 191397194 | H_c_261k11 |
| 1 | 191814996 | 191815172 | H_c_75m02 |
| 1 | 191929985 | 191930146 | H_c_54c23 |
| 1 | 192236193 | 192236386 | H_c_11i19 |
| 1 | 192420065 | 192420212 | H_c_95f24 |
| 1 | 19281586 | 19282286 | H_c_149l05_M |
| 1 | 19323133 | 19324140 | H_c_265d23_M |
| 1 | 19383227 | 19384908 | H_c_273c09 |
| 1 | 193846531 | 193847418 | H_c_225l13 |
| 1 | 193901763 | 193902487 | H_c_102h17_M |
| 1 | 194475517 | 194477314 | H_c_215l02_M |
| 1 | 194603228 | 194604016 | H_c_90n14_M |
| 1 | 194612248 | 194612595 | H_c_9o15_M |
| 1 | 194625476 | 194625616 | H_c_238n01 |
| 1 | 1947938 | 1949904 | H_c_105e11 |
| 1 | 194857526 | 194858379 | H_c_163b12 |
| 1 | 195435905 | 195436103 | H_c134m15 |
| 1 | 19555665 | 19558086 | H_c137i21_M |
| 1 | 195939013 | 195939157 | H_c_97g08 |
| 1 | 196245831 | 196245916 | H_c_103g17 |
| 1 | 19668485 | 19669496 | H_c_254f20 |
| 1 | 1967176 | 1968255 | H_c_71p07 |
| 1 | 196735168 | 196735476 | H_c_250g09_M |
| 1 | 196740250 | 196740806 | H_c_267i10 |
| 1 | 196743358 | 196743724 | H_c_59n21_M |
| 1 | 196751160 | 196751362 | H_c_150i23 |
| 1 | 196915473 | 196915859 | H_c_216e07 |
| 1 | 197003093 | 197003588 | H_c_150k20 |
| 1 | 19715487 | 19717073 | H_c_27h21_M |
| 1 | 197321202 | 197321730 | H_c_175e18 |
| 1 | 19736098 | 19738766 | H_c_23n09_M |
| 1 | 197370044 | 197371086 | H_c_27b21_M |
| 1 | 197439532 | 197440863 | H_c_239a05_M |
| 1 | 197573082 | 197575825 | H_c_217b06_M |
| 1 | 197590879 | 197592315 | H_c_197b20_M |
| 1 | 19765972 | 19768385 | H_c_267n21 |
| 1 | 197723981 | 197724629 | H_c_186i01_M |
| 1 | 197814621 | 197816806 | H_c_14n23_M |
| 1 | 197854813 | 197855137 | H_c_125i20_M |
| 1 | 197871858 | 197872469 | H_c_32g24 |
| 1 | 197983565 | 197985772 | H_c_84e21 |
| 1 | 198099497 | 198100832 | H_c_208h07_M |
| 1 | 198113536 | 198113702 | H_c_266d16 |
| 1 | 1982241 | 1983717 | H_c_103a11_M |
| 1 | 198238568 | 198240457 | H_c_23h13_M |
| 1 | 198348148 | 198350409 | H_c_124f02_M |
| 1 | 198440620 | 198442423 | H_c_163o06 |
| 1 | 198529759 | 198530055 | H_c_245p20_M |
| 1 | 198589011 | 198590201 | H_c_91c16_M |
| 1 | 198682840 | 198684398 | H_c_13o09_M |
| 1 | 19870698 | 19872569 | H_c_59m09 |
| 1 | 198844760 | 198845819 | H_c_224e09_M |
| 1 | 198964295 | 198964494 | H_c_210m07 |
| 1 | 199042041 | 199043039 | H_c_190b22 |
| 1 | 199049140 | 199050313 | H_c_4c08 |
| 1 | 199360716 | 199361266 | H_c144p03 |
| 1 | 199426244 | 199426469 | H_c_108n23 |
| 1 | 199511634 | 199513030 | H_c_209o21_M |
| 1 | 19953974 | 19954774 | H_c_47k03_M |
| 1 | 199561488 | 199562656 | H_c_148i15_M |
| 1 | 199667118 | 199668609 | H_c132l18 |
| 1 | 199707759 | 199708663 | H_c_115o17 |
| 1 | 199726892 | 199727846 | H_c_258n17_M |
| 1 | 199817886 | 199818921 | H_c_84d04 |
| 1 | 199828410 | 199828979 | H_c_77e03_M |
| 1 | 200005947 | 200006497 | H_c_43b09_M |
| 1 | 200027442 | 200028800 | H_c_234b07_M |
| 1 | 200081322 | 200081445 | H_c_93k03 |
| 1 | 200129488 | 200129575 | H_c_81g03 |
| 1 | 200773603 | 200775417 | H_c_145f08_M |
| 1 | 200852015 | 200853470 | H_c_7c20 |
| 1 | 200891019 | 200891805 | H_c_66m16 |
| 1 | 201060241 | 201060822 | H_c_21a01 |
| 1 | 201078818 | 201079172 | H_c_174b12_M |
| 1 | 201111716 | 201112931 | H_c_67p16_M |
| 1 | 201194788 | 201196193 | H_c_115i02 |
| 1 | 2012950 | 2014660 | H_c_99c02 |
| 1 | 2012977 | 2014660 | H_c_99d17 |
| 1 | 201384790 | 201386594 | H_c_75m03_M |
| 1 | 201528448 | 201531030 | H_c_191p10 |
| 1 | 201605874 | 201606042 | H_c143i12 |
| 1 | 20183720 | 20185321 | H_c_268h20_M |
| 1 | 201928363 | 201929191 | H_c_72m14_M |
| 1 | 201949517 | 201951836 | H_c_125e01_M |
| 1 | 202021864 | 202022776 | H_c_193f07_M |
| 1 | 202043030 | 202045453 | H_c_209p17 |
| 1 | 202157007 | 202158592 | H_c_113l22_M |
| 1 | 202319133 | 202319243 | H_c_219b09 |
| 1 | 202331724 | 202333365 | H_c_63f13_M |
| 1 | 202380588 | 202381791 | H_c_17h12_M |
| 1 | 202450034 | 202451281 | H_c_191e10_M |
| 1 | 202475808 | 202476364 | H_c_183j10_M |
| 1 | 202513142 | 202514552 | H_c_199l10_M |
| 1 | 202539999 | 202540277 | H_c140p07 |
| 1 | 202550366 | 202551025 | H_c_96h13 |
| 1 | 202766360 | 202768664 | H_c_25k21_M |
| 1 | 203068301 | 203069921 | H_c_224f22_M |
| 1 | 203073467 | 203073838 | H_c_79p09 |
| 1 | 203118455 | 203119880 | H_c_12i10_M |
| 1 | 203171865 | 203174629 | H_c_36f21_M |
| 1 | 203196958 | 203197798 | H_c136f15_M |
| 1 | 203246617 | 203248105 | H_c_62i07_M |
| 1 | 203470744 | 203472123 | H_c_195n17 |
| 1 | 203611971 | 203615981 | H_c_35l18_M |
| 1 | 203691599 | 203691754 | H_c_203h13_M |
| 1 | 203882542 | 203883745 | H_c_273a11_M |
| 1 | 204003622 | 204003808 | H_c_217k03 |
| 1 | 204016043 | 204016768 | H_c_115g17_M |
| 1 | 204206613 | 204207604 | H_c_15f17 |
| 1 | 20437951 | 20438623 | H_c_29d23_M |
| 1 | 204430322 | 204431453 | H_c_102n23 |
| 1 | 204472263 | 204473161 | H_c_163c11 |
| 1 | 204486895 | 204487414 | H_c_232l22 |
| 1 | 204520561 | 204521252 | H_c_33j22_M |
| 1 | 204803767 | 204806279 | H_c_77n19_M |
| 1 | 20517787 | 20518627 | H_c_272e19 |
| 1 | 205382356 | 205382486 | H_c_7a15 |
| 1 | 205390098 | 205390167 | H_c_14g01 |
| 1 | 205536935 | 205537012 | H_c_180g17 |
| 1 | 205609418 | 205609575 | H_c_9k18 |
| 1 | 205793133 | 205794453 | H_c_57h11 |
| 1 | 20624197 | 20626692 | H_c139k09_M |
| 1 | 206366604 | 206368207 | H_c_123a14 |
| 1 | 206379650 | 206379786 | H_c_197f12 |
| 1 | 206389403 | 206390141 | H_c_11o04_M |
| 1 | 206794125 | 206795729 | H_c_147m22_M |
| 1 | 206812866 | 206814303 | H_c_125g17_M |
| 1 | 206854049 | 206854590 | H_c_96a24 |
| 1 | 207044995 | 207045145 | H_c_50e08 |
| 1 | 20705008 | 20705860 | H_c_113d24_M |

TABLE 1-continued

| | | | |
|---|---|---|---|
| 1 | 207289099 | 207289238 | H_c_43o11 |
| 1 | 20732334 | 20733944 | H_c_202n13_M |
| 1 | 207362150 | 207362902 | H_c_15e08 |
| 1 | 207820319 | 207821769 | H_c_259o18_M |
| 1 | 207887516 | 207889649 | H_c131k13 |
| 1 | 207944187 | 207944886 | H_c_130b20_M |
| 1 | 207977971 | 207978928 | H_c_163g17 |
| 1 | 20803194 | 20805207 | H_c_52c02_M |
| 1 | 208077143 | 208077587 | H_c_45i01 |
| 1 | 208139251 | 208141859 | H_c_262n01_M |
| 1 | 208391621 | 208392882 | H_c_62o22_M |
| 1 | 20843257 | 20843416 | H_c_57d19 |
| 1 | 20846149 | 20846350 | H_c135l03 |
| 1 | 208543657 | 208543798 | H_c_267j23 |
| 1 | 208596505 | 208597882 | H_c_170c11_M |
| 1 | 208719451 | 208719541 | H_c_84j22 |
| 1 | 208846115 | 208848300 | H_c_160f02_M |
| 1 | 208975344 | 208976878 | H_c_116b07_M |
| 1 | 208994331 | 208995792 | H_c_253i11_M |
| 1 | 209119738 | 209120889 | H_c_26m06_M |
| 1 | 209169228 | 209170768 | H_c_258p22_M |
| 1 | 209260631 | 209262404 | H_c_272c22_M |
| 1 | 209301934 | 209302154 | H_c_221g06 |
| 1 | 209419534 | 209420963 | H_c_246d24_M |
| 1 | 209512078 | 209513940 | H_c_150k17 |
| 1 | 2095281 | 2097829 | H_c_266m03_M |
| 1 | 209576790 | 209577506 | H_c_251b18_M |
| 1 | 209612693 | 209613502 | H_c_190b18_M |
| 1 | 209722985 | 209723229 | H_c_272l03 |
| 1 | 210221683 | 210221840 | H_c_29k15 |
| 1 | 210323330 | 210324262 | H_c_6k10 |
| 1 | 210469285 | 210469520 | H_c_195o17 |
| 1 | 210493847 | 210493982 | H_c132p05 |
| 1 | 210544082 | 210550850 | H_c134f24_M_M |
| 1 | 210748803 | 210749730 | H_c_124k24 |
| 1 | 210842363 | 210843459 | H_c_140n24_M |
| 1 | 211112661 | 211113196 | H_c_84n24_M |
| 1 | 211164822 | 211165579 | H_c_189g20 |
| 1 | 211643988 | 211645624 | H_c_247d12 |
| 1 | 211677323 | 211677472 | H_c_18g11 |
| 1 | 212139866 | 212139968 | H_c_146h04 |
| 1 | 213139370 | 213139496 | H_c_258g21 |
| 1 | 213498420 | 213498525 | H_c_200j04 |
| 1 | 213606545 | 213606657 | H_c_92e08 |
| 1 | 213651382 | 213651750 | H_c143b09 |
| 1 | 213696791 | 213701527 | H_c_44j16_M_M |
| 1 | 213834782 | 213834887 | H_c_205e13 |
| 1 | 21415739 | 21417447 | H_c_122i07 |
| 1 | 214300883 | 214301003 | H_c138a09 |
| 1 | 214486667 | 214487186 | H_c_33i12 |
| 1 | 214726949 | 214727404 | H_c_25f02 |
| 1 | 214846714 | 214847433 | H_c_67j20 |
| 1 | 214906642 | 214907911 | H_c_190g01_M |
| 1 | 215015147 | 215015362 | H_c_13l14 |
| 1 | 2157140 | 2158822 | H_c_238i11 |
| 1 | 215735340 | 215735914 | H_c_254b08_M |
| 1 | 21580365 | 21581414 | H_c_73e07 |
| 1 | 216036936 | 216037608 | H_c_108j12 |
| 1 | 216222554 | 216222904 | H_c144m21 |
| 1 | 216489379 | 216490737 | H_c_129b18_M |
| 1 | 216607722 | 216608485 | H_c142e03_M |
| 1 | 216655668 | 216656446 | H_c_113j08 |
| 1 | 21693578 | 21694672 | H_c_41e03_M |
| 1 | 217089475 | 217091287 | H_c_200g20_M |
| 1 | 21721802 | 21724202 | H_c_202k08 |
| 1 | 217251853 | 217252624 | H_c_42g17_M |
| 1 | 21731019 | 21731625 | H_c_209j11_M |
| 1 | 21739661 | 21742370 | H_c_240b22_M |
| 1 | 217440086 | 217442279 | H_c_45h20_M |
| 1 | 217676841 | 217676979 | H_c_200n21 |
| 1 | 218304156 | 218305934 | H_c_50p02_M |
| 1 | 218500518 | 218500653 | H_c_181f11 |
| 1 | 218558546 | 218558706 | H_c_199h23 |
| 1 | 219027142 | 219027724 | H_c_32a04_M |
| 1 | 219086553 | 219086796 | H_c_224d22 |
| 1 | 219179081 | 219181072 | H_c_56j18_M |
| 1 | 219274157 | 219274867 | H_c139e14 |
| 1 | 219376444 | 219377718 | H_c_26j20 |
| 1 | 219686272 | 219688973 | H_c_217o11 |
| 1 | 219907971 | 219909914 | H_c_129a22_M |
| 1 | 22008346 | 22009721 | H_c_85c15 |
| 1 | 220206584 | 220207884 | H_c_62m01 |
| 1 | 220242921 | 220244017 | H_c_262n11_M |
| 1 | 220339656 | 220340989 | H_c_63d03_M |
| 1 | 220570416 | 220570503 | H_c_32b13 |
| 1 | 220608307 | 220609535 | H_c_159g20_M |
| 1 | 220677311 | 220678354 | H_c_100o24_M |
| 1 | 220824208 | 220825332 | H_c_62i23 |
| 1 | 220927811 | 220930201 | H_c132p11_M |
| 1 | 220946175 | 220946275 | H_c_63b09 |
| 1 | 22097286 | 22098254 | H_c_215n21 |
| 1 | 221110480 | 221112085 | H_c_1h13_M |
| 1 | 221423870 | 221424585 | H_c_84o11_M |
| 1 | 221884055 | 221884140 | H_c131b01 |
| 1 | 221921357 | 221923274 | H_c_85j23_M |
| 1 | 22214013 | 22214229 | H_c_236h08_M |
| 1 | 222146851 | 222148559 | H_c137g22_M |
| 1 | 222304408 | 222304935 | H_c_197o22_M |
| 1 | 222375861 | 222378675 | H_c_64m16_M |
| 1 | 222405572 | 222406665 | H_c_57g15 |
| 1 | 222417904 | 222419623 | H_c_121j01 |
| 1 | 222493489 | 222494082 | H_c_18j12_M |
| 1 | 222557665 | 222557782 | H_c_179i05 |
| 1 | 222577081 | 222579510 | H_c_4i04_M |
| 1 | 222603936 | 222604579 | H_c_198n23_M |
| 1 | 222639013 | 222639096 | H_c_13l10 |
| 1 | 222680463 | 222681634 | H_c_71p22_M |
| 1 | 222717752 | 222718740 | H_c_129f17 |
| 1 | 223042770 | 223044318 | H_c_86d18_M |
| 1 | 223197484 | 223198371 | H_c_101d22 |
| 1 | 22322378 | 22322617 | H_c_124m11 |
| 1 | 223230997 | 223233431 | H_c_147b14_M |
| 1 | 223364718 | 223365443 | H_c_134m19_M |
| 1 | 223433842 | 223436945 | H_c_18n11_M |
| 1 | 223812304 | 223813381 | H_c_95b07_M |
| 1 | 224053412 | 224055698 | H_c_234p05_M |
| 1 | 224228966 | 224231040 | H_c_158k05_M |
| 1 | 224285628 | 224285843 | H_c_34a04 |
| 1 | 224381427 | 224382399 | H_c139g14 |
| 1 | 224440581 | 224443083 | H_c_67n24_M |
| 1 | 224500544 | 224503824 | H_c_52k09_M |
| 1 | 224552616 | 224554618 | H_c_44l15_M |
| 1 | 224576425 | 224577999 | H_c_234o20_M |
| 1 | 224596026 | 224597921 | H_c_130a17_M |
| 1 | 224603134 | 224605102 | H_c_187f09 |
| 1 | 224659880 | 224661355 | H_c_97b12_M |
| 1 | 224666412 | 224668775 | H_c_50m11 |
| 1 | 224741387 | 224741649 | H_c_102a11 |
| 1 | 224769991 | 224772486 | H_c_252d13 |
| 1 | 224910108 | 224911374 | H_c_77c22 |
| 1 | 224940358 | 224941190 | H_c_151e10 |
| 1 | 224953902 | 224954046 | H_c_244o21 |
| 1 | 224963731 | 224963877 | H_c134j12 |
| 1 | 224981389 | 224983619 | H_c_64d11_M |
| 1 | 225177486 | 225178714 | H_c_198a14 |
| 1 | 22522804 | 22524554 | H_c_170j03_M |
| 1 | 225318223 | 225318454 | H_c_254n16_M |
| 1 | 225713263 | 225714331 | H_c_235g24 |
| 1 | 225784391 | 225785904 | H_c_240e17_M |
| 1 | 225849729 | 225849916 | H_c_169j24 |
| 1 | 225873827 | 225878078 | H_c141c05_M |
| 1 | 225950116 | 225950903 | H_c_233g08_M |
| 1 | 226000216 | 226002153 | H_c_84g04 |
| 1 | 226067513 | 226069389 | H_c_210m10_M |
| 1 | 226509170 | 226510989 | H_c_73f06_M |
| 1 | 226867576 | 226869455 | H_c_154g08 |
| 1 | 227084327 | 227085515 | H_c_127a11_M |
| 1 | 227420558 | 227422027 | H_c_4e08_M |
| 1 | 227604438 | 227606830 | H_c_31j22_M |
| 1 | 227777985 | 227780364 | H_c_253n21 |
| 1 | 22781621 | 22783912 | H_c_232d24 |
| 1 | 227863209 | 227865375 | H_c_118n19_M |
| 1 | 227970693 | 227971317 | H_c_86l16 |
| 1 | 228144695 | 228144918 | H_c_146f15 |
| 1 | 228558259 | 228558332 | H_c_53l12 |
| 1 | 228625162 | 228626806 | H_c_109k04 |
| 1 | 228914107 | 228914211 | H_c_225p22 |
| 1 | 229071719 | 229072981 | H_c_180o21_M |
| 1 | 229392921 | 229393348 | H_c139h19_M |
| 1 | 229730106 | 229730245 | H_c_120h18 |

TABLE 1-continued

| | | | |
|---|---|---|---|
| 1 | 229737697 | 229738701 | H_c_99m08 |
| 1 | 229769725 | 229771427 | H_c_124i02_M |
| 1 | 230055742 | 230057713 | H_c_58d10 |
| 1 | 230128692 | 230128758 | H_c_54n07 |
| 1 | 230346682 | 230348082 | H_c_157h12 |
| 1 | 230656545 | 230657889 | H_c_155i14_M |
| 1 | 230815542 | 230816617 | H_c_30n04_M |
| 1 | 23090986 | 23092284 | H_c_37d05_M |
| 1 | 230920229 | 230921824 | H_c_216m14_M |
| 1 | 231042103 | 231042942 | H_c_55k03_M |
| 1 | 231088085 | 231088255 | H_c_9l12 |
| 1 | 231316063 | 231316250 | H_c_114f24 |
| 1 | 23145341 | 23145448 | H_c_222b24_M |
| 1 | 231650135 | 231651812 | H_c_26e10_M |
| 1 | 231816001 | 231818193 | H_c_152f10_M |
| 1 | 231963004 | 231963093 | H_c_262n22 |
| 1 | 231992995 | 231995007 | H_c_90d13_M |
| 1 | 232071082 | 232072622 | H_c_97i02 |
| 1 | 232138340 | 232140115 | H_c_215g09_M |
| 1 | 232355517 | 232357179 | H_c_236f24 |
| 1 | 23239836 | 23240883 | H_c_222h11 |
| 1 | 23249007 | 23249814 | H_c_5m14 |
| 1 | 232552972 | 232555304 | H_c_173k08_M |
| 1 | 232631316 | 232633101 | H_c_211m16 |
| 1 | 232679133 | 232679211 | H_c_215k02 |
| 1 | 232701433 | 232701531 | H_c_121p11 |
| 1 | 232770736 | 232771839 | H_c_248j23_M |
| 1 | 232786396 | 232786476 | H_c_28m17 |
| 1 | 232814582 | 232814835 | H_c_234p20 |
| 1 | 23288301 | 23289815 | H_c_207k20_M |
| 1 | 232884526 | 232885572 | H_c_119h03_M |
| 1 | 233012563 | 233013897 | H_c_210k14_M |
| 1 | 233053978 | 233054062 | H_c_103k20 |
| 1 | 233174926 | 233176841 | H_c_42l16_M |
| 1 | 233285122 | 233285341 | H_c_45g16 |
| 1 | 233531272 | 233532802 | H_c_56m11_M |
| 1 | 233751100 | 233751252 | H_c_238d15 |
| 1 | 233984536 | 233984773 | H_c_74c05_M |
| 1 | 23415284 | 23416678 | H_c_212o09_M |
| 1 | 23440464 | 23440820 | H_c_49p13_M |
| 1 | 23495592 | 23496922 | H_c_6k03_M |
| 1 | 23497175 | 23497471 | H_c_16a08 |
| 1 | 235469382 | 235469457 | H_c_264g23 |
| 1 | 235778429 | 235778567 | H_c_48o20 |
| 1 | 235875614 | 235877297 | H_c_59b14_M |
| 1 | 235923542 | 235924386 | H_c_92o23 |
| 1 | 23601154 | 23603214 | H_c_162l18_M |
| 1 | 236027003 | 236027164 | H_c_54d07 |
| 1 | 23629779 | 23631413 | H_c_213m05_M |
| 1 | 23634120 | 23634460 | H_c_50c16 |
| 1 | 23640074 | 23640732 | H_c_71n02_M |
| 1 | 236487048 | 236487630 | H_c_212o24_M |
| 1 | 236581052 | 236583195 | H_c_178i11_M |
| 1 | 236631722 | 236633399 | H_c_233m12 |
| 1 | 236672068 | 236672237 | H_c_125g12 |
| 1 | 23689968 | 23691814 | H_c_89h15_M |
| 1 | 236981514 | 236983169 | H_c138f07 |
| 1 | 237432109 | 237432345 | H_c_208b09 |
| 1 | 237665063 | 237665258 | H_c_74j22 |
| 1 | 237815630 | 237815729 | H_c_59f04 |
| 1 | 237845309 | 237846806 | H_c_9h11_M |
| 1 | 237913065 | 237914284 | H_c_48e01_M |
| 1 | 238008202 | 238009236 | H_c132g18 |
| 1 | 238128822 | 238130389 | H_c_250g22 |
| 1 | 23814680 | 23816057 | H_c_16e23_M |
| 1 | 238234621 | 238234730 | H_c_213j18 |
| 1 | 23850 | 23850588 | H_c_110k02_M |
| 1 | 23871117 | 23873519 | H_c_97e02_M |
| 1 | 238890265 | 238890460 | H_c_119m12 |
| 1 | 239013260 | 239014865 | H_c_73d19_M |
| 1 | 239040009 | 239040122 | H_c_94d01 |
| 1 | 239204930 | 239205047 | H_c_42j01 |
| 1 | 239245818 | 239245965 | H_c_129j15 |
| 1 | 239336754 | 239336966 | H_c_14h22 |
| 1 | 23938961 | 23940321 | H_c_144i23_M |
| 1 | 239590706 | 239591331 | H_c_12a16 |
| 1 | 239974311 | 239975002 | H_c_33n04 |
| 1 | 239743311 | 239744971 | H_c_174f16_M |
| 1 | 240259317 | 240259472 | H_c139l14 |
| 1 | 24030969 | 24032100 | H_c141h05_M |
| 1 | 240338690 | 240340945 | H_c_84i23_M |
| 1 | 240406454 | 240406967 | H_c_147k21 |
| 1 | 24051514 | 24052484 | H_c_129f04_M |
| 1 | 240940313 | 240941630 | H_c_87n17_M |
| 1 | 240950465 | 240951325 | H_c_22o22_M |
| 1 | 241141811 | 241143250 | H_c_2j15_M |
| 1 | 241183644 | 241183730 | H_c_244j16 |
| 1 | 241323998 | 241325213 | H_c_21f15_M |
| 1 | 241352205 | 241354278 | H_c_114e23_M |
| 1 | 241407991 | 241408862 | H_c_116c03_M |
| 1 | 241459330 | 241460536 | H_c131g03_M |
| 1 | 241643227 | 241646964 | H_c_25f23_M |
| 1 | 241702163 | 241702306 | H_c_275d10 |
| 1 | 241975043 | 241975232 | H_c_248c24 |
| 1 | 242190701 | 242190768 | H_c_1f08 |
| 1 | 242220403 | 242220507 | H_c_165p02 |
| 1 | 24246775 | 24247169 | H_c_161l18 |
| 1 | 242489199 | 242489359 | H_c_179e10 |
| 1 | 24258703 | 24259548 | H_c_227l06_M |
| 1 | 242960180 | 242960302 | H_c_79i03 |
| 1 | 243212940 | 243214130 | H_c_49n07_M |
| 1 | 243252976 | 243253206 | H_c_43k17 |
| 1 | 243278111 | 243278681 | H_c_55j05_M |
| 1 | 243496556 | 243497648 | H_c138e12 |
| 1 | 243593154 | 243593950 | H_c144c06_M |
| 1 | 243600442 | 243601997 | H_c_247l23_M |
| 1 | 243699666 | 243700435 | H_c144n20 |
| 1 | 243792683 | 243792845 | H_c_73a24 |
| 1 | 243820116 | 243822920 | H_c_63c07 |
| 1 | 243836904 | 243837648 | H_c_91c14 |
| 1 | 24393276 | 24394177 | H_c_202a18_M |
| 1 | 244128675 | 244129228 | H_c_199j15_M |
| 1 | 244346396 | 244347435 | H_c_193k09 |
| 1 | 24484711 | 24485598 | H_c_11b24 |
| 1 | 245341841 | 245343049 | H_c_57f18_M |
| 1 | 245360747 | 245362988 | H_c_215m10_M |
| 1 | 245409618 | 245410732 | H_c_243l22 |
| 1 | 24568902 | 24569003 | H_c_193i09 |
| 1 | 24627669 | 24628346 | H_c_130g09 |
| 1 | 24714055 | 24715778 | H_c_11l22_M |
| 1 | 24742469 | 24742565 | H_c_231p09 |
| 1 | 24815878 | 24817937 | H_c_193l23 |
| 1 | 24875270 | 24875404 | H_c_92j24 |
| 1 | 24919567 | 24920750 | H_c_79n22_M |
| 1 | 25001188 | 25005859 | H_c_178h04_M |
| 1 | 2509388 | 2513212 | H_c_199e18_M |
| 1 | 25105528 | 25106242 | H_c_183c09 |
| 1 | 25212174 | 25212597 | H_c_193d21 |
| 1 | 25223489 | 25223644 | H_c_48g22 |
| 1 | 25303668 | 25304710 | H_c_84a22_M |
| 1 | 25318253 | 25319890 | H_c_178f12_M |
| 1 | 25409561 | 25410799 | H_c_29d02_M |
| 1 | 25501650 | 25503697 | H_c_11c04_M |
| 1 | 25810325 | 25811340 | H_c_81k16_M |
| 1 | 25829498 | 25831566 | H_c_120c09_M |
| 1 | 25867757 | 25870524 | H_c_49e14 |
| 1 | 25884993 | 25887237 | H_c_203o10 |
| 1 | 25916074 | 25917816 | H_c_204e06_M |
| 1 | 25933128 | 25933834 | H_c_117d11 |
| 1 | 26045774 | 26045925 | H_c_149f09_M |
| 1 | 26121751 | 26123274 | H_c_195o13 |
| 1 | 26171238 | 26176500 | H_c_161e23_M |
| 1 | 26235542 | 26236624 | H_c_36d12 |
| 1 | 26244246 | 26245272 | H_c_104h14_M |
| 1 | 26346602 | 26348627 | H_c_61e10 |
| 1 | 26370024 | 26370976 | H_c_27n09 |
| 1 | 26483022 | 26483983 | H_c_9f17_M |
| 1 | 26510656 | 26511120 | H_c_63j14_M |
| 1 | 26539577 | 26540933 | H_c142k03_M |
| 1 | 26630844 | 26632393 | H_c_190n11_M |
| 1 | 26703123 | 26703364 | H_c_125d14 |
| 1 | 26797810 | 26799267 | H_c_16g20_M |
| 1 | 26836687 | 26838901 | H_c139e17 |
| 1 | 26900062 | 26901906 | H_c_198a16 |
| 1 | 26910607 | 26911574 | H_c_6b01_M |
| 1 | 26970146 | 26971835 | H_c_273b07_M |
| 1 | 27023414 | 27023693 | H_c_271c03 |
| 1 | 27041905 | 27043382 | H_c_56f23 |
| 1 | 27244818 | 27246394 | H_c_48h03 |
| 1 | 2728241 | 2730424 | H_c_111h18 |

TABLE 1-continued

| | | | |
|---|---|---|---|
| 1 | 27331788 | 27333335 | H_c134i09 |
| 1 | 27376774 | 27378031 | H_c_89c01_M |
| 1 | 27392727 | 27394738 | H_c_212e20 |
| 1 | 27401952 | 27403637 | H_c_225i12_M |
| 1 | 27644639 | 27645363 | H_c_242m03 |
| 1 | 27670094 | 27670987 | H_c_66d11_M |
| 1 | 27736205 | 27737295 | H_c_124o02_M |
| 1 | 27783242 | 27784551 | H_c_30c18_M |
| 1 | 27840812 | 27842140 | H_c_39g15_M |
| 1 | 27882668 | 27883826 | H_c_64c17_M |
| 1 | 27924573 | 27925965 | H_c140k24_M |
| 1 | 27970142 | 27972177 | H_c_146k01 |
| 1 | 28098568 | 28099507 | H_c_157m21_M |
| 1 | 2822967 | 2825609 | H_c_22d18 |
| 1 | 28245891 | 28247162 | H_c_24e15 |
| 1 | 28257760 | 28258081 | H_c_114f19_M |
| 1 | 28269781 | 28271542 | H_c_207g07_M |
| 1 | 28379881 | 28380978 | H_c_264o22 |
| 1 | 28665033 | 28667871 | H_c_63n03 |
| 1 | 28699631 | 28700889 | H_c_194d15_M |
| 1 | 28728617 | 28729465 | H_c144d21_M |
| 1 | 28739329 | 28740976 | H_c_33k05 |
| 1 | 28883816 | 28884935 | H_c_39p09_M |
| 1 | 28959002 | 28960790 | H_c_57o11_M |
| 1 | 29034275 | 29035725 | H_c_169b07_M |
| 1 | 29061056 | 29062462 | H_c_82k21_M |
| 1 | 29267231 | 29272184 | H_c_4o06_M |
| 1 | 29327803 | 29329566 | H_c_100k21_M |
| 1 | 29377801 | 29378398 | H_c_254p04_M |
| 1 | 3005720 | 3008613 | H_c_89l13_M |
| 1 | 3013158 | 3013735 | H_c_170k18_M |
| 1 | 30148320 | 30148524 | H_c_195c09 |
| 1 | 30223679 | 30225220 | H_c_194h17 |
| 1 | 30441357 | 30441650 | H_c_74o14 |
| 1 | 30774825 | 30774933 | H_c_164k23 |
| 1 | 30859932 | 30862436 | H_c141f07_M |
| 1 | 31015719 | 31017930 | H_c_60i24 |
| 1 | 31207023 | 31208108 | H_c_77j16_M |
| 1 | 3123486 | 3123618 | H_c_258o01 |
| 1 | 31296504 | 31297724 | H_c_239n19 |
| 1 | 31380457 | 31382918 | H_c_129e01_M |
| 1 | 31554610 | 31557720 | H_c_154b15_M |
| 1 | 31720036 | 31722248 | H_c_112k24 |
| 1 | 31747681 | 31747957 | H_c_67j06 |
| 1 | 31751799 | 31753238 | H_c_15b18_M |
| 1 | 31778296 | 31780499 | H_c_145o24_M |
| 1 | 3186987 | 3187790 | H_c_207c12_M |
| 1 | 31894997 | 31898128 | H_c132c11_M |
| 1 | 32071974 | 32073575 | H_c_210b15_M |
| 1 | 32078653 | 32080183 | H_c_81d18 |
| 1 | 32147764 | 32149610 | H_c_190a18_M |
| 1 | 32207566 | 32208587 | H_c_31d04_M |
| 1 | 32313898 | 32314913 | H_c_178g09_M |
| 1 | 32340065 | 32340653 | H_c_61p11_M |
| 1 | 32374593 | 32375803 | H_c_42m18_M |
| 1 | 32409936 | 32411796 | H_c_74b05_M |
| 1 | 32426603 | 32427425 | H_c_112h09 |
| 1 | 32469098 | 32470297 | H_c_71d12_M |
| 1 | 32486009 | 32486881 | H_c_14e21 |
| 1 | 32496018 | 32497101 | H_c_2o11_M |
| 1 | 3262428 | 3263433 | H_c_153o20_M |
| 1 | 32635026 | 32635846 | H_c_43a17 |
| 1 | 32745570 | 32745654 | H_c_7e05 |
| 1 | 32837059 | 32837384 | H_c_85h17_M |
| 1 | 32851406 | 32852069 | H_c_159g10 |
| 1 | 32875692 | 32877233 | H_c_120c16_M |
| 1 | 32951619 | 32953499 | H_c137p04 |
| 1 | 33003370 | 33006249 | H_c_76e24_M |
| 1 | 33035091 | 33036560 | H_c_27j02_M |
| 1 | 33107264 | 33108092 | H_c_2b09_M |
| 1 | 33185668 | 33187866 | H_c_271c09 |
| 1 | 33215428 | 33215986 | H_c_224c07_M |
| 1 | 33262170 | 33262334 | H_c_201p14_M |
| 1 | 33315291 | 33316505 | H_c_261g15 |
| 1 | 3332998 | 3333621 | H_c_2f22 |
| 1 | 33390470 | 33391579 | H_c_169p16 |
| 1 | 33435281 | 33436846 | H_c141l19 |
| 1 | 33441033 | 33443664 | H_c_208a07 |
| 1 | 33483861 | 33485527 | H_c_130f12_M |
| 1 | 33606914 | 33607754 | H_c_163c05_M |
| 1 | 33800114 | 33800264 | H_c_261a07 |
| 1 | 33893847 | 33893980 | H_c_171m02_M |
| 1 | 34298168 | 34300042 | H_c_81b10_M |
| 1 | 3470740 | 3471162 | H_c_97a07 |
| 1 | 34751048 | 34751300 | H_c_79k16 |
| 1 | 34910736 | 34910846 | H_c_244a15 |
| 1 | 34962444 | 34962657 | H_c_74k09 |
| 1 | 35019204 | 35021602 | H_c_250a20_M |
| 1 | 35062740 | 35065373 | H_c_248f18 |
| 1 | 35166109 | 35166739 | H_c_87n19_M |
| 1 | 35228823 | 35228895 | H_c_50f16 |
| 1 | 35326516 | 35328334 | H_c_71j21_M |
| 1 | 35403598 | 35404075 | H_c_179e04 |
| 1 | 3550733 | 3553214 | H_c_228d11_M |
| 1 | 35691273 | 35692760 | H_c_34k20 |
| 1 | 35708033 | 35712678 | H_c_160g15_M |
| 1 | 35851921 | 35853812 | H_c_66c12_M |
| 1 | 35903891 | 35905494 | H_c_190m17_M |
| 1 | 35941628 | 35944036 | H_c_92c17 |
| 1 | 36017336 | 36019043 | H_c_3c22_M |
| 1 | 36065317 | 36066366 | H_c_60g04_M |
| 1 | 36218595 | 36219241 | H_c_188b06 |
| 1 | 36283702 | 36284305 | H_c_241d05 |
| 1 | 36289738 | 36291205 | H_c_258l20 |
| 1 | 36347034 | 36349254 | H_c_160k10 |
| 1 | 36358533 | 36359234 | H_c_130c02_M |
| 1 | 36519651 | 36521325 | H_c_246j05_M |
| 1 | 36531963 | 36532850 | H_c_212m06_M |
| 1 | 36584752 | 36586221 | H_c_224f21 |
| 1 | 36598582 | 36599285 | H_c_62k11_M |
| 1 | 3711346 | 3713478 | H_c_98m10_M |
| 1 | 37167305 | 37170092 | H_c_15g05_M |
| 1 | 37321028 | 37321281 | H_c_43k02 |
| 1 | 37326849 | 37326976 | H_c_58o08 |
| 1 | 3735334 | 3736475 | H_c_121l22_M |
| 1 | 37381603 | 37383733 | H_c_192c02 |
| 1 | 37608727 | 37609958 | H_c_251k24_M |
| 1 | 37619010 | 37620567 | H_c_215l12 |
| 1 | 37648284 | 37649980 | H_c_252k19_M |
| 1 | 37688589 | 37688994 | H_c_218d04_M |
| 1 | 37730136 | 37730817 | H_c_26c24 |
| 1 | 37826151 | 37827890 | H_c_19e06_M |
| 1 | 37887249 | 37889488 | H_c_121g18_M |
| 1 | 37895855 | 37897877 | H_c_71j01_M |
| 1 | 37928141 | 37930846 | H_c_204c22_M |
| 1 | 37942408 | 37943647 | H_c_166o02_M |
| 1 | 3796224 | 3798000 | H_c_34f22_M |
| 1 | 38065313 | 38067475 | H_c_187i07 |
| 1 | 38139042 | 38140672 | H_c_4j06_M |
| 1 | 38147151 | 38147755 | H_c_171m04_M |
| 1 | 38179138 | 38179440 | H_c_169d22 |
| 1 | 38181586 | 38184004 | H_c_274p20_M |
| 1 | 38351873 | 38353478 | H_c_28o12 |
| 1 | 3839175 | 3841920 | H_c_126h06_M |
| 1 | 38676281 | 38677508 | H_c_32e12 |
| 1 | 38773230 | 38773341 | H_c_201d03 |
| 1 | 38815169 | 38815311 | H_c_71c23 |
| 1 | 38938423 | 38938616 | H_c_62g12 |
| 1 | 38952269 | 38953400 | H_c_154i01_M |
| 1 | 38993582 | 38995535 | H_c_150d17 |
| 1 | 3907220 | 3907295 | H_c_52c15 |
| 1 | 39125639 | 39127035 | H_c_76o21_M |
| 1 | 39239334 | 39241155 | H_c_93p19_M |
| 1 | 3924147 | 3925688 | H_c_97p20 |
| 1 | 39283219 | 39283399 | H_c_75l10 |
| 1 | 39340329 | 39340519 | H_c_28b17 |
| 1 | 39503928 | 39504054 | H_c_196e24 |
| 1 | 39543153 | 39544441 | H_c139i10_M |
| 1 | 39710003 | 39711023 | H_c_32g23_M |
| 1 | 39773591 | 39776050 | H_c_211d11_M |
| 1 | 39806032 | 39808206 | H_c_121n06_M |
| 1 | 39824921 | 39827211 | H_c_101e16 |
| 1 | 39872962 | 39875075 | H_c_105m10 |
| 1 | 40078069 | 40078197 | H_c_28m20 |
| 1 | 40089518 | 40090610 | H_c_250g02 |
| 1 | 40174671 | 40175630 | H_c_44m10_M |
| 1 | 40213280 | 40214870 | H_c_251h24 |
| 1 | 40231860 | 40232292 | H_c_81c04_M |
| 1 | 40295612 | 40296849 | H_c_154m04_M |
| 1 | 40392287 | 40393483 | H_c_186d23_M |

TABLE 1-continued

| | | | |
|---|---|---|---|
| 1 | 40449884 | 40451265 | H_c_157g17 |
| 1 | 40451284 | 40452498 | H_c_151c02 |
| 1 | 40508194 | 40509459 | H_c_148j07_M |
| 1 | 40582107 | 40582277 | H_c_52h11 |
| 1 | 40584427 | 40585601 | H_c_170j16_M |
| 1 | 40612261 | 40612758 | H_c_171n23 |
| 1 | 40643316 | 40644457 | H_c_72m22 |
| 1 | 40826325 | 40827081 | H_c_66f17_M |
| 1 | 40842918 | 40843085 | H_c_232n09 |
| 1 | 40994852 | 40997479 | H_c_115a05_M |
| 1 | 41005127 | 41005239 | H_c_15m17 |
| 1 | 41018337 | 41019507 | H_c_196b14_M |
| 1 | 41376010 | 41377768 | H_c_188c07_M |
| 1 | 41499875 | 41501501 | H_c_41h10 |
| 1 | 41515841 | 41518347 | H_c_36h17 |
| 1 | 41619431 | 41621319 | H_c142h16 |
| 1 | 41630438 | 41632483 | H_c_57j20_M |
| 1 | 41650414 | 41651991 | H_c_228b17_M |
| 1 | 42052605 | 42053326 | H_c_170h17_M |
| 1 | 42169936 | 42172138 | H_c_228l19_M |
| 1 | 42469404 | 42470583 | H_c_29e08_M |
| 1 | 42514742 | 42516034 | H_c_1e08_M |
| 1 | 4255768 | 4256006 | H_c_252n07 |
| 1 | 42590525 | 42591984 | H_c144d03_M |
| 1 | 42792976 | 42793233 | H_c_201o04_M |
| 1 | 42901027 | 42902735 | H_c_168m20 |
| 1 | 42951586 | 42952374 | H_c_120i20_M |
| 1 | 42980929 | 42982071 | H_c_271h05 |
| 1 | 43058076 | 43059088 | H_c_86n10 |
| 1 | 43091922 | 43094088 | H_c_154h18_M |
| 1 | 43306021 | 43307838 | H_c_184m18 |
| 1 | 43483005 | 43484584 | H_c_24p15 |
| 1 | 43493352 | 43493714 | H_c137c01_M |
| 1 | 43502359 | 43503975 | H_c_124i24_M |
| 1 | 43587380 | 43588843 | H_c_272c19_M |
| 1 | 43698824 | 43701095 | H_c_254o13_M |
| 1 | 43841843 | 43843141 | H_c_271d19 |
| 1 | 44004028 | 44004275 | H_c143c14 |
| 1 | 44080953 | 44083226 | H_c_257a24_M |
| 1 | 44109217 | 44110791 | H_c_170h06 |
| 1 | 44113660 | 44115147 | H_c_153n10_M |
| 1 | 44158420 | 44160131 | H_c_249f11 |
| 1 | 44164714 | 44166130 | H_c_76a05_M |
| 1 | 44347985 | 44349419 | H_c_229b02 |
| 1 | 44489614 | 44490298 | H_c137j03_M |
| 1 | 44539614 | 44543264 | H_c_11p08_M |
| 1 | 44543507 | 44543873 | H_c_36j16 |
| 1 | 44552122 | 44553301 | H_c_1l15_M |
| 1 | 44574932 | 44575266 | H_c_227h17 |
| 1 | 44765682 | 44767523 | H_c_133a24_M |
| 1 | 44808810 | 44809956 | H_c_259n15 |
| 1 | 44841764 | 44841864 | H_c_194m10_M |
| 1 | 44858047 | 44860438 | H_c_39l19_M |
| 1 | 44909782 | 44911212 | H_c_14l16 |
| 1 | 44918660 | 44922845 | H_c135l09_M |
| 1 | 44934148 | 44936285 | H_c_65a05_M |
| 1 | 44964819 | 44966642 | H_c_251m04 |
| 1 | 44976084 | 44978330 | H_c_85a10_M |
| 1 | 45120862 | 45121553 | H_c_34h11_M |
| 1 | 45145199 | 45146450 | H_c_72d03_M |
| 1 | 45340192 | 45342052 | H_c_45c01_M |
| 1 | 45438740 | 45439022 | H_c_63h17_M |
| 1 | 45442012 | 45442182 | H_c_237h08 |
| 1 | 45461312 | 45463206 | H_c_16h10_M |
| 1 | 45463468 | 45464801 | H_c_264f03 |
| 1 | 45474599 | 45475486 | H_c140k16 |
| 1 | 45633974 | 45635329 | H_c_21c16 |
| 1 | 45685195 | 45685836 | H_c_234n14 |
| 1 | 45718993 | 45720099 | H_c_227o01_M |
| 1 | 45795128 | 45795216 | H_c_69h17 |
| 1 | 45820678 | 45822128 | H_c_28o09_M |
| 1 | 45927593 | 45928703 | H_c_67a09_M |
| 1 | 45980494 | 45982156 | H_c_36n13_M |
| 1 | 46310349 | 46311502 | H_c143f17_M |
| 1 | 46374800 | 46376542 | H_c_44f10 |
| 1 | 46480027 | 46482075 | H_c140f20 |
| 1 | 46518068 | 46519957 | H_c_71i22_M |
| 1 | 46624919 | 46627052 | H_c_15b01_M |
| 1 | 46643739 | 46645952 | H_c_76g03_M |
| 1 | 46663298 | 46663511 | H_c_77g02_M |
| 1 | 46665865 | 46668063 | H_c_224i13_M |
| 1 | 46721089 | 46723271 | H_c_238l07_M |
| 1 | 46793686 | 46795515 | H_c_123p02 |
| 1 | 46896919 | 46897161 | H_c_58p20 |
| 1 | 47402996 | 47404662 | H_c_94i14_M |
| 1 | 47408436 | 47410128 | H_c_21n20_M |
| 1 | 47491577 | 47492072 | H_c_98n24 |
| 1 | 47511030 | 47512622 | H_c_83p02_M |
| 1 | 47614720 | 47615231 | H_c_85g16_M |
| 1 | 47621787 | 47622926 | H_c_49p19_M |
| 1 | 47625695 | 47628050 | H_c142i01 |
| 1 | 47685235 | 47686059 | H_c_272b22_M |
| 1 | 47710566 | 47711022 | H_c_243l08 |
| 1 | 47771045 | 47772274 | H_c_213m16_M |
| 1 | 47886204 | 47888811 | H_c_71n23 |
| 1 | 47902877 | 47903369 | H_c_86h09 |
| 1 | 48052903 | 48053037 | H_c_4g11 |
| 1 | 48322426 | 48322527 | H_c_77f22 |
| 1 | 48649191 | 48650275 | H_c_119b08 |
| 1 | 48669533 | 48669772 | H_c_237g19 |
| 1 | 48769896 | 48770032 | H_c_113i22 |
| 1 | 48893603 | 48893788 | H_c_25f24 |
| 1 | 49194160 | 49194251 | H_c_196p23 |
| 1 | 49793694 | 49793851 | H_c_243m15 |
| 1 | 50005893 | 50006088 | H_c_76a06 |
| 1 | 50510277 | 50511675 | H_c_129i08_M |
| 1 | 50594439 | 50601783 | H_c_188f06_M_M |
| 1 | 50603314 | 50604705 | H_c_146n01_M |
| 1 | 50608003 | 50609499 | H_c_208k06 |
| 1 | 50747033 | 50747200 | H_c_101p19 |
| 1 | 50884387 | 50884532 | H_c_32j21 |
| 1 | 51137854 | 51138143 | H_c_240d17_M |
| 1 | 51145699 | 51147431 | H_c_148d13_M |
| 1 | 51155261 | 51156390 | H_c_154o24_M |
| 1 | 51413655 | 51415023 | H_c_269g12_M |
| 1 | 51507762 | 51508613 | H_c_127a18 |
| 1 | 51521975 | 51522897 | H_c_211l15_M |
| 1 | 51696320 | 51697215 | H_c_195m03 |
| 1 | 51906927 | 51907977 | H_c_85m22 |
| 1 | 52101167 | 52101259 | H_c140g06 |
| 1 | 52166519 | 52168557 | H_c_6f13_M |
| 1 | 52211211 | 52211717 | H_c_90n22_M |
| 1 | 52319390 | 52320889 | H_c_15j16_M |
| 1 | 5242988 | 5243243 | H_c_270c03 |
| 1 | 52542741 | 52544268 | H_c_274l05_M |
| 1 | 52546136 | 52546649 | H_c_110h16 |
| 1 | 52730290 | 52731796 | H_c_109a14 |
| 1 | 52779705 | 52781669 | H_c_98f13_M |
| 1 | 52875201 | 52876166 | H_c_155f14 |
| 1 | 52880625 | 52881208 | H_c_103d13 |
| 1 | 53020079 | 53021353 | H_c_18f01_M |
| 1 | 5307342 | 5309179 | H_c_185e20 |
| 1 | 53098932 | 53099606 | H_c_254h22 |
| 1 | 53374198 | 53375054 | H_c_44l12_M |
| 1 | 53397862 | 53398524 | H_c_122l14_M |
| 1 | 53915318 | 53915908 | H_c_27b02_M |
| 1 | 54067209 | 54067550 | H_c_59a09 |
| 1 | 54122970 | 54124403 | H_c_157h15_M |
| 1 | 5431758 | 5431860 | H_c139m17 |
| 1 | 54652222 | 54653864 | H_c_216i02 |
| 1 | 54665813 | 54667514 | H_c_205i02_M |
| 1 | 54824337 | 54824465 | H_c_253d06 |
| 1 | 54893140 | 54893883 | H_c_19p18_M |
| 1 | 54941736 | 54942608 | H_c_42h17_M |
| 1 | 54965914 | 54966191 | H_c_72p15 |
| 1 | 54977746 | 54980091 | H_c_274m05 |
| 1 | 55065204 | 55066071 | H_c_129d23_M |
| 1 | 55158106 | 55158282 | H_c_215b01_M |
| 1 | 55217155 | 55218699 | H_c_84d23 |
| 1 | 55392706 | 55393738 | H_c_69c13_M |
| 1 | 55784138 | 55784326 | H_c_167e04 |
| 1 | 55827441 | 55827616 | H_c_75p09 |
| 1 | 56085514 | 56085717 | H_c_79e08 |
| 1 | 56462727 | 56462855 | H_c_162a07 |
| 1 | 56655202 | 56655795 | H_c_90a17_M |
| 1 | 56755828 | 56757010 | H_c_93g09_M |
| 1 | 56822303 | 56823910 | H_c_23n15_M |
| 1 | 57077179 | 57077328 | H_c_272o20 |
| 1 | 57255483 | 57255613 | H_c_124n17 |
| 1 | 57599946 | 57602509 | H_c_94k23_M |

TABLE 1-continued

| | | | |
|---|---|---|---|
| 1 | 57635755 | 57635922 | H_c_258a11 |
| 1 | 58272511 | 58272607 | H_c_80f23 |
| 1 | 58427421 | 58428489 | H_c_252m19_M |
| 1 | 58693363 | 58693546 | H_c_55k14_M |
| 1 | 58723839 | 58724580 | H_c_154d14_M |
| 1 | 58753726 | 58755342 | H_c_53i06 |
| 1 | 58836652 | 58836760 | H_c_60j22 |
| 1 | 58959839 | 58963971 | H_c_160m16_M |
| 1 | 58991474 | 58993572 | H_c_4l11_M |
| 1 | 59080822 | 59082166 | H_c_205g04_M |
| 1 | 59366562 | 59366765 | H_c_265h02 |
| 1 | 59473862 | 59474861 | H_c_210i07_M |
| 1 | 59583112 | 59583567 | H_c_6e22 |
| 1 | 59592102 | 59592173 | H_c_53p05 |
| 1 | 59991713 | 59993535 | H_c_112m24 |
| 1 | 6019233 | 6020880 | H_c_191k03 |
| 1 | 60579319 | 60579498 | H_c_76k17 |
| 1 | 60648167 | 60648444 | H_c_77a04 |
| 1 | 60699704 | 60699792 | H_c_164j20 |
| 1 | 6092963 | 6094929 | H_c_148b12 |
| 1 | 61220500 | 61221599 | H_c_32a19_M |
| 1 | 61227838 | 61229163 | H_c_242l04_M |
| 1 | 61231504 | 61232611 | H_c_206m05 |
| 1 | 61234821 | 61235086 | H_c_38h07_M |
| 1 | 61260261 | 61260700 | H_c_232d08 |
| 1 | 61303323 | 61303415 | H_c_24c13_M |
| 1 | 6173409 | 6174736 | H_c_100h20_M |
| 1 | 61902677 | 61902895 | H_c_207e06 |
| 1 | 61919789 | 61920951 | H_c_35n20_M |
| 1 | 6193205 | 6195195 | H_c_208n03 |
| 1 | 6199564 | 6204086 | H_c_172i20_M_M |
| 1 | 6229853 | 6230752 | H_c_21o18_M |
| 1 | 6236281 | 6236757 | H_c_67o12_M |
| 1 | 6243069 | 6245425 | H_c_202n23_M |
| 1 | 62496639 | 62498829 | H_c_229a09_M |
| 1 | 6254296 | 6256906 | H_c_50m21_M |
| 1 | 62613561 | 62615540 | H_c_46a15_M |
| 1 | 62865203 | 62866438 | H_c_66g04_M |
| 1 | 63251589 | 63251876 | H_c_82f13_M |
| 1 | 63494485 | 63497739 | H_c_4h06_M |
| 1 | 63499160 | 63502561 | H_c_98d10_M |
| 1 | 63507739 | 63507961 | H_c_237l10 |
| 1 | 63544342 | 63545946 | H_c132c10 |
| 1 | 63700466 | 63701590 | H_c_175f23_M |
| 1 | 63771203 | 63772264 | H_c_96c10_M |
| 1 | 63774632 | 63774832 | H_c_81d08 |
| 1 | 6385950 | 6388691 | H_c_209p09 |
| 1 | 6404022 | 6404169 | H_c_224a06 |
| 1 | 6412548 | 6414872 | H_c_178b05_M |
| 1 | 6417409 | 6419073 | H_c_266m11_M |
| 1 | 64289219 | 64289450 | H_c_241h23 |
| 1 | 64331841 | 64332081 | H_c_2b04 |
| 1 | 6460262 | 6460961 | H_c_201a06 |
| 1 | 64647547 | 64649606 | H_c_272c06_M |
| 1 | 64682871 | 64683832 | H_c_90o12 |
| 1 | 6469178 | 6470466 | H_c_266k11 |
| 1 | 64876251 | 64877918 | H_c133k16 |
| 1 | 6491033 | 6492168 | H_c_188h24_M |
| 1 | 64921023 | 64923767 | H_c134j02_M |
| 1 | 65026113 | 65026303 | H_c132o16 |
| 1 | 65169692 | 65170208 | H_c_149b03 |
| 1 | 65179727 | 65180736 | H_c_257m22_M |
| 1 | 65244091 | 65245486 | H_c_195i11 |
| 1 | 65326587 | 65327119 | H_c_272j18_M |
| 1 | 65431980 | 65433471 | H_c_65k16 |
| 1 | 65443385 | 65443694 | H_c_77h15_M |
| 1 | 65443473 | 65443695 | H_c_266g09 |
| 1 | 65443699 | 65444031 | H_c_90b15 |
| 1 | 6547871 | 6549146 | H_c_110d16_M |
| 1 | 65597430 | 65598747 | H_c142o22_M |
| 1 | 65629278 | 65629490 | H_c_192p21 |
| 1 | 65702933 | 65704020 | H_c_191i19_M |
| 1 | 6572798 | 6575045 | H_c_241c09_M |
| 1 | 6595963 | 6597699 | H_c144c16_M |
| 1 | 6607358 | 6610145 | H_c_3j10_M |
| 1 | 66132633 | 66133624 | H_c_35j10 |
| 1 | 6619060 | 6620476 | H_c_85l08_M |
| 1 | 66533590 | 66533782 | H_c_6h24 |
| 1 | 66616913 | 66617007 | H_c_222p24_M |
| 1 | 6695199 | 6696628 | H_c_102m24_M |
| 1 | 67092231 | 67092326 | H_c_115b08 |
| 1 | 67102303 | 67102928 | H_c_127h11 |
| 1 | 67107440 | 67108578 | H_c_236a12_M |
| 1 | 67230998 | 67232404 | H_c_64b08_M |
| 1 | 67484934 | 67485829 | H_c_205b17_M |
| 1 | 6778954 | 6781835 | H_c_170n10 |
| 1 | 67911310 | 67912520 | H_c_162f09_M |
| 1 | 68010314 | 68011580 | H_c_31i16_M |
| 1 | 68408546 | 68409629 | H_c_56a22_M |
| 1 | 68674200 | 68675110 | H_c131m01_M |
| 1 | 69398858 | 69399669 | H_c_163c12 |
| 1 | 69703722 | 69703835 | H_c_152k14_M |
| 1 | 69744887 | 69746609 | H_c_39o07_M |
| 1 | 7001373 | 7001571 | H_c_239c08_M |
| 1 | 70308799 | 70308995 | H_c_122e18 |
| 1 | 70383290 | 70383474 | H_c_82f08_M |
| 1 | 70398867 | 70399310 | H_c_83l11_M |
| 1 | 70851569 | 70851754 | H_c_248c03 |
| 1 | 70982943 | 70983035 | H_c139p04 |
| 1 | 71224522 | 71225921 | H_c_14c19_M |
| 1 | 71393262 | 71393425 | H_c139g01 |
| 1 | 71593092 | 71593172 | H_c_79d03 |
| 1 | 71711467 | 71711536 | H_c_63l16 |
| 1 | 71947745 | 71948079 | H_c_215m17 |
| 1 | 72040320 | 72040440 | H_c_39p18 |
| 1 | 72380553 | 72380645 | H_c_63a21 |
| 1 | 72459416 | 72460791 | H_c_177f10 |
| 1 | 72518918 | 72519046 | H_c_61e07_M |
| 1 | 7318182 | 7318280 | H_c_17e02 |
| 1 | 73817410 | 73817502 | H_c_168e16 |
| 1 | 73867173 | 73868439 | H_c_230e15 |
| 1 | 74024162 | 74024380 | H_c_266g08 |
| 1 | 74250248 | 74250454 | H_c_274m04 |
| 1 | 74808980 | 74809137 | H_c_204a01 |
| 1 | 74850949 | 74852066 | H_c_27b06 |
| 1 | 75302230 | 75303674 | H_c_251b19 |
| 1 | 75306264 | 75306339 | H_c_67l20 |
| 1 | 75314008 | 75315330 | H_c_62h17_M |
| 1 | 75792211 | 75794503 | H_c_178a18_M |
| 1 | 75974301 | 75975256 | H_c_256b05 |
| 1 | 76295801 | 76295978 | H_c_229o09 |
| 1 | 7698168 | 7700428 | H_c_222i04 |
| 1 | 77045191 | 77047100 | H_c_234n09_M |
| 1 | 77068525 | 77068683 | H_c_222i10 |
| 1 | 77459041 | 77460957 | H_c_274o08_M |
| 1 | 77540152 | 77540261 | H_c_265e01 |
| 1 | 77687458 | 77687545 | H_c_214d18 |
| 1 | 7775674 | 7777227 | H_c_125n09 |
| 1 | 7777354 | 7779564 | H_c_85k05 |
| 1 | 77860586 | 77861607 | H_c_60h15_M |
| 1 | 78065740 | 78066950 | H_c_162l02 |
| 1 | 78070879 | 78073067 | H_c_26d21 |
| 1 | 78156629 | 78156938 | H_c_124m05 |
| 1 | 78219299 | 78219462 | H_c_70b16 |
| 1 | 78223353 | 78224217 | H_c_152b19_M |
| 1 | 78668537 | 78670166 | H_c_8h21_M |
| 1 | 78689505 | 78689635 | H_c_66e04 |
| 1 | 79361610 | 79361841 | H_c_78a04 |
| 1 | 7948196 | 7948990 | H_c133e08 |
| 1 | 7955812 | 7956386 | H_c_10a02_M |
| 1 | 79978159 | 79978322 | H_c_69c15 |
| 1 | 8019808 | 8021891 | H_c_118b06_M |
| 1 | 80451083 | 80451169 | H_c_81d06 |
| 1 | 80915963 | 80916145 | H_c_114g03 |
| 1 | 81474320 | 81474543 | H_c_3g09 |
| 1 | 81486846 | 81487022 | H_c_111g23 |
| 1 | 81909035 | 81909334 | H_c_86p17 |
| 1 | 81978123 | 81981071 | H_c_162a11_M |
| 1 | 8211133 | 8212091 | H_c_253a14_M |
| 1 | 82216141 | 82216309 | H_c_229c09 |
| 1 | 82700010 | 82700137 | H_c_161n10 |
| 1 | 82874999 | 82875129 | H_c_78l17 |
| 1 | 8312191 | 8313233 | H_c_32i14_M |
| 1 | 8360200 | 8360390 | H_c_244n21 |
| 1 | 83944265 | 83944449 | H_c_114g15 |
| 1 | 84175949 | 84177490 | H_c_225k08 |
| 1 | 84254996 | 84256719 | H_c_243c02_M |
| 1 | 84476050 | 84477508 | H_c_4i10_M |
| 1 | 84656924 | 84657155 | H_c_78h02 |
| 1 | 84684084 | 84684654 | H_c_168o15 |

TABLE 1-continued

| | | | |
|---|---|---|---|
| 1 | 84902152 | 84902301 | H_c_68i07 |
| 1 | 85070013 | 85071385 | H_c_103j06_M |
| 1 | 85174510 | 85176314 | H_c_151i12_M |
| 1 | 85225067 | 85226257 | H_c_66c15_M |
| 1 | 85377889 | 85379921 | H_c_199a11_M |
| 1 | 85436586 | 85437974 | H_c_190j14_M |
| 1 | 85489516 | 85490255 | H_c_74f07 |
| 1 | 85641975 | 85643217 | H_c_104k08_M |
| 1 | 85758130 | 85759310 | H_c_83d16_M |
| 1 | 85793711 | 85794203 | H_c_89m11 |
| 1 | 85885044 | 85886440 | H_c_25j02 |
| 1 | 86180941 | 86181097 | H_c_214f18 |
| 1 | 86240566 | 86240685 | H_c_103f04_M |
| 1 | 86332386 | 86334091 | H_c_162a23 |
| 1 | 86397274 | 86397337 | H_c_84p17 |
| 1 | 86490785 | 86490962 | H_c_213m21_M |
| 1 | 86829697 | 86829822 | H_c_208g19 |
| 1 | 86882110 | 86883369 | H_c_160l21_M |
| 1 | 8697163 | 8697965 | H_c_166n14_M |
| 1 | 87329719 | 87330144 | H_c_120j18 |
| 1 | 87505661 | 87506770 | H_c_87c10_M |
| 1 | 87509024 | 87510013 | H_c_25g02 |
| 1 | 87868799 | 87869018 | H_c_39j13 |
| 1 | 878862 | 880898 | H_c_28d16_M |
| 1 | 87977708 | 87977887 | H_c136f21 |
| 1 | 88023058 | 88023221 | H_c_99g17 |
| 1 | 8811802 | 8812464 | H_c_100e11_M |
| 1 | 88640324 | 88640514 | H_c_194f10_M |
| 1 | 88713869 | 88713969 | H_c143e14 |
| 1 | 88861679 | 88862745 | H_c_11i20_M |
| 1 | 89068504 | 89069521 | H_c_191h24_M |
| 1 | 89701733 | 89703094 | H_c_151c17_M |
| 1 | 897316 | 899136 | H_c_78d10 |
| 1 | 89809874 | 89811814 | H_c_58i24_M |
| 1 | 899139 | 900455 | H_c_53o19_M |
| 1 | 89998205 | 89999261 | H_c_11c03 |
| 1 | 90020731 | 90021964 | H_c_246e01 |
| 1 | 900456 | 900648 | H_c137d16_M |
| 1 | 90094402 | 90094633 | H_c_240i02 |
| 1 | 90172201 | 90173266 | H_c_190a15_M |
| 1 | 90836403 | 90836592 | H_c_38p17 |
| 1 | 90887939 | 90888907 | H_c_164e20 |
| 1 | 90894345 | 90896671 | H_c_71o23_M |
| 1 | 90907994 | 90908231 | H_c_63k08 |
| 1 | 91012969 | 91014179 | H_c_56h24_M |
| 1 | 91028059 | 91029959 | H_c_217g15_M |
| 1 | 91198959 | 91199994 | H_c_40b16_M |
| 1 | 9122087 | 9123602 | H_c_107n04_M |
| 1 | 9134520 | 9134847 | H_c_119j01_M |
| 1 | 915721 | 917489 | H_c_139p02_M |
| 1 | 91581611 | 91582569 | H_c_5c09_M |
| 1 | 91678275 | 91678521 | H_c_93k19_M |
| 1 | 9176260 | 9177543 | H_c_178g01_M |
| 1 | 91782457 | 91782754 | H_c_150h14 |
| 1 | 92212000 | 92212147 | H_c_188h21 |
| 1 | 92234292 | 92234419 | H_c143c04 |
| 1 | 92257642 | 92258650 | H_c_30g08 |
| 1 | 9228443 | 9229654 | H_c_42m24 |
| 1 | 9246219 | 9246373 | H_c_210e15 |
| 1 | 92535945 | 92536088 | H_c_262c02 |
| 1 | 92653131 | 92654314 | H_c_81a03 |
| 1 | 92662225 | 92664529 | H_c_26n03_M |
| 1 | 92678363 | 92678486 | H_c_185m22 |
| 1 | 9273858 | 9276710 | H_c_182o16 |
| 1 | 9286539 | 9288011 | H_c_123b11_M |
| 1 | 92962710 | 92962919 | H_c_9e20 |
| 1 | 93009853 | 93010194 | H_c_192h10 |
| 1 | 93013611 | 93013708 | H_c133a07 |
| 1 | 93138505 | 93139789 | H_c_13h13_M |
| 1 | 93244281 | 93244413 | H_c_102h23 |
| 1 | 93256718 | 93257683 | H_c_125m10 |
| 1 | 93357597 | 93358736 | H_c_27b13_M |
| 1 | 934321 | 936169 | H_c_172a05 |
| 1 | 93522907 | 93524190 | H_c_224a16_M |
| 1 | 93561233 | 93561475 | H_c_236f02 |
| 1 | 936173 | 938849 | H_c_90m23 |
| 1 | 93637089 | 93637258 | H_c_65p06 |
| 1 | 93969241 | 93969372 | H_c_15m02 |
| 1 | 94023726 | 94025757 | H_c_100g16_M |
| 1 | 94056565 | 94056887 | H_c_118f10_M |
| 1 | 9423141 | 9423544 | H_c_68d02 |
| 1 | 94530923 | 94531050 | H_c_238j11 |
| 1 | 94595590 | 94596917 | H_c_102l11_M |
| 1 | 94718812 | 94719767 | H_c_190j01_M |
| 1 | 94997207 | 94998324 | H_c_2m07_M |
| 1 | 95103355 | 95105581 | H_c_13c21 |
| 1 | 95294619 | 95294930 | H_c_268d04_M |
| 1 | 95294925 | 95295587 | H_c_269j05_M |
| 1 | 95411234 | 95412323 | H_c_182f12 |
| 1 | 9582137 | 9583850 | H_c_10g24_M |
| 1 | 96059261 | 96059461 | H_c_186p02 |
| 1 | 9621030 | 9621872 | H_c_8d24 |
| 1 | 96226512 | 96226658 | H_c_270b04 |
| 1 | 96774304 | 96774396 | H_c_14f05_M |
| 1 | 9681273 | 9684792 | H_c136d24_M |
| 1 | 975192 | 977296 | H_c_83p09_M |
| 1 | 98097937 | 98098805 | H_c_71c07_M |
| 1 | 9817077 | 9818882 | H_c_78i19 |
| 1 | 98222694 | 98227406 | H_c_44j24_M_M |
| 1 | 98230912 | 98231713 | H_c_170p18_M |
| 1 | 98250217 | 98250343 | H_c_229i21 |
| 1 | 9831399 | 9831561 | H_c_202n15 |
| 1 | 98403250 | 98403361 | H_c_3l06 |
| 1 | 98838762 | 98839923 | H_c_5g05_M |
| 1 | 99033626 | 99033767 | H_c_100m02 |
| 1 | 9903892 | 9905126 | H_c_207h14_M |
| 1 | 99181356 | 99182813 | H_c_37b14_M |
| 1 | 99345855 | 99346008 | H_c_11k18 |
| 1 | 99441687 | 99442701 | H_c_85e24 |
| 1 | 99726471 | 99726567 | H_c_77i15 |
| 1 | 9991295 | 9993046 | H_c_154g22_M |
| 2 | 100266996 | 100267167 | H_c_232i14 |
| 2 | 100377045 | 100377208 | H_c_156c22 |
| 2 | 100395588 | 100397628 | H_c_97g23_M |
| 2 | 100492173 | 100492966 | H_c_176h09_M |
| 2 | 100893075 | 100894709 | H_c_120b21_M |
| 2 | 100961732 | 100961824 | H_c_57f15 |
| 2 | 101076583 | 101077435 | H_c_68e20 |
| 2 | 101225382 | 101226787 | H_c_176f18 |
| 2 | 101327588 | 101328548 | H_c_201b24 |
| 2 | 10133764 | 10134857 | H_c_4g10 |
| 2 | 10134921 | 10135361 | H_c_17f20_M |
| 2 | 101382857 | 101384062 | H_c_229e03 |
| 2 | 101461514 | 101462732 | H_c_84l03_M |
| 2 | 101548787 | 101550026 | H_c_14b05_M |
| 2 | 101772026 | 101773417 | H_c_178i13 |
| 2 | 10212691 | 10214080 | H_c_34o15_M |
| 2 | 102217187 | 102218193 | H_c_100m12_M |
| 2 | 102261828 | 102263366 | H_c_20a18_M |
| 2 | 102324682 | 102326532 | H_c_220k15 |
| 2 | 102654735 | 102654924 | H_c_216i11_M |
| 2 | 102684765 | 102684894 | H_c_213o23 |
| 2 | 102811332 | 102812196 | H_c_100d04 |
| 2 | 103689187 | 103689259 | H_c_88f22 |
| 2 | 103726797 | 103726908 | H_c_162i15 |
| 2 | 10391760 | 10394576 | H_c_124o19_M |
| 2 | 10394790 | 10395297 | H_c_177o04_M |
| 2 | 104152327 | 104154192 | H_c_215j10 |
| 2 | 104296665 | 104296816 | H_c_232h06 |
| 2 | 104733067 | 104734795 | H_c_209h23 |
| 2 | 104803456 | 104803542 | H_c_171h02 |
| 2 | 104917282 | 104919171 | H_c_7k06_M |
| 2 | 104919328 | 104920472 | H_c_16m01_M |
| 2 | 104927423 | 104928810 | H_c_214o06_M |
| 2 | 104932679 | 104933043 | H_c_123o24 |
| 2 | 104948137 | 104948905 | H_c_48f17_M |
| 2 | 105112467 | 105113674 | H_c_195m16_M |
| 2 | 105218763 | 105219909 | H_c_188m22_M |
| 2 | 105403897 | 105406230 | H_c_201c02 |
| 2 | 105412183 | 105412727 | H_c_152n08 |
| 2 | 105436958 | 105437059 | H_c133j11 |
| 2 | 105473325 | 105474894 | H_c_80o10_M |
| 2 | 105819338 | 105820614 | H_c_145g10_M |
| 2 | 106140133 | 106141118 | H_c_28n11_M |
| 2 | 10615649 | 10617448 | H_c_247g24 |
| 2 | 106268714 | 106269547 | H_c_224a18 |
| 2 | 106723828 | 106723988 | H_c_201e10 |
| 2 | 106960752 | 106962890 | H_c_186f19_M |
| 2 | 10780019 | 10781772 | H_c_77k10_M |
| 2 | 108060910 | 108062059 | H_c_110l23_M |

TABLE 1-continued

| | | | |
|---|---|---|---|
| 2 | 10811654 | 10813041 | H_c_214g03_M |
| 2 | 108300160 | 108300231 | H_c_213m10 |
| 2 | 108365677 | 108365756 | H_c_25h08 |
| 2 | 108561470 | 108561724 | H_c_168b18 |
| 2 | 108608809 | 108609970 | H_c_204i14 |
| 2 | 108861474 | 108862195 | H_c_104b07_M |
| 2 | 10905302 | 10905400 | H_c_47m06_M |
| 2 | 109190401 | 109190705 | H_c_34l02 |
| 2 | 109274304 | 109274691 | H_c_58n16_M |
| 2 | 109728259 | 109730965 | H_c_182h09_M |
| 2 | 11002566 | 11004211 | H_c_66f02_M |
| 2 | 110186775 | 110187194 | H_c_94l12 |
| 2 | 110326988 | 110327809 | H_c_105p03 |
| 2 | 111143429 | 111143501 | H_c_253b24 |
| 2 | 111205724 | 111207341 | H_c_90k13_M |
| 2 | 111515168 | 111517114 | H_c_4n03 |
| 2 | 111591482 | 111597442 | H_c_128fl2_M_M |
| 2 | 111891649 | 111891730 | H_c137i03 |
| 2 | 11204813 | 11205008 | H_c_63j17 |
| 2 | 112357385 | 112358429 | H_c_175a18_M |
| 2 | 112371527 | 112373734 | H_c_68j24_M |
| 2 | 112527897 | 112530035 | H_c_208h10_M |
| 2 | 112611824 | 112614519 | H_c_267j21 |
| 2 | 112655254 | 112655985 | H_c_69b23_M |
| 2 | 112728166 | 112729063 | H_c_122o02 |
| 2 | 112748982 | 112749622 | H_c_271k12_M |
| 2 | 112953825 | 112955317 | H_c_163a19 |
| 2 | 112955636 | 112956960 | H_c_12j18_M |
| 2 | 113016098 | 113016619 | H_c_266n18 |
| 2 | 113057750 | 113058182 | H_c_27e15 |
| 2 | 113237891 | 113238933 | H_c_266d02 |
| 2 | 113630584 | 113631678 | H_c_245h09_M |
| 2 | 113672220 | 113673482 | H_c_84e08_M |
| 2 | 113677191 | 113679093 | H_c_193n03 |
| 2 | 113724939 | 113725600 | H_c_76p03 |
| 2 | 113750782 | 113752501 | H_c_55a01_M |
| 2 | 114152028 | 114152243 | H_c_218c10 |
| 2 | 114229935 | 114231342 | H_c_186b17_M |
| 2 | 114333542 | 114333643 | H_c133n13_M |
| 2 | 11434172 | 11436229 | H_c_111b18_M |
| 2 | 114363401 | 114364740 | H_c_9k24_M |
| 2 | 114473258 | 114473659 | H_c_153i08_M |
| 2 | 115052856 | 115052960 | H_c_83o17 |
| 2 | 115153811 | 115153981 | H_c_183f19_M |
| 2 | 11556184 | 11557173 | H_c_43d21 |
| 2 | 115636177 | 115636536 | H_c_267p15_M |
| 2 | 115694373 | 115694652 | H_c_156k09 |
| 2 | 115733826 | 115733892 | H_c_31k19_M |
| 2 | 115825967 | 115826060 | H_c_262p04 |
| 2 | 116120126 | 116120233 | H_c_271j13 |
| 2 | 116858094 | 116858242 | H_c_97c18 |
| 2 | 116890933 | 116891113 | H_c_45f07 |
| 2 | 117037177 | 117037289 | H_c_12d13 |
| 2 | 117200214 | 117201209 | H_c_226h02 |
| 2 | 11760017 | 11761160 | H_c_213k24_M |
| 2 | 11834270 | 11838094 | H_c_28o08_M |
| 2 | 118487047 | 118488581 | H_c_69l21_M |
| 2 | 118561688 | 118562994 | H_c_26k23_M |
| 2 | 118659946 | 118660728 | H_c_30p12_M |
| 2 | 118697755 | 118698696 | H_c_77j01_M |
| 2 | 118783929 | 118784077 | H_c_167p21_M |
| 2 | 119248148 | 119248681 | H_c_51a11_M |
| 2 | 119308364 | 119310127 | H_c_225o16_M |
| 2 | 119315098 | 119316377 | H_c_53j07 |
| 2 | 119318391 | 119325355 | H_c138i07_M_M |
| 2 | 119329417 | 119331845 | H_c_28e02_M |
| 2 | 119485901 | 119485751 | H_c_178b20 |
| 2 | 119697333 | 119698588 | H_c_244e17_M |
| 2 | 119840443 | 119842031 | H_c_2h10_M |
| 2 | 119905565 | 119906944 | H_c_168m06_M |
| 2 | 119997814 | 119998795 | H_c_162i07_M |
| 2 | 120017699 | 120018898 | H_c_42d23_M |
| 2 | 120119121 | 120119441 | H_c_202n21 |
| 2 | 120233277 | 120234620 | H_c_108n24 |
| 2 | 120284591 | 120284709 | H_c_22o17 |
| 2 | 120303198 | 120303312 | H_c_67p07 |
| 2 | 120319884 | 120320073 | H_c138a24 |
| 2 | 120374803 | 120374939 | H_c_32i19 |
| 2 | 120460248 | 120460338 | H_c_117g01 |
| 2 | 120486546 | 120487292 | H_c_206p19_M |
| 2 | 120565670 | 120565787 | H_c_39n06 |
| 2 | 120725867 | 120727183 | H_c_194m17_M |
| 2 | 120825280 | 120825462 | H_c_165n09 |
| 2 | 121060304 | 121061775 | H_c_248h03_M |
| 2 | 121208976 | 121210962 | H_c_214b19 |
| 2 | 121210957 | 121211477 | H_c_89p04_M |
| 2 | 121272142 | 121273530 | H_c_273e17 |
| 2 | 121635613 | 121636777 | H_c_200d04_M |
| 2 | 121708555 | 121709401 | H_c_157f13 |
| 2 | 121758022 | 121759804 | H_c_267o21_M |
| 2 | 121858979 | 121859113 | H_c_92m21 |
| 2 | 122123271 | 122123918 | H_c_148j04_M |
| 2 | 122210614 | 122211120 | H_c_68i23_M |
| 2 | 122228973 | 122229979 | H_c_105a19_M |
| 2 | 122539464 | 122539580 | H_c_96b04 |
| 2 | 123144909 | 123145115 | H_c_101l14 |
| 2 | 123838108 | 123838209 | H_c_105o07 |
| 2 | 124308437 | 124308760 | H_c_9g21 |
| 2 | 125300193 | 125300515 | H_c_243m16 |
| 2 | 125520218 | 125520442 | H_c_93g21 |
| 2 | 125984626 | 125984729 | H_c_228k08 |
| 2 | 126145674 | 126145776 | H_c_150l19 |
| 2 | 126428865 | 126428974 | H_c_209g06 |
| 2 | 126666553 | 126666800 | H_c_84c20 |
| 2 | 126755626 | 126755723 | H_c_189l21 |
| 2 | 126757270 | 126757527 | H_c_163c03_M |
| 2 | 126963058 | 126963149 | H_c_116h02 |
| 2 | 127129836 | 127130674 | H_c_36h16_M |
| 2 | 127250387 | 127250868 | H_c_48p21 |
| 2 | 127251335 | 127251678 | H_c_112c18 |
| 2 | 127579271 | 127581826 | H_c_195h12_M |
| 2 | 127586831 | 127587090 | H_c_148o18 |
| 2 | 127692409 | 127694153 | H_c_220m21_M |
| 2 | 127766964 | 127768163 | H_c_227g09 |
| 2 | 127860722 | 127862223 | H_c_163c23_M |
| 2 | 127881528 | 127882810 | H_c_185p03_M |
| 2 | 127889538 | 127890948 | H_c_149j10_M |
| 2 | 127999725 | 128000784 | H_c_265c06_M |
| 2 | 128038737 | 128040195 | H_c_222f08 |
| 2 | 12807062 | 12809682 | H_c_82p01_M |
| 2 | 128169293 | 128169788 | H_c_152i12 |
| 2 | 128284535 | 128285413 | H_c_23e01 |
| 2 | 128331555 | 128332254 | H_c_74b20_M |
| 2 | 128401672 | 128401777 | H_c_231i01_M |
| 2 | 128439740 | 128439810 | H_c_220p15 |
| 2 | 128500228 | 128501389 | H_c_71n12_M |
| 2 | 128564721 | 128565595 | H_c_150j20_M |
| 2 | 128706636 | 128707703 | H_c_214p22_M |
| 2 | 128722998 | 128723085 | H_c_5k15 |
| 2 | 128746156 | 128748902 | H_c_177f17 |
| 2 | 128790948 | 128793404 | H_c_125b05_M |
| 2 | 128795675 | 128797388 | H_c_267g22 |
| 2 | 129211937 | 129212178 | H_c_210n12 |
| 2 | 129371297 | 129371376 | H_c_39m01 |
| 2 | 129569390 | 129569563 | H_c_16j12 |
| 2 | 13022372 | 13022541 | H_c_75n06 |
| 2 | 130815415 | 130817156 | H_c_6c23_M |
| 2 | 130845727 | 130847136 | H_c_23h22_M |
| 2 | 130973768 | 130973846 | H_c_221i14 |
| 2 | 131347506 | 131348457 | H_c_213g15 |
| 2 | 131388346 | 131389808 | H_c_49j03_M |
| 2 | 131555211 | 131555847 | H_c_190b03 |
| 2 | 131625818 | 131627606 | H_c_103d15_M |
| 2 | 131684064 | 131684848 | H_c_199p23_M |
| 2 | 131696449 | 131697251 | H_c_34i21_M |
| 2 | 131775392 | 131775572 | H_c_86f18 |
| 2 | 132015685 | 132017015 | H_c_41p01 |
| 2 | 132821403 | 132821509 | H_c_239o24 |
| 2 | 132845660 | 132849695 | H_c_166k17_M |
| 2 | 132856390 | 132859143 | H_c_205b15_M |
| 2 | 132865699 | 132867482 | H_c_154e12 |
| 2 | 133153928 | 133154188 | H_c_116g01 |
| 2 | 13316239 | 13316352 | H_c_167h14 |
| 2 | 133260308 | 133262136 | H_c_13b03_M |
| 2 | 133458372 | 133458513 | H_c_114a07 |
| 2 | 133547608 | 133547704 | H_c_268l19_M |
| 2 | 133856840 | 133858143 | H_c_145c15 |
| 2 | 134858269 | 134858383 | H_c_225f19_M |
| 2 | 135308657 | 135310876 | H_c_74b17_M |
| 2 | 135503123 | 135503269 | H_c_160n24 |

TABLE 1-continued

| | | | |
|---|---|---|---|
| 2 | 135509657 | 135511293 | H_c_168f13_M |
| 2 | 136068191 | 136068355 | H_c_111f17 |
| 2 | 136121751 | 136123549 | H_c_235n04_M |
| 2 | 136134351 | 136134440 | H_c_54g14 |
| 2 | 136211406 | 136211822 | H_c_39h24 |
| 2 | 13625666 | 13625810 | H_c_152m04 |
| 2 | 136576356 | 136577540 | H_c_103g16_M |
| 2 | 136593894 | 136594450 | H_c_38n16 |
| 2 | 136708093 | 136708379 | H_c_30l18_M |
| 2 | 136708873 | 136710559 | H_c_198h06_M |
| 2 | 136969854 | 136970435 | H_c_39a10 |
| 2 | 137014722 | 137015135 | H_c_199f01_M |
| 2 | 137282711 | 137282902 | H_c_157l17 |
| 2 | 137355976 | 137357765 | H_c_262g21_M |
| 2 | 138237078 | 138237321 | H_c_201f07 |
| 2 | 138404151 | 138404293 | H_c_233m19 |
| 2 | 138693592 | 138693900 | H_c_193g24 |
| 2 | 138862499 | 138862718 | H_c_126p18_M |
| 2 | 13894210 | 13894584 | H_c_201i06 |
| 2 | 139092399 | 139093960 | H_c_33h11 |
| 2 | 139370766 | 139372678 | H_c_235l10_M |
| 2 | 139598813 | 139598923 | H_c_4e13 |
| 2 | 140018899 | 140018999 | H_c_74g11 |
| 2 | 140246370 | 140246565 | H_c_171h24 |
| 2 | 140641 | 140725 | H_c_31l22 |
| 2 | 14092085 | 14092222 | H_c_22k06_M |
| 2 | 140922815 | 140922960 | H_c_11n07 |
| 2 | 14127541 | 14127610 | H_c_64e05 |
| 2 | 141388756 | 141388776 | H_c_57l03 |
| 2 | 141469278 | 141469434 | H_c_120g14 |
| 2 | 142046644 | 142046786 | H_c_251i22 |
| 2 | 142115734 | 142115839 | H_c_229g21 |
| 2 | 142381427 | 142381540 | H_c_159c15 |
| 2 | 142454816 | 142454978 | H_c_103g08 |
| 2 | 142689682 | 142689774 | H_c_213a03 |
| 2 | 142721554 | 142722375 | H_c_267j22_M |
| 2 | 143061512 | 143061748 | H_c_106o05 |
| 2 | 143075459 | 143075841 | H_c_254b19_M |
| 2 | 143671948 | 143672069 | H_c_271b02_M |
| 2 | 143978645 | 143978721 | H_c_212o12 |
| 2 | 144242435 | 144242668 | H_c_1i21 |
| 2 | 144447918 | 144448210 | H_c_190e18 |
| 2 | 144527894 | 144528961 | H_c_20h15_M |
| 2 | 145068094 | 145068234 | H_c_179m17 |
| 2 | 145106854 | 145109314 | H_c_64g03_M |
| 2 | 145115427 | 145116175 | H_c_79e09 |
| 2 | 146155701 | 146155782 | H_c_14j08 |
| 2 | 1463109 | 1465594 | H_c_247j15 |
| 2 | 146638856 | 146638922 | H_c_4k10 |
| 2 | 147159084 | 147159201 | H_c_49n14_M |
| 2 | 147170358 | 147170630 | H_c_213o05 |
| 2 | 14723624 | 14726504 | H_c_258o10 |
| 2 | 147786670 | 147786847 | H_c_75e03 |
| 2 | 147831694 | 147831783 | H_c_29j11 |
| 2 | 148190620 | 148190782 | H_c_84i03 |
| 2 | 148220246 | 148220405 | H_c_115h10 |
| 2 | 148295856 | 148295920 | H_c_96b19 |
| 2 | 148434859 | 148436151 | H_c_70p18 |
| 2 | 148658391 | 148658487 | H_c_217l04 |
| 2 | 148979161 | 148979238 | H_c_39f04 |
| 2 | 149235137 | 149237332 | H_c_77m19_M |
| 2 | 149466295 | 149467345 | H_c_216k07_M |
| 2 | 149720454 | 149721529 | H_c_201c18_M |
| 2 | 150000063 | 150000277 | H_c_180i24 |
| 2 | 150560176 | 150560253 | H_c131b08 |
| 2 | 151133909 | 151134116 | H_c_77n18 |
| 2 | 151767808 | 151767917 | H_c_44k19 |
| 2 | 151943432 | 151944130 | H_c_230c05 |
| 2 | 151971078 | 151971860 | H_c_157g09 |
| 2 | 152091712 | 152092796 | H_c_209n18_M |
| 2 | 152169290 | 152169522 | H_c_21o03 |
| 2 | 152509541 | 152510805 | H_c_212n10 |
| 2 | 152584819 | 152584938 | H_c_222c11 |
| 2 | 15269808 | 15270074 | H_c_28c06 |
| 2 | 152857326 | 152858578 | H_c_270o19_M |
| 2 | 153016850 | 153018408 | H_c_82i02_M |
| 2 | 153209625 | 153209818 | H_c_64f15_M |
| 2 | 15326366 | 15326588 | H_c_101a13_M |
| 2 | 153561609 | 153561724 | H_c_80p01 |
| 2 | 153817736 | 153817831 | H_c_10b03 |
| 2 | 153946167 | 153946293 | H_c_122b23 |
| 2 | 154157928 | 154161088 | H_c_29p19_M |
| 2 | 154555022 | 154555632 | H_c_109b08 |
| 2 | 15465624 | 15465795 | H_c_147g19 |
| 2 | 154675742 | 154675894 | H_c_37m16 |
| 2 | 154681376 | 154681619 | H_c_17i07 |
| 2 | 154731894 | 154732006 | H_c_70d03 |
| 2 | 155379685 | 155380360 | H_c_45l11 |
| 2 | 155899438 | 155901191 | H_c_69k01_M |
| 2 | 15650950 | 15651338 | H_c_202e17 |
| 2 | 156787999 | 156788086 | H_c_180n22 |
| 2 | 15682161 | 15683012 | H_c_274g08_M |
| 2 | 157001781 | 157003898 | H_c_145k09_M |
| 2 | 157013868 | 157015734 | H_c137a21_M |
| 2 | 157023490 | 157024899 | H_c_169h08_M |
| 2 | 157081947 | 157082704 | H_c_129e22_M |
| 2 | 157117349 | 157118961 | H_c_5e06_M |
| 2 | 158310055 | 158311190 | H_c_42a04 |
| 2 | 158500056 | 158500147 | H_c_251h07 |
| 2 | 158504961 | 158505529 | H_c_153p15_M |
| 2 | 158556294 | 158556422 | H_c_25h06_M |
| 2 | 158558435 | 158559724 | H_c_204h20 |
| 2 | 158591016 | 158591313 | H_c_25m08 |
| 2 | 159138149 | 159140832 | H_c136i10_M |
| 2 | 15933571 | 15935139 | H_c_46g24 |
| 2 | 159650230 | 159651924 | H_c_90e09_M |
| 2 | 159680469 | 159680742 | H_c_34n21 |
| 2 | 159871149 | 159871277 | H_c_93d19 |
| 2 | 159967738 | 159969046 | H_c_139n02_M |
| 2 | 160195001 | 160195086 | H_c132n10 |
| 2 | 16032732 | 16034015 | H_c_185i03_M |
| 2 | 160374069 | 160374168 | H_c_265i05 |
| 2 | 160393985 | 160395253 | H_c_146k12_M |
| 2 | 160479640 | 160480307 | H_c_11o15_M |
| 2 | 160586091 | 160587323 | H_c_68f10 |
| 2 | 160743834 | 160745340 | H_c_249i19 |
| 2 | 160951826 | 160952617 | H_c_170h15 |
| 2 | 16103230 | 16104742 | H_c_189d07_M |
| 2 | 161089006 | 161090255 | H_c_194b10 |
| 2 | 161174558 | 161175954 | H_c_125g06_M |
| 2 | 161494183 | 161494512 | H_c_31a04 |
| 2 | 161652532 | 161652625 | H_c_109e10 |
| 2 | 161842384 | 161842937 | H_c_22l18 |
| 2 | 161920774 | 161921524 | H_c_28b16_M |
| 2 | 162050092 | 162050166 | H_c_157m03 |
| 2 | 162096014 | 162100862 | H_c_103k03_M_M |
| 2 | 162105026 | 162106323 | H_c_122e03 |
| 2 | 162108877 | 162110586 | H_c_273a19_M |
| 2 | 162755142 | 162756873 | H_c_146g05_M |
| 2 | 162849318 | 162849570 | H_c_221f11 |
| 2 | 162999729 | 163000826 | H_c_107c22 |
| 2 | 163521362 | 163522520 | H_c_47i01_M |
| 2 | 163824713 | 163824803 | H_c_44f04 |
| 2 | 163895223 | 163895361 | H_c_207d05 |
| 2 | 164202368 | 164202476 | H_c_22e06 |
| 2 | 164417821 | 164419213 | H_c_168a23_M |
| 2 | 164709540 | 164709653 | H_c_145j13 |
| 2 | 16482322 | 16482518 | H_c143a20_M |
| 2 | 165060110 | 165060260 | H_c_177m11 |
| 2 | 165108100 | 165108245 | H_c_242h11 |
| 2 | 165302795 | 165304154 | H_c_3f17_M |
| 2 | 165471583 | 165471697 | H_c_251j03 |
| 2 | 165522518 | 165524407 | H_c_66g05_M |
| 2 | 16610495 | 16611495 | H_c_209f12_M |
| 2 | 166253598 | 166253670 | H_c_67p15 |
| 2 | 166537997 | 166538128 | H_c_72c02 |
| 2 | 166616624 | 166616893 | H_c_125i12 |
| 2 | 166635368 | 166636836 | H_c_75p14_M |
| 2 | 167047764 | 167047866 | H_c_204i07 |
| 2 | 167057227 | 167058836 | H_c_4c09 |
| 2 | 167208780 | 167208992 | H_c_179f24 |
| 2 | 167222512 | 167222875 | H_c_14j06 |
| 2 | 167320361 | 167320477 | H_c_17n14 |
| 2 | 167559045 | 167559192 | H_c_73f22 |
| 2 | 16777823 | 16778683 | H_c_62m06 |
| 2 | 167915121 | 167915316 | H_c_66l14 |
| 2 | 167974309 | 167975694 | H_c133h12_M |
| 2 | 168160205 | 168160316 | H_c_12m08 |
| 2 | 168732607 | 168732794 | H_c_185p13 |
| 2 | 16890498 | 16890597 | H_c_184c06 |

TABLE 1-continued

| | | | |
|---|---|---|---|
| 2 | 168929079 | 168930201 | H_c_250d24_M |
| 2 | 169137585 | 169139268 | H_c_53d18_M |
| 2 | 169237931 | 169238006 | H_c_81f08 |
| 2 | 16951954 | 16952771 | H_c_151m22 |
| 2 | 169564738 | 169564842 | H_c_31f20 |
| 2 | 170046150 | 170046865 | H_c_121c05_M |
| 2 | 170359632 | 170359756 | H_c_237a20_M |
| 2 | 170375944 | 170376844 | H_c_74b08 |
| 2 | 170415664 | 170416530 | H_c_216n13_M |
| 2 | 170449767 | 170450919 | H_c_145b03_M |
| 2 | 170480989 | 170482104 | H_c_73b22_M |
| 2 | 170506624 | 170507771 | H_c_34c17 |
| 2 | 171394943 | 171399395 | H_c_11e02_M |
| 2 | 171408982 | 171409210 | H_c_5j02 |
| 2 | 171452648 | 171453661 | H_c_161g19 |
| 2 | 171497780 | 171498157 | H_c_211b04_M |
| 2 | 171503623 | 171505702 | H_c_83n18_M |
| 2 | 1716635 | 1718898 | H_c_153e16_M |
| 2 | 171841718 | 171841948 | H_c_39o21 |
| 2 | 172084384 | 172084570 | H_c_19d10 |
| 2 | 172115582 | 172116792 | H_c_63g21_M |
| 2 | 172205047 | 172205392 | H_c_244m15_M |
| 2 | 172246831 | 172246981 | H_c_62g05 |
| 2 | 172484185 | 172484335 | H_c_158p19 |
| 2 | 172575647 | 172576610 | H_c_90f04 |
| 2 | 172604397 | 172604910 | H_c_16c03_M |
| 2 | 172659817 | 172659938 | H_c_209c09 |
| 2 | 172689761 | 172690876 | H_c_128c23_M |
| 2 | 172770470 | 172771932 | H_c_216d03_M |
| 2 | 172775020 | 172781565 | H_c_153e04_M_M |
| 2 | 172785072 | 172794362 | H_c_273f22_M_M_M |
| 2 | 172924084 | 172925863 | H_c_270e17 |
| 2 | 173052086 | 173052358 | H_c_38n24 |
| 2 | 173117420 | 173118455 | H_c_252j08_M |
| 2 | 173245654 | 173247069 | H_c_107f07_M |
| 2 | 173425132 | 173426667 | H_c_20o08 |
| 2 | 173765849 | 173766629 | H_c_36i23_M |
| 2 | 173772469 | 173772650 | H_c_166a08 |
| 2 | 174044730 | 174045664 | H_c_66o14_M |
| 2 | 174178338 | 174178431 | H_c136c09 |
| 2 | 174702681 | 174704176 | H_c_169m15_M |
| 2 | 174938025 | 174939308 | H_c_1d07 |
| 2 | 175017296 | 175018631 | H_c_75g15 |
| 2 | 175024941 | 175028035 | H_c_86e24_M_M |
| 2 | 175030215 | 175034788 | H_c_244p13_M_M |
| 2 | 175176386 | 175177726 | H_c_12m24 |
| 2 | 175255684 | 175255831 | H_c_217i22 |
| 2 | 175694822 | 175696036 | H_c_181i18_M |
| 2 | 175850914 | 175851100 | H_c_79a12 |
| 2 | 175897256 | 175897443 | H_c_88f17 |
| 2 | 17641455 | 17642160 | H_c_60k01 |
| 2 | 176489439 | 176489530 | H_c_155d12 |
| 2 | 176691395 | 176692763 | H_c_268p14_M |
| 2 | 176757207 | 176758826 | H_c_169e03_M |
| 2 | 176769353 | 176775984 | H_c_48g09_M_M |
| 2 | 176778001 | 176779171 | H_c_36p13_M |
| 2 | 176797175 | 176798560 | H_c_41c23_M |
| 2 | 176806597 | 176807394 | H_c_230g11 |
| 2 | 176811978 | 176813438 | H_c_183l06_M |
| 2 | 176819567 | 176821127 | H_c_244m24_M |
| 2 | 176830654 | 176831569 | H_c142a18_M |
| 2 | 176849952 | 176851382 | H_c_51b01 |
| 2 | 176854635 | 176855517 | H_c_44c20 |
| 2 | 176861440 | 176862896 | H_c_92e23_M |
| 2 | 176868619 | 176869018 | H_c_100k03 |
| 2 | 176878506 | 176880145 | H_c_13i12_M |
| 2 | 176959761 | 176960295 | H_c_274j15_M |
| 2 | 177073682 | 177073793 | H_c_19e07 |
| 2 | 1771768 | 1772357 | H_c_19j21_M |
| 2 | 177327531 | 177328699 | H_c_149n01_M |
| 2 | 177573367 | 177573514 | H_c_129g16 |
| 2 | 177902559 | 177903771 | H_c_187f22_M |
| 2 | 177953505 | 177955296 | H_c_99b17_M |
| 2 | 178306271 | 178309442 | H_c_60f05_M |
| 2 | 178416733 | 178416844 | H_c_55m15 |
| 2 | 178447841 | 178448127 | H_c_168k06 |
| 2 | 17856099 | 17857621 | H_c_6b03_M |
| 2 | 178652827 | 178652966 | H_c_99h24 |
| 2 | 178768854 | 178769012 | H_c_14c16_M |
| 2 | 178802430 | 178803524 | H_c_96d03_M |
| 2 | 179133371 | 179133469 | H_c144j13 |
| 2 | 179140720 | 179141737 | H_c132c15_M |
| 2 | 179267801 | 179267976 | H_c_100d24 |
| 2 | 179909003 | 179909150 | H_c_231g04 |
| 2 | 179954109 | 179955245 | H_c_145j23_M |
| 2 | 180551579 | 180551859 | H_c_28c17_M |
| 2 | 180696885 | 180697394 | H_c_69j04 |
| 2 | 181299484 | 181299575 | H_c_223f20 |
| 2 | 181670251 | 181671723 | H_c_248g20_M |
| 2 | 181961681 | 181961829 | H_c_162m20 |
| 2 | 182147412 | 182148657 | H_c_157n02 |
| 2 | 182244656 | 182244757 | H_c_233j03 |
| 2 | 182346622 | 182347140 | H_c139e07 |
| 2 | 182372879 | 182374656 | H_c_201f11_M |
| 2 | 183070803 | 183070886 | H_c_106m05 |
| 2 | 183406150 | 183406825 | H_c_119e09_M |
| 2 | 183520854 | 183521084 | H_c_40o04 |
| 2 | 183613144 | 183613353 | H_c_221c07 |
| 2 | 183727501 | 183729020 | H_c_37o12_M |
| 2 | 184030303 | 184030375 | H_c_42l02 |
| 2 | 184253236 | 184253435 | H_c_90g16 |
| 2 | 184687089 | 184687188 | H_c_7c11 |
| 2 | 185288416 | 185289336 | H_c_119g15_M |
| 2 | 185318676 | 185318774 | H_c_234b09 |
| 2 | 18557403 | 18558261 | H_c_83a23 |
| 2 | 18662712 | 18663978 | H_c_225e14_M |
| 2 | 186773645 | 186773719 | H_c_61k03 |
| 2 | 187176220 | 187177193 | H_c_177f01 |
| 2 | 187279897 | 187280974 | H_c133m23_M |
| 2 | 18729720 | 18729904 | H_c_156f18 |
| 2 | 187538987 | 187539596 | H_c_48f22 |
| 2 | 187829752 | 187829819 | H_c_95j22 |
| 2 | 188044735 | 188044849 | H_c_41i05 |
| 2 | 188067575 | 188067640 | H_c_242k23 |
| 2 | 188748964 | 188749079 | H_c_72e11 |
| 2 | 188981983 | 188982973 | H_c_9c11_M |
| 2 | 188987038 | 188987256 | H_c_191e17 |
| 2 | 189004809 | 189004909 | H_c_72l23 |
| 2 | 190130710 | 190131467 | H_c_89j23 |
| 2 | 190189316 | 190189393 | H_c_241b04 |
| 2 | 190213355 | 190213498 | H_c_47c06 |
| 2 | 190251195 | 190251316 | H_c_102k22 |
| 2 | 190270764 | 190271517 | H_c_149n19_M |
| 2 | 190364371 | 190365579 | H_c_29l06_M |
| 2 | 190452726 | 190453105 | H_c_32e22_M |
| 2 | 190473923 | 190475072 | H_c_150c19 |
| 2 | 190870366 | 190871461 | H_c_234g13 |
| 2 | 191033722 | 191034533 | H_c_38h22_M |
| 2 | 191224131 | 191225290 | H_c_82b08_M |
| 2 | 191338447 | 191340068 | H_c_243f03_M |
| 2 | 191450530 | 191452332 | H_c_22e10 |
| 2 | 191570058 | 191572448 | H_c_220c24_M |
| 2 | 191710380 | 191711424 | H_c_26i15_M |
| 2 | 191760302 | 191760401 | H_c_105j13 |
| 2 | 191935083 | 191937183 | H_c_110p07_M |
| 2 | 191942132 | 191942264 | H_c_78h12 |
| 2 | 192175978 | 192176187 | H_c138c16 |
| 2 | 192367771 | 192368889 | H_c_16j16_M |
| 2 | 192635408 | 192635480 | H_c_154i07 |
| 2 | 192884622 | 192886632 | H_c_114j23_M |
| 2 | 193320151 | 193320395 | H_c_16g10 |
| 2 | 193457707 | 193457826 | H_c_127e18 |
| 2 | 19468721 | 19472219 | H_c_214i09_M |
| 2 | 194746275 | 194746631 | H_c_39k13 |
| 2 | 19477038 | 19479505 | H_c_86o14_M |
| 2 | 19482749 | 19483367 | H_c_3k15_M |
| 2 | 19484853 | 19485305 | H_c_22m10 |
| 2 | 196347118 | 196348658 | H_c_208b12_M |
| 2 | 196596538 | 196596660 | H_c_173h12 |
| 2 | 196758361 | 196759342 | H_c_233k20 |
| 2 | 196856362 | 196856593 | H_c_117i05 |
| 2 | 196861010 | 196862759 | H_c_122i12 |
| 2 | 197282624 | 197284236 | H_c_210p22_M |
| 2 | 197616830 | 197617356 | H_c_198h04_M |
| 2 | 197999800 | 198001369 | H_c_215o12_M |
| 2 | 198124766 | 198124932 | H_c_247j04 |
| 2 | 198143464 | 198144223 | H_c_155d10_M |
| 2 | 198189477 | 198191059 | H_c_195b17 |
| 2 | 198205519 | 198207134 | H_c_13a15_M |
| 2 | 198390901 | 198390963 | H_c_200d22_M |

TABLE 1-continued

| | | | |
|---|---|---|---|
| 2 | 198395037 | 198396038 | H_c__221f09_M |
| 2 | 198475177 | 198477145 | H_c__190g13_M |
| 2 | 198494398 | 198496006 | H_c143b07_M |
| 2 | 199686997 | 199687107 | H_c__256c10 |
| 2 | 200143564 | 200143697 | H_c__108h21 |
| 2 | 200147111 | 200149595 | H_c__5d13_M |
| 2 | 200152342 | 200155206 | H_c__94i23_M |
| 2 | 200159438 | 200162253 | H_c__7e10_M |
| 2 | 20022593 | 20023618 | H_c__119k24_M |
| 2 | 200240075 | 200240207 | H_c__128m08 |
| 2 | 200540887 | 200541603 | H_c__210g16_M |
| 2 | 200565370 | 200565625 | H_c__61d11 |
| 2 | 200601174 | 200602381 | H_c__265e21_M |
| 2 | 200645314 | 200646404 | H_c__41i24_M |
| 2 | 200845361 | 200845533 | H_c__74l20 |
| 2 | 20091793 | 20091916 | H_c139k24 |
| 2 | 200996578 | 200998179 | H_c__204a18_M |
| 2 | 201027399 | 201027496 | H_c__149n22 |
| 2 | 20111069 | 20112016 | H_c__114g07_M |
| 2 | 201199670 | 201200623 | H_c__17m18_M |
| 2 | 201216410 | 201216750 | H_c__216c12 |
| 2 | 201276180 | 201276478 | H_c__196h17_M |
| 2 | 20133035 | 20134084 | H_c__232a18_M |
| 2 | 201501585 | 201503198 | H_c__122e14_M |
| 2 | 201554289 | 201555208 | H_c__68l16_M |
| 2 | 201639731 | 201639920 | H_c__47f07 |
| 2 | 201653459 | 201654187 | H_c__101e22 |
| 2 | 201805576 | 201807210 | H_c__6h21_M |
| 2 | 202141241 | 202142629 | H_c__69f05_M |
| 2 | 202332816 | 202333134 | H_c__59a01_M |
| 2 | 202470392 | 202472425 | H_c__89j07_M |
| 2 | 202575439 | 202575680 | H_c__17p13 |
| 2 | 202723244 | 202725611 | H_c__21p06 |
| 2 | 202861502 | 202862000 | H_c__167f21 |
| 2 | 202869017 | 202869157 | H_c__195c24 |
| 2 | 202927912 | 202929214 | H_c__9c24_M |
| 2 | 203066186 | 203067955 | H_c__87n23_M |
| 2 | 203324743 | 203325006 | H_c__29k10_M |
| 2 | 203561397 | 203562173 | H_c__16d06_M |
| 2 | 203602234 | 203603257 | H_c__1l21 |
| 2 | 203704767 | 203705440 | H_c__97a15 |
| 2 | 203727528 | 203727613 | H_c__42b21 |
| 2 | 203789829 | 203789962 | H_c__19f19 |
| 2 | 203872615 | 203872816 | H_c__221e22_M |
| 2 | 203928889 | 203930063 | H_c__17m16_M |
| 2 | 20416768 | 20416885 | H_c__265g10 |
| 2 | 204224851 | 204226166 | H_c__20o22_M |
| 2 | 204354503 | 204354597 | H_c__180m10 |
| 2 | 204498604 | 204498709 | H_c__210c06 |
| 2 | 204651441 | 204651726 | H_c__31m08 |
| 2 | 20471422 | 20472684 | H_c__85d05_M |
| 2 | 20522916 | 20523093 | H_c__207n14 |
| 2 | 205235280 | 205236637 | H_c__39b02_M |
| 2 | 205617980 | 205618082 | H_c__196j05 |
| 2 | 20568435 | 20569977 | H_c__120e11_M |
| 2 | 205695665 | 205695787 | H_c__107j13 |
| 2 | 205861102 | 205861291 | H_c__2e20 |
| 2 | 206372029 | 206376366 | H_c__185d05_M_M |
| 2 | 206849214 | 206849879 | H_c__187m17_M |
| 2 | 207133289 | 207134612 | H_c__18g08_M |
| 2 | 207202238 | 207202427 | H_c__161i21 |
| 2 | 207473366 | 207473663 | H_c__150i13 |
| 2 | 207697367 | 207697731 | H_c__267d16 |
| 2 | 20784795 | 20788546 | H_c__27h13_M |
| 2 | 207855685 | 207857275 | H_c__268c12 |
| 2 | 20791909 | 20793386 | H_c__123h07_M |
| 2 | 208219166 | 208221213 | H_c__71n14_M |
| 2 | 208314712 | 208316195 | H_c__3h19_M |
| 2 | 208401885 | 208402743 | H_c__176m09_M |
| 2 | 208456971 | 208461584 | H_c__206p06_M_M |
| 2 | 208880156 | 208880313 | H_c__210n03 |
| 2 | 208944579 | 208945943 | H_c__206a02_M |
| 2 | 208963539 | 208963665 | H_c__149i09 |
| 2 | 209096581 | 209097536 | H_c__25i03_M |
| 2 | 20943998 | 20944875 | H_c__234j21 |
| 2 | 210025513 | 210025598 | H_c__216h13 |
| 2 | 210113481 | 210117073 | H_c__35l13_M |
| 2 | 210461505 | 210462546 | H_c__123l09_M |
| 2 | 21059157 | 21059299 | H_c__65b18 |
| 2 | 210614441 | 210614599 | H_c144l06 |
| 2 | 210692638 | 210693411 | H_c__56f13 |
| 2 | 210860475 | 210862017 | H_c__88n06_M |
| 2 | 210914810 | 210915840 | H_c__83k08_M |
| 2 | 211067542 | 211067734 | H_c__76g08 |
| 2 | 211166511 | 211166833 | H_c__218j11 |
| 2 | 211387207 | 211387307 | H_c__72a17 |
| 2 | 21177306 | 21180104 | H_c__213k06_M |
| 2 | 212098571 | 212098656 | H_c__69h06 |
| 2 | 212342391 | 212342529 | H_c__175f08 |
| 2 | 212872128 | 212872288 | H_c__56e14 |
| 2 | 213226956 | 213228449 | H_c__76g18_M |
| 2 | 213387000 | 213387092 | H_c__242p16 |
| 2 | 213806089 | 213806224 | H_c__208c12 |
| 2 | 213841698 | 213842688 | H_c__55a22 |
| 2 | 214584039 | 214584148 | H_c__160b15 |
| 2 | 214834281 | 214834389 | H_c__94c01 |
| 2 | 215016668 | 215016872 | H_c__183g06 |
| 2 | 215130550 | 215130697 | H_c__99m16 |
| 2 | 215499489 | 215500554 | H_c__153l08_M |
| 2 | 215705746 | 215705982 | H_c__45g18 |
| 2 | 216001170 | 216002825 | H_c__87a13_M |
| 2 | 216053032 | 216053277 | H_c__258g02 |
| 2 | 216125614 | 216126816 | H_c__48d03 |
| 2 | 216490132 | 216490222 | H_c__210p09 |
| 2 | 216702918 | 216703804 | H_c__50c15_M |
| 2 | 216739906 | 216740087 | H_c__151j19 |
| 2 | 216799299 | 216800011 | H_c__108h13_M |
| 2 | 216929630 | 216929734 | H_c__67m15 |
| 2 | 217028904 | 217029090 | H_c131i09 |
| 2 | 217061352 | 217063016 | H_c__8j21_M |
| 2 | 217322623 | 217324885 | H_c__30e12 |
| 2 | 217384245 | 217385111 | H_c__202o14 |
| 2 | 217654977 | 217655111 | H_c__15j24 |
| 2 | 218906628 | 218908267 | H_c__11p19_M |
| 2 | 218982189 | 218982917 | H_c__216j15_M |
| 2 | 219057797 | 219058478 | H_c__198l04_M |
| 2 | 21908594 | 21908771 | H_c__247p04_M |
| 2 | 219088538 | 219091570 | H_c__235l14_M |
| 2 | 219257923 | 219259549 | H_c__165p07_M |
| 2 | 219349019 | 219350661 | H_c__23j04_M |
| 2 | 219361637 | 219363354 | H_c__46g12 |
| 2 | 219400925 | 219401586 | H_c__67o17_M |
| 2 | 219471855 | 219472873 | H_c__67k16 |
| 2 | 21954180 | 21954360 | H_c__266f02 |
| 2 | 219548891 | 219551653 | H_c139d06_M |
| 2 | 219560940 | 219562145 | H_c__45m02 |
| 2 | 219570276 | 219574537 | H_c__157b17_M |
| 2 | 219587846 | 219588208 | H_c__4l10 |
| 2 | 219671537 | 219675960 | H_c__6j22_M |
| 2 | 219682922 | 219685149 | H_c__245k13_M |
| 2 | 219688542 | 219688707 | H_c__275j18_M |
| 2 | 219748565 | 219749854 | H_c__26h21 |
| 2 | 219850334 | 219851328 | H_c__44b05_M |
| 2 | 219868020 | 219869324 | H_c__163o07_M |
| 2 | 219896414 | 219897461 | H_c__55d05_M |
| 2 | 219908150 | 219909621 | H_c__270n18 |
| 2 | 219918550 | 219920222 | H_c__164j01_M |
| 2 | 219933165 | 219933937 | H_c__46p11_M |
| 2 | 219944360 | 219944971 | H_c__159j11 |
| 2 | 219983851 | 219985706 | H_c__70d10_M |
| 2 | 220048959 | 220049374 | H_c__26f01 |
| 2 | 220077607 | 220079066 | H_c__230d01_M |
| 2 | 220108225 | 220109547 | H_c__29e19_M |
| 2 | 220124894 | 220125947 | H_c__22m05_M |
| 2 | 220174259 | 220175884 | H_c__26e12 |
| 2 | 220204547 | 220205479 | H_c__1c13 |
| 2 | 220231470 | 220234712 | H_c__220g16_M |
| 2 | 220260323 | 220263074 | H_c__145i04 |
| 2 | 220287347 | 220288870 | H_c__97a02 |
| 2 | 220867736 | 220867805 | H_c__8g06 |
| 2 | 220993993 | 220994198 | H_c__208l22 |
| 2 | 221715081 | 221715321 | H_c__39l11 |
| 2 | 221924213 | 221924310 | H_c__245j11 |
| 2 | 22198180 | 22198303 | H_c__206g05 |
| 2 | 222260570 | 222264466 | H_c__149g03_M |
| 2 | 222588813 | 222588893 | H_c__192g14 |
| 2 | 222981090 | 222981707 | H_c__79e24_M |
| 2 | 222986964 | 222988269 | H_c__187g02_M |
| 2 | 222993287 | 222994249 | H_c__121h16 |
| 2 | 222996341 | 222997637 | H_c131c11 |

TABLE 1-continued

| | | | |
|---|---|---|---|
| 2 | 223002246 | 223002918 | H_c_199e17 |
| 2 | 223008388 | 223011158 | H_c_106i24_M |
| 2 | 223114000 | 223115318 | H_c_66c04 |
| 2 | 223345908 | 223346431 | H_c_214m02 |
| 2 | 223360941 | 223362288 | H_c_182h15_M |
| 2 | 223550797 | 223551833 | H_c_274c16 |
| 2 | 223595724 | 223595862 | H_c_258l07 |
| 2 | 224277366 | 224277460 | H_c_139c02 |
| 2 | 224647333 | 224647967 | H_c_92p16_M |
| 2 | 224728810 | 224730319 | H_c135c02__M |
| 2 | 224973225 | 224973476 | H_c_194k01 |
| 2 | 225132093 | 225133032 | H_c_169b11_M |
| 2 | 225197987 | 225198071 | H_c_124c06 |
| 2 | 225275297 | 225275912 | H_c_1c21 |
| 2 | 22562113 | 22562355 | H_c_102o03_M |
| 2 | 225986293 | 225986465 | H_c_22e23 |
| 2 | 226141383 | 226141542 | H_c133i02 |
| 2 | 226212810 | 226213004 | H_c_71n17 |
| 2 | 2266896 | 2268085 | H_c_66b21 |
| 2 | 226988263 | 226988488 | H_c_213h21 |
| 2 | 2271637 | 2272011 | H_c_228o15 |
| 2 | 227481650 | 227482372 | H_c_202f14 |
| 2 | 227486650 | 227490502 | H_c_91i06_M |
| 2 | 227526190 | 227526624 | H_c144k10_M |
| 2 | 227854052 | 227855325 | H_c_7m10_M |
| 2 | 227945621 | 227945725 | H_c_157k07 |
| 2 | 228015320 | 228015920 | H_c_189o16_M |
| 2 | 228162213 | 228165172 | H_c_47g21_M_M |
| 2 | 228318558 | 228318633 | H_c_173i18 |
| 2 | 228561488 | 228562135 | H_c_7e13 |
| 2 | 228747446 | 228747915 | H_c_228m15 |
| 2 | 228871271 | 228872460 | H_c_29o03 |
| 2 | 228960876 | 228960856 | H_c_169a20 |
| 2 | 229772734 | 229773031 | H_c_6i06 |
| 2 | 229940331 | 229940494 | H_c131n06 |
| 2 | 229960716 | 229961960 | H_c_57d09_M |
| 2 | 230255112 | 230255215 | H_c_215p19 |
| 2 | 230578348 | 230578424 | H_c_34f20_M |
| 2 | 230611405 | 230613176 | H_c_176e08_M |
| 2 | 230661912 | 230662035 | H_c_54b21_M |
| 2 | 230757941 | 230759041 | H_c_28j24_M |
| 2 | 231101832 | 231104489 | H_c_205p18 |
| 2 | 231321219 | 231321411 | H_c_163p17 |
| 2 | 231402789 | 231404500 | H_c_68o24 |
| 2 | 231421892 | 231422069 | H_c_226j07 |
| 2 | 231517679 | 231520041 | H_c_72k13_M |
| 2 | 231538183 | 231538617 | H_c_44n07_M |
| 2 | 231554821 | 231555537 | H_c_22h11_M |
| 2 | 231558837 | 231559865 | H_c_145n21 |
| 2 | 231680235 | 231681560 | H_c_149g11_M |
| 2 | 231726874 | 231729130 | H_c_217f17_M |
| 2 | 231742091 | 231743808 | H_c_119p18_M |
| 2 | 231888471 | 231889547 | H_c_258e19_M |
| 2 | 232084876 | 232087227 | H_c_172o19_M |
| 2 | 232101810 | 232102873 | H_c_50p07 |
| 2 | 232153971 | 232155278 | H_c_32m23_M |
| 2 | 232204447 | 232205030 | H_c_261b24_M |
| 2 | 232220030 | 232220963 | H_c_121m09_M |
| 2 | 232293909 | 232296554 | H_c_11k20 |
| 2 | 232352192 | 232353356 | H_c_183i13_M |
| 2 | 232370789 | 232372133 | H_c_125d15 |
| 2 | 232398891 | 232401342 | H_c_9e12_M |
| 2 | 232476317 | 232477179 | H_c_176i01_M |
| 2 | 232605617 | 232605849 | H_c_261i07 |
| 2 | 232651200 | 232652418 | H_c_126h04_M |
| 2 | 233071286 | 233073064 | H_c_82g05 |
| 2 | 233192623 | 233194695 | H_c_45n17_M |
| 2 | 233215908 | 233218637 | H_c_156j12 |
| 2 | 233240339 | 233241900 | H_c_43n18_M |
| 2 | 233295073 | 233296400 | H_c_274h06 |
| 2 | 233323015 | 233324645 | H_c_247o05_M |
| 2 | 233566080 | 233567596 | H_c_189f04 |
| 2 | 233617441 | 233619436 | H_c_210l13 |
| 2 | 233777253 | 233777471 | H_c_239c10 |
| 2 | 233942018 | 233942740 | H_c_64d16_M |
| 2 | 234044888 | 234046422 | H_c_22o08_M |
| 2 | 234086333 | 234088516 | H_c_242b24 |
| 2 | 234463361 | 234463570 | H_c_56e01_M |
| 2 | 234544411 | 234545691 | H_c_7f12_M |
| 2 | 235135983 | 235136759 | H_c_57e10 |
| 2 | 235643318 | 235643960 | H_c_27n03_M |
| 2 | 235703795 | 235704387 | H_c_109b12 |
| 2 | 236059695 | 236059771 | H_c_158o17 |
| 2 | 236184182 | 236185977 | H_c143c21_M |
| 2 | 236250692 | 236250834 | H_c_210e16 |
| 2 | 236275577 | 236275743 | H_c_106a23 |
| 2 | 236359978 | 236362314 | H_c_101p12_M |
| 2 | 236854812 | 236855681 | H_c_66f18_M |
| 2 | 236857703 | 236859028 | H_c_26h13_M |
| 2 | 236862043 | 236864553 | H_c_186o08_M |
| 2 | 236869177 | 236870241 | H_c_35e14_M |
| 2 | 236927837 | 236928668 | H_c_8b24_M |
| 2 | 237153740 | 237153965 | H_c_267i14 |
| 2 | 237197562 | 237198482 | H_c_41g10 |
| 2 | 237258026 | 237258710 | H_c_103f18 |
| 2 | 237738943 | 237739027 | H_c_191m24 |
| 2 | 237776261 | 237776522 | H_c_30f23_M |
| 2 | 237908334 | 237909218 | H_c_23d16 |
| 2 | 238165528 | 238166745 | H_c_123o18 |
| 2 | 238176973 | 238178363 | H_c_90d19_M |
| 2 | 238317380 | 238318972 | H_c_157a05 |
| 2 | 238348000 | 238348255 | H_c_147b19 |
| 2 | 238381815 | 238383766 | H_c_92i16_M |
| 2 | 238548910 | 238550960 | H_c_202g06_M |
| 2 | 238646136 | 238647532 | H_c_56k02_M |
| 2 | 238657079 | 238658615 | H_c_15c07_M |
| 2 | 238751051 | 238752162 | H_c_161j13_M |
| 2 | 238758678 | 238758836 | H_c_27g22 |
| 2 | 238848584 | 238850047 | H_c_223f06_M |
| 2 | 238854027 | 238855063 | H_c_202g15_M |
| 2 | 238929286 | 238933057 | H_c_261j22_M |
| 2 | 238978615 | 238980224 | H_c_163i04 |
| 2 | 239116078 | 239118574 | H_c_226n23_M |
| 2 | 239162458 | 239162617 | H_c_234k10_M |
| 2 | 239537065 | 239537981 | H_c_43d13_M |
| 2 | 240057468 | 240060313 | H_c_149m03_M_M |
| 2 | 24060527 | 24062152 | H_c_225f14_M |
| 2 | 240684415 | 240685616 | H_c_113p19_M |
| 2 | 241034287 | 241035286 | H_c_177f16 |
| 2 | 241179284 | 241181219 | H_c_115h02 |
| 2 | 241216527 | 241217689 | H_c_145d11_M |
| 2 | 241219406 | 241220996 | H_c_77n12_M |
| 2 | 241224762 | 241226954 | H_c_202l03_M |
| 2 | 241245313 | 241246739 | H_c_209i01_M |
| 2 | 241331492 | 241333196 | H_c_185j03_M |
| 2 | 24144121 | 24145517 | H_c_257j24_M |
| 2 | 241478294 | 241480336 | H_c_80f06_M |
| 2 | 241491555 | 241493180 | H_c_275h18_M |
| 2 | 241523663 | 241523880 | H_c_101j05 |
| 2 | 241575218 | 241577144 | H_c_4c20_M |
| 2 | 241657999 | 241659963 | H_c_40k07_M |
| 2 | 241808329 | 241810678 | H_c_29d17_M |
| 2 | 241876548 | 241878066 | H_c_42j22 |
| 2 | 241931432 | 241932435 | H_c_193e21_M |
| 2 | 241974097 | 241976237 | H_c_15d07_M |
| 2 | 24210417 | 24211989 | H_c_215j15_M |
| 2 | 242166864 | 242169045 | H_c_271l17 |
| 2 | 242218062 | 242220525 | H_c_27c16_M |
| 2 | 242269029 | 242270120 | H_c_66a08_M |
| 2 | 242295686 | 242297572 | H_c_154e05_M |
| 2 | 242345777 | 242347241 | H_c_205m16_M |
| 2 | 242360723 | 242362708 | H_c_154p03_M |
| 2 | 242392891 | 242395148 | H_c_3j12_M |
| 2 | 242420648 | 242422196 | H_c_19p17 |
| 2 | 242505369 | 242506649 | H_c_28d09_M |
| 2 | 24257586 | 24258791 | H_c143f15_M |
| 2 | 24494259 | 24495786 | H_c_86i04_M |
| 2 | 24590648 | 24590728 | H_c_232a15 |
| 2 | 24625001 | 24626956 | H_c_7i12_M |
| 2 | 25105585 | 25107083 | H_c_188b15 |
| 2 | 25175351 | 25177171 | H_c_23p15_M |
| 2 | 25265633 | 25267173 | H_c_224n13 |
| 2 | 25295484 | 25296595 | H_c_248a11 |
| 2 | 25349722 | 25351140 | H_c_4l16 |
| 2 | 25386274 | 25388640 | H_c_157j04 |
| 2 | 253916 | 255441 | H_c_250e06 |
| 2 | 25445341 | 25446270 | H_c_97c15 |
| 2 | 25496311 | 25496915 | H_c_231c19 |
| 2 | 25510613 | 25511659 | H_c_66e05_M |
| 2 | 25807351 | 25808949 | H_c_98a01_M |

TABLE 1-continued

| | | | |
|---|---|---|---|
| 2 | 26011901 | 26013464 | H_c_222f20 |
| 2 | 26071416 | 26071559 | H_c_265i21 |
| 2 | 26114481 | 26117316 | H_c_66l12 |
| 2 | 26168091 | 26169493 | H_c_30h07_M |
| 2 | 26318573 | 26320083 | H_c_25e13_M |
| 2 | 26479939 | 26481078 | H_c_205a11_M |
| 2 | 26514934 | 26515208 | H_c_35j05 |
| 2 | 26528098 | 26528230 | H_c_19a02 |
| 2 | 26897950 | 26899192 | H_c_6m19_M |
| 2 | 26919863 | 26921203 | H_c_88o18_M |
| 2 | 26981008 | 26981622 | H_c_122p16_M |
| 2 | 26981830 | 26984662 | H_c_208e11_M |
| 2 | 27043989 | 27044083 | H_c_120m23_M |
| 2 | 27104336 | 27105953 | H_c_57o01_M |
| 2 | 27166813 | 27168061 | H_c_90e14_M |
| 2 | 27184228 | 27187165 | H_c_70e11_M |
| 2 | 27205515 | 27207619 | H_c_52c13_M |
| 2 | 27220041 | 27221423 | H_c_191d19_M |
| 2 | 27226311 | 27227287 | H_c_105m07 |
| 2 | 27268619 | 27269380 | H_c_232p20_M |
| 2 | 27351695 | 27352582 | H_c139n09_M |
| 2 | 27397675 | 27400013 | H_c_73b21_M |
| 2 | 27421526 | 27421635 | H_c_206b09 |
| 2 | 27441940 | 27443977 | H_c_121i19_M |
| 2 | 27490778 | 27492312 | H_c_71a02_M |
| 2 | 27504158 | 27505972 | H_c_28c10_M |
| 2 | 27514589 | 27515785 | H_c_81b08_M |
| 2 | 27543412 | 27544400 | H_c_151i22_M |
| 2 | 27562712 | 27564905 | H_c_172h01_M |
| 2 | 27574875 | 27577444 | H_c_68k04_M |
| 2 | 27624062 | 27624522 | H_c_6n10 |
| 2 | 27629064 | 27630073 | H_c_182h01 |
| 2 | 277455 | 280521 | H_c_114i03_M |
| 2 | 27899330 | 27900710 | H_c_26m01 |
| 2 | 27905883 | 27906716 | H_c_268a06_M |
| 2 | 28024051 | 28025430 | H_c_55f24 |
| 2 | 28133546 | 28133714 | H_c_179e15 |
| 2 | 28357738 | 28358014 | H_c_150p15 |
| 2 | 28524166 | 28527866 | H_c_182m23_M |
| 2 | 28565974 | 28567235 | H_c_39e22_M |
| 2 | 28701278 | 28701668 | H_c_27l24_M |
| 2 | 28885750 | 28887183 | H_c_191o02_M |
| 2 | 2894144 | 2894369 | H_c_187a07 |
| 2 | 28944842 | 28945933 | H_c_254j23_M |
| 2 | 29004290 | 29005123 | H_c_192a13_M |
| 2 | 29028982 | 29029980 | H_c_237n21_M |
| 2 | 29249670 | 29250598 | H_c_97i15_M |
| 2 | 30004489 | 30004599 | H_c_68h06 |
| 2 | 30055613 | 30056473 | H_c_99a04_M |
| 2 | 30280693 | 30281068 | H_c_105e03 |
| 2 | 30365483 | 30367669 | H_c139m09_M |
| 2 | 30428352 | 30428518 | H_c144k17 |
| 2 | 30480857 | 30481642 | H_c_230e08_M |
| 2 | 30581616 | 30582310 | H_c_39a20_M |
| 2 | 30665232 | 30665483 | H_c_128p17 |
| 2 | 30827967 | 30828088 | H_c_185c09 |
| 2 | 3115948 | 3117041 | H_c_56l15_M |
| 2 | 31272313 | 31273556 | H_c_39h22_M |
| 2 | 3135553 | 3136809 | H_c_247f03 |
| 2 | 31368644 | 31368816 | H_c_87b03_M |
| 2 | 31389150 | 31389337 | H_c_6d02 |
| 2 | 31642619 | 31642736 | H_c_99h02 |
| 2 | 31716993 | 31719152 | H_c_49i15_M |
| 2 | 31940010 | 31941387 | H_c_183a04_M |
| 2 | 32147545 | 32148624 | H_c_194d10 |
| 2 | 32176477 | 32176960 | H_c_264d06_M |
| 2 | 32199917 | 32201136 | H_c_28e11_M |
| 2 | 32302385 | 32302905 | H_c_259e23 |
| 2 | 3243740 | 3245814 | H_c_121o08_M |
| 2 | 32493237 | 32495191 | H_c_147m23_M |
| 2 | 32764535 | 32765340 | H_c_6h22 |
| 2 | 32873397 | 32873672 | H_c_174e11 |
| 2 | 33083021 | 33083642 | H_c_247e19 |
| 2 | 33099446 | 33099571 | H_c_70e04 |
| 2 | 33317357 | 33317488 | H_c_218i10 |
| 2 | 33735550 | 33736353 | H_c_121m11 |
| 2 | 33897877 | 33898977 | H_c_8m08 |
| 2 | 34530435 | 34530659 | H_c_209j12 |
| 2 | 34539476 | 34539566 | H_c_186d14 |
| 2 | 34841928 | 34842061 | H_c_39h10 |
| 2 | 35166 | 36934 | H_c_98b21_M |
| 2 | 35326429 | 35326743 | H_c133l13 |
| 2 | 35848511 | 35848653 | H_c_259l10 |
| 2 | 36449005 | 36449188 | H_c_38g17 |
| 2 | 36736502 | 36737125 | H_c132g12_M |
| 2 | 37104769 | 37105722 | H_c_89k03_M |
| 2 | 37222462 | 37223705 | H_c_79f17 |
| 2 | 37295154 | 37296572 | H_c_72j13_M |
| 2 | 37369785 | 37370804 | H_c_86o10 |
| 2 | 37381426 | 37381599 | H_c_116k16 |
| 2 | 37462878 | 37464184 | H_c144a19_M |
| 2 | 37483046 | 37484157 | H_c_145l07_M |
| 2 | 37657416 | 37657480 | H_c_250d21 |
| 2 | 37757286 | 37757509 | H_c_1i05 |
| 2 | 37809776 | 37811383 | H_c_66b04_M |
| 2 | 38063754 | 38064746 | H_c_213j05_M |
| 2 | 38212833 | 38216276 | H_c_27e23_M |
| 2 | 38215438 | 38216278 | H_c_74h06 |
| 2 | 38514963 | 38516065 | H_c131k14_M |
| 2 | 38654408 | 38654566 | H_c_16b19 |
| 2 | 38674737 | 38675258 | H_c_186l13 |
| 2 | 38889186 | 38890475 | H_c_6g21_M |
| 2 | 39098101 | 39099756 | H_c143h08_M |
| 2 | 39258600 | 39260368 | H_c_73p20 |
| 2 | 39382356 | 39384098 | H_c_256j14_M |
| 2 | 39575506 | 39576982 | H_c_151c19_M |
| 2 | 39620552 | 39620644 | H_c_118c03 |
| 2 | 39696943 | 39697023 | H_c133j21 |
| 2 | 39804385 | 39805942 | H_c_219i09 |
| 2 | 39917672 | 39918359 | H_c_176k15 |
| 2 | 40114103 | 40114228 | H_c_213p07 |
| 2 | 40171394 | 40171729 | H_c_99f11 |
| 2 | 40257787 | 40257908 | H_c_43o02 |
| 2 | 40270388 | 40270719 | H_c_214c03 |
| 2 | 40590774 | 40591366 | H_c_207b12 |
| 2 | 40776872 | 40776967 | H_c_74o19 |
| 2 | 40916621 | 40916754 | H_c_170n13 |
| 2 | 41268976 | 41269163 | H_c_66m07 |
| 2 | 41663635 | 41663836 | H_c_49a11 |
| 2 | 41715165 | 41715395 | H_c_50d15 |
| 2 | 42098253 | 42098438 | H_c_163b21 |
| 2 | 42185576 | 42187533 | H_c_38m23_M |
| 2 | 42238957 | 42240781 | H_c_204k16_M |
| 2 | 42500106 | 42500505 | H_c_93o14 |
| 2 | 42678710 | 42678837 | H_c_160e19 |
| 2 | 42706546 | 42708557 | H_c_41e07_M |
| 2 | 42795306 | 42795372 | H_c_61o04 |
| 2 | 42948567 | 42950245 | H_c_28e20_M |
| 2 | 43113428 | 43116301 | H_c_188l11 |
| 2 | 43222773 | 43222981 | H_c_186p07 |
| 2 | 43239782 | 43240298 | H_c_120g11 |
| 2 | 43364285 | 43365799 | H_c_177h12_M |
| 2 | 43734554 | 43734961 | H_c_5a05_M |
| 2 | 43775749 | 43776557 | H_c_224a08_M |
| 2 | 43845083 | 43845227 | H_c_175e23 |
| 2 | 44134415 | 44135399 | H_c_76f21_M |
| 2 | 44306442 | 44308526 | H_c_107e08 |
| 2 | 44499740 | 44501495 | H_c_12d16_M |
| 2 | 44941262 | 44942373 | H_c_63e03_M |
| 2 | 45067372 | 45068879 | H_c_12j19 |
| 2 | 45073095 | 45074354 | H_c138c07_M |
| 2 | 45077026 | 45083751 | H_c_196a11_M_M |
| 2 | 45139144 | 45140801 | H_c_121e18_M |
| 2 | 45143492 | 45144191 | H_c_86m01 |
| 2 | 45146183 | 45148241 | H_c_6h02_M |
| 2 | 45148242 | 45149152 | H_c_119g01_M |
| 2 | 45151198 | 45153902 | H_c_101i05_M |
| 2 | 45307569 | 45309273 | H_c_192g23_M |
| 2 | 45718157 | 45718260 | H_c135a11 |
| 2 | 45749930 | 45750287 | H_c_70n16 |
| 2 | 457938 | 459066 | H_c_110l16_M |
| 2 | 45865340 | 45865523 | H_c_190c13 |
| 2 | 46435273 | 46438680 | H_c_85c14_M_M |
| 2 | 46458385 | 46458531 | H_c_168h08 |
| 2 | 46680994 | 46683292 | H_c_204c01 |
| 2 | 46755108 | 46756088 | H_c_77e07_M |
| 2 | 46836959 | 46838726 | H_c_85i06_M |
| 2 | 46894612 | 46894694 | H_c_31b06 |
| 2 | 47054376 | 47055256 | H_c_207j15_M |
| 2 | 47148259 | 47148507 | H_c_74p22_M |

TABLE 1-continued

| | | | |
|---|---|---|---|
| 2 | 47314378 | 47315522 | H_c139h17_M |
| 2 | 47507799 | 47509070 | H_c_149l24 |
| 2 | 47541510 | 47542450 | H_c_43e08_M |
| 2 | 47659608 | 47660656 | H_c_204g05_M |
| 2 | 47707347 | 47710094 | H_c_244d06 |
| 2 | 47710096 | 47711639 | H_c_148k05_M |
| 2 | 47781672 | 47781912 | H_c_88m05 |
| 2 | 47815536 | 47815730 | H_c_26e08 |
| 2 | 47922846 | 47923164 | H_c_29l16_M |
| 2 | 48043615 | 48045185 | H_c_259e22_M |
| 2 | 48052601 | 48052801 | H_c_180n07 |
| 2 | 48250020 | 48251225 | H_c_245p22_M |
| 2 | 4845257 | 4845959 | H_c_203i20 |
| 2 | 48452884 | 48454500 | H_c_52a03_M |
| 2 | 48578830 | 48580222 | H_c_249h15_M |
| 2 | 48627975 | 48628066 | H_c_244h04 |
| 2 | 48667799 | 48669592 | H_c_243c03_M |
| 2 | 48779630 | 48779711 | H_c_245e15 |
| 2 | 48893334 | 48894733 | H_c_57e15 |
| 2 | 49123985 | 49124099 | H_c_67d13 |
| 2 | 4919537 | 4922309 | H_c_89p08_M |
| 2 | 49336415 | 49336595 | H_c_3e08 |
| 2 | 5005181 | 5005254 | H_c_186c19 |
| 2 | 50484901 | 50486828 | H_c_122i03_M |
| 2 | 5060400 | 5061893 | H_c_52d05_M |
| 2 | 50625922 | 50626086 | H_c_49g04 |
| 2 | 50771221 | 50771392 | H_c_215j07 |
| 2 | 50795105 | 50795264 | H_c_196c17 |
| 2 | 51170609 | 51171390 | H_c_167l07 |
| 2 | 51310214 | 51310421 | H_c_5n09 |
| 2 | 51713562 | 51713639 | H_c_9b08 |
| 2 | 51726646 | 51726798 | H_c_16b04 |
| 2 | 51997257 | 51997422 | H_c142m16 |
| 2 | 52002704 | 52002775 | H_c_199h03_M |
| 2 | 52083953 | 52084118 | H_c_209l22 |
| 2 | 52762692 | 52762847 | H_c_122m10 |
| 2 | 52841763 | 52841843 | H_c_58j02 |
| 2 | 53071885 | 53071970 | H_c_178j10 |
| 2 | 53491856 | 53491970 | H_c_231b14 |
| 2 | 53664618 | 53664806 | H_c_40c09 |
| 2 | 53857458 | 53857551 | H_c140m05 |
| 2 | 53925300 | 53926496 | H_c_45k03_M |
| 2 | 54051882 | 54051964 | H_c_65o17 |
| 2 | 54108817 | 54110231 | H_c_154e22_M |
| 2 | 54254194 | 54254876 | H_c_34l24_M |
| 2 | 54469251 | 54469902 | H_c_154g01_M |
| 2 | 54594646 | 54596869 | H_c_245f04_M |
| 2 | 54637908 | 54638016 | H_c_215l05_M |
| 2 | 54696324 | 54697218 | H_c_73b23_M |
| 2 | 54810400 | 54810488 | H_c140k04 |
| 2 | 54861912 | 54864279 | H_c_102k09_M |
| 2 | 55187307 | 55189798 | H_c_86j12_M |
| 2 | 55362073 | 55362887 | H_c_62m04 |
| 2 | 55420512 | 55421503 | H_c_76i13_M |
| 2 | 55514780 | 55514877 | H_c_72m07 |
| 2 | 55558293 | 55559296 | H_c_5e16_M |
| 2 | 55755715 | 55756900 | H_c_167b21_M |
| 2 | 56062194 | 56063006 | H_c_144c08 |
| 2 | 56322303 | 56324328 | H_c_3i14_M |
| 2 | 57060526 | 57060607 | H_c131l15 |
| 2 | 57394883 | 57394996 | H_c_8g21 |
| 2 | 57523388 | 57523542 | H_c_93l20 |
| 2 | 5763586 | 5764400 | H_c_104i15_M |
| 2 | 57680844 | 57680937 | H_c_223b06 |
| 2 | 57740521 | 57740743 | H_c_18c16 |
| 2 | 57817712 | 57817925 | H_c137f05 |
| 2 | 5782417 | 5784976 | H_c_109i05_M |
| 2 | 57953448 | 57953556 | H_c_274i03_M |
| 2 | 57974498 | 57974745 | H_c_95e02 |
| 2 | 57994193 | 57994407 | H_c_89o20 |
| 2 | 58185138 | 58186102 | H_c134b24_M |
| 2 | 58379693 | 58380516 | H_c_261a04_M |
| 2 | 58560483 | 58560660 | H_c_64i04 |
| 2 | 58720622 | 58720696 | H_c_232d11 |
| 2 | 59288189 | 59288386 | H_c_150p20 |
| 2 | 59919202 | 59919295 | H_c136b07 |
| 2 | 60483898 | 60484094 | H_c_187l12 |
| 2 | 60688181 | 60693872 | H_c_87o19_M_M |
| 2 | 60720072 | 60721104 | H_c_151j11_M |
| 2 | 60874286 | 60874717 | H_c_16a21_M |
| 2 | 60894785 | 60895918 | H_c_224o17 |
| 2 | 61019649 | 61019994 | H_c_29j16_M |
| 2 | 61065612 | 61065681 | H_c_54o15 |
| 2 | 61204345 | 61205586 | H_c_167j11_M |
| 2 | 61315566 | 61317521 | H_c_54i05 |
| 2 | 61592903 | 61594429 | H_c_100p01 |
| 2 | 61608980 | 61610501 | H_c_86p06_M |
| 2 | 61902519 | 61904002 | H_c_264l13_M |
| 2 | 62026412 | 62027612 | H_c_44c08_M |
| 2 | 62183415 | 62183511 | H_c_25c17 |
| 2 | 62595297 | 62596525 | H_c_225b11 |
| 2 | 626348 | 627137 | H_c_163i07_M |
| 2 | 62709764 | 62710334 | H_c_238b22 |
| 2 | 62843631 | 62845280 | H_c_116i23_M |
| 2 | 63007429 | 63007569 | H_c_71g21 |
| 2 | 63186052 | 63195389 | H_c_187d09_M_M |
| 2 | 63197565 | 63199088 | H_c_98p07_M |
| 2 | 63726978 | 63728086 | H_c135b12_M |
| 2 | 63978949 | 63980656 | H_c_221m07_M |
| 2 | 64282349 | 64283745 | H_c_205h15_M |
| 2 | 64580098 | 64580270 | H_c_22o09 |
| 2 | 64592981 | 64593935 | H_c_231k10 |
| 2 | 64662811 | 64664044 | H_c_67j13_M |
| 2 | 64701512 | 64701622 | H_c_71o08 |
| 2 | 64747353 | 64748760 | H_c_13i03_M |
| 2 | 64792024 | 64793593 | H_c_7b12 |
| 2 | 64889407 | 64889932 | H_c140i11_M |
| 2 | 64906455 | 64907310 | H_c_132d11 |
| 2 | 64997744 | 64999807 | H_c_206b20 |
| 2 | 65077734 | 65078753 | H_c_81h17 |
| 2 | 65194282 | 65196088 | H_c_49a09_M |
| 2 | 65366359 | 65367203 | H_c_212c02_M |
| 2 | 65569273 | 65571671 | H_c_100c11_M |
| 2 | 65574347 | 65575560 | H_c_123j07_M |
| 2 | 66564178 | 66565946 | H_c_83i19_M |
| 2 | 66572649 | 66573685 | H_c_192l15 |
| 2 | 66584408 | 66584627 | H_c_170n16 |
| 2 | 666023 | 667605 | H_c_183e19_M |
| 2 | 66714477 | 66715733 | H_c_208a14_M |
| 2 | 66720657 | 66721037 | H_c_124f21 |
| 2 | 66894940 | 66895051 | H_c_66a06 |
| 2 | 66971548 | 66971863 | H_c132p01 |
| 2 | 67536057 | 67536826 | H_c_89a03 |
| 2 | 68201697 | 68201871 | H_c_86m14_M |
| 2 | 68295883 | 68296703 | H_c_53k09 |
| 2 | 68314523 | 68314646 | H_c_178h24 |
| 2 | 68390200 | 68392117 | H_c_195o20_M |
| 2 | 68458029 | 68458826 | H_c_212f08_M |
| 2 | 68605417 | 68606763 | H_c_245c17_M |
| 2 | 6863951 | 6864169 | H_c_76a02 |
| 2 | 69152042 | 69152835 | H_c_28c16_M |
| 2 | 69176105 | 69176217 | H_c_99p18 |
| 2 | 69302451 | 69302645 | H_c137l08 |
| 2 | 69374545 | 69374659 | H_c_212f24 |
| 2 | 69390142 | 69390314 | H_c_211e12 |
| 2 | 69437941 | 69438201 | H_c_101b17 |
| 2 | 69445210 | 69446453 | H_c_36g20_M |
| 2 | 69525417 | 69526745 | H_c_11a15_M |
| 2 | 6955585 | 6957420 | H_c_161k11 |
| 2 | 69707611 | 69707718 | H_c_104m03 |
| 2 | 69781631 | 69782910 | H_c141f13_M |
| 2 | 69841869 | 69842031 | H_c_109d10 |
| 2 | 69880004 | 69881176 | H_c_66o17_M |
| 2 | 70053029 | 70054607 | H_c_206o18 |
| 2 | 7007581 | 7009209 | H_c_182i21_M |
| 2 | 7014898 | 7016131 | H_c_190n24 |
| 2 | 70226124 | 70226633 | H_c_129a05 |
| 2 | 70329213 | 70330243 | H_c_218c08 |
| 2 | 70395903 | 70397453 | H_c_216k09_M |
| 2 | 70432039 | 70433182 | H_c_75d13 |
| 2 | 70439917 | 70441064 | H_c_244i19_M |
| 2 | 70691572 | 70693288 | H_c_165o03_M |
| 2 | 70905921 | 70906757 | H_c_109k01_M |
| 2 | 70928877 | 70929724 | H_c_34k03 |
| 2 | 71026144 | 71028256 | H_c_251c07_M |
| 2 | 71039820 | 71041187 | H_c142f16_M |
| 2 | 71117076 | 71118233 | H_c_251e07_M |
| 2 | 71132245 | 71134195 | H_c_27j18_M |
| 2 | 71206373 | 71208374 | H_c_40a14_M |
| 2 | 71268376 | 71269701 | H_c_56c08_M |

TABLE 1-continued

| | | | |
|---|---|---|---|
| 2 | 71305954 | 71306149 | H_c_274h08 |
| 2 | 71364983 | 71365767 | H_c_39k22_M |
| 2 | 71415102 | 71415995 | H_c_110m02_M |
| 2 | 71470325 | 71471434 | H_c_35f08_M |
| 2 | 71592628 | 71595492 | H_c_130n23 |
| 2 | 71604288 | 71606192 | H_c_169i13 |
| 2 | 7188007 | 7188183 | H_c_214j20_M |
| 2 | 72057147 | 72057225 | H_c_245f07 |
| 2 | 72198450 | 72198531 | H_c_80l03 |
| 2 | 72260943 | 72261191 | H_c_184e02 |
| 2 | 72281714 | 72283860 | H_c_54b23_M |
| 2 | 72285937 | 72287535 | H_c_65b13 |
| 2 | 72629600 | 72629710 | H_c_89g07 |
| 2 | 72827594 | 72827674 | H_c_68c11 |
| 2 | 72963872 | 72964983 | H_c_120k08_M |
| 2 | 73025658 | 73026584 | H_c_165n17 |
| 2 | 73054943 | 73055498 | H_c_274l13_M |
| 2 | 73058657 | 73059397 | H_c_80g11_M |
| 2 | 73062827 | 73063828 | H_c_213e17 |
| 2 | 73251029 | 73252421 | H_c_42c19 |
| 2 | 73313367 | 73315209 | H_c_128b10_M |
| 2 | 73315214 | 73316615 | H_c_266b21 |
| 2 | 73341328 | 73342415 | H_c_66h06_M |
| 2 | 73353020 | 73353773 | H_c_85d15_M |
| 2 | 73371214 | 73372184 | H_c_98h09_M |
| 2 | 73372939 | 73373696 | H_c_9l03_M |
| 2 | 73407099 | 73408749 | H_c_30p01_M |
| 2 | 73422770 | 73423822 | H_c_268k22_M |
| 2 | 73524241 | 73525641 | H_c_46d11_M |
| 2 | 73918401 | 73919232 | H_c_244l16_M |
| 2 | 73967530 | 73968266 | H_c_166o06 |
| 2 | 74065418 | 74066187 | H_c_186h17_M |
| 2 | 7407308 | 7407451 | H_c_55a20_M |
| 2 | 74122743 | 74125614 | H_c_268k14 |
| 2 | 74140884 | 74142046 | H_c_226h16 |
| 2 | 74157227 | 74157382 | H_c_8g07_M |
| 2 | 74258884 | 74259577 | H_c_20a23 |
| 2 | 74286069 | 74287458 | H_c_194k14_M |
| 2 | 74317083 | 74317929 | H_c_73k09_M |
| 2 | 74529962 | 74530947 | H_c_73b13_M |
| 2 | 74560011 | 74561425 | H_c_253i22_M |
| 2 | 74593495 | 74594570 | H_c_267c14 |
| 2 | 74603361 | 74604213 | H_c133j16_M |
| 2 | 74610854 | 74611292 | H_c_90k16 |
| 2 | 74636389 | 74638276 | H_c_239e14_M |
| 2 | 74640965 | 74642247 | H_c_107h03 |
| 2 | 74646633 | 74647066 | H_c_113m19_M |
| 2 | 74653318 | 74655712 | H_c_149e07 |
| 2 | 74687487 | 74689431 | H_c_209d17_M |
| 2 | 74786370 | 74787380 | H_c_27m12_M |
| 2 | 74792729 | 74793919 | H_c_29k24_M |
| 2 | 74811853 | 74812024 | H_c_52d13 |
| 2 | 74854119 | 74854656 | H_c_149l15_M |
| 2 | 74971955 | 74974054 | H_c_24e20_M |
| 2 | 75096803 | 75097837 | H_c_210g20_M |
| 2 | 75181291 | 75181623 | H_c_186d02 |
| 2 | 75337085 | 75339689 | H_c_169b03_M |
| 2 | 75442561 | 75442648 | H_c_27e17 |
| 2 | 75698702 | 75700141 | H_c_245c14 |
| 2 | 75747539 | 75748273 | H_c_67b22 |
| 2 | 75785222 | 75786216 | H_c_128g03_M |
| 2 | 75849019 | 75850062 | H_c_229a21_M |
| 2 | 76470594 | 76470728 | H_c_174a04 |
| 2 | 77058884 | 77058963 | H_c_1o01 |
| 2 | 77203845 | 77203918 | H_c_110m03 |
| 2 | 77501569 | 77501682 | H_c136h08 |
| 2 | 7880085 | 7880163 | H_c_2h16 |
| 2 | 78939621 | 78939762 | H_c_145i11 |
| 2 | 79324567 | 79324675 | H_c_69l04 |
| 2 | 79651185 | 79652391 | H_c_116k18_M |
| 2 | 80440912 | 80441974 | H_c_4m06_M |
| 2 | 80461255 | 80461770 | H_c_109a03 |
| 2 | 8069101 | 8070207 | H_c_20b01 |
| 2 | 81008458 | 81008614 | H_c_26f19 |
| 2 | 81413927 | 81414095 | H_c_145h22_M |
| 2 | 81581794 | 81581915 | H_c_2m02 |
| 2 | 82269492 | 82269592 | H_c_259e17 |
| 2 | 8338674 | 8339906 | H_c_19c03 |
| 2 | 83821109 | 83821322 | H_c_185d22_M |
| 2 | 84146372 | 84146513 | H_c_175f20 |
| 2 | 84375951 | 84376031 | H_c_63j19 |
| 2 | 84597141 | 84598256 | H_c_109p07 |
| 2 | 8481102 | 8482569 | H_c_212i14 |
| 2 | 85019337 | 85020209 | H_c_3b16_M |
| 2 | 85043723 | 85044794 | H_c_82g21 |
| 2 | 85064462 | 85065124 | H_c_92n11 |
| 2 | 85109180 | 85109312 | H_c_108p04 |
| 2 | 85155290 | 85155418 | H_c_123g16 |
| 2 | 85271229 | 85273133 | H_c_164c01_M |
| 2 | 85331806 | 85332101 | H_c_189d17 |
| 2 | 85576083 | 85576908 | H_c_247g12_M |
| 2 | 85657824 | 85658068 | H_c_275c14 |
| 2 | 85677292 | 85678894 | H_c_123h15_M |
| 2 | 85733762 | 85734409 | H_c_38p20 |
| 2 | 85741479 | 85741716 | H_c_129d12_M |
| 2 | 85750251 | 85751367 | H_c_82f21 |
| 2 | 85754117 | 85755881 | H_c_37h14_M |
| 2 | 8585313 | 8585715 | H_c_163d05 |
| 2 | 85892588 | 85893816 | H_c_83o19_M |
| 2 | 8589678 | 8589773 | H_c_64o19 |
| 2 | 85918516 | 85919874 | H_c_181n22 |
| 2 | 86014446 | 86014774 | H_c_190h18 |
| 2 | 86027295 | 86028075 | H_c_106d04_M |
| 2 | 86244623 | 86245246 | H_c_151c03_M |
| 2 | 86333713 | 86334540 | H_c_98n23_M |
| 2 | 86476157 | 86476889 | H_c_33e07_M |
| 2 | 8657151 | 8657459 | H_c_72c11 |
| 2 | 86579926 | 86581223 | H_c_150j14_M |
| 2 | 8674155 | 8674826 | H_c_83d18_M |
| 2 | 86927613 | 86928857 | H_c_94f10_M |
| 2 | 8769479 | 8770242 | H_c_145e06_M |
| 2 | 8775617 | 8776940 | H_c_65k12_M |
| 2 | 8827812 | 8828045 | H_c_2l06 |
| 2 | 88308639 | 88310293 | H_c_57l11_M |
| 2 | 88590104 | 88591723 | H_c_198l10_M |
| 2 | 88765143 | 88766640 | H_c_51l12_M |
| 2 | 88829764 | 88830932 | H_c_62i09_M |
| 2 | 89078257 | 89078350 | H_c_192i15 |
| 2 | 8927726 | 8928519 | H_c_197l13_M |
| 2 | 89446084 | 89446243 | H_c_66k01 |
| 2 | 89803848 | 89804073 | H_c_170l21 |
| 2 | 9093730 | 9095441 | H_c_204b06_M |
| 2 | 91092009 | 91093523 | H_c_204l03 |
| 2 | 91743610 | 91744447 | H_c_235l18 |
| 2 | 935609 | 937350 | H_c_240g16_M |
| 2 | 9387592 | 9388337 | H_c_251n02 |
| 2 | 9428726 | 9430210 | H_c_152c13_M |
| 2 | 94948945 | 94949965 | H_c_162h15 |
| 2 | 94984258 | 94986975 | H_c_60c05 |
| 2 | 95017047 | 95017142 | H_c_5l04 |
| 2 | 95085737 | 95087173 | H_c_195i05 |
| 2 | 95113301 | 95113913 | H_c140n14_M |
| 2 | 95124221 | 95125438 | H_c_234n03 |
| 2 | 95246105 | 95248266 | H_c_6m15_M |
| 2 | 95253322 | 95253712 | H_c_83f11_M |
| 2 | 95294735 | 95295276 | H_c_274a06_M |
| 2 | 95316053 | 95316165 | H_c_215m24 |
| 2 | 95432975 | 95433783 | H_c_259o07 |
| 2 | 9564656 | 9566556 | H_c_87h14_M |
| 2 | 96201409 | 96204846 | H_c_194h15_M |
| 2 | 96287772 | 96287993 | H_c_46c01 |
| 2 | 96295657 | 96296737 | H_c_119e21 |
| 2 | 96300373 | 96301552 | H_c_2d08_M |
| 2 | 96338543 | 96338833 | H_c_187j02 |
| 2 | 96346624 | 96347170 | H_c_213a22 |
| 2 | 96352726 | 96355200 | H_c_199h09_M |
| 2 | 96392621 | 96393602 | H_c_258f16 |
| 2 | 96409233 | 96410408 | H_c139g11_M |
| 2 | 96423038 | 96423786 | H_c_83h21_M |
| 2 | 9646884 | 9647357 | H_c_68g14 |
| 2 | 965479 | 965574 | H_c_118m22 |
| 2 | 96725350 | 96726300 | H_c_130b24_M |
| 2 | 96848395 | 96850419 | H_c_197j06 |
| 2 | 96926845 | 96927870 | H_c_192k09_M |
| 2 | 96945053 | 96946707 | H_c_213h11_M |
| 2 | 97738294 | 97739217 | H_c_55f11_M |
| 2 | 98070082 | 98071702 | H_c_9j22_M |
| 2 | 98161852 | 98162513 | H_c_91l09_M |
| 2 | 98259382 | 98260307 | H_c_272m21_M |
| 2 | 98404328 | 98404494 | H_c_199h24 |

TABLE 1-continued

| | | | |
|---|---|---|---|
| 2 | 98421110 | 98422184 | H_c_128g15 |
| 2 | 98683190 | 98683764 | H_c_146g06_M |
| 2 | 98777760 | 98777852 | H_c_115g02 |
| 2 | 98896606 | 98898638 | H_c_33j06_M |
| 2 | 99041645 | 99041751 | H_c_120p24 |
| 2 | 99066412 | 99066592 | H_c_216a09 |
| 2 | 99215540 | 99216633 | H_c_171g15_M |
| 2 | 99232559 | 99232655 | H_c_69e21 |
| 2 | 9925627 | 9926037 | H_c_66f12 |
| 2 | 9933842 | 9934548 | H_c144d20_M |
| 2 | 99411765 | 99413072 | H_c_32d01 |
| 2 | 99564009 | 99566236 | H_c_106p06_M |
| 2 | 99866601 | 99866822 | H_c_237c15 |
| 3 | 100102323 | 100103742 | H_c_202p02_M |
| 3 | 101019258 | 101019733 | H_c_275g09_M |
| 3 | 101077527 | 101078364 | H_c_21j02_M |
| 3 | 101117031 | 101117128 | H_c_117a06 |
| 3 | 10132064 | 10133233 | H_c_22p14_M |
| 3 | 101462185 | 101463324 | H_c_81h10_M |
| 3 | 101578873 | 101579102 | H_c_182o07 |
| 3 | 101601852 | 101602729 | H_c_39d17_M |
| 3 | 101693840 | 101694281 | H_c_249f01_M |
| 3 | 10181327 | 10182179 | H_c_162l08_M |
| 3 | 101883344 | 101884530 | H_c_200c16_M |
| 3 | 101910708 | 101911742 | H_c_33g11_M |
| 3 | 10264903 | 10266289 | H_c_1m04_M |
| 3 | 102877538 | 102878839 | H_c_251k14 |
| 3 | 102925903 | 102927302 | H_c_105a04_M |
| 3 | 102980047 | 102981609 | H_c_151d07_M |
| 3 | 103047000 | 103047197 | H_c_4o01 |
| 3 | 103050531 | 103051019 | H_c_22b13_M |
| 3 | 103216543 | 103216645 | H_c_62o13 |
| 3 | 103365385 | 103365695 | H_c_227e03 |
| 3 | 103369227 | 103369350 | H_c_185c21 |
| 3 | 10337304 | 10338074 | H_c_82n05 |
| 3 | 103767533 | 103767629 | H_c_199c22 |
| 3 | 10431830 | 10431962 | H_c_163o24 |
| 3 | 105463820 | 105463982 | H_c_159d21 |
| 3 | 106088958 | 106089163 | H_c_167m24 |
| 3 | 106570815 | 106571245 | H_c_200g12_M |
| 3 | 107070136 | 107071478 | H_c_188e07 |
| 3 | 107086352 | 107086568 | H_c_191l12_M |
| 3 | 107181409 | 107181521 | H_c_145m13 |
| 3 | 10723413 | 10725505 | H_c_80g12_M |
| 3 | 10759331 | 10761107 | H_c_146e19 |
| 3 | 10832349 | 10833754 | H_c_148o07 |
| 3 | 108370329 | 108370428 | H_c_169l17 |
| 3 | 108632268 | 108633708 | H_c_234b20_M |
| 3 | 108723880 | 108727130 | H_c141o12_M |
| 3 | 108902981 | 108903926 | H_c_174g13 |
| 3 | 108923999 | 108924212 | H_c_268l14_M |
| 3 | 109129311 | 109129934 | H_c_80b02 |
| 3 | 109292089 | 109293306 | H_c_94b10 |
| 3 | 109315086 | 109315361 | H_c_225l22 |
| 3 | 109642751 | 109642862 | H_c_183d09_M |
| 3 | 109690018 | 109690162 | H_c138a17 |
| 3 | 109790446 | 109791444 | H_c_57h24 |
| 3 | 110196880 | 110196957 | H_c131p22 |
| 3 | 110548741 | 110548874 | H_c_169g16 |
| 3 | 110600368 | 110600733 | H_c_224d13 |
| 3 | 110920369 | 110920467 | H_c_256d01 |
| 3 | 111225962 | 111226051 | H_c_151k08 |
| 3 | 111251029 | 111251164 | H_c_249e13 |
| 3 | 111446013 | 111446202 | H_c_58n14 |
| 3 | 111513015 | 111513146 | H_c_90l16 |
| 3 | 112273056 | 112274045 | H_c_63k06_M |
| 3 | 112686949 | 112690748 | H_c_246n16_M |
| 3 | 112773022 | 112773125 | H_c_118p07 |
| 3 | 11288845 | 11289554 | H_c_199o09 |
| 3 | 113060777 | 113061856 | H_c_111i03_M |
| 3 | 11315548 | 11315857 | H_c_90h12 |
| 3 | 113206297 | 113206671 | H_c_108e07 |
| 3 | 113287006 | 113288388 | H_c_40f16 |
| 3 | 113317895 | 113318125 | H_c_62m13 |
| 3 | 113342629 | 113342776 | H_c_174f08 |
| 3 | 113763050 | 113764619 | H_c_95a24_M |
| 3 | 114092412 | 114092530 | H_c_271a11 |
| 3 | 114192334 | 114193001 | H_c_270l14_M |
| 3 | 114202590 | 114202698 | H_c_4p07 |
| 3 | 114220232 | 114221476 | H_c_173n23_M |
| 3 | 114412917 | 114414465 | H_c_123l13 |
| 3 | 114461246 | 114461341 | H_c_30o18_M |
| 3 | 114484616 | 114487130 | H_c_194i05 |
| 3 | 114720179 | 114720253 | H_c_241m07 |
| 3 | 114734170 | 114735412 | H_c_28k01 |
| 3 | 114897189 | 114898462 | H_c_90f15_M |
| 3 | 114910902 | 114911073 | H_c136i01 |
| 3 | 114947048 | 114948062 | H_c_69l18_M |
| 3 | 115039784 | 115040566 | H_c_1b10 |
| 3 | 115148985 | 115150228 | H_c133g20 |
| 3 | 115518215 | 115518370 | H_c_203b23 |
| 3 | 116214687 | 116214817 | H_c_120o03 |
| 3 | 116326570 | 116326725 | H_c139j10 |
| 3 | 116349427 | 116349883 | H_c_169b14_M |
| 3 | 116430717 | 116430853 | H_c_104a08 |
| 3 | 116599805 | 116599986 | H_c_148j06 |
| 3 | 116859545 | 116860278 | H_c_3a14_M |
| 3 | 116908035 | 116908456 | H_c_80h02 |
| 3 | 116985381 | 116986517 | H_c_9d20 |
| 3 | 11735453 | 11737323 | H_c_36g01_M |
| 3 | 117366904 | 117366995 | H_c_152j08 |
| 3 | 117646468 | 117646753 | H_c_9o16 |
| 3 | 11781660 | 11781858 | H_c_201g09 |
| 3 | 1178673 | 1178912 | H_c_11e10 |
| 3 | 11787278 | 11788370 | H_c_1e02 |
| 3 | 11862637 | 11863586 | H_c_101n12 |
| 3 | 119143752 | 119144001 | H_c_110n20 |
| 3 | 119400308 | 119400612 | H_c_64f02 |
| 3 | 119468750 | 119468866 | H_c_262i12 |
| 3 | 12021018 | 12021834 | H_c_243g15_M |
| 3 | 120234651 | 120237007 | H_c_80n11_M |
| 3 | 120375613 | 120375731 | H_c_187c24 |
| 3 | 120495479 | 120496638 | H_c_257d04_M |
| 3 | 120523833 | 120525004 | H_c_117f18 |
| 3 | 120670014 | 120671018 | H_c_219h17_M |
| 3 | 120697300 | 120697774 | H_c_163g09 |
| 3 | 120780857 | 120781610 | H_c_264n04 |
| 3 | 120878401 | 120878986 | H_c_93c24 |
| 3 | 120904333 | 120905214 | H_c_156e20 |
| 3 | 121204372 | 121204500 | H_c_101g07 |
| 3 | 121486550 | 121487339 | H_c_79c02_M |
| 3 | 121508068 | 121509667 | H_c_186h09 |
| 3 | 121550167 | 121551233 | H_c_107e04_M |
| 3 | 121651786 | 121653355 | H_c_75n17_M |
| 3 | 121797503 | 121797783 | H_c_185f18 |
| 3 | 122109169 | 122110702 | H_c_117i11_M |
| 3 | 122846036 | 122846467 | H_c_79c23 |
| 3 | 123036397 | 123036800 | H_c_14j19_M |
| 3 | 12304007 | 12305414 | H_c_173a18 |
| 3 | 123223236 | 123224594 | H_c_74o01_M |
| 3 | 123385081 | 123386351 | H_c_245j10_M |
| 3 | 12351789 | 12351915 | H_c_73i10 |
| 3 | 123583532 | 123586074 | H_c_195e10_M |
| 3 | 12362187 | 12362542 | H_c_231j21_M |
| 3 | 123778932 | 123779606 | H_c_68i03 |
| 3 | 123882044 | 123882822 | H_c_69f20_M |
| 3 | 123994948 | 123997314 | H_c131m22_M |
| 3 | 124064477 | 124064569 | H_c_56o06 |
| 3 | 124113634 | 124116070 | H_c_9h18 |
| 3 | 124123402 | 124124814 | H_c_182j05_M |
| 3 | 124205790 | 124205965 | H_c_130a22_M |
| 3 | 124228047 | 124229891 | H_c_57a18_M |
| 3 | 124268392 | 124269367 | H_c_267f05_M |
| 3 | 124293627 | 124293867 | H_c_210h19 |
| 3 | 124693266 | 124693404 | H_c_59d09 |
| 3 | 124785950 | 124787542 | H_c_26g02_M |
| 3 | 125071317 | 125073052 | H_c_104f23 |
| 3 | 125785952 | 125786847 | H_c_57o13 |
| 3 | 12589400 | 12589642 | H_c138a19_M |
| 3 | 126087796 | 126089712 | H_c_155a13 |
| 3 | 126256835 | 126257870 | H_c_59m04_M |
| 3 | 126342268 | 126343859 | H_c_112f15_M |
| 3 | 126558465 | 126559226 | H_c_18f14 |
| 3 | 126575854 | 126577146 | H_c_42n18_M |
| 3 | 126721140 | 126721910 | H_c_273c18 |
| 3 | 12679770 | 12680617 | H_c_119g16 |
| 3 | 126813594 | 126813760 | H_c_187k15 |
| 3 | 126965733 | 126968405 | H_c_157k12_M |
| 3 | 127206773 | 127207400 | H_c_40f14 |
| 3 | 127243275 | 127243406 | H_c_78a19 |

TABLE 1-continued

| | | | |
|---|---|---|---|
| 3 | 127256759 | 127259170 | H_c_125h03 |
| 3 | 127284974 | 127286005 | H_c_125d02_M |
| 3 | 127334709 | 127336546 | H_c_157c09 |
| 3 | 127381305 | 127382153 | H_c_9n10 |
| 3 | 127414419 | 127414941 | H_c_91i13_M |
| 3 | 127469111 | 127469270 | H_c_239f22_M |
| 3 | 127590365 | 127592674 | H_c_183e16_M |
| 3 | 127676252 | 127677907 | H_c_1f24 |
| 3 | 127855968 | 127856897 | H_c_124e21_M |
| 3 | 127905200 | 127906661 | H_c_63o21 |
| 3 | 12832408 | 12834547 | H_c_262e17 |
| 3 | 128337138 | 128337260 | H_c_62e06_M |
| 3 | 128539395 | 128541333 | H_c_71l23 |
| 3 | 128572913 | 128575504 | H_c_206b11 |
| 3 | 128656768 | 128657883 | H_c141l08 |
| 3 | 128660668 | 128663200 | H_c_79b07 |
| 3 | 128748714 | 128749946 | H_c_88i05 |
| 3 | 128792428 | 128793233 | H_c_236g13_M |
| 3 | 128799292 | 128800328 | H_c_226l10 |
| 3 | 128830107 | 128831823 | H_c_21m03_M |
| 3 | 12884458 | 12886756 | H_c_251h02 |
| 3 | 128872038 | 128876306 | H_c_214e07_M |
| 3 | 129116669 | 129117453 | H_c_232i12_M |
| 3 | 129207755 | 129208975 | H_c142k23 |
| 3 | 129271160 | 129271297 | H_c_201f24 |
| 3 | 129277036 | 129278459 | H_c137m14_M |
| 3 | 129278462 | 129278718 | H_c_90a18_M |
| 3 | 129354975 | 129355598 | H_c_214p04_M |
| 3 | 129627417 | 129628560 | H_c_147d15_M |
| 3 | 129633826 | 129635960 | H_c_151i14_M |
| 3 | 129648479 | 129650066 | H_c_215n14 |
| 3 | 129690761 | 129700113 | H_c_42c18_M_M_M |
| 3 | 129756453 | 129757923 | H_c_63k23_M |
| 3 | 129808800 | 129810688 | H_c_168d15_M |
| 3 | 129819223 | 129819725 | H_c_38i10_M |
| 3 | 129854448 | 129855981 | H_c_77l02 |
| 3 | 12985630 | 12985752 | H_c_199l15 |
| 3 | 129882188 | 129883014 | H_c_266i16_M |
| 3 | 129927371 | 129928538 | H_c_84e14_M |
| 3 | 130194563 | 130195829 | H_c_24k12 |
| 3 | 130202255 | 130205709 | H_c_15d18_M |
| 3 | 130322059 | 130324727 | H_c_82j10_M |
| 3 | 130362293 | 130363453 | H_c_11p03_M |
| 3 | 130384510 | 130385863 | H_c_240d18_M |
| 3 | 130480139 | 130481137 | H_c_196b22_M |
| 3 | 130516427 | 130518207 | H_c_237a04 |
| 3 | 130640992 | 130642257 | H_c_148k16 |
| 3 | 130828224 | 130829607 | H_c_162o02_M |
| 3 | 13089625 | 13091098 | H_c_202h18_M |
| 3 | 131094433 | 131095886 | H_c_46i15 |
| 3 | 131712982 | 131713046 | H_c_184j15 |
| 3 | 132095201 | 132096375 | H_c_124k19_M |
| 3 | 13220974 | 13221140 | H_c_79m10_M |
| 3 | 13229549 | 13229703 | H_c_33d08 |
| 3 | 132813138 | 132813285 | H_c_124m23 |
| 3 | 132906354 | 132906453 | H_c_69m22 |
| 3 | 132954955 | 132955083 | H_c_184n19 |
| 3 | 13298651 | 13299879 | H_c_219m02_M |
| 3 | 133236404 | 133236891 | H_c_86a18 |
| 3 | 133262301 | 133262352 | H_c_124a05 |
| 3 | 133545327 | 133545524 | H_c_73e16 |
| 3 | 133618665 | 133619581 | H_c_151d04_M |
| 3 | 133861631 | 133862426 | H_c_151d12 |
| 3 | 133923398 | 133924897 | H_c_33a17_M |
| 3 | 134046226 | 134046477 | H_c_267o12 |
| 3 | 134239572 | 134240344 | H_c_180j13_M |
| 3 | 13434530 | 13436596 | H_c_190i22_M |
| 3 | 13436597 | 13437332 | H_c_19n10_M |
| 3 | 134715005 | 134715155 | H_c142m04 |
| 3 | 134774716 | 134776266 | H_c144d15_M |
| 3 | 134947094 | 134949156 | H_c_125n11 |
| 3 | 13495783 | 13497591 | H_c_29i14_M |
| 3 | 135007165 | 135007721 | H_c_214k01 |
| 3 | 135095435 | 135096922 | H_c_101g14 |
| 3 | 135096923 | 135097644 | H_c_70j09_M |
| 3 | 135166749 | 135169063 | H_c_226m01 |
| 3 | 135199872 | 135202252 | H_c_37c12_M |
| 3 | 135230191 | 135231249 | H_c_87k17_M |
| 3 | 135451153 | 135452348 | H_c_219o06_M |
| 3 | 135512876 | 135515513 | H_c_81g18_M |
| 3 | 135575298 | 135576065 | H_c_71p10_M |
| 3 | 135608176 | 135608870 | H_c_87e10 |
| 3 | 135686792 | 135688263 | H_c_15c24_M |
| 3 | 135802463 | 135802622 | H_c_267l09_M |
| 3 | 135996662 | 135998646 | H_c_176e04 |
| 3 | 136051435 | 136051711 | H_c_189a09 |
| 3 | 136631935 | 136632138 | H_c_124p09 |
| 3 | 13666691 | 13667407 | H_c_57d02_M |
| 3 | 136708502 | 136708780 | H_c_23m10 |
| 3 | 136897047 | 136897204 | H_c_169l19 |
| 3 | 137166771 | 137167678 | H_c_211e02_M |
| 3 | 137396560 | 137397740 | H_c_127c10_M |
| 3 | 137433957 | 137434050 | H_c_11d20 |
| 3 | 137451659 | 137452306 | H_c_12d22_M |
| 3 | 137570541 | 137570733 | H_c_129h17 |
| 3 | 137952685 | 137954582 | H_c_23c19 |
| 3 | 138063454 | 138064445 | H_c_267l12 |
| 3 | 138246024 | 138246212 | H_c_80h20 |
| 3 | 138531227 | 138531308 | H_c_226m07 |
| 3 | 138568105 | 138568260 | H_c_26l14 |
| 3 | 138793461 | 138793652 | H_c_57m16_M |
| 3 | 13894793 | 13898022 | H_c_20j11_M |
| 3 | 138966024 | 138967544 | H_c_110e09 |
| 3 | 138969581 | 138972850 | H_c_86j21_M_M |
| 3 | 13911287 | 13912464 | H_c_270i07_M |
| 3 | 139316444 | 139317240 | H_c_95d11_M |
| 3 | 139375663 | 139376349 | H_c_108g23_M |
| 3 | 139388467 | 139389733 | H_c_77g23_M |
| 3 | 139531017 | 139531771 | H_c_25i05 |
| 3 | 139549491 | 139550684 | H_c_37d17_M |
| 3 | 139635939 | 139636872 | H_c_213e09_M |
| 3 | 139743272 | 139745398 | H_c_246d18 |
| 3 | 139855638 | 139855821 | H_c_151a21_M |
| 3 | 139971458 | 139971558 | H_c_252a19 |
| 3 | 140035720 | 140037067 | H_c_160j24 |
| 3 | 140117005 | 140118005 | H_c_122l17 |
| 3 | 140138439 | 140141924 | H_c_199d11_M |
| 3 | 140150906 | 140152599 | H_c_84k09_M |
| 3 | 140161680 | 140162770 | H_c_250i20 |
| 3 | 140590736 | 140591655 | H_c_151a05 |
| 3 | 140740800 | 140741451 | H_c_10f02_M |
| 3 | 140878942 | 140879719 | H_c_74g17_M |
| 3 | 141136038 | 141138340 | H_c_154a17_M |
| 3 | 14140812 | 14142388 | H_c_115j02 |
| 3 | 141631338 | 141631570 | H_c_258a09 |
| 3 | 141775568 | 141775712 | H_c_178f07 |
| 3 | 14194479 | 14195397 | H_c144b24_M |
| 3 | 142603359 | 142604788 | H_c_7b03_M |
| 3 | 142688341 | 142689442 | H_c_30k22_M |
| 3 | 142817894 | 142818036 | H_c_62o04 |
| 3 | 142861331 | 142862159 | H_c_258l21 |
| 3 | 142939539 | 142940320 | H_c_98d13 |
| 3 | 143215357 | 143215602 | H_c_196e10 |
| 3 | 143350328 | 143351640 | H_c_80k20_M |
| 3 | 143392231 | 143392332 | H_c_184b22 |
| 3 | 143426412 | 143427292 | H_c_82l06_M |
| 3 | 143601669 | 143601759 | H_c_150k22 |
| 3 | 143648721 | 143649928 | H_c_182e21_M |
| 3 | 143779506 | 143780728 | H_c_232l03_M |
| 3 | 143797639 | 143798254 | H_c_111g08_M |
| 3 | 143871763 | 143872019 | H_c_75i20 |
| 3 | 143925372 | 143926699 | H_c_186j02_M |
| 3 | 144010252 | 144010472 | H_c_70n03 |
| 3 | 144090082 | 144090982 | H_c_20n21_M |
| 3 | 144163246 | 144165690 | H_c_200c15_M |
| 3 | 14418456 | 14420661 | H_c_17j22_M |
| 3 | 144198021 | 144198171 | H_c_45k22 |
| 3 | 144202827 | 144203423 | H_c_48i21_M |
| 3 | 144320425 | 144323946 | H_c_12e16_M |
| 3 | 144409857 | 144409974 | H_c_70o05 |
| 3 | 144701050 | 144701301 | H_c_26j14_M |
| 3 | 144793858 | 144793975 | H_c_114d17 |
| 3 | 145173168 | 145174805 | H_c_232d07 |
| 3 | 145235970 | 145236045 | H_c_183i17 |
| 3 | 1452965 | 1453037 | H_c_223a11 |
| 3 | 145438458 | 145438598 | H_c_71j23 |
| 3 | 14564328 | 14566337 | H_c_175i24 |
| 3 | 145740253 | 145740370 | H_c_243k23 |
| 3 | 146075061 | 146075175 | H_c_175f05 |
| 3 | 14618119 | 14620119 | H_c_11k03 |

TABLE 1-continued

| | | | |
|---|---|---|---|
| 3 | 146708662 | 146708830 | H_c_73h05 |
| 3 | 146942529 | 146942631 | H_c_235g03 |
| 3 | 147360684 | 147361845 | H_c_8o08 |
| 3 | 147451013 | 147452645 | H_c_52b03_M |
| 3 | 147669619 | 147670380 | H_c_14a09 |
| 3 | 14815303 | 14815417 | H_c_38d13 |
| 3 | 148557179 | 148557262 | H_c_49e21 |
| 3 | 148588683 | 148594450 | H_c_42j13_M_M |
| 3 | 148609209 | 148611466 | H_c_190m24_M |
| 3 | 148620471 | 148622226 | H_c_225m05_M |
| 3 | 149260650 | 149260740 | H_c_22m02 |
| 3 | 14937020 | 14937151 | H_c_58n19 |
| 3 | 14963894 | 14965504 | H_c_251i10_M |
| 3 | 149695034 | 149695183 | H_c_183m20 |
| 3 | 149898061 | 149898864 | H_c_59h13_M |
| 3 | 150191759 | 150192905 | H_c_168o11 |
| 3 | 150329679 | 150330058 | H_c_123a22 |
| 3 | 150332223 | 150332332 | H_c_63a24 |
| 3 | 15081045 | 15082150 | H_c_150e09 |
| 3 | 150856734 | 150859236 | H_c_14f23_M |
| 3 | 151608632 | 151611721 | H_c_32i20_M |
| 3 | 151745985 | 151747719 | H_c_244j13_M |
| 3 | 151803941 | 151804449 | H_c_57i09_M |
| 3 | 151904515 | 151904688 | H_c_73c02 |
| 3 | 151962815 | 151964235 | H_c_48a08_M |
| 3 | 15222429 | 15223488 | H_c135b21 |
| 3 | 152285273 | 152287397 | H_c_23o21_M |
| 3 | 152937525 | 152937602 | H_c_15c14 |
| 3 | 153444903 | 153444992 | H_c_73f02 |
| 3 | 153468891 | 153469920 | H_c_89h02_M |
| 3 | 15348195 | 15349638 | H_c_39g16_M |
| 3 | 153717046 | 153717137 | H_c_63e05 |
| 3 | 154034989 | 154035823 | H_c_67m08 |
| 3 | 154180505 | 154180747 | H_c_186l12 |
| 3 | 154361525 | 154364005 | H_c_222j12 |
| 3 | 154372801 | 154372954 | H_c_191k19 |
| 3 | 15443835 | 15444801 | H_c_94f13_M |
| 3 | 154455162 | 154455235 | H_c_189e08 |
| 3 | 154729143 | 154729259 | H_c_4k05 |
| 3 | 154756914 | 154757036 | H_c_27o20 |
| 3 | 154905413 | 154905520 | H_c_204b16 |
| 3 | 155321458 | 155323255 | H_c_209l07_M |
| 3 | 155628785 | 155629776 | H_c_251e10 |
| 3 | 155668424 | 155668504 | H_c_11i16 |
| 3 | 155818607 | 155818769 | H_c_108b14 |
| 3 | 156675739 | 156675851 | H_c_121f23 |
| 3 | 156944531 | 156945905 | H_c_123n17_M |
| 3 | 156995992 | 156996080 | H_c_40i01 |
| 3 | 157006231 | 157006899 | H_c_24j23_M |
| 3 | 15702991 | 15703208 | H_c_111e24 |
| 3 | 157054306 | 157055081 | H_c_272h09 |
| 3 | 157070234 | 157072356 | H_c_261b18_M |
| 3 | 15768708 | 15768794 | H_c_43l01 |
| 3 | 157874453 | 157876810 | H_c_182c19_M |
| 3 | 157980801 | 157980968 | H_c_119f03_M |
| 3 | 158016374 | 158017815 | H_c_83p19_M |
| 3 | 158026361 | 158027377 | H_c_210l16 |
| 3 | 158050874 | 158051344 | H_c_265o13 |
| 3 | 158084641 | 158084813 | H_c_89l01 |
| 3 | 158187895 | 158188115 | H_c144l14 |
| 3 | 158359706 | 158361984 | H_c_16i10_M |
| 3 | 158375177 | 158375805 | H_c_113b06_M |
| 3 | 158466501 | 158466822 | H_c_11o16_M |
| 3 | 158637882 | 158638626 | H_c_184h04 |
| 3 | 158679943 | 158680153 | H_c_48e08 |
| 3 | 15875450 | 15877097 | H_c_4g09_M |
| 3 | 159298144 | 159298843 | H_c_162h01_M |
| 3 | 159302880 | 159306823 | H_c_7l15_M |
| 3 | 159310604 | 159311282 | H_c_208k24 |
| 3 | 159557599 | 159557757 | H_c_241b15 |
| 3 | 159745104 | 159745113 | H_c_45h15 |
| 3 | 159798862 | 159799022 | H_c_104d24 |
| 3 | 159844804 | 159845413 | H_c_95i06 |
| 3 | 159932290 | 159933685 | H_c_64j15_M |
| 3 | 160002164 | 160002840 | H_c_70a17_M |
| 3 | 160283938 | 160284174 | H_c_121e04 |
| 3 | 160638773 | 160638986 | H_c_237i07 |
| 3 | 160641310 | 160641848 | H_c_107l14 |
| 3 | 160941325 | 160941558 | H_c_236c17 |
| 3 | 160964500 | 160965866 | H_c_91p14_M |
| 3 | 161051254 | 161051467 | H_c_124o06 |
| 3 | 161295190 | 161295385 | H_c_269b05_M |
| 3 | 161339702 | 161339894 | H_c_220e22 |
| 3 | 161425878 | 161427728 | H_c_84f19 |
| 3 | 161500701 | 161500902 | H_c_16g11 |
| 3 | 161624846 | 161624955 | H_c_1p09 |
| 3 | 161649603 | 161651232 | H_c_198m15_M |
| 3 | 161765201 | 161766773 | H_c_112e16_M |
| 3 | 162305096 | 162306113 | H_c_101c19 |
| 3 | 162325165 | 162325248 | H_c140p04 |
| 3 | 162498074 | 162498199 | H_c_166h15 |
| 3 | 162572627 | 162572934 | H_c_273g21 |
| 3 | 162587533 | 162587755 | H_c_32h23 |
| 3 | 16281448 | 16282000 | H_c_272f10_M |
| 3 | 163209262 | 163209373 | H_c_1p02 |
| 3 | 163598973 | 163599169 | H_c_121k21 |
| 3 | 163802591 | 163802743 | H_c_203m07_M |
| 3 | 164318114 | 164318225 | H_c_27d18 |
| 3 | 165065371 | 165065458 | H_c_126k12 |
| 3 | 165183579 | 165183967 | H_c_5a20_M |
| 3 | 16529271 | 16530748 | H_c_56b09_M |
| 3 | 165446278 | 165446484 | H_c_78n14 |
| 3 | 165462345 | 165462531 | H_c_213n08 |
| 3 | 165595747 | 165595889 | H_c_84j24 |
| 3 | 166216705 | 166216892 | H_c_85n15 |
| 3 | 166397093 | 166397666 | H_c_12a04 |
| 3 | 16770216 | 16770362 | H_c_184n17 |
| 3 | 167907188 | 167907323 | H_c_154l22_M |
| 3 | 168934779 | 168936464 | H_c_35o21_M |
| 3 | 16900012 | 16902187 | H_c_257a16_M |
| 3 | 169295169 | 169297050 | H_c_100e24_M |
| 3 | 169450058 | 169450865 | H_c_68j01_M |
| 3 | 170458034 | 170458318 | H_c_257g10 |
| 3 | 17059985 | 17060053 | H_c_91f14 |
| 3 | 170804251 | 170804375 | H_c_67l09 |
| 3 | 170830088 | 170830329 | H_c_218c05 |
| 3 | 170961384 | 170961461 | H_c_124i22 |
| 3 | 170973200 | 170974361 | H_c_215m19_M |
| 3 | 171138404 | 171138693 | H_c_200k17 |
| 3 | 171143045 | 171143330 | H_c_150b05 |
| 3 | 171166704 | 171167759 | H_c_50j15 |
| 3 | 171239052 | 171239264 | H_c_86l09_M |
| 3 | 171381517 | 171382481 | H_c_165n15 |
| 3 | 171422380 | 171423584 | H_c_48m11 |
| 3 | 171618738 | 171620698 | H_c_72i05_M |
| 3 | 171779240 | 171779328 | H_c_164h20_M |
| 3 | 171784602 | 171786989 | H_c_236a09_M |
| 3 | 172070607 | 172070915 | H_c_152f01_M |
| 3 | 172179408 | 172179592 | H_c_109i01 |
| 3 | 172431294 | 172431384 | H_c_124f11 |
| 3 | 172661360 | 172661879 | H_c_247b12_M |
| 3 | 173013397 | 173013586 | H_c_10k08 |
| 3 | 173222174 | 173222405 | H_c_60n18 |
| 3 | 173240570 | 173241522 | H_c_113o11_M |
| 3 | 173363619 | 173363807 | H_c_94f18 |
| 3 | 17343620 | 17343735 | H_c_80c19 |
| 3 | 173580480 | 173580565 | H_c_210h13 |
| 3 | 173951011 | 173951758 | H_c_183k22_M |
| 3 | 174183577 | 174183685 | H_c_114k09 |
| 3 | 174188052 | 174188179 | H_c_186b05 |
| 3 | 174525659 | 174525829 | H_c_228o16 |
| 3 | 174595727 | 174598880 | H_c_203i14_M |
| 3 | 174803447 | 174803534 | H_c_273k09 |
| 3 | 174862994 | 174863174 | H_c_100a18 |
| 3 | 175641246 | 175642059 | H_c_113o13_M |
| 3 | 176194187 | 176194773 | H_c_151e03_M |
| 3 | 176366139 | 176366560 | H_c_45i07 |
| 3 | 176797873 | 176797933 | H_c_274l03 |
| 3 | 176957578 | 176957740 | H_c_146g01 |
| 3 | 17758446 | 17759949 | H_c_68j07_M |
| 3 | 178396909 | 178399029 | H_c_273f15_M |
| 3 | 178559999 | 178560854 | H_c_63a01 |
| 3 | 178815980 | 178816211 | H_c143m21 |
| 3 | 179026640 | 179026957 | H_c_270a23 |
| 3 | 179836411 | 179838546 | H_c_20h14 |
| 3 | 180076221 | 180076370 | H_c_249d07 |
| 3 | 180271572 | 180272581 | H_c_243n05_M |
| 3 | 180348460 | 180349599 | H_c_61g06 |
| 3 | 180522930 | 180524361 | H_c_91e17_M |
| 3 | 180763482 | 180764270 | H_c_82i16_M |

TABLE 1-continued

| | | | |
|---|---|---|---|
| 3 | 180805046 | 180805211 | H_c_72l18_M |
| 3 | 180853217 | 180854147 | H_c_83j16_M |
| 3 | 181181584 | 181181701 | H_c_92m16 |
| 3 | 181237022 | 181237948 | H_c_149o10 |
| 3 | 181293252 | 181294998 | H_c_200n19 |
| 3 | 181424181 | 181424290 | H_c_31i22 |
| 3 | 181552140 | 181552306 | H_c_214k10 |
| 3 | 181879602 | 181880629 | H_c_174g22_M |
| 3 | 182189188 | 182190517 | H_c_87c19 |
| 3 | 18219319 | 18219449 | H_c_188l16 |
| 3 | 182517540 | 182517633 | H_c_86d12 |
| 3 | 182832039 | 182832120 | H_c_95f01 |
| 3 | 182895405 | 182896767 | H_c_18d04_M |
| 3 | 182919534 | 182920556 | H_c_118c08 |
| 3 | 182924807 | 182924923 | H_c_266b05 |
| 3 | 182927110 | 182927442 | H_c_102k01 |
| 3 | 183272377 | 183272447 | H_c_106p05 |
| 3 | 183882777 | 183883615 | H_c_52f18_M |
| 3 | 183993732 | 183995021 | H_c_96d21 |
| 3 | 184180159 | 184181885 | H_c_24j12 |
| 3 | 184298966 | 184300397 | H_c_124d02_M |
| 3 | 184362837 | 184365123 | H_c_75k09_M |
| 3 | 184379202 | 184380432 | H_c_40d05 |
| 3 | 18441534 | 18441696 | H_c144k12_M |
| 3 | 18442016 | 18442697 | H_c_113l17_M |
| 3 | 184453543 | 184455507 | H_c_202n03_M |
| 3 | 18459296 | 18461261 | H_c_6g10 |
| 3 | 18459524 | 18461261 | H_c_214b12_M |
| 3 | 184628539 | 184629876 | H_c_249d18 |
| 3 | 184647649 | 184648527 | H_c_270h05 |
| 3 | 184712689 | 184712761 | H_c_197a17 |
| 3 | 184835895 | 184837637 | H_c_21p11_M |
| 3 | 184863642 | 184863835 | H_c_73e05 |
| 3 | 184898046 | 184898787 | H_c_10h14 |
| 3 | 185025317 | 185026711 | H_c_59j02_M |
| 3 | 18514575 | 18514811 | H_c_9o07 |
| 3 | 185217113 | 185218895 | H_c_179e03_M |
| 3 | 185355383 | 185356491 | H_c_77a19_M |
| 3 | 185420556 | 185421932 | H_c_24k14 |
| 3 | 185428954 | 185431953 | H_c_20f02_M |
| 3 | 185449434 | 185451132 | H_c_163p24_M |
| 3 | 185458404 | 185462675 | H_c_123a13_M |
| 3 | 185462734 | 185463348 | H_c_265e06_M |
| 3 | 185499227 | 185500410 | H_c_268f10_M |
| 3 | 185514845 | 185516023 | H_c_210o03 |
| 3 | 185535841 | 185537065 | H_c_120e16_M |
| 3 | 185563790 | 185565820 | H_c_156j23 |
| 3 | 185713831 | 185714462 | H_c_71k12_M |
| 3 | 185725721 | 185726749 | H_c_256e21_M |
| 3 | 185761664 | 185762872 | H_c_4j02_M |
| 3 | 185783467 | 185785304 | H_c_265f09_M |
| 3 | 185801999 | 185802624 | H_c_122m16_M |
| 3 | 186012550 | 186013008 | H_c_151a11_M |
| 3 | 186105079 | 186105272 | H_c144j05 |
| 3 | 186255240 | 186255351 | H_c_129l13 |
| 3 | 186352712 | 186355391 | H_c_196d23 |
| 3 | 18639121 | 18639219 | H_c_1o17_M |
| 3 | 186454349 | 186454716 | H_c_222b23 |
| 3 | 186698834 | 186699973 | H_c_168h18_M |
| 3 | 186786820 | 186787360 | H_c_266c24 |
| 3 | 187023719 | 187023958 | H_c_145f17_M |
| 3 | 187138417 | 187138893 | H_c_65c16_M |
| 3 | 187394006 | 187395207 | H_c_215a06 |
| 3 | 187561024 | 187563387 | H_c_243d23_M |
| 3 | 18765769 | 18765961 | H_c_69p09_M |
| 3 | 187767499 | 187768222 | H_c_16f09 |
| 3 | 187770631 | 187771963 | H_c_72e13_M |
| 3 | 187972924 | 187974119 | H_c_27p10 |
| 3 | 187983585 | 187984864 | H_c_65m14_M |
| 3 | 188006599 | 188007332 | H_c132d01_M |
| 3 | 188130816 | 188131226 | H_c133h05_M |
| 3 | 188339187 | 188340219 | H_c_20f12 |
| 3 | 188940380 | 188941667 | H_c_33j23_M |
| 3 | 188944079 | 188946812 | H_c_96a18_M |
| 3 | 189351116 | 189351204 | H_c_123j02 |
| 3 | 189353968 | 189355209 | H_c_87f13_M |
| 3 | 189818107 | 189818206 | H_c_212k07 |
| 3 | 18990275 | 18990429 | H_c_36c14 |
| 3 | 189911904 | 189912063 | H_c_264g03 |
| 3 | 190445212 | 190445334 | H_c_232g16 |
| 3 | 190809355 | 190809431 | H_c_188e18 |
| 3 | 191083113 | 191083344 | H_c142g12 |
| 3 | 191320632 | 191321667 | H_c_272d06_M |
| 3 | 191522809 | 191522963 | H_c_62j20_M |
| 3 | 19162942 | 19164201 | H_c_67p22 |
| 3 | 19164313 | 19165462 | H_c_273m03 |
| 3 | 191776246 | 191776365 | H_c_32e21 |
| 3 | 192063245 | 192063721 | H_c_263g15_M |
| 3 | 192265652 | 192265848 | H_c_232p21 |
| 3 | 192529528 | 192530136 | H_c_212j11 |
| 3 | 192628987 | 192629084 | H_c132b24_M |
| 3 | 192670530 | 192670614 | H_c_20e23 |
| 3 | 193543362 | 193543707 | H_c135e16 |
| 3 | 193608359 | 193610932 | H_c133a01_M |
| 3 | 193630687 | 193630796 | H_c_163f08 |
| 3 | 193670110 | 193670373 | H_c_257e19 |
| 3 | 193714752 | 193716286 | H_c_213b18_M |
| 3 | 193760561 | 193760711 | H_c_19i08 |
| 3 | 193806225 | 193806342 | H_c_113e07 |
| 3 | 194372033 | 194372285 | H_c_224e02 |
| 3 | 194441032 | 194442213 | H_c_12k12_M |
| 3 | 194783005 | 194784279 | H_c_111c04 |
| 3 | 194793497 | 194793926 | H_c_183p06 |
| 3 | 195092978 | 195093048 | H_c_270c07 |
| 3 | 195258605 | 195259248 | H_c_270b02 |
| 3 | 195270435 | 195271955 | H_c_89c03_M |
| 3 | 195334308 | 195335683 | H_c_23k14_M |
| 3 | 195341682 | 195342628 | H_c139f02_M |
| 3 | 195404489 | 195405015 | H_c_163b16_M |
| 3 | 195496952 | 195497546 | H_c_79k09 |
| 3 | 195516175 | 195516543 | H_c_104c12_M |
| 3 | 195598677 | 195600432 | H_c_74p08_M |
| 3 | 195834712 | 195836051 | H_c_12e08_M |
| 3 | 195873649 | 195874816 | H_c_252o10_M |
| 3 | 195887782 | 195890553 | H_c_9c19_M |
| 3 | 196247754 | 196248029 | H_c_159b23 |
| 3 | 196288246 | 196289317 | H_c_273e16 |
| 3 | 196378416 | 196378597 | H_c_20d13 |
| 3 | 196460405 | 196463465 | H_c_88f12_M |
| 3 | 196472673 | 196473809 | H_c_205k05_M |
| 3 | 196644151 | 196645929 | H_c_21d11_M |
| 3 | 196750870 | 196752121 | H_c_107b04_M |
| 3 | 19678837 | 19678992 | H_c_172e16 |
| 3 | 197109923 | 197112338 | H_c_80e14_M |
| 3 | 197123243 | 197125001 | H_c_94j13_M |
| 3 | 19718876 | 19719726 | H_c_61h13 |
| 3 | 197296577 | 197297625 | H_c_159c10 |
| 3 | 197422814 | 197423389 | H_c_165j01 |
| 3 | 197502271 | 197503520 | H_c_70l03_M |
| 3 | 197532740 | 197533993 | H_c_46a12_M |
| 3 | 197647533 | 197648192 | H_c144c03_M |
| 3 | 197717981 | 197719730 | H_c_128b12_M |
| 3 | 197743747 | 197744913 | H_c_178k14 |
| 3 | 197783333 | 197784665 | H_c_127j11 |
| 3 | 197847547 | 197849563 | H_c139d12_M |
| 3 | 197853672 | 197855382 | H_c_67l11_M |
| 3 | 197926479 | 197928798 | H_c_209m07_M |
| 3 | 197954839 | 197956531 | H_c_196d16_M |
| 3 | 198157191 | 198158191 | H_c_62g19_M |
| 3 | 198184281 | 198185382 | H_c_214f12 |
| 3 | 198512618 | 198513819 | H_c_19l23_M |
| 3 | 198725029 | 198725719 | H_c_125a11 |
| 3 | 198769116 | 198771489 | H_c_93i24_M |
| 3 | 198951091 | 198952456 | H_c_190p21_M |
| 3 | 198964567 | 198966007 | H_c_213i20_M |
| 3 | 199165340 | 199165613 | H_c_25a13 |
| 3 | 199174968 | 199176221 | H_c_89m03_M |
| 3 | 199222197 | 199222332 | H_c135b03 |
| 3 | 199295295 | 199297093 | H_c_43l03 |
| 3 | 199328498 | 199329382 | H_c_15e22 |
| 3 | 19963036 | 19964611 | H_c_197l19_M |
| 3 | 19975594 | 19975855 | H_c142m08 |
| 3 | 20056143 | 20057914 | H_c_108n20_M |
| 3 | 20202246 | 20202952 | H_c_218c01_M |
| 3 | 21091642 | 21091710 | H_c_196n02 |
| 3 | 2115036 | 2116968 | H_c_72l08 |
| 3 | 21215611 | 21215738 | H_c_254b18 |
| 3 | 213253 | 215202 | H_c_185i11_M |
| 3 | 21697348 | 21697489 | H_c_169d14_M |
| 3 | 22388427 | 22389295 | H_c_247c18 |

TABLE 1-continued

| | | | |
|---|---|---|---|
| 3 | 22420326 | 22420427 | H_c_195a22 |
| 3 | 22440487 | 22440561 | H_c_3c12 |
| 3 | 22736078 | 22736359 | H_c_73m05 |
| 3 | 23022191 | 23022314 | H_c136l10 |
| 3 | 23826793 | 23827661 | H_c_22i11_M |
| 3 | 23932807 | 23933986 | H_c_218a15_M |
| 3 | 23961233 | 23963044 | H_c_33k14 |
| 3 | 24510694 | 24512102 | H_c_104d05_M |
| 3 | 24537808 | 24539079 | H_c_220n22_M |
| 3 | 24845341 | 24847330 | H_c136e07 |
| 3 | 25680433 | 25681845 | H_c_266g19_M |
| 3 | 25799223 | 25800485 | H_c_145e19_M |
| 3 | 25806241 | 25807053 | H_c_7g02_M |
| 3 | 25968846 | 25968940 | H_c_265a21 |
| 3 | 26466555 | 26466873 | H_c_26f10 |
| 3 | 26639218 | 26641480 | H_c_51g24_M |
| 3 | 26849881 | 26850029 | H_c_236d20 |
| 3 | 27111412 | 27111555 | H_c_152k19 |
| 3 | 27136161 | 27137136 | H_c_63c10 |
| 3 | 27499771 | 27501202 | H_c_22k20 |
| 3 | 27649176 | 27650034 | H_c_61m09 |
| 3 | 27731181 | 27732127 | H_c_47f20_M |
| 3 | 27737249 | 27741476 | H_c_264f02_M |
| 3 | 28216083 | 28217822 | H_c_126e22 |
| 3 | 28257788 | 28258552 | H_c_181b17_M |
| 3 | 28364420 | 28366154 | H_c_170k21 |
| 3 | 28591554 | 28593061 | H_c_165m07_M |
| 3 | 28639945 | 28640093 | H_c_258j07 |
| 3 | 28708612 | 28708818 | H_c_42g24_M |
| 3 | 28954635 | 28954751 | H_c_237b12 |
| 3 | 29096295 | 29096455 | H_c_24l07 |
| 3 | 29100845 | 29100986 | H_c_151h11 |
| 3 | 29404032 | 29404101 | H_c135h01 |
| 3 | 29844200 | 29844378 | H_c_216d17_M |
| 3 | 2987435 | 2987634 | H_c_245p18 |
| 3 | 30311642 | 30311844 | H_c_109i15 |
| 3 | 30469737 | 30469836 | H_c_39n16 |
| 3 | 30622638 | 30624195 | H_c_72e03 |
| 3 | 30722314 | 30722378 | H_c_1b21 |
| 3 | 30911039 | 30911300 | H_c_42c13_M |
| 3 | 31398367 | 31398545 | H_c_235d21 |
| 3 | 3143401 | 3144751 | H_c_192e14_M |
| 3 | 3150424 | 3150583 | H_c_194k22 |
| 3 | 31548259 | 31550503 | H_c_69p17_M |
| 3 | 31765248 | 31765385 | H_c_34k17 |
| 3 | 31773895 | 31774044 | H_c_38p13 |
| 3 | 3196065 | 3196655 | H_c_12l02_M |
| 3 | 31996942 | 31998446 | H_c_37h09_M |
| 3 | 32021908 | 32022065 | H_c_163b01 |
| 3 | 32048260 | 32048363 | H_c_184a02_M |
| 3 | 32254376 | 32256576 | H_c_52a22_M |
| 3 | 32406644 | 32409407 | H_c_158h08_M |
| 3 | 32518662 | 32519746 | H_c_190d01_M |
| 3 | 32586446 | 32587951 | H_c_1m05_M |
| 3 | 32701500 | 32702247 | H_c_164h12_M |
| 3 | 32797265 | 32798349 | H_c_28k19_M |
| 3 | 32833101 | 32834365 | H_c143d19_M |
| 3 | 32834367 | 32835676 | H_c_54j13 |
| 3 | 32919095 | 32920788 | H_c_234h04_M |
| 3 | 3302270 | 3302971 | H_c_193f14 |
| 3 | 33051634 | 33051772 | H_c_194j22 |
| 3 | 33112613 | 33113947 | H_c_221j21_M |
| 3 | 33130126 | 33131366 | H_c_211b03_M |
| 3 | 33234810 | 33235852 | H_c_75p19 |
| 3 | 33293682 | 33294245 | H_c_170n12 |
| 3 | 33366173 | 33366387 | H_c_210p24 |
| 3 | 33455777 | 33457926 | H_c_3k22_M |
| 3 | 33513732 | 33513819 | H_c_62k09 |
| 3 | 33734253 | 33735035 | H_c_50m01 |
| 3 | 33842616 | 33842947 | H_c132d05 |
| 3 | 34230431 | 34231438 | H_c_153b14_M |
| 3 | 34270731 | 34270938 | H_c_73c03 |
| 3 | 34843626 | 34883817 | H_c_45e03 |
| 3 | 35402535 | 35402759 | H_c_221f04 |
| 3 | 35807900 | 35808046 | H_c_257i10 |
| 3 | 3604897 | 3605107 | H_c_21j23 |
| 3 | 36084580 | 36084696 | H_c_157o21 |
| 3 | 36396377 | 36397666 | H_c_96b17 |
| 3 | 36780260 | 36781827 | H_c_107n20_M |
| 3 | 3683834 | 3684223 | H_c_238h20 |
| 3 | 36960373 | 36962776 | H_c_150d21_M |
| 3 | 37009074 | 37010366 | H_c_79l08_M |
| 3 | 37192296 | 37193381 | H_c133b06 |
| 3 | 37259137 | 37260217 | H_c_121e14 |
| 3 | 37467916 | 37469802 | H_c_235e07_M |
| 3 | 37597304 | 37597456 | H_c_69f14 |
| 3 | 37861697 | 37861784 | H_c_170n02 |
| 3 | 38040865 | 38042121 | H_c_231i17 |
| 3 | 38045745 | 38047194 | H_c_43e22_M |
| 3 | 38055591 | 38056657 | H_c_31n13 |
| 3 | 38152674 | 38155678 | H_c_218b07_M |
| 3 | 3815561 | 3818114 | H_c_124n06_M |
| 3 | 38181192 | 38182846 | H_c_25g08_M |
| 3 | 38215401 | 38215492 | H_c_269a16 |
| 3 | 38226864 | 38227079 | H_c_31l01 |
| 3 | 38513477 | 38513587 | H_c_118p23 |
| 3 | 38664981 | 38666531 | H_c_265b03_M |
| 3 | 39068180 | 39069097 | H_c_98j21 |
| 3 | 39123541 | 39124685 | H_c_15c15 |
| 3 | 39193924 | 39194865 | H_c_202f03 |
| 3 | 39196943 | 39198155 | H_c_27k15_M |
| 3 | 39238915 | 39239001 | H_c_126f02 |
| 3 | 39399750 | 39401015 | H_c_185b05_M |
| 3 | 39422773 | 39423660 | H_c_180o04 |
| 3 | 39518977 | 39519422 | H_c133c18_M |
| 3 | 40325450 | 40326850 | H_c_22d20_M |
| 3 | 40473672 | 40474201 | H_c_78e04_M |
| 3 | 40540933 | 40541819 | H_c_35m10_M |
| 3 | 41215082 | 41215997 | H_c_79p21_M |
| 3 | 42029712 | 42030961 | H_c_195b22_M |
| 3 | 42033080 | 42033315 | H_c_219k11_M |
| 3 | 42363593 | 42363781 | H_c_84n07 |
| 3 | 42517577 | 42519916 | H_c_197i05_M |
| 3 | 42598022 | 42598607 | H_c_39p04 |
| 3 | 42606538 | 42608200 | H_c_202g04_M |
| 3 | 42616610 | 42617983 | H_c_123c17_M |
| 3 | 42670911 | 42671384 | H_c_256e22_M |
| 3 | 42701536 | 42702670 | H_c_130b14_M |
| 3 | 42789441 | 42789907 | H_c_244f22 |
| 3 | 42820307 | 42821515 | H_c_93n24_M |
| 3 | 42896779 | 42899430 | H_c_54f09_M |
| 3 | 42995380 | 42996513 | H_c_87j10_M |
| 3 | 43302674 | 43304058 | H_c_19j11 |
| 3 | 43310078 | 43310262 | H_c_38g05 |
| 3 | 43351318 | 43351408 | H_c_34h24 |
| 3 | 43637819 | 43638958 | H_c_186m09 |
| 3 | 43706734 | 43708217 | H_c_86f11_M |
| 3 | 43910769 | 43911025 | H_c_19n22_M |
| 3 | 4392274 | 4392682 | H_c_172g05 |
| 3 | 44011465 | 44013464 | H_c_89j11_M |
| 3 | 44015308 | 44016549 | H_c_185j12_M |
| 3 | 44030536 | 44030875 | H_c_190j19_M |
| 3 | 44354500 | 44355489 | H_c_257m16_M |
| 3 | 44489282 | 44489374 | H_c_45m09 |
| 3 | 44571356 | 44572003 | H_c_177n08 |
| 3 | 44600745 | 44602167 | H_c_62k03 |
| 3 | 44641077 | 44642060 | H_c_40e20_M |
| 3 | 44701847 | 44702284 | H_c_162i20 |
| 3 | 44745982 | 44746413 | H_c_17g04_M |
| 3 | 4483480 | 4483980 | H_c_20g15_M |
| 3 | 44878082 | 44878981 | H_c_90a16_M |
| 3 | 44991715 | 44992953 | H_c_93b03_M |
| 3 | 45161880 | 45163274 | H_c_250o19 |
| 3 | 45241430 | 45243283 | H_c_51a20_M |
| 3 | 45404910 | 45405659 | H_c_181h19 |
| 3 | 45609669 | 45611169 | H_c143b03 |
| 3 | 45704749 | 45706347 | H_c_186a23_M |
| 3 | 45812368 | 45813052 | H_c_121j15 |
| 3 | 46011485 | 46012431 | H_c_200g05_M |
| 3 | 46582571 | 46583200 | H_c_34o16 |
| 3 | 46716350 | 46718520 | H_c_128k16 |
| 3 | 46862052 | 46864137 | H_c_169i02 |
| 3 | 46908562 | 46909029 | H_c_164f08_M |
| 3 | 46992762 | 46998208 | H_c_216i09_M |
| 3 | 47025386 | 47026135 | H_c_230a16 |
| 3 | 47095997 | 47096273 | H_c_162k04 |
| 3 | 47167604 | 47167777 | H_c_229a04 |
| 3 | 47179503 | 47180677 | H_c_33d09 |
| 3 | 47298257 | 47300045 | H_c_93e10_M |
| 3 | 47396727 | 47398137 | H_c_254k20_M |

TABLE 1-continued

| | | | |
|---|---|---|---|
| 3 | 47491825 | 47492802 | H_c_42h20_M |
| 3 | 47529804 | 47530590 | H_c_35p21_M |
| 3 | 47818754 | 47820603 | H_c_52f11_M |
| 3 | 47841127 | 47842283 | H_c_64d17_M |
| 3 | 48104503 | 48106028 | H_c_211h05_M |
| 3 | 48317249 | 48318361 | H_c_101f17_M |
| 3 | 48445199 | 48447097 | H_c_57m18 |
| 3 | 48516072 | 48517561 | H_c_261k18_M |
| 3 | 48568616 | 48570330 | H_c_104h18 |
| 3 | 48621378 | 48622700 | H_c_218j21_M |
| 3 | 48647314 | 48648039 | H_c_207o09 |
| 3 | 48672887 | 48675772 | H_c_76a04 |
| 3 | 48676076 | 48677843 | H_c_224d02_M |
| 3 | 48697707 | 48698583 | H_c_165i08_M |
| 3 | 48729043 | 48730472 | H_c_182m20_M |
| 3 | 48765153 | 48765313 | H_c_218c18 |
| 3 | 4884178 | 4885844 | H_c_199j01_M |
| 3 | 48859478 | 48860527 | H_c_70i04 |
| 3 | 48910786 | 48911795 | H_c_214c04 |
| 3 | 48931071 | 48932061 | H_c139k12_M |
| 3 | 48955715 | 48955793 | H_c_73e09 |
| 3 | 49002394 | 49003584 | H_c_84n08_M |
| 3 | 49029657 | 49035033 | H_c144l18_M_M |
| 3 | 49040933 | 49042071 | H_c_269o12_M |
| 3 | 49105564 | 49106560 | H_c_74b15_M |
| 3 | 49116516 | 49117322 | H_c_162g02 |
| 3 | 49178129 | 49179475 | H_c_66j07 |
| 3 | 49288866 | 49289697 | H_c_116a08_M |
| 3 | 49352393 | 49353073 | H_c_207h20 |
| 3 | 49423813 | 49424962 | H_c_68l08_M |
| 3 | 49441471 | 49441827 | H_c_100p09_M |
| 3 | 49481841 | 49483518 | H_c_90l19 |
| 3 | 49552284 | 49552736 | H_c_87a19_M |
| 3 | 49566421 | 49567535 | H_c_249f14_M |
| 3 | 49639851 | 49641403 | H_c_21h21_M |
| 3 | 49735653 | 49737024 | H_c_172k23 |
| 3 | 49798214 | 49799966 | H_c_274l09_M |
| 3 | 49881938 | 49882439 | H_c_73b07 |
| 3 | 4994692 | 4996002 | H_c_182j04 |
| 3 | 49952150 | 49953444 | H_c140o13_M |
| 3 | 50101242 | 50102074 | H_c_106h13 |
| 3 | 50165929 | 50168360 | H_c_237b22_M |
| 3 | 50207012 | 50208493 | H_c135k15_M |
| 3 | 50217443 | 50217994 | H_c_62p13_M |
| 3 | 50217995 | 50219461 | H_c_211g04 |
| 3 | 50272227 | 50273866 | H_c_31i24_M |
| 3 | 50279876 | 50280062 | H_c_74a06 |
| 3 | 50304136 | 50305107 | H_c_249d15 |
| 3 | 50311355 | 50313084 | H_c_95m08_M |
| 3 | 50331648 | 50333936 | H_c_208j09_M |
| 3 | 50339055 | 50341056 | H_c_70n09_M |
| 3 | 50348727 | 50349873 | H_c_212k20_M |
| 3 | 50370499 | 50372449 | H_c_235j15_M |
| 3 | 50376638 | 50378277 | H_c_83e04_M |
| 3 | 5042341 | 5044024 | H_c_270a15_M |
| 3 | 50514569 | 50516424 | H_c_20l21_M |
| 3 | 50579899 | 50582136 | H_c_194m21_M |
| 3 | 50629152 | 50630897 | H_c_130b22_M |
| 3 | 50685805 | 50688093 | H_c_187i17_M |
| 3 | 50685877 | 50688096 | H_c_208j21 |
| 3 | 5112462 | 5113238 | H_c_69g19 |
| 3 | 51396649 | 51398407 | H_c_105k05_M |
| 3 | 51547244 | 51548249 | H_c_12n06_M |
| 3 | 51678236 | 51680631 | H_c_257j13 |
| 3 | 51715507 | 51717348 | H_c_70o14_M |
| 3 | 51982596 | 51984575 | H_c_224i06_M |
| 3 | 51991883 | 51992910 | H_c_56a06_M |
| 3 | 52004553 | 52005148 | H_c_212b02 |
| 3 | 5203917 | 5206047 | H_c_197c24_M |
| 3 | 52064252 | 52066795 | H_c_272k19_M |
| 3 | 52162303 | 52163546 | H_c_146g14_M |
| 3 | 52206850 | 52207188 | H_c_35m21 |
| 3 | 52285617 | 52288163 | H_c_249g22_M |
| 3 | 5235659 | 5235809 | H_c_51a03 |
| 3 | 52418297 | 52419957 | H_c_175b04 |
| 3 | 52463771 | 52466087 | H_c_151e13_M |
| 3 | 52541984 | 52544463 | H_c_259n21_M |
| 3 | 52545157 | 52545933 | H_c_214f10 |
| 3 | 52694374 | 52695294 | H_c_71h22_M |
| 3 | 52712997 | 52715234 | H_c_64e03_M |
| 3 | 52715236 | 52716323 | H_c_86h05_M |
| 3 | 52779518 | 52780424 | H_c_271m15 |
| 3 | 52906352 | 52907164 | H_c_79e18_M |
| 3 | 53053690 | 53056481 | H_c_147f20 |
| 3 | 53165316 | 53166525 | H_c_126b18_M |
| 3 | 53200530 | 53200767 | H_c_151n03 |
| 3 | 53264505 | 53265100 | H_c_208b21_M |
| 3 | 5334456 | 5334670 | H_c_32d07_M |
| 3 | 53356403 | 53358088 | H_c_259b21_M |
| 3 | 53504498 | 53505530 | H_c_150o16 |
| 3 | 53604188 | 53604271 | H_c_80i09 |
| 3 | 53854711 | 53856017 | H_c_19o05_M |
| 3 | 53887066 | 53887285 | H_c_208c22 |
| 3 | 53890695 | 53891748 | H_c_56n20_M |
| 3 | 53900520 | 53901097 | H_c_70k03_M |
| 3 | 54096641 | 54098087 | H_c_258c04_M |
| 3 | 54106587 | 54106719 | H_c_247f09 |
| 3 | 54132463 | 54133257 | H_c_184j12 |
| 3 | 5460605 | 5460939 | H_c_98d09 |
| 3 | 54950752 | 54950845 | H_c_228l20 |
| 3 | 552246 | 553088 | H_c_168i23 |
| 3 | 55493959 | 55497523 | H_c_274a05_M |
| 3 | 55648689 | 55648773 | H_c_39k14 |
| 3 | 55741693 | 55743027 | H_c_38h13 |
| 3 | 56030327 | 56030440 | H_c_83a02 |
| 3 | 56270042 | 56270180 | H_c_199m19 |
| 3 | 56325173 | 56325369 | H_c_222p03_M |
| 3 | 56476801 | 56477932 | H_c_26g08_M |
| 3 | 56691151 | 56692901 | H_c_112l24 |
| 3 | 56810364 | 56811403 | H_c_272c15 |
| 3 | 56900708 | 56900784 | H_c_111e19 |
| 3 | 57087652 | 57089063 | H_c_203l07 |
| 3 | 57165975 | 57166821 | H_c_256i15 |
| 3 | 57173278 | 57174580 | H_c_7d22_M |
| 3 | 57236396 | 57237405 | H_c_95n13_M |
| 3 | 57237409 | 57237662 | H_c_26f13_M |
| 3 | 57255670 | 57255774 | H_c_2d07 |
| 3 | 57516533 | 57517543 | H_c_266m04_M |
| 3 | 57653286 | 57654116 | H_c_155h12 |
| 3 | 57716927 | 57718215 | H_c_190j06_M |
| 3 | 57847716 | 57847838 | H_c_55k05_M |
| 3 | 57968277 | 57970448 | H_c_115n06_M |
| 3 | 58138420 | 58139238 | H_c_92a09 |
| 3 | 58198089 | 58198544 | H_c_70b14_M |
| 3 | 58292745 | 58294445 | H_c_15p03_M |
| 3 | 58394135 | 58394913 | H_c_29f09_M |
| 3 | 5843263 | 5843420 | H_c_251g13 |
| 3 | 58451778 | 58453382 | H_c_30d11_M |
| 3 | 58546262 | 58548120 | H_c_84k14_M |
| 3 | 59010241 | 59011307 | H_c_164h14_M |
| 3 | 59109243 | 59109332 | H_c_100e23 |
| 3 | 59546407 | 59546548 | H_c_84h14 |
| 3 | 61211630 | 61212488 | H_c_261b03 |
| 3 | 61521263 | 61524885 | H_c_202h21_M_M |
| 3 | 62004785 | 62004929 | H_c_85a14 |
| 3 | 62050097 | 62050232 | H_c134k24_M |
| 3 | 62279479 | 62279851 | H_c_269n06_M |
| 3 | 62329308 | 62330087 | H_c_6k17_M |
| 3 | 62332382 | 62334221 | H_c_79c10_M |
| 3 | 62337295 | 62338191 | H_c_75k02_M |
| 3 | 62617165 | 62617391 | H_c134i23 |
| 3 | 62767084 | 62767270 | H_c_125h22 |
| 3 | 62834351 | 62836121 | H_c_166i24_M |
| 3 | 63823416 | 63825397 | H_c_237f23_M |
| 3 | 63872321 | 63874198 | H_c_102f23_M |
| 3 | 63983734 | 63984424 | H_c_13k15_M |
| 3 | 64405900 | 64406538 | H_c_173j13 |
| 3 | 64646006 | 64647465 | H_c_69a20_M |
| 3 | 65316896 | 65317956 | H_c_159i10_M |
| 3 | 65455862 | 65456216 | H_c_217c13_M |
| 3 | 65509696 | 65510647 | H_c137g12 |
| 3 | 65631731 | 65631836 | H_c_227l23 |
| 3 | 65997854 | 66001006 | H_c_202o13_M |
| 3 | 6619755 | 6619897 | H_c_47c19 |
| 3 | 6636490 | 6636794 | H_c_235b11 |
| 3 | 66632440 | 66634454 | H_c_27n04 |
| 3 | 66834771 | 66835423 | H_c_204f24 |
| 3 | 66861716 | 66862076 | H_c_205m18 |
| 3 | 67131441 | 67131935 | H_c_268e19_M |
| 3 | 67632348 | 67632436 | H_c_116a21 |

TABLE 1-continued

| | | | |
|---|---|---|---|
| 3 | 67732870 | 67733004 | H_c_249i08 |
| 3 | 67787311 | 67787693 | H_c_193k23_M |
| 3 | 68113258 | 68113350 | H_c_266k03 |
| 3 | 6877772 | 6879905 | H_c_95b17_M |
| 3 | 68896055 | 68896244 | H_c_213b06 |
| 3 | 69063966 | 69064852 | H_c_68o19 |
| 3 | 69144759 | 69145873 | H_c_119j15_M |
| 3 | 69211607 | 69212357 | H_c_54b10_M |
| 3 | 69216897 | 69217415 | H_c_97k12 |
| 3 | 69517568 | 69518869 | H_c_181h03_M |
| 3 | 69673319 | 69675260 | H_c_9g23 |
| 3 | 70161865 | 70161949 | H_c_120a11 |
| 3 | 70189857 | 70189943 | H_c_140l22_M |
| 3 | 70546363 | 70546504 | H_c_50e09 |
| 3 | 7099383 | 7099501 | H_c_7b06_M |
| 3 | 71196541 | 71197004 | H_c_83l02_M |
| 3 | 71234747 | 71234863 | H_c_120p21 |
| 3 | 71291797 | 71292206 | H_c_66i22 |
| 3 | 71715344 | 71716269 | H_c_67j16_M |
| 3 | 71856254 | 71858033 | H_c_161l11_M |
| 3 | 71885027 | 71887044 | H_c_189b02_M |
| 3 | 72408769 | 72408943 | H_c_120l12 |
| 3 | 72420190 | 72420463 | H_c_171h04 |
| 3 | 72441741 | 72441852 | H_c_128h22 |
| 3 | 72578381 | 72578920 | H_c_80a19_M |
| 3 | 72614546 | 72615192 | H_c_160e15 |
| 3 | 7274995 | 7275171 | H_c_237k24 |
| 3 | 72870616 | 72871014 | H_c_67d19 |
| 3 | 728911 | 729040 | H_c_20g02 |
| 3 | 72979834 | 72980502 | H_c_56k23_M |
| 3 | 73019251 | 73020487 | H_c_82a20_M |
| 3 | 73755442 | 73757481 | H_c_212b23_M |
| 3 | 74508704 | 74508795 | H_c_31i06_M |
| 3 | 74745929 | 74746817 | H_c_49n02_M |
| 3 | 7519317 | 7519407 | H_c_216p15_M |
| 3 | 75922285 | 75922549 | H_c_82f01 |
| 3 | 76043143 | 76043258 | H_c_220m10 |
| 3 | 76242177 | 76242262 | H_c_178c11 |
| 3 | 7639385 | 7639736 | H_c_204b15 |
| 3 | 76714854 | 76715051 | H_c_213f10 |
| 3 | 76816759 | 76816936 | H_c_147b05 |
| 3 | 77171330 | 77172070 | H_c_241c03 |
| 3 | 77253572 | 77253686 | H_c_265k20 |
| 3 | 77538527 | 77538733 | H_c_172f07 |
| 3 | 77732479 | 77732574 | H_c_39m11 |
| 3 | 7843200 | 7843288 | H_c_232i02 |
| 3 | 788246 | 788370 | H_c_231f02 |
| 3 | 78921867 | 78922161 | H_c_93k17 |
| 3 | 78950819 | 78951086 | H_c_17c22 |
| 3 | 79277674 | 79277782 | H_c_111n15 |
| 3 | 79334747 | 79334903 | H_c_256g19 |
| 3 | 79804203 | 79804279 | H_c_39m06 |
| 3 | 79869290 | 79869379 | H_c132a23 |
| 3 | 79898047 | 79898855 | H_c_56h09_M |
| 3 | 80344052 | 80344194 | H_c_114p23_M |
| 3 | 80389240 | 80389349 | H_c_49d16 |
| 3 | 80575353 | 80575605 | H_c_212p02 |
| 3 | 80621697 | 80621795 | H_c_129n03 |
| 3 | 81593925 | 81594002 | H_c_196f09 |
| 3 | 81620793 | 81620915 | H_c_41d13 |
| 3 | 81892796 | 81893687 | H_c_18k14_M |
| 3 | 83616614 | 83616767 | H_c_84f11 |
| 3 | 8518246 | 8518481 | H_c_73d23_M |
| 3 | 85676106 | 85676213 | H_c_111i10 |
| 3 | 85970078 | 85970207 | H_c_266j12 |
| 3 | 86615094 | 86615247 | H_c_33h08_M |
| 3 | 86692143 | 86692223 | H_c_24o01 |
| 3 | 86827110 | 86827184 | H_c_59a24 |
| 3 | 87095740 | 87095905 | H_c_197e04 |
| 3 | 87113517 | 87113627 | H_c_176a15 |
| 3 | 87121869 | 87123431 | H_c_216l11_M |
| 3 | 87358512 | 87359357 | H_c_210d18_M |
| 3 | 87616835 | 87617078 | H_c_6p21 |
| 3 | 8766846 | 8767104 | H_c_84p07 |
| 3 | 8771718 | 8771839 | H_c143b16 |
| 3 | 8783782 | 8785447 | H_c_10m17_M |
| 3 | 88189848 | 88191940 | H_c_145e11_M |
| 3 | 88483242 | 88483466 | H_c_216k24 |
| 3 | 88609656 | 88609738 | H_c_164b01 |
| 3 | 88679810 | 88679950 | H_c_130a07_M |
| 3 | 88930345 | 88930715 | H_c_11n19 |
| 3 | 89402019 | 89402335 | H_c_195l17 |
| 3 | 8979932 | 8980233 | H_c_202k12_M |
| 3 | 89927776 | 89927910 | H_c_18m19 |
| 3 | 89959600 | 89959684 | H_c_187a12 |
| 3 | 90416349 | 90416594 | H_c_192e05 |
| 3 | 9152606 | 9153269 | H_c133c04 |
| 3 | 95174735 | 95175730 | H_c_16j20 |
| 3 | 95181170 | 95182200 | H_c_92i08_M |
| 3 | 95230444 | 95230570 | H_c_181k01 |
| 3 | 95264084 | 95265056 | H_c_66i08_M |
| 3 | 9569937 | 9570911 | H_c_186g07_M |
| 3 | 95729394 | 95729474 | H_c_31g10 |
| 3 | 9617257 | 9619713 | H_c_187k03_M |
| 3 | 96545883 | 96545971 | H_c_175a22 |
| 3 | 9665596 | 9667339 | H_c_38b23_M |
| 3 | 9720121 | 9722516 | H_c_92e08_M |
| 3 | 9747478 | 9749353 | H_c_74d21_M |
| 3 | 97587399 | 97587633 | H_c_184d09 |
| 3 | 97599383 | 97599485 | H_c_129b08 |
| 3 | 97725932 | 97726051 | H_c_11j17 |
| 3 | 9786093 | 9786826 | H_c_129a07 |
| 3 | 98014751 | 98016864 | H_c131o17_M |
| 3 | 9808982 | 9809582 | H_c_227j10 |
| 3 | 98106146 | 98106216 | H_c_19c10 |
| 3 | 9826149 | 9827460 | H_c_49j14_M |
| 3 | 98385222 | 98385348 | H_c_29c20 |
| 3 | 98847476 | 98847632 | H_c_157i08 |
| 3 | 98965773 | 98966533 | H_c_265c15 |
| 3 | 99022854 | 99024089 | H_c_188d24_M |
| 3 | 9907170 | 9907873 | H_c_240g23 |
| 3 | 99173027 | 99174344 | H_c_118c06_M |
| 3 | 99201109 | 99201276 | H_c_86c21 |
| 3 | 99207609 | 99207737 | H_c_42d14 |
| 3 | 9931615 | 9934435 | H_c_101a05_M |
| 3 | 9949228 | 9951289 | H_c_39o22_M |
| 3 | 99794209 | 99795697 | H_c_8k05_M |
| 3 | 99933590 | 99934873 | H_c_10d06_M |
| 4 | 100163417 | 100163489 | H_c_128e15 |
| 4 | 100206399 | 100207619 | H_c_76o06_M |
| 4 | 100273529 | 100274799 | H_c_31a16 |
| 4 | 100366677 | 100366715 | H_c134j08 |
| 4 | 100727461 | 100727587 | H_c_215f10 |
| 4 | 100788230 | 100788429 | H_c_58d07 |
| 4 | 10085023 | 10085136 | H_c_235j03_M |
| 4 | 101172722 | 101173103 | H_c_106g17_M |
| 4 | 101224244 | 101225598 | H_c_2f18_M |
| 4 | 10134231 | 10135948 | H_c_120p05_M |
| 4 | 101411970 | 101412132 | H_c_64l06_M |
| 4 | 101436424 | 101436494 | H_c_212h20 |
| 4 | 101467986 | 101469143 | H_c_42g11 |
| 4 | 101491865 | 101492018 | H_c_189d22 |
| 4 | 102337666 | 102337797 | H_c_21d15 |
| 4 | 102584359 | 102584540 | H_c_235j09_M |
| 4 | 102624644 | 102627300 | H_c_74e06_M |
| 4 | 10285750 | 10285868 | H_c_202d03_M |
| 4 | 103068686 | 103069619 | H_c_17j12 |
| 4 | 103590906 | 103591013 | H_c_201d18 |
| 4 | 103622605 | 103624148 | H_c_227j11_M |
| 4 | 10373027 | 10373122 | H_c_19k22 |
| 4 | 103779183 | 103780438 | H_c_26h19_M |
| 4 | 104038684 | 104040033 | H_c_51d19_M |
| 4 | 104147561 | 104148284 | H_c_2i18_M |
| 4 | 104298341 | 104298521 | H_c_166l07_M |
| 4 | 104354745 | 104355683 | H_c_106m04_M |
| 4 | 104438379 | 104438476 | H_c_91c23 |
| 4 | 104476826 | 104477295 | H_c_106l15_M |
| 4 | 105325476 | 105325587 | H_c_153j13_M |
| 4 | 105769200 | 105770866 | H_c_199l22 |
| 4 | 106079555 | 106079733 | H_c_22i09 |
| 4 | 106424776 | 106425892 | H_c_38e20_M |
| 4 | 106751900 | 106753050 | H_c_191h23_M |
| 4 | 106986855 | 106988111 | H_c_10h09 |
| 4 | 107173457 | 107175441 | H_c_265e17 |
| 4 | 107335279 | 107335502 | H_c_81m01 |
| 4 | 107856430 | 107856626 | H_c_129i16 |
| 4 | 108313900 | 108316401 | H_c_86j16_M |
| 4 | 10860454 | 10860558 | H_c_161m09 |
| 4 | 108998290 | 108999528 | H_c_161j14_M |
| 4 | 109103466 | 109104270 | H_c_68k17_M |

TABLE 1-continued

| | | | |
|---|---|---|---|
| 4 | 109202726 | 109202816 | H_c_27d07_M |
| 4 | 109209549 | 109211069 | H_c_252o13_M |
| 4 | 109268177 | 109269217 | H_c_18h15_M |
| 4 | 109340384 | 109340557 | H_c_30i03 |
| 4 | 109447232 | 109448299 | H_c_124d01 |
| 4 | 109451166 | 109452887 | H_c_14c23_M |
| 4 | 109507072 | 109507189 | H_c_274m16 |
| 4 | 109518016 | 109518246 | H_c_219h06 |
| 4 | 109831481 | 109831554 | H_c_9c03 |
| 4 | 109899023 | 109899914 | H_c_54k01_M |
| 4 | 11002918 | 11003074 | H_c_190f20_M |
| 4 | 110041150 | 110041840 | H_c_127a15 |
| 4 | 110331300 | 110331483 | H_c_200k03_M |
| 4 | 110580259 | 110581442 | H_c_161f08_M |
| 4 | 110701278 | 110701437 | H_c_222e03 |
| 4 | 110712018 | 110713307 | H_c_117b17_M |
| 4 | 110838717 | 110840013 | H_c_5h11_M |
| 4 | 110981794 | 110982520 | H_c_108b06_M |
| 4 | 111008235 | 111009031 | H_c_234g07 |
| 4 | 11105054 | 11107694 | H_c_198i24 |
| 4 | 111474994 | 111476000 | H_c_274d09_M |
| 4 | 111890047 | 111890706 | H_c_189a15 |
| 4 | 111899541 | 111901862 | H_c_77n08_M |
| 4 | 111910937 | 111912077 | H_c_217e22_M |
| 4 | 112288902 | 112288974 | H_c_10j11 |
| 4 | 112758429 | 112758638 | H_c_233h19 |
| 4 | 112921957 | 112922055 | H_c143a21 |
| 4 | 113066983 | 113067091 | H_c_239l07_M |
| 4 | 113423409 | 113425084 | H_c_106p14_M |
| 4 | 113510100 | 113511269 | H_c_50g21_M |
| 4 | 113793071 | 113795631 | H_c_46a05_M |
| 4 | 113801309 | 113803043 | H_c_124b03_M |
| 4 | 113914973 | 113915135 | H_c_201a15_M |
| 4 | 113983897 | 113985670 | H_c_75m09_M |
| 4 | 114275537 | 114275628 | H_c_274n14 |
| 4 | 114481144 | 114481262 | H_c_179c18 |
| 4 | 114942723 | 114942957 | H_c_220p02_M |
| 4 | 1149678 | 1151781 | H_c_115e24_M |
| 4 | 115039609 | 115040799 | H_c_189j22_M |
| 4 | 115173809 | 115173961 | H_c_63l10 |
| 4 | 115195221 | 115195546 | H_c_188c04 |
| 4 | 115257686 | 115259009 | H_c_99h05 |
| 4 | 1156127 | 1156227 | H_c_85m20 |
| 4 | 115876935 | 115878676 | H_c_105h13_M |
| 4 | 117615929 | 117616109 | H_c_66h12 |
| 4 | 117743026 | 117743193 | H_c_40a07 |
| 4 | 118016454 | 118016594 | H_c_25e06 |
| 4 | 118204635 | 118205349 | H_c_113c03 |
| 4 | 118631178 | 118631330 | H_c_97m05 |
| 4 | 118741525 | 118741759 | H_c_229k20 |
| 4 | 118749739 | 118749850 | H_c_79l11 |
| 4 | 119311842 | 119312813 | H_c_49l01 |
| 4 | 119557664 | 119557929 | H_c137i08_M |
| 4 | 119630592 | 119632172 | H_c_28c02 |
| 4 | 119963872 | 119964463 | H_c_178a14_M |
| 4 | 120114528 | 120115108 | H_c_109b17_M |
| 4 | 120490862 | 120492030 | H_c_158i19 |
| 4 | 120579338 | 120579768 | H_c_31a07_M |
| 4 | 120905743 | 120908067 | H_c_15n22_M |
| 4 | 121245787 | 121245892 | H_c_258d19 |
| 4 | 121252934 | 121253072 | H_c_23m17 |
| 4 | 121470273 | 121470928 | H_c_112c19 |
| 4 | 121542265 | 121542424 | H_c_211o14 |
| 4 | 121642088 | 121642319 | H_c_43e03 |
| 4 | 12216976 | 12217049 | H_c_19k14 |
| 4 | 122200833 | 122202070 | H_c135k21_M |
| 4 | 122351083 | 122351723 | H_c_206b04 |
| 4 | 122922744 | 122922922 | H_c_31g20 |
| 4 | 122949565 | 122949823 | H_c_226a06 |
| 4 | 122974893 | 122976279 | H_c_86j07_M |
| 4 | 122990094 | 122991614 | H_c_214b09 |
| 4 | 123043239 | 123044231 | H_c_22c03 |
| 4 | 123078646 | 123078813 | H_c_202j22 |
| 4 | 123101864 | 123102878 | H_c_19m22_M |
| 4 | 123229375 | 123231041 | H_c_83n17_M |
| 4 | 123277826 | 123277933 | H_c_166l12 |
| 4 | 123287253 | 123287384 | H_c_198d23 |
| 4 | 123430811 | 123431719 | H_c_43i23_M |
| 4 | 123660659 | 123660722 | H_c_71d15 |
| 4 | 123857999 | 123858411 | H_c_79k02 |
| 4 | 124105201 | 124106563 | H_c_166i07_M |
| 4 | 124200753 | 124201344 | H_c_5a12_M |
| 4 | 124449798 | 124449962 | H_c_40l23_M |
| 4 | 124676078 | 124677835 | H_c_182m13_M |
| 4 | 124784501 | 124784751 | H_c138a08 |
| 4 | 124894658 | 124894931 | H_c_32b15_M |
| 4 | 125990539 | 125991958 | H_c_228m05 |
| 4 | 126324491 | 126324639 | H_c_206j22 |
| 4 | 126593249 | 126595897 | H_c137l16_M |
| 4 | 126713926 | 126714017 | H_c_73g05 |
| 4 | 126801758 | 126801851 | H_c_63c17 |
| 4 | 126884844 | 126884933 | H_c_161o07 |
| 4 | 127855793 | 127855901 | H_c_187h13 |
| 4 | 12794278 | 12794385 | H_c_6e09 |
| 4 | 128057727 | 128058029 | H_c_54a12 |
| 4 | 128228877 | 128228983 | H_c_180j14_M |
| 4 | 128251713 | 128251956 | H_c_113a10 |
| 4 | 1284708 | 1285025 | H_c_68j21 |
| 4 | 128911491 | 128911965 | H_c_126g10 |
| 4 | 129060244 | 129061477 | H_c_128e11_M |
| 4 | 129159455 | 129160573 | H_c_13f15_M |
| 4 | 129242705 | 129244935 | H_c_234j20_M |
| 4 | 129339368 | 129341489 | H_c_160j03_M |
| 4 | 129565778 | 129567418 | H_c_265k22_M |
| 4 | 129885145 | 129885301 | H_c_30b18 |
| 4 | 130088401 | 130091442 | H_c_207b18_M |
| 4 | 130100699 | 130100810 | H_c_12o22 |
| 4 | 13153088 | 13153185 | H_c_76f01 |
| 4 | 13161773 | 13162438 | H_c_97a08 |
| 4 | 13200080 | 13201492 | H_c_117b02_M |
| 4 | 13213892 | 13214135 | H_c_259p05 |
| 4 | 132160106 | 132160206 | H_c_265m14 |
| 4 | 13219597 | 13223057 | H_c_124d15_M |
| 4 | 13224704 | 13225936 | H_c_41g07 |
| 4 | 13271448 | 13271673 | H_c_2f03_M |
| 4 | 132802788 | 132802947 | H_c_236b08 |
| 4 | 1329834 | 1331440 | H_c_47e21_M |
| 4 | 13305067 | 13306304 | H_c_3f16_M |
| 4 | 133524497 | 133524722 | H_c_165k02 |
| 4 | 133884059 | 133884291 | H_c_244f05_M |
| 4 | 134427709 | 134431410 | H_c_114m17_M |
| 4 | 135115876 | 135115968 | H_c_85i02 |
| 4 | 135303035 | 135303039 | H_c_247b14 |
| 4 | 13535419 | 13535702 | H_c_147i04 |
| 4 | 135480166 | 135480564 | H_c_209d22_M |
| 4 | 135555106 | 135555398 | H_c_179i10 |
| 4 | 135807577 | 135807780 | H_c143f20 |
| 4 | 136060461 | 136060581 | H_c_254d11 |
| 4 | 136169257 | 136169402 | H_c_45o08 |
| 4 | 136485766 | 136485841 | H_c_163g06 |
| 4 | 136990904 | 136990975 | H_c_121i20 |
| 4 | 136994540 | 136994632 | H_c_195o06 |
| 4 | 137227989 | 137228081 | H_c_80c11 |
| 4 | 13754966 | 13757577 | H_c_221k19 |
| 4 | 138449855 | 138450049 | H_c_25p20 |
| 4 | 1386459 | 1389111 | H_c142h18_M |
| 4 | 138939956 | 138940099 | H_c_274i06 |
| 4 | 1390565 | 1391587 | H_c_62o16_M |
| 4 | 139342388 | 139343056 | H_c_8p09 |
| 4 | 139703297 | 139703453 | H_c_85o19 |
| 4 | 1397740 | 1398063 | H_c132b04_M |
| 4 | 1398280 | 1399271 | H_c_35p16_M |
| 4 | 139907631 | 139907840 | H_c_181m15 |
| 4 | 139960649 | 139960781 | H_c_119k08 |
| 4 | 140099432 | 140099570 | H_c_122a11 |
| 4 | 140294417 | 140295215 | H_c_7k03 |
| 4 | 140362239 | 140363453 | H_c_145c09_M |
| 4 | 140418688 | 140418882 | H_c_51d02 |
| 4 | 140558575 | 140559264 | H_c_95b09 |
| 4 | 140579865 | 140580335 | H_c_106c16 |
| 4 | 140731871 | 140733441 | H_c_86g12_M |
| 4 | 140736378 | 140736527 | H_c_7f11 |
| 4 | 140834088 | 140836172 | H_c_201l03_M |
| 4 | 141013806 | 141014935 | H_c_151e23_M |
| 4 | 141090300 | 141090450 | H_c_33a11 |
| 4 | 141198545 | 141198694 | H_c141p15 |
| 4 | 141384045 | 141384147 | H_c_234d05 |
| 4 | 141531363 | 141532379 | H_c_16i06_M |
| 4 | 14154298 | 14154431 | H_c_200b03 |
| 4 | 141662499 | 141662634 | H_c133p02_M |

TABLE 1-continued

| | | | |
|---|---|---|---|
| 4 | 141776225 | 141777196 | H_c_27e14_M |
| 4 | 141802557 | 141803438 | H_c_173i14_M |
| 4 | 141811108 | 141811270 | H_c_74h12 |
| 4 | 141847094 | 141848144 | H_c_249b07 |
| 4 | 142034447 | 142035655 | H_c_121p15_M |
| 4 | 142410947 | 142412389 | H_c_73m24_M |
| 4 | 142611190 | 142612567 | H_c_218d14 |
| 4 | 143073098 | 143073196 | H_c_267m01 |
| 4 | 144042966 | 144043058 | H_c_9n05 |
| 4 | 144124470 | 144126301 | H_c_166i15_M |
| 4 | 144306179 | 144306323 | H_c_111n11 |
| 4 | 144463220 | 144464993 | H_c_18e17_M |
| 4 | 144614561 | 144616118 | H_c_50n20_M |
| 4 | 144791697 | 144793073 | H_c_163i11_M |
| 4 | 145108529 | 145108601 | H_c_62j12 |
| 4 | 145190268 | 145191202 | H_c_59d19 |
| 4 | 14540689 | 14541015 | H_c_270g19 |
| 4 | 145923907 | 145925996 | H_c_8k14_M |
| 4 | 146376373 | 146377897 | H_c_245p11_M |
| 4 | 146458993 | 146459746 | H_c_172g19 |
| 4 | 146745831 | 146745903 | H_c144f03 |
| 4 | 146760217 | 146761728 | H_c_94k17 |
| 4 | 14679023 | 14683154 | H_c_175g24_M |
| 4 | 146897703 | 146898389 | H_c_103e07_M |
| 4 | 147011547 | 147012383 | H_c_42c03_M |
| 4 | 147214747 | 147216713 | H_c_147p22_M |
| 4 | 147379932 | 147380050 | H_c_99n01 |
| 4 | 147799484 | 147801913 | H_c_161g20_M |
| 4 | 147915825 | 147918210 | H_c_238g19_M |
| 4 | 147918506 | 147919779 | H_c_8p20_M |
| 4 | 147933460 | 147934569 | H_c_170j13_M |
| 4 | 1481158 | 1482493 | H_c_161d05 |
| 4 | 148223982 | 148225214 | H_c_99j24 |
| 4 | 148273412 | 148273749 | H_c_32e04 |
| 4 | 148759644 | 148760698 | H_c_188o23_M |
| 4 | 148962440 | 148963408 | H_c_89b21_M |
| 4 | 149011178 | 149011694 | H_c_72c23 |
| 4 | 1490114 | 1490270 | H_c_88k01_M |
| 4 | 149721996 | 149724727 | H_c_91d04_M |
| 4 | 1503590 | 1503823 | H_c_17n15_M |
| 4 | 15084725 | 15084857 | H_c_30j07 |
| 4 | 151356997 | 151358352 | H_c_162k03_M |
| 4 | 151401646 | 151401849 | H_c_129a14 |
| 4 | 152293644 | 152294795 | H_c134n20_M |
| 4 | 152377742 | 152378934 | H_c_38g13_M |
| 4 | 152603880 | 152604325 | H_c_2j08_M |
| 4 | 152687380 | 152688817 | H_c_11e12_M |
| 4 | 152944594 | 152944784 | H_c_15l11 |
| 4 | 153039851 | 153039977 | H_c_119c21 |
| 4 | 15332344 | 15334082 | H_c_123f13_M |
| 4 | 15359080 | 15359324 | H_c_73p11 |
| 4 | 153790115 | 153790212 | H_c_34o06_M |
| 4 | 15380583 | 15383439 | H_c_249g12_M |
| 4 | 153958404 | 153959613 | H_c_122f19 |
| 4 | 154057945 | 154059591 | H_c_125a02_M |
| 4 | 154179712 | 154179854 | H_c_231c15 |
| 4 | 154283651 | 154283775 | H_c_215j09_M |
| 4 | 154354385 | 154354500 | H_c_22l19 |
| 4 | 154432075 | 154432651 | H_c_13f18_M |
| 4 | 154500948 | 154502173 | H_c_243m05_M |
| 4 | 154527850 | 154528449 | H_c_105k14 |
| 4 | 15456124 | 15457013 | H_c_274l12_M |
| 4 | 154623181 | 154623931 | H_c_7e09_M |
| 4 | 154744172 | 154745933 | H_c_196c22 |
| 4 | 1547548 | 1549159 | H_c_196g11_M |
| 4 | 154838585 | 154838790 | H_c_195d10 |
| 4 | 154962593 | 154963947 | H_c_204a14_M |
| 4 | 155013771 | 155013940 | H_c_50g16 |
| 4 | 155017303 | 155017414 | H_c_168c14 |
| 4 | 155037931 | 155039641 | H_c_77f04_M |
| 4 | 15505349 | 15505618 | H_c_195g04 |
| 4 | 155069178 | 155070447 | H_c_120p11 |
| 4 | 155694693 | 155694825 | H_c_233f08 |
| 4 | 155770370 | 155771110 | H_c_8i05_M |
| 4 | 155828522 | 155829403 | H_c136d09_M |
| 4 | 15583849 | 15584364 | H_c_219o19_M |
| 4 | 155901276 | 155901539 | H_c_274o12_M |
| 4 | 156022527 | 156023014 | H_c_122j01_M |
| 4 | 156059919 | 156060961 | H_c_42p18 |
| 4 | 156655236 | 156655967 | H_c_273c21_M |
| 4 | 156837411 | 156837572 | H_c_210i14 |
| 4 | 156945370 | 156947098 | H_c133h19_M |
| 4 | 156991166 | 156991320 | H_c_272l13 |
| 4 | 157231975 | 157233388 | H_c_85p07 |
| 4 | 157403319 | 157403474 | H_c_149b12_M |
| 4 | 15760284 | 15761856 | H_c_73f13 |
| 4 | 157967239 | 157967448 | H_c_187o13 |
| 4 | 158249911 | 158251197 | H_c132i02_M |
| 4 | 158354507 | 158355654 | H_c_56j09_M |
| 4 | 158498784 | 158499958 | H_c_1d01_M |
| 4 | 158500119 | 158501298 | H_c_163h18 |
| 4 | 15862699 | 15862828 | H_c135a01 |
| 4 | 158747233 | 158748308 | H_c_201e06 |
| 4 | 15903783 | 15905582 | H_c137g19_M |
| 4 | 159126340 | 159126502 | H_c_129m19 |
| 4 | 159269696 | 159269794 | H_c_183l24 |
| 4 | 15929943 | 15930085 | H_c_135c12 |
| 4 | 159510682 | 159510810 | H_c_146m18 |
| 4 | 159536826 | 159536929 | H_c_29k12 |
| 4 | 159635386 | 159635545 | H_c_259b08 |
| 4 | 159777886 | 159778075 | H_c_229c02 |
| 4 | 159798186 | 159798279 | H_c_85e10 |
| 4 | 160047215 | 160047432 | H_c143g06_M |
| 4 | 160381121 | 160383198 | H_c142i20_M |
| 4 | 160452083 | 160452287 | H_c_158g03 |
| 4 | 160682539 | 160682807 | H_c_56i15 |
| 4 | 160814636 | 160814835 | H_c_244p03 |
| 4 | 160919905 | 160920057 | H_c_122a09 |
| 4 | 161167155 | 161167229 | H_c_145g22 |
| 4 | 161531705 | 161532781 | H_c_102j15_M |
| 4 | 161898518 | 161898658 | H_c_202f19 |
| 4 | 162515077 | 162515163 | H_c_71b24 |
| 4 | 162593991 | 162594133 | H_c_115g13 |
| 4 | 162790004 | 162790121 | H_c142j13 |
| 4 | 163120334 | 163120416 | H_c_97f14 |
| 4 | 163442946 | 163443430 | H_c_96b07 |
| 4 | 163466805 | 163466944 | H_c_163p08 |
| 4 | 163918133 | 163918235 | H_c_70j22 |
| 4 | 164444643 | 164446267 | H_c_206m02_M |
| 4 | 164560483 | 164560623 | H_c_57d12 |
| 4 | 164610569 | 164611881 | H_c_82e21_M |
| 4 | 164622420 | 164623464 | H_c_61i01_M |
| 4 | 164717271 | 164717467 | H_c_4j08 |
| 4 | 1652710 | 1654923 | H_c_53e08 |
| 4 | 16532262 | 16532384 | H_c_109j13 |
| 4 | 165471278 | 165471378 | H_c_209a10 |
| 4 | 165661974 | 165662991 | H_c_40d17 |
| 4 | 165945156 | 165945337 | H_c_58j20_M |
| 4 | 166390897 | 166391843 | H_c_254d06_M |
| 4 | 166485616 | 166486853 | H_c_230f03_M |
| 4 | 166605977 | 166606725 | H_c_74d01_M |
| 4 | 166657501 | 166659147 | H_c_24l14_M |
| 4 | 166957671 | 166957745 | H_c_5n13 |
| 4 | 166962994 | 166963197 | H_c_16i01 |
| 4 | 166982237 | 166982331 | H_c_166p09 |
| 4 | 167016232 | 167016333 | H_c_83p18 |
| 4 | 167152069 | 167153516 | H_c_62o08_M |
| 4 | 167447326 | 167447458 | H_c_27e16_M |
| 4 | 167565488 | 167565647 | H_c_147d20 |
| 4 | 1680011 | 1681837 | H_c_205b20_M |
| 4 | 168826345 | 168826423 | H_c_94p24 |
| 4 | 169346355 | 169346511 | H_c_74c14 |
| 4 | 169666266 | 169666416 | H_c_21n18 |
| 4 | 169735182 | 169735334 | H_c_10b19_M |
| 4 | 169748077 | 169748272 | H_c_7g05 |
| 4 | 169827679 | 169827789 | H_c_217k23 |
| 4 | 169927059 | 169927643 | H_c_192j21 |
| 4 | 170127678 | 170129323 | H_c_272d07_M |
| 4 | 170173383 | 170174426 | H_c_184d18_M |
| 4 | 170306042 | 170306774 | H_c_158k11_M |
| 4 | 170566066 | 170566362 | H_c_110i14_M |
| 4 | 170907985 | 170908716 | H_c_210d11_M |
| 4 | 170915489 | 170916620 | H_c_154o03_M |
| 4 | 171321494 | 171322829 | H_c134i05_M |
| 4 | 171384632 | 171386492 | H_c_184i15_M |
| 4 | 171429512 | 171430720 | H_c_110h11 |
| 4 | 171765764 | 171765879 | H_c_41k11 |
| 4 | 171877625 | 171877798 | H_c142m12 |
| 4 | 17189332 | 17190262 | H_c_253e23_M |
| 4 | 172360131 | 172360219 | H_c_170e10 |

TABLE 1-continued

| | | | |
|---|---|---|---|
| 4 | 17253991 | 17255579 | H_c__155j19 |
| 4 | 17255581 | 17255887 | H_c__6g19__M |
| 4 | 172586136 | 172586225 | H_c132h23 |
| 4 | 173038893 | 173038987 | H_c__65o10 |
| 4 | 173108709 | 173110177 | H_c__81a07__M |
| 4 | 173261956 | 173262151 | H_c131m06 |
| 4 | 173791034 | 173791266 | H_c__174b16 |
| 4 | 173958318 | 173958432 | H_c__183a12 |
| 4 | 174417681 | 174417761 | H_c__23j19 |
| 4 | 174463997 | 174466204 | H_c141k11__M |
| 4 | 174468268 | 174468433 | H_c__50o20 |
| 4 | 17459166 | 17460359 | H_c__204p17__M |
| 4 | 174629259 | 174630464 | H_c__197j22__M |
| 4 | 174665606 | 174668259 | H_c__2b02__M |
| 4 | 174796792 | 174797562 | H_c__212f13 |
| 4 | 174803500 | 174805851 | H_c__36i09 |
| 4 | 174815291 | 174815419 | H_c__144j04 |
| 4 | 174817660 | 174818731 | H_c138b20__M |
| 4 | 174820922 | 174825783 | H_c__237b10__M__M |
| 4 | 174827120 | 174827813 | H_c__19e03 |
| 4 | 174832558 | 174834170 | H_c__155k14 |
| 4 | 17488147 | 17489639 | H_c__241f09__M |
| 4 | 175078583 | 175078681 | H_c__29g03 |
| 4 | 175647088 | 175647329 | H_c__213m23 |
| 4 | 175791246 | 175791530 | H_c__84p04 |
| 4 | 175818253 | 175818559 | H_c__34l22__M |
| 4 | 176125130 | 176125268 | H_c__165o15__M |
| 4 | 176365344 | 176365611 | H_c__179f19 |
| 4 | 176657798 | 176658001 | H_c144f05 |
| 4 | 176862467 | 176862611 | H_c__13c03 |
| 4 | 176969954 | 176970124 | H_c__218h09 |
| 4 | 176983243 | 176983504 | H_c__204k09 |
| 4 | 17698837 | 17700394 | H_c__104i23 |
| 4 | 177394156 | 177394280 | H_c__35d10 |
| 4 | 177615907 | 177616750 | H_c__185f08__M |
| 4 | 178088374 | 178090152 | H_c__230i09 |
| 4 | 178255975 | 178256204 | H_c__8d01 |
| 4 | 178488625 | 178488725 | H_c__114p24 |
| 4 | 178596118 | 178596450 | H_c132p15 |
| 4 | 178606047 | 178606488 | H_c__94e13 |
| 4 | 178738740 | 178738914 | H_c__91e10 |
| 4 | 178875645 | 178875846 | H_c__15l22 |
| 4 | 179908384 | 179908571 | H_c__39g03 |
| 4 | 180289011 | 180289264 | H_c__220p09 |
| 4 | 180568788 | 180565922 | H_c__95e18 |
| 4 | 181343134 | 181343266 | H_c__66e18 |
| 4 | 181354069 | 181355814 | H_c131e07__M |
| 4 | 181545481 | 181545553 | H_c__7b08 |
| 4 | 181618538 | 181618683 | H_c144e23__M |
| 4 | 181704362 | 181704495 | H_c__95c03__M |
| 4 | 182011834 | 182012075 | H_c__182f10 |
| 4 | 182196585 | 182196692 | H_c__18i09 |
| 4 | 1824195 | 1826149 | H_c__123n22__M |
| 4 | 182868412 | 182868628 | H_c__117k02 |
| 4 | 183091138 | 183091306 | H_c__106a06 |
| 4 | 183146336 | 183146466 | H_c__202m13 |
| 4 | 183438842 | 183441446 | H_c__114n19__M |
| 4 | 183744466 | 183745629 | H_c__55l20__M |
| 4 | 1838798 | 1841296 | H_c__125j07 |
| 4 | 184084815 | 184084920 | H_c__64i14 |
| 4 | 184102540 | 184102967 | H_c__145a21__M |
| 4 | 184125040 | 184126125 | H_c__251d16 |
| 4 | 184213092 | 184214161 | H_c__14d06 |
| 4 | 184394290 | 184396415 | H_c__82f06__M |
| 4 | 184694562 | 184694941 | H_c__8c14 |
| 4 | 184740205 | 184741643 | H_c__237p23__M |
| 4 | 184800331 | 184802719 | H_c__243l12__M |
| 4 | 185019212 | 185019951 | H_c__155g06 |
| 4 | 185061662 | 185061896 | H_c__31j04 |
| 4 | 185093359 | 185094926 | H_c__241k07 |
| 4 | 185201480 | 185203839 | H_c__64d21__M |
| 4 | 185461163 | 185461495 | H_c__247g16 |
| 4 | 185464640 | 185465352 | H_c__250f03 |
| 4 | 185579949 | 185580663 | H_c__75f23 |
| 4 | 185770372 | 185771756 | H_c__198g09__M |
| 4 | 185945464 | 185946286 | H_c134m14__M |
| 4 | 186024630 | 186024899 | H_c__200l19 |
| 4 | 186314663 | 186317706 | H_c__216l15__M__M |
| 4 | 186423617 | 186425147 | H_c__118k17__M |
| 4 | 186439372 | 186440312 | H_c__73e18__M |
| 4 | 186500081 | 186500469 | H_c__273h21__M |
| 4 | 186505556 | 186507186 | H_c__45p09__M |
| 4 | 186691951 | 186693116 | H_c__244j23__M |
| 4 | 186721872 | 186722620 | H_c__127p09__M |
| 4 | 186770420 | 186770502 | H_c__240j23 |
| 4 | 186893932 | 186894053 | H_c__233i05 |
| 4 | 186897376 | 186897491 | H_c__149k05 |
| 4 | 187366106 | 187366297 | H_c__181i11 |
| 4 | 187400937 | 187402258 | H_c__28f03__M |
| 4 | 187440857 | 187441734 | H_c__145p09 |
| 4 | 187487015 | 187488694 | H_c__69f19__M |
| 4 | 187500473 | 187500903 | H_c__47l16__M |
| 4 | 187744078 | 187744156 | H_c__149f13 |
| 4 | 187851733 | 187852159 | H_c__224d05__M |
| 4 | 187996298 | 187996523 | H_c__231o19 |
| 4 | 188022865 | 188023771 | H_c__86a05__M |
| 4 | 188301425 | 188301596 | H_c__270o03 |
| 4 | 188308092 | 188308342 | H_c__195h08 |
| 4 | 188898605 | 188898728 | H_c__192m17 |
| 4 | 189291178 | 189292490 | H_c__69a05 |
| 4 | 189428606 | 189428761 | H_c__82a05 |
| 4 | 190023199 | 190023403 | H_c__147a10 |
| 4 | 190232903 | 190233013 | H_c__163d10 |
| 4 | 190275597 | 190275699 | H_c__36a04 |
| 4 | 19078434 | 19078634 | H_c__55b17 |
| 4 | 190864536 | 190864723 | H_c__183i06 |
| 4 | 191070180 | 191070309 | H_c__197g08 |
| 4 | 191098393 | 191098495 | H_c__59b21 |
| 4 | 191106722 | 191107351 | H_c__161l09 |
| 4 | 191314880 | 191317543 | H_c__189b11 |
| 4 | 19254745 | 19254819 | H_c__274f19__M |
| 4 | 1977587 | 1978692 | H_c__169l23__M |
| 4 | 19929392 | 19933198 | H_c__211j07__M__M |
| 4 | 2008929 | 2010292 | H_c__272m07__M |
| 4 | 2010340 | 2011895 | H_c__55i14 |
| 4 | 20378064 | 20378661 | H_c__13m02 |
| 4 | 20428806 | 20428968 | H_c__58p15 |
| 4 | 20625561 | 20625642 | H_c134k20 |
| 4 | 21376526 | 21376616 | H_c__220g20 |
| 4 | 21943584 | 21943661 | H_c__203i24 |
| 4 | 2210572 | 2211630 | H_c__1g18__M |
| 4 | 22193093 | 22194786 | H_c__245k11__M |
| 4 | 2230057 | 2233329 | H_c__166g05__M |
| 4 | 22452100 | 22452225 | H_c__151g22__M |
| 4 | 22615496 | 22615628 | H_c__270m10 |
| 4 | 2332101 | 2333606 | H_c__112j23 |
| 4 | 2333607 | 2335201 | H_c__83c12__M |
| 4 | 23631942 | 23632034 | H_c__45f17 |
| 4 | 23662239 | 23662407 | H_c__49o15 |
| 4 | 2371051 | 2371414 | H_c__70f16 |
| 4 | 2385704 | 2388192 | H_c__20j23 |
| 4 | 23908493 | 23908704 | H_c__120b23 |
| 4 | 23938504 | 23938623 | H_c__27i15__M |
| 4 | 24137151 | 24137230 | H_c__211p23 |
| 4 | 24147864 | 24151454 | H_c__1942j4__M |
| 4 | 24166967 | 24167170 | H_c__20a09 |
| 4 | 24262363 | 24262746 | H_c__242h13__M |
| 4 | 2437580 | 2439047 | H_c__11h04__M |
| 4 | 24476571 | 24478717 | H_c__3i06__M |
| 4 | 24589787 | 24591380 | H_c__227p23__M |
| 4 | 24641935 | 24642125 | H_c__212m10 |
| 4 | 24766427 | 24766950 | H_c__57p12 |
| 4 | 24911582 | 24912548 | H_c__210p03__M |
| 4 | 25054536 | 25055605 | H_c__105n20__M |
| 4 | 25162675 | 25162747 | H_c__181l13 |
| 4 | 25344531 | 25344655 | H_c__232h22 |
| 4 | 25421832 | 25422191 | H_c__243d12 |
| 4 | 25590225 | 25592629 | H_c__118a03__M |
| 4 | 25877773 | 25878020 | H_c__179o20 |
| 4 | 26535037 | 26539855 | H_c__7j22__M__M |
| 4 | 26762620 | 26762875 | H_c__97i13__M |
| 4 | 27224788 | 27225003 | H_c__102d18 |
| 4 | 2793684 | 2795643 | H_c__192k15__M |
| 4 | 2802793 | 2803433 | H_c__201f23 |
| 4 | 2830636 | 2832998 | H_c__107g05 |
| 4 | 28507500 | 28507576 | H_c__179a17 |
| 4 | 2855490 | 2857669 | H_c__210f20__M |
| 4 | 28636397 | 28636519 | H_c__30o24 |
| 4 | 29475020 | 29475182 | H_c__207e02 |
| 4 | 29563895 | 29564068 | H_c__121g11 |

TABLE 1-continued

| | | | |
|---|---|---|---|
| 4 | 3001568 | 3003154 | H_c__32e23_M |
| 4 | 30395031 | 30401131 | H_c__211h10_M_M |
| 4 | 30482647 | 30482804 | H_c__171k11 |
| 4 | 3080162 | 3081092 | H_c__115i10_M |
| 4 | 30954211 | 30954396 | H_c__197o12 |
| 4 | 3111709 | 3114192 | H_c__221e14_M |
| 4 | 31350542 | 31350635 | H_c__165l01 |
| 4 | 31402774 | 31402909 | H_c__20h13 |
| 4 | 3151083 | 3151217 | H_c__72n16 |
| 4 | 31774228 | 31774491 | H_c__5l05 |
| 4 | 31856918 | 31857011 | H_c__193o03 |
| 4 | 320137 | 321361 | H_c__15e13_M |
| 4 | 32319953 | 32320045 | H_c__89a18 |
| 4 | 32461256 | 32461447 | H_c139n19 |
| 4 | 33073446 | 33073594 | H_c__43b21 |
| 4 | 33155774 | 33155863 | H_c__107h24_M |
| 4 | 3330592 | 3333387 | H_c__20f17 |
| 4 | 33638700 | 33638808 | H_c__49j02 |
| 4 | 35331727 | 35331876 | H_c__26l11 |
| 4 | 35490462 | 35490609 | H_c__45e08 |
| 4 | 3570364 | 3572064 | H_c__230p15_M |
| 4 | 35971620 | 35971754 | H_c__176j15 |
| 4 | 36034373 | 36034536 | H_c__148e06 |
| 4 | 36068077 | 36069084 | H_c__104d13_M |
| 4 | 36248266 | 36248403 | H_c__25i21_M |
| 4 | 36661806 | 36661875 | H_c__42i18 |
| 4 | 36672201 | 36672558 | H_c__7k11 |
| 4 | 36986034 | 36986243 | H_c__22j17 |
| 4 | 37067688 | 37069546 | H_c__82d02_M |
| 4 | 37107958 | 37108093 | H_c__71m24 |
| 4 | 37277379 | 37278280 | H_c__268p22_M |
| 4 | 37555072 | 37555199 | H_c__230a12 |
| 4 | 37558399 | 37558769 | H_c__159m14 |
| 4 | 37714442 | 37715737 | H_c__208b07_M |
| 4 | 37800828 | 37802210 | H_c__78a06 |
| 4 | 38287832 | 38287922 | H_c143f09 |
| 4 | 38487165 | 38489645 | H_c__73g07_M |
| 4 | 38498646 | 38499294 | H_c__251o19 |
| 4 | 38640587 | 38640748 | H_c__203k01 |
| 4 | 38691709 | 38692788 | H_c__2d09_M |
| 4 | 39006316 | 39006773 | H_c__90p07_M |
| 4 | 3910488 | 3910970 | H_c__87g02_M |
| 4 | 3918219 | 3918660 | H_c__105o08 |
| 4 | 39270288 | 39271834 | H_c__181o21 |
| 4 | 39282307 | 39283471 | H_c__186m17_M |
| 4 | 39351655 | 39352556 | H_c133h04_M |
| 4 | 39462405 | 39463619 | H_c__223a21_M |
| 4 | 39689522 | 39689711 | H_c__148c17 |
| 4 | 39800593 | 39802399 | H_c__97f17_M |
| 4 | 39827989 | 39828117 | H_c__185l15 |
| 4 | 40443274 | 40444499 | H_c__266o10 |
| 4 | 40472573 | 40472908 | H_c__56a21_M |
| 4 | 40592629 | 40593466 | H_c__101h07_M |
| 4 | 40699503 | 40700981 | H_c__90g18 |
| 4 | 41056721 | 41059663 | H_c__125i13_M |
| 4 | 41099604 | 41100896 | H_c__31k21 |
| 4 | 41202839 | 41204590 | H_c__191g18_M |
| 4 | 41418353 | 41418565 | H_c__253c06 |
| 4 | 41588256 | 41589370 | H_c__73d04_M |
| 4 | 41594056 | 41595118 | H_c__129i02 |
| 4 | 41721023 | 41721743 | H_c__112d08 |
| 4 | 42214124 | 42214212 | H_c__219o01 |
| 4 | 42239723 | 42241773 | H_c__65m22_M |
| 4 | 42498798 | 42500775 | H_c__101o07 |
| 4 | 43006246 | 43006342 | H_c__51e07 |
| 4 | 43160701 | 43160825 | H_c__19h09 |
| 4 | 4367785 | 4368188 | H_c__206p12 |
| 4 | 43916836 | 43916960 | H_c__124c17_M |
| 4 | 4409646 | 4410519 | H_c__5l23_M |
| 4 | 44509610 | 44509934 | H_c__19i11 |
| 4 | 44521033 | 44522022 | H_c__43j03 |
| 4 | 44569141 | 44570195 | H_c131j03_M |
| 4 | 44591796 | 44593095 | H_c__146g12 |
| 4 | 45550835 | 45550953 | H_c__47d01_M |
| 4 | 46232529 | 46233647 | H_c140k17 |
| 4 | 46324959 | 46325165 | H_c__117m12 |
| 4 | 46835940 | 46837170 | H_c__120m13 |
| 4 | 4695084 | 4695595 | H_c__270f03_M |
| 4 | 47306269 | 47306800 | H_c__66h09 |
| 4 | 47327791 | 47328630 | H_c__77k12 |
| 4 | 4758299 | 4758440 | H_c132h14 |
| 4 | 47679470 | 47681005 | H_c__86n17_M |
| 4 | 47859079 | 47860439 | H_c__103a09 |
| 4 | 48091959 | 48092165 | H_c__116a01 |
| 4 | 48108780 | 48109434 | H_c__46h22 |
| 4 | 48112233 | 48113333 | H_c131m05_M |
| 4 | 48183984 | 48185835 | H_c__49c05_M |
| 4 | 482832 | 483420 | H_c__91h19_M |
| 4 | 48325963 | 48328222 | H_c__41f22_M |
| 4 | 48332757 | 48334739 | H_c__85a21_M |
| 4 | 48621994 | 48623121 | H_c__253b10 |
| 4 | 48673633 | 48674506 | H_c__189k21 |
| 4 | 48748884 | 48749786 | H_c__80c04_M |
| 4 | 48828661 | 48829713 | H_c__176m10 |
| 4 | 4975608 | 4980389 | H_c142p23_M_M |
| 4 | 4981017 | 4983043 | H_c__81j01_M |
| 4 | 4986401 | 4986569 | H_c138a11 |
| 4 | 4991022 | 4991792 | H_c132c04 |
| 4 | 5170855 | 5172495 | H_c__129e02_M |
| 4 | 52549654 | 52552145 | H_c__79e21 |
| 4 | 52744773 | 52746366 | H_c139k06_M |
| 4 | 52758296 | 52758508 | H_c__210j24_M |
| 4 | 5320648 | 5320853 | H_c__221k17 |
| 4 | 53458034 | 53459181 | H_c__6l15_M |
| 4 | 54025546 | 54025618 | H_c__127g03 |
| 4 | 54072477 | 54073189 | H_c__229l10_M |
| 4 | 54084552 | 54085460 | H_c__65p02_M |
| 4 | 54214747 | 54214898 | H_c__196g10 |
| 4 | 54409430 | 54410689 | H_c__247k24 |
| 4 | 54770714 | 54772297 | H_c__87j04_M |
| 4 | 54807050 | 54808252 | H_c__217a24_M |
| 4 | 54816703 | 54817259 | H_c__217f11_M |
| 4 | 54855693 | 54857065 | H_c__224d07_M |
| 4 | 54936950 | 54937951 | H_c__109b24 |
| 4 | 54939993 | 54941355 | H_c__68g16_M |
| 4 | 55345288 | 55345402 | H_c__22g02 |
| 4 | 55364219 | 55366304 | H_c__148c23_M |
| 4 | 55831053 | 55832974 | H_c__130c14_M |
| 4 | 55832975 | 55833210 | H_c__80m02_M |
| 4 | 55864601 | 55865519 | H_c__232h20 |
| 4 | 5596993 | 5597068 | H_c__17f24 |
| 4 | 56053011 | 56054286 | H_c__258o10 |
| 4 | 56102551 | 56103809 | H_c__51k05_M |
| 4 | 56252665 | 56254699 | H_c__32c11_M |
| 4 | 56258933 | 56259004 | H_c__25p22 |
| 4 | 56342819 | 56343617 | H_c__20g16_M |
| 4 | 56560547 | 56561307 | H_c__129j17 |
| 4 | 56655626 | 56656476 | H_c__22i05_M |
| 4 | 56755595 | 56756846 | H_c__11h17_M |
| 4 | 57094076 | 57095038 | H_c__202e21 |
| 4 | 57212314 | 57213071 | H_c__38d01_M |
| 4 | 57237156 | 57238625 | H_c__1k05 |
| 4 | 57362319 | 57363492 | H_c__219o08_M |
| 4 | 57614673 | 57616533 | H_c__45e19_M |
| 4 | 57683614 | 57684824 | H_c__74f21_M |
| 4 | 57812808 | 57812996 | H_c__87o16 |
| 4 | 57816566 | 57817782 | H_c__59a19_M |
| 4 | 5796207 | 5796432 | H_c__106n20 |
| 4 | 58035474 | 58035568 | H_c__170b10 |
| 4 | 5827663 | 5832003 | H_c__272d15_M |
| 4 | 58280720 | 58280859 | H_c__29n17 |
| 4 | 58720234 | 58720363 | H_c132c08 |
| 4 | 59125879 | 59125957 | H_c__223j09 |
| 4 | 59294221 | 59294346 | H_c__8k06 |
| 4 | 5974889 | 5975058 | H_c__209n12 |
| 4 | 6012075 | 6013435 | H_c__149f19_M |
| 4 | 60150312 | 60150455 | H_c__198c24 |
| 4 | 60261873 | 60262218 | H_c__13l20 |
| 4 | 60673853 | 60674023 | H_c__89n16 |
| 4 | 6127681 | 6128402 | H_c__118o05_M |
| 4 | 61336011 | 61336295 | H_c__176h17 |
| 4 | 61478118 | 61478288 | H_c__81o13 |
| 4 | 61894280 | 61896579 | H_c__67b04_M |
| 4 | 61955065 | 61955149 | H_c__53e02 |
| 4 | 62057848 | 62058052 | H_c__36o14 |
| 4 | 62309164 | 62309311 | H_c__127h04 |
| 4 | 6318062 | 6320847 | H_c__120i10_M |
| 4 | 6341613 | 6342722 | H_c__102f12_M |
| 4 | 63743997 | 63744084 | H_c__149b01 |
| 4 | 63937645 | 63937761 | H_c__93j18_M |

TABLE 1-continued

| | | | |
|---|---|---|---|
| 4 | 6428208 | 6429291 | H_c__270i12 |
| 4 | 64394355 | 64394475 | H_c__77d19 |
| 4 | 646625 | 648033 | H_c__51c13_M |
| 4 | 64761685 | 64761776 | H_c__51d23 |
| 4 | 64891353 | 64891535 | H_c__93g22 |
| 4 | 6520576 | 6520842 | H_c__173i04_M |
| 4 | 657318 | 660030 | H_c134e18_M |
| 4 | 6590231 | 6591274 | H_c__183k20 |
| 4 | 66055473 | 66055606 | H_c__40m16_M |
| 4 | 66364666 | 66365418 | H_c__191g09_M |
| 4 | 66377087 | 66377289 | H_c137f11 |
| 4 | 66426992 | 66427104 | H_c__33h04 |
| 4 | 6682201 | 6684469 | H_c__223f24 |
| 4 | 6694294 | 6696722 | H_c__30n11_M |
| 4 | 67026617 | 67026705 | H_c__204l12 |
| 4 | 672966 | 673084 | H_c__42h09_M |
| 4 | 6701146 | 6701277 | H_c__36j20 |
| 4 | 6783328 | 6786164 | H_c__14f08_M |
| 4 | 6793623 | 6794978 | H_c__82n20 |
| 4 | 68094212 | 68094547 | H_c__170a13 |
| 4 | 6829583 | 6829913 | H_c__19j04_M |
| 4 | 6835757 | 6836770 | H_c__124m01_M |
| 4 | 68394856 | 68395906 | H_c__221e06_M |
| 4 | 68478285 | 68478378 | H_c__108o16 |
| 4 | 68825822 | 68825901 | H_c__70h09 |
| 4 | 689208 | 689633 | H_c__251c12 |
| 4 | 6901918 | 6903895 | H_c__161c12_M |
| 4 | 7029049 | 7031697 | H_c__248i20 |
| 4 | 70595916 | 70596709 | H_c__78j12 |
| 4 | 71230402 | 71230477 | H_c__60b21 |
| 4 | 7186854 | 7189143 | H_c__225i10 |
| 4 | 71918938 | 71919140 | H_c__101c07_M |
| 4 | 71935138 | 71936693 | H_c__80g15_M |
| 4 | 72069616 | 72071751 | H_c__51k07 |
| 4 | 7223183 | 7225861 | H_c__213a18_M |
| 4 | 72417079 | 72418710 | H_c__206b16_M |
| 4 | 72567659 | 72567826 | H_c__116j01 |
| 4 | 7270908 | 7271685 | H_c__246i21 |
| 4 | 72728608 | 72728721 | H_c__197m08 |
| 4 | 73108807 | 73109120 | H_c__9m10 |
| 4 | 73410867 | 73410954 | H_c__175o18 |
| 4 | 73661759 | 73662078 | H_c141d10_M |
| 4 | 73799600 | 73800357 | H_c__236e15 |
| 4 | 74370556 | 74370693 | H_c__56d20 |
| 4 | 74488768 | 74490270 | H_c__34d04_M |
| 4 | 74925354 | 74925441 | H_c__44n16_M |
| 4 | 75077889 | 75079162 | H_c__247m09 |
| 4 | 75144548 | 75144700 | H_c__193h15 |
| 4 | 75388472 | 75389453 | H_c__25d19 |
| 4 | 7552947 | 7555794 | H_c__185o01_M |
| 4 | 75595472 | 75596243 | H_c__266f07_M |
| 4 | 75675704 | 75676433 | H_c__273k20 |
| 4 | 756957 | 758164 | H_c__253j03 |
| 4 | 75717691 | 75717162 | H_c__77a18 |
| 4 | 76215185 | 76215752 | H_c__166a06_M |
| 4 | 76765780 | 76765881 | H_c__96j04 |
| 4 | 76796501 | 76797356 | H_c__27j20_M |
| 4 | 76955229 | 76956157 | H_c__97h22 |
| 4 | 77006734 | 77007710 | H_c__261a10 |
| 4 | 77036918 | 77037052 | H_c__164b16 |
| 4 | 77086358 | 77086558 | H_c__179f07 |
| 4 | 77218061 | 77219658 | H_c__83o02_M |
| 4 | 77269210 | 77269455 | H_c__154n12_M |
| 4 | 77426111 | 77426930 | H_c__183d16 |
| 4 | 77491601 | 77492808 | H_c__1f04_M |
| 4 | 77529389 | 77530932 | H_c__10i04_M |
| 4 | 77584247 | 77585933 | H_c__28b10_M |
| 4 | 77698900 | 77700059 | H_c__58g21 |
| 4 | 778282 | 779797 | H_c__150p13 |
| 4 | 77832461 | 77832584 | H_c__102f19 |
| 4 | 77966383 | 77966454 | H_c__161g02 |
| 4 | 78174710 | 78176832 | H_c__238k09_M |
| 4 | 78227321 | 78229685 | H_c__111m21_M |
| 4 | 78267746 | 78267848 | H_c__83k23 |
| 4 | 78353470 | 78355004 | H_c__241f19 |
| 4 | 78436062 | 78437095 | H_c__118a18 |
| 4 | 7849372 | 7850053 | H_c__239i06 |
| 4 | 79098536 | 79098699 | H_c__95b16_M |
| 4 | 79335484 | 79337940 | H_c__258a07_M |
| 4 | 79405495 | 79405658 | H_c__253c02 |
| 4 | 79511563 | 79511748 | H_c__36e14 |
| 4 | 79829758 | 79831087 | H_c__239f10 |
| 4 | 80054088 | 80055215 | H_c__201n20_M |
| 4 | 80216958 | 80218047 | H_c__48n17_M |
| 4 | 80575293 | 80577206 | H_c__97c07 |
| 4 | 8058168 | 8060423 | H_c__4o19_M |
| 4 | 80632657 | 80632817 | H_c__43m05 |
| 4 | 8065858 | 8066073 | H_c__8e22 |
| 4 | 81015989 | 81016215 | H_c__30c06 |
| 4 | 81350324 | 81351929 | H_c__24a16_M |
| 4 | 81357731 | 81357881 | H_c__92o20 |
| 4 | 81461710 | 81463137 | H_c__169a07_M |
| 4 | 81544335 | 81545484 | H_c__232j11 |
| 4 | 81613989 | 81614618 | H_c__5e03_M |
| 4 | 81835510 | 81835617 | H_c__37b09 |
| 4 | 82308770 | 82310579 | H_c__232g17_M |
| 4 | 82492488 | 82493735 | H_c__198e23_M |
| 4 | 82749317 | 82750471 | H_c__116i05_M |
| 4 | 82854008 | 82854151 | H_c__22n10_M |
| 4 | 83242066 | 83242241 | H_c__115e14 |
| 4 | 83321885 | 83322875 | H_c__161j24 |
| 4 | 83452868 | 83452960 | H_c__274p16 |
| 4 | 83563159 | 83564955 | H_c__203i16_M |
| 4 | 83651104 | 83652979 | H_c__250i02_M |
| 4 | 83706910 | 83709643 | H_c__6j03_M |
| 4 | 83839500 | 83841143 | H_c__24d09_M |
| 4 | 8389524 | 8390572 | H_c__10j02 |
| 4 | 84168990 | 84169943 | H_c__3o22_M |
| 4 | 84178458 | 84179448 | H_c__201f21_M |
| 4 | 84290491 | 84291720 | H_c__69d24_M |
| 4 | 84313183 | 84313611 | H_c__29a05 |
| 4 | 84387683 | 84389701 | H_c__174i19_M |
| 4 | 84562499 | 84563276 | H_c__75m22_M |
| 4 | 84727305 | 84727412 | H_c__194h13 |
| 4 | 84762807 | 84763735 | H_c134b20 |
| 4 | 84877293 | 84877420 | H_c__169k14 |
| 4 | 85170950 | 85171066 | H_c__38e04 |
| 4 | 8547132 | 8548580 | H_c__195n09_M |
| 4 | 8560082 | 8561600 | H_c__225i20_M |
| 4 | 85759809 | 85762266 | H_c__46l12_M |
| 4 | 85771049 | 85771927 | H_c__58o23_M |
| 4 | 85780046 | 85780396 | H_c__31j10 |
| 4 | 85860567 | 85862484 | H_c144j15_M |
| 4 | 86243905 | 86244978 | H_c__109h05_M |
| 4 | 86435126 | 86435276 | H_c__52c21 |
| 4 | 87306013 | 87306150 | H_c__4j15 |
| 4 | 87434919 | 87435357 | H_c__212e01_M |
| 4 | 87490057 | 87490120 | H_c__218g18_M |
| 4 | 87871900 | 87873401 | H_c__25b22_M |
| 4 | 88170018 | 88171011 | H_c__52b04 |
| 4 | 88213047 | 88214181 | H_c143d12_M |
| 4 | 88285239 | 88285886 | H_c__70d18_M |
| 4 | 88290176 | 88290337 | H_c__30j08 |
| 4 | 88331507 | 88331633 | H_c__83n01 |
| 4 | 88497901 | 88499782 | H_c__84h12_M |
| 4 | 88700601 | 88701598 | H_c__116h03_M |
| 4 | 89437496 | 89437594 | H_c__74o08 |
| 4 | 89561196 | 89562767 | H_c__103n16_M |
| 4 | 89735214 | 89736340 | H_c__221n20_M |
| 4 | 89870139 | 89871314 | H_c__167g12_M |
| 4 | 9002190 | 9003960 | H_c__271n24 |
| 4 | 90388858 | 90390202 | H_c__108b22_M |
| 4 | 90533360 | 90533476 | H_c__25p17 |
| 4 | 90585564 | 90586531 | H_c143g19_M |
| 4 | 91056419 | 91056522 | H_c__13c20 |
| 4 | 91065140 | 91065256 | H_c__167p19 |
| 4 | 91114387 | 91115722 | H_c__36e07_M |
| 4 | 91464799 | 91464957 | H_c__226p15 |
| 4 | 915200 | 916240 | H_c__91a21_M |
| 4 | 91544742 | 91544845 | H_c__76f02 |
| 4 | 916244 | 916362 | H_c135c18_M |
| 4 | 91693858 | 91693960 | H_c__115a07 |
| 4 | 92043076 | 92043214 | H_c__122a06 |
| 4 | 92117916 | 92118045 | H_c__191o11 |
| 4 | 92286456 | 92286555 | H_c__213a06 |
| 4 | 92642745 | 92642868 | H_c__117b06 |
| 4 | 93583446 | 93584148 | H_c__246k13_M |
| 4 | 94898117 | 94898305 | H_c__16i03 |
| 4 | 95107055 | 95108393 | H_c__272i21_M |
| 4 | 95113061 | 95113282 | H_c__265a09_M |

TABLE 1-continued

| | | | |
|---|---|---|---|
| 4 | 95129390 | 95129526 | H_c__9j19 |
| 4 | 95386753 | 95386958 | H_c__238f18 |
| 4 | 9546334 | 9546601 | H_c__173d03 |
| 4 | 95485796 | 95486106 | H_c__269m15__M |
| 4 | 96821 | 97924 | H_c__38b07__M |
| 4 | 9696141 | 9698268 | H_c__59d20__M |
| 4 | 9703282 | 9703349 | H_c__156f22 |
| 4 | 97158031 | 97158168 | H_c__100d21 |
| 4 | 97714310 | 97714449 | H_c__56k14__M |
| 4 | 97760285 | 97760376 | H_c__98n01 |
| 4 | 97771815 | 97771945 | H_c132b18 |
| 4 | 9793668 | 9795075 | H_c__89f24__M |
| 4 | 980662 | 981673 | H_c__193d05__M |
| 4 | 98182225 | 98182287 | H_c__259e08 |
| 4 | 993112 | 997302 | H_c__89i23__M |
| 4 | 99489679 | 99489789 | H_c__102n22 |
| 4 | 99720698 | 99720835 | H_c__272b09 |
| 4 | 99936304 | 99937873 | H_c__181o19__M |
| 5 | 100264658 | 100265360 | H_c__266h14 |
| 5 | 100437433 | 100437805 | H_c__3m24 |
| 5 | 100728154 | 100728324 | H_c__75k11 |
| 5 | 100796321 | 100796577 | H_c__121b24 |
| 5 | 101313979 | 101314062 | H_c__68k16 |
| 5 | 101490405 | 101490626 | H_c__93k07 |
| 5 | 101659136 | 101660662 | H_c__194j16__M |
| 5 | 101948791 | 101948904 | H_c142d24 |
| 5 | 101993370 | 101993483 | H_c__108e21 |
| 5 | 102220010 | 102220187 | H_c__173d23 |
| 5 | 102229347 | 102229881 | H_c__156d04__M |
| 5 | 102402641 | 102403117 | H_c__41d09__M |
| 5 | 102543493 | 102543578 | H_c133i07 |
| 5 | 102622011 | 102623298 | H_c__94e16__M |
| 5 | 10302696 | 10303933 | H_c__27e05__M |
| 5 | 103457668 | 103457779 | H_c__229f09 |
| 5 | 103499263 | 103499378 | H_c__128j10 |
| 5 | 10384708 | 10387185 | H_c__22c06__M |
| 5 | 10405964 | 10407621 | H_c__244p04__M |
| 5 | 10494559 | 10495518 | H_c__45g23__M |
| 5 | 10509950 | 10512563 | H_c__223b15__M |
| 5 | 1056988 | 1058254 | H_c__21g22__M |
| 5 | 105898132 | 105898291 | H_c__163g24 |
| 5 | 105979 | 107960 | H_c__242g14__M |
| 5 | 1061891 | 1063566 | H_c__160j20__M |
| 5 | 10636828 | 10636984 | H_c__120b14 |
| 5 | 106751666 | 106751827 | H_c__183l16 |
| 5 | 106883392 | 106883574 | H_c__74c19 |
| 5 | 107032955 | 107035236 | H_c__68m23__M |
| 5 | 107290783 | 107290880 | H_c__55l02__M |
| 5 | 107744090 | 107745633 | H_c__120c07 |
| 5 | 107745659 | 107746249 | H_c__211b23__M |
| 5 | 10814346 | 10814630 | H_c__247m12__M |
| 5 | 108309722 | 108309806 | H_c__157i23 |
| 5 | 108772770 | 108774097 | H_c__78c03 |
| 5 | 109052597 | 109054540 | H_c139o20__M |
| 5 | 110083142 | 110083412 | H_c__96e18 |
| 5 | 110193554 | 110193683 | H_c__10j13 |
| 5 | 110434255 | 110437292 | H_c__237f14__M |
| 5 | 110587116 | 110588651 | H_c__199b11__M |
| 5 | 111090279 | 111090746 | H_c__229d07 |
| 5 | 111120449 | 111121959 | H_c__93m17__M |
| 5 | 111336674 | 111336817 | H_c__185a20 |
| 5 | 111523840 | 111524818 | H_c__68k05__M |
| 5 | 111554906 | 111555048 | H_c__237b07 |
| 5 | 111635300 | 111635444 | H_c140k22 |
| 5 | 111694402 | 111694602 | H_c__245c10 |
| 5 | 111782362 | 111784166 | H_c__115d16__M |
| 5 | 112070902 | 112071841 | H_c__162e24__M |
| 5 | 112284971 | 112286053 | H_c__51e22__M |
| 5 | 112339745 | 112341015 | H_c__30h04__M |
| 5 | 112353221 | 112353308 | H_c__274c21 |
| 5 | 112448819 | 112449077 | H_c__145o13 |
| 5 | 112694600 | 112694708 | H_c__6n24 |
| 5 | 112810794 | 112810944 | H_c__196g07 |
| 5 | 112851089 | 112852724 | H_c__111k01__M |
| 5 | 112877117 | 112877958 | H_c__51b07 |
| 5 | 112980409 | 112982079 | H_c__14l06 |
| 5 | 113002715 | 113002831 | H_c__207e10 |
| 5 | 11333567 | 11333695 | H_c__77o19 |
| 5 | 113418613 | 113419136 | H_c__227h06__M |
| 5 | 113700211 | 113700323 | H_c__261i09 |
| 5 | 113724887 | 113725679 | H_c__68f19 |
| 5 | 113725724 | 113727075 | H_c__82l08__M |
| 5 | 113925072 | 113925739 | H_c__227k02 |
| 5 | 11437295 | 11438660 | H_c__17i14__M |
| 5 | 114437617 | 114437705 | H_c__108e13 |
| 5 | 114532686 | 114534466 | H_c__45l16__M |
| 5 | 114542614 | 114544357 | H_c__191l09__M |
| 5 | 114659862 | 114660553 | H_c__230b18__M |
| 5 | 114907828 | 114908796 | H_c__180o10 |
| 5 | 114965391 | 114966069 | H_c__154g09__M |
| 5 | 114989016 | 114990166 | H_c__47d09__M |
| 5 | 115180494 | 115180804 | H_c__258p13 |
| 5 | 115204879 | 115206586 | H_c__86l21__M |
| 5 | 115249897 | 115250100 | H_c__269i13__M |
| 5 | 115325849 | 115327075 | H_c__209b01 |
| 5 | 115353766 | 115353893 | H_c__84j10 |
| 5 | 115448704 | 115449114 | H_c__68i15 |
| 5 | 115935856 | 115938853 | H_c__259m02__M |
| 5 | 116687775 | 116688133 | H_c__15c20 |
| 5 | 116742995 | 116743095 | H_c__56c19 |
| 5 | 116884462 | 116884535 | H_c__13g07 |
| 5 | 117037301 | 117037520 | H_c__146m20 |
| 5 | 117395476 | 117395699 | H_c__22k23 |
| 5 | 11762593 | 11762736 | H_c__11d07 |
| 5 | 117650615 | 117650792 | H_c__183g21 |
| 5 | 117753671 | 117754008 | H_c__179f18 |
| 5 | 117776666 | 117776792 | H_c__266o03 |
| 5 | 118026418 | 118026498 | H_c__12j15 |
| 5 | 118058248 | 118058563 | H_c__2b19 |
| 5 | 118073246 | 118073323 | H_c__12p01 |
| 5 | 118210127 | 118210198 | H_c__100p03 |
| 5 | 118217481 | 118217549 | H_c__47h03__M |
| 5 | 118351620 | 118352356 | H_c__20g18 |
| 5 | 118423429 | 118423725 | H_c__200c04 |
| 5 | 118434347 | 118435481 | H_c__210n24__M |
| 5 | 118631986 | 118632787 | H_c__82c18__M |
| 5 | 118719128 | 118719799 | H_c__157e04__M |
| 5 | 118851782 | 118852215 | H_c__146i07 |
| 5 | 118861214 | 118861354 | H_c__268n01 |
| 5 | 119827452 | 119828239 | H_c__195i24__M |
| 5 | 121387559 | 121387680 | H_c__43h18__M |
| 5 | 121440321 | 121441878 | H_c138g13__M |
| 5 | 121862789 | 121862949 | H_c__155d01 |
| 5 | 122138349 | 122139349 | H_c__92d22__M |
| 5 | 122261551 | 122261770 | H_c__189d13 |
| 5 | 122400585 | 122400911 | H_c__80g07__M |
| 5 | 122451590 | 122454826 | H_c__9f10__M |
| 5 | 122463210 | 122463827 | H_c__154i22__M |
| 5 | 122641163 | 122642177 | H_c__176h21 |
| 5 | 122786498 | 122787209 | H_c__39j20 |
| 5 | 122875412 | 122876681 | H_c__14d10__M |
| 5 | 123432853 | 123432931 | H_c__231f13 |
| 5 | 12354893 | 12355011 | H_c__40p07 |
| 5 | 123590007 | 123590174 | H_c__129i18 |
| 5 | 123819600 | 123819664 | H_c__44b19 |
| 5 | 123823695 | 123825849 | H_c__124k14__M |
| 5 | 124015245 | 124015710 | H_c__55i05__M |
| 5 | 124376812 | 124377006 | H_c__150b09 |
| 5 | 124451498 | 124453286 | H_c__95d13 |
| 5 | 125028548 | 125028703 | H_c__30l24 |
| 5 | 125056748 | 125056855 | H_c__216m15 |
| 5 | 125299804 | 125299913 | H_c__219j15 |
| 5 | 125414545 | 125414665 | H_c__125h24 |
| 5 | 125494527 | 125494648 | H_c__2j04 |
| 5 | 125963914 | 125965421 | H_c__183j14__M |
| 5 | 126139991 | 126142994 | H_c__73b18__M |
| 5 | 126390816 | 126391003 | H_c__231h07 |
| 5 | 126393193 | 126395909 | H_c__111k14 |
| 5 | 126436917 | 126437303 | H_c__205b03__M |
| 5 | 126592677 | 126593848 | H_c__166i01__M |
| 5 | 126652004 | 126652120 | H_c__152f07 |
| 5 | 126743796 | 126744421 | H_c__28a09 |
| 5 | 127264872 | 127265084 | H_c__23g11 |
| 5 | 127446345 | 127448466 | H_c__69b07__M |
| 5 | 127521070 | 127521205 | H_c__6e03 |
| 5 | 127564959 | 127565452 | H_c__174i12__M |
| 5 | 127900320 | 127903010 | H_c__187f13 |
| 5 | 128267669 | 128267892 | H_c__92f21 |
| 5 | 128328546 | 128329426 | H_c__170p08 |
| 5 | 128457735 | 128459115 | H_c__274f18 |

TABLE 1-continued

| | | | |
|---|---|---|---|
| 5 | 128822942 | 128825544 | H_c_101b12_M |
| 5 | 128951794 | 128952015 | H_c_272k23_M |
| 5 | 130527753 | 130529156 | H_c_116e06_M |
| 5 | 130534175 | 130535279 | H_c_151a13 |
| 5 | 130627116 | 130628352 | H_c_50l20_M |
| 5 | 130652054 | 130652346 | H_c_150d15 |
| 5 | 130998356 | 130998894 | H_c_235l08_M |
| 5 | 131620259 | 131622003 | H_c_170j22 |
| 5 | 131634730 | 131635849 | H_c_156f03 |
| 5 | 131732911 | 131734395 | H_c_53h10_M |
| 5 | 131773808 | 131775026 | H_c_129c01_M |
| 5 | 131840817 | 131841299 | H_c_209p01 |
| 5 | 131854259 | 131855563 | H_c_204h07_M |
| 5 | 131920155 | 131920866 | H_c_18o05 |
| 5 | 132019587 | 132020922 | H_c_169d16_M |
| 5 | 132110207 | 132111856 | H_c_10j23_M |
| 5 | 132176822 | 132179143 | H_c_91k20 |
| 5 | 132229643 | 132230774 | H_c_70f14 |
| 5 | 132273081 | 132273167 | H_c_217j10 |
| 5 | 132327141 | 132327782 | H_c_239b16 |
| 5 | 132389603 | 132390788 | H_c_206k13 |
| 5 | 132415267 | 132416359 | H_c_272p13_M |
| 5 | 132535584 | 132535678 | H_c_212i01 |
| 5 | 132575281 | 132575513 | H_c_217i07_M |
| 5 | 132709990 | 132710244 | H_c_8n06_M |
| 5 | 133476365 | 133479986 | H_c_213j03_M |
| 5 | 133532646 | 133533014 | H_c_271j20_M |
| 5 | 133540100 | 133540840 | H_c_149g07_M |
| 5 | 133588790 | 133590444 | H_c_201p21_M |
| 5 | 133730250 | 133731061 | H_c_19g22_M |
| 5 | 133734570 | 133735756 | H_c_153g19_M |
| 5 | 133828415 | 133830782 | H_c_70i16 |
| 5 | 133889247 | 133891801 | H_c_154i23_M |
| 5 | 134011961 | 134012529 | H_c_74j11_M |
| 5 | 134101430 | 134102758 | H_c_9h16_M |
| 5 | 134122108 | 134123080 | H_c_52d15_M |
| 5 | 134128051 | 134128339 | H_c_70a22 |
| 5 | 134209419 | 134210299 | H_c_196f15_M |
| 5 | 134237906 | 134238442 | H_c_14c18_M |
| 5 | 134267878 | 134269237 | H_c_16b20_M |
| 5 | 134396467 | 134400115 | H_c_245f03_M |
| 5 | 134413725 | 134416221 | H_c_21h11 |
| 5 | 134470201 | 134470279 | H_c134m17 |
| 5 | 134554425 | 134556404 | H_c_213c10_M |
| 5 | 1346011 | 1348894 | H_c_120p10 |
| 5 | 134630482 | 134630573 | H_c_159g05 |
| 5 | 134761950 | 134763359 | H_c_71f03_M |
| 5 | 134852638 | 134854124 | H_c_73i16_M |
| 5 | 134898452 | 134899578 | H_c_85b10_M |
| 5 | 134907087 | 134908426 | H_c_240e16_M |
| 5 | 134941761 | 134943260 | H_c_233d07_M |
| 5 | 135166932 | 135167036 | H_c_180k24 |
| 5 | 135292955 | 135294466 | H_c_10b08_M |
| 5 | 135317220 | 135317327 | H_c_192f09_M |
| 5 | 135391783 | 135393472 | H_c_167h12_M |
| 5 | 135496150 | 135497278 | H_c_73n23 |
| 5 | 135547647 | 135547767 | H_c_51f02 |
| 5 | 135743310 | 135743436 | H_c_157p16 |
| 5 | 136180280 | 136180512 | H_c_236d13 |
| 5 | 136227023 | 136227196 | H_c_84d03 |
| 5 | 136352522 | 136352640 | H_c_42e09 |
| 5 | 136395081 | 136395228 | H_c_91i11 |
| 5 | 136603033 | 136603155 | H_c_270c18 |
| 5 | 136861772 | 136863020 | H_c_36i13_M |
| 5 | 137094024 | 137094199 | H_c_199j04_M |
| 5 | 137116726 | 137118692 | H_c_168b19_M |
| 5 | 137252828 | 137253123 | H_c_30k04_M |
| 5 | 137395920 | 137397389 | H_c_86i08_M |
| 5 | 137439616 | 137439698 | H_c_100n12 |
| 5 | 137605404 | 137605930 | H_c_153i12_M |
| 5 | 137611016 | 137612365 | H_c_156i14 |
| 5 | 137637533 | 137638591 | H_c_209l01 |
| 5 | 137695296 | 137695739 | H_c_249n11_M |
| 5 | 137701293 | 137702718 | H_c135f18_M |
| 5 | 137795544 | 137795645 | H_c_187p16 |
| 5 | 137802249 | 137802882 | H_c_11p17_M |
| 5 | 137855093 | 137856347 | H_c_223i05_M |
| 5 | 137906136 | 137907764 | H_c_93g13_M |
| 5 | 137938226 | 137939447 | H_c_83i15_M |
| 5 | 138116277 | 138117833 | H_c_86k08_M |
| 5 | 138185669 | 138185767 | H_c_275k16_M |
| 5 | 138218209 | 138218347 | H_c_202d10 |
| 5 | 138459621 | 138459828 | H_c_71g17 |
| 5 | 138561101 | 138562355 | H_c_42c23_M |
| 5 | 138637594 | 138638060 | H_c132d09 |
| 5 | 138657147 | 138658148 | H_c_100i19_M |
| 5 | 138704158 | 138705751 | H_c_89a21_M |
| 5 | 138731077 | 138731310 | H_c_93g14_M |
| 5 | 138755521 | 138758773 | H_c_68d23_M |
| 5 | 138802208 | 138803964 | H_c_113i08 |
| 5 | 138831740 | 138833011 | H_c_125l22 |
| 5 | 138877018 | 138878492 | H_c_30a05_M |
| 5 | 138920817 | 138922142 | H_c_83j14_M |
| 5 | 138997541 | 138999338 | H_c_253m06 |
| 5 | 139007594 | 139010426 | H_c143a15_M |
| 5 | 139027978 | 139028373 | H_c141p22_M |
| 5 | 139056109 | 139057610 | H_c_34h05 |
| 5 | 139069466 | 139071331 | H_c_78e22_M |
| 5 | 139105172 | 139107692 | H_c_100m10_M |
| 5 | 139111733 | 139113198 | H_c_73i14 |
| 5 | 139146200 | 139148084 | H_c_265e19_M |
| 5 | 139155351 | 139156782 | H_c_271m24_M |
| 5 | 139207696 | 139208571 | H_c_149k09 |
| 5 | 139263206 | 139264304 | H_c_47i09_M |
| 5 | 139269261 | 139269340 | H_c_170i22 |
| 5 | 139293424 | 139293501 | H_c_66f23 |
| 5 | 139327435 | 139328947 | H_c_212p12 |
| 5 | 139466910 | 139468214 | H_c_72j11 |
| 5 | 139516751 | 139518442 | H_c136f07 |
| 5 | 139534148 | 139536137 | H_c_91e24_M |
| 5 | 139650426 | 139650600 | H_c_58f10_M |
| 5 | 139760065 | 139762480 | H_c_51l02_M |
| 5 | 139907020 | 139908494 | H_c_196c15_M |
| 5 | 139916813 | 139917662 | H_c_21k03_M |
| 5 | 139923464 | 139924890 | H_c_8h22_M |
| 5 | 140007787 | 140007964 | H_c_198p19 |
| 5 | 140050228 | 140051682 | H_c_17e07 |
| 5 | 140161346 | 140161511 | H_c_100c10 |
| 5 | 140242417 | 140244444 | H_c_29b04_M |
| 5 | 140285982 | 140286196 | H_c_41p04_M |
| 5 | 140322057 | 140322148 | H_c_244e07 |
| 5 | 140326006 | 140327125 | H_c_16i09_M |
| 5 | 140461048 | 140461187 | H_c_239e18 |
| 5 | 14064209 | 14065222 | H_c_247e24_M |
| 5 | 140710823 | 140712293 | H_c_248e14 |
| 5 | 140767536 | 140768294 | H_c_91f03_M |
| 5 | 140777287 | 140777950 | H_c_212d05 |
| 5 | 14080171 | 14080266 | H_c138a03 |
| 5 | 140844665 | 140847537 | H_c_25h23 |
| 5 | 140850186 | 140853010 | H_c_193o05_M |
| 5 | 140872280 | 140873624 | H_c_253a22 |
| 5 | 140978165 | 140979301 | H_c_33i14_M |
| 5 | 140996151 | 140999000 | H_c_103j04 |
| 5 | 141009939 | 141011606 | H_c_149n07 |
| 5 | 141041378 | 141043161 | H_c_2e15_M |
| 5 | 141061844 | 141062852 | H_c142h08_M |
| 5 | 141208839 | 141210018 | H_c_100a20_M |
| 5 | 141235602 | 141239438 | H_c_239j09_M |
| 5 | 141273355 | 141274352 | H_c_45m14_M |
| 5 | 141282469 | 141284148 | H_c_2g24_M |
| 5 | 141371703 | 141372956 | H_c_26n16_M |
| 5 | 141411621 | 141411774 | H_c_20i18 |
| 5 | 141458787 | 141458993 | H_c_149o11 |
| 5 | 141467799 | 141469185 | H_c_108a12 |
| 5 | 14156601 | 14156704 | H_c_23l11 |
| 5 | 141682923 | 141684928 | H_c139i23_M |
| 5 | 141716372 | 141717839 | H_c_238d10_M |
| 5 | 14195964 | 14198512 | H_c_245m24 |
| 5 | 142130098 | 142131356 | H_c132k09_M |
| 5 | 142172508 | 142172653 | H_c134n11 |
| 5 | 142592973 | 142593190 | H_c_82p23 |
| 5 | 142762338 | 142764454 | H_c_206m24_M |
| 5 | 142888858 | 142888939 | H_c_249m24 |
| 5 | 143101993 | 143102121 | H_c_36l02 |
| 5 | 1432464 | 1433901 | H_c_8j23_M |
| 5 | 143524776 | 143524989 | H_c_36k14 |
| 5 | 143564695 | 143565087 | H_c_92n18_M |
| 5 | 1438456 | 1439779 | H_c_122f10_M |
| 5 | 143896750 | 143896868 | H_c_264j11 |
| 5 | 144367082 | 144367221 | H_c_18n07 |

TABLE 1-continued

| | | | |
|---|---|---|---|
| 5 | 144469490 | 144469701 | H_c_74l05 |
| 5 | 144525822 | 144526001 | H_c_79d17 |
| 5 | 144680 | 145959 | H_c_83f22_M |
| 5 | 144723437 | 144723668 | H_c_196l19_M |
| 5 | 14494563 | 14494722 | H_c_62p24 |
| 5 | 145144558 | 145144626 | H_c_40l19 |
| 5 | 14515161 | 14515434 | H_c_274p06 |
| 5 | 145182527 | 145182691 | H_c_67m10 |
| 5 | 145296327 | 145296984 | H_c140l17 |
| 5 | 145542128 | 145542711 | H_c_38d16 |
| 5 | 145606282 | 145606451 | H_c_181n21 |
| 5 | 145692910 | 145694623 | H_c_204n13 |
| 5 | 145705259 | 145706183 | H_c_82e17_M |
| 5 | 145806606 | 145807682 | H_c_249c19_M |
| 5 | 146237535 | 146238539 | H_c_105j21_M |
| 5 | 146274215 | 146274318 | H_c_199a19 |
| 5 | 14633919 | 14636229 | H_c_59n11_M |
| 5 | 146811753 | 146814245 | H_c_147g21 |
| 5 | 146868843 | 146870590 | H_c_171o20 |
| 5 | 14717256 | 14718264 | H_c_17p04_M |
| 5 | 147187907 | 147188046 | H_c_240i20 |
| 5 | 14722775 | 14722901 | H_c_68d17 |
| 5 | 147628771 | 147628883 | H_c_227o12 |
| 5 | 147703645 | 147703913 | H_c_98b19 |
| 5 | 148013052 | 148014660 | H_c_106j06_M |
| 5 | 14805105 | 14805262 | H_c_186o04 |
| 5 | 148185410 | 148187461 | H_c_8g15_M |
| 5 | 148500614 | 148501797 | H_c_57o24_M |
| 5 | 148631082 | 148632636 | H_c_243i21 |
| 5 | 148658512 | 148658743 | H_c_52k02 |
| 5 | 148705230 | 148705628 | H_c_99e13_M |
| 5 | 148910380 | 148911510 | H_c_5j13_M |
| 5 | 149049904 | 149051309 | H_c_126c23 |
| 5 | 149205148 | 149206543 | H_c_44k10 |
| 5 | 14924246 | 14925719 | H_c_107f11_M |
| 5 | 149320033 | 149321156 | H_c_265c05 |
| 5 | 149359655 | 149361261 | H_c_56c03_M |
| 5 | 149547144 | 149551665 | H_c_86g20_M |
| 5 | 149661479 | 149662558 | H_c_194l10 |
| 5 | 149717217 | 149717912 | H_c_148b22_M |
| 5 | 149809223 | 149809607 | H_c_173k15 |
| 5 | 1498123 | 1500268 | H_c_17o19_M |
| 5 | 1498188 | 1500315 | H_c_264h12_M |
| 5 | 149844872 | 149846559 | H_c_214j13_M |
| 5 | 149983769 | 149986299 | H_c_224a19 |
| 5 | 150059895 | 150060917 | H_c_107k12_M |
| 5 | 150118474 | 150119080 | H_c_237i12_M |
| 5 | 150440197 | 150441180 | H_c_27g23_M |
| 5 | 150446207 | 150447536 | H_c_186j16 |
| 5 | 150454636 | 150455455 | H_c_84l11 |
| 5 | 150517115 | 150518458 | H_c_79h16 |
| 5 | 151130670 | 151132932 | H_c_218f05_M |
| 5 | 151284412 | 151284569 | H_c_248p16 |
| 5 | 151852975 | 151853149 | H_c_76j02 |
| 5 | 152471181 | 152471302 | H_c_4m03 |
| 5 | 152851082 | 152852040 | H_c_269g10_M |
| 5 | 153056039 | 153056206 | H_c_169m09 |
| 5 | 153548918 | 153550918 | H_c_192m02 |
| 5 | 153804480 | 153807202 | H_c_100a24 |
| 5 | 153837433 | 153837797 | H_c_164i21 |
| 5 | 154114775 | 154117247 | H_c_39n17_M |
| 5 | 154217073 | 154218705 | H_c_37i06_M |
| 5 | 154297050 | 154298170 | H_c_176b04 |
| 5 | 154300676 | 154300910 | H_c_213f19_M |
| 5 | 154325706 | 154326868 | H_c_27o13 |
| 5 | 154465116 | 154655388 | H_c_77h01 |
| 5 | 15465934 | 15466060 | H_c_20e11_M |
| 5 | 154666651 | 154666768 | H_c_265l18 |
| 5 | 155087265 | 155088787 | H_c_17m02_M |
| 5 | 15552962 | 15554014 | H_c_2m20_M |
| 5 | 155540261 | 155540328 | H_c_214o13 |
| 5 | 156501927 | 156502525 | H_c_265d02 |
| 5 | 156625220 | 156627313 | H_c_1i18 |
| 5 | 156744884 | 156744977 | H_c_246n23 |
| 5 | 156819219 | 156820268 | H_c_227j15_M |
| 5 | 156933608 | 156935642 | H_c_71a13_M |
| 5 | 156979295 | 156980005 | H_c140n08 |
| 5 | 157093405 | 157093556 | H_c_183b12 |
| 5 | 157103128 | 157104547 | H_c_241l08_M |
| 5 | 157218322 | 157218897 | H_c_75i09 |
| 5 | 157825115 | 157825249 | H_c_208m09_M |
| 5 | 1578924 | 1579181 | H_c_129i17 |
| 5 | 158458660 | 158459111 | H_c_91f19_M |
| 5 | 158463173 | 158466336 | H_c_129j23_M |
| 5 | 158567576 | 158569519 | H_c_209m20 |
| 5 | 158622497 | 158623408 | H_c_275h08 |
| 5 | 159132689 | 159133415 | H_c_12l15_M |
| 5 | 159275761 | 159276246 | H_c_14g03_M |
| 5 | 159484373 | 159486528 | H_c_235e19 |
| 5 | 159547504 | 159549165 | H_c_101d15 |
| 5 | 159558468 | 159559699 | H_c_213g17_M |
| 5 | 159631046 | 159631316 | H_c_96i05 |
| 5 | 159729908 | 159730647 | H_c_162k14 |
| 5 | 159781469 | 159781734 | H_c_47k13_M |
| 5 | 160165086 | 160165207 | H_c_160a03 |
| 5 | 160906618 | 160908134 | H_c_122i24_M |
| 5 | 161026063 | 161026314 | H_c_121n07 |
| 5 | 16231938 | 16233306 | H_c_46d15_M |
| 5 | 162796946 | 162797759 | H_c136a20_M |
| 5 | 162819176 | 162820882 | H_c_48l04 |
| 5 | 162865038 | 162865772 | H_c_74c15_M |
| 5 | 162925573 | 162926244 | H_c_48i04_M |
| 5 | 163220864 | 163220979 | H_c_163e23 |
| 5 | 163348277 | 163348481 | H_c_246a23_M |
| 5 | 163356704 | 163356830 | H_c141o13 |
| 5 | 1646011 | 1648048 | H_c_55e13_M |
| 5 | 164702167 | 164702311 | H_c_69g03 |
| 5 | 16518101 | 16519526 | H_c_41d21_M |
| 5 | 165648014 | 165648181 | H_c_169k03_M |
| 5 | 166188273 | 166188938 | H_c_57d18 |
| 5 | 166293353 | 166293456 | H_c_160d13 |
| 5 | 166337762 | 166339132 | H_c_258b13_M |
| 5 | 166510506 | 166510648 | H_c_204k06 |
| 5 | 166538258 | 166538423 | H_c_87o07 |
| 5 | 16668881 | 16671201 | H_c_55b09_M |
| 5 | 167060096 | 167060247 | H_c_124k23 |
| 5 | 167364209 | 167364281 | H_c_157o07 |
| 5 | 167845704 | 167846796 | H_c_63j06_M |
| 5 | 167888184 | 167890195 | H_c_244m19_M |
| 5 | 167938225 | 167939627 | H_c137d21_M |
| 5 | 168193217 | 168193388 | H_c_49d05 |
| 5 | 168282147 | 168282515 | H_c142p06 |
| 5 | 168556351 | 168556533 | H_c_36e21 |
| 5 | 168576013 | 168576199 | H_c_234f02 |
| 5 | 168996551 | 168997691 | H_c_249b24_M |
| 5 | 16915715 | 16915808 | H_c_209j22 |
| 5 | 169398710 | 169399490 | H_c_230h10 |
| 5 | 169621751 | 169622628 | H_c_92p04 |
| 5 | 169863224 | 169864817 | H_c143e02_M |
| 5 | 16988424 | 16989661 | H_c_187a20_M |
| 5 | 170620339 | 170620539 | H_c_55a07 |
| 5 | 1706486 | 1708821 | H_c_231b21 |
| 5 | 170667343 | 170676560 | H_c_265d14_M_M |
| 5 | 170722743 | 170722841 | H_c_156g18 |
| 5 | 170778719 | 170780416 | H_c_221d17 |
| 5 | 171366597 | 171366851 | H_c_38i08 |
| 5 | 171464526 | 171466941 | H_c_8c01_M |
| 5 | 171531497 | 171532732 | H_c_208f06 |
| 5 | 171547107 | 171548312 | H_c_20g17 |
| 5 | 171642893 | 171644383 | H_c_4h18 |
| 5 | 171814235 | 171814496 | H_c_186d03_M |
| 5 | 172000314 | 172001573 | H_c_76e16_M |
| 5 | 172076468 | 172076686 | H_c_130c18 |
| 5 | 172129630 | 172132331 | H_c_245i14_M |
| 5 | 172318139 | 172319830 | H_c_11m15_M |
| 5 | 172343130 | 172343960 | H_c133j24 |
| 5 | 172415609 | 172417227 | H_c_68m09_M |
| 5 | 172588363 | 172588591 | H_c_221c11_M |
| 5 | 172591733 | 172595016 | H_c_84l17_M |
| 5 | 172598066 | 172599018 | H_c_3n12_M |
| 5 | 172603492 | 172604424 | H_c_107o20_M |
| 5 | 17269766 | 17272545 | H_c_267k20 |
| 5 | 172975509 | 172976571 | H_c_210p19_M |
| 5 | 173247366 | 173248207 | H_c_261e10 |
| 5 | 173670320 | 173672584 | H_c_132b13_M |
| 5 | 174052056 | 174053020 | H_c_4g18 |
| 5 | 174084000 | 174085118 | H_c_55j19 |
| 5 | 174091687 | 174093278 | H_c_185j22_M |
| 5 | 174095311 | 174095479 | H_c_187f14_M |
| 5 | 174110634 | 174111059 | H_c139i09_M |

TABLE 1-continued

| | | | |
|---|---|---|---|
| 5 | 17423737 | 17424032 | H_c_243k12 |
| 5 | 174613574 | 174614935 | H_c_181b24_M |
| 5 | 174803234 | 174804836 | H_c139l15_M |
| 5 | 174837913 | 174839185 | H_c_120e07 |
| 5 | 175017111 | 175018903 | H_c_72k17 |
| 5 | 175154923 | 175157724 | H_c_68m10_M |
| 5 | 175678149 | 175678217 | H_c_21d16 |
| 5 | 175721089 | 175722324 | H_c_50c02_M |
| 5 | 175747602 | 175749339 | H_c_264f18_M |
| 5 | 175775275 | 175776698 | H_c_225h15_M |
| 5 | 175806539 | 175808705 | H_c_74m05_M |
| 5 | 175895580 | 175897103 | H_c_54m21_M |
| 5 | 175988847 | 175990395 | H_c_247f24_M |
| 5 | 176006666 | 176008497 | H_c_181f08 |
| 5 | 176175679 | 176178078 | H_c_59e14_M |
| 5 | 176221627 | 176222830 | H_c_98h21 |
| 5 | 176291727 | 176291886 | H_c_203a15 |
| 5 | 176365588 | 176366406 | H_c_97e13 |
| 5 | 176366411 | 176366613 | H_c_53f01_M |
| 5 | 176445973 | 176447584 | H_c_272l20 |
| 5 | 176662464 | 176663228 | H_c_76l07_M |
| 5 | 176722462 | 176723212 | H_c_52d03 |
| 5 | 176730047 | 176732390 | H_c140m08_M |
| 5 | 176758439 | 176760562 | H_c_117f22 |
| 5 | 176785414 | 176787460 | H_c_212c08_M |
| 5 | 176832033 | 176833615 | H_c_83l17 |
| 5 | 176855382 | 176858080 | H_c_50d11_M |
| 5 | 176875910 | 176877584 | H_c_95f03_M |
| 5 | 176912419 | 176914761 | H_c_6f16_M |
| 5 | 176951450 | 176952443 | H_c_31n09 |
| 5 | 176958685 | 176960377 | H_c_73g02_M |
| 5 | 177139885 | 177139944 | H_c_17l14 |
| 5 | 177344333 | 177345702 | H_c_253i09_M |
| 5 | 177490096 | 177491059 | H_c_43l09 |
| 5 | 177511838 | 177511992 | H_c_214m14 |
| 5 | 177563479 | 177565261 | H_c_6p15 |
| 5 | 177735700 | 177736240 | H_c_13b22 |
| 5 | 177935057 | 177936972 | H_c_90g19_M |
| 5 | 177948746 | 177950672 | H_c_30g03_M |
| 5 | 177986270 | 177987245 | H_c_216p04_M |
| 5 | 178088051 | 178090909 | H_c_105d18 |
| 5 | 178255049 | 178256229 | H_c_192k13_M |
| 5 | 178300055 | 178301712 | H_c_128f14 |
| 5 | 178353941 | 178354953 | H_c_83i02_M |
| 5 | 178383130 | 178383843 | H_c_145m06_M |
| 5 | 178419761 | 178421042 | H_c_6l13_M |
| 5 | 178702007 | 178706536 | H_c_65d10_M |
| 5 | 178742040 | 178742108 | H_c_217a13 |
| 5 | 1789076 | 1789292 | H_c_194g01 |
| 5 | 178909878 | 178910924 | H_c_84h15_M |
| 5 | 178918618 | 178920002 | H_c_77j13_M |
| 5 | 178982811 | 178984375 | H_c_219o03_M |
| 5 | 179037579 | 179039181 | H_c_78i16 |
| 5 | 179057806 | 179059163 | H_c134m21_M |
| 5 | 179092283 | 179093651 | H_c_26i19_M |
| 5 | 179154119 | 179156525 | H_c_239a18_M |
| 5 | 179164389 | 179167935 | H_c_234o06_M |
| 5 | 179217849 | 179219078 | H_c_81g13_M |
| 5 | 179247395 | 179249312 | H_c_106d03 |
| 5 | 179265762 | 179268598 | H_c_186j24 |
| 5 | 179430855 | 179431991 | H_c_152k07_M |
| 5 | 179449715 | 179450586 | H_c_245g13 |
| 5 | 179520288 | 179522230 | H_c_11f21 |
| 5 | 17952989 | 17953194 | H_c_2l16_M |
| 5 | 179566926 | 179569507 | H_c_100c16 |
| 5 | 179650587 | 179652531 | H_c_173l03_M |
| 5 | 179695776 | 179695776 | H_c_65o14 |
| 5 | 179711285 | 179713875 | H_c_185e07_M |
| 5 | 179949723 | 179952221 | H_c_84j08 |
| 5 | 180008086 | 180009978 | H_c_191g03 |
| 5 | 180161909 | 180163114 | H_c_11c16_M |
| 5 | 180190470 | 180192105 | H_c_223e19_M |
| 5 | 180220416 | 180221516 | H_c_175c03 |
| 5 | 180412124 | 180413546 | H_c_74k21_M |
| 5 | 180457453 | 180461154 | H_c_187d24_M |
| 5 | 180472608 | 180474615 | H_c_267a04_M |
| 5 | 180519185 | 180521056 | H_c_23g01 |
| 5 | 180543444 | 180543979 | H_c_88j21 |
| 5 | 180550779 | 180552033 | H_c_91b17_M |
| 5 | 180581623 | 180582537 | H_c_64h01 |
| 5 | 180603041 | 180603718 | H_c_6m08_M |
| 5 | 180605969 | 180607616 | H_c_40f01 |
| 5 | 180619779 | 180623009 | H_c_92m07_M |
| 5 | 180632229 | 180633300 | H_c_122b08 |
| 5 | 18462464 | 18462563 | H_c_96c05 |
| 5 | 18523069 | 18523209 | H_c_200h18 |
| 5 | 1852361 | 1853268 | H_c_106l09 |
| 5 | 1854275 | 1855107 | H_c_73c23_M |
| 5 | 18604915 | 18605024 | H_c_79o10 |
| 5 | 18772415 | 18773843 | H_c_185g07 |
| 5 | 18920529 | 18920641 | H_c_237d21 |
| 5 | 19014386 | 19014462 | H_c_63f24 |
| 5 | 1902680 | 1905122 | H_c_252o23 |
| 5 | 19177521 | 19177662 | H_c_65c06 |
| 5 | 1929020 | 1930196 | H_c_195m24_M |
| 5 | 19290441 | 19290551 | H_c_127h21 |
| 5 | 1932437 | 1933641 | H_c_73h04_M |
| 5 | 1935965 | 1936544 | H_c_150g22_M |
| 5 | 1936549 | 1942299 | H_c_166p21_M_M |
| 5 | 19926237 | 19926427 | H_c_24e11 |
| 5 | 20677890 | 20677965 | H_c_210l14 |
| 5 | 20720898 | 20721104 | H_c_206b17 |
| 5 | 21089294 | 21089431 | H_c_172b03 |
| 5 | 21603443 | 21603722 | H_c_207j21 |
| 5 | 22265494 | 22265661 | H_c_47d15 |
| 5 | 22909671 | 22909772 | H_c_154j09_M |
| 5 | 2304215 | 2305812 | H_c_64d13 |
| 5 | 23537025 | 23537129 | H_c_72a18 |
| 5 | 23579404 | 23579759 | H_c_216e20_M |
| 5 | 24233829 | 24233978 | H_c_75o16 |
| 5 | 24630127 | 24630271 | H_c_174e08 |
| 5 | 24672543 | 24672849 | H_c_88n04 |
| 5 | 25054534 | 25054689 | H_c_83c02 |
| 5 | 25246276 | 25246376 | H_c_218n19 |
| 5 | 25405464 | 25405667 | H_c_66k13 |
| 5 | 25859993 | 25860140 | H_c_94p22 |
| 5 | 26111960 | 26112241 | H_c_259a07 |
| 5 | 26144431 | 26144521 | H_c_239a22 |
| 5 | 26812126 | 26812356 | H_c_175a19 |
| 5 | 271247 | 272164 | H_c_33n07 |
| 5 | 27209074 | 27209620 | H_c_226f15 |
| 5 | 27781801 | 27781915 | H_c_216l10 |
| 5 | 27857429 | 27857572 | H_c_19a19_M |
| 5 | 2791563 | 2793744 | H_c_50b05_M |
| 5 | 2796555 | 2796805 | H_c_248l02_M |
| 5 | 28003060 | 28003180 | H_c_173c13 |
| 5 | 2801244 | 2803248 | H_c_19b22_M |
| 5 | 28036135 | 28036303 | H_c_170p23 |
| 5 | 2808104 | 2810086 | H_c_9g10_M |
| 5 | 29126186 | 29126314 | H_c_106o16 |
| 5 | 29934951 | 29935112 | H_c_171b24 |
| 5 | 30219967 | 30220219 | H_c_13k02 |
| 5 | 31229522 | 31230321 | H_c_88p08_M |
| 5 | 31315990 | 31316396 | H_c_216m04 |
| 5 | 31445449 | 31445612 | H_c_152i16 |
| 5 | 31567443 | 31568439 | H_c143j14_M |
| 5 | 31674481 | 31675975 | H_c_247h23_M |
| 5 | 31787535 | 31787696 | H_c135a21 |
| 5 | 32209361 | 32210717 | H_c_66j10_M |
| 5 | 32259202 | 32260222 | H_c_215f02 |
| 5 | 32340561 | 32340827 | H_c_134o16_M |
| 5 | 32347814 | 32349813 | H_c_269n16_M |
| 5 | 32479829 | 32480947 | H_c_213c07 |
| 5 | 3250148 | 3251154 | H_c_71l05 |
| 5 | 32621316 | 32622258 | H_c_57l05_M |
| 5 | 32745876 | 32748939 | H_c_250b02_M |
| 5 | 32946504 | 32946692 | H_c_79p19 |
| 5 | 32971941 | 32972144 | H_c_20e09_M |
| 5 | 33104733 | 33105008 | H_c_38l04 |
| 5 | 33127975 | 33129299 | H_c_30b23 |
| 5 | 3318661 | 3318937 | H_c_66a13 |
| 5 | 33476117 | 33477386 | H_c_175a17_M |
| 5 | 33727168 | 33727381 | H_c_31c22 |
| 5 | 33971851 | 33974110 | H_c_49i10_M |
| 5 | 34043384 | 34044147 | H_c_103d23 |
| 5 | 34076926 | 34077268 | H_c_209f15 |
| 5 | 34645949 | 34646141 | H_c_176h18 |
| 5 | 34693271 | 34693796 | H_c_94o18 |
| 5 | 3482704 | 3482872 | H_c_27d20 |
| 5 | 34950954 | 34951846 | H_c_81g14_M |

TABLE 1-continued

| | | | |
|---|---|---|---|
| 5 | 34964896 | 34966202 | H_c_39c13_M |
| 5 | 34973043 | 34973150 | H_c_54b12 |
| 5 | 3516054 | 3516182 | H_c_30p16 |
| 5 | 35265889 | 35266850 | H_c_245j06_M |
| 5 | 35652306 | 35654439 | H_c_217c21_M |
| 5 | 36187240 | 36188083 | H_c_72o20_M |
| 5 | 36193472 | 36193602 | H_c_118i21 |
| 5 | 36276751 | 36278491 | H_c_128j08_M |
| 5 | 3643426 | 3649969 | H_c_173k22_M_M |
| 5 | 3651777 | 3657734 | H_c_192e09_M |
| 5 | 36703424 | 36703499 | H_c_199n03_M |
| 5 | 36725745 | 36726501 | H_c_152b12_M |
| 5 | 36911624 | 36913666 | H_c_87i05_M |
| 5 | 37284728 | 37285463 | H_c_117l05 |
| 5 | 373270 | 376742 | H_c_13l24_M |
| 5 | 37527950 | 37528045 | H_c_23g03 |
| 5 | 37612376 | 37612443 | H_c_61i06 |
| 5 | 37870105 | 37870648 | H_c_196h22 |
| 5 | 37872719 | 37873918 | H_c_209o09_M |
| 5 | 3797030 | 3797116 | H_c_16n18 |
| 5 | 38057424 | 38057774 | H_c_80e11 |
| 5 | 38132868 | 38133103 | H_c_112h19 |
| 5 | 38294621 | 38294823 | H_c_122a20_M |
| 5 | 38354676 | 38355681 | H_c139e10 |
| 5 | 38436547 | 38436770 | H_c_64f09 |
| 5 | 38506179 | 38506485 | H_c_49g05 |
| 5 | 38591843 | 38593160 | H_c_165i01_M |
| 5 | 38675956 | 38676054 | H_c_211d13 |
| 5 | 3876309 | 3876526 | H_c_266e09 |
| 5 | 38881406 | 38883059 | H_c_121c04_M |
| 5 | 39109242 | 39111068 | H_c_13h20_M |
| 5 | 3929435 | 3929514 | H_c_31o22 |
| 5 | 39393584 | 39393715 | H_c_215p23 |
| 5 | 39460615 | 39461367 | H_c_4d01_M |
| 5 | 39509634 | 39509731 | H_c_41d02 |
| 5 | 40564002 | 40564198 | H_c_124f07 |
| 5 | 40714961 | 40718159 | H_c_167j14_M |
| 5 | 40790900 | 40792221 | H_c_271f03_M |
| 5 | 40833365 | 40834485 | H_c_128i11_M |
| 5 | 40987270 | 40987500 | H_c_213i06 |
| 5 | 41286024 | 41286140 | H_c_233g16 |
| 5 | 41545803 | 41546536 | H_c_213p02 |
| 5 | 41905007 | 41906383 | H_c_116g15_M |
| 5 | 41939530 | 41940639 | H_c_156i21 |
| 5 | 42459195 | 42460947 | H_c_18j02_M |
| 5 | 425018 | 427483 | H_c_206i20_M |
| 5 | 42986539 | 42988743 | H_c_92d12_M |
| 5 | 43027674 | 43029803 | H_c_257n16_M |
| 5 | 43029825 | 43029978 | H_c_41k07_M |
| 5 | 43076634 | 43079485 | H_c_130d08_M |
| 5 | 43156603 | 43158126 | H_c_15a18_M |
| 5 | 43227368 | 43229015 | H_c_43j15 |
| 5 | 43348811 | 43349805 | H_c_145j11_M |
| 5 | 43381641 | 43381819 | H_c_58i14 |
| 5 | 43423310 | 43423517 | H_c_259a08 |
| 5 | 43592110 | 43593452 | H_c_86h10_M |
| 5 | 43638283 | 43640024 | H_c_100j12 |
| 5 | 44844787 | 44845739 | H_c_266j07_M |
| 5 | 45731571 | 45732500 | H_c_86k22_M |
| 5 | 46093574 | 46093747 | H_c_209h08 |
| 5 | 46135761 | 46135894 | H_c_74g12 |
| 5 | 495147 | 496690 | H_c_21c18 |
| 5 | 49989054 | 49989241 | H_c_41f01 |
| 5 | 49997874 | 49998597 | H_c_94n04 |
| 5 | 50301337 | 50301758 | H_c_32d03 |
| 5 | 50611091 | 50611180 | H_c_274a08 |
| 5 | 50650063 | 50650141 | H_c_199o21 |
| 5 | 50714359 | 50715085 | H_c_162o23_M |
| 5 | 51783777 | 51783910 | H_c_111h05 |
| 5 | 5192842 | 5193991 | H_c_75j12_M |
| 5 | 52119591 | 52120208 | H_c_225p03 |
| 5 | 52131520 | 52132233 | H_c_170b17_M |
| 5 | 52226338 | 52226936 | H_c_272l01 |
| 5 | 52320344 | 52321348 | H_c_27k01_M |
| 5 | 52440968 | 52441771 | H_c_21b17 |
| 5 | 52810345 | 52810673 | H_c_63j12 |
| 5 | 52811407 | 52813935 | H_c134i19_M |
| 5 | 52820901 | 52820994 | H_c_126k17 |
| 5 | 52944652 | 52945031 | H_c_251o03 |
| 5 | 53275660 | 53275766 | H_c_19d23 |
| 5 | 53575893 | 53576040 | H_c144f04 |
| 5 | 53641623 | 53642979 | H_c_30j09_M |
| 5 | 53680585 | 53680713 | H_c_251a15 |
| 5 | 53849085 | 53851649 | H_c_80n10 |
| 5 | 54008717 | 54008820 | H_c_176j19 |
| 5 | 54029643 | 54029767 | H_c_84c22 |
| 5 | 54215031 | 54216294 | H_c_100l17 |
| 5 | 54504788 | 54505974 | H_c_71f19_M |
| 5 | 54551717 | 54555559 | H_c_73p14_M |
| 5 | 54558092 | 54559199 | H_c_163g02_M |
| 5 | 54564429 | 54565549 | H_c_28f24_M |
| 5 | 54638816 | 54640038 | H_c_64f13 |
| 5 | 54715527 | 54715732 | H_c_176h19_M |
| 5 | 5475623 | 5476307 | H_c140o19 |
| 5 | 54792180 | 54792242 | H_c136e19 |
| 5 | 54865724 | 54867014 | H_c_160h07_M |
| 5 | 54896733 | 54896878 | H_c_230f24 |
| 5 | 55043026 | 55044394 | H_c_6a02_M |
| 5 | 5506288 | 5506457 | H_c_20i03_M |
| 5 | 55152698 | 55153807 | H_c_115b11_M |
| 5 | 55326114 | 55327166 | H_c_171k17_M |
| 5 | 5547635 | 5548491 | H_c_184o16 |
| 5 | 55831221 | 55831316 | H_c_56d19 |
| 5 | 55964738 | 55964829 | H_c_109c09 |
| 5 | 56003592 | 56003666 | H_c_66h10 |
| 5 | 56145943 | 56148758 | H_c_202h15 |
| 5 | 56240483 | 56241741 | H_c_152d07_M |
| 5 | 56283065 | 56284732 | H_c_227n02_M |
| 5 | 56504633 | 56506413 | H_c_207b14_M |
| 5 | 57026361 | 57026523 | H_c_91h14 |
| 5 | 57614899 | 57615020 | H_c_266p08 |
| 5 | 576688 | 578277 | H_c_66k22_M |
| 5 | 57778732 | 57778973 | H_c_211p03_M |
| 5 | 580793 | 582225 | H_c_130e13_M |
| 5 | 58332918 | 58333035 | H_c_256g20 |
| 5 | 5894932 | 5895321 | H_c137d14 |
| 5 | 59067454 | 59067580 | H_c_51k19 |
| 5 | 59224533 | 59226011 | H_c_8i08 |
| 5 | 59634051 | 59634179 | H_c_243n02 |
| 5 | 60031362 | 60032207 | H_c_208d08_M |
| 5 | 60083941 | 60084150 | H_c_108f11_M |
| 5 | 60173902 | 60176299 | H_c_248g02_M |
| 5 | 60276218 | 60277240 | H_c_179e20 |
| 5 | 60383654 | 60383812 | H_c_13m03 |
| 5 | 60493407 | 60494694 | H_c_74g08_M |
| 5 | 60665072 | 60665783 | H_c_146l19_M |
| 5 | 60957246 | 60958702 | H_c_127a09_M |
| 5 | 61637468 | 61638645 | H_c_168d20_M |
| 5 | 61734955 | 61735726 | H_c_96f06_M |
| 5 | 61744001 | 61744951 | H_c_201f02 |
| 5 | 62348469 | 62348573 | H_c_223f15 |
| 5 | 62739147 | 62739352 | H_c_26b12 |
| 5 | 6282092 | 6282288 | H_c_35c24 |
| 5 | 63315478 | 63315565 | H_c_57g20 |
| 5 | 63402376 | 63402502 | H_c_5e24 |
| 5 | 63497113 | 63497738 | H_c136b24_M |
| 5 | 63574065 | 63576082 | H_c_88j11 |
| 5 | 63675799 | 63675883 | H_c132f11 |
| 5 | 63836897 | 63838363 | H_c_175m19_M |
| 5 | 64021741 | 64022794 | H_c_59k18_M |
| 5 | 64224262 | 64224441 | H_c_152e08 |
| 5 | 64522532 | 64522766 | H_c_90a13 |
| 5 | 64582568 | 64582710 | H_c_191e14 |
| 5 | 64607462 | 64607728 | H_c_89k10 |
| 5 | 64879896 | 64879994 | H_c_146j03 |
| 5 | 64894469 | 64895244 | H_c_220k10 |
| 5 | 6512801 | 6512899 | H_c_169f14 |
| 5 | 65384562 | 65384678 | H_c_43c24 |
| 5 | 65475471 | 65476312 | H_c_199h13_M |
| 5 | 65758556 | 65758648 | H_c_182a13 |
| 5 | 65927418 | 65928840 | H_c_51e02 |
| 5 | 66268738 | 66268975 | H_c_164k08 |
| 5 | 66283619 | 66283882 | H_c_191n16_M |
| 5 | 6635990 | 6636976 | H_c139k07_M |
| 5 | 664729 | 666154 | H_c_4d22_M |
| 5 | 6685732 | 6687440 | H_c_39h02_M |
| 5 | 67048497 | 67048745 | H_c_109k24 |
| 5 | 67546468 | 67548542 | H_c_18d20_M |
| 5 | 67619938 | 67620780 | H_c_104h15_M |
| 5 | 6765786 | 6767966 | H_c_29k19_M |

TABLE 1-continued

| | | | |
|---|---|---|---|
| 5 | 67727064 | 67727173 | H_c_130d14 |
| 5 | 68082768 | 68082916 | H_c_42m01 |
| 5 | 68425322 | 68426265 | H_c_89n04_M |
| 5 | 68520977 | 68521482 | H_c_73k04 |
| 5 | 68549182 | 68550020 | H_c_191o06_M |
| 5 | 68746443 | 68747299 | H_c_266i23_M |
| 5 | 68824034 | 68826097 | H_c_152e22_M |
| 5 | 70787256 | 70787768 | H_c_119i08 |
| 5 | 70918399 | 70919353 | H_c_57i23 |
| 5 | 71438365 | 71440723 | H_c_244o06_M |
| 5 | 71639486 | 71640794 | H_c_87p10_M |
| 5 | 72147528 | 72148636 | H_c131k20 |
| 5 | 72179586 | 72180695 | H_c_157j08_M |
| 5 | 72286871 | 72288306 | H_c_14k14 |
| 5 | 72451325 | 72452529 | H_c_264h21_M |
| 5 | 72629829 | 72631397 | H_c_175j12_M |
| 5 | 72632280 | 72635600 | H_c_152p18_M |
| 5 | 72642967 | 72643468 | H_c_251b05 |
| 5 | 72711593 | 72713948 | H_c_101d24_M |
| 5 | 72751300 | 72751578 | H_c_122o09_M |
| 5 | 72767876 | 72769426 | H_c_19a05_M |
| 5 | 72775571 | 72776155 | H_c_84l16 |
| 5 | 72778620 | 72780829 | H_c_87d17 |
| 5 | 72782716 | 72783821 | H_c_25d13_M |
| 5 | 72897112 | 72897441 | H_c_261c08 |
| 5 | 72957242 | 72958500 | H_c_188k19_M |
| 5 | 73104410 | 73104519 | H_c_266c04 |
| 5 | 73136529 | 73136884 | H_c_87d14 |
| 5 | 73489734 | 73489867 | H_c_188g19 |
| 5 | 73532331 | 73532465 | H_c_201c06 |
| 5 | 73971355 | 73973148 | H_c_103m16_M |
| 5 | 74114172 | 74114280 | H_c_112h22 |
| 5 | 7411623 | 7411764 | H_c_98i20 |
| 5 | 74354434 | 74354566 | H_c_126p11 |
| 5 | 74384163 | 74385850 | H_c_35c16_M |
| 5 | 74423010 | 74423111 | H_c_226k10 |
| 5 | 74568362 | 74568740 | H_c_154g04_M |
| 5 | 74668673 | 74668821 | H_c_89a23_M |
| 5 | 74842329 | 74843848 | H_c_65m03_M |
| 5 | 74912812 | 74913033 | H_c_64l16 |
| 5 | 75048818 | 75049028 | H_c_207h19 |
| 5 | 75413129 | 75416557 | H_c_155c03_M |
| 5 | 75730437 | 75730545 | H_c_155h07 |
| 5 | 75734185 | 75735937 | H_c_265d07_M |
| 5 | 76037594 | 76037879 | H_c_26g09 |
| 5 | 76046557 | 76048357 | H_c_42h07_M |
| 5 | 76150401 | 76151240 | H_c_34c22 |
| 5 | 76284562 | 76286021 | H_c_81b20_M |
| 5 | 76359372 | 76359451 | H_c_195d21_M |
| 5 | 76361657 | 76362670 | H_c_69m03 |
| 5 | 76407910 | 76409624 | H_c_169o20_M |
| 5 | 76418813 | 76418947 | H_c_60b15_M |
| 5 | 76511551 | 76513549 | H_c_216m12_M |
| 5 | 76968029 | 76969185 | H_c_79c19 |
| 5 | 76970322 | 76971101 | H_c_85g17_M |
| 5 | 76976724 | 76976966 | H_c_202k15_M |
| 5 | 77107163 | 77108190 | H_c_274p22 |
| 5 | 77123286 | 77123370 | H_c134i17 |
| 5 | 77183034 | 77184579 | H_c_72d18_M |
| 5 | 77289554 | 77289830 | H_c_179g15_M |
| 5 | 77304083 | 77304589 | H_c_208b11 |
| 5 | 77439827 | 77440247 | H_c_26b13 |
| 5 | 77625670 | 77626521 | H_c_53g16 |
| 5 | 77691371 | 77692812 | H_c_116d08_M |
| 5 | 77841836 | 77842183 | H_c_119k22_M |
| 5 | 77972066 | 77972271 | H_c_210m15 |
| 5 | 78316003 | 78317101 | H_c_241c20 |
| 5 | 78339216 | 78339345 | H_c_259n17 |
| 5 | 78400962 | 78402299 | H_c_251l21 |
| 5 | 78442768 | 78444167 | H_c_82j06 |
| 5 | 78567176 | 78569464 | H_c_179d16_M |
| 5 | 78573911 | 78574131 | H_c_218c06 |
| 5 | 78844973 | 78846138 | H_c_46d04 |
| 5 | 78977888 | 78978082 | H_c_153p03_M |
| 5 | 79215975 | 79216221 | H_c_158j12 |
| 5 | 7921604 | 7923102 | H_c_5d14_M |
| 5 | 79322117 | 79322956 | H_c_51n13 |
| 5 | 79366324 | 79367507 | H_c133i24 |
| 5 | 79475999 | 79476103 | H_c_169f19 |
| 5 | 79586796 | 79588815 | H_c_188l05_M |
| 5 | 79731669 | 79731982 | H_c_77h16 |
| 5 | 79738989 | 79740306 | H_c_101c14_M |
| 5 | 79819333 | 79819968 | H_c_4i15_M |
| 5 | 79899753 | 79902415 | H_c_151g05_M |
| 5 | 79985571 | 79986767 | H_c_55j21 |
| 5 | 80291374 | 80293215 | H_c_207i05_M |
| 5 | 80519928 | 80520183 | H_c_7k01 |
| 5 | 80725347 | 80726383 | H_c_10g21_M |
| 5 | 81082983 | 81083642 | H_c_245f08_M |
| 5 | 81303253 | 81304185 | H_c_120l21_M |
| 5 | 81609522 | 81610088 | H_c_219p10_M |
| 5 | 82193425 | 82193563 | H_c_203l17 |
| 5 | 82803984 | 82806313 | H_c_18i12_M |
| 5 | 83053161 | 83054121 | H_c_40j04_M |
| 5 | 83715180 | 83716693 | H_c_154c19_M |
| 5 | 84716543 | 84716766 | H_c_197d17 |
| 5 | 84809924 | 84810069 | H_c_6g11 |
| 5 | 8603367 | 8603473 | H_c_123b05 |
| 5 | 86425704 | 86425871 | H_c_9m16_M |
| 5 | 86599161 | 86600571 | H_c_253i04 |
| 5 | 86702035 | 86702233 | H_c_16j24 |
| 5 | 86743740 | 86744672 | H_c_155j01 |
| 5 | 87292513 | 87292584 | H_c_199m08 |
| 5 | 87472627 | 87472743 | H_c_127e19 |
| 5 | 87599843 | 87600858 | H_c_108l13 |
| 5 | 87605827 | 87605964 | H_c_63d09 |
| 5 | 87824452 | 87824550 | H_c_18f24 |
| 5 | 87860347 | 87860567 | H_c_244a24 |
| 5 | 87904626 | 87904633 | H_c_56g10 |
| 5 | 87984138 | 87984243 | H_c_45l14 |
| 5 | 88011335 | 88012744 | H_c_70h13 |
| 5 | 88022643 | 88022842 | H_c_213k18 |
| 5 | 88203963 | 88204087 | H_c_117d02 |
| 5 | 88812966 | 88813087 | H_c_224b20 |
| 5 | 89243210 | 89243344 | H_c_157d13 |
| 5 | 89486356 | 89486450 | H_c_232k14_M |
| 5 | 89530302 | 89530397 | H_c_72d02 |
| 5 | 89805379 | 89806168 | H_c_203k20_M |
| 5 | 89860581 | 89861896 | H_c_234n11_M |
| 5 | 90518738 | 90518846 | H_c_44l23 |
| 5 | 90612059 | 90612530 | H_c_152c12_M |
| 5 | 90653605 | 90653797 | H_c_207o08 |
| 5 | 90711580 | 90712298 | H_c_118d14 |
| 5 | 90714918 | 90715497 | H_c_258h24_M |
| 5 | 91356419 | 91356509 | H_c_246l20 |
| 5 | 91369963 | 91370056 | H_c_18k11 |
| 5 | 91433122 | 91433271 | H_c_165p14 |
| 5 | 91444362 | 91444560 | H_c_65m02 |
| 5 | 91628284 | 91628549 | H_c_229b04 |
| 5 | 91863768 | 91864182 | H_c_165l17 |
| 5 | 91935169 | 91935272 | H_c_245p13 |
| 5 | 92927454 | 92927682 | H_c_44p14 |
| 5 | 92931942 | 92935037 | H_c_105k24_M |
| 5 | 9293674 | 9293783 | H_c_36p22 |
| 5 | 92941173 | 92946837 | H_c_49i09_M_M |
| 5 | 92949002 | 92950681 | H_c_169h23_M |
| 5 | 92957722 | 92957830 | H_c_33a09 |
| 5 | 92965657 | 92966137 | H_c_214j01 |
| 5 | 92973410 | 92973551 | H_c_16l08_M |
| 5 | 92982057 | 92983228 | H_c_160d02_M |
| 5 | 93245848 | 93245960 | H_c_147n21 |
| 5 | 93301506 | 93301548 | H_c_17j03 |
| 5 | 93912687 | 93912756 | H_c_38p12 |
| 5 | 9423245 | 9423322 | H_c142i07 |
| 5 | 94480473 | 94480609 | H_c_39j14 |
| 5 | 945253 | 946626 | H_c_56d16_M |
| 5 | 94552477 | 94552590 | H_c_245n23 |
| 5 | 94618351 | 94618444 | H_c_51n24 |
| 5 | 94645201 | 94646903 | H_c_273p17_M |
| 5 | 94916220 | 94917104 | H_c_44g09_M |
| 5 | 95007890 | 95008420 | H_c_59k23 |
| 5 | 95092586 | 95093616 | H_c_4f18_M |
| 5 | 95177540 | 95177745 | H_c_259a18 |
| 5 | 95316510 | 95316645 | H_c_250g18 |
| 5 | 95321534 | 95323181 | H_c_176f08_M |
| 5 | 95630058 | 95630157 | H_c_36n23 |
| 5 | 95695332 | 95695435 | H_c_168j22 |
| 5 | 9597808 | 9599774 | H_c_149n20_M |
| 5 | 96023651 | 96025000 | H_c_163h10_M |
| 5 | 96168808 | 96170176 | H_c_91o22 |

TABLE 1-continued

| | | | |
|---|---|---|---|
| 5 | 96205117 | 96205311 | H_c_37j23 |
| 5 | 96296647 | 96298000 | H_c_36h18_M |
| 5 | 96305148 | 96305287 | H_c_185c20 |
| 5 | 96500633 | 96500762 | H_c_196i10 |
| 5 | 96773720 | 96773926 | H_c_8j22 |
| 5 | 97876155 | 97876343 | H_c_216j07 |
| 5 | 98132456 | 98134269 | H_c_18a12_M |
| 5 | 98136903 | 98138224 | H_c_251d17 |
| 5 | 98291596 | 98293435 | H_c_160b16_M |
| 5 | 99166796 | 99166874 | H_c_230b22 |
| 5 | 99589719 | 99589884 | H_c_34m22 |
| 5 | 99898771 | 99899686 | H_c_122l04 |
| 6 | 100113817 | 100113925 | H_c_220p07 |
| 6 | 100122829 | 100124287 | H_c_242n10_M |
| 6 | 100143142 | 100144007 | H_c_84e05 |
| 6 | 100157704 | 100158661 | H_c_273f17_M |
| 6 | 100167690 | 100169466 | H_c_33h15_M |
| 6 | 100173115 | 100174012 | H_c_9e13_M |
| 6 | 100299550 | 100299630 | H_c_232d06 |
| 6 | 100547986 | 100549023 | H_c_21n14_M |
| 6 | 100789884 | 100789962 | H_c_270e03 |
| 6 | 100967629 | 100967727 | H_c_258m17 |
| 6 | 101001603 | 101002666 | H_c_31e10 |
| 6 | 101019518 | 101020097 | H_c_262j02_M |
| 6 | 101024100 | 101026430 | H_c_206n19_M |
| 6 | 101114878 | 101114950 | H_c_40l18 |
| 6 | 101435735 | 101436281 | H_c141e11_M |
| 6 | 101954174 | 101954389 | H_c_128n04 |
| 6 | 10221331 | 10221806 | H_c_27h19 |
| 6 | 102374070 | 102374147 | H_c139p21 |
| 6 | 103207945 | 103208055 | H_c_68i16 |
| 6 | 103233832 | 103233922 | H_c_153i09 |
| 6 | 104254596 | 104254757 | H_c_90g21 |
| 6 | 104791333 | 104791465 | H_c_237f03 |
| 6 | 104835500 | 104835848 | H_c_181p24 |
| 6 | 10489408 | 10492032 | H_c_87m19_M |
| 6 | 10492917 | 10493630 | H_c_4f07_M |
| 6 | 10497601 | 10497671 | H_c_202e14 |
| 6 | 10512245 | 10512903 | H_c_197h18_M |
| 6 | 10520280 | 10520497 | H_c_216k19_M |
| 6 | 10526540 | 10528580 | H_c_251g11 |
| 6 | 10534001 | 10534943 | H_c_123k16_M |
| 6 | 105408517 | 105408719 | H_c_175i09 |
| 6 | 105413782 | 105414731 | H_c_43i04_M |
| 6 | 105494614 | 105496257 | H_c_178h15 |
| 6 | 105507481 | 105508425 | H_c_82l20 |
| 6 | 105518753 | 105518962 | H_c_40h05_M |
| 6 | 105690942 | 105692346 | H_c_18j07_M |
| 6 | 105733447 | 105735188 | H_c132p22_M |
| 6 | 105957065 | 105958450 | H_c_70h20_M |
| 6 | 106535956 | 106536656 | H_c_16f16 |
| 6 | 106546102 | 106549912 | H_c_40l24_M |
| 6 | 106640905 | 106641188 | H_c_152d05_M |
| 6 | 107064744 | 107067737 | H_c_211d16_M |
| 6 | 107183890 | 107184155 | H_c_246g06_M |
| 6 | 107455740 | 107456802 | H_c_87k10 |
| 6 | 107542016 | 107544230 | H_c_83i05_M |
| 6 | 107756865 | 107757055 | H_c_94i07 |
| 6 | 107916666 | 107918835 | H_c_269e03_M |
| 6 | 108061323 | 108063158 | H_c_23a07 |
| 6 | 10827785 | 10831500 | H_c_179c08_M |
| 6 | 108385334 | 108386403 | H_c_205k10_M |
| 6 | 108501730 | 108503163 | H_c_6d14_M |
| 6 | 108542751 | 108546668 | H_c140o24_M |
| 6 | 108585661 | 108586262 | H_c_192i13 |
| 6 | 108591529 | 108598180 | H_c132b20_M_M |
| 6 | 108603785 | 108605436 | H_c_195k16 |
| 6 | 108722591 | 108723894 | H_c_121j05_M |
| 6 | 108732201 | 108732392 | H_c_86g22 |
| 6 | 108985118 | 108988655 | H_c_28i15_M_M |
| 6 | 109276180 | 109276883 | H_c_108g20 |
| 6 | 109436796 | 109438263 | H_c_201c03_M |
| 6 | 109522344 | 109523248 | H_c_49j01_M |
| 6 | 109809828 | 109810931 | H_c_92k12_M |
| 6 | 109867923 | 109869693 | H_c_108e23_M |
| 6 | 109910784 | 109911665 | H_c_81i16 |
| 6 | 10991715 | 10993071 | H_c_240o22 |
| 6 | 110118999 | 110119732 | H_c_185b18 |
| 6 | 110405752 | 110406844 | H_c_52g18_M |
| 6 | 110606519 | 110608142 | H_c_30n15_M |
| 6 | 110674257 | 110674359 | H_c_212g07 |
| 6 | 110785505 | 110786618 | H_c132h13 |
| 6 | 110791061 | 110791308 | H_c_127g13 |
| 6 | 111302953 | 111304418 | H_c_52a02_M |
| 6 | 111386218 | 111387044 | H_c_52b08_M |
| 6 | 111409771 | 111409966 | H_c_252i09_M |
| 6 | 11151476 | 11153465 | H_c_80n04 |
| 6 | 111514960 | 111515371 | H_c_154h15_M |
| 6 | 111515374 | 111516572 | H_c_59o02_M |
| 6 | 111686746 | 111688278 | H_c_93a08_M |
| 6 | 111909908 | 111911863 | H_c_2d18 |
| 6 | 11201492 | 11202725 | H_c_59h15 |
| 6 | 112116443 | 112116638 | H_c_39n15_M |
| 6 | 112162842 | 112163170 | H_c_84b04 |
| 6 | 112192405 | 112192534 | H_c_149h21 |
| 6 | 112515241 | 112515614 | H_c_163h08_M |
| 6 | 112681499 | 112683293 | H_c_121b06_M |
| 6 | 113485335 | 113485419 | H_c_29b23 |
| 6 | 113992259 | 113993191 | H_c_113j14 |
| 6 | 114286399 | 114288549 | H_c_80e09_M |
| 6 | 114397609 | 114399575 | H_c_239g16_M |
| 6 | 114527245 | 114527320 | H_c_163g01 |
| 6 | 114769298 | 114769551 | H_c_85f11 |
| 6 | 114926767 | 114926924 | H_c_127o05 |
| 6 | 115156362 | 115156561 | H_c_79h12 |
| 6 | 115263523 | 115263860 | H_c_197b21_M |
| 6 | 115490180 | 115490299 | H_c_176f04 |
| 6 | 115694119 | 115694203 | H_c_50l11 |
| 6 | 115702680 | 115703291 | H_c_177k12 |
| 6 | 116358333 | 116358409 | H_c_184n11 |
| 6 | 116400966 | 116401050 | H_c_60d20 |
| 6 | 11645446 | 11646733 | H_c_22m23_M |
| 6 | 116503822 | 116503931 | H_c_102f09 |
| 6 | 116798368 | 116799737 | H_c_64i13 |
| 6 | 116889649 | 116890755 | H_c_53m13_M |
| 6 | 117304411 | 117305576 | H_c_79i10 |
| 6 | 117693389 | 117694219 | H_c_19l20_M |
| 6 | 117697991 | 117698937 | H_c_209j04_M |
| 6 | 117911004 | 117911452 | H_c_89d06 |
| 6 | 117975356 | 117976542 | H_c_11b10_M |
| 6 | 118029792 | 118030507 | H_c_44l24_M |
| 6 | 118102764 | 118104130 | H_c_209j20 |
| 6 | 11814331 | 11814458 | H_c_202a15 |
| 6 | 118334513 | 118336595 | H_c_46b01 |
| 6 | 118492701 | 118492884 | H_c_225m24 |
| 6 | 119066692 | 119066753 | H_c_273m23 |
| 6 | 119078148 | 119079875 | H_c_189j23_M |
| 6 | 119265758 | 119265890 | H_c_116m04 |
| 6 | 119275386 | 119275535 | H_c_15h08 |
| 6 | 119297000 | 119298412 | H_c_46c19_M |
| 6 | 119440822 | 119442293 | H_c_195l24_M |
| 6 | 119711109 | 119712256 | H_c_74b11_M |
| 6 | 119712248 | 119713471 | H_c_36b06_M |
| 6 | 119974804 | 119974906 | H_c_72b08 |
| 6 | 120107221 | 120107389 | H_c_1l08 |
| 6 | 120589103 | 120589197 | H_c_193j15 |
| 6 | 121034507 | 121034672 | H_c_219p02 |
| 6 | 12119431 | 12121672 | H_c_91h02_M |
| 6 | 121218930 | 121219081 | H_c_15i09 |
| 6 | 121697098 | 121697969 | H_c_120l06_M |
| 6 | 121873654 | 121874039 | H_c_70o20 |
| 6 | 122033659 | 122033781 | H_c_19o11 |
| 6 | 122128402 | 122128503 | H_c_233m10 |
| 6 | 122336044 | 122336270 | H_c_18n13 |
| 6 | 122561721 | 122561814 | H_c_180n06 |
| 6 | 122635934 | 122636049 | H_c_73c21 |
| 6 | 122761984 | 122763247 | H_c_121j20_M |
| 6 | 122972822 | 122973575 | H_c_216n03_M |
| 6 | 1231403 | 1231574 | H_c_195c17 |
| 6 | 123151620 | 123152958 | H_c_83m10_M |
| 6 | 123358710 | 123359946 | H_c_167o22 |
| 6 | 123754789 | 123755055 | H_c_252a22 |
| 6 | 124165759 | 124167311 | H_c_267k23_M |
| 6 | 124219056 | 124219119 | H_c_211d17 |
| 6 | 124675072 | 124675310 | H_c_224d03 |
| 6 | 124792809 | 124792963 | H_c_265h13 |
| 6 | 124948869 | 124949070 | H_c_113e22 |
| 6 | 125020608 | 125020686 | H_c_50b10 |
| 6 | 125157856 | 125157989 | H_c_188f01 |
| 6 | 125230084 | 125230199 | H_c_222j09 |

TABLE 1-continued

| | | | |
|---|---|---|---|
| 6 | 125324400 | 125326420 | H_c_268g15_M |
| 6 | 125429975 | 125430038 | H_c_89k05 |
| 6 | 125461481 | 125462918 | H_c138h20 |
| 6 | 125516362 | 125517702 | H_c_66b12 |
| 6 | 125664228 | 125665670 | H_c_162g23 |
| 6 | 1256645 | 1259248 | H_c_120b03_M |
| 6 | 125726367 | 125727104 | H_c_51a10 |
| 6 | 126111889 | 126113083 | H_c_4o05_M |
| 6 | 1261440 | 1262817 | H_c_31l24 |
| 6 | 126153101 | 126154544 | H_c_202p14_M |
| 6 | 126255700 | 126255804 | H_c_128c21 |
| 6 | 126319391 | 126320416 | H_c_195n08_M |
| 6 | 126349473 | 126349669 | H_c_233n19 |
| 6 | 126415353 | 126415495 | H_c_32a16 |
| 6 | 126425515 | 126425794 | H_c_192e18 |
| 6 | 126702928 | 126703299 | H_c_28a13_M |
| 6 | 126717616 | 126717779 | H_c_160h14 |
| 6 | 127121121 | 127121204 | H_c_226m04 |
| 6 | 127481983 | 127482938 | H_c_204n21 |
| 6 | 12755316 | 12755533 | H_c_42j16 |
| 6 | 127607174 | 127607277 | H_c134o21_M |
| 6 | 127629327 | 127630509 | H_c_233m24_M |
| 6 | 127702080 | 127702181 | H_c_4h16 |
| 6 | 127705875 | 127706783 | H_c_123n21_M |
| 6 | 127877203 | 127879629 | H_c_120n11_M |
| 6 | 12858050 | 12858615 | H_c_223f04 |
| 6 | 128881698 | 128882711 | H_c_248k21 |
| 6 | 12962151 | 12962367 | H_c_36h10 |
| 6 | 129850380 | 129850819 | H_c_172b19 |
| 6 | 130236873 | 130236936 | H_c_184e13 |
| 6 | 130381132 | 130381535 | H_c_186i19 |
| 6 | 130727849 | 130729628 | H_c_186e14_M |
| 6 | 130994738 | 130994887 | H_c_181l19 |
| 6 | 13121479 | 13122607 | H_c_205b12 |
| 6 | 131424889 | 131426371 | H_c_56l05_M |
| 6 | 131818079 | 131818175 | H_c_63k09 |
| 6 | 131899334 | 131899473 | H_c144c02 |
| 6 | 132170627 | 132171452 | H_c_99j05_M |
| 6 | 132312784 | 132314735 | H_c_266k17_M |
| 6 | 1323379 | 1324411 | H_c_216b05_M |
| 6 | 1324420 | 1325248 | H_c_7a23 |
| 6 | 132562137 | 132562386 | H_c_206g18 |
| 6 | 132763729 | 132765130 | H_c_6f18 |
| 6 | 132853478 | 132853946 | H_c_230p19 |
| 6 | 13286628 | 13286776 | H_c_57p01 |
| 6 | 132965582 | 132965678 | H_c_268b03 |
| 6 | 133082866 | 133084329 | H_c136i16 |
| 6 | 133177373 | 133177536 | H_c_124k22_M |
| 6 | 133308285 | 133308461 | H_c_170j14 |
| 6 | 133603236 | 133605094 | H_c_2e21_M |
| 6 | 133844894 | 133845002 | H_c_128b16 |
| 6 | 1338671 | 1338935 | H_c_207j08_M |
| 6 | 134217383 | 134217719 | H_c_254e10 |
| 6 | 134258455 | 134259173 | H_c_17k20_M |
| 6 | 134314842 | 134316574 | H_c_160m23_M |
| 6 | 13436299 | 13437047 | H_c_67m09_M |
| 6 | 134537216 | 134539497 | H_c_170f07_M |
| 6 | 134640838 | 134641131 | H_c_97f13 |
| 6 | 13530734 | 13530958 | H_c_114d08 |
| 6 | 135531317 | 135531457 | H_c_103m23 |
| 6 | 135543549 | 135546112 | H_c_57b04_M |
| 6 | 135826358 | 135826828 | H_c_259m18 |
| 6 | 135860130 | 135860980 | H_c_58n24_M |
| 6 | 136652001 | 136652748 | H_c135c23_M |
| 6 | 13682218 | 13683835 | H_c_44k17_M |
| 6 | 136912139 | 136913994 | H_c139n03_M |
| 6 | 137154494 | 137156163 | H_c_217d08 |
| 6 | 137185236 | 137186231 | H_c_64b16 |
| 6 | 13722349 | 13724008 | H_c_110h14 |
| 6 | 137283600 | 137283781 | H_c143l07 |
| 6 | 137352793 | 137353159 | H_c_106n13_M |
| 6 | 137406988 | 137407993 | H_c_214b10_M |
| 6 | 137581802 | 137582416 | H_c_24o19_M |
| 6 | 137851046 | 137851919 | H_c_98p11_M |
| 6 | 137855837 | 137857050 | H_c_261f08 |
| 6 | 137860263 | 137861546 | H_c_77d06_M |
| 6 | 138072341 | 138072607 | H_c_183n14 |
| 6 | 138123125 | 138124235 | H_c_19h17 |
| 6 | 138228959 | 138230571 | H_c_89n23_M |
| 6 | 138469569 | 138470943 | H_c_67n11 |
| 6 | 138523671 | 138525364 | H_c_23a09_M |
| 6 | 138766607 | 138767500 | H_c_252n16 |
| 6 | 139054764 | 139056519 | H_c_264h14 |
| 6 | 13921817 | 13922919 | H_c_257k21 |
| 6 | 139350050 | 139351313 | H_c_175h11_M |
| 6 | 139497656 | 139498888 | H_c_63e23 |
| 6 | 139661126 | 139661212 | H_c_160d03 |
| 6 | 139737104 | 139737611 | H_c_62l20_M |
| 6 | 140018508 | 140018714 | H_c139n15 |
| 6 | 140319402 | 140319548 | H_c_41d07_M |
| 6 | 14032740 | 14033861 | H_c_7j14_M |
| 6 | 141008191 | 141008315 | H_c_13e11 |
| 6 | 14104521 | 14104757 | H_c_195m20 |
| 6 | 141192135 | 141192233 | H_c_167h07 |
| 6 | 141330279 | 141330405 | H_c140j11 |
| 6 | 141478703 | 141478818 | H_c_157b20 |
| 6 | 14225372 | 14226537 | H_c_192d24_M |
| 6 | 142509708 | 142510288 | H_c_88j05_M |
| 6 | 142664237 | 142665478 | H_c_162j24_M |
| 6 | 14318989 | 14320042 | H_c_228i23 |
| 6 | 143289311 | 143290423 | H_c_6c11_M |
| 6 | 143307446 | 143309536 | H_c_28f02_M |
| 6 | 143422891 | 143424795 | H_c_235a09_M |
| 6 | 143725762 | 143725938 | H_c_32a07 |
| 6 | 143813146 | 143814117 | H_c_150n01_M |
| 6 | 143899311 | 143900578 | H_c_53h05 |
| 6 | 144040590 | 144041240 | H_c_30h03 |
| 6 | 144132622 | 144132735 | H_c_217m03 |
| 6 | 144205978 | 144206583 | H_c140j04 |
| 6 | 144293051 | 144293172 | H_c_159e11 |
| 6 | 144370507 | 144371794 | H_c_33b01 |
| 6 | 144426782 | 144427588 | H_c_108d18_M |
| 6 | 144458004 | 144458722 | H_c_244l06 |
| 6 | 144512722 | 144513752 | H_c_155c17 |
| 6 | 144647510 | 144650105 | H_c_185i14_M |
| 6 | 144698095 | 144698223 | H_c_97g18 |
| 6 | 144704938 | 144705119 | H_c_232e11 |
| 6 | 144756313 | 144756672 | H_c_56j07 |
| 6 | 144763137 | 144763311 | H_c_21f02 |
| 6 | 145051261 | 145051345 | H_c_3a07_M |
| 6 | 146097370 | 146098651 | H_c_172d16 |
| 6 | 146177151 | 146178681 | H_c_71f08_M |
| 6 | 146326414 | 146327227 | H_c_150j12_M |
| 6 | 146390335 | 146391566 | H_c_195n03 |
| 6 | 14668255 | 14668395 | H_c_221e03 |
| 6 | 146797350 | 146797782 | H_c_91h08 |
| 6 | 146906031 | 146907343 | H_c_264g04_M |
| 6 | 147566454 | 147567496 | H_c_97p22 |
| 6 | 147773253 | 147773374 | H_c_117e18 |
| 6 | 147785336 | 147785422 | H_c_32k21 |
| 6 | 147869598 | 147872584 | H_c_60k05_M |
| 6 | 149679584 | 149681278 | H_c_129f15_M |
| 6 | 149813400 | 149815042 | H_c_70g18_M |
| 6 | 149852142 | 149852314 | H_c_150a17 |
| 6 | 1500176 | 1500732 | H_c_210f19_M |
| 6 | 150131274 | 150131558 | H_c_274g09_M |
| 6 | 150162310 | 150163948 | H_c_5b12 |
| 6 | 150162379 | 150163948 | H_c_184o13 |
| 6 | 150276392 | 150278093 | H_c_210h10_M |
| 6 | 150355035 | 150355248 | H_c_169b19_M |
| 6 | 150402025 | 150405394 | H_c_189o24_M |
| 6 | 150418093 | 150418733 | H_c_30n12_M |
| 6 | 150621832 | 150621991 | H_c_13c05 |
| 6 | 151012872 | 151014361 | H_c139j23_M |
| 6 | 151278644 | 151280389 | H_c_6p03 |
| 6 | 151630167 | 151630362 | H_c_215g11 |
| 6 | 151653630 | 151654994 | H_c_61n09 |
| 6 | 151803187 | 151803724 | H_c_51b10_M |
| 6 | 151865092 | 151866117 | H_c_93g19_M |
| 6 | 151906895 | 151907683 | H_c_240b03 |
| 6 | 152297265 | 152297385 | H_c_53i22 |
| 6 | 152715294 | 152715650 | H_c_74j13_M |
| 6 | 153049647 | 153050809 | H_c_26g23_M |
| 6 | 153396320 | 153397137 | H_c_271k21 |
| 6 | 153416065 | 153416680 | H_c_80f10 |
| 6 | 15352891 | 15357659 | H_c_66h19_M_M |
| 6 | 153542976 | 153543505 | H_c_241f14_M |
| 6 | 153543504 | 153545010 | H_c_217e18_M |
| 6 | 15364179 | 15364450 | H_c_60g02 |
| 6 | 153692616 | 153692700 | H_c_36k19 |

TABLE 1-continued

| | | | |
|---|---|---|---|
| 6 | 154277385 | 154277485 | H_c_119e17 |
| 6 | 154439103 | 154439204 | H_c_227j02 |
| 6 | 154452294 | 154453124 | H_c_49j08_M |
| 6 | 154557492 | 154557647 | H_c_13k11 |
| 6 | 154921913 | 154924235 | H_c_187m19_M |
| 6 | 1549417 | 1550802 | H_c_74k19 |
| 6 | 155408283 | 155409484 | H_c_91e19_M |
| 6 | 1554112 | 1555178 | H_c_234c03_M |
| 6 | 1555183 | 1557437 | H_c_30k12_M |
| 6 | 15565089 | 15565226 | H_c_220j12 |
| 6 | 155727611 | 155728035 | H_c_6k02 |
| 6 | 155766477 | 155766814 | H_c_25e10 |
| 6 | 1559118 | 1559265 | H_c_210f15_M |
| 6 | 156032272 | 156032404 | H_c_54j03 |
| 6 | 156443983 | 156444206 | H_c_16g17 |
| 6 | 1570067 | 1570756 | H_c_33h01_M |
| 6 | 157038310 | 157038419 | H_c_60m07 |
| 6 | 157100049 | 157101031 | H_c_83a22_M |
| 6 | 157189967 | 157191865 | H_c_16a15_M |
| 6 | 157287342 | 157287482 | H_c_91j21 |
| 6 | 157434168 | 157435178 | H_c_84d12_M |
| 6 | 15770381 | 15771404 | H_c_88p18 |
| 6 | 157714858 | 157715195 | H_c_254j11 |
| 6 | 157771315 | 157773851 | H_c141k22_M |
| 6 | 158214010 | 158215815 | H_c_60b18_M |
| 6 | 158372415 | 158374181 | H_c_102l10_M |
| 6 | 158559157 | 158560022 | H_c_194k07_M |
| 6 | 158623050 | 158624659 | H_c_113f23_M |
| 6 | 158703860 | 158703977 | H_c_184o24 |
| 6 | 158927584 | 158929130 | H_c_16d04 |
| 6 | 158951120 | 158952295 | H_c_99c23_M |
| 6 | 159035547 | 159036665 | H_c_54n14_M |
| 6 | 159164450 | 159164670 | H_c_229e08 |
| 6 | 159209704 | 159211194 | H_c_241l04 |
| 6 | 159261019 | 159261922 | H_c_151b23_M |
| 6 | 159390693 | 159391853 | H_c_169d03 |
| 6 | 159559471 | 159562760 | H_c_199n06_M |
| 6 | 159697690 | 159697867 | H_c_61k10 |
| 6 | 160010002 | 160010133 | H_c_193d19 |
| 6 | 160016067 | 160016205 | H_c_120p23 |
| 6 | 160083956 | 160085479 | H_c_32i11_M |
| 6 | 160117860 | 160119617 | H_c_251d09_M |
| 6 | 160135673 | 160135824 | H_c_117e07 |
| 6 | 160152772 | 160155004 | H_c_58p08_M |
| 6 | 160180127 | 160181510 | H_c_1n18_M |
| 6 | 160360102 | 160361318 | H_c_19a17_M |
| 6 | 160738045 | 160740507 | H_c_98h24 |
| 6 | 160746100 | 160747374 | H_c_103g19 |
| 6 | 160911298 | 160912284 | H_c_28b05_M |
| 6 | 161322126 | 161323071 | H_c_2k05 |
| 6 | 161382763 | 161384239 | H_c_247m14 |
| 6 | 16236968 | 16238185 | H_c_265d17 |
| 6 | 162618572 | 162618660 | H_c_111j13 |
| 6 | 162864803 | 162864970 | H_c_64h05 |
| 6 | 163119204 | 163119704 | H_c_26m12_M |
| 6 | 16346770 | 16347161 | H_c131j19_M |
| 6 | 163539791 | 163540831 | H_c_116c02 |
| 6 | 163543144 | 163543615 | H_c_17d09 |
| 6 | 163804542 | 163807360 | H_c_82j01_M |
| 6 | 164021607 | 164023299 | H_c_158n23 |
| 6 | 164846797 | 164846990 | H_c135j01 |
| 6 | 164891732 | 164892016 | H_c142f18 |
| 6 | 165231787 | 165231855 | H_c_24i15 |
| 6 | 165392075 | 165393412 | H_c_6f22 |
| 6 | 165582944 | 165583263 | H_c_112h13 |
| 6 | 166047603 | 166048744 | H_c_259d07 |
| 6 | 166201485 | 166201765 | H_c_261d04 |
| 6 | 166268876 | 166269056 | H_c_105o19 |
| 6 | 16635413 | 16635551 | H_c_215n24 |
| 6 | 166371977 | 166373087 | H_c_199e12_M |
| 6 | 16643982 | 16643985 | H_c_9h24 |
| 6 | 166550182 | 166552850 | H_c_12d06_M |
| 6 | 166659581 | 166659837 | H_c_235g05 |
| 6 | 166726124 | 166726978 | H_c_127g20_M |
| 6 | 166921873 | 166922848 | H_c_215n18 |
| 6 | 167122582 | 167122686 | H_c_102i02 |
| 6 | 167246075 | 167247078 | H_c_233g2_M |
| 6 | 167303714 | 167303822 | H_c_158l05 |
| 6 | 167339059 | 167341467 | H_c_214f11_M |
| 6 | 167381938 | 167383922 | H_c_156a04_M |
| 6 | 167462475 | 167463045 | H_c_72n17 |
| 6 | 1677883 | 1679084 | H_c_261c13_M |
| 6 | 167953491 | 167953591 | H_c_29k16 |
| 6 | 168014514 | 168016241 | H_c_205m20_M |
| 6 | 168044714 | 168047107 | H_c_116b12_M |
| 6 | 168254263 | 168255354 | H_c_79d06_M |
| 6 | 168363338 | 168363458 | H_c_228m20 |
| 6 | 168538117 | 168539244 | H_c_205k18 |
| 6 | 168659976 | 168661720 | H_c_167o17 |
| 6 | 16869982 | 16870378 | H_c133i06 |
| 6 | 168760562 | 168760872 | H_c_206h03 |
| 6 | 168928759 | 168928883 | H_c_103d18 |
| 6 | 169102388 | 169102515 | H_c_7n20_M |
| 6 | 169469419 | 169471653 | H_c_247b06_M |
| 6 | 16967174 | 16967262 | H_c_109i20 |
| 6 | 169919269 | 169920714 | H_c_185c01_M |
| 6 | 169969017 | 169970135 | H_c_236b14_M |
| 6 | 170255723 | 170256937 | H_c144j03_M |
| 6 | 170517015 | 170517263 | H_c_33m18_M |
| 6 | 170521815 | 170524157 | H_c_205g06_M |
| 6 | 170532385 | 170533892 | H_c_58p04_M |
| 6 | 170721252 | 170723761 | H_c_42l10_M |
| 6 | 170779669 | 170780246 | H_c_161n12 |
| 6 | 170810962 | 170811792 | H_c_94k07_M |
| 6 | 17123636 | 17124929 | H_c_246n17_M |
| 6 | 17371550 | 17371759 | H_c_119a16 |
| 6 | 17388563 | 17390262 | H_c_57m11_M |
| 6 | 17501328 | 17502688 | H_c_258p01_M |
| 6 | 17708340 | 17709912 | H_c_27k21_M |
| 6 | 17814519 | 17815384 | H_c_178g11_M |
| 6 | 17873122 | 17873221 | H_c_56c22 |
| 6 | 1796705 | 1796813 | H_c_117c09 |
| 6 | 18229584 | 18231365 | H_c_55n13_M |
| 6 | 18263038 | 18263956 | H_c_99c17_M |
| 6 | 18313149 | 18313334 | H_c_8h05 |
| 6 | 1834291 | 1834391 | H_c_88j01 |
| 6 | 18353821 | 18353916 | H_c_265h15 |
| 6 | 18371865 | 18373196 | H_c_206d05 |
| 6 | 18385400 | 18386299 | H_c_258c10 |
| 6 | 18495473 | 18495826 | H_c_2f06 |
| 6 | 18567853 | 18568029 | H_c_206c07 |
| 6 | 18779963 | 18780163 | H_c_99d11_M |
| 6 | 18893703 | 18893963 | H_c_111n06 |
| 6 | 19178311 | 19178400 | H_c_6g17 |
| 6 | 19210268 | 19210371 | H_c_234p09_M |
| 6 | 19679280 | 19679410 | H_c_38p04_M |
| 6 | 1973792 | 1973870 | H_c_72h15 |
| 6 | 19912556 | 19913399 | H_c_237l09_M |
| 6 | 19945022 | 19947689 | H_c_41p24_M |
| 6 | 20320083 | 20321354 | H_c_212c16 |
| 6 | 20509509 | 20512723 | H_c_1b01_M |
| 6 | 20546660 | 20546764 | H_c_186e07 |
| 6 | 2073382 | 2074271 | H_c_252f15_M |
| 6 | 2126468 | 2126600 | H_c_273o18 |
| 6 | 21695091 | 21696926 | H_c_54c09_M |
| 6 | 21702043 | 21704045 | H_c_3k16_M |
| 6 | 2171741 | 2171865 | H_c_40j03 |
| 6 | 21772342 | 21772782 | H_c_71o11_M |
| 6 | 2189998 | 2191853 | H_c_222p19_M |
| 6 | 22476230 | 22476389 | H_c_209j21 |
| 6 | 24422967 | 24423115 | H_c_258g09 |
| 6 | 24465445 | 24468846 | H_c_150m17_M |
| 6 | 24602502 | 24607641 | H_c_139o15_M |
| 6 | 24754127 | 24754935 | H_c_110j04_M |
| 6 | 24774477 | 24775702 | H_c_172e21_M |
| 6 | 24882967 | 24883656 | H_c_6j18_M |
| 6 | 25043725 | 25043819 | H_c_202i13 |
| 6 | 25386831 | 25388674 | H_c_3c19 |
| 6 | 25740051 | 25740187 | H_c_252j05 |
| 6 | 26006394 | 26006599 | H_c_78j15 |
| 6 | 26020365 | 26020444 | H_c_164f10 |
| 6 | 26027267 | 26027413 | H_c_171a23 |
| 6 | 26099919 | 26101132 | H_c_91h24_M |
| 6 | 26128560 | 26130156 | H_c_197o17_M |
| 6 | 26135149 | 26135655 | H_c_167g16_M |
| 6 | 26139830 | 26140423 | H_c138p15 |
| 6 | 2614307 | 2615031 | H_c_233o13 |
| 6 | 26212335 | 26212555 | H_c_88c06 |
| 6 | 26264196 | 26265173 | H_c_97n16 |
| 6 | 26279909 | 26280395 | H_c_170j04_M |

TABLE 1-continued

| | | | |
|---|---|---|---|
| 6 | 26313311 | 26313633 | H_c_67n21 |
| 6 | 26324457 | 26324648 | H_c_25e23 |
| 6 | 26348608 | 26348808 | H_c_69e06_M |
| 6 | 26381563 | 26381629 | H_c_167o08 |
| 6 | 26427309 | 26427380 | H_c_89n19 |
| 6 | 26608484 | 26610348 | H_c_213j09_M |
| 6 | 26628950 | 26629256 | H_c_25n05_M |
| 6 | 26646385 | 26647042 | H_c_198p13_M |
| 6 | 26658506 | 26658967 | H_c_228i19 |
| 6 | 26713441 | 26713547 | H_c_51a13 |
| 6 | 27095647 | 27096266 | H_c_167f14_M |
| 6 | 2710028 | 2712039 | H_c_168m17_M |
| 6 | 27172179 | 27173084 | H_c_231m13 |
| 6 | 27207565 | 27207845 | H_c_26h06 |
| 6 | 2723262 | 2723640 | H_c_226l23_M |
| 6 | 27323433 | 27328200 | H_c142j23_M_M |
| 6 | 27343701 | 27343905 | H_c_86i10_M |
| 6 | 27360080 | 27360323 | H_c_235a08 |
| 6 | 27387628 | 27388868 | H_c_230c23 |
| 6 | 27464704 | 27465184 | H_c_109k22 |
| 6 | 27548501 | 27549478 | H_c_226c09_M |
| 6 | 27571139 | 27571325 | H_c_75a19 |
| 6 | 27659792 | 27659935 | H_c_214o24 |
| 6 | 27706390 | 27707331 | H_c_151m11 |
| 6 | 27756301 | 27756502 | H_c_146p12_M |
| 6 | 27802474 | 27802570 | H_c_230b11 |
| 6 | 27833058 | 27834564 | H_c_212m21_M |
| 6 | 2786335 | 2787775 | H_c_6p02 |
| 6 | 27943092 | 27943482 | H_c136h11 |
| 6 | 27949136 | 27949429 | H_c_220f03_M |
| 6 | 28155940 | 28157249 | H_c_9b18 |
| 6 | 2819448 | 2822079 | H_c_215o14 |
| 6 | 28199695 | 28200755 | H_c_262g23_M |
| 6 | 28212385 | 28213219 | H_c_201n03_M |
| 6 | 28217095 | 28218050 | H_c_121k04 |
| 6 | 28283300 | 28283596 | H_c_119n09_M |
| 6 | 28334751 | 28335793 | H_c_171p20_M |
| 6 | 28357011 | 28357506 | H_c_230c21 |
| 6 | 284007 | 284216 | H_c_110n23 |
| 6 | 28475030 | 28475759 | H_c_103e15_M |
| 6 | 2847677 | 2848927 | H_c_96g22 |
| 6 | 28518990 | 28519368 | H_c_191g01_M |
| 6 | 28549985 | 28550136 | H_c_171m16 |
| 6 | 28662620 | 28663203 | H_c_90n17 |
| 6 | 28691976 | 28692301 | H_c_188f14_M |
| 6 | 28742224 | 28742330 | H_c_55o14_M |
| 6 | 28814658 | 28815016 | H_c_33j09 |
| 6 | 28914582 | 28915005 | H_c_160f03_M |
| 6 | 28941099 | 28943612 | H_c_59d05 |
| 6 | 28960259 | 28961461 | H_c_230p21 |
| 6 | 28971898 | 28972768 | H_c_231d01 |
| 6 | 28998686 | 29000477 | H_c_265d11 |
| 6 | 29064172 | 29064615 | H_c_12k14_M |
| 6 | 29081455 | 29081623 | H_c_45f03 |
| 6 | 29087011 | 29087523 | H_c_88l14 |
| 6 | 29105001 | 29105119 | H_c_216g18 |
| 6 | 2916072 | 2917098 | H_c_254n03_M |
| 6 | 29255990 | 29256135 | H_c_121g20 |
| 6 | 2944308 | 2946584 | H_c_6k15_M |
| 6 | 29628810 | 29629946 | H_c_12f16 |
| 6 | 29643820 | 29645017 | H_c_43o12_M |
| 6 | 29677926 | 29678098 | H_c_28c03 |
| 6 | 29707669 | 29710334 | H_c_83l01_M |
| 6 | 29755495 | 29757129 | H_c_95b10 |
| 6 | 29797622 | 29800389 | H_c_54b16_M |
| 6 | 29925835 | 29926423 | H_c_111c22 |
| 6 | 2998242 | 2999949 | H_c_69g13_M |
| 6 | 3013370 | 3014383 | H_c_182a18 |
| 6 | 30149125 | 30151460 | H_c_222o16 |
| 6 | 30176315 | 30176992 | H_c_54a05_M |
| 6 | 30288551 | 30289599 | H_c_253c03_M |
| 6 | 30402127 | 30403467 | H_c140j21_M |
| 6 | 30420678 | 30421483 | H_c_177g02 |
| 6 | 30433385 | 30434051 | H_c_68h11 |
| 6 | 30565077 | 30566453 | H_c_32m04 |
| 6 | 30631360 | 30633587 | H_c_98i01 |
| 6 | 3063245 | 3064552 | H_c_66b16_M |
| 6 | 30646875 | 30647377 | H_c131i04_M |
| 6 | 30693384 | 30693637 | H_c_234c22 |
| 6 | 30722544 | 30723752 | H_c_180i16_M |
| 6 | 30748318 | 30748956 | H_c_18h18 |
| 6 | 30793050 | 30793198 | H_c_113a15 |
| 6 | 30818128 | 30820423 | H_c_211l18_M |
| 6 | 3102449 | 3103529 | H_c_153k15_M |
| 6 | 3107777 | 3108786 | H_c_239a13 |
| 6 | 31125652 | 31125732 | H_c_173m15 |
| 6 | 31272592 | 31274602 | H_c_30j22 |
| 6 | 31381007 | 31381816 | H_c_242o06 |
| 6 | 31474994 | 31476305 | H_c_24j17_M |
| 6 | 31621613 | 31622778 | H_c_40i10 |
| 6 | 31656286 | 31658993 | H_c_145o15_M |
| 6 | 31695852 | 31697632 | H_c_38e12_M |
| 6 | 3172379 | 3175274 | H_c_125g04_M |
| 6 | 31740635 | 31742389 | H_c_233n01_M |
| 6 | 31756500 | 31757682 | H_c_149n02_M |
| 6 | 31805173 | 31805318 | H_c_219a15_M |
| 6 | 31815405 | 31816038 | H_c_101f12_M |
| 6 | 31882105 | 31882944 | H_c_103h23_M |
| 6 | 31897164 | 31897756 | H_c_85j01 |
| 6 | 31910193 | 31911480 | H_c_246b02_M |
| 6 | 31939831 | 31940371 | H_c_192a06 |
| 6 | 31971952 | 31973506 | H_c_37f22_M |
| 6 | 3203804 | 3205160 | H_c_60c18_M |
| 6 | 32046545 | 32048210 | H_c_254o15_M |
| 6 | 32162476 | 32164086 | H_c_196e08_M |
| 6 | 32203725 | 32204224 | H_c_264m15 |
| 6 | 32224360 | 32227038 | H_c_68o09_M |
| 6 | 32271149 | 32272894 | H_c_59m12 |
| 6 | 32913217 | 32913397 | H_c_232m23 |
| 6 | 32928294 | 32930364 | H_c_214h08_M |
| 6 | 33043847 | 33044853 | H_c_229a05_M |
| 6 | 33119880 | 33120169 | H_c_56h13 |
| 6 | 33267074 | 33269359 | H_c_228o21_M |
| 6 | 33275742 | 33276329 | H_c_127g22_M |
| 6 | 33324353 | 33325519 | H_c_77p02_M |
| 6 | 33352623 | 33353093 | H_c_188h14_M |
| 6 | 3335655 | 3335820 | H_c_56i11 |
| 6 | 33373649 | 33375697 | H_c_105f14_M |
| 6 | 33388876 | 33392907 | H_c_185k07_M |
| 6 | 33392910 | 33393540 | H_c_208h16 |
| 6 | 33397940 | 33399157 | H_c_10h05_M |
| 6 | 33466771 | 33467407 | H_c_272l21 |
| 6 | 33485654 | 33487228 | H_c_174f04_M |
| 6 | 33495257 | 33496799 | H_c_239i22 |
| 6 | 33502430 | 33504718 | H_c_47n05_M |
| 6 | 33530048 | 33530588 | H_c_64h22 |
| 6 | 33545530 | 33545816 | H_c_37c03 |
| 6 | 33707915 | 33709824 | H_c_145e18_M |
| 6 | 33787082 | 33788114 | H_c_41f18_M |
| 6 | 33863594 | 33864968 | H_c_83c01 |
| 6 | 34218809 | 34220856 | H_c_82n23_M |
| 6 | 34220862 | 34221561 | H_c_159h20_M |
| 6 | 34271590 | 34273058 | H_c_19e19 |
| 6 | 34310212 | 34314312 | H_c_72m17_M |
| 6 | 34323924 | 34325320 | H_c_47f13_M |
| 6 | 34470870 | 34471069 | H_c_63i04 |
| 6 | 34540635 | 34542469 | H_c_29c16_M |
| 6 | 3454351 | 3454488 | H_c_45b20 |
| 6 | 34602843 | 34603372 | H_c_202m11_M |
| 6 | 34664013 | 34665505 | H_c_100j22 |
| 6 | 34833074 | 34833487 | H_c_23f10_M |
| 6 | 34867191 | 34868802 | H_c_33h20_M |
| 6 | 34964686 | 34965682 | H_c_114d01 |
| 6 | 35288928 | 35290929 | H_c_114j13 |
| 6 | 35334907 | 35335972 | H_c_145l19 |
| 6 | 35373068 | 35373183 | H_c_44a13 |
| 6 | 35418054 | 35419320 | H_c_65c22_M |
| 6 | 35543639 | 35544679 | H_c_212g05_M |
| 6 | 35763647 | 35764982 | H_c_176e15_M |
| 6 | 35802997 | 35804127 | H_c_116c14 |
| 6 | 35807685 | 35808029 | H_c_186j06 |
| 6 | 35851933 | 35852871 | H_c_258n09_M |
| 6 | 35886931 | 35887066 | H_c_214k20 |
| 6 | 35995844 | 35997200 | H_c_74p02_M |
| 6 | 36099867 | 36100677 | H_c_35h03_M |
| 6 | 36103354 | 36104624 | H_c_41a01 |
| 6 | 36205786 | 36207854 | H_c_195a02_M |
| 6 | 36271977 | 36273263 | H_c_40k18_M |
| 6 | 36317684 | 36317890 | H_c_93h07 |
| 6 | 36461782 | 36464189 | H_c_52b16 |

TABLE 1-continued

| | | | |
|---|---|---|---|
| 6 | 36518548 | 36519253 | H_c_66k10_M |
| 6 | 36622783 | 36623458 | H_c_208b17_M |
| 6 | 36669767 | 36670221 | H_c_31h20_M |
| 6 | 36702473 | 36705018 | H_c_212a09_M |
| 6 | 36754044 | 36756545 | H_c_272p23_M |
| 6 | 3695193 | 3696086 | H_c_11l01_M |
| 6 | 3696096 | 3697754 | H_c_44a21 |
| 6 | 37061084 | 37062688 | H_c_224j15 |
| 6 | 37082436 | 37084332 | H_c_18o01 |
| 6 | 37244840 | 37247660 | H_c_207e22_M |
| 6 | 37457381 | 37457475 | H_c_160f10 |
| 6 | 37508718 | 37509776 | H_c132i12 |
| 6 | 37611479 | 37612328 | H_c_211c04_M |
| 6 | 37644357 | 37645094 | H_c_88n16 |
| 6 | 37699197 | 37701044 | H_c142n18 |
| 6 | 37725500 | 37726448 | H_c_70a10 |
| 6 | 37771618 | 37775202 | H_c_45j04_M |
| 6 | 37894286 | 37896511 | H_c_244f14_M |
| 6 | 3793991 | 3796124 | H_c_267c09_M |
| 6 | 3826773 | 3826888 | H_c134i02 |
| 6 | 38778316 | 38778889 | H_c135m18 |
| 6 | 38790562 | 38791655 | H_c_212i22_M |
| 6 | 39190375 | 39191150 | H_c_8l24_M |
| 6 | 39304231 | 39305517 | H_c_71n18_M |
| 6 | 39388257 | 39390652 | H_c_222o23 |
| 6 | 39541706 | 39541866 | H_c135i03 |
| 6 | 3963430 | 3964200 | H_c_129g17 |
| 6 | 39800406 | 39801362 | H_c_5j11 |
| 6 | 39867554 | 39868514 | H_c_8i10_M |
| 6 | 40009664 | 40010486 | H_c_167g06 |
| 6 | 40204579 | 40204802 | H_c_35m13 |
| 6 | 40441374 | 40441551 | H_c_91e11 |
| 6 | 40660373 | 40665334 | H_c_205l02_M |
| 6 | 40767987 | 40769013 | H_c_196f17 |
| 6 | 4080318 | 4081508 | H_c_67j08_M |
| 6 | 41046639 | 41046715 | H_c_249a21 |
| 6 | 41148173 | 41149937 | H_c_45n18_M |
| 6 | 41176521 | 41176923 | H_c_5k11 |
| 6 | 41394529 | 41396150 | H_c_105b10 |
| 6 | 41447727 | 41450180 | H_c133g19_M |
| 6 | 41451116 | 41451237 | H_c_243o02 |
| 6 | 41482618 | 41483039 | H_c_211i22 |
| 6 | 41503540 | 41504294 | H_c_124m24_M |
| 6 | 41579493 | 41580784 | H_c_169f22_M |
| 6 | 41623424 | 41625555 | H_c_45n21_M |
| 6 | 41758804 | 41760945 | H_c_8m23_M |
| 6 | 41863149 | 41863577 | H_c_220k16 |
| 6 | 41970592 | 41971368 | H_c_192k13_M |
| 6 | 41997067 | 41997903 | H_c_183o19_M |
| 6 | 42015874 | 42018063 | H_c_46f08_M |
| 6 | 42123708 | 42126765 | H_c_5i19_M |
| 6 | 42217733 | 42221293 | H_c_28g09_M |
| 6 | 42527867 | 42529481 | H_c_127b21_M |
| 6 | 42802838 | 42803930 | H_c_187l02 |
| 6 | 42820828 | 42822045 | H_c_268g05_M |
| 6 | 42857522 | 42859639 | H_c_92h11_M |
| 6 | 42966032 | 42967256 | H_c_170b20_M |
| 6 | 43004773 | 43006093 | H_c_169a09_M |
| 6 | 43036442 | 43037027 | H_c_212j08_M |
| 6 | 43054032 | 43055116 | H_c_107m13_M |
| 6 | 43059478 | 43061193 | H_c_13m15 |
| 6 | 43089335 | 43090209 | H_c_69c19 |
| 6 | 43097000 | 43097824 | H_c_202g05_M |
| 6 | 43151635 | 43153123 | H_c_165p09_M |
| 6 | 43225591 | 43225701 | H_c_37a15 |
| 6 | 43303660 | 43305245 | H_c_18l20_M |
| 6 | 43349504 | 43352287 | H_c_72j23_M |
| 6 | 43360444 | 43361965 | H_c_30c08_M |
| 6 | 43383568 | 43384563 | H_c_261c05_M |
| 6 | 43444198 | 43445666 | H_c_250e20_M |
| 6 | 43457984 | 43458979 | H_c_116d13 |
| 6 | 43585312 | 43586887 | H_c_195i16_M |
| 6 | 4368035 | 4368219 | H_c138h03 |
| 6 | 43705093 | 43705621 | H_c_43h15_M |
| 6 | 43720920 | 43722002 | H_c_251l11 |
| 6 | 43746829 | 43748439 | H_c_130j12 |
| 6 | 43763349 | 43763678 | H_c_2f17_M |
| 6 | 43844288 | 43845896 | H_c_222b21 |
| 6 | 43845900 | 43846096 | H_c_186f17_M |
| 6 | 44077921 | 44078836 | H_c_240k20_M |
| 6 | 44148089 | 44150272 | H_c_236a22 |
| 6 | 44152175 | 44152547 | H_c_188o09_M |
| 6 | 44203033 | 44204776 | H_c_229g22_M |
| 6 | 44259284 | 44260438 | H_c131j07 |
| 6 | 44294772 | 44295864 | H_c139o11 |
| 6 | 44299027 | 44299679 | H_c_253e07_M |
| 6 | 44313443 | 44314157 | H_c_177g21 |
| 6 | 44321349 | 4322736 | H_c_45h24 |
| 6 | 44331109 | 44333916 | H_c_214h12 |
| 6 | 44340568 | 44341577 | H_c_102m23 |
| 6 | 44345780 | 44347695 | H_c_26a12_M |
| 6 | 44350887 | 44353129 | H_c_72c12 |
| 6 | 44371871 | 44374193 | H_c_261l24 |
| 6 | 44388515 | 44389217 | H_c_13h16_M |
| 6 | 44463099 | 44464495 | H_c136g16_M |
| 6 | 45126265 | 45126345 | H_c137e13 |
| 6 | 45453129 | 45454104 | H_c_164h04_M |
| 6 | 45455771 | 45455906 | H_c140o04 |
| 6 | 45495422 | 45499696 | H_c_91a14_M |
| 6 | 45738737 | 45739894 | H_c_64j24 |
| 6 | 45862302 | 45862826 | H_c_216a20_M |
| 6 | 46090803 | 46091356 | H_c_31k09_M |
| 6 | 46205378 | 46206146 | H_c_39g14_M |
| 6 | 46568725 | 46568837 | H_c_73c15 |
| 6 | 46671664 | 46671733 | H_c_249e04 |
| 6 | 46728051 | 46729241 | H_c_94h09_M |
| 6 | 46809856 | 46811260 | H_c_127g15_M |
| 6 | 46945949 | 46946088 | H_c_245l19 |
| 6 | 47182193 | 47182301 | H_c142m15 |
| 6 | 47371908 | 47371996 | H_c_91h21 |
| 6 | 47383995 | 47385911 | H_c_72m15_M |
| 6 | 47553112 | 47554378 | H_c_167o16_M |
| 6 | 47577089 | 47577272 | H_c_46g09 |
| 6 | 47852803 | 47852890 | H_c_197e18 |
| 6 | 47893205 | 47893327 | H_c_9m05 |
| 6 | 48144341 | 48144917 | H_c_98n21_M |
| 6 | 48461674 | 48461870 | H_c_92k21 |
| 6 | 48558068 | 48558220 | H_c_60j03 |
| 6 | 48641713 | 48641869 | H_c_45i02 |
| 6 | 48727577 | 48727669 | H_c_249j03 |
| 6 | 4887052 | 4887312 | H_c_147k09 |
| 6 | 49211420 | 49211565 | H_c_192k02 |
| 6 | 49290829 | 49290933 | H_c_36o13 |
| 6 | 4948960 | 4949707 | H_c_120p13 |
| 6 | 49578502 | 49578601 | H_c133g12 |
| 6 | 49625999 | 49627188 | H_c_122e01 |
| 6 | 5030666 | 5032151 | H_c_103m18_M |
| 6 | 5034396 | 5034528 | H_c_49o11_M |
| 6 | 5078073 | 5078634 | H_c_209j13 |
| 6 | 50895070 | 50895621 | H_c_28g18_M |
| 6 | 50898818 | 50901855 | H_c_165k04_M |
| 6 | 50925944 | 50926714 | H_c_127n18_M |
| 6 | 51325925 | 51326098 | H_c_68o15 |
| 6 | 51378065 | 51378229 | H_c_31p22 |
| 6 | 51468659 | 51468873 | H_c_54a18_M |
| 6 | 51499318 | 51500171 | H_c140g08 |
| 6 | 51606464 | 51606629 | H_c_117g03 |
| 6 | 5182046 | 5182187 | H_c_79c09 |
| 6 | 5205544 | 5206806 | H_c_13i23_M |
| 6 | 52257144 | 52257965 | H_c_266i05_M |
| 6 | 52334663 | 52336375 | H_c_184l21_M |
| 6 | 52392521 | 52393186 | H_c_9l17_M |
| 6 | 52549945 | 52550520 | H_c_241f16 |
| 6 | 52636780 | 52637753 | H_c_13j19 |
| 6 | 52643565 | 52644312 | H_c_46d22_M |
| 6 | 52953826 | 52954001 | H_c_215h21 |
| 6 | 53037990 | 53039283 | H_c_208i22_M |
| 6 | 53315674 | 53315875 | H_c_258d12_M |
| 6 | 53321008 | 53322134 | H_c_37a20 |
| 6 | 53332081 | 53332721 | H_c_82c02_M |
| 6 | 53516858 | 53518221 | H_c139o05 |
| 6 | 53520459 | 53521665 | H_c_235c14_M |
| 6 | 5353963 | 5354141 | H_c_76c14_M |
| 6 | 5363617 | 5364347 | H_c_117m24 |
| 6 | 53703848 | 53704039 | H_c_68n02 |
| 6 | 53767455 | 53768434 | H_c_6i05_M |
| 6 | 53875292 | 53875557 | H_c_8l06_M |
| 6 | 54130585 | 54130691 | H_c_241n02_M |
| 6 | 54818800 | 54820142 | H_c_239i13 |
| 6 | 54842702 | 54842788 | H_c_274f12_M |

TABLE 1-continued

| | | | |
|---|---|---|---|
| 6 | 54951345 | 54951552 | H_c_222o13 |
| 6 | 55116219 | 55116444 | H_c_235m17 |
| 6 | 55255001 | 55255257 | H_c_96e24 |
| 6 | 55551549 | 55552058 | H_c_84i24 |
| 6 | 56626659 | 56626744 | H_c_170a03 |
| 6 | 56665353 | 56665581 | H_c_69h21 |
| 6 | 56815745 | 56817213 | H_c_229i12_M |
| 6 | 56927118 | 56928919 | H_c_125i11_M |
| 6 | 57144484 | 57145785 | H_c_20j12_M |
| 6 | 57194142 | 57195356 | H_c_245b01_M |
| 6 | 57304734 | 57304914 | H_c_262h08 |
| 6 | 57562312 | 57562514 | H_c_113f15 |
| 6 | 57839540 | 57839624 | H_c_11e11 |
| 6 | 58885965 | 58887997 | H_c_172f18_M |
| 6 | 5941898 | 5942644 | H_c_82i22_M |
| 6 | 5947877 | 5949342 | H_c_183o14_M |
| 6 | 5952674 | 5954663 | H_c_70e03_M |
| 6 | 620518 | 622386 | H_c_15l15 |
| 6 | 6260583 | 6260734 | H_c_191j13 |
| 6 | 62780091 | 62780302 | H_c_214g01 |
| 6 | 62924229 | 62924327 | H_c_104g14 |
| 6 | 63053525 | 63054067 | H_c_185h12_M |
| 6 | 63120019 | 63120214 | H_c_195f14 |
| 6 | 6337285 | 6338914 | H_c_100l10 |
| 6 | 63588901 | 63589052 | H_c_47p15 |
| 6 | 637335 | 639267 | H_c_110p18_M |
| 6 | 64070498 | 64070602 | H_c_149i24 |
| 6 | 64340090 | 64341664 | H_c_122e07_M |
| 6 | 64403424 | 64404667 | H_c_187c09_M |
| 6 | 6491471 | 6492262 | H_c139k19_M |
| 6 | 65135152 | 65135305 | H_c_10e24 |
| 6 | 65168511 | 65168742 | H_c_73o02 |
| 6 | 65601221 | 65601333 | H_c_9m17 |
| 6 | 66715698 | 66715840 | H_c_257f24 |
| 6 | 66950884 | 66951056 | H_c_153n03_M |
| 6 | 67344766 | 67344938 | H_c_15k15_M |
| 6 | 67487900 | 67488008 | H_c_117d21 |
| 6 | 67848116 | 67848249 | H_c_16a11 |
| 6 | 68415461 | 68415647 | H_c_53d09 |
| 6 | 68528815 | 68528942 | H_c_246k24 |
| 6 | 69248865 | 69248974 | H_c_25a07 |
| 6 | 69401187 | 69402260 | H_c_164b12_M |
| 6 | 69960557 | 69960672 | H_c_153c17_M |
| 6 | 6996547 | 6998136 | H_c137c16_M |
| 6 | 70051839 | 70051994 | H_c_222a14 |
| 6 | 7022233 | 7022431 | H_c137e21 |
| 6 | 7052338 | 7054572 | H_c_82d01_M |
| 6 | 70633757 | 70634469 | H_c_71j10_M |
| 6 | 70634007 | 70634463 | H_c_72a07 |
| 6 | 70836581 | 70836656 | H_c_54f16 |
| 6 | 7085578 | 7086640 | H_c_3j09_M |
| 6 | 71179597 | 71180905 | H_c_272k14_M |
| 6 | 71333189 | 71333905 | H_c_85k22 |
| 6 | 71433793 | 71435159 | H_c_209i23_M |
| 6 | 7144273 | 7144350 | H_c_181j22 |
| 6 | 71475083 | 71475223 | H_c_78c20 |
| 6 | 71722042 | 71724076 | H_c_39m24_M |
| 6 | 71968554 | 71968814 | H_c_92e11 |
| 6 | 7205211 | 7207741 | H_c_36l23 |
| 6 | 72186411 | 72187496 | H_c_79m18_M |
| 6 | 7257509 | 7258676 | H_c_148i13 |
| 6 | 72652686 | 72654159 | H_c_76o04 |
| 6 | 72715722 | 72715826 | H_c_232n14 |
| 6 | 72948627 | 72949726 | H_c_99c04 |
| 6 | 73372768 | 73372927 | H_c_251b04 |
| 6 | 73387617 | 73389559 | H_c_100f09 |
| 6 | 73389560 | 73389809 | H_c_196j06_M |
| 6 | 7349091 | 7349305 | H_c_166k09 |
| 6 | 73536322 | 73536442 | H_c_48c11 |
| 6 | 73796744 | 73797523 | H_c_244b08 |
| 6 | 73821101 | 73821274 | H_c_24i22 |
| 6 | 74029096 | 74030095 | H_c_79o05_M |
| 6 | 74081038 | 74081715 | H_c_42g01 |
| 6 | 74286318 | 74287770 | H_c_36d11_M |
| 6 | 74419667 | 74420104 | H_c_64g19 |
| 6 | 74462562 | 74462886 | H_c_205f19_M |
| 6 | 74609385 | 74609492 | H_c_203b19 |
| 6 | 74714090 | 74715223 | H_c_233f04 |
| 6 | 74791704 | 74791873 | H_c_34k18 |
| 6 | 75030748 | 75030855 | H_c_106h08 |
| 6 | 75367507 | 75367589 | H_c_232l23_M |
| 6 | 75744891 | 75745043 | H_c_82b01 |
| 6 | 75786114 | 75786230 | H_c_119g22_M |
| 6 | 75971209 | 75972517 | H_c_152n02_M |
| 6 | 76216549 | 76216760 | H_c_34e15 |
| 6 | 76367976 | 76369300 | H_c_105i13_M |
| 6 | 76514986 | 76516209 | H_c_100f04_M |
| 6 | 76640354 | 76640477 | H_c_271o05 |
| 6 | 7671228 | 7673185 | H_c_1j03_M |
| 6 | 76728297 | 76728462 | H_c_70k02 |
| 6 | 76911491 | 76911659 | H_c_187n21 |
| 6 | 77299046 | 77300480 | H_c_227j04 |
| 6 | 77383565 | 77383656 | H_c_121k23 |
| 6 | 77738248 | 77739375 | H_c_37k21 |
| 6 | 77776144 | 77776260 | H_c_226m02_M |
| 6 | 7795620 | 7795764 | H_c_47c21 |
| 6 | 78144171 | 78144277 | H_c_54i18 |
| 6 | 78229031 | 78231263 | H_c_23p02_M |
| 6 | 78387755 | 78387959 | H_c_202m15 |
| 6 | 7855070 | 7856945 | H_c_63j15_M |
| 6 | 78830536 | 78830881 | H_c_104a04 |
| 6 | 79342722 | 79342866 | H_c_221g14 |
| 6 | 79633810 | 79634540 | H_c_55p22 |
| 6 | 79843337 | 79843651 | H_c_101d01_M |
| 6 | 80174290 | 80174468 | H_c_95e13 |
| 6 | 80291066 | 80291294 | H_c_129c23_M |
| 6 | 80353416 | 80353539 | H_c_266b12 |
| 6 | 80396942 | 80398382 | H_c_66o15_M |
| 6 | 8047472 | 8048064 | H_c_227d06_M |
| 6 | 80713451 | 80714929 | H_c_22m19_M |
| 6 | 80770845 | 80771518 | H_c_171m20_M |
| 6 | 80872766 | 80873431 | H_c_217h04_M |
| 6 | 81018359 | 81018466 | H_c_13k21 |
| 6 | 81665080 | 81665243 | H_c_154a09_M |
| 6 | 81750123 | 81750409 | H_c_50n16 |
| 6 | 82398027 | 82398255 | H_c_25f09_M |
| 6 | 82517945 | 82520035 | H_c_83p08_M |
| 6 | 82699540 | 82699799 | H_c_77d23 |
| 6 | 83013324 | 83015111 | H_c_130i19_M |
| 6 | 83126541 | 83126644 | H_c_32g21 |
| 6 | 83130123 | 83132117 | H_c_258d10_M |
| 6 | 83606282 | 83606430 | H_c_169g13 |
| 6 | 83833903 | 83834719 | H_c_7c07_M |
| 6 | 83959272 | 83960233 | H_c_192b17_M |
| 6 | 84196767 | 84198614 | H_c_187a10_M |
| 6 | 84474429 | 84476053 | H_c_46h24_M |
| 6 | 84619602 | 84620326 | H_c_60k03_M |
| 6 | 84686273 | 84686353 | H_c_49n08 |
| 6 | 84799820 | 84800483 | H_c_35f18_M |
| 6 | 85528590 | 85531318 | H_c_239l13_M |
| 6 | 85539737 | 85541038 | H_c_10b14_M |
| 6 | 85929518 | 85929655 | H_c_238k15 |
| 6 | 85988210 | 85988379 | H_c_214e19 |
| 6 | 86157096 | 86157185 | H_c_152h12 |
| 6 | 86215848 | 86217095 | H_c_62i08_M |
| 6 | 86359126 | 86360749 | H_c_53n08_M |
| 6 | 86445076 | 86445921 | H_c_42o05_M |
| 6 | 86883418 | 86883587 | H_c_90f1 |
| 6 | 87685374 | 87685658 | H_c_55n20 |
| 6 | 87703090 | 87704561 | H_c_7l04 |
| 6 | 87888630 | 87889577 | H_c_44a16_M |
| 6 | 87918036 | 87919384 | H_c_89k19 |
| 6 | 87921238 | 87923185 | H_c_116j22 |
| 6 | 88057364 | 88057612 | H_c_57b14 |
| 6 | 88088634 | 88089493 | H_c_96d14 |
| 6 | 88174317 | 88175118 | H_c_226p05 |
| 6 | 88238807 | 88239888 | H_c_124k01_M |
| 6 | 88249564 | 88250999 | H_c_60g13 |
| 6 | 88288079 | 88289892 | H_c_173j14_M |
| 6 | 88355974 | 88356846 | H_c_98e04_M |
| 6 | 88467463 | 88468897 | H_c_130a18_M |
| 6 | 88813944 | 88814640 | H_c_197c02_M |
| 6 | 88932084 | 88933759 | H_c_188a02_M |
| 6 | 89249459 | 89249885 | H_c_60e21 |
| 6 | 89694703 | 89694782 | H_c_167l08 |
| 6 | 89729403 | 89730389 | H_c_27j23_M |
| 6 | 89846687 | 89848527 | H_c_122n20_M |
| 6 | 89883659 | 89884935 | H_c_129a11 |
| 6 | 89912213 | 89913626 | H_c_41p07_M |
| 6 | 89995320 | 89995487 | H_c_120h06 |

TABLE 1-continued

| | | |
|---|---|---|
| 6 | 90118539 | 90119637 | H_c_29l19_M |
| 6 | 90177495 | 90179310 | H_c_249f22_M |
| 6 | 90199255 | 90200407 | H_c_252j16_M |
| 6 | 90404780 | 90405338 | H_c_81e03_M |
| 6 | 90586003 | 90586472 | H_c_163n11_M |
| 6 | 90596148 | 90596724 | H_c_74i09 |
| 6 | 90811891 | 90811970 | H_c_111f19 |
| 6 | 91062430 | 91063957 | H_c_83m17 |
| 6 | 91300867 | 91300994 | H_c_210g23 |
| 6 | 91352520 | 91353753 | H_c_220c17 |
| 6 | 91887923 | 91888144 | H_c_24g16 |
| 6 | 92052652 | 92052995 | H_c_121k24 |
| 6 | 92749742 | 92749828 | H_c_147d24 |
| 6 | 93035108 | 93035279 | H_c_117f05 |
| 6 | 93529923 | 93530026 | H_c_268n07 |
| 6 | 93713688 | 93713806 | H_c_3g10 |
| 6 | 94183070 | 94185833 | H_c_11f12_M |
| 6 | 94508099 | 94508205 | H_c_148m24 |
| 6 | 9541070 | 9541303 | H_c_70a13 |
| 6 | 95416564 | 95416700 | H_c_111n18 |
| 6 | 95553207 | 95553318 | H_c_271j14 |
| 6 | 96131746 | 96132415 | H_c_216j17_M |
| 6 | 96658549 | 96658643 | H_c_53p01 |
| 6 | 97299599 | 97299843 | H_c_10l13 |
| 6 | 97391368 | 97392155 | H_c_272m13_M |
| 6 | 97449928 | 97450085 | H_c_206b19 |
| 6 | 97478709 | 97479516 | H_c_81h08_M |
| 6 | 97549377 | 97549584 | H_c_113g17 |
| 6 | 97715075 | 97715235 | H_c_92p12 |
| 6 | 97837304 | 97837953 | H_c_119g18_M |
| 6 | 98173472 | 98173616 | H_c_104c09_M |
| 6 | 98202011 | 98202127 | H_c_85k01 |
| 6 | 984196 | 984400 | H_c_52j05 |
| 6 | 98527549 | 98527728 | H_c_197c18 |
| 6 | 98764311 | 98764436 | H_c_95g10 |
| 6 | 99070534 | 99070693 | H_c_29f11_M |
| 6 | 9936638 | 9936793 | H_c_211g02 |
| 6 | 99386846 | 99390910 | H_c_63c02_M |
| 6 | 99399712 | 99400148 | H_c_38a12_M |
| 6 | 99501649 | 99503435 | H_c_192j13 |
| 6 | 99811134 | 99811315 | H_c_82m06 |
| 6 | 99903511 | 99904680 | H_c_77d21 |
| 7 | 100068646 | 100071150 | H_c_55a02 |
| 7 | 100079620 | 100079931 | H_c_121i17 |
| 7 | 100094231 | 100095505 | H_c_15i02_M |
| 7 | 100116994 | 100117997 | H_c_31f15_M |
| 7 | 100137554 | 100138053 | H_c_54l24_M |
| 7 | 100348553 | 100349879 | H_c_28m11 |
| 7 | 100390788 | 100392278 | H_c_273g09 |
| 7 | 100408164 | 100410398 | H_c_53j01_M |
| 7 | 100415683 | 100417794 | H_c_203j20_M |
| 7 | 100438455 | 100439175 | H_c_95c15_M |
| 7 | 100453615 | 100454672 | H_c_264p01_M |
| 7 | 100480471 | 100482163 | H_c_86f09_M |
| 7 | 100488566 | 100489377 | H_c_197p20 |
| 7 | 100599510 | 100601004 | H_c_182f14_M |
| 7 | 100924928 | 100925813 | H_c_188p18_M |
| 7 | 100980098 | 100981252 | H_c_55n15 |
| 7 | 101189210 | 101189874 | H_c_248e09 |
| 7 | 101282103 | 101282201 | H_c_102e01_M |
| 7 | 101522191 | 101524334 | H_c_122b19_M |
| 7 | 101554738 | 101555527 | H_c_79i01 |
| 7 | 101629764 | 101630965 | H_c_84m24 |
| 7 | 101666974 | 101668283 | H_c_150o23 |
| 7 | 101673140 | 101674259 | H_c_44e03 |
| 7 | 101698734 | 101699679 | H_c_225j06_M |
| 7 | 102308802 | 102310048 | H_c_30b16_M |
| 7 | 1023691 | 1025453 | H_c_73c20 |
| 7 | 102383060 | 102384345 | H_c_22j04 |
| 7 | 102531518 | 102532401 | H_c_2n10_M |
| 7 | 10262374 | 10262647 | H_c_160e23 |
| 7 | 102679538 | 102680762 | H_c_129a13_M |
| 7 | 103223217 | 103224690 | H_c_204d15_M |
| 7 | 103330753 | 103330976 | H_c_95d06 |
| 7 | 103340235 | 103340853 | H_c_270d04 |
| 7 | 103442222 | 103442649 | H_c_40a11 |
| 7 | 103589459 | 103589984 | H_c_118c24 |
| 7 | 1036168 | 1037338 | H_c_208c13_M |
| 7 | 104217953 | 104219097 | H_c_71h07_M |
| 7 | 104246707 | 104247761 | H_c_125o11_M |
| 7 | 1043189 | 1047109 | H_c_101i08_M |
| 7 | 104622134 | 104623910 | H_c_71k09_M |
| 7 | 104755834 | 104756959 | H_c_190h07_M |
| 7 | 104766393 | 104767180 | H_c_87a03 |
| 7 | 1047790 | 1049980 | H_c_43g05_M |
| 7 | 104917488 | 104917577 | H_c143b18 |
| 7 | 105023758 | 105023958 | H_c_245d13 |
| 7 | 105110510 | 105111967 | H_c_20h23_M |
| 7 | 10528258 | 10528437 | H_c_252l19 |
| 7 | 105346051 | 105347096 | H_c_57m13_M |
| 7 | 105501510 | 105501626 | H_c_20i07 |
| 7 | 1055024 | 1055415 | H_c_169c05_M |
| 7 | 105518473 | 105519371 | H_c_19l18_M |
| 7 | 105712209 | 105712293 | H_c_170m19 |
| 7 | 105894002 | 105895581 | H_c_85c11_M |
| 7 | 1059545 | 1060851 | H_c_72j02_M |
| 7 | 105983229 | 105983558 | H_c_258n24 |
| 7 | 106403717 | 106404412 | H_c_64f24 |
| 7 | 106435329 | 106435412 | H_c135c08 |
| 7 | 106814313 | 106815226 | H_c_15h12_M |
| 7 | 106895336 | 106896543 | H_c_174f15 |
| 7 | 106978285 | 106979202 | H_c_200n09_M |
| 7 | 107125327 | 107125750 | H_c_87i24_M |
| 7 | 107237110 | 107237959 | H_c_113m03 |
| 7 | 107244214 | 107244295 | H_c_194c02 |
| 7 | 10753105 | 10753575 | H_c_202i09_M |
| 7 | 107588496 | 107588596 | H_c_158m03 |
| 7 | 107686423 | 107686512 | H_c_154j20_M |
| 7 | 107760071 | 107761162 | H_c_234j15_M |
| 7 | 107804129 | 107805049 | H_c_42p21_M |
| 7 | 10786451 | 10787075 | H_c_25f13_M |
| 7 | 108654425 | 108654569 | H_c132j03 |
| 7 | 108752856 | 108752959 | H_c_39p12 |
| 7 | 109246100 | 109246198 | H_c_146b10 |
| 7 | 109377654 | 109377864 | H_c_112i01 |
| 7 | 109515175 | 109515595 | H_c140h08 |
| 7 | 109563119 | 109563935 | H_c_107k03 |
| 7 | 109898115 | 109898521 | H_c_34m18_M |
| 7 | 110083634 | 110083782 | H_c_62n02_M |
| 7 | 1102822 | 1104165 | H_c_61d05 |
| 7 | 110502217 | 110502360 | H_c_64h04 |
| 7 | 110795965 | 110796814 | H_c_116e16_M |
| 7 | 111100740 | 111101038 | H_c_253j22 |
| 7 | 111221967 | 111222238 | H_c_176d11 |
| 7 | 111334365 | 111334520 | H_c_152n23 |
| 7 | 111385496 | 111385634 | H_c_5h02 |
| 7 | 111439191 | 111441379 | H_c_32g13 |
| 7 | 111539775 | 111539940 | H_c_84m05 |
| 7 | 111625231 | 111626296 | H_c_30m23_M |
| 7 | 111684440 | 111685571 | H_c_204d18_M |
| 7 | 112023649 | 112024741 | H_c_225b24 |
| 7 | 112064614 | 112064748 | H_c_163g21_M |
| 7 | 112173506 | 112174413 | H_c_237l05_M |
| 7 | 112320307 | 112320664 | H_c_50m09_M |
| 7 | 11292346 | 11292447 | H_c_199o17_M |
| 7 | 113059256 | 113059447 | H_c_19o13 |
| 7 | 113318519 | 113322018 | H_c_33n17_M |
| 7 | 11336849 | 11337266 | H_c_201e12 |
| 7 | 114155608 | 114157362 | H_c_108c23_M |
| 7 | 114277062 | 114277173 | H_c_70j01 |
| 7 | 114472502 | 114472640 | H_c_244k10 |
| 7 | 115443473 | 115445004 | H_c_76m19_M |
| 7 | 115559818 | 115559946 | H_c_75m01 |
| 7 | 115759018 | 115760334 | H_c_8n23_M |
| 7 | 115865158 | 115865261 | H_c_151e14 |
| 7 | 115905619 | 115906870 | H_c_54b02_M |
| 7 | 116096217 | 116097510 | H_c_19b23_M |
| 7 | 116187134 | 116188470 | H_c_27k20_M |
| 7 | 11644573 | 11645481 | H_c_79f16_M |
| 7 | 116898892 | 116899117 | H_c_88k23 |
| 7 | 117106557 | 117107830 | H_c_237e14_M |
| 7 | 11710910 | 11711060 | H_c137a01 |
| 7 | 117417836 | 117418510 | H_c_179a21 |
| 7 | 117788266 | 117788385 | H_c_104o13 |
| 7 | 118110893 | 118111492 | H_c_179d04 |
| 7 | 11924242 | 11925369 | H_c_169c19 |
| 7 | 119304983 | 119305087 | H_c_239d13 |
| 7 | 119506402 | 119507967 | H_c_19c17_M |
| 7 | 119640683 | 119640750 | H_c_199i14 |
| 7 | 119716164 | 119716400 | H_c_8f18 |

TABLE 1-continued

| | | | |
|---|---|---|---|
| 7 | 120090988 | 120091735 | H_c_75n02_M |
| 7 | 120184327 | 120185613 | H_c_265d20_M |
| 7 | 120222230 | 120223021 | H_c_154o17_M |
| 7 | 12023717 | 12024729 | H_c_84b17 |
| 7 | 120243141 | 120243230 | H_c_177n17 |
| 7 | 12033127 | 12033197 | H_c_124d03 |
| 7 | 120419019 | 120419166 | H_c_78j21 |
| 7 | 120563546 | 120564213 | H_c_158l06_M |
| 7 | 120589764 | 120589946 | H_c_56c16 |
| 7 | 120629471 | 120630651 | H_c_184g01_M |
| 7 | 120877242 | 120877810 | H_c_192c16_M |
| 7 | 121106755 | 121107404 | H_c_49i14_M |
| 7 | 121260130 | 121260234 | H_c_60m22 |
| 7 | 121336852 | 121336956 | H_c_36g19 |
| 7 | 121534693 | 121534787 | H_c_210l03 |
| 7 | 121539722 | 121540273 | H_c_202m20 |
| 7 | 121540460 | 121541241 | H_c_245g08 |
| 7 | 121544487 | 121546075 | H_c_1m07_M |
| 7 | 121571021 | 121571274 | H_c_108f12 |
| 7 | 122119672 | 122121220 | H_c_86c14_M |
| 7 | 12216418 | 12217893 | H_c_223g11_M |
| 7 | 122414616 | 122414889 | H_c_8o14 |
| 7 | 1225046 | 1226113 | H_c_86k21_M |
| 7 | 122742466 | 122742638 | H_c_89o04 |
| 7 | 123303337 | 123303544 | H_c_82a15 |
| 7 | 123942120 | 123942223 | H_c_201g19 |
| 7 | 123997632 | 124000148 | H_c_152j15 |
| 7 | 124185211 | 124185349 | H_c_69b18 |
| 7 | 124439401 | 124439600 | H_c_79d18 |
| 7 | 124614508 | 124614659 | H_c_46k14 |
| 7 | 124679753 | 124680130 | H_c_17k21 |
| 7 | 124746285 | 124746426 | H_c_14b17 |
| 7 | 124767431 | 124767431 | H_c_54m23 |
| 7 | 12500109 | 12500651 | H_c_187i22_M |
| 7 | 12529254 | 12529467 | H_c_221f17 |
| 7 | 125694444 | 125694686 | H_c_170b05 |
| 7 | 125701029 | 125701116 | H_c_152i24 |
| 7 | 125892618 | 125893021 | H_c_26l18 |
| 7 | 126221848 | 126221933 | H_c_66k09 |
| 7 | 126422348 | 126422633 | H_c_239g13 |
| 7 | 126485132 | 126488120 | H_c_73b04_M |
| 7 | 126581347 | 126582287 | H_c_91h23_M |
| 7 | 126626596 | 126627500 | H_c_11o12_M |
| 7 | 126772609 | 126772774 | H_c_96b13 |
| 7 | 126821585 | 126822839 | H_c_2n02_M |
| 7 | 126885524 | 126886743 | H_c_120g20 |
| 7 | 127205775 | 127207125 | H_c_264c10 |
| 7 | 127266207 | 127266840 | H_c_87j15_M |
| 7 | 127337525 | 127338469 | H_c_163b09_M |
| 7 | 12735727 | 12736114 | H_c_256l22 |
| 7 | 127401558 | 127403143 | H_c_272f02 |
| 7 | 127505580 | 127506548 | H_c_127g02 |
| 7 | 127584360 | 127587114 | H_c_274l08_M |
| 7 | 127594335 | 127596162 | H_c_58p10 |
| 7 | 127639391 | 127640623 | H_c_98g16 |
| 7 | 127642911 | 127644505 | H_c_87i19_M |
| 7 | 127677670 | 127679462 | H_c_130e16 |
| 7 | 127972972 | 127973991 | H_c_265b06_M |
| 7 | 128023942 | 128026478 | H_c_26m21 |
| 7 | 12806380 | 12806630 | H_c_216n10_M |
| 7 | 128064388 | 128065618 | H_c_1j21_M |
| 7 | 128096500 | 128097682 | H_c_134m08_M |
| 7 | 128102962 | 128103727 | H_c_75e20_M |
| 7 | 128170464 | 128172556 | H_c_221j16_M |
| 7 | 128421656 | 128423785 | H_c_198k04_M |
| 7 | 128458338 | 128459361 | H_c_215f05 |
| 7 | 128667396 | 128668682 | H_c_16h16_M |
| 7 | 128735588 | 128737513 | H_c_68l18_M |
| 7 | 128852693 | 128852828 | H_c132e07 |
| 7 | 129012113 | 129015007 | H_c_106i03_M |
| 7 | 129015525 | 129015892 | H_c_195h07_M |
| 7 | 129058541 | 129060577 | H_c_266j02 |
| 7 | 129185741 | 129187001 | H_c_220k04 |
| 7 | 129303737 | 129304983 | H_c_6i24 |
| 7 | 129726724 | 129726922 | H_c_58f04 |
| 7 | 129809993 | 129811340 | H_c_195c19_M |
| 7 | 129874618 | 129876345 | H_c_185k03_M |
| 7 | 130250184 | 130250450 | H_c_71m17_M |
| 7 | 130469418 | 130470491 | H_c_27a16_M |
| 7 | 130697868 | 130699270 | H_c_185k13_M |
| 7 | 131050759 | 131051979 | H_c138e19_M |
| 7 | 131271131 | 131271235 | H_c_4j18 |
| 7 | 1316392 | 1318045 | H_c_172c14_M |
| 7 | 131718049 | 131720234 | H_c140j07 |
| 7 | 13189033 | 13189350 | H_c_145o07 |
| 7 | 132104031 | 132104208 | H_c_44f13 |
| 7 | 132223761 | 132224479 | H_c_14g06 |
| 7 | 133458254 | 133459358 | H_c_242m21_M |
| 7 | 133601134 | 133601418 | H_c_209p05_M |
| 7 | 133633049 | 133633326 | H_c_210d06 |
| 7 | 13366660 | 13366799 | H_c_199g24 |
| 7 | 133969830 | 133970121 | H_c_29j24 |
| 7 | 134109452 | 134109582 | H_c_11h06 |
| 7 | 134128212 | 134129095 | H_c_64g10_M |
| 7 | 13418725 | 13418871 | H_c_264i13 |
| 7 | 134312668 | 134313130 | H_c_208d10_M |
| 7 | 1343317 | 1344798 | H_c_70b02 |
| 7 | 134334960 | 134335130 | H_c144a14 |
| 7 | 134337593 | 134339292 | H_c_259g23 |
| 7 | 13434837 | 13435042 | H_c_111b20 |
| 7 | 134352956 | 134353840 | H_c_192e24_M |
| 7 | 134372582 | 134372742 | H_c_48h20 |
| 7 | 134531843 | 134532016 | H_c_29h24 |
| 7 | 134651634 | 134652591 | H_c_267c24 |
| 7 | 134803249 | 134804899 | H_c_152a22_M |
| 7 | 134948219 | 134948340 | H_c_214a21 |
| 7 | 135025269 | 135025542 | H_c_115g08 |
| 7 | 135725353 | 135725471 | H_c_3m18 |
| 7 | 135798126 | 135798244 | H_c_126e17 |
| 7 | 136011059 | 136013501 | H_c135b07_M |
| 7 | 136262380 | 136262609 | H_c_88m06 |
| 7 | 136988491 | 136989521 | H_c_211b05_M |
| 7 | 137082812 | 137082896 | H_c_149e14 |
| 7 | 137099337 | 137099427 | H_c_9a21 |
| 7 | 137143460 | 137144519 | H_c_275j23 |
| 7 | 137601974 | 137603238 | H_c_60m18 |
| 7 | 137738739 | 137738871 | H_c_37g22 |
| 7 | 138120194 | 138120324 | H_c_153l17_M |
| 7 | 138177371 | 138178858 | H_c_218b10 |
| 7 | 138250348 | 138252075 | H_c_100h09_M |
| 7 | 13830061 | 13830241 | H_c_66d16 |
| 7 | 138372820 | 138374487 | H_c_42i21_M |
| 7 | 138436684 | 138436854 | H_c_184o05 |
| 7 | 138483223 | 138483607 | H_c_151p01_M |
| 7 | 138501378 | 138501724 | H_c_75e17_M |
| 7 | 138623929 | 138626583 | H_c_121n12_M |
| 7 | 138928663 | 138931858 | H_c_238f07_M |
| 7 | 139215357 | 139216276 | H_c_42c01_M |
| 7 | 139328573 | 139330999 | H_c_52g06_M |
| 7 | 139345167 | 139345349 | H_c_265l21_M |
| 7 | 139382505 | 139383996 | H_c_58n12_M |
| 7 | 139550591 | 139551835 | H_c_29j23_M |
| 7 | 139631317 | 139632904 | H_c_230d08_M |
| 7 | 139650592 | 139650708 | H_c_38h05 |
| 7 | 139792742 | 139793976 | H_c_88g07_M |
| 7 | 139825591 | 139827905 | H_c_194b03_M |
| 7 | 139849191 | 139850281 | H_c_109o09_M |
| 7 | 140167711 | 140168335 | H_c_247e16_M |
| 7 | 140225510 | 140227847 | H_c_28g16_M |
| 7 | 140732414 | 140732507 | H_c_37d09 |
| 7 | 140791200 | 140791289 | H_c_30o20 |
| 7 | 140854266 | 140855420 | H_c_149l02_M |
| 7 | 14149176 | 14149261 | H_c_91i05 |
| 7 | 141877648 | 141877741 | H_c_44a03 |
| 7 | 142030821 | 142031059 | H_c_154p23_M |
| 7 | 142274721 | 142276001 | H_c_39e13 |
| 7 | 142501584 | 142502827 | H_c_226o05_M |
| 7 | 142574731 | 142577385 | H_c_130a13_M |
| 7 | 142594163 | 142594582 | H_c_76k19_M |
| 7 | 142622482 | 142622877 | H_c_50h04_M |
| 7 | 142627848 | 142628205 | H_c_87m23 |
| 7 | 143036434 | 143037084 | H_c_268l11_M |
| 7 | 143264886 | 143265021 | H_c_125e11 |
| 7 | 143970406 | 143970990 | H_c_16b21_M |
| 7 | 145250400 | 145251980 | H_c_212d18_M |
| 7 | 145722176 | 145722255 | H_c_19b11 |
| 7 | 145887234 | 145887326 | H_c_235m15 |
| 7 | 146136937 | 146137219 | H_c_108f05 |
| 7 | 147160537 | 147160633 | H_c_31m20 |
| 7 | 147832825 | 147834644 | H_c_195h15_M |

TABLE 1-continued

| | | | |
|---|---|---|---|
| 7 | 147958166 | 147958300 | H_c_195j12 |
| 7 | 148017904 | 148019549 | H_c_155d23_M |
| 7 | 148075453 | 148076048 | H_c_158p17 |
| 7 | 148110663 | 148112269 | H_c_237d22 |
| 7 | 148117960 | 148118146 | H_c_130i20 |
| 7 | 148162741 | 148163426 | H_c_3f15_M |
| 7 | 148199885 | 148201266 | H_c_166n07_M |
| 7 | 148262152 | 148262944 | H_c_229o16 |
| 7 | 148281672 | 148283528 | H_c_3g19_M |
| 7 | 148330032 | 148330940 | H_c_209f07_M |
| 7 | 148373951 | 148375290 | H_c_273o22_M |
| 7 | 148396424 | 148396905 | H_c_81f21_M |
| 7 | 148419723 | 148420895 | H_c_252o08 |
| 7 | 148425409 | 148425612 | H_c_58j04 |
| 7 | 148555953 | 148557418 | H_c_243k16_M |
| 7 | 148557504 | 148558133 | H_c_75o21 |
| 7 | 148594054 | 148596109 | H_c_47l14_M |
| 7 | 148631699 | 148633092 | H_c_63d04 |
| 7 | 148758697 | 148759911 | H_c_48f23_M |
| 7 | 148848444 | 148850602 | H_c_65e20_M |
| 7 | 148972850 | 148974171 | H_c_3j16_M |
| 7 | 149007965 | 149009286 | H_c_274n20_M |
| 7 | 149457460 | 149458492 | H_c_150m16 |
| 7 | 149474907 | 149477285 | H_c_16a24 |
| 7 | 149487760 | 149488691 | H_c_150o12 |
| 7 | 149502957 | 149504245 | H_c_84k15_M |
| 7 | 149513413 | 149514106 | H_c_29n21_M |
| 7 | 149539345 | 149540207 | H_c_31m24_M |
| 7 | 14975686 | 14975786 | H_c_101n22 |
| 7 | 149934279 | 149936891 | H_c_31c19 |
| 7 | 150089329 | 150090735 | H_c_79m12 |
| 7 | 150146971 | 150149115 | H_c_264f04_M |
| 7 | 150162375 | 150163694 | H_c_59f15_M |
| 7 | 150185474 | 150186206 | H_c_123b13 |
| 7 | 150193669 | 150195172 | H_c_237e07 |
| 7 | 150215010 | 150215839 | H_c_65m20_M |
| 7 | 150248809 | 150251573 | H_c_8e03_M |
| 7 | 150361429 | 150362511 | H_c_34f10 |
| 7 | 150366644 | 150368653 | H_c132f02_M |
| 7 | 150386306 | 150386818 | H_c_270k19_M |
| 7 | 150410688 | 150411935 | H_c_148f18 |
| 7 | 150437668 | 150439220 | H_c_57a07 |
| 7 | 150475893 | 150476801 | H_c_8e21_M |
| 7 | 150515861 | 150517056 | H_c_117l04_M |
| 7 | 150543843 | 150545745 | H_c_246c10_M |
| 7 | 150582828 | 150583845 | H_c_81l20_M |
| 7 | 150654651 | 150655163 | H_c_229b09 |
| 7 | 150766416 | 150767439 | H_c_45j09_M |
| 7 | 150917287 | 150918252 | H_c_241l12 |
| 7 | 15100282 | 15100386 | H_c_52h15 |
| 7 | 151010213 | 151013566 | H_c_228k22_M |
| 7 | 151160220 | 151160961 | H_c_18l05 |
| 7 | 151544766 | 151544853 | H_c_111c09 |
| 7 | 151597916 | 151599779 | H_c_180n17 |
| 7 | 151810434 | 151811147 | H_c_157k08 |
| 7 | 151894310 | 151895071 | H_c_3k09_M |
| 7 | 152029049 | 152029381 | H_c_102j19 |
| 7 | 152059473 | 152061063 | H_c_83k19_M |
| 7 | 152093326 | 152093459 | H_c_123c12 |
| 7 | 153020624 | 153023370 | H_c_162c05_M |
| 7 | 153814118 | 153814218 | H_c_174i15 |
| 7 | 153926135 | 153926629 | H_c_271e13 |
| 7 | 153978274 | 153980138 | H_c_93j09 |
| 7 | 154023025 | 154024054 | H_c_76g17 |
| 7 | 154526321 | 154528631 | H_c_110a22_M |
| 7 | 154635584 | 154637312 | H_c_126b15_M |
| 7 | 154663568 | 154666935 | H_c133d12_M |
| 7 | 154673696 | 154675494 | H_c_84l18_M |
| 7 | 154742791 | 154743855 | H_c141o14_M |
| 7 | 154744914 | 154746100 | H_c_268d03_M |
| 7 | 154749383 | 154752078 | H_c_87o06_M |
| 7 | 154758263 | 154761003 | H_c_8c24_M |
| 7 | 154763423 | 154763909 | H_c_113m23 |
| 7 | 154801486 | 154802567 | H_c_267m12 |
| 7 | 154825575 | 154825881 | H_c_7a19_M |
| 7 | 154936107 | 154937374 | H_c_120n01_M |
| 7 | 15498310 | 15499979 | H_c_186h08_M |
| 7 | 155079319 | 155080071 | H_c_54b11 |
| 7 | 155100549 | 155101135 | H_c_16h17_M |
| 7 | 155104075 | 155104606 | H_c_225h14_M |
| 7 | 155474610 | 155474830 | H_c_170l11 |
| 7 | 1555118 | 1555642 | H_c_116j12 |
| 7 | 155898774 | 155900233 | H_c_85f22_M |
| 7 | 15590351 | 15590521 | H_c_165n06 |
| 7 | 155908241 | 155909295 | H_c_151h14 |
| 7 | 156183070 | 156186124 | H_c_169o23_M |
| 7 | 156241673 | 156243052 | H_c_8f03_M |
| 7 | 156291695 | 156298453 | H_c_32b17_M_M_M |
| 7 | 156310105 | 156314451 | H_c_6j05_M_M |
| 7 | 156423217 | 156423332 | H_c_243h03_M |
| 7 | 156430363 | 156432175 | H_c_97h18_M |
| 7 | 156628498 | 156630198 | H_c_42i07_M |
| 7 | 156794684 | 156795292 | H_c_213n18 |
| 7 | 156868624 | 156869124 | H_c_157e01 |
| 7 | 156884288 | 156887164 | H_c_48j09 |
| 7 | 156904718 | 156906623 | H_c_162c04_M |
| 7 | 156976416 | 156978524 | H_c_217d16 |
| 7 | 156980695 | 156981720 | H_c_38j21_M |
| 7 | 157339118 | 157340554 | H_c_206n24 |
| 7 | 157861500 | 157862536 | H_c_151h07 |
| 7 | 157880482 | 157881140 | H_c_270d03_M |
| 7 | 157995890 | 157997696 | H_c132h12_M |
| 7 | 158060899 | 158061037 | H_c_5k14_M |
| 7 | 158148070 | 158149256 | H_c_83m04_M |
| 7 | 158322594 | 158323239 | H_c_179p17 |
| 7 | 158353834 | 158354445 | H_c_99l08_M |
| 7 | 158435980 | 158436119 | H_c_194f01_M |
| 7 | 16233758 | 16234610 | H_c_148c14_M |
| 7 | 16458484 | 16459677 | H_c_82i05_M |
| 7 | 16566214 | 16567342 | H_c_167j19_M |
| 7 | 17111237 | 17112389 | H_c_8d18_M |
| 7 | 17900523 | 17900610 | H_c_106p11 |
| 7 | 18015908 | 18016041 | H_c_16d16 |
| 7 | 18353978 | 18354224 | H_c_99n20 |
| 7 | 18492592 | 18492668 | H_c_88o06 |
| 7 | 18650695 | 18650901 | H_c_42b16 |
| 7 | 1892203 | 1893834 | H_c_252i05 |
| 7 | 18925058 | 18925812 | H_c_229o22 |
| 7 | 18929196 | 18931626 | H_c_275j05_M |
| 7 | 18957310 | 18958293 | H_c_187e05_M |
| 7 | 18990632 | 18990778 | H_c_183b08 |
| 7 | 1958707 | 1959556 | H_c_61j07 |
| 7 | 19969417 | 19969658 | H_c_275o09_M |
| 7 | 20143014 | 20145121 | H_c_74i11_M |
| 7 | 20367287 | 20367445 | H_c_163f07 |
| 7 | 2045112 | 2046510 | H_c_36e23_M |
| 7 | 20518706 | 20518870 | H_c_270d13 |
| 7 | 2054629 | 2056991 | H_c_121m17_M |
| 7 | 20590423 | 20591514 | H_c_204j15_M |
| 7 | 20596363 | 20600177 | H_c137h13_M_M |
| 7 | 20603833 | 20604470 | H_c_161o03_M |
| 7 | 20610497 | 20611522 | H_c_32i05_M |
| 7 | 21202845 | 21203066 | H_c_106j02 |
| 7 | 21239594 | 21241102 | H_c_11f01 |
| 7 | 21302836 | 21302963 | H_c_98k16 |
| 7 | 2166796 | 2168882 | H_c_241f10_M |
| 7 | 21757447 | 21759599 | H_c133k07_M |
| 7 | 21895479 | 21896417 | H_c_44j09_M |
| 7 | 22165295 | 22165412 | H_c_150o08 |
| 7 | 2216664 | 2217099 | H_c_159e23 |
| 7 | 22667089 | 22667447 | H_c_98d20 |
| 7 | 22826080 | 22827399 | H_c_20j10 |
| 7 | 22994434 | 22995212 | H_c_161f04 |
| 7 | 23018755 | 23019259 | H_c_62h14_M |
| 7 | 23111905 | 23112867 | H_c_117l18_M |
| 7 | 23281989 | 23282982 | H_c_111g05_M |
| 7 | 23286707 | 23287477 | H_c_117e13_M |
| 7 | 2331510 | 2332582 | H_c_122e04 |
| 7 | 2332621 | 2333601 | H_c_38i04 |
| 7 | 23344013 | 23344731 | H_c_36h15_M |
| 7 | 23410029 | 23410873 | H_c_161a15_M |
| 7 | 23497051 | 23497165 | H_c_188a04_M |
| 7 | 2367203 | 2368773 | H_c_128p08_M |
| 7 | 2370832 | 2372685 | H_c_20b03_M |
| 7 | 24385641 | 24387218 | H_c_186n03_M |
| 7 | 244040 | 244685 | H_c_33p08 |
| 7 | 2444465 | 2446626 | H_c_150g05 |
| 7 | 24508523 | 24508701 | H_c_130b17 |
| 7 | 24569356 | 24570979 | H_c_98e22_M |
| 7 | 24772608 | 24772790 | H_c_163f10 |

TABLE 1-continued

| | | | |
|---|---|---|---|
| 7 | 2478047 | 2479576 | H_c_123h21 |
| 7 | 24791944 | 24793720 | H_c_65i22_M |
| 7 | 24938154 | 24938850 | H_c_49m16 |
| 7 | 24992498 | 24994317 | H_c_100f01 |
| 7 | 2500754 | 2502340 | H_c_1k14_M |
| 7 | 25156927 | 25157057 | H_c_43d09 |
| 7 | 25664193 | 25665990 | H_c_213a11_M |
| 7 | 25669582 | 25670202 | H_c_166a13 |
| 7 | 25763295 | 25764696 | H_c132e04_M |
| 7 | 25964114 | 25966100 | H_c_68n01_M |
| 7 | 26012909 | 26015359 | H_c_213j04_M |
| 7 | 26104557 | 26105313 | H_c_157c21_M |
| 7 | 26188783 | 26189746 | H_c_48f03_M |
| 7 | 26210846 | 26212427 | H_c_64i08_M |
| 7 | 26418993 | 26419118 | H_c_86k05 |
| 7 | 2656465 | 2658225 | H_c_185e22 |
| 7 | 26670294 | 26670506 | H_c_109b10_M |
| 7 | 26914598 | 26915461 | H_c_264n22_M |
| 7 | 26942712 | 26943592 | H_c_113c24 |
| 7 | 26960032 | 26960857 | H_c_153e10_M |
| 7 | 26962711 | 26964363 | H_c_84d01_M |
| 7 | 26967719 | 26970122 | H_c_10g18_M |
| 7 | 26973281 | 26974274 | H_c_30f18_M |
| 7 | 26981096 | 26983339 | H_c_166i21_M |
| 7 | 26986063 | 26987508 | H_c_191a19_M |
| 7 | 26997227 | 26999422 | H_c_60c06_M |
| 7 | 27000829 | 27002362 | H_c_166l24 |
| 7 | 27005357 | 27005820 | H_c_101c13_M |
| 7 | 27012978 | 27013928 | H_c_244n19_M |
| 7 | 27018300 | 27018488 | H_c_159c14 |
| 7 | 27033181 | 27033742 | H_c_206g12 |
| 7 | 27038303 | 27039983 | H_c_148m19 |
| 7 | 27048193 | 27048980 | H_c_44e02_M |
| 7 | 27055364 | 27057033 | H_c_72f13_M |
| 7 | 27058357 | 27059765 | H_c_90k05 |
| 7 | 27064275 | 27065601 | H_c_40p18_M |
| 7 | 27246124 | 27246277 | H_c_61d06 |
| 7 | 27475447 | 27476093 | H_c_273b23_M |
| 7 | 27552826 | 27554060 | H_c_12p07_M |
| 7 | 27775650 | 27775724 | H_c_271a05 |
| 7 | 27957033 | 27957116 | H_c_182h19 |
| 7 | 27992400 | 27993890 | H_c_82e24 |
| 7 | 28163086 | 28163310 | H_c140n22 |
| 7 | 28220830 | 28223386 | H_c_258j09_M |
| 7 | 28666706 | 28667602 | H_c_8g04_M |
| 7 | 287039 | 289313 | H_c_185d17 |
| 7 | 28958663 | 28959418 | H_c_53l13 |
| 7 | 29006788 | 29008591 | H_c_231d05_M |
| 7 | 29376326 | 29377220 | H_c_73f10_M |
| 7 | 29617923 | 29620780 | H_c_91k07_M |
| 7 | 29762453 | 29764661 | H_c_16g13 |
| 7 | 29801638 | 29803035 | H_c_18f16 |
| 7 | 29840734 | 29842827 | H_c_155f23_M |
| 7 | 29947404 | 29949789 | H_c_137j10_M |
| 7 | 30097051 | 30097686 | H_c_50a24 |
| 7 | 30317147 | 30318305 | H_c_67p04_M |
| 7 | 30407362 | 30408370 | H_c_167p18_M |
| 7 | 30494640 | 30495958 | H_c_83e02_M |
| 7 | 30583827 | 30584912 | H_c_125d12_M |
| 7 | 30665687 | 30668138 | H_c_151f21 |
| 7 | 30677143 | 30677307 | H_c_149l20 |
| 7 | 30864604 | 30866839 | H_c_103d19_M |
| 7 | 31030475 | 31030620 | H_c_161k05 |
| 7 | 31148844 | 31149870 | H_c_89p18_M |
| 7 | 31345817 | 31346013 | H_c_99p08 |
| 7 | 3183213 | 3183320 | H_c_87c05 |
| 7 | 31883040 | 31884946 | H_c_3d01 |
| 7 | 32111219 | 32112790 | H_c136g05_M |
| 7 | 32240654 | 32241411 | H_c_127p17_M |
| 7 | 32307874 | 32308916 | H_c_47g05_M |
| 7 | 32347280 | 32347432 | H_c_208a19 |
| 7 | 32704007 | 32705653 | H_c_209l18_M |
| 7 | 32734804 | 32735082 | H_c_256i20 |
| 7 | 32769923 | 32771128 | H_c_195e20_M |
| 7 | 33380144 | 33380257 | H_c_21f04 |
| 7 | 33716822 | 33717370 | H_c_17g08 |
| 7 | 33717406 | 33718819 | H_c_62e16_M |
| 7 | 33823355 | 33823455 | H_c_57a16 |
| 7 | 34103519 | 34103679 | H_c_55j14 |
| 7 | 34160770 | 34160842 | H_c_10f07 |
| 7 | 34205295 | 34205429 | H_c_273l18 |
| 7 | 34849500 | 34851053 | H_c_31h10_M |
| 7 | 35066064 | 35068015 | H_c_26b23_M |
| 7 | 35070471 | 35071684 | H_c_116g12 |
| 7 | 35073764 | 35074999 | H_c_204p22_M |
| 7 | 35163661 | 35164519 | H_c_6h01 |
| 7 | 35507222 | 35508471 | H_c_93o19_M |
| 7 | 35612887 | 35614837 | H_c_237g17_M |
| 7 | 35965622 | 35966939 | H_c_247e03_M |
| 7 | 36179466 | 36180326 | H_c_127d05_M |
| 7 | 36202445 | 36203378 | H_c_272g06_M |
| 7 | 36452824 | 36454280 | H_c_264o03 |
| 7 | 36538174 | 36540136 | H_c_213o14 |
| 7 | 3661196 | 3661299 | H_c_42f19 |
| 7 | 36666749 | 36666847 | H_c_77e09 |
| 7 | 36896784 | 36897134 | H_c_11e16_M |
| 7 | 37416646 | 37416758 | H_c_22c11 |
| 7 | 37446995 | 37447177 | H_c_19o07 |
| 7 | 37610295 | 37610413 | H_c_113b07 |
| 7 | 37728611 | 37730307 | H_c_8j06_M |
| 7 | 37733421 | 37734506 | H_c_157f20 |
| 7 | 37990833 | 37991258 | H_c_218e11_M |
| 7 | 38364745 | 38364868 | H_c_125g05 |
| 7 | 38443634 | 38444356 | H_c_166i03_M |
| 7 | 38938157 | 38938361 | H_c_156k20 |
| 7 | 39226734 | 39227494 | H_c_235k20_M |
| 7 | 39279139 | 39279219 | H_c141l10 |
| 7 | 39315004 | 39315167 | H_c_197j10 |
| 7 | 3940999 | 3943055 | H_c_229a17 |
| 7 | 39435699 | 39437098 | H_c139m14_M |
| 7 | 39545564 | 39546627 | H_c_117d24_M |
| 7 | 39646006 | 39647098 | H_c_39j07 |
| 7 | 39762288 | 39764945 | H_c_125e03 |
| 7 | 39946847 | 39948266 | H_c_183l07_M |
| 7 | 40352717 | 40352911 | H_c_146h08 |
| 7 | 40365893 | 40366060 | H_c_50b17 |
| 7 | 41746711 | 41746926 | H_c_98i13 |
| 7 | 41925483 | 41925708 | H_c_185a08 |
| 7 | 4194775 | 4194935 | H_c_55d07 |
| 7 | 42040604 | 42041439 | H_c_129j07 |
| 7 | 42049156 | 42050386 | H_c_127m13_M |
| 7 | 4260722 | 4261007 | H_c_198o11 |
| 7 | 42657070 | 42657262 | H_c_56f03 |
| 7 | 42700778 | 42700984 | H_c_73e12 |
| 7 | 42724365 | 42725169 | H_c_30o13 |
| 7 | 42744731 | 42745726 | H_c_15m03 |
| 7 | 43209512 | 43209659 | H_c_70f19 |
| 7 | 43395577 | 43396583 | H_c_59p20_M |
| 7 | 43541696 | 43542808 | H_c_230a03_M |
| 7 | 43570804 | 43572213 | H_c_95f18_M |
| 7 | 43681718 | 43682818 | H_c_27a11_M |
| 7 | 43718969 | 43719733 | H_c_26g14_M |
| 7 | 43738780 | 43739855 | H_c_266p16_M |
| 7 | 43894960 | 43895560 | H_c_204a13 |
| 7 | 43916856 | 43918294 | H_c134d02_M |
| 7 | 43923480 | 43926106 | H_c_239l17 |
| 7 | 43936029 | 43937294 | H_c_209i11 |
| 7 | 44058690 | 44060563 | H_c_267c05 |
| 7 | 44122189 | 44122992 | H_c_85h22_M |
| 7 | 44281171 | 44281348 | H_c_56k07 |
| 7 | 44303019 | 44303860 | H_c_258e10_M |
| 7 | 44386606 | 44387312 | H_c_70h08_M |
| 7 | 44393443 | 44395278 | H_c_217g13_M |
| 7 | 44418920 | 44420201 | H_c_13a01 |
| 7 | 4454708 | 4455438 | H_c_77f24_M |
| 7 | 44561099 | 44562637 | H_c_30e07_M |
| 7 | 44660479 | 44661748 | H_c_270l13_M |
| 7 | 44811775 | 44813551 | H_c_235g17_M |
| 7 | 44901429 | 44902922 | H_c_9f22_M |
| 7 | 44924105 | 44924983 | H_c137i04_M |
| 7 | 45062085 | 45062311 | H_c_117d12 |
| 7 | 45701263 | 45702489 | H_c_112j08_M |
| 7 | 45733321 | 45734569 | H_c_114f09_M |
| 7 | 4587652 | 4589088 | H_c_24n16_M |
| 7 | 4604622 | 4606133 | H_c_28g13_M |
| 7 | 46087776 | 46087935 | H_c_66i04 |
| 7 | 46182893 | 46183123 | H_c131l22 |
| 7 | 4658697 | 4659012 | H_c_38f09 |
| 7 | 4674476 | 4675321 | H_c_93m22_M |
| 7 | 4679451 | 4680264 | H_c_98c06 |

TABLE 1-continued

| | | | |
|---|---|---|---|
| 7 | 46865256 | 46867159 | H_c_86g14_M |
| 7 | 4695711 | 4696887 | H_c_18j03_M |
| 7 | 47058137 | 47058863 | H_c_243k15 |
| 7 | 47274009 | 47274570 | H_c_225d15 |
| 7 | 47393692 | 47395327 | H_c_146g16 |
| 7 | 47732592 | 47732664 | H_c_101n07 |
| 7 | 47792048 | 47792746 | H_c_202p22_M |
| 7 | 47847847 | 47849762 | H_c_169d07_M |
| 7 | 47901795 | 47902734 | H_c_160i13_M |
| 7 | 48099189 | 48100494 | H_c_176m02 |
| 7 | 48254274 | 48254438 | H_c_24c24_M |
| 7 | 49357989 | 49358090 | H_c_269i16 |
| 7 | 49590187 | 49592095 | H_c_68i13_M |
| 7 | 49938137 | 49938315 | H_c_241m13 |
| 7 | 5002886 | 5003645 | H_c_198b18_M |
| 7 | 50119544 | 50121809 | H_c_216d16 |
| 7 | 50186984 | 50187176 | H_c_122j23 |
| 7 | 50291798 | 50292655 | H_c_30e08_M |
| 7 | 50406072 | 50406435 | H_c_19m10 |
| 7 | 50437365 | 50437474 | H_c_44g03 |
| 7 | 50503427 | 50504144 | H_c132b03 |
| 7 | 50526284 | 50526573 | H_c_129f19 |
| 7 | 50623871 | 50624072 | H_c_90o21 |
| 7 | 50634071 | 50635387 | H_c_154o14_M |
| 7 | 50635388 | 50635768 | H_c_30e18_M |
| 7 | 50978936 | 50979123 | H_c132i01 |
| 7 | 51157290 | 51159353 | H_c_52j21 |
| 7 | 51588715 | 51588843 | H_c_40p09 |
| 7 | 51767137 | 51767275 | H_c_93a23 |
| 7 | 5231496 | 5234739 | H_c_68e08_M |
| 7 | 523562 | 523680 | H_c133l16 |
| 7 | 5235978 | 5237358 | H_c_77o18_M |
| 7 | 5240724 | 5241964 | H_c_251g17_M |
| 7 | 52540515 | 52540691 | H_c_70e08 |
| 7 | 52666341 | 52666483 | H_c_67d02 |
| 7 | 52942382 | 52942486 | H_c139j06 |
| 7 | 52974411 | 52974521 | H_c_36g21 |
| 7 | 53060732 | 53061372 | H_c_258g04 |
| 7 | 5325173 | 5327212 | H_c_63b10_M |
| 7 | 53497695 | 53497888 | H_c_14k07 |
| 7 | 5367023 | 5370584 | H_c137d11_M |
| 7 | 5374889 | 5377009 | H_c_189p23_M |
| 7 | 54383841 | 54384188 | H_c_59g09 |
| 7 | 54386915 | 54389320 | H_c_169g15 |
| 7 | 54775076 | 54775884 | H_c139o02 |
| 7 | 54860681 | 54862449 | H_c_46d01_M |
| 7 | 54984908 | 54985589 | H_c_103j12 |
| 7 | 55311117 | 55311351 | H_c_5j19 |
| 7 | 55314370 | 55314950 | H_c_214a03 |
| 7 | 55413420 | 55414640 | H_c_73c04_M |
| 7 | 55728810 | 55730085 | H_c_43k14_M |
| 7 | 55793699 | 55794270 | H_c_126f04 |
| 7 | 55806112 | 55807150 | H_c_119i04_M |
| 7 | 55893048 | 55894317 | H_c_76e17 |
| 7 | 55906012 | 55907169 | H_c_22m14_M |
| 7 | 5592530 | 5594922 | H_c_33c17_M |
| 7 | 55957760 | 55958685 | H_c_193m08 |
| 7 | 568620 | 570363 | H_c_99d24 |
| 7 | 57294775 | 57295974 | H_c_82o14 |
| 7 | 57411105 | 57411279 | H_c_65h18 |
| 7 | 57738987 | 57739957 | H_c_267c19_M |
| 7 | 583140 | 583696 | H_c_270h01 |
| 7 | 5871445 | 5872340 | H_c_49f01_M |
| 7 | 5894094 | 5894755 | H_c_9d02 |
| 7 | 5917228 | 5918688 | H_c_113a16_M |
| 7 | 6084475 | 6086199 | H_c_69c05_M |
| 7 | 61413058 | 61413249 | H_c_243e24_M |
| 7 | 61414419 | 61414757 | H_c_34j05_M |
| 7 | 61503903 | 61506588 | H_c_266k09 |
| 7 | 6259399 | 6261382 | H_c_229d02 |
| 7 | 628538 | 630016 | H_c_245a03_M |
| 7 | 6296261 | 6297118 | H_c_273e22_M |
| 7 | 63000870 | 63001823 | H_c136l08 |
| 7 | 630021 | 630786 | H_c_50e02 |
| 7 | 63086133 | 63087354 | H_c_39h09 |
| 7 | 6316232 | 6317318 | H_c_11g23_M |
| 7 | 63391738 | 63391960 | H_c_236h20 |
| 7 | 6343310 | 6344914 | H_c_244i05 |
| 7 | 63471526 | 63474319 | H_c_122g21_M |
| 7 | 6348589 | 6350828 | H_c_240g22 |
| 7 | 63793514 | 63794332 | H_c_26a05 |
| 7 | 63851759 | 63852607 | H_c144p01 |
| 7 | 6389011 | 6391163 | H_c_268g21_M |
| 7 | 6402336 | 6403571 | H_c_2n18 |
| 7 | 64143353 | 64144939 | H_c_238c02_M |
| 7 | 64156422 | 64157003 | H_c_221m03 |
| 7 | 6427692 | 6428304 | H_c_29m19_M |
| 7 | 644874 | 645001 | H_c_109a21 |
| 7 | 64659534 | 64660690 | H_c134l03_M |
| 7 | 6476291 | 6477683 | H_c_57p18 |
| 7 | 64782061 | 64783271 | H_c_238g07 |
| 7 | 64984340 | 64986169 | H_c_17m15 |
| 7 | 65113014 | 65115201 | H_c_190a11 |
| 7 | 6519011 | 6520008 | H_c_59p15_M |
| 7 | 65322417 | 65323222 | H_c_199c05_M |
| 7 | 65414153 | 65416339 | H_c_202o22_M |
| 7 | 65501180 | 65501954 | H_c_11e14 |
| 7 | 65537281 | 65539068 | H_c_3e02_M |
| 7 | 65542435 | 65542701 | H_c_99p20 |
| 7 | 65563245 | 65563975 | H_c_162m15 |
| 7 | 65650145 | 65650901 | H_c_39i20 |
| 7 | 65829954 | 65830972 | H_c_203k02_M |
| 7 | 65876805 | 65878595 | H_c_125c05 |
| 7 | 66211347 | 66212207 | H_c_34f09 |
| 7 | 66475292 | 66475552 | H_c_14b01 |
| 7 | 66766990 | 66767134 | H_c142c11 |
| 7 | 67167828 | 67167996 | H_c_206g16 |
| 7 | 67903231 | 67904264 | H_c_112d20 |
| 7 | 68067441 | 68067544 | H_c_160d07 |
| 7 | 68491759 | 68491945 | H_c_36m10_M |
| 7 | 68508674 | 68510300 | H_c_51h18_M |
| 7 | 688943 | 691064 | H_c_45g06_M |
| 7 | 69603126 | 69604665 | H_c_171p21 |
| 7 | 69604665 | 69605152 | H_c_68f13_M |
| 7 | 69711640 | 69711769 | H_c_23g10_M |
| 7 | 69875076 | 69875350 | H_c_206o15 |
| 7 | 6995049 | 6996273 | H_c_55f10_M |
| 7 | 70040698 | 70043273 | H_c_259c03_M |
| 7 | 70242181 | 70242278 | H_c_33l14 |
| 7 | 70397807 | 70398115 | H_c_73a15 |
| 7 | 70762592 | 70762701 | H_c_253l05 |
| 7 | 71185604 | 71185740 | H_c_231m22 |
| 7 | 71342289 | 71342475 | H_c_203a20 |
| 7 | 71840149 | 71840250 | H_c_153m15_M |
| 7 | 72282248 | 72283489 | H_c_252d22 |
| 7 | 72292673 | 72295037 | H_c_74i08_M |
| 7 | 72380151 | 72381410 | H_c141i24_M |
| 7 | 72415829 | 72417044 | H_c_91m11 |
| 7 | 72435763 | 72438082 | H_c_5e10_M |
| 7 | 72482595 | 72483549 | H_c_32i13 |
| 7 | 72526786 | 72528073 | H_c_232a21 |
| 7 | 72541727 | 72542940 | H_c_205d20_M |
| 7 | 72584507 | 72585543 | H_c_84k07 |
| 7 | 72597139 | 72598718 | H_c140i02 |
| 7 | 72627307 | 72629845 | H_c_240a17_M |
| 7 | 72691970 | 72692122 | H_c_114b19 |
| 7 | 72699812 | 72702122 | H_c_87g13 |
| 7 | 72818107 | 72818369 | H_c_37m15 |
| 7 | 72994714 | 72994800 | H_c_113j12 |
| 7 | 73147293 | 73150073 | H_c_202b07_M |
| 7 | 73313075 | 73314884 | H_c_201g24 |
| 7 | 73339622 | 73340136 | H_c_6i21 |
| 7 | 73516048 | 73517797 | H_c_69c07_M |
| 7 | 7379571 | 7380322 | H_c_198f19_M |
| 7 | 73933441 | 73934276 | H_c_216d05_M |
| 7 | 7453416 | 7454169 | H_c133m15 |
| 7 | 74912198 | 74914395 | H_c_122p17 |
| 7 | 75011969 | 75013904 | H_c_273j01 |
| 7 | 75087096 | 75088535 | H_c_83d02 |
| 7 | 75130958 | 75131064 | H_c_29j13 |
| 7 | 75188138 | 75189499 | H_c_109i11 |
| 7 | 75267296 | 75269061 | H_c_170j15_M |
| 7 | 75321251 | 75322733 | H_c_129h14 |
| 7 | 75508943 | 75509550 | H_c_120i02 |
| 7 | 75516082 | 75518197 | H_c140j24 |
| 7 | 75533557 | 75535587 | H_c_27e24 |
| 7 | 75540957 | 75542634 | H_c_200a14_M |
| 7 | 75576566 | 75577145 | H_c_6o15 |
| 7 | 75591247 | 75593168 | H_c_182p11 |
| 7 | 75632083 | 75633589 | H_c_123l17_M |

TABLE 1-continued

| | | | |
|---|---|---|---|
| 7 | 75653696 | 75655158 | H_c_222e02 |
| 7 | 75667010 | 75668223 | H_c_36l11_M |
| 7 | 75789805 | 75790848 | H_c_56e10 |
| 7 | 76689427 | 76690840 | H_c_166j21 |
| 7 | 76810447 | 76812572 | H_c_97j22_M |
| 7 | 76902080 | 76902163 | H_c_30m03 |
| 7 | 76970050 | 76971556 | H_c_11m06_M |
| 7 | 77036890 | 77037045 | H_c_34m14 |
| 7 | 77072685 | 77073446 | H_c_128b17_M |
| 7 | 77293256 | 77294577 | H_c_94e20 |
| 7 | 77443681 | 77443963 | H_c_122c07 |
| 7 | 77742735 | 77742806 | H_c_208m14 |
| 7 | 7781261 | 7782930 | H_c_191g23_M |
| 7 | 77844829 | 77844911 | H_c_75n10 |
| 7 | 78221990 | 78222146 | H_c_206m15 |
| 7 | 78258439 | 78258625 | H_c_146l03 |
| 7 | 78619681 | 78619772 | H_c_5m21 |
| 7 | 78726024 | 78728633 | H_c_205a08_M |
| 7 | 787770 | 789279 | H_c138i24_M |
| 7 | 78810589 | 78810832 | H_c_91k17 |
| 7 | 79155382 | 79155456 | H_c_77c12 |
| 7 | 79408150 | 79409776 | H_c_234h08_M |
| 7 | 79445700 | 79445907 | H_c_94d18 |
| 7 | 79605721 | 79605822 | H_c_22m17 |
| 7 | 79925385 | 79925462 | H_c_204a04 |
| 7 | 80192685 | 80193472 | H_c_227i06_M |
| 7 | 80299399 | 80299487 | H_c133k24 |
| 7 | 80472233 | 80472516 | H_c_110o23 |
| 7 | 8074126 | 8075567 | H_c_163h07_M |
| 7 | 80938243 | 80938328 | H_c_270e16 |
| 7 | 81008227 | 81008339 | H_c_235b19 |
| 7 | 81037333 | 81037488 | H_c_81n02 |
| 7 | 81287105 | 81287224 | H_c_76j21 |
| 7 | 8137468 | 8137628 | H_c_229k21 |
| 7 | 81537420 | 81537542 | H_c_13k17 |
| 7 | 81959611 | 81959720 | H_c_127g04 |
| 7 | 82133832 | 82133923 | H_c_65j10 |
| 7 | 82153257 | 82153436 | H_c_125p19_M |
| 7 | 82217101 | 82217194 | H_c_211m18 |
| 7 | 8227538 | 8227652 | H_c_71f22 |
| 7 | 82435985 | 82437013 | H_c_147c08_M |
| 7 | 8245775 | 8247121 | H_c_241c02 |
| 7 | 8245804 | 8248962 | H_c_41d06_M |
| 7 | 82998460 | 82998536 | H_c_155e21 |
| 7 | 83668630 | 83668801 | H_c_22p20 |
| 7 | 840049 | 842026 | H_c_178e07_M |
| 7 | 85542297 | 85542363 | H_c_104j23 |
| 7 | 856200 | 857762 | H_c_112a20_M |
| 7 | 86025149 | 86025318 | H_c_43o05_M |
| 7 | 86332806 | 86333946 | H_c_191g06 |
| 7 | 86425951 | 86427203 | H_c_248p18 |
| 7 | 86454577 | 86454705 | H_c_242d14 |
| 7 | 86493504 | 86494772 | H_c_175a05_M |
| 7 | 86748991 | 86750019 | H_c_67p08 |
| 7 | 86826984 | 86827171 | H_c_48h07 |
| 7 | 86874102 | 86875165 | H_c_164i03 |
| 7 | 86902250 | 86903238 | H_c_205n16_M |
| 7 | 87149590 | 87151116 | H_c_162j12_M |
| 7 | 87207851 | 87208644 | H_c_18n06_M |
| 7 | 87216655 | 87216816 | H_c_57h21 |
| 7 | 87493654 | 87494376 | H_c_33i24 |
| 7 | 8751252 | 8751377 | H_c_110n04 |
| 7 | 87580555 | 87581051 | H_c_119k23_M |
| 7 | 87967861 | 87967941 | H_c_214k17 |
| 7 | 87985702 | 87985789 | H_c_275n06 |
| 7 | 88032673 | 88034000 | H_c_18o09_M |
| 7 | 88052751 | 88052854 | H_c_5c06 |
| 7 | 88376664 | 88376792 | H_c_251e19 |
| 7 | 88597850 | 88598135 | H_c_181e05 |
| 7 | 89484765 | 89486165 | H_c_95c09_M |
| 7 | 89495920 | 89496060 | H_c_54k05 |
| 7 | 89594561 | 89595625 | H_c_25n09 |
| 7 | 89869387 | 89871118 | H_c_233j16_M |
| 7 | 899443 | 900348 | H_c_217g21 |
| 7 | 91168860 | 91168957 | H_c_99d19 |
| 7 | 91407618 | 91408528 | H_c_36j05 |
| 7 | 91452724 | 91453446 | H_c_38l08_M |
| 7 | 91519139 | 91521237 | H_c_273o02 |
| 7 | 91611098 | 91611196 | H_c_147h14 |
| 7 | 91703309 | 91703492 | H_c_214o09 |
| 7 | 91721242 | 91722165 | H_c_170c22 |
| 7 | 91793743 | 91793825 | H_c_89k07 |
| 7 | 91801812 | 91802648 | H_c_121p18_M |
| 7 | 9193412 | 9193519 | H_c_189f17 |
| 7 | 91970509 | 91970657 | H_c_162f08 |
| 7 | 92087149 | 92087299 | H_c_60e18 |
| 7 | 92106911 | 92110935 | H_c_202j19_M_M |
| 7 | 92366857 | 92367003 | H_c131k17_M |
| 7 | 92505664 | 92506183 | H_c_4k16_M |
| 7 | 92756097 | 92756178 | H_c_63e17 |
| 7 | 92848718 | 92849864 | H_c_107p19_M |
| 7 | 92928421 | 92928565 | H_c_35d05 |
| 7 | 93086184 | 93086321 | H_c_174a21_M |
| 7 | 93163977 | 93165195 | H_c_118k19_M |
| 7 | 93231364 | 93231463 | H_c_66j20 |
| 7 | 93259836 | 93259941 | H_c_76f19 |
| 7 | 93277978 | 93278587 | H_c_51h10 |
| 7 | 9369122 | 9369383 | H_c_125n10 |
| 7 | 93783740 | 93784547 | H_c_154p02 |
| 7 | 93835225 | 93835342 | H_c_257o20 |
| 7 | 94181657 | 94182254 | H_c_173k01 |
| 7 | 94339646 | 94339777 | H_c_186g01 |
| 7 | 94669775 | 94670783 | H_c_8e14_M |
| 7 | 94870075 | 94870769 | H_c_68p05 |
| 7 | 95046235 | 95047249 | H_c_91i01_M |
| 7 | 950837 | 951523 | H_c_14n17_M |
| 7 | 95349504 | 95349873 | H_c_21b12 |
| 7 | 95595000 | 95596588 | H_c_94g22_M |
| 7 | 95816500 | 95816572 | H_c_159e09 |
| 7 | 96222447 | 96222566 | H_c_139d15 |
| 7 | 96266215 | 96266783 | H_c_230j13 |
| 7 | 96273636 | 96273842 | H_c_163m11_M |
| 7 | 96277483 | 96277693 | H_c_218o18 |
| 7 | 96297726 | 96298821 | H_c_21i18_M |
| 7 | 96302626 | 96302755 | H_c_59g12 |
| 7 | 96391297 | 96391944 | H_c_32o04_M |
| 7 | 96453210 | 96453295 | H_c_167p22_M |
| 7 | 96577095 | 96577188 | H_c_231i15 |
| 7 | 97007149 | 97007763 | H_c_161g13 |
| 7 | 972266 | 973573 | H_c_270g24_M |
| 7 | 97380659 | 97381524 | H_c_77k03 |
| 7 | 97524791 | 97526624 | H_c_178d11 |
| 7 | 97554610 | 97557089 | H_c_127n22_M |
| 7 | 97674141 | 97675652 | H_c_245a24 |
| 7 | 97736450 | 97736604 | H_c_8i17 |
| 7 | 97743652 | 97744925 | H_c140n10 |
| 7 | 97883579 | 97883750 | H_c_76m12_M |
| 7 | 97890219 | 97892315 | H_c_145b19_M |
| 7 | 97910921 | 97911029 | H_c_51m05_M |
| 7 | 97947450 | 97947626 | H_c_183k19_M |
| 7 | 98055389 | 98057525 | H_c_60f06 |
| 7 | 98111629 | 98112803 | H_c_56i23 |
| 7 | 98120690 | 98122284 | H_c_190c18_M |
| 7 | 98134642 | 98134818 | H_c_105k18 |
| 7 | 982666 | 984856 | H_c_238n21_M |
| 7 | 98529975 | 98531958 | H_c_52j04 |
| 7 | 98567816 | 98568449 | H_c_109h01_M |
| 7 | 98634450 | 98636948 | H_c_147d13_M |
| 7 | 98650390 | 98652138 | H_c_24g10 |
| 7 | 98680587 | 98681897 | H_c_191f09_M |
| 7 | 98708015 | 98708641 | H_c_117n06 |
| 7 | 98714951 | 98715627 | H_c_82e08_M |
| 7 | 98741356 | 98742770 | H_c_64a04_M |
| 7 | 98788634 | 98788742 | H_c_123a19_M |
| 7 | 98793843 | 98795228 | H_c_167m19 |
| 7 | 98800089 | 98801608 | H_c_44d08_M |
| 7 | 98852436 | 98853299 | H_c_111b12 |
| 7 | 98858830 | 98859637 | H_c_31a24_M |
| 7 | 989966 | 990278 | H_c_208i14 |
| 7 | 99161221 | 99162068 | H_c_3e18_M |
| 7 | 99323667 | 99324398 | H_c_121f19 |
| 7 | 99342632 | 99343165 | H_c_37b10 |
| 7 | 99367872 | 99369530 | H_c142m20_M |
| 7 | 99391021 | 99392353 | H_c_149l23 |
| 7 | 99400277 | 99401271 | H_c_107c07_M |
| 7 | 99419338 | 99420483 | H_c_223e23_M |
| 7 | 99513240 | 99515907 | H_c_68i24_M |
| 7 | 99669970 | 99674013 | H_c_119g24_M |
| 7 | 99677620 | 99678770 | H_c_72b17 |
| 7 | 99692872 | 99693336 | H_c_42a08 |

TABLE 1-continued

| | | | |
|---|---|---|---|
| 7 | 99781107 | 99782198 | H_c__27g19_M |
| 7 | 99827837 | 99828950 | H_c__31a10_M |
| 7 | 99854506 | 99855412 | H_c__125e15_M |
| 7 | 99873974 | 99876347 | H_c__7i10_M |
| 7 | 99897060 | 99898814 | H_c__187a09_M |
| 7 | 99947234 | 99948855 | H_c__217k06 |
| 7 | 99962462 | 99964294 | H_c__216n07_M |
| 8 | 100021085 | 100026448 | H_c__41j01_M_M |
| 8 | 100042421 | 100042566 | H_c__232g01_M |
| 8 | 100055287 | 100056064 | H_c__172o08 |
| 8 | 100338853 | 100338947 | H_c__89p15 |
| 8 | 100350522 | 100350623 | H_c__88o14 |
| 8 | 100481509 | 100481763 | H_c__245a15_M |
| 8 | 100830363 | 100830456 | H_c__19c16 |
| 8 | 100974583 | 100975343 | H_c__93m11 |
| 8 | 101187095 | 101187976 | H_c__75p12 |
| 8 | 101226723 | 101227569 | H_c__88g10 |
| 8 | 101294239 | 101295193 | H_c144h03_M |
| 8 | 101391275 | 101392230 | H_c__87a10_M |
| 8 | 101640629 | 101641505 | H_c__54k13_M |
| 8 | 101730253 | 101731291 | H_c__82a16_M |
| 8 | 101802108 | 101804416 | H_c__161i09_M |
| 8 | 101988395 | 101990541 | H_c__67f11_M |
| 8 | 102207358 | 102208666 | H_c__7i22 |
| 8 | 102280798 | 102280960 | H_c__1j08_M |
| 8 | 102286309 | 102287746 | H_c__68p20 |
| 8 | 10229758 | 10230152 | H_c__194k17_M |
| 8 | 102305250 | 102306269 | H_c__241o13_M |
| 8 | 102414087 | 102414804 | H_c__207f18 |
| 8 | 102574396 | 102575740 | H_c__188l23_M |
| 8 | 102812114 | 102812276 | H_c__119b10 |
| 8 | 103131280 | 103131599 | H_c__116a19 |
| 8 | 103204843 | 103206225 | H_c__124h23_M |
| 8 | 103319680 | 103321411 | H_c__164j14 |
| 8 | 103475694 | 103475788 | H_c144j14 |
| 8 | 103492926 | 103494580 | H_c__235i02 |
| 8 | 103682368 | 103682618 | H_c__72g07_M |
| 8 | 103890910 | 103892459 | H_c__7h10_M |
| 8 | 103944200 | 103946169 | H_c__163i05_M |
| 8 | 104102089 | 104102863 | H_c__39o08 |
| 8 | 104111578 | 104111709 | H_c__84g09 |
| 8 | 104221721 | 104223186 | H_c__21j10 |
| 8 | 104379893 | 104380953 | H_c__26c04_M |
| 8 | 104452640 | 104453844 | H_c__254o24_M |
| 8 | 104495888 | 104497267 | H_c__166i11_M |
| 8 | 104599371 | 104599729 | H_c__93c11 |
| 8 | 104727674 | 104727768 | H_c__187e20 |
| 8 | 104897891 | 104898028 | H_c__48c12 |
| 8 | 10491552 | 10493325 | H_c__47n02_M |
| 8 | 105091790 | 105091885 | H_c__120c17 |
| 8 | 105547803 | 105548660 | H_c__200h10_M |
| 8 | 105669458 | 105671412 | H_c__48l12_M |
| 8 | 106134581 | 106134701 | H_c__69d16_M |
| 8 | 10624664 | 10625960 | H_c__35m01_M |
| 8 | 10627901 | 10628545 | H_c144d11_M |
| 8 | 106400652 | 106401464 | H_c__92k22_M |
| 8 | 10646535 | 10646665 | H_c__252i10 |
| 8 | 107209238 | 107209503 | H_c__22j01 |
| 8 | 107269511 | 107269724 | H_c__152f23 |
| 8 | 107351157 | 107352708 | H_c__17h01_M |
| 8 | 107739060 | 107740003 | H_c__72b04 |
| 8 | 107999497 | 107999584 | H_c__34l16 |
| 8 | 108387535 | 108387639 | H_c__91j20 |
| 8 | 108631746 | 108631923 | H_c__149l04 |
| 8 | 10910682 | 10912319 | H_c__43l13 |
| 8 | 109163318 | 109165374 | H_c__87a12_M |
| 8 | 109524743 | 109525604 | H_c__178j13_M |
| 8 | 10953861 | 10954894 | H_c__197i21_M |
| 8 | 109721149 | 109721262 | H_c__212h12 |
| 8 | 110414827 | 110415442 | H_c__244f21 |
| 8 | 110620631 | 110621748 | H_c__244f06 |
| 8 | 110663577 | 110663677 | H_c__101b07 |
| 8 | 110725810 | 110726631 | H_c__205e05_M |
| 8 | 111026782 | 111026897 | H_c__163c20_M |
| 8 | 111055101 | 111056619 | H_c__35l16 |
| 8 | 111344316 | 111344575 | H_c__203n09 |
| 8 | 111452585 | 111452714 | H_c__128e03 |
| 8 | 111461322 | 111461420 | H_c__36p21 |
| 8 | 11179197 | 11179823 | H_c__52b24_M |
| 8 | 11241943 | 11243228 | H_c__212m22 |
| 8 | 113105886 | 113105991 | H_c__185p07 |
| 8 | 11360493 | 11362836 | H_c__29o05_M |
| 8 | 114294712 | 114294811 | H_c__78b17 |
| 8 | 114516148 | 114516343 | H_c__7p17_M |
| 8 | 11457642 | 11459849 | H_c__54p17_M |
| 8 | 115133074 | 115133276 | H_c__35g22 |
| 8 | 115463475 | 115463626 | H_c__200i12 |
| 8 | 11574296 | 11576515 | H_c__103m12_M |
| 8 | 11588050 | 11588918 | H_c__88e19 |
| 8 | 11592240 | 11593073 | H_c__200n17_M |
| 8 | 11597212 | 11597540 | H_c__160e22_M |
| 8 | 11598842 | 11599404 | H_c__208j12 |
| 8 | 11599407 | 11605366 | H_c__151j05_M_M |
| 8 | 116081060 | 116081158 | H_c__145i08 |
| 8 | 116226005 | 116226075 | H_c__28f04 |
| 8 | 116360535 | 116360664 | H_c__67e16 |
| 8 | 116440883 | 116440973 | H_c__9g01 |
| 8 | 116457690 | 116457895 | H_c__199d01_M |
| 8 | 11664230 | 11665250 | H_c__24p05_M |
| 8 | 116729428 | 116730045 | H_c__8e12 |
| 8 | 116749783 | 116750803 | H_c__274n23_M |
| 8 | 116884639 | 116884761 | H_c__254o14 |
| 8 | 116933800 | 116933911 | H_c__130f13 |
| 8 | 11696577 | 11698149 | H_c__127c21_M |
| 8 | 116969980 | 116970158 | H_c__41k04 |
| 8 | 11722099 | 11722251 | H_c__20i22 |
| 8 | 117407159 | 117407270 | H_c__91d15 |
| 8 | 11753739 | 11753816 | H_c__50c04 |
| 8 | 117595859 | 117596052 | H_c__112i24 |
| 8 | 11762328 | 11763821 | H_c__241a23_M |
| 8 | 117758126 | 117758366 | H_c__159h17 |
| 8 | 117836538 | 117837462 | H_c__87m03 |
| 8 | 117955438 | 117956527 | H_c137g13 |
| 8 | 11797236 | 11797326 | H_c__119l13 |
| 8 | 11798793 | 11798939 | H_c__58n20 |
| 8 | 118019435 | 118020485 | H_c__212j20 |
| 8 | 118491525 | 118491626 | H_c__160a10 |
| 8 | 118602032 | 118602785 | H_c__120f11 |
| 8 | 119394966 | 119395204 | H_c__48c20 |
| 8 | 119562776 | 119562945 | H_c139j15 |
| 8 | 119703201 | 119704058 | H_c__166n12 |
| 8 | 120289388 | 120290848 | H_c__225o04_M |
| 8 | 120815348 | 120815493 | H_c__81b04 |
| 8 | 120936712 | 120937961 | H_c__180h06_M |
| 8 | 120954770 | 120955938 | H_c__41f24_M |
| 8 | 121097337 | 121097448 | H_c__87a17 |
| 8 | 121437867 | 121438014 | H_c__1i19 |
| 8 | 121500755 | 121500848 | H_c__245h18_M |
| 8 | 121892684 | 121893278 | H_c__70d22_M |
| 8 | 122150181 | 122150287 | H_c__66b14 |
| 8 | 122326617 | 122326695 | H_c__203j11 |
| 8 | 123861414 | 123862249 | H_c__41d20_M |
| 8 | 123862501 | 123863498 | H_c__84i22_M |
| 8 | 124122923 | 124123780 | H_c__42o04_M |
| 8 | 124153737 | 124154614 | H_c__46h18 |
| 8 | 124322229 | 124323045 | H_c__228k07 |
| 8 | 124354946 | 124356919 | H_c__73i06 |
| 8 | 124477135 | 124478347 | H_c__194e18_M |
| 8 | 124579462 | 124579541 | H_c__81b13 |
| 8 | 124622012 | 124623377 | H_c__41k10_M |
| 8 | 124849276 | 124850483 | H_c__196b15_M |
| 8 | 125114273 | 125114367 | H_c__38e17 |
| 8 | 125177997 | 125178219 | H_c__223d22 |
| 8 | 125355526 | 125357531 | H_c__213n22 |
| 8 | 125451549 | 125454717 | H_c__216e22_M_M |
| 8 | 125620230 | 125620979 | H_c__180k05_M |
| 8 | 125809625 | 125810401 | H_c__81d11_M |
| 8 | 126079295 | 126080541 | H_c__83p14_M |
| 8 | 126172613 | 126173636 | H_c__170h16_M |
| 8 | 126201490 | 126201705 | H_c__71c15 |
| 8 | 126215813 | 126215916 | H_c133g05 |
| 8 | 12655663 | 12657974 | H_c__124m03 |
| 8 | 126639782 | 126639940 | H_c__80h22 |
| 8 | 127147506 | 127147624 | H_c__237d23 |
| 8 | 127637592 | 127638709 | H_c__94g10_M |
| 8 | 127639893 | 127640025 | H_c__55c10_M |
| 8 | 128012883 | 128012984 | H_c__39p01 |
| 8 | 12853216 | 12854402 | H_c__114p09_M |
| 8 | 128818526 | 128820520 | H_c__17e23_M |
| 8 | 128875226 | 128876418 | H_c142h24 |

TABLE 1-continued

| | | | |
|---|---|---|---|
| 8 | 128998734 | 129000637 | H_c__237o14 |
| 8 | 12982122 | 12982423 | H_c__1e21 |
| 8 | 13034245 | 13036079 | H_c__7a02_M |
| 8 | 130485075 | 130485206 | H_c__190d19_M |
| 8 | 130791473 | 130791759 | H_c__5c22_M |
| 8 | 131438583 | 131440576 | H_c__70e14_M |
| 8 | 131524158 | 131525265 | H_c__74b07_M |
| 8 | 131972252 | 131972619 | H_c__46f07 |
| 8 | 132121332 | 132124113 | H_c__89a15_M |
| 8 | 132553087 | 132553217 | H_c__152f02 |
| 8 | 132985248 | 132986321 | H_c139j02_M |
| 8 | 133136303 | 133137893 | H_c__116f02 |
| 8 | 133561488 | 133563309 | H_c__78b22_M |
| 8 | 133756024 | 133757444 | H_c__58o20 |
| 8 | 133967454 | 133967837 | H_c__109j04 |
| 8 | 134377265 | 134379293 | H_c__193l11_M |
| 8 | 134601073 | 134603037 | H_c__38o09 |
| 8 | 134650942 | 134652010 | H_c__174b20_M |
| 8 | 134652127 | 134654280 | H_c__44l03_M |
| 8 | 134765820 | 134765902 | H_c__89h16 |
| 8 | 134950925 | 134951973 | H_c__66i14 |
| 8 | 135047464 | 135047570 | H_c__92k24 |
| 8 | 135198827 | 135198957 | H_c__113h11 |
| 8 | 135793780 | 135794828 | H_c__52e23_M |
| 8 | 135860349 | 135860471 | H_c144g11 |
| 8 | 135912829 | 135914514 | H_c__225j21_M |
| 8 | 136537420 | 136539392 | H_c__215g15 |
| 8 | 136652391 | 136652665 | H_c__274b11 |
| 8 | 136685474 | 136685592 | H_c__157j01 |
| 8 | 136818345 | 136818446 | H_c__8b06 |
| 8 | 136925865 | 136926097 | H_c135d15 |
| 8 | 137628239 | 137628428 | H_c__274g16 |
| 8 | 137810766 | 137812177 | H_c__118n15 |
| 8 | 138241734 | 138241920 | H_c136a13 |
| 8 | 138246780 | 138247128 | H_c__58d21 |
| 8 | 138698208 | 138698385 | H_c__51c22 |
| 8 | 13910085 | 13910210 | H_c131a17 |
| 8 | 139577854 | 139579186 | H_c__163e17_M |
| 8 | 140711695 | 140713126 | H_c__78c19_M |
| 8 | 140801889 | 140801980 | H_c__127d18 |
| 8 | 141013265 | 141014688 | H_c__8b12 |
| 8 | 141156293 | 141157378 | H_c__62o06 |
| 8 | 141246991 | 141247092 | H_c__247c07 |
| 8 | 141395717 | 141395821 | H_c__78i02 |
| 8 | 141536175 | 141537978 | H_c__128e13_M |
| 8 | 141589949 | 141591692 | H_c__120m20_M |
| 8 | 141676961 | 141678059 | H_c__196i12 |
| 8 | 141713923 | 141715540 | H_c__188d07_M |
| 8 | 141804382 | 141804582 | H_c138f08 |
| 8 | 142027527 | 142027713 | H_c__217g09 |
| 8 | 142079356 | 142081531 | H_c__79p11_M |
| 8 | 142140428 | 142140544 | H_c__70a06_M |
| 8 | 142177693 | 142177783 | H_c__212m08 |
| 8 | 142216940 | 142217512 | H_c__44f18 |
| 8 | 142284429 | 142286148 | H_c__251j16_M |
| 8 | 142462077 | 142462570 | H_c143g10 |
| 8 | 142469924 | 142471977 | H_c__108a15_M |
| 8 | 142496613 | 142497603 | H_c__39g01_M |
| 8 | 142586156 | 142588432 | H_c__199m12 |
| 8 | 143588564 | 143590992 | H_c__91b19 |
| 8 | 143747985 | 143748987 | H_c__100j05_M |
| 8 | 143804787 | 143806539 | H_c__152p04_M |
| 8 | 143817463 | 143818375 | H_c__101c01_M |
| 8 | 143855325 | 143856500 | H_c__205g05 |
| 8 | 144398950 | 144401667 | H_c__68o13_M |
| 8 | 144419807 | 144421649 | H_c__37h03_M |
| 8 | 144441682 | 144445352 | H_c__234m07_M |
| 8 | 144486270 | 144489093 | H_c__41a19_M |
| 8 | 144555231 | 144556573 | H_c__149j16 |
| 8 | 144582239 | 144584724 | H_c__149k11 |
| 8 | 144670463 | 144672776 | H_c__85h20 |
| 8 | 144693893 | 144695181 | H_c__195j22_M |
| 8 | 144724638 | 144726937 | H_c__124j10 |
| 8 | 144762073 | 144763417 | H_c__78g20_M |
| 8 | 144770382 | 144771625 | H_c__21n08_M |
| 8 | 144788975 | 144789963 | H_c__15i23_M |
| 8 | 144837873 | 144839648 | H_c__273n24_M |
| 8 | 144914904 | 144915776 | H_c__212e04 |
| 8 | 144924426 | 144926874 | H_c__269c13_M |
| 8 | 144968855 | 144970146 | H_c__262j05_M |
| 8 | 145097682 | 145101260 | H_c__179e11_M |
| 8 | 145119356 | 145123621 | H_c__181p23_M |
| 8 | 145135985 | 145136928 | H_c__6k20_M |
| 8 | 145186827 | 145188115 | H_c__4d11_M |
| 8 | 145204930 | 145206174 | H_c__153n13_M |
| 8 | 145208762 | 145211130 | H_c__58m04_M |
| 8 | 145235906 | 145237885 | H_c__164f18 |
| 8 | 145485447 | 145486540 | H_c__49m12_M |
| 8 | 145605139 | 145606283 | H_c__119p06 |
| 8 | 145673782 | 145674819 | H_c__262n16_M |
| 8 | 145771661 | 145771873 | H_c__223h07 |
| 8 | 145775455 | 145777180 | H_c__214l23 |
| 8 | 145883064 | 145884251 | H_c__41i11_M |
| 8 | 145908364 | 145910114 | H_c__39g22_M |
| 8 | 145925892 | 145927198 | H_c__208d20_M |
| 8 | 145950878 | 145954598 | H_c__86k19_M |
| 8 | 145988036 | 145990095 | H_c__262j12_M |
| 8 | 145994478 | 145995610 | H_c__163g12_M |
| 8 | 146021953 | 146024452 | H_c__98e11_M |
| 8 | 146048174 | 146049820 | H_c__199c11_M |
| 8 | 146096825 | 146098668 | H_c__226m18_M |
| 8 | 146098671 | 146098973 | H_c__212o22_M |
| 8 | 146198380 | 146199774 | H_c__123a10_M |
| 8 | 146247105 | 146249167 | H_c__258e07_M |
| 8 | 14957975 | 14958185 | H_c__35h14_M |
| 8 | 15138523 | 15139502 | H_c__8k07_M |
| 8 | 15441595 | 15442887 | H_c__13l02 |
| 8 | 15749561 | 15749751 | H_c__129d17 |
| 8 | 15758633 | 15760439 | H_c__78e09_M |
| 8 | 15806697 | 15806854 | H_c__183i16_M |
| 8 | 1635562 | 1637746 | H_c__85i11_M |
| 8 | 16372663 | 16372807 | H_c__244p07 |
| 8 | 16408674 | 16409103 | H_c__102a09 |
| 8 | 16903272 | 16904017 | H_c__81l22 |
| 8 | 1698474 | 1700673 | H_c__155a08 |
| 8 | 17028946 | 17029046 | H_c__13k07 |
| 8 | 17057330 | 17059197 | H_c__241f04_M |
| 8 | 17147538 | 17149617 | H_c__44e24_M |
| 8 | 17314705 | 17315449 | H_c__37l16 |
| 8 | 17380037 | 17380235 | H_c__222i08_M |
| 8 | 17478667 | 17479878 | H_c__145i09_M |
| 8 | 17561178 | 17561456 | H_c__26n24 |
| 8 | 1758693 | 1760503 | H_c__147a18_M |
| 8 | 17696551 | 17696772 | H_c138k16 |
| 8 | 17824198 | 17825565 | H_c__236c16_M |
| 8 | 17985553 | 17986590 | H_c__91c10_M |
| 8 | 18287839 | 18289575 | H_c__225c19_M |
| 8 | 18485012 | 18485257 | H_c__3g12 |
| 8 | 18915140 | 18916204 | H_c__69o11_M |
| 8 | 1908995 | 1910481 | H_c__254c03 |
| 8 | 19185690 | 19185777 | H_c__74a16 |
| 8 | 19215197 | 19216398 | H_c__61c02_M |
| 8 | 19254324 | 19254455 | H_c__18b08_M |
| 8 | 1936502 | 1939090 | H_c__4m17_M |
| 8 | 1958609 | 1959869 | H_c142f09 |
| 8 | 19604325 | 19605491 | H_c__6h10_M |
| 8 | 19650351 | 19650469 | H_c__69c06 |
| 8 | 19658216 | 19659977 | H_c__177m17_M |
| 8 | 19718489 | 19719448 | H_c__7j08 |
| 8 | 19841118 | 19842334 | H_c__148c07_M |
| 8 | 20204147 | 20206121 | H_c__7k08 |
| 8 | 20399326 | 20399483 | H_c__168a24 |
| 8 | 20561963 | 20562092 | H_c__237h14 |
| 8 | 2061322 | 2063199 | H_c__83b19_M |
| 8 | 21443641 | 21443791 | H_c__12j07 |
| 8 | 21700627 | 21703843 | H_c__121a07_M |
| 8 | 21810332 | 21811769 | H_c__181k16 |
| 8 | 21816297 | 21818925 | H_c__265d01 |
| 8 | 21832935 | 21834134 | H_c__65p11_M |
| 8 | 21923559 | 21923863 | H_c__125m21 |
| 8 | 21961759 | 21962987 | H_c__226d08_M |
| 8 | 21979776 | 21980801 | H_c__190e07_M |
| 8 | 2199572 | 2199925 | H_c__15f09_M |
| 8 | 2204222 | 2204313 | H_c__203c12 |
| 8 | 22051829 | 22055398 | H_c__262f18_M |
| 8 | 22158212 | 22159200 | H_c__63h12_M |
| 8 | 22354018 | 22355213 | H_c__173k09 |
| 8 | 22478247 | 22481096 | H_c__16l18 |
| 8 | 22511476 | 22513426 | H_c__5c13 |
| 8 | 22517584 | 22519108 | H_c144m22_M |

TABLE 1-continued

| | | | |
|---|---|---|---|
| 8 | 22777898 | 22779656 | H_c133c11_M |
| 8 | 22912509 | 22913799 | H_c_63h04_M |
| 8 | 23076866 | 23077276 | H_c_12h11_M |
| 8 | 23201235 | 23202391 | H_c_48j20 |
| 8 | 23316053 | 23317604 | H_c_35m18_M |
| 8 | 23370642 | 23371912 | H_c_188c19_M |
| 8 | 23441662 | 23443416 | H_c_30p24_M |
| 8 | 23611473 | 23611632 | H_c_42i05 |
| 8 | 23619161 | 23620837 | H_c_235b14_M |
| 8 | 23627795 | 23628318 | H_c_18a21_M |
| 8 | 23640014 | 23640799 | H_c131j16 |
| 8 | 23957951 | 23958183 | H_c_109n07 |
| 8 | 2467746 | 2468794 | H_c_1k11_M |
| 8 | 24826707 | 24828562 | H_c_120h10_M |
| 8 | 24868675 | 24870760 | H_c_183l12_M |
| 8 | 24913305 | 24914499 | H_c_115a01_M |
| 8 | 25097391 | 25098845 | H_c_22j10_M |
| 8 | 25229249 | 25229348 | H_c_120h07 |
| 8 | 25371109 | 25373189 | H_c_82e02_M |
| 8 | 25397475 | 25397765 | H_c_92e09 |
| 8 | 2571900 | 2573388 | H_c_274g13_M |
| 8 | 25783158 | 25783241 | H_c_100c23 |
| 8 | 25808698 | 25808876 | H_c144d23 |
| 8 | 2589400 | 2589472 | H_c_81j24 |
| 8 | 25953287 | 25954666 | H_c_234l13 |
| 8 | 25956861 | 25961457 | H_c_41o19_M_M |
| 8 | 25963524 | 25964809 | H_c_107j12 |
| 8 | 2606813 | 2606961 | H_c_1e14 |
| 8 | 26296000 | 26297341 | H_c_247e18_M |
| 8 | 26361671 | 26362044 | H_c_189d11 |
| 8 | 26427818 | 26428936 | H_c_70b03_M |
| 8 | 26490135 | 26491638 | H_c_192l20_M |
| 8 | 26777273 | 26779884 | H_c_35l12_M |
| 8 | 26974932 | 26975061 | H_c_74o06 |
| 8 | 27196298 | 27196442 | H_c_121e19 |
| 8 | 27238947 | 27239689 | H_c_9d16_M |
| 8 | 27404506 | 27404935 | H_c_19k08_M |
| 8 | 27504835 | 27504979 | H_c_235n13 |
| 8 | 27527340 | 27528493 | H_c_205g19_M |
| 8 | 27546074 | 27547911 | H_c_229i07_M |
| 8 | 27685522 | 27686131 | H_c_16f02_M |
| 8 | 27925527 | 27925717 | H_c_176h04 |
| 8 | 28217852 | 28218075 | H_c_18e16 |
| 8 | 28264432 | 28266423 | H_c139b13 |
| 8 | 28298415 | 28300264 | H_c_247d03 |
| 8 | 28314373 | 28316108 | H_c_189d05_M |
| 8 | 28430179 | 28430408 | H_c_208e02 |
| 8 | 28535647 | 28536822 | H_c_5e09_M |
| 8 | 28557417 | 28557510 | H_c_259m16 |
| 8 | 28614405 | 28615928 | H_c_244j08_M |
| 8 | 28725718 | 28725990 | H_c_114b16 |
| 8 | 29261383 | 29265864 | H_c_174c21_M_M |
| 8 | 29322281 | 29322501 | H_c_97e06 |
| 8 | 2976887 | 2977143 | H_c_209n15 |
| 8 | 30059671 | 30060502 | H_c_15g06 |
| 8 | 30072161 | 30073269 | H_c_27b07_M |
| 8 | 30094263 | 30094390 | H_c_35f16 |
| 8 | 30132720 | 30134231 | H_c_120c08 |
| 8 | 30297863 | 30298085 | H_c_39k09 |
| 8 | 30360844 | 30362601 | H_c_153o03_M |
| 8 | 30455019 | 30455125 | H_c_233o20 |
| 8 | 30634684 | 30635507 | H_c_68l21_M |
| 8 | 30704323 | 30705490 | H_c_88l07 |
| 8 | 30788948 | 30790078 | H_c_124p06_M |
| 8 | 30820824 | 30821029 | H_c_100f23 |
| 8 | 30888712 | 30889762 | H_c132o10 |
| 8 | 31008766 | 31011437 | H_c_199d07_M |
| 8 | 31392087 | 31392267 | H_c_267b11 |
| 8 | 31616147 | 31618008 | H_c_123i05 |
| 8 | 32524845 | 32526580 | H_c_35n21_M |
| 8 | 32554758 | 32554825 | H_c_32e15 |
| 8 | 32871302 | 32871456 | H_c_237d11 |
| 8 | 33449590 | 33450411 | H_c_241e15_M |
| 8 | 33460645 | 33462638 | H_c_23n20_M |
| 8 | 33491347 | 33492270 | H_c_100l16 |
| 8 | 33543409 | 33544685 | H_c_71p02_M |
| 8 | 33575179 | 33576860 | H_c_145g21 |
| 8 | 33985674 | 33985810 | H_c_191g19_M |
| 8 | 34385121 | 34385343 | H_c_176j16 |
| 8 | 34815687 | 34815898 | H_c_224e17 |
| 8 | 35212053 | 35213504 | H_c_240f04_M |
| 8 | 3546150 | 3546434 | H_c_265f17_M |
| 8 | 3561606 | 3561806 | H_c_108h22 |
| 8 | 3632019 | 3632230 | H_c_240h04 |
| 8 | 36467297 | 36467392 | H_c134j16 |
| 8 | 37017955 | 37018179 | H_c_81e23 |
| 8 | 37039325 | 37039411 | H_c_100l15 |
| 8 | 37244047 | 37244183 | H_c_24c18_M |
| 8 | 37346340 | 37346573 | H_c_153g15_M |
| 8 | 37544871 | 37544968 | H_c_215o11 |
| 8 | 37670861 | 37672303 | H_c_8m22_M |
| 8 | 37676899 | 37678308 | H_c_151h16 |
| 8 | 37712843 | 37714396 | H_c_114l01_M |
| 8 | 37738703 | 37739974 | H_c_72l16_M |
| 8 | 37860685 | 37861571 | H_c_238b06 |
| 8 | 37874111 | 37876196 | H_c141d22_M |
| 8 | 37876201 | 37876798 | H_c_123p14_M |
| 8 | 37941852 | 37943349 | H_c_76d24_M |
| 8 | 38006909 | 38009667 | H_c_59k17 |
| 8 | 38115872 | 38116095 | H_c_108d10 |
| 8 | 38154037 | 38154309 | H_c_171f01 |
| 8 | 38207601 | 38209139 | H_c_231l13_M |
| 8 | 38245172 | 38246375 | H_c_254f14_M |
| 8 | 38304726 | 38304860 | H_c_244e21 |
| 8 | 38357864 | 38359290 | H_c_206l13_M |
| 8 | 38359355 | 38359947 | H_c_65e16_M |
| 8 | 38362988 | 38363803 | H_c_27f06_M |
| 8 | 38442862 | 38443214 | H_c136i08 |
| 8 | 38627554 | 38628563 | H_c_199g23_M |
| 8 | 38660219 | 38660809 | H_c_63e08 |
| 8 | 38733310 | 38734782 | H_c_40e09 |
| 8 | 38763601 | 38764126 | H_c132h02_M |
| 8 | 38877463 | 38877906 | H_c_79g18 |
| 8 | 38950820 | 38951561 | H_c_19p11_M |
| 8 | 38972829 | 38974258 | H_c_234i03_M |
| 8 | 38988405 | 38988495 | H_c_252o15 |
| 8 | 39084130 | 39084805 | H_c_179f20_M |
| 8 | 39093878 | 39093962 | H_c_121n18 |
| 8 | 39432088 | 39432203 | H_c_54k18 |
| 8 | 4007024 | 4007141 | H_c_57m24 |
| 8 | 40134192 | 40134456 | H_c_204l15 |
| 8 | 4122430 | 4122600 | H_c_201g10 |
| 8 | 41280456 | 41281591 | H_c_214g17 |
| 8 | 41398821 | 41398916 | H_c_56k05 |
| 8 | 41466425 | 41468155 | H_c134o11 |
| 8 | 41554126 | 41555436 | H_c_60g22_M |
| 8 | 41621532 | 41623462 | H_c_145c19_M |
| 8 | 41630047 | 41630727 | H_c134c15_M |
| 8 | 41630730 | 41630917 | H_c_209h17 |
| 8 | 41701707 | 41702852 | H_c_125m16 |
| 8 | 41743216 | 41744278 | H_c_42m20 |
| 8 | 41773673 | 41775010 | H_c_207j02_M |
| 8 | 42021262 | 42021483 | H_c_19b15 |
| 8 | 42116558 | 42117734 | H_c_149m08_M |
| 8 | 42128407 | 42130469 | H_c_189l07_M |
| 8 | 42257571 | 42257717 | H_c_230h23 |
| 8 | 42368258 | 42369066 | H_c_50k05_M |
| 8 | 42515332 | 42516930 | H_c_248o19_M |
| 8 | 42872086 | 42872310 | H_c_33b12_M |
| 8 | 43213834 | 43214139 | H_c_225d12 |
| 8 | 43220577 | 43221965 | H_c_41i03_M |
| 8 | 4333309 | 4333448 | H_c133a15 |
| 8 | 43575393 | 43575559 | H_c_206i14 |
| 8 | 43772750 | 43772901 | H_c_229h10 |
| 8 | 43845263 | 43845431 | H_c_224i24 |
| 8 | 43915926 | 43916018 | H_c_115o03 |
| 8 | 47404774 | 47407441 | H_c_246o20 |
| 8 | 47647598 | 47647842 | H_c_265a23_M |
| 8 | 48219206 | 48220359 | H_c139i13 |
| 8 | 48223037 | 48223280 | H_c_212b21 |
| 8 | 48315732 | 48315854 | H_c133h02 |
| 8 | 48335753 | 48336679 | H_c_11k22_M |
| 8 | 4836247 | 4836776 | H_c_229b20 |
| 8 | 4837248 | 4840390 | H_c_68c21_M |
| 8 | 484145 | 485988 | H_c_211f16_M |
| 8 | 48504630 | 48504711 | H_c_208d03 |
| 8 | 48643074 | 48643234 | H_c_211d12 |
| 8 | 48731474 | 48731733 | H_c_54n12 |
| 8 | 48811841 | 48814238 | H_c_247o06_M |
| 8 | 48933937 | 48934138 | H_c_173i21 |

TABLE 1-continued

| | | | |
|---|---|---|---|
| 8 | 49034885 | 49036480 | H_c_10j12_M |
| 8 | 49082501 | 49084021 | H_c_244i24_M |
| 8 | 49108781 | 49109023 | H_c_167n02 |
| 8 | 49407411 | 49407811 | H_c_230k10 |
| 8 | 49471019 | 49472220 | H_c_186c05 |
| 8 | 49810227 | 49810597 | H_c_262k19 |
| 8 | 49945043 | 49945845 | H_c_82d13_M |
| 8 | 50045340 | 50045430 | H_c_271m16 |
| 8 | 50177204 | 50178775 | H_c_259f17 |
| 8 | 50657097 | 50659467 | H_c_190c17_M |
| 8 | 50984788 | 50986151 | H_c_151m23 |
| 8 | 50986640 | 50986989 | H_c_128d08 |
| 8 | 51312220 | 51312355 | H_c_173a20 |
| 8 | 52694861 | 52695097 | H_c_49i20 |
| 8 | 52818510 | 52820105 | H_c136e15 |
| 8 | 52843347 | 52843466 | H_c_102p21 |
| 8 | 52973905 | 52974843 | H_c_182g14_M |
| 8 | 52976804 | 52976946 | H_c_225p06 |
| 8 | 53547721 | 53547903 | H_c_164h05 |
| 8 | 53639993 | 53641324 | H_c_9j18_M |
| 8 | 53772266 | 53772351 | H_c_16k22 |
| 8 | 53788751 | 53790065 | H_c_2d22 |
| 8 | 54325479 | 54327205 | H_c_199b19_M |
| 8 | 54787552 | 54788008 | H_c_32d11 |
| 8 | 54956884 | 54958185 | H_c_85j15 |
| 8 | 54986292 | 54986368 | H_c_11h02 |
| 8 | 5502990 | 5503095 | H_c_43h13 |
| 8 | 55096892 | 55097734 | H_c_92l07_M |
| 8 | 55176208 | 55177513 | H_c_128a16_M |
| 8 | 55249762 | 55250002 | H_c_241l22_M |
| 8 | 55473708 | 55473902 | H_c_79c13 |
| 8 | 55534041 | 55535220 | H_c_15b09_M |
| 8 | 55541413 | 55542810 | H_c_203h21_M |
| 8 | 55792222 | 55792337 | H_c_83n19 |
| 8 | 55862202 | 55862326 | H_c_180i09 |
| 8 | 5591655 | 5591804 | H_c_175d06 |
| 8 | 55986982 | 55987127 | H_c_198i21 |
| 8 | 56176165 | 56178764 | H_c_11g04_M |
| 8 | 56847796 | 56848652 | H_c_109j12_M |
| 8 | 56915368 | 56915601 | H_c_235j10 |
| 8 | 56954512 | 56955848 | H_c_116a13_M |
| 8 | 57149112 | 57150330 | H_c_111p04_M |
| 8 | 57151604 | 57151716 | H_c_71d18 |
| 8 | 57188007 | 57188578 | H_c_82e01_M |
| 8 | 57231998 | 57232731 | H_c_86p20_M |
| 8 | 57286637 | 57287453 | H_c_85i24_M |
| 8 | 57394611 | 57395369 | H_c_265b12_M |
| 8 | 57520663 | 57521700 | H_c_207c09_M |
| 8 | 57702842 | 57703043 | H_c_107m24 |
| 8 | 57770540 | 57770603 | H_c_234b13 |
| 8 | 58068421 | 58069161 | H_c_124c11 |
| 8 | 58217216 | 58218329 | H_c_61h10 |
| 8 | 58795930 | 58796030 | H_c_254l12 |
| 8 | 589402 | 590435 | H_c_152k13 |
| 8 | 59069158 | 59070404 | H_c_244j21_M |
| 8 | 59202173 | 59202321 | H_c_50f22 |
| 8 | 59220500 | 59221099 | H_c_95g08_M |
| 8 | 59486324 | 59487010 | H_c_119k15_M |
| 8 | 59627678 | 59628869 | H_c_169d08_M |
| 8 | 59733418 | 59735234 | H_c_46j18_M |
| 8 | 59813878 | 59814071 | H_c_225o19 |
| 8 | 60193713 | 60195930 | H_c_133c10_M |
| 8 | 60335104 | 60335192 | H_c_72f24 |
| 8 | 60852378 | 60852518 | H_c_173i01 |
| 8 | 61355515 | 61356989 | H_c_101a01_M |
| 8 | 61591222 | 61592894 | H_c_170b11_M |
| 8 | 61661888 | 61662141 | H_c_201a20 |
| 8 | 61727093 | 61727939 | H_c_72p20_M |
| 8 | 61728432 | 61728751 | H_c_172j22 |
| 8 | 61753982 | 61755799 | H_c_208a09_M |
| 8 | 61984836 | 61985716 | H_c_28m22_M |
| 8 | 62362959 | 62363794 | H_c_70c11 |
| 8 | 62418270 | 62418526 | H_c_225p05 |
| 8 | 6250493 | 6252256 | H_c_63d23 |
| 8 | 62788866 | 62790171 | H_c_209g14_M |
| 8 | 63033120 | 63033413 | H_c_84h08 |
| 8 | 63938202 | 63939997 | H_c134a07 |
| 8 | 64077549 | 64077781 | H_c_162o16 |
| 8 | 64113552 | 64114713 | H_c_206m01_M |
| 8 | 64160520 | 64161304 | H_c_182e10 |
| 8 | 64243158 | 64244269 | H_c_28f15_M |
| 8 | 64442174 | 64442409 | H_c_274h15 |
| 8 | 64457524 | 64457681 | H_c_19m15 |
| 8 | 64735009 | 64735215 | H_c_10i19 |
| 8 | 64790851 | 64791037 | H_c_116n04 |
| 8 | 65265141 | 65265268 | H_c_200p09_M |
| 8 | 65444229 | 65446637 | H_c_59l10_M |
| 8 | 6552993 | 6554111 | H_c_252g17_M |
| 8 | 65530909 | 65531111 | H_c_49k24 |
| 8 | 65655405 | 65656635 | H_c_17f02_M |
| 8 | 65683116 | 65683220 | H_c_219j20_M |
| 8 | 65979614 | 65979689 | H_c_3b07 |
| 8 | 66381100 | 66381244 | H_c_216b17_M |
| 8 | 66488249 | 66488341 | H_c_231h18 |
| 8 | 66719174 | 66719988 | H_c_195p12 |
| 8 | 66719989 | 66720072 | H_c_178i21 |
| 8 | 6678398 | 6680804 | H_c_93i14_M |
| 8 | 66799090 | 66799157 | H_c_52c06 |
| 8 | 66915892 | 66918099 | H_c_271m07 |
| 8 | 67057402 | 67057551 | H_c132f05 |
| 8 | 67187351 | 67187668 | H_c_219m23 |
| 8 | 67251626 | 67252623 | H_c_171m12_M |
| 8 | 67299644 | 67300104 | H_c_50k19 |
| 8 | 67503008 | 67505073 | H_c_188b22_M |
| 8 | 67507040 | 67507597 | H_c_237k19_M |
| 8 | 676802 | 679081 | H_c_272a08_M |
| 8 | 67687030 | 67688621 | H_c_60a17_M |
| 8 | 67787055 | 67787864 | H_c_108f18_M |
| 8 | 67922428 | 67922600 | H_c_91j22 |
| 8 | 67999939 | 68000605 | H_c_254k03_M |
| 8 | 68035950 | 68038383 | H_c_36g22_M |
| 8 | 68103188 | 68103839 | H_c_159i02 |
| 8 | 68136595 | 68137030 | H_c_245f01_M |
| 8 | 68277222 | 68277355 | H_c_62m17 |
| 8 | 68417525 | 68419200 | H_c_101n23_M |
| 8 | 68501489 | 68501614 | H_c_106g23 |
| 8 | 68896722 | 68896873 | H_c_223n24 |
| 8 | 69026846 | 69027705 | H_c_88b16_M |
| 8 | 69115972 | 69116077 | H_c_166h12 |
| 8 | 69405473 | 69406547 | H_c134l22_M |
| 8 | 69824518 | 69824672 | H_c140n04_M |
| 8 | 70003327 | 70003540 | H_c_160h12 |
| 8 | 70078092 | 70078439 | H_c_188d20 |
| 8 | 705368 | 705484 | H_c_180l01 |
| 8 | 70907036 | 70910193 | H_c_189g23_M |
| 8 | 71145693 | 71147853 | H_c_123n11_M |
| 8 | 71403505 | 71403568 | H_c_257g02 |
| 8 | 71682210 | 71683574 | H_c_4i19_M |
| 8 | 71743479 | 71744292 | H_c_250e21_M |
| 8 | 72165075 | 72165478 | H_c_210k11 |
| 8 | 72313415 | 72313564 | H_c_84o10 |
| 8 | 72431836 | 72431942 | H_c_37o24 |
| 8 | 72621924 | 72623245 | H_c_92h20_M |
| 8 | 72631481 | 72632954 | H_c_147f03_M |
| 8 | 72916996 | 72919599 | H_c_30a11_M |
| 8 | 73079673 | 73080547 | H_c_207d18_M |
| 8 | 73143915 | 73144015 | H_c_72k11 |
| 8 | 73150213 | 73150863 | H_c_128n14 |
| 8 | 73611238 | 73612393 | H_c_42l11_M |
| 8 | 73871325 | 73871413 | H_c_232i04 |
| 8 | 74167146 | 74168308 | H_c_73d09 |
| 8 | 74368624 | 74371010 | H_c_181m05_M |
| 8 | 74548563 | 74548885 | H_c_214a02 |
| 8 | 74820528 | 74822519 | H_c_196k24_M |
| 8 | 74953031 | 74954133 | H_c_84f23_M |
| 8 | 75046737 | 75047350 | H_c_15f08 |
| 8 | 75050686 | 75051583 | H_c_265i15_M |
| 8 | 75260006 | 75260182 | H_c_215d01 |
| 8 | 75395031 | 75396685 | H_c_226k19 |
| 8 | 7581325 | 7583947 | H_c_77l07_M |
| 8 | 76003704 | 76003846 | H_c134l07 |
| 8 | 76058956 | 76059779 | H_c_80c16_M |
| 8 | 76241902 | 76242006 | H_c139i02 |
| 8 | 76481885 | 76483341 | H_c_88a08_M |
| 8 | 76781354 | 76781658 | H_c_34h18 |
| 8 | 77366066 | 77366170 | H_c_80e03 |
| 8 | 775803 | 776038 | H_c_181l22 |
| 8 | 77702737 | 77702864 | H_c_66h07 |
| 8 | 77752571 | 77753138 | H_c_87b12 |
| 8 | 78402819 | 78402904 | H_c_17b03 |

TABLE 1-continued

| | | | |
|---|---|---|---|
| 8 | 78599661 | 78599825 | H_c_204h09 |
| 8 | 78757139 | 78757309 | H_c_160k15 |
| 8 | 79236419 | 79236575 | H_c_160d24 |
| 8 | 79533412 | 79533654 | H_c143g04 |
| 8 | 79590967 | 79591317 | H_c_168d08_M |
| 8 | 79740524 | 79741335 | H_c_226m16_M |
| 8 | 79879232 | 79880225 | H_c_93e20 |
| 8 | 79976160 | 79976313 | H_c_231n16 |
| 8 | 79980281 | 79980516 | H_c_7c17 |
| 8 | 80687353 | 80688416 | H_c_195g01 |
| 8 | 80709105 | 80709227 | H_c_15b05 |
| 8 | 80842126 | 80843907 | H_c_65k07_M |
| 8 | 80858311 | 80859337 | H_c_53d19_M |
| 8 | 80966178 | 80967023 | H_c_7f17_M |
| 8 | 81002808 | 81002967 | H_c_145j15 |
| 8 | 81104392 | 81105190 | H_c_40o06 |
| 8 | 81245835 | 81246966 | H_c_11lg11 |
| 8 | 81560356 | 81564205 | H_c_28e21_M_M |
| 8 | 81652656 | 81653736 | H_c_272g22_M |
| 8 | 81761936 | 81762444 | H_c_63c05 |
| 8 | 81904349 | 81904423 | H_c_1j16 |
| 8 | 81947607 | 81949413 | H_c_91d03 |
| 8 | 82000164 | 82000385 | H_c_64g01_M |
| 8 | 82186284 | 82187067 | H_c_248n05_M |
| 8 | 82760814 | 82761141 | H_c_93m14_M |
| 8 | 82795250 | 82796294 | H_c_89k04 |
| 8 | 82806531 | 82807439 | H_c_214d10 |
| 8 | 8280993 | 8282026 | H_c_42n13 |
| 8 | 82916975 | 82917714 | H_c_127m20_M |
| 8 | 82931133 | 82931233 | H_c_46n14 |
| 8 | 82992569 | 82992699 | H_c_95k10 |
| 8 | 8335474 | 8335761 | H_c_85c21_M |
| 8 | 83507437 | 83507615 | H_c_150k05 |
| 8 | 83912099 | 83912168 | H_c_38e03 |
| 8 | 84206578 | 84206845 | H_c_39b13_M |
| 8 | 84794385 | 84794542 | H_c_155i22 |
| 8 | 84874723 | 84874882 | H_c_275e07 |
| 8 | 85188295 | 85188415 | H_c_165f18 |
| 8 | 85219872 | 85219960 | H_c_7g15 |
| 8 | 85256817 | 85259902 | H_c_82b07_M |
| 8 | 85829812 | 85830100 | H_c_52j10 |
| 8 | 8596471 | 8598376 | H_c_11j13_M |
| 8 | 86206757 | 86207229 | H_c_13c14_M |
| 8 | 86276614 | 86277549 | H_c_242f08_M |
| 8 | 86296152 | 86296238 | H_c144a10 |
| 8 | 86319818 | 86320522 | H_c_146g19_M |
| 8 | 86562673 | 86563928 | H_c_180p13_M |
| 8 | 87099839 | 87099989 | H_c_192j19 |
| 8 | 87318839 | 87318937 | H_c_204e24 |
| 8 | 87364400 | 87364516 | H_c_183k07 |
| 8 | 87423646 | 87424901 | H_c_240b06_M |
| 8 | 87523673 | 87523792 | H_c_217c14_M |
| 8 | 87595591 | 87596593 | H_c_203i09_M |
| 8 | 8787479 | 8788953 | H_c_22i07_M |
| 8 | 88192450 | 88192578 | H_c_35d12 |
| 8 | 88251261 | 88251361 | H_c_168h14 |
| 8 | 88839279 | 88839466 | H_c_161h19 |
| 8 | 89101907 | 89101999 | H_c_180k19_M |
| 8 | 89408274 | 89409208 | H_c_43k20 |
| 8 | 89421735 | 89421877 | H_c_226e20 |
| 8 | 89489563 | 89489706 | H_c_163d20 |
| 8 | 90330912 | 90331067 | H_c_155b14 |
| 8 | 9045863 | 9046974 | H_c_259h06_M |
| 8 | 90838623 | 90840135 | H_c_4p10_M |
| 8 | 90951725 | 90951938 | H_c_226l15 |
| 8 | 90983281 | 90984547 | H_c_112p01_M |
| 8 | 91065378 | 91066186 | H_c_173g22 |
| 8 | 91082511 | 91083595 | H_c_125o01_M |
| 8 | 91093418 | 91093557 | H_c_30e14 |
| 8 | 91200474 | 91200642 | H_c_230i21 |
| 8 | 91746575 | 91748171 | H_c_226b06 |
| 8 | 92066026 | 92066794 | H_c_66b15 |
| 8 | 92151379 | 92151619 | H_c_36m21_M |
| 8 | 92382654 | 92382733 | H_c_78e02 |
| 8 | 92849232 | 92849465 | H_c_59f16 |
| 8 | 92938674 | 92938843 | H_c_70g20 |
| 8 | 93058138 | 93058286 | H_c_195g20 |
| 8 | 93182878 | 93183745 | H_c_40j13 |
| 8 | 93874830 | 93875290 | H_c_193d09 |
| 8 | 94046873 | 94047722 | H_c_61b01 |
| 8 | 94248563 | 94248706 | H_c_69f04 |
| 8 | 94715677 | 94715862 | H_c_65l22 |
| 8 | 94781469 | 94782402 | H_c_99b14_M |
| 8 | 94821839 | 94822683 | H_c_186b18_M |
| 8 | 9499992 | 9500152 | H_c_268p19_M |
| 8 | 95122877 | 95124110 | H_c_106p01_M |
| 8 | 95343375 | 95343889 | H_c_265a11_M |
| 8 | 95408718 | 95408904 | H_c_99j01 |
| 8 | 95555944 | 95556627 | H_c_35i10_M |
| 8 | 95581022 | 95581095 | H_c_114k19 |
| 8 | 95634808 | 95635325 | H_c_91f06_M |
| 8 | 95721429 | 95724291 | H_c_223p23 |
| 8 | 95800732 | 95801801 | H_c_212f01_M |
| 8 | 95904185 | 95905114 | H_c_88p16_M |
| 8 | 95971306 | 95971435 | H_c_88j10 |
| 8 | 95975563 | 95978453 | H_c_99g14_M |
| 8 | 96005623 | 96005698 | H_c_36o20 |
| 8 | 96105435 | 96106578 | H_c_252j22_M |
| 8 | 96153494 | 96154971 | H_c_11h03 |
| 8 | 96214614 | 96216050 | H_c_8c13_M |
| 8 | 96350051 | 96351029 | H_c_74a23_M |
| 8 | 96577273 | 96577333 | H_c_57o05 |
| 8 | 96693975 | 96694118 | H_c_229d18 |
| 8 | 97232472 | 97232647 | H_c_150o06 |
| 8 | 97239076 | 97240089 | H_c_241p17 |
| 8 | 97342470 | 97344446 | H_c_211o20_M |
| 8 | 97574642 | 97576976 | H_c_146h15_M |
| 8 | 9797894 | 9798250 | H_c_77g13_M |
| 8 | 9800534 | 9802205 | H_c_8j13_M |
| 8 | 98129553 | 98129945 | H_c_95h17_M |
| 8 | 98358421 | 98359735 | H_c_219m13 |
| 8 | 98725440 | 98726655 | H_c_259l09_M |
| 8 | 98856106 | 98858110 | H_c_59a05_M |
| 8 | 98949984 | 98951430 | H_c_102f11_M |
| 8 | 99127458 | 99127868 | H_c_14b09_M |
| 8 | 99145619 | 99146464 | H_c_29b13 |
| 8 | 99190031 | 99190318 | H_c_243k20 |
| 8 | 99198079 | 99199326 | H_c_125b19_M |
| 8 | 99375032 | 99376053 | H_c_39n20 |
| 8 | 9949070 | 9949985 | H_c_210b23_M |
| 8 | 99507819 | 99510301 | H_c_262o18 |
| 8 | 99647446 | 99647607 | H_c_56e22 |
| 9 | 100153986 | 100154253 | H_c_168a18 |
| 9 | 100194159 | 100195148 | H_c_89e10 |
| 9 | 100219005 | 100219246 | H_c_169e17 |
| 9 | 100268594 | 100269630 | H_c_2m10 |
| 9 | 100314133 | 100316071 | H_c_48j15_M |
| 9 | 100440487 | 100440890 | H_c142f20_M |
| 9 | 100870593 | 100872145 | H_c_201d23 |
| 9 | 101185714 | 101185849 | H_c_9m12 |
| 9 | 101375134 | 101376167 | H_c_230c07 |
| 9 | 101578991 | 101580777 | H_c_268n08 |
| 9 | 10180924 | 10181104 | H_c_275p20 |
| 9 | 101998785 | 101998959 | H_c_73h16 |
| 9 | 1032590 | 1032965 | H_c_222g11_M |
| 9 | 1035134 | 1036115 | H_c_28e03_M |
| 9 | 103935406 | 103936034 | H_c_110n03 |
| 9 | 1041366 | 1042356 | H_c_262i04 |
| 9 | 104769624 | 104770158 | H_c_151e07 |
| 9 | 104810321 | 104810521 | H_c_212g04_M |
| 9 | 105085722 | 105087649 | H_c132b11_M |
| 9 | 105103021 | 105103276 | H_c_36h13_M |
| 9 | 105171713 | 105171803 | H_c_215i19 |
| 9 | 105241021 | 105241098 | H_c_10k23 |
| 9 | 105426769 | 105426846 | H_c_252m22 |
| 9 | 105456442 | 105456590 | H_c144e24 |
| 9 | 105497787 | 105498531 | H_c_229f18 |
| 9 | 105535874 | 105537599 | H_c_71p04_M |
| 9 | 10602144 | 10603065 | H_c_99l07 |
| 9 | 10615260 | 10615345 | H_c144b14 |
| 9 | 106704053 | 106704516 | H_c_1o21_M |
| 9 | 106718102 | 106718254 | H_c_104j01 |
| 9 | 106764147 | 106764426 | H_c_31g16 |
| 9 | 106883409 | 106883575 | H_c_44i13 |
| 9 | 107041360 | 107041508 | H_c_16l24 |
| 9 | 107096240 | 107096650 | H_c_64c02 |
| 9 | 107124727 | 107125981 | H_c_259e19_M |
| 9 | 107328585 | 107332374 | H_c_76g19_M |
| 9 | 107480020 | 107480366 | H_c_110e15 |
| 9 | 107499059 | 107499364 | H_c_169j07 |

TABLE 1-continued

| | | | |
|---|---|---|---|
| 9 | 107610403 | 107610640 | H_c__77d07_M |
| 9 | 10766053 | 10766186 | H_c__76e01 |
| 9 | 107866815 | 107867087 | H_c__157p14_M |
| 9 | 108635905 | 108636032 | H_c141k16 |
| 9 | 108775557 | 108776708 | H_c__247n15_M |
| 9 | 108854481 | 108855908 | H_c__15d14_M |
| 9 | 108961660 | 108961918 | H_c__239c06 |
| 9 | 109160276 | 109160564 | H_c__6g06 |
| 9 | 109341320 | 109341996 | H_c139a07 |
| 9 | 109482065 | 109482810 | H_c__194f08_M |
| 9 | 109587765 | 109587925 | H_c__115n15 |
| 9 | 109621568 | 109622586 | H_c__61o10_M |
| 9 | 109720921 | 109721145 | H_c137e19 |
| 9 | 109890970 | 109891928 | H_c__157o20 |
| 9 | 110097287 | 110099138 | H_c__69d03 |
| 9 | 110180057 | 110180266 | H_c__83b20 |
| 9 | 11036169 | 11036323 | H_c__68a19 |
| 9 | 110420653 | 110422158 | H_c144j16_M |
| 9 | 110550806 | 110550943 | H_c__5c05_M |
| 9 | 110698409 | 110698760 | H_c__72k02 |
| 9 | 110879456 | 110881125 | H_c__176p02_M |
| 9 | 111324420 | 111326546 | H_c__5f02_M |
| 9 | 111366700 | 111367383 | H_c__22a05 |
| 9 | 111372846 | 111373174 | H_c__161g24 |
| 9 | 111440336 | 111442398 | H_c__29f24_M |
| 9 | 111472813 | 111473623 | H_c__181a17 |
| 9 | 111502883 | 111504547 | H_c__274p10 |
| 9 | 111691820 | 111691940 | H_c__252g11 |
| 9 | 111738769 | 111739809 | H_c__86k09_M |
| 9 | 112016526 | 112018686 | H_c140p03_M |
| 9 | 112221358 | 112222385 | H_c__182e15_M |
| 9 | 112328172 | 112329704 | H_c__88c16 |
| 9 | 112377644 | 112377890 | H_c137b05 |
| 9 | 112559872 | 112560327 | H_c__176o07 |
| 9 | 112591726 | 112593939 | H_c__184p14_M |
| 9 | 112731213 | 112733154 | H_c143e13 |
| 9 | 112898234 | 112898990 | H_c136d03_M |
| 9 | 112953181 | 112953569 | H_c__150p06_M |
| 9 | 112954491 | 112955058 | H_c__229j04_M |
| 9 | 112992460 | 112993583 | H_c138k19 |
| 9 | 113062347 | 113063465 | H_c__217e06_M |
| 9 | 113066650 | 113066790 | H_c__171i07 |
| 9 | 113191254 | 113191772 | H_c__71o04_M |
| 9 | 113242257 | 113243426 | H_c__24b18 |
| 9 | 113252146 | 113252616 | H_c__45i22_M |
| 9 | 113529329 | 113530373 | H_c__74d03 |
| 9 | 113717633 | 113718735 | H_c__89f11 |
| 9 | 113995859 | 113998003 | H_c__47k16_M |
| 9 | 114946119 | 114946284 | H_c__18g17 |
| 9 | 115060850 | 115061072 | H_c__89p10 |
| 9 | 115454755 | 115454864 | H_c__153h22_M |
| 9 | 115845369 | 115845577 | H_c__60i17 |
| 9 | 116431797 | 116433354 | H_c131i11 |
| 9 | 116451345 | 116451552 | H_c__51k04 |
| 9 | 116708397 | 116709552 | H_c__212f14 |
| 9 | 117228326 | 117228900 | H_c__1k17 |
| 9 | 117254347 | 117257326 | H_c__27h14_M |
| 9 | 117586702 | 117587411 | H_c__36k02_M |
| 9 | 118117150 | 118117320 | H_c__155e24 |
| 9 | 118144581 | 118144982 | H_c__208p16 |
| 9 | 118392336 | 118392445 | H_c__19d21 |
| 9 | 118650458 | 118651630 | H_c__48j18 |
| 9 | 118808123 | 118808225 | H_c__248j10 |
| 9 | 119211633 | 119212111 | H_c136d07 |
| 9 | 119667664 | 119667771 | H_c__62o19 |
| 9 | 119700633 | 119700773 | H_c__229c18 |
| 9 | 120415840 | 120416673 | H_c__178a13 |
| 9 | 120554991 | 120557228 | H_c__222f07 |
| 9 | 120634834 | 120635577 | H_c__48h09_M |
| 9 | 120684584 | 120685047 | H_c__214c09_M |
| 9 | 120717381 | 120719911 | H_c__124h16_M |
| 9 | 121042729 | 121044053 | H_c__210c24_M |
| 9 | 121120604 | 121121115 | H_c__21a24 |
| 9 | 121141014 | 121142524 | H_c__24m12_M |
| 9 | 121210380 | 121212661 | H_c__266c22_M |
| 9 | 121389181 | 121392995 | H_c__4b08_M |
| 9 | 121440109 | 121440723 | H_c__74k12 |
| 9 | 121440943 | 121441804 | H_c__32a06_M |
| 9 | 121492999 | 121493934 | H_c__270m23_M |
| 9 | 121540358 | 121542503 | H_c__190h04 |
| 9 | 121578007 | 121579208 | H_c__187f19 |
| 9 | 121759697 | 121759830 | H_c__94b12 |
| 9 | 121875879 | 121875988 | H_c__202k22 |
| 9 | 121933599 | 121935737 | H_c__70a11 |
| 9 | 121950225 | 121950389 | H_c__151d13_M |
| 9 | 121967540 | 121969213 | H_c__214n20 |
| 9 | 122060090 | 122063420 | H_c__101g13_M |
| 9 | 122069762 | 122071483 | H_c__186l20_M |
| 9 | 122106085 | 122106854 | H_c__107p16_M |
| 9 | 122188265 | 122189421 | H_c__13g19_M |
| 9 | 122247281 | 122248601 | H_c__10k12 |
| 9 | 122365633 | 122365804 | H_c__31n05 |
| 9 | 122670376 | 122670571 | H_c__253c11 |
| 9 | 122747230 | 122747480 | H_c__162a10 |
| 9 | 122772771 | 122773701 | H_c__33n18 |
| 9 | 122782205 | 122783254 | H_c__275i19 |
| 9 | 122931566 | 122931771 | H_c__24o18 |
| 9 | 123109158 | 123111316 | H_c__251e08_M |
| 9 | 123770923 | 123772355 | H_c__59c01_M |
| 9 | 123853196 | 123857465 | H_c__230j22_M |
| 9 | 123858973 | 123860002 | H_c__19n13 |
| 9 | 123887331 | 123888273 | H_c__51l04 |
| 9 | 124098211 | 124101039 | H_c__148b17 |
| 9 | 124324333 | 124329038 | H_c__185n11_M |
| 9 | 124611394 | 124614287 | H_c__45c21_M |
| 9 | 124618468 | 124620452 | H_c__48k20 |
| 9 | 124679797 | 124682583 | H_c__153f09_M |
| 9 | 124694788 | 124696343 | H_c141e09_M |
| 9 | 124703168 | 124704207 | H_c__87i23_M |
| 9 | 124710480 | 124711878 | H_c__9m03_M |
| 9 | 124782286 | 124783161 | H_c__129d11_M |
| 9 | 124981446 | 124981671 | H_c144b17 |
| 9 | 124984349 | 124985789 | H_c__158o04 |
| 9 | 125031554 | 125032934 | H_c__167h18_M |
| 9 | 125041611 | 125042886 | H_c__46b03 |
| 9 | 125082381 | 125084257 | H_c__171p06 |
| 9 | 125102942 | 125104334 | H_c136a03_M |
| 9 | 125347770 | 125347906 | H_c__5b23 |
| 9 | 125548419 | 125549886 | H_c__6e16_M |
| 9 | 125587842 | 125590297 | H_c__59m20_M |
| 9 | 125671902 | 125672106 | H_c__171f21 |
| 9 | 125731530 | 125732187 | H_c__209i22_M |
| 9 | 126167793 | 126170486 | H_c__208k22_M |
| 9 | 126319641 | 126319974 | H_c__150j16 |
| 9 | 126341273 | 126341960 | H_c__216d18 |
| 9 | 126355477 | 126356638 | H_c__91f20 |
| 9 | 126362453 | 126362602 | H_c__65f09 |
| 9 | 126455431 | 126458611 | H_c__151f17_M |
| 9 | 126465366 | 126468297 | H_c__218b17_M |
| 9 | 126480434 | 126480578 | H_c__97k21_M |
| 9 | 126524281 | 126525686 | H_c__7c21_M |
| 9 | 126577503 | 126577640 | H_c__69n01 |
| 9 | 126647026 | 126647400 | H_c__210j15_M |
| 9 | 126665253 | 126666413 | H_c__208b13 |
| 9 | 126701820 | 126703299 | H_c__88k18_M |
| 9 | 126756002 | 126757701 | H_c__33f11_M |
| 9 | 127065644 | 127068142 | H_c__180k21 |
| 9 | 127238866 | 127240855 | H_c__248p06 |
| 9 | 127265994 | 127267139 | H_c__233h09_M |
| 9 | 127293027 | 127294882 | H_c__208o12_M |
| 9 | 127409672 | 127411850 | H_c__68k08_M |
| 9 | 127453462 | 127455307 | H_c__229f23_M |
| 9 | 127612725 | 127614945 | H_c__123k09_M |
| 9 | 127618055 | 127620142 | H_c__207m22 |
| 9 | 127643825 | 127645952 | H_c__29l05_M |
| 9 | 127718748 | 127720784 | H_c__141i13 |
| 9 | 127740323 | 127741854 | H_c__92b24_M |
| 9 | 127757346 | 127759270 | H_c__103c24 |
| 9 | 127763473 | 127764376 | H_c__52j15_M |
| 9 | 127778887 | 127780641 | H_c__42e17_M |
| 9 | 127909686 | 127911417 | H_c__231n06 |
| 9 | 127968718 | 127969615 | H_c__129j06_M |
| 9 | 128031761 | 128034221 | H_c__70d15_M |
| 9 | 128044154 | 128046793 | H_c__34p22_M |
| 9 | 128091330 | 128092410 | H_c__8n08 |
| 9 | 128117053 | 128118919 | H_c__182l10 |
| 9 | 128163885 | 128165201 | H_c__208b03_M |
| 9 | 128181879 | 128183884 | H_c__178f19 |
| 9 | 128212534 | 128213663 | H_c__96a23 |
| 9 | 128268454 | 128268624 | H_c__167o12 |

TABLE 1-continued

| | | | |
|---|---|---|---|
| 9 | 128297556 | 128299396 | H_c__63k14_M |
| 9 | 128346269 | 128347045 | H_c__81f24 |
| 9 | 128393729 | 128395062 | H_c__33m13 |
| 9 | 12844878 | 12845310 | H_c__217h20_M |
| 9 | 128498167 | 128499014 | H_c__265m05_M |
| 9 | 128530404 | 128532724 | H_c__216a23 |
| 9 | 128543031 | 128545084 | H_c__35l06_M |
| 9 | 128565630 | 128566631 | H_c__3i13_M |
| 9 | 128613247 | 128615027 | H_c__209p12_M |
| 9 | 128660320 | 128660473 | H_c__1l11 |
| 9 | 128670031 | 128671660 | H_c__97b13 |
| 9 | 128723798 | 128725146 | H_c__103k21_M |
| 9 | 128787672 | 128790469 | H_c__100e09_M |
| 9 | 128869119 | 128870517 | H_c__94m19 |
| 9 | 128878205 | 128879561 | H_c__220p16_M |
| 9 | 128922272 | 128923779 | H_c__182n22 |
| 9 | 128952134 | 128953221 | H_c__98p05 |
| 9 | 129014942 | 129016894 | H_c__124m10_M |
| 9 | 129016898 | 129017404 | H_c__143b24_M |
| 9 | 129178728 | 129178850 | H_c__209a20_M |
| 9 | 129224765 | 129226626 | H_c__129b16_M |
| 9 | 129255002 | 129256505 | H_c__13m23_M |
| 9 | 129277342 | 129278896 | H_c__125g07 |
| 9 | 129278954 | 129280304 | H_c139n14_M |
| 9 | 129302507 | 129303160 | H_c__204d14_M |
| 9 | 129324242 | 129324947 | H_c__51f08 |
| 9 | 129330181 | 129332113 | H_c__179g03 |
| 9 | 129337855 | 129338263 | H_c__107n19 |
| 9 | 129391173 | 129392614 | H_c__195g07_M |
| 9 | 129461472 | 129462625 | H_c__204e09_M |
| 9 | 129467893 | 129468504 | H_c__164g15_M |
| 9 | 129482734 | 129485467 | H_c__187b12 |
| 9 | 129506217 | 129508366 | H_c__192l03_M |
| 9 | 129603873 | 129605711 | H_c__31i02 |
| 9 | 129644883 | 129645559 | H_c__273l01 |
| 9 | 129676926 | 129678048 | H_c__186l11_M |
| 9 | 129727581 | 129729038 | H_c__225g04_M |
| 9 | 129884067 | 129885382 | H_c__210n19_M |
| 9 | 129885385 | 129886026 | H_c__234f22 |
| 9 | 129895286 | 129896141 | H_c__80o16 |
| 9 | 130012585 | 130015397 | H_c__224f08 |
| 9 | 130022870 | 130025310 | H_c__248i05 |
| 9 | 130107067 | 130108642 | H_c__11l04 |
| 9 | 130336744 | 130339047 | H_c__189h20_M |
| 9 | 130483918 | 130485096 | H_c135c01_M |
| 9 | 130528319 | 130528489 | H_c__73j21_M |
| 9 | 130562946 | 130566384 | H_c__207l23_M |
| 9 | 130569155 | 130573788 | H_c__189a20_M |
| 9 | 130585721 | 130587527 | H_c__189n20 |
| 9 | 130843103 | 130844725 | H_c__17j24_M |
| 9 | 130913865 | 130915183 | H_c__125g20 |
| 9 | 130951706 | 130952082 | H_c__231j23 |
| 9 | 131001015 | 131002475 | H_c__30d09 |
| 9 | 131030325 | 131031022 | H_c__35h13_M |
| 9 | 131156263 | 131158360 | H_c__195p14 |
| 9 | 131181360 | 131183737 | H_c__272p03_M |
| 9 | 131187343 | 131188594 | H_c__215o05 |
| 9 | 131277403 | 131279145 | H_c__195e06 |
| 9 | 131407691 | 131409503 | H_c__178j15 |
| 9 | 131426755 | 131428217 | H_c__158d15 |
| 9 | 131450442 | 131452207 | H_c__211m14 |
| 9 | 131458812 | 131460321 | H_c__33j20 |
| 9 | 131644276 | 131645854 | H_c__270l12_M |
| 9 | 13178877 | 13179096 | H_c__29f01 |
| 9 | 131789889 | 131790698 | H_c__78f23 |
| 9 | 13182071 | 13182240 | H_c__50j23_M |
| 9 | 132066694 | 132069464 | H_c__196d03_M |
| 9 | 132259285 | 132260364 | H_c__3g16_M |
| 9 | 132311592 | 132312446 | H_c__114e09 |
| 9 | 132314468 | 132316169 | H_c__11p14_M |
| 9 | 132391519 | 132392021 | H_c__102m02 |
| 9 | 132412914 | 132413040 | H_c__75n24 |
| 9 | 132484104 | 132487355 | H_c__93f14_M |
| 9 | 132491356 | 132495944 | H_c__110b06_M |
| 9 | 132574693 | 132576027 | H_c__93b14 |
| 9 | 13267883 | 13269770 | H_c__160n12_M |
| 9 | 132782207 | 132783595 | H_c__50n15_M |
| 9 | 132849049 | 132850343 | H_c__28i22_M |
| 9 | 133025262 | 133026615 | H_c__201f08_M |
| 9 | 13303942 | 13304036 | H_c__272c03 |
| 9 | 133048441 | 133049842 | H_c__204n09_M |
| 9 | 133055836 | 133057704 | H_c__239f24 |
| 9 | 133179556 | 133181075 | H_c__186k23_M |
| 9 | 133231784 | 133233510 | H_c__181g20_M |
| 9 | 133244551 | 133245305 | H_c__234c21_M |
| 9 | 133252525 | 133253776 | H_c__202n18_M |
| 9 | 133271533 | 133272738 | H_c__181j15_M |
| 9 | 133312005 | 133313271 | H_c__169n04_M |
| 9 | 133323037 | 133324898 | H_c__30k07_M |
| 9 | 133354582 | 133355610 | H_c__52j08_M |
| 9 | 133373493 | 133374528 | H_c__125b16 |
| 9 | 133428084 | 133429903 | H_c__195b14_M |
| 9 | 133553372 | 133553564 | H_c__79l14_M |
| 9 | 133595961 | 133598354 | H_c__257f06_M |
| 9 | 133683808 | 133685164 | H_c__148h20 |
| 9 | 133700927 | 133701858 | H_c__227h21 |
| 9 | 13378931 | 13378999 | H_c__125i17 |
| 9 | 133937504 | 133941493 | H_c__193n16_M |
| 9 | 133961877 | 133963984 | H_c__47m08_M |
| 9 | 134029943 | 134030587 | H_c__19d05 |
| 9 | 134057749 | 134060452 | H_c__2c06_M |
| 9 | 134394868 | 134396951 | H_c__235h13_M |
| 9 | 134618761 | 134621218 | H_c__120e10 |
| 9 | 134759197 | 134761273 | H_c__155f05 |
| 9 | 134867530 | 134867897 | H_c__28h16 |
| 9 | 135192839 | 135194138 | H_c__251f14_M |
| 9 | 135198496 | 135198733 | H_c__56o07 |
| 9 | 135204156 | 135204317 | H_c__239l15 |
| 9 | 135359785 | 135362451 | H_c__170i23 |
| 9 | 135464332 | 135465946 | H_c__114n01 |
| 9 | 135530379 | 135530874 | H_c139h03_M |
| 9 | 135596497 | 135599370 | H_c__209c23 |
| 9 | 135616148 | 135620228 | H_c__146k08_M |
| 9 | 135666929 | 135669791 | H_c__129h01 |
| 9 | 135819363 | 135821103 | H_c__12f03_M |
| 9 | 135831110 | 135832932 | H_c__229j16 |
| 9 | 136024295 | 136026842 | H_c__248n01_M |
| 9 | 136167072 | 136169913 | H_c__207e23_M |
| 9 | 136212143 | 136213843 | H_c__176m16_M |
| 9 | 136235922 | 136237886 | H_c__88o09_M |
| 9 | 136310407 | 136311531 | H_c__21a04_M |
| 9 | 136314847 | 136318211 | H_c__78a21_M |
| 9 | 136322239 | 136323363 | H_c__272k07_M |
| 9 | 136533137 | 136534413 | H_c__85m21_M |
| 9 | 136568864 | 136570775 | H_c__102b23_M |
| 9 | 136579786 | 136581725 | H_c__171p14_M |
| 9 | 136652910 | 136656301 | H_c__264i05_M |
| 9 | 136714150 | 136717235 | H_c__21g05_M |
| 9 | 136748432 | 136751186 | H_c__178g10 |
| 9 | 136882033 | 136883246 | H_c__211j12_M |
| 9 | 136934589 | 136935951 | H_c__222o24 |
| 9 | 136977558 | 136979116 | H_c__226h07_M |
| 9 | 136991450 | 136993750 | H_c__97b23 |
| 9 | 137018166 | 137021294 | H_c__257d02_M |
| 9 | 137035330 | 137037065 | H_c__247g07_M |
| 9 | 137056192 | 137057962 | H_c__66i07 |
| 9 | 137212950 | 137217602 | H_c__234n12_M |
| 9 | 137298985 | 137301246 | H_c__33k19_M |
| 9 | 137309151 | 137310340 | H_c__92o15_M |
| 9 | 137326442 | 137329242 | H_c__113l24_M |
| 9 | 137375200 | 137376527 | H_c__171g20_M |
| 9 | 137410929 | 137412511 | H_c__249a12_M |
| 9 | 137586359 | 137588340 | H_c__63f14 |
| 9 | 137592926 | 137594571 | H_c__85c19_M |
| 9 | 137721587 | 137722756 | H_c__245h16_M |
| 9 | 137748770 | 137749544 | H_c__123d17_M |
| 9 | 137774888 | 137775553 | H_c__169i23_M |
| 9 | 137994284 | 137994413 | H_c__29p10_M |
| 9 | 138191519 | 138194374 | H_c__17o05_M |
| 9 | 138396818 | 138396933 | H_c140h15 |
| 9 | 14154294 | 14154408 | H_c__261k17 |
| 9 | 14302818 | 14303391 | H_c__27h06_M |
| 9 | 14304910 | 14306208 | H_c__254f18_M |
| 9 | 14335759 | 14336677 | H_c__75n16 |
| 9 | 14337170 | 14338474 | H_c__87n04_M |
| 9 | 14349155 | 14349274 | H_c__161l07 |
| 9 | 14418727 | 14419486 | H_c__93f13 |
| 9 | 14682895 | 14683667 | H_c__88o13_M |
| 9 | 15296089 | 15298032 | H_c__101g15_M |
| 9 | 15412632 | 15413319 | H_c__101h19_M |

TABLE 1-continued

| | | | |
|---|---|---|---|
| 9 | 15416021 | 15416172 | H_c_72j06 |
| 9 | 15500353 | 15501632 | H_c_149h13_M |
| 9 | 15542166 | 15543575 | H_c_121m10_M |
| 9 | 15941856 | 15942027 | H_c_55h23 |
| 9 | 16300282 | 16301373 | H_c_184o18 |
| 9 | 16718959 | 16719109 | H_c_245f06 |
| 9 | 16859844 | 16861977 | H_c_82b24_M |
| 9 | 17448744 | 17448769 | H_c_119d10 |
| 9 | 17509108 | 17509256 | H_c_30e24_M |
| 9 | 17568602 | 17569856 | H_c_145n09_M |
| 9 | 17896394 | 17897667 | H_c_24g18_M |
| 9 | 18609349 | 18609448 | H_c_54g19 |
| 9 | 18776344 | 18776472 | H_c_59h17 |
| 9 | 19038876 | 19040029 | H_c_29g10_M |
| 9 | 19092901 | 19093076 | H_c_105p19 |
| 9 | 19116742 | 19118070 | H_c_38m10_M |
| 9 | 19219506 | 19221441 | H_c_127l08_M |
| 9 | 19260992 | 19261068 | H_c_160a06 |
| 9 | 19453106 | 19455150 | H_c_71j14 |
| 9 | 19501666 | 19501990 | H_c_223i21_M |
| 9 | 1974304 | 1974462 | H_c_164a07 |
| 9 | 19778496 | 19780237 | H_c_42p02_M |
| 9 | 19798953 | 19799074 | H_c_79e11 |
| 9 | 19858309 | 19858502 | H_c_15b22 |
| 9 | 19924629 | 19924884 | H_c_28p06_M |
| 9 | 19989377 | 19989589 | H_c_114o15 |
| 9 | 2004806 | 2008178 | H_c_249e18_M |
| 9 | 20167991 | 20168057 | H_c_144d13 |
| 9 | 20253215 | 20253416 | H_c_229g05 |
| 9 | 204490 | 205614 | H_c_232h09 |
| 9 | 20612435 | 20612686 | H_c_12c12_M |
| 9 | 21549089 | 21550626 | H_c_125g19_M |
| 9 | 21954688 | 21955236 | H_c_184l15 |
| 9 | 21958301 | 21959108 | H_c_61e08 |
| 9 | 21964356 | 21964982 | H_c_193k03 |
| 9 | 21983371 | 21986139 | H_c_105n04_M |
| 9 | 21998598 | 21999619 | H_c_70c14_M |
| 9 | 22013421 | 22016169 | H_c_43j04 |
| 9 | 22436824 | 22437832 | H_c_247i08_M |
| 9 | 23213818 | 23213927 | H_c_230m24 |
| 9 | 23627689 | 23627869 | H_c_47m20_M |
| 9 | 23810626 | 23812228 | H_c_142l09_M |
| 9 | 23892428 | 23892571 | H_c144j02 |
| 9 | 24224121 | 24224238 | H_c_17f14 |
| 9 | 2439629 | 2439806 | H_c_236i24 |
| 9 | 24701382 | 24701472 | H_c_199o11 |
| 9 | 24721759 | 24721900 | H_c_97m16 |
| 9 | 24800295 | 24800505 | H_c_150m14 |
| 9 | 25554512 | 25554638 | H_c_247j07 |
| 9 | 255908 | 256016 | H_c_244c03 |
| 9 | 25667387 | 25668804 | H_c_59h18_M |
| 9 | 2611077 | 2613420 | H_c_195p07_M |
| 9 | 26303618 | 26303709 | H_c_101b09 |
| 9 | 26546521 | 26546625 | H_c_115e12 |
| 9 | 26882231 | 26883017 | H_c_68d05_M |
| 9 | 26936719 | 26937547 | H_c_253a21_M |
| 9 | 27001539 | 27001683 | H_c_173j01 |
| 9 | 27281068 | 27281161 | H_c_272g17 |
| 9 | 2748934 | 2749262 | H_c_30p10_M |
| 9 | 27518973 | 27520193 | H_c_230c12_M |
| 9 | 27562805 | 27563944 | H_c_76j08_M |
| 9 | 27860191 | 27860300 | H_c_127f09 |
| 9 | 27995330 | 27995403 | H_c_22n18 |
| 9 | 28059538 | 28059836 | H_c_63g01 |
| 9 | 28617093 | 28617264 | H_c_72i22 |
| 9 | 29201871 | 29203795 | H_c_236c06_M |
| 9 | 29303393 | 29303483 | H_c_126p05 |
| 9 | 2932245 | 2932351 | H_c_42b18 |
| 9 | 29507634 | 29507704 | H_c_199a09 |
| 9 | 29986201 | 29986302 | H_c_257m24 |
| 9 | 30413220 | 30413313 | H_c133h18 |
| 9 | 31122978 | 31123248 | H_c_214c17 |
| 9 | 3170843 | 3172067 | H_c_153c09_M |
| 9 | 32010918 | 32011390 | H_c_177j06 |
| 9 | 32374302 | 32375419 | H_c_8a20_M |
| 9 | 32540436 | 32542585 | H_c_247n12_M |
| 9 | 32562712 | 32563636 | H_c_113d15_M |
| 9 | 32772453 | 32774095 | H_c_30k08_M |
| 9 | 33014775 | 33016420 | H_c_252o04 |
| 9 | 33034166 | 33034289 | H_c_119i16 |
| 9 | 33066531 | 33066850 | H_c_108l08_M |
| 9 | 33156628 | 33157897 | H_c_199i03_M |
| 9 | 33279961 | 33281093 | H_c_70o01 |
| 9 | 33361852 | 33363263 | H_c_264e08 |
| 9 | 33437291 | 33437809 | H_c_213f13_M |
| 9 | 33666983 | 33667532 | H_c_34p11 |
| 9 | 33806520 | 33808591 | H_c137g05_M |
| 9 | 34038228 | 34039768 | H_c_192e19 |
| 9 | 34116192 | 34117015 | H_c_259e14_M |
| 9 | 34318642 | 34319603 | H_c_123l14_M |
| 9 | 34366281 | 34368125 | H_c_267d01 |
| 9 | 34369467 | 34371882 | H_c_253a15_M |
| 9 | 34446768 | 34449350 | H_c_20i15_M |
| 9 | 34510997 | 34513524 | H_c_267e12 |
| 9 | 34578072 | 34579748 | H_c_190h01_M |
| 9 | 34600455 | 34602644 | H_c_94n17_M |
| 9 | 34618721 | 34619646 | H_c_254m16_M |
| 9 | 34626776 | 34628115 | H_c_95a10 |
| 9 | 34635529 | 34638242 | H_c_272h06 |
| 9 | 34654696 | 34655841 | H_c_108e09_M |
| 9 | 34690906 | 34691937 | H_c_128i12 |
| 9 | 34947359 | 34949282 | H_c_265l15 |
| 9 | 34979277 | 34980632 | H_c_41i17_M |
| 9 | 35061624 | 35062905 | H_c_181j06_M |
| 9 | 35069039 | 35070274 | H_c_228m04_M |
| 9 | 35091655 | 35093715 | H_c_45p01 |
| 9 | 35100826 | 35101807 | H_c_149m06_M |
| 9 | 35151929 | 35152442 | H_c_5d16 |
| 9 | 3515341 | 3516985 | H_c_197l17_M |
| 9 | 35593912 | 35596190 | H_c_123c22_M |
| 9 | 35636492 | 35637259 | H_c_228i05_M |
| 9 | 35647193 | 35649360 | H_c_127n17_M |
| 9 | 35653796 | 35655489 | H_c_57n22_M |
| 9 | 35680377 | 35681640 | H_c137k18 |
| 9 | 35721719 | 35723521 | H_c_219h23_M |
| 9 | 35738822 | 35740008 | H_c_113e14_M |
| 9 | 35804529 | 35805306 | H_c13l110_M |
| 9 | 36026383 | 36027596 | H_c_21o09_M |
| 9 | 36053536 | 36053648 | H_c_13h14 |
| 9 | 36125757 | 36128004 | H_c_265n20_M |
| 9 | 36155518 | 36156915 | H_c_245c03 |
| 9 | 36164284 | 36164471 | H_c_90b03 |
| 9 | 36180417 | 36181367 | H_c_19j06_M |
| 9 | 36247857 | 36248874 | H_c_20g14 |
| 9 | 36389958 | 36391556 | H_c_177i01 |
| 9 | 36562250 | 36563222 | H_c_81j08_M |
| 9 | 36729491 | 36729735 | H_c132e08_M |
| 9 | 36973787 | 36977838 | H_c_171b18_M |
| 9 | 36992354 | 36993068 | H_c_39k01_M |
| 9 | 36999661 | 36999833 | H_c_127h12 |
| 9 | 37015377 | 37018269 | H_c_105p15_M |
| 9 | 37019124 | 37020923 | H_c133l04 |
| 9 | 37025027 | 37028675 | H_c_265n12_M |
| 9 | 37176928 | 37177082 | H_c_229k08_M |
| 9 | 37412449 | 37412980 | H_c_270d02_M |
| 9 | 37454694 | 37456079 | H_c_127f03 |
| 9 | 37464901 | 37465078 | H_c_181k06 |
| 9 | 37475752 | 37475979 | H_c_274e04_M |
| 9 | 37565697 | 37566723 | H_c_273e10_M |
| 9 | 37582349 | 37582763 | H_c_197n03_M |
| 9 | 37640121 | 37641312 | H_c_243c15_M |
| 9 | 37774397 | 37777682 | H_c_56h15_M |
| 9 | 37787421 | 37787486 | H_c_61o08 |
| 9 | 37790478 | 37791976 | H_c_58k24 |
| 9 | 37893306 | 37894608 | H_c_195i22_M |
| 9 | 37993099 | 37995244 | H_c144d12 |
| 9 | 38382357 | 38383795 | H_c_171j04 |
| 9 | 38413723 | 38414788 | H_c_43b05 |
| 9 | 38609884 | 38612545 | H_c_6i23 |
| 9 | 38622189 | 38622396 | H_c_60d12 |
| 9 | 3936572 | 3936815 | H_c_200a06 |
| 9 | 4188318 | 4188393 | H_c_171p02 |
| 9 | 4287319 | 4290329 | H_c_186o22_M |
| 9 | 4480201 | 4481100 | H_c_66e22_M |
| 9 | 4652116 | 4653566 | H_c_224i12 |
| 9 | 4656185 | 4656733 | H_c_226f22 |
| 9 | 4669288 | 4670274 | H_c_61i05_M |
| 9 | 4730487 | 4733806 | H_c_31m13_M |
| 9 | 4782030 | 4783774 | H_c_76b09_M |
| 9 | 4894368 | 4894612 | H_c_77f01 |

TABLE 1-continued

| | | | |
|---|---|---|---|
| 9 | 493654 | 495600 | H_c143l08_M |
| 9 | 4974896 | 4975761 | H_c134f12_M |
| 9 | 5161300 | 5161433 | H_c__38j01 |
| 9 | 5427559 | 5427953 | H_c__68g09_M |
| 9 | 5618557 | 5619797 | H_c__200l05_M |
| 9 | 5804139 | 5804408 | H_c__184g12_M |
| 9 | 5822482 | 5823459 | H_c__146j04_M |
| 9 | 6144192 | 6144265 | H_c__101g17 |
| 9 | 6402379 | 6404278 | H_c__20a21_M |
| 9 | 65548730 | 65549472 | H_c__180g03_M |
| 9 | 6635731 | 6636025 | H_c__180h24_M |
| 9 | 6670891 | 6672191 | H_c__217l20_M |
| 9 | 6705921 | 6706834 | H_c__62f16_M |
| 9 | 6747895 | 6748532 | H_c__211e18_M |
| 9 | 68548941 | 68550507 | H_c__6k14_M |
| 9 | 68624458 | 68625576 | H_c__33n15 |
| 9 | 68880101 | 68880778 | H_c__76h21 |
| 9 | 68965394 | 68966621 | H_c__129b14_M |
| 9 | 69018056 | 69019092 | H_c__222c06_M |
| 9 | 69168772 | 69170439 | H_c__168g05_M |
| 9 | 69515640 | 69517681 | H_c__11b03 |
| 9 | 69604002 | 69604717 | H_c__57c08 |
| 9 | 70103217 | 70103951 | H_c__15i19_M |
| 9 | 7023162 | 7023354 | H_c__161l02 |
| 9 | 70256951 | 70257101 | H_c__208l19_M |
| 9 | 70262852 | 70265603 | H_c__20e06_M |
| 9 | 70392845 | 70393015 | H_c__162l01 |
| 9 | 71236528 | 71236654 | H_c__274e11 |
| 9 | 71291178 | 71291984 | H_c__29j24_M |
| 9 | 715012 | 715254 | H_c__232o18 |
| 9 | 71612577 | 71612854 | H_c__213j20_M |
| 9 | 71632064 | 71632188 | H_c__47i16_M |
| 9 | 71694876 | 71694995 | H_c__99g16 |
| 9 | 71754534 | 71755535 | H_c__245k04_M |
| 9 | 7209116 | 7209180 | H_c__102j10 |
| 9 | 72208289 | 72209952 | H_c__227c03_M |
| 9 | 72249430 | 72249514 | H_c__245j05 |
| 9 | 72669526 | 72669673 | H_c__168d16 |
| 9 | 73813411 | 73813538 | H_c__203k22_M |
| 9 | 7394246 | 7394643 | H_c__119b07_M |
| 9 | 74149819 | 74149956 | H_c__266n20 |
| 9 | 74287922 | 74288048 | H_c__53l21 |
| 9 | 74341228 | 74343598 | H_c__262b10_M |
| 9 | 74731291 | 74732369 | H_c__162j10 |
| 9 | 74796263 | 74797463 | H_c__178f06_M |
| 9 | 74931762 | 74933390 | H_c__243c04_M |
| 9 | 75236679 | 75236759 | H_c__118p13 |
| 9 | 75381584 | 75381712 | H_c__101o11 |
| 9 | 7549590 | 7549749 | H_c__49a10 |
| 9 | 75735096 | 75736422 | H_c__219k14_M |
| 9 | 75885433 | 75885596 | H_c__121o03 |
| 9 | 7605467 | 7606465 | H_c__59b22 |
| 9 | 76101173 | 76101301 | H_c__70i08 |
| 9 | 76303434 | 76304030 | H_c__146l08_M |
| 9 | 76416168 | 76416504 | H_c__46p07 |
| 9 | 76750236 | 76751033 | H_c__96a10_M |
| 9 | 76856275 | 76859159 | H_c__74l18_M |
| 9 | 76860581 | 76861261 | H_c__246h09 |
| 9 | 76863668 | 76867893 | H_c139f09_M |
| 9 | 77021487 | 77022944 | H_c__93m12_M |
| 9 | 77492156 | 77493618 | H_c__66f01_M |
| 9 | 77699981 | 77700072 | H_c__191b17 |
| 9 | 77874732 | 77877307 | H_c131m13_M |
| 9 | 78080251 | 78081209 | H_c__215j14_M |
| 9 | 78140968 | 78142268 | H_c__9e11_M |
| 9 | 78321924 | 78322016 | H_c__117p13 |
| 9 | 78492378 | 78492507 | H_c__84g22 |
| 9 | 79007457 | 79007603 | H_c__59n04 |
| 9 | 79415073 | 79418030 | H_c__226h20_M |
| 9 | 79463804 | 79463974 | H_c__246a07_M |
| 9 | 80179932 | 80180082 | H_c__98e02 |
| 9 | 81314221 | 81314340 | H_c__191h06 |
| 9 | 81368984 | 81369225 | H_c__8b22 |
| 9 | 81507416 | 81507625 | H_c__32i17_M |
| 9 | 81531678 | 81531839 | H_c__3f23_M |
| 9 | 81534016 | 81534594 | H_c__181n11_M |
| 9 | 82906739 | 82907915 | H_c__94n22_M |
| 9 | 83063564 | 83063980 | H_c__158p23 |
| 9 | 831207 | 833029 | H_c__26k18 |
| 9 | 83339084 | 83339229 | H_c__175a12 |
| 9 | 83466953 | 83468210 | H_c__32a22 |
| 9 | 83551556 | 83552914 | H_c__272g16_M |
| 9 | 83647665 | 83649682 | H_c__120c13 |
| 9 | 8369446 | 8369600 | H_c__187g16 |
| 9 | 83765305 | 83766262 | H_c__270k15 |
| 9 | 83823846 | 83825965 | H_c__224g22_M |
| 9 | 84037808 | 84037958 | H_c__7j10 |
| 9 | 84512587 | 84514553 | H_c__35a15_M |
| 9 | 84659379 | 84659453 | H_c__118f08 |
| 9 | 84911930 | 84912143 | H_c__249j19 |
| 9 | 85585365 | 85586867 | H_c__91f02_M |
| 9 | 85785152 | 85786363 | H_c132c02_M |
| 9 | 85864693 | 85864904 | H_c__234m08_M |
| 9 | 8588291 | 8588378 | H_c__177i18 |
| 9 | 85943185 | 85944798 | H_c__1g20_M |
| 9 | 86091071 | 86091147 | H_c__73i09 |
| 9 | 86126512 | 86127362 | H_c__116j23 |
| 9 | 86198275 | 86199489 | H_c__114m20 |
| 9 | 86792007 | 86792382 | H_c__272n15 |
| 9 | 86858245 | 86858636 | H_c__35o09 |
| 9 | 86992900 | 86993588 | H_c__79g13 |
| 9 | 87110055 | 87110237 | H_c__8f14 |
| 9 | 87341921 | 87343291 | H_c__114n09_M |
| 9 | 8748684 | 8748855 | H_c__108o05 |
| 9 | 87570093 | 87571216 | H_c__79l17 |
| 9 | 87818734 | 87819462 | H_c__90p06_M |
| 9 | 87827467 | 87827596 | H_c__178c20 |
| 9 | 87920646 | 87922168 | H_c__76e14 |
| 9 | 88232075 | 88232380 | H_c__31m03 |
| 9 | 88378317 | 88380980 | H_c__254b12 |
| 9 | 8847259 | 8848226 | H_c__116l22_M |
| 9 | 88739835 | 88740001 | H_c__181d06 |
| 9 | 89018628 | 89018760 | H_c__167k22 |
| 9 | 89021797 | 89023101 | H_c__224g15_M |
| 9 | 89079134 | 89079573 | H_c__34k10 |
| 9 | 89154647 | 89155408 | H_c__121p22_M |
| 9 | 89155452 | 89156360 | H_c__43n20_M |
| 9 | 89162420 | 89163418 | H_c__247o19_M |
| 9 | 89449221 | 89451244 | H_c__271c07_M |
| 9 | 89819535 | 89819855 | H_c__4l13 |
| 9 | 90152671 | 90152856 | H_c__228n08 |
| 9 | 90484367 | 90484932 | H_c__35n02_M |
| 9 | 90643079 | 90644392 | H_c__81i10_M |
| 9 | 90917194 | 90917762 | H_c__85l03 |
| 9 | 91035247 | 91035795 | H_c__9f21_M |
| 9 | 91047910 | 91048113 | H_c__44e09 |
| 9 | 9108364 | 9108599 | H_c__164a18_M |
| 9 | 91262867 | 91266967 | H_c__30i10_M_M |
| 9 | 91523646 | 91523910 | H_c__210b10 |
| 9 | 91728069 | 91728458 | H_c__94o10 |
| 9 | 91790394 | 91792648 | H_c__14i14_M |
| 9 | 91935172 | 91935404 | H_c__195l13 |
| 9 | 91956490 | 91957494 | H_c__28h18 |
| 9 | 92167287 | 92168140 | H_c__239i09_M |
| 9 | 92604559 | 92607423 | H_c__265f03 |
| 9 | 92649119 | 92651213 | H_c__173b23_M |
| 9 | 92898803 | 92901274 | H_c__38d04 |
| 9 | 92936947 | 92937476 | H_c__52c09 |
| 9 | 92973495 | 92976362 | H_c__199f09_M |
| 9 | 93024703 | 93027537 | H_c__76f16 |
| 9 | 93034588 | 93035654 | H_c__117j07 |
| 9 | 93130194 | 93131978 | H_c__183a22 |
| 9 | 93278847 | 93279292 | H_c__231d04 |
| 9 | 93292535 | 93294944 | H_c__115i01_M |
| 9 | 93408236 | 93409257 | H_c135f03_M |
| 9 | 93661016 | 93662759 | H_c__13g11 |
| 9 | 93666278 | 93668632 | H_c141n02 |
| 9 | 93726701 | 93726844 | H_c__208n24 |
| 9 | 93787045 | 93788361 | H_c__112f14_M |
| 9 | 93792603 | 93793366 | H_c__145i21 |
| 9 | 93800990 | 93801294 | H_c__94m04 |
| 9 | 93871827 | 93873019 | H_c__123m15_M |
| 9 | 94100929 | 94101719 | H_c__67a13 |
| 9 | 94479616 | 94481687 | H_c__25b05 |
| 9 | 94568296 | 94568962 | H_c__78h05_M |
| 9 | 94846179 | 94848153 | H_c__102n07_M |
| 9 | 94890071 | 94890528 | H_c__122e12 |
| 9 | 95158642 | 95159924 | H_c__27b20_M |
| 9 | 95190895 | 95192781 | H_c__263j15 |
| 9 | 95290565 | 95290744 | H_c__106b02 |

TABLE 1-continued

| | | | |
|---|---|---|---|
| 9 | 95347545 | 95349327 | H_c_86l19_M |
| 9 | 95352134 | 95353300 | H_c_84b16_M |
| 9 | 95358647 | 95359638 | H_c_46b05_M |
| 9 | 9536645 | 9536773 | H_c137f21 |
| 9 | 95467225 | 95469371 | H_c_176g12 |
| 9 | 95653787 | 95653869 | H_c_35l14 |
| 9 | 95716796 | 95718214 | H_c_164i09_M |
| 9 | 95862671 | 95863147 | H_c142o16_M |
| 9 | 959484 | 959791 | H_c_34p10 |
| 9 | 96060818 | 96062005 | H_c_12d24 |
| 9 | 96224771 | 96225944 | H_c_79k22_M |
| 9 | 96259027 | 96261395 | H_c_130g01_M |
| 9 | 962607 | 963860 | H_c_210a20 |
| 9 | 96291494 | 96293108 | H_c_53d11_M |
| 9 | 96344815 | 96344922 | H_c137m07 |
| 9 | 96374526 | 96374721 | H_c_27j24_M |
| 9 | 96408753 | 96409072 | H_c_164e05_M |
| 9 | 96460928 | 96461952 | H_c_29g11_M |
| 9 | 96496162 | 96497551 | H_c_66o11_M |
| 9 | 96528559 | 96528996 | H_c134n14_M |
| 9 | 96561408 | 96562208 | H_c_32g04_M |
| 9 | 96656358 | 96656512 | H_c_156e15 |
| 9 | 966677 | 967790 | H_c_2j01_M |
| 9 | 96695838 | 96696552 | H_c_6a10 |
| 9 | 96881005 | 96881308 | H_c_111g02 |
| 9 | 96918299 | 96919736 | H_c134l12 |
| 9 | 97253355 | 97254537 | H_c_183h04_M |
| 9 | 97343174 | 97344214 | H_c_146n05_M |
| 9 | 97474884 | 97476113 | H_c_151m03_M |
| 9 | 97538345 | 97539260 | H_c_125f16_M |
| 9 | 97645170 | 97645939 | H_c132m12 |
| 9 | 97689026 | 97690888 | H_c_234b15 |
| 9 | 97693369 | 97697288 | H_c_103n01_M |
| 9 | 97700146 | 97700485 | H_c_87e17 |
| 9 | 97823427 | 97826643 | H_c_77g05_M_M |
| 9 | 97826645 | 97827475 | H_c144o17_M |
| 9 | 97897893 | 97899116 | H_c_227i23 |
| 9 | 97929048 | 97929979 | H_c_169j15_M |
| 9 | 97960475 | 97961281 | H_c_200k07_M |
| 9 | 98097225 | 98098364 | H_c_175h24_M |
| 9 | 98417116 | 98418365 | H_c_91a04 |
| 9 | 98464399 | 98464612 | H_c_266b19 |
| 9 | 98510938 | 98511074 | H_c_268m21_M |
| 9 | 98637872 | 98638809 | H_c_162h16_M |
| 9 | 98649301 | 98649842 | H_c_62p15_M |
| 9 | 98785488 | 98786566 | H_c_30a21_M |
| 9 | 98816824 | 98817046 | H_c_27f23_M |
| 9 | 99063208 | 99064619 | H_c_155c14_M |
| 9 | 99661263 | 99671111 | H_c_147b13_M_M_M |
| 9 | 99711930 | 99712423 | H_c_270k21 |
| 9 | 99939925 | 99941812 | H_c_36d24_M |
| 10 | 100016826 | 100018754 | H_c_5f07 |
| 10 | 100109312 | 100109523 | H_c_187o08 |
| 10 | 100195865 | 100197069 | H_c_127c03_M |
| 10 | 100217605 | 100218444 | H_c_28i20 |
| 10 | 100382211 | 100382418 | H_c_8l21 |
| 10 | 100398867 | 100398981 | H_c_113i24 |
| 10 | 100941906 | 100941998 | H_c_167d23 |
| 10 | 100981751 | 100984255 | H_c_26k09_M |
| 10 | 10120522 | 10120635 | H_c_70p20 |
| 10 | 101279485 | 101280331 | H_c_83j20_M |
| 10 | 101284450 | 101290863 | H_c_173a03_M_M |
| 10 | 101369453 | 101372674 | H_c_14h01_M_M |
| 10 | 101481517 | 101482303 | H_c_121d10 |
| 10 | 101758918 | 101760318 | H_c_179o22_M |
| 10 | 101864807 | 101865231 | H_c_221i11 |
| 10 | 101935221 | 101935939 | H_c_185b12_M |
| 10 | 102016777 | 102017593 | H_c_12k18 |
| 10 | 102035275 | 102036877 | H_c136b22 |
| 10 | 102095941 | 102097071 | H_c_130c21_M |
| 10 | 102231893 | 102233314 | H_c_21i02_M |
| 10 | 102268983 | 102269743 | H_c_81e18_M |
| 10 | 102285366 | 102286046 | H_c_196j21 |
| 10 | 102311345 | 102313032 | H_c_78a11_M |
| 10 | 1023809 | 1024909 | H_c_267n24_M |
| 10 | 102381532 | 102381674 | H_c_36p04 |
| 10 | 102404411 | 102405171 | H_c_101g23 |
| 10 | 102420647 | 102420797 | H_c_168c22_M |
| 10 | 102430529 | 102431225 | H_c_54i20 |
| 10 | 102459296 | 102461273 | H_c_81i05_M |
| 10 | 102463540 | 102466086 | H_c_121b01_M_M |
| 10 | 102474248 | 102475117 | H_c_111k12 |
| 10 | 102479134 | 102480866 | H_c_15a15_M |
| 10 | 102484801 | 102486548 | H_c_161d14_M |
| 10 | 102486611 | 102487539 | H_c_121b11 |
| 10 | 102492409 | 102498562 | H_c_82f19_M_M |
| 10 | 102577282 | 102581279 | H_c_268p01_M |
| 10 | 102657634 | 102657873 | H_c_237o19 |
| 10 | 102662275 | 102663305 | H_c_111o05_M |
| 10 | 102718577 | 102719998 | H_c135b24_M |
| 10 | 102736720 | 102739315 | H_c_241c12_M |
| 10 | 102746590 | 102747650 | H_c_115a17_M |
| 10 | 102798022 | 102798345 | H_c_249c12_M |
| 10 | 102810472 | 102812959 | H_c_81n18_M |
| 10 | 102873109 | 102874069 | H_c139j11 |
| 10 | 102880817 | 102883334 | H_c_9j10 |
| 10 | 102888484 | 102890428 | H_c_120a08 |
| 10 | 102932611 | 102932750 | H_c_95b02 |
| 10 | 102964600 | 102964822 | H_c_68h16 |
| 10 | 102969896 | 102972869 | H_c_156h15_M |
| 10 | 102976749 | 102978852 | H_c_209g18_M |
| 10 | 102985982 | 102986278 | H_c_168l23 |
| 10 | 103033930 | 103035432 | H_c_35l17_M |
| 10 | 103041073 | 103042507 | H_c_59h16_M |
| 10 | 103315996 | 103321564 | H_c_258i13_M |
| 10 | 103443728 | 103445536 | H_c_253c04_M |
| 10 | 103519888 | 103520940 | H_c_70g12 |
| 10 | 103524987 | 103533215 | H_c_33d23_M_M |
| 10 | 103567396 | 103567989 | H_c_77f11_M |
| 10 | 103590485 | 103591557 | H_c_208g13 |
| 10 | 103805336 | 103806250 | H_c_205m22_M |
| 10 | 103863405 | 103865285 | H_c_2k11_M |
| 10 | 103870264 | 103870739 | H_c_39h23_M |
| 10 | 103882624 | 103883917 | H_c_68j18_M |
| 10 | 103901946 | 103902923 | H_c136a24 |
| 10 | 103975798 | 103976876 | H_c_206m11 |
| 10 | 103989914 | 103991843 | H_c_257k13_M |
| 10 | 104144166 | 104145263 | H_c_85c08_M |
| 10 | 104147675 | 104149685 | H_c_175c20 |
| 10 | 104167879 | 104172113 | H_c_243m21_M |
| 10 | 104199306 | 104200934 | H_c_140p17_M |
| 10 | 104210980 | 104211539 | H_c_33c06_M |
| 10 | 104251575 | 104254915 | H_c_22d23_M_M |
| 10 | 104391873 | 104392593 | H_c_167h11_M |
| 10 | 104409480 | 104411484 | H_c_22g20 |
| 10 | 104463937 | 104464876 | H_c_14c15_M |
| 10 | 104667127 | 104669491 | H_c138d20_M |
| 10 | 104942211 | 104944175 | H_c_249f18_M |
| 10 | 105026860 | 105028047 | H_c_246e10_M |
| 10 | 105117374 | 105118652 | H_c_41g20_M |
| 10 | 105145808 | 105146686 | H_c_86k16 |
| 10 | 105156301 | 105156493 | H_c_80f04 |
| 10 | 105201515 | 105203108 | H_c132i20 |
| 10 | 105206980 | 105209387 | H_c_7m09 |
| 10 | 105242090 | 105244651 | H_c_161h17_M |
| 10 | 105304527 | 105305905 | H_c_197p08 |
| 10 | 105334103 | 105335615 | H_c_2b24_M |
| 10 | 105604328 | 105605847 | H_c_247e23_M |
| 10 | 105716254 | 105717391 | H_c_170h20_M |
| 10 | 105870691 | 105872144 | H_c_240a08_M |
| 10 | 105957744 | 105957870 | H_c_93f17 |
| 10 | 105981263 | 105982358 | H_c_42k20 |
| 10 | 106018405 | 106019124 | H_c_36l19_M |
| 10 | 106024547 | 106025145 | H_c_112b08 |
| 10 | 106087265 | 106088284 | H_c_204d17_M |
| 10 | 106377575 | 106377754 | H_c_188a24 |
| 10 | 106388415 | 106391868 | H_c_187k07_M |
| 10 | 106512454 | 106512747 | H_c_203h10 |
| 10 | 106944676 | 106944837 | H_c_2f23 |
| 10 | 107145936 | 107146198 | H_c_84a09 |
| 10 | 107374496 | 107374638 | H_c_34j03 |
| 10 | 107579432 | 107579622 | H_c_37i23 |
| 10 | 107724984 | 107725686 | H_c_174b11 |
| 10 | 1078669 | 1078803 | H_c_89d19 |
| 10 | 108101803 | 108101870 | H_c_43g14 |
| 10 | 1084194 | 1085905 | H_c_84l04_M |
| 10 | 108694407 | 108694505 | H_c_222n09_M |
| 10 | 108912786 | 108914982 | H_c_1d19_M |
| 10 | 10903781 | 10903913 | H_c139i07 |
| 10 | 109204870 | 109205050 | H_c_97c23 |

TABLE 1-continued

| | | | |
|---|---|---|---|
| 10 | 1092095 | 1093461 | H_c_207a24 |
| 10 | 109910567 | 109910760 | H_c_22a07_M |
| 10 | 110155554 | 110155703 | H_c_56k09 |
| 10 | 110321057 | 110321434 | H_c_150l22 |
| 10 | 110625312 | 110625401 | H_c_21m22_M |
| 10 | 110681388 | 110681465 | H_c_267k10 |
| 10 | 110736574 | 110736655 | H_c_94n01 |
| 10 | 11080693 | 11080983 | H_c_101j15 |
| 10 | 110847718 | 110847804 | H_c131f18 |
| 10 | 11099813 | 11100806 | H_c_82h11_M |
| 10 | 111206243 | 111207181 | H_c_11n01_M |
| 10 | 111472667 | 111472735 | H_c_41p12 |
| 10 | 111672522 | 111673578 | H_c_57i14_M |
| 10 | 111685135 | 111685271 | H_c_34n24 |
| 10 | 111959222 | 111961171 | H_c_27h24 |
| 10 | 112053989 | 112054943 | H_c_82a22_M |
| 10 | 112246974 | 112249275 | H_c_7i23_M |
| 10 | 112317083 | 112318084 | H_c_71f11_M |
| 10 | 112393387 | 112394798 | H_c_211f08 |
| 10 | 112422061 | 112422664 | H_c_15i15_M |
| 10 | 112516349 | 112518411 | H_c_121h13 |
| 10 | 112826562 | 112829505 | H_c135g01_M |
| 10 | 113026991 | 113027126 | H_c_19f09 |
| 10 | 113151585 | 113151804 | H_c_193i22 |
| 10 | 11372427 | 11372562 | H_c_102h14 |
| 10 | 113767725 | 113768010 | H_c_150j04 |
| 10 | 114195876 | 114197485 | H_c_229j23_M |
| 10 | 114539800 | 114541171 | H_c_199l06 |
| 10 | 114699978 | 114701259 | H_c_101c11 |
| 10 | 114876321 | 114876834 | H_c_85b21 |
| 10 | 115239646 | 115239763 | H_c_27o24 |
| 10 | 115545340 | 115545442 | H_c_163j11 |
| 10 | 115792558 | 115795378 | H_c_26j22_M |
| 10 | 115923063 | 115924424 | H_c131m08 |
| 10 | 115953764 | 115953915 | H_c_29j17 |
| 10 | 116146892 | 116147190 | H_c_3f22 |
| 10 | 116293196 | 116294604 | H_c_195c02 |
| 10 | 116381476 | 116382234 | H_c_22d24_M |
| 10 | 116517401 | 116518188 | H_c_30m15_M |
| 10 | 116571172 | 116572251 | H_c_152k06 |
| 10 | 116842531 | 116844090 | H_c_195i10_M |
| 10 | 11693049 | 11694226 | H_c_76h07_M |
| 10 | 118019908 | 118023511 | H_c_128b03_M |
| 10 | 118123977 | 118124153 | H_c_167m11 |
| 10 | 118151128 | 118151287 | H_c_126j03 |
| 10 | 11824201 | 11825183 | H_c_77i24_M |
| 10 | 118490917 | 118492751 | H_c_43o08 |
| 10 | 118537559 | 118537831 | H_c_187n22 |
| 10 | 118598488 | 118599581 | H_c_253b20_M |
| 10 | 118670485 | 118670699 | H_c_168i17 |
| 10 | 118754001 | 118755231 | H_c_2g07_M |
| 10 | 118911914 | 118918207 | H_c_91c02_M_M |
| 10 | 118965242 | 118967188 | H_c_63h01_M |
| 10 | 118989516 | 118991874 | H_c_5o17_M |
| 10 | 11905083 | 11906014 | H_c_191f10_M |
| 10 | 119116054 | 119116125 | H_c_34j06 |
| 10 | 119122906 | 119125667 | H_c_105h11_M |
| 10 | 119164055 | 119164136 | H_c_145i02 |
| 10 | 119283840 | 119287753 | H_c_23m04_M_M |
| 10 | 119292118 | 119296331 | H_c_177d10_M_M |
| 10 | 11951051 | 11952874 | H_c_148m04 |
| 10 | 119548447 | 119548542 | H_c_170k05 |
| 10 | 119610070 | 119610265 | H_c_259j24 |
| 10 | 119795763 | 119797285 | H_c_38m20_M |
| 10 | 119886349 | 119886474 | H_c_18f07 |
| 10 | 120052912 | 120053021 | H_c_116e11 |
| 10 | 120092190 | 120092553 | H_c_77g03 |
| 10 | 120310466 | 120310674 | H_c_30c22 |
| 10 | 120343454 | 120346291 | H_c_31c16_M |
| 10 | 120503428 | 120505002 | H_c_149d01_M |
| 10 | 120513744 | 120513884 | H_c_170l05 |
| 10 | 120616536 | 120616738 | H_c_149a16 |
| 10 | 120778669 | 120780585 | H_c_102g19 |
| 10 | 120852840 | 120854541 | H_c_12j21_M |
| 10 | 12090705 | 12090800 | H_c_99k14 |
| 10 | 120914564 | 120915876 | H_c_12i22 |
| 10 | 120956227 | 120957055 | H_c_245o04_M |
| 10 | 121400309 | 121401968 | H_c_36l06_M |
| 10 | 12150522 | 12151776 | H_c_102m19_M |
| 10 | 121621509 | 121624231 | H_c_155f17_M |
| 10 | 121628883 | 121629037 | H_c_273l10 |
| 10 | 121641728 | 121642764 | H_c_62l08_M |
| 10 | 121749285 | 121749459 | H_c139j22 |
| 10 | 121811753 | 121811872 | H_c_210h22 |
| 10 | 121828173 | 121828367 | H_c_127d24 |
| 10 | 12192523 | 12192664 | H_c_128i15 |
| 10 | 122046385 | 122046552 | H_c_179d01 |
| 10 | 12210857 | 12212106 | H_c_56i06_M |
| 10 | 122205813 | 122207834 | H_c_19m07 |
| 10 | 122293458 | 122293670 | H_c_173k24 |
| 10 | 122363991 | 122364467 | H_c_17k22 |
| 10 | 122698472 | 122698754 | H_c_4l08_M |
| 10 | 122728931 | 122729313 | H_c_181l08_M |
| 10 | 12277206 | 12278004 | H_c134c12_M |
| 10 | 123097500 | 123099211 | H_c_148c18 |
| 10 | 123147275 | 123147497 | H_c_199k05 |
| 10 | 123346562 | 123348344 | H_c_21h03 |
| 10 | 123358162 | 123358849 | H_c_76m08 |
| 10 | 123667952 | 123668036 | H_c_160o24 |
| 10 | 123677092 | 123678334 | H_c_200l10 |
| 10 | 123723813 | 123725263 | H_c_177p06_M |
| 10 | 123753127 | 123754011 | H_c_221d03 |
| 10 | 123862007 | 123863249 | H_c_117a10_M |
| 10 | 123863259 | 123863486 | H_c_265a18_M |
| 10 | 123911855 | 123914319 | H_c_155i06_M |
| 10 | 124060458 | 124060621 | H_c_225c07 |
| 10 | 124123897 | 124124826 | H_c_154h07 |
| 10 | 124210418 | 124212078 | H_c_106g20_M |
| 10 | 124578019 | 124579439 | H_c_258g10 |
| 10 | 124629322 | 124629894 | H_c_27i12 |
| 10 | 124703140 | 124704584 | H_c_51p10 |
| 10 | 124729374 | 124730356 | H_c_31k02_M |
| 10 | 124758238 | 124758425 | H_c_127i03 |
| 10 | 124882600 | 124892260 | H_c_107e24_M_M_M |
| 10 | 124895449 | 124898781 | H_c143d16_M |
| 10 | 124900862 | 124904657 | H_c_235a18_M |
| 10 | 12512880 | 12513071 | H_c_83i06 |
| 10 | 125414235 | 125416728 | H_c_147j21_M |
| 10 | 125640144 | 125642510 | H_c_182k06_M |
| 10 | 125741106 | 125741634 | H_c_57f05 |
| 10 | 126096713 | 126097501 | H_c142g20_M |
| 10 | 126125803 | 126129176 | H_c_264h15_M |
| 10 | 126171461 | 126171595 | H_c_15m14 |
| 10 | 126202170 | 126202581 | H_c_128l22 |
| 10 | 126212142 | 126213622 | H_c_20n23 |
| 10 | 126235438 | 126235562 | H_c_67h08 |
| 10 | 126395256 | 126395489 | H_c_171i23 |
| 10 | 126470089 | 126471055 | H_c_216d23_M |
| 10 | 126480114 | 126480803 | H_c_174a01_M |
| 10 | 126595104 | 126596493 | H_c_91b08 |
| 10 | 126829732 | 126831146 | H_c_122c19_M |
| 10 | 127397338 | 127398233 | H_c_28i24_M |
| 10 | 127501354 | 127502430 | H_c_57o17_M |
| 10 | 127574168 | 127575580 | H_c_75i21 |
| 10 | 128065898 | 128067648 | H_c_75k04_M |
| 10 | 128098625 | 128098709 | H_c_182a21 |
| 10 | 128883843 | 128885627 | H_c_227k03 |
| 10 | 128921857 | 128922040 | H_c_195o18 |
| 10 | 129222346 | 129222493 | H_c_26d10_M |
| 10 | 129424252 | 129426526 | H_c_7d20_M |
| 10 | 129571748 | 129572884 | H_c_60h05 |
| 10 | 129594783 | 129596677 | H_c_95o05_M |
| 10 | 129813631 | 129814924 | H_c_30e13_M |
| 10 | 129837911 | 129838850 | H_c_159c06 |
| 10 | 129898455 | 129899811 | H_c136i06 |
| 10 | 129974723 | 129975387 | H_c_35n11_M |
| 10 | 130228392 | 130229867 | H_c_12b06_M |
| 10 | 13083007 | 13084005 | H_c_38a20_M |
| 10 | 130919914 | 130920060 | H_c_273i20 |
| 10 | 131154374 | 131156342 | H_c_192c10_M |
| 10 | 131251813 | 131251977 | H_c_46n22 |
| 10 | 131262772 | 131262932 | H_c_94o05 |
| 10 | 131401366 | 131401451 | H_c_73p21 |
| 10 | 131542274 | 131542417 | H_c_225g19 |
| 10 | 131646969 | 131648928 | H_c_241e12_M |
| 10 | 131652882 | 131661766 | H_c_159j05_M_M_M |
| 10 | 13181890 | 13183208 | H_c_268c18_M |
| 10 | 131823001 | 131825354 | H_c_34p07_M |
| 10 | 131877735 | 131879426 | H_c_68l13 |
| 10 | 131988475 | 131990204 | H_c_37l18 |

TABLE 1-continued

| | | | |
|---|---|---|---|
| 10 | 132119945 | 132120031 | H_c_155c22 |
| 10 | 13212565 | 13212643 | H_c_81b14 |
| 10 | 132487238 | 132488877 | H_c139a17 |
| 10 | 132654651 | 132654870 | H_c_222m10 |
| 10 | 132999049 | 133001170 | H_c132n17 |
| 10 | 13344727 | 13346015 | H_c_187l04_M |
| 10 | 13357641 | 13358665 | H_c_16e09 |
| 10 | 133644862 | 133646982 | H_c_187h23 |
| 10 | 133699834 | 133700608 | H_c_92i03_M |
| 10 | 13381284 | 13382283 | H_c_99p16_M |
| 10 | 133848945 | 133850768 | H_c_254a23_M |
| 10 | 133895148 | 133895803 | H_c_5b09 |
| 10 | 133994402 | 133996064 | H_c_208n20_M |
| 10 | 134059935 | 134061132 | H_c_50m05_M |
| 10 | 134116515 | 134117373 | H_c_261i14_M |
| 10 | 134200249 | 134200804 | H_c_25h19_M |
| 10 | 13429145 | 13431112 | H_c_171f16_M |
| 10 | 134408186 | 134409780 | H_c_184i10 |
| 10 | 134448320 | 134449934 | H_c_108g24_M |
| 10 | 134605001 | 134606485 | H_c144h10_M |
| 10 | 134790154 | 134791553 | H_c_85f17_M |
| 10 | 134799768 | 134801699 | H_c_176f13 |
| 10 | 134826295 | 134827483 | H_c_34h15 |
| 10 | 134932088 | 134935028 | H_c_4m01_M |
| 10 | 134962420 | 134964845 | H_c_42o17_M |
| 10 | 135010793 | 135012015 | H_c_154g03_M |
| 10 | 135038562 | 135038891 | H_c_92g21_M |
| 10 | 135075133 | 135076238 | H_c_229k23_M |
| 10 | 135080116 | 135082076 | H_c_101b06_M |
| 10 | 135125139 | 135126037 | H_c_47o14_M |
| 10 | 135187662 | 135187787 | H_c_159i12 |
| 10 | 13521102 | 13522770 | H_c_173a14_M |
| 10 | 135222402 | 135223063 | H_c_207c23 |
| 10 | 135230391 | 135232279 | H_c_6a06_M |
| 10 | 135389775 | 135390477 | H_c_264e07 |
| 10 | 13610278 | 13611407 | H_c144k11_M |
| 10 | 1394439 | 1396370 | H_c_242k03 |
| 10 | 13973475 | 13974322 | H_c_15b04_M |
| 10 | 14635572 | 14635777 | H_c_190d24 |
| 10 | 14686436 | 14686819 | H_c_195f10 |
| 10 | 14863560 | 14863746 | H_c_205c23 |
| 10 | 14919621 | 14921223 | H_c_253m21 |
| 10 | 14960229 | 14961383 | H_c_215p08_M |
| 10 | 15023813 | 15023897 | H_c_157n08 |
| 10 | 15035302 | 15036218 | H_c_196d24 |
| 10 | 15041009 | 15042138 | H_c_33a06_M |
| 10 | 15170666 | 15170955 | H_c_56l07_M |
| 10 | 15249756 | 15250075 | H_c_268c24_M |
| 10 | 15452112 | 15453292 | H_c_72h04 |
| 10 | 15453289 | 15453624 | H_c_39f21_M |
| 10 | 15520959 | 15522052 | H_c_130g03 |
| 10 | 15801270 | 15802351 | H_c_76j15 |
| 10 | 15838937 | 15839236 | H_c137f10 |
| 10 | 15939199 | 15939322 | H_c_125p03 |
| 10 | 16121215 | 16121361 | H_c_58l06 |
| 10 | 16404013 | 16404287 | H_c_266j09 |
| 10 | 16601915 | 16604319 | H_c_84n02_M |
| 10 | 16898695 | 16899543 | H_c_65a03_M |
| 10 | 170572 | 173371 | H_c_199f02_M |
| 10 | 17282924 | 17283982 | H_c_121k13 |
| 10 | 17310344 | 17312245 | H_c_226j01_M |
| 10 | 17472156 | 17472302 | H_c_16g22 |
| 10 | 17535176 | 17537199 | H_c141j03_M |
| 10 | 1768401 | 1770067 | H_c_123m23 |
| 10 | 17698852 | 17699934 | H_c_243b06_M |
| 10 | 18356322 | 18356487 | H_c_118o13 |
| 10 | 18469062 | 18470409 | H_c133g24 |
| 10 | 18980273 | 18980716 | H_c_199j02 |
| 10 | 18987841 | 18989164 | H_c142j15_M |
| 10 | 19193412 | 19193542 | H_c132k16 |
| 10 | 19846088 | 19846169 | H_c_73l12 |
| 10 | 20144452 | 20146499 | H_c_104i06_M |
| 10 | 21159701 | 21161993 | H_c_184d07_M |
| 10 | 21541272 | 21541484 | H_c_49h03_M |
| 10 | 21783845 | 21783923 | H_c_199j05 |
| 10 | 21822853 | 21826466 | H_c_29n02_M |
| 10 | 21839111 | 21839497 | H_c_110o16 |
| 10 | 21845044 | 21846545 | H_c132k15 |
| 10 | 21854722 | 21856688 | H_c_108o22_M |
| 10 | 21863562 | 21864444 | H_c_233k18 |
| 10 | 2228296 | 2228403 | H_c_15c03 |
| 10 | 22331797 | 22332978 | H_c_48g06 |
| 10 | 22557911 | 22558434 | H_c_167n09_M |
| 10 | 22571051 | 22571145 | H_c_45p06 |
| 10 | 22581638 | 22582780 | H_c_99d13_M |
| 10 | 22644844 | 22645897 | H_c_177p13_M |
| 10 | 22663263 | 22666148 | H_c_214f06_M |
| 10 | 22669284 | 22670385 | H_c_265l12 |
| 10 | 22765449 | 22767096 | H_c_16d01 |
| 10 | 22805680 | 22805955 | H_c_77n14 |
| 10 | 23042108 | 23044010 | H_c_82e12_M |
| 10 | 23163545 | 23163623 | H_c_61c03 |
| 10 | 23260320 | 23260456 | H_c140m24 |
| 10 | 23381394 | 23381681 | H_c_83j06 |
| 10 | 23423740 | 23425187 | H_c_215i09_M |
| 10 | 23502100 | 23504130 | H_c_28g20_M |
| 10 | 23527740 | 23528639 | H_c_78i20 |
| 10 | 23672486 | 23673798 | H_c_193h14 |
| 10 | 23767567 | 23769574 | H_c_28d23 |
| 10 | 24022444 | 24025113 | H_c_81m17_M |
| 10 | 24338709 | 24338814 | H_c_162m23 |
| 10 | 24795766 | 24795959 | H_c_218a18_M |
| 10 | 24848638 | 24848898 | H_c_7b09 |
| 10 | 25051474 | 25052200 | H_c_121i05 |
| 10 | 25281043 | 25281348 | H_c_12p23_M |
| 10 | 25345265 | 25345957 | H_c136a08_M |
| 10 | 25503799 | 25505690 | H_c_76f17_M |
| 10 | 25513752 | 25514245 | H_c132i24 |
| 10 | 26539133 | 26539286 | H_c_57j07 |
| 10 | 26543448 | 26547669 | H_c_218o09_M |
| 10 | 26720537 | 26721846 | H_c_216a17_M |
| 10 | 26767013 | 26768224 | H_c_82c01_M |
| 10 | 27428840 | 27429678 | H_c_252h04_M |
| 10 | 27483680 | 27484839 | H_c_232k18_M |
| 10 | 27569110 | 27571227 | H_c_157o04_M |
| 10 | 27581454 | 27581958 | H_c_35j11 |
| 10 | 27832986 | 27833858 | H_c_62n06 |
| 10 | 28071091 | 28075782 | H_c_101f11_M_M |
| 10 | 28183250 | 28183393 | H_c_207g21 |
| 10 | 28243556 | 28243745 | H_c_209c11 |
| 10 | 2826479 | 2826657 | H_c_18g06 |
| 10 | 28693305 | 28693448 | H_c_73b14 |
| 10 | 28860954 | 28863108 | H_c_30n08_M |
| 10 | 28997473 | 28998183 | H_c_14e11 |
| 10 | 29005764 | 29007907 | H_c_147j23 |
| 10 | 29044703 | 29044820 | H_c_239g23 |
| 10 | 29050983 | 29051175 | H_c_66h02_M |
| 10 | 29090539 | 29090740 | H_c_125g09 |
| 10 | 30062147 | 30062410 | H_c_13n11 |
| 10 | 30063939 | 30066506 | H_c_224b15_M |
| 10 | 30354860 | 30356568 | H_c_4l09 |
| 10 | 30387708 | 30389494 | H_c_78k08_M |
| 10 | 30677692 | 30678754 | H_c_270a22 |
| 10 | 30762254 | 30764048 | H_c_262d07_M |
| 10 | 30903453 | 30903632 | H_c_230i03 |
| 10 | 3098579 | 3100239 | H_c_65k06_M |
| 10 | 3100240 | 3101554 | H_c_3a22_M |
| 10 | 31333467 | 31333550 | H_c_105m08 |
| 10 | 31360398 | 31361205 | H_c_108c09_M |
| 10 | 31361240 | 31361526 | H_c131i20 |
| 10 | 31647146 | 31649909 | H_c_205o10_M |
| 10 | 31932273 | 31933438 | H_c_221h13 |
| 10 | 3204628 | 3205005 | H_c_101p23_M |
| 10 | 32256976 | 32258020 | H_c_125b03_M |
| 10 | 3229654 | 3229969 | H_c_106j12 |
| 10 | 32384424 | 32385620 | H_c_206l06_M |
| 10 | 32650730 | 32650831 | H_c_49f07 |
| 10 | 32674848 | 32675684 | H_c131c15_M |
| 10 | 32675687 | 32676806 | H_c_69a10_M |
| 10 | 3271887 | 3272189 | H_c_20k13 |
| 10 | 32742134 | 32742281 | H_c_100m01 |
| 10 | 32774940 | 32775502 | H_c_126e23_M |
| 10 | 33286215 | 33287559 | H_c_67h12_M |
| 10 | 33346867 | 33347050 | H_c_116c13 |
| 10 | 33662952 | 33666290 | H_c_238l10_M |
| 10 | 33669240 | 33669324 | H_c_25e01 |
| 10 | 33717405 | 33717561 | H_c_84a15 |
| 10 | 34022327 | 34022414 | H_c_125f11 |
| 10 | 34448502 | 34448641 | H_c_119e16_M |
| 10 | 34604717 | 34604945 | H_c_194k13_M |

TABLE 1-continued

| | | | |
|---|---|---|---|
| 10 | 34836233 | 34836468 | H_c_149b14 |
| 10 | 35131416 | 35131596 | H_c_101p21 |
| 10 | 35142880 | 35144664 | H_c_6h20 |
| 10 | 35145015 | 35145148 | H_c140k09_M |
| 10 | 35203917 | 35204006 | H_c_272j03 |
| 10 | 35419053 | 35419645 | H_c143e05_M |
| 10 | 35854221 | 35854330 | H_c_154n11 |
| 10 | 35936448 | 35938007 | H_c_129h10_M |
| 10 | 35971350 | 35972335 | H_c_187p14_M |
| 10 | 3816768 | 3818375 | H_c_30g04_M |
| 10 | 38472208 | 38472276 | H_c_73j16 |
| 10 | 3892885 | 3893078 | H_c_152d11 |
| 10 | 3976895 | 3977081 | H_c_196b12 |
| 10 | 41766185 | 41766726 | H_c_2e16 |
| 10 | 41786358 | 41786529 | H_c_129i09 |
| 10 | 41814906 | 41815022 | H_c_43f16 |
| 10 | 41919942 | 41920126 | H_c_5k10 |
| 10 | 41976109 | 41976169 | H_c_199o14 |
| 10 | 42568498 | 42570940 | H_c_49a14_M |
| 10 | 42652115 | 42652732 | H_c_208p22 |
| 10 | 42713035 | 42714713 | H_c_52j19_M |
| 10 | 42748667 | 42749534 | H_c_36g16 |
| 10 | 42890948 | 42893347 | H_c_119a07 |
| 10 | 42988978 | 42989115 | H_c_58n21 |
| 10 | 43120108 | 43120704 | H_c_122o08 |
| 10 | 43177172 | 43178777 | H_c_271b09_M |
| 10 | 43211597 | 43213089 | H_c_178e02_M |
| 10 | 43222572 | 43223079 | H_c_196f14 |
| 10 | 43223098 | 43225786 | H_c137m15_M |
| 10 | 43252057 | 43253089 | H_c_18h22 |
| 10 | 43270418 | 43272200 | H_c_83i08_M |
| 10 | 43389498 | 43390248 | H_c_182m02 |
| 10 | 43463690 | 43465083 | H_c_9o03_M |
| 10 | 43504893 | 43506263 | H_c_9g18_M |
| 10 | 43630129 | 43630296 | H_c_265d09 |
| 10 | 43729504 | 43729813 | H_c_80m20 |
| 10 | 43937341 | 43937493 | H_c_157m08 |
| 10 | 43978017 | 43978129 | H_c_59k01 |
| 10 | 43999280 | 43999366 | H_c_243a22 |
| 10 | 44036622 | 44036742 | H_c_199h17 |
| 10 | 44059470 | 44059622 | H_c_6a15 |
| 10 | 44125913 | 44126945 | H_c_132c07 |
| 10 | 44144435 | 44144595 | H_c_210o07 |
| 10 | 44202069 | 44202609 | H_c_19g24_M |
| 10 | 44679553 | 44681222 | H_c_145j03_M |
| 10 | 44774642 | 44775771 | H_c_105f11_M |
| 10 | 44816083 | 44816973 | H_c_5p20_M |
| 10 | 44895119 | 44895424 | H_c_42n08 |
| 10 | 45188754 | 45190576 | H_c137d20 |
| 10 | 45234324 | 45235568 | H_c_120e18_M |
| 10 | 45409672 | 45410572 | H_c_226o14 |
| 10 | 45487517 | 45489281 | H_c_208m04_M |
| 10 | 46390521 | 46391122 | H_c_65k08_M |
| 10 | 46411451 | 46414030 | H_c_210j06_M |
| 10 | 46427904 | 46428860 | H_c_111k21_M |
| 10 | 46499667 | 46501178 | H_c_160a16 |
| 10 | 47080899 | 47083005 | H_c_59m14 |
| 10 | 47974443 | 47976042 | H_c_11d03 |
| 10 | 48156075 | 48156286 | H_c_158l21 |
| 10 | 4858332 | 4859320 | H_c_94a01 |
| 10 | 49184402 | 49185626 | H_c_70b22_M |
| 10 | 49188070 | 49188251 | H_c_149i19 |
| 10 | 49223051 | 49223147 | H_c_197g05 |
| 10 | 49245141 | 49245260 | H_c_66j23 |
| 10 | 49257189 | 49257395 | H_c_49k05 |
| 10 | 49401670 | 49402903 | H_c144c20_M |
| 10 | 49437007 | 49437222 | H_c_186h16 |
| 10 | 49482561 | 49483070 | H_c_252n09 |
| 10 | 49532317 | 49534709 | H_c_84o04 |
| 10 | 49560971 | 49561052 | H_c_267h13 |
| 10 | 49992842 | 49994111 | H_c_92i06_M |
| 10 | 50125900 | 50126068 | H_c_40g10 |
| 10 | 50272584 | 50274145 | H_c_183b14_M |
| 10 | 50416704 | 50417371 | H_c_185c19_M |
| 10 | 50438679 | 50438903 | H_c_13h06 |
| 10 | 50491787 | 50492688 | H_c136h17 |
| 10 | 50556792 | 50558113 | H_c_83l13 |
| 10 | 50639857 | 50642569 | H_c_197a01_M |
| 10 | 51040475 | 51041406 | H_c_239a04 |
| 10 | 51242064 | 51242845 | H_c_267h07 |
| 10 | 51847765 | 51848284 | H_c_157o02_M |
| 10 | 52052635 | 52055338 | H_c135g09_M |
| 10 | 52420508 | 52422312 | H_c_231l10_M |
| 10 | 52504094 | 52504797 | H_c_57g18_M |
| 10 | 53129220 | 53129686 | H_c_185i16_M |
| 10 | 53438127 | 53438348 | H_c_157c05 |
| 10 | 53743801 | 53745035 | H_c_185b08 |
| 10 | 54626532 | 54626624 | H_c_43d04 |
| 10 | 54883513 | 54883707 | H_c_274j06 |
| 10 | 55483103 | 55483333 | H_c_101a08 |
| 10 | 56143605 | 56143701 | H_c_223g10 |
| 10 | 56283594 | 56285334 | H_c_59c17 |
| 10 | 56384865 | 56384937 | H_c_2i06 |
| 10 | 56461304 | 56462010 | H_c_172j24_M |
| 10 | 56477784 | 56477881 | H_c_253d20 |
| 10 | 56599322 | 56599411 | H_c_28b11 |
| 10 | 57060089 | 57061655 | H_c_229k12 |
| 10 | 57066409 | 57066529 | H_c_159h19 |
| 10 | 57331643 | 57331805 | H_c_12d23 |
| 10 | 5747707 | 5749199 | H_c_159g24_M |
| 10 | 5766363 | 5767801 | H_c_76a10_M |
| 10 | 5774362 | 5774982 | H_c_86b22 |
| 10 | 57790421 | 57791339 | H_c_56p05 |
| 10 | 57819942 | 57820118 | H_c_162e20 |
| 10 | 58270427 | 58270548 | H_c_46h09 |
| 10 | 58538190 | 58538323 | H_c_210g01 |
| 10 | 59030792 | 59030944 | H_c144k13 |
| 10 | 59155772 | 59155970 | H_c_234o09 |
| 10 | 5922224 | 5923308 | H_c_261e14 |
| 10 | 59696461 | 59698200 | H_c_92a17_M |
| 10 | 5972379 | 5972887 | H_c_106a05 |
| 10 | 59764591 | 59765375 | H_c_2j17_M |
| 10 | 59814687 | 59815598 | H_c_193m17_M |
| 10 | 59824840 | 59824918 | H_c_37e21 |
| 10 | 60511193 | 60511280 | H_c_19h03 |
| 10 | 60605458 | 60607176 | H_c_127j02_M |
| 10 | 60694988 | 60695419 | H_c_87l19 |
| 10 | 60778928 | 60779091 | H_c_24p03 |
| 10 | 60792145 | 60792547 | H_c_69j07_M |
| 10 | 60964170 | 60964362 | H_c_124b19 |
| 10 | 61138575 | 61140450 | H_c_125d10_M |
| 10 | 61600152 | 61600310 | H_c_3f19 |
| 10 | 6170614 | 6172270 | H_c_32d15 |
| 10 | 62095449 | 62095580 | H_c_20i11 |
| 10 | 62162475 | 62163539 | H_c_273l02 |
| 10 | 62208020 | 62208827 | H_c_107n03 |
| 10 | 6226135 | 6228458 | H_c_74j10_M |
| 10 | 62372846 | 62375056 | H_c_188f11_M |
| 10 | 62430460 | 62431957 | H_c_194d12 |
| 10 | 62633278 | 62633440 | H_c_241m15_M |
| 10 | 6282677 | 6285758 | H_c_225n23_M |
| 10 | 63092460 | 63093149 | H_c_108i02_M |
| 10 | 63332821 | 63333424 | H_c133l19_M |
| 10 | 63362039 | 63362224 | H_c_111m19 |
| 10 | 63529703 | 63529774 | H_c_227m07 |
| 10 | 63697924 | 63698635 | H_c_226i06_M |
| 10 | 63803672 | 63804628 | H_c_122g12_M |
| 10 | 63833858 | 63834061 | H_c_244l08 |
| 10 | 64234185 | 64236003 | H_c_203n06 |
| 10 | 64244559 | 64245913 | H_c_245i21_M |
| 10 | 64246833 | 64249105 | H_c_209c13_M |
| 10 | 64374435 | 64374590 | H_c_24m16 |
| 10 | 6450952 | 6451102 | H_c_202p15 |
| 10 | 64894815 | 64896308 | H_c_27a04_M |
| 10 | 64907382 | 64907522 | H_c_36l20 |
| 10 | 65059848 | 65060561 | H_c_166o08_M |
| 10 | 65362159 | 65362339 | H_c_113i19 |
| 10 | 6661552 | 6662729 | H_c_9j16_M |
| 10 | 67988341 | 67988448 | H_c_97k04 |
| 10 | 68481978 | 68482114 | H_c_189f14 |
| 10 | 68721277 | 68721442 | H_c_249g03_M |
| 10 | 68763516 | 68763618 | H_c_259o23 |
| 10 | 69193719 | 69194272 | H_c_199e04_M |
| 10 | 69278683 | 69279809 | H_c_90j09 |
| 10 | 69314393 | 69315187 | H_c_212j22_M |
| 10 | 69371208 | 69371302 | H_c_204p10 |
| 10 | 6938540 | 6938798 | H_c_253a04 |
| 10 | 69625059 | 69625185 | H_c_160f09 |
| 10 | 69660808 | 69662180 | H_c_214j22 |
| 10 | 69760934 | 69762714 | H_c_127a17_M |

TABLE 1-continued

| | | | |
|---|---|---|---|
| 10 | 69836190 | 69837442 | H_c138a21_M |
| 10 | 69901221 | 69902533 | H_c__7m04 |
| 10 | 69956621 | 69957482 | H_c__145h01 |
| 10 | 69989905 | 69991213 | H_c__27c21 |
| 10 | 70150814 | 70151600 | H_c__175i20_M |
| 10 | 70255921 | 70258295 | H_c__11m22_M |
| 10 | 70310862 | 70310976 | H_c__201f12 |
| 10 | 70330592 | 70330846 | H_c__100k20_M |
| 10 | 70385571 | 70386855 | H_c__123n18_M |
| 10 | 70418293 | 70419371 | H_c__242e22 |
| 10 | 70553441 | 70554461 | H_c__199b21_M |
| 10 | 70838633 | 70838981 | H_c__211a14 |
| 10 | 70880895 | 70881817 | H_c__118o11 |
| 10 | 70998366 | 70999116 | H_c__58k12 |
| 10 | 71001636 | 71004071 | H_c__11g09_M |
| 10 | 71059446 | 71060958 | H_c__251d05 |
| 10 | 71482483 | 71484097 | H_c__112h06_M |
| 10 | 71561793 | 71562821 | H_c__20j09_M |
| 10 | 71574737 | 71576898 | H_c__27k18_M |
| 10 | 71599387 | 71601279 | H_c__17k23_M |
| 10 | 71662595 | 71663586 | H_c__152e05_M |
| 10 | 71811232 | 71813170 | H_c__147i22 |
| 10 | 71833764 | 71834680 | H_c__248l23 |
| 10 | 71870526 | 71871471 | H_c__83a10 |
| 10 | 71887927 | 71889844 | H_c__208k09_M |
| 10 | 71907374 | 71909581 | H_c__236c13_M |
| 10 | 72245375 | 72246486 | H_c__116f15 |
| 10 | 72317327 | 72318392 | H_c__17c21 |
| 10 | 72334753 | 72336555 | H_c__123f03 |
| 10 | 72642072 | 72643456 | H_c__225j18 |
| 10 | 72643570 | 72644169 | H_c__196f24_M |
| 10 | 72647030 | 72647826 | H_c__9p10 |
| 10 | 72748826 | 72749778 | H_c__196p08_M |
| 10 | 72784063 | 72786203 | H_c__238l15 |
| 10 | 72806377 | 72807592 | H_c__71p09 |
| 10 | 72826157 | 72828301 | H_c__194l12_M |
| 10 | 73200850 | 73203481 | H_c__234m15_M |
| 10 | 73393130 | 73395292 | H_c__184l04_M |
| 10 | 73516692 | 73518138 | H_c__31n14 |
| 10 | 73645542 | 73645952 | H_c__84p18_M |
| 10 | 73703028 | 73704379 | H_c__130h01_M |
| 10 | 73727599 | 73728487 | H_c__94j23 |
| 10 | 73749101 | 73749985 | H_c__103l08 |
| 10 | 73784126 | 73785284 | H_c__99e06_M |
| 10 | 74055352 | 74056280 | H_c__87e19 |
| 10 | 74207331 | 74207474 | H_c__198g11 |
| 10 | 74525824 | 74527005 | H_c__22e22_M |
| 10 | 74597167 | 74598414 | H_c__189l09_M |
| 10 | 74676457 | 74677342 | H_c__95g01 |
| 10 | 74682074 | 74682451 | H_c__222f04_M |
| 10 | 74842840 | 74844003 | H_c__26m19_M |
| 10 | 7488219 | 7490230 | H_c133l12_M |
| 10 | 7492146 | 7495499 | H_c__69i21_M |
| 10 | 74982984 | 74983071 | H_c__6k09 |
| 10 | 75076847 | 75078024 | H_c__39j09 |
| 10 | 75201918 | 75203624 | H_c__196g23_M |
| 10 | 75303270 | 75305603 | H_c__177n24 |
| 10 | 75340228 | 75342316 | H_c__217g10_M |
| 10 | 75387226 | 75387386 | H_c__161o01 |
| 10 | 75606134 | 75607308 | H_c__274m01_M |
| 10 | 76253947 | 76257262 | H_c__94o17_M |
| 10 | 7626542 | 7626618 | H_c__1k10 |
| 10 | 76419397 | 76419473 | H_c__208m03 |
| 10 | 76473308 | 76474223 | H_c__207k08 |
| 10 | 76528632 | 76529621 | H_c__203a10 |
| 10 | 76540895 | 76542137 | H_c__203b17 |
| 10 | 76639123 | 76641221 | H_c__226j14_M |
| 10 | 76663770 | 76666112 | H_c__204m05_M |
| 10 | 76724281 | 76724675 | H_c__245c19_M |
| 10 | 76825576 | 76827102 | H_c__150i07_M |
| 10 | 76829585 | 76831688 | H_c132g05_M |
| 10 | 76837790 | 76839638 | H_c__11l24_M |
| 10 | 76839692 | 76839900 | H_c__176f14 |
| 10 | 76860455 | 76861871 | H_c__169f03_M |
| 10 | 77762393 | 77762845 | H_c__72p07 |
| 10 | 7818774 | 7820902 | H_c__111c24 |
| 10 | 78282077 | 78282253 | H_c__231m03 |
| 10 | 78463363 | 78463708 | H_c__168n12 |
| 10 | 7869427 | 7870641 | H_c__129j16_M |
| 10 | 78869026 | 78869843 | H_c__18n01 |
| 10 | 7900071 | 7901464 | H_c__78l07 |
| 10 | 79288419 | 79288524 | H_c__239b15 |
| 10 | 79355616 | 79357191 | H_c__84k11 |
| 10 | 79463343 | 79464230 | H_c__18e02_M |
| 10 | 79732386 | 79733410 | H_c__210e07_M |
| 10 | 7996804 | 7997976 | H_c__153n02 |
| 10 | 80129649 | 80129768 | H_c__95f21 |
| 10 | 8033005 | 8033092 | H_c__231i14 |
| 10 | 80402846 | 80404755 | H_c__118d11_M |
| 10 | 80480587 | 80482018 | H_c__158h16 |
| 10 | 80496168 | 80500223 | H_c__203a03_M_M |
| 10 | 80636852 | 80639562 | H_c__235i09 |
| 10 | 8115607 | 8117309 | H_c__150o15_M |
| 10 | 8131491 | 8132758 | H_c__59a08_M |
| 10 | 8135264 | 8137775 | H_c__54n24_M |
| 10 | 8137777 | 8138533 | H_c__20f21_M |
| 10 | 81731091 | 81732423 | H_c__6m21_M |
| 10 | 81828188 | 81829175 | H_c__75g18_M |
| 10 | 818585 | 820998 | H_c__203p13 |
| 10 | 81954639 | 81955552 | H_c__188c15_M |
| 10 | 81958624 | 81958724 | H_c__64d05 |
| 10 | 82157907 | 82158860 | H_c__265f10_M |
| 10 | 82203138 | 82204952 | H_c__244p02 |
| 10 | 82767781 | 82767923 | H_c__220i01 |
| 10 | 82807005 | 82807184 | H_c__241p21 |
| 10 | 82928004 | 82928074 | H_c__60l23 |
| 10 | 83033418 | 83033558 | H_c__216e13_M |
| 10 | 83236837 | 83236882 | H_c__59b13 |
| 10 | 83312525 | 83312684 | H_c__129c20 |
| 10 | 83314794 | 83314956 | H_c__259g05 |
| 10 | 84360669 | 84360738 | H_c__26d14 |
| 10 | 84372974 | 84373089 | H_c__163h09 |
| 10 | 85473027 | 85473115 | H_c__78k02 |
| 10 | 85777275 | 85777539 | H_c142a20_M |
| 10 | 85944096 | 85945503 | H_c__90e15_M |
| 10 | 86077769 | 86079056 | H_c__233j14_M |
| 10 | 86289787 | 86291114 | H_c__209l02 |
| 10 | 86596291 | 86596495 | H_c__121f17_M |
| 10 | 86836472 | 86836751 | H_c__240j02 |
| 10 | 86851512 | 86852164 | H_c__117e14 |
| 10 | 87556418 | 87556582 | H_c__71m21 |
| 10 | 88012971 | 88013489 | H_c__232h13_M |
| 10 | 88112804 | 88113976 | H_c__38j02 |
| 10 | 88125907 | 88127356 | H_c__54k02_M |
| 10 | 88149362 | 88151846 | H_c__55h06_M |
| 10 | 88270605 | 88272164 | H_c135c16_M |
| 10 | 88381691 | 88382214 | H_c__222i09_M |
| 10 | 88461139 | 88461626 | H_c__68m04_M |
| 10 | 88505330 | 88506957 | H_c__3g17_M |
| 10 | 88718192 | 88721707 | H_c__216p07_M |
| 10 | 88844609 | 88845742 | H_c__27i16_M |
| 10 | 89091401 | 89092835 | H_c__21g01 |
| 10 | 89253979 | 89255497 | H_c__166h08 |
| 10 | 89409076 | 89410190 | H_c__164d01 |
| 10 | 89567842 | 89568109 | H_c__70i06_M |
| 10 | 89611243 | 89613869 | H_c__243n03_M |
| 10 | 90320090 | 90320209 | H_c__270i06 |
| 10 | 90332162 | 90333283 | H_c__28e17_M |
| 10 | 90406757 | 90406841 | H_c__161i04 |
| 10 | 90629701 | 90630921 | H_c__122m19_M |
| 10 | 90957524 | 90957910 | H_c__77b21_M |
| 10 | 91134552 | 91134838 | H_c__195b07 |
| 10 | 91164375 | 91165380 | H_c__65d16_M |
| 10 | 91284835 | 91286133 | H_c__82l03_M |
| 10 | 91289212 | 91289416 | H_c144e19 |
| 10 | 91393826 | 91395309 | H_c142h06_M |
| 10 | 91586298 | 91587325 | H_c__188a23 |
| 10 | 91978227 | 91978378 | H_c__101o21 |
| 10 | 92458330 | 92458487 | H_c__166p24 |
| 10 | 92607398 | 92608101 | H_c__60d09 |
| 10 | 92694757 | 92694920 | H_c__28i09 |
| 10 | 92911973 | 92913724 | H_c__181i07 |
| 10 | 92970157 | 92970968 | H_c__123h03_M |
| 10 | 93159082 | 93160762 | H_c__247h22_M |
| 10 | 93382497 | 93383438 | H_c__208c23 |
| 10 | 93547968 | 93548959 | H_c__266h15 |
| 10 | 93629984 | 93630062 | H_c__42a14_M |
| 10 | 93637006 | 93637215 | H_c__63j08_M |
| 10 | 93637218 | 93637389 | H_c__153n01_M |
| 10 | 93657729 | 93659397 | H_c__86b10 |

TABLE 1-continued

| | | | |
|---|---|---|---|
| 10 | 93673379 | 93674034 | H_c__13c06_M |
| 10 | 93989016 | 93990540 | H_c__44j20_M |
| 10 | 94040138 | 94041533 | H_c__89m06 |
| 10 | 94170390 | 94170927 | H_c__234c08 |
| 10 | 94322788 | 94324415 | H_c__211h04_M |
| 10 | 94341292 | 94343421 | H_c__120k09_M |
| 10 | 94439167 | 94440567 | H_c__212g16_M |
| 10 | 94809441 | 94810452 | H_c__88l09_M |
| 10 | 94815533 | 94819076 | H_c__215n15_M |
| 10 | 94822627 | 94825309 | H_c__163g20_M |
| 10 | 95045683 | 95045767 | H_c__210a13 |
| 10 | 95246029 | 95246857 | H_c__31o16_M |
| 10 | 95246534 | 95246873 | H_c142o21 |
| 10 | 95317294 | 95318175 | H_c__243a03 |
| 10 | 95451889 | 95452857 | H_c__236a20 |
| 10 | 95643623 | 95644358 | H_c__164j21_M |
| 10 | 95937334 | 95937498 | H_c__234i23 |
| 10 | 96151792 | 96153696 | H_c__188o10 |
| 10 | 96295095 | 96296015 | H_c__125o13_M |
| 10 | 96933021 | 96933980 | H_c__127h19_M |
| 10 | 97034102 | 97035161 | H_c139f14 |
| 10 | 97040107 | 97041152 | H_c__22d05_M |
| 10 | 97044634 | 97045878 | H_c__49f22 |
| 10 | 97310946 | 97311521 | H_c__72i15 |
| 10 | 97376289 | 97376811 | H_c__103j22 |
| 10 | 97405688 | 97406742 | H_c__222o11_M |
| 10 | 97443853 | 97444135 | H_c__3b19 |
| 10 | 97657098 | 97658054 | H_c__218h03_M |
| 10 | 97752562 | 97752817 | H_c__199i02 |
| 10 | 97792916 | 97794351 | H_c__41i07_M |
| 10 | 97880130 | 97880686 | H_c__158p12_M |
| 10 | 98124014 | 98125626 | H_c__107i13 |
| 10 | 98145190 | 98145948 | H_c__95b20 |
| 10 | 98214162 | 98214340 | H_c__92a14 |
| 10 | 98262833 | 98264277 | H_c__72k19_M |
| 10 | 98335961 | 98337078 | H_c__3l15_M |
| 10 | 98505858 | 98505931 | H_c__11j01 |
| 10 | 98581564 | 98583198 | H_c__36f19_M |
| 10 | 98634007 | 98634077 | H_c__104j15 |
| 10 | 98807567 | 98809555 | H_c__241e19 |
| 10 | 98934470 | 98936248 | H_c__71n06 |
| 10 | 98945888 | 98946730 | H_c__54d03 |
| 10 | 99070623 | 99071527 | H_c__194f17_M |
| 10 | 99083431 | 99085404 | H_c__8b04_M |
| 10 | 99149811 | 99151009 | H_c131g08 |
| 10 | 99175595 | 99176302 | H_c__35m17 |
| 10 | 99195097 | 99196371 | H_c__267l03 |
| 10 | 99247838 | 99250019 | H_c__48g15_M |
| 10 | 99389763 | 99391434 | H_c__158j21 |
| 10 | 99436192 | 99437575 | H_c__6n03_M |
| 10 | 99450785 | 99452991 | H_c__1c16 |
| 10 | 99462780 | 99464879 | H_c__202f20_M |
| 10 | 99486751 | 99487668 | H_c__185g22_M |
| 10 | 99599163 | 99601114 | H_c__135i01_M |
| 10 | 99724593 | 99724866 | H_c__96b01 |
| 11 | 100503110 | 100505920 | H_c__63e13_M |
| 11 | 100561766 | 100561931 | H_c__150j19 |
| 11 | 100958086 | 100959646 | H_c__48a17 |
| 11 | 100964623 | 100964704 | H_c__176p07 |
| 11 | 101290624 | 101291613 | H_c__4k08_M |
| 11 | 101344198 | 101344310 | H_c__160g22 |
| 11 | 101423151 | 101423881 | H_c__4n14_M |
| 11 | 101595491 | 101595588 | H_c__74c09 |
| 11 | 101722660 | 101723483 | H_c__116d22_M |
| 11 | 101779262 | 101779356 | H_c__53g03 |
| 11 | 101828149 | 101829204 | H_c__53a14_M |
| 11 | 10211715 | 10211787 | H_c__45d24_M |
| 11 | 102485026 | 102485837 | H_c__145k12_M |
| 11 | 10271506 | 10273193 | H_c__9c04_M |
| 11 | 10281694 | 10285020 | H_c__7b15_M |
| 11 | 10285952 | 10286130 | H_c__189m24 |
| 11 | 103539718 | 103540336 | H_c__4r24_M |
| 11 | 104081599 | 104081754 | H_c__10m13 |
| 11 | 10428006 | 10429453 | H_c__69d09_M |
| 11 | 10443540 | 10445557 | H_c__21b15_M |
| 11 | 104985850 | 104986754 | H_c__110p17_M |
| 11 | 10499133 | 10499407 | H_c139m16 |
| 11 | 105017246 | 105017371 | H_c__106p17 |
| 11 | 105592641 | 105592729 | H_c__43j13 |
| 11 | 105886528 | 105886624 | H_c__226p19 |
| 11 | 106392982 | 106395691 | H_c__70f15_M |
| 11 | 10674602 | 10674881 | H_c__105n02_M |
| 11 | 106774161 | 106774264 | H_c__43l06 |
| 11 | 106833805 | 106833913 | H_c__31i17 |
| 11 | 10684185 | 10684279 | H_c__185c24 |
| 11 | 106966953 | 106967574 | H_c__251i13 |
| 11 | 107234372 | 107234877 | H_c__231f16 |
| 11 | 10728944 | 10730110 | H_c__208f04_M |
| 11 | 107303861 | 107305376 | H_c__122m08_M |
| 11 | 107384699 | 107385261 | H_c__244f20_M |
| 11 | 107496482 | 107497848 | H_c__160b08_M |
| 11 | 107598271 | 107599316 | H_c__31b22_M |
| 11 | 107843274 | 107843713 | H_c__23j01 |
| 11 | 10785850 | 10787914 | H_c__52k18 |
| 11 | 107873872 | 107874888 | H_c__241j14_M |
| 11 | 107968569 | 107969436 | H_c__30f08 |
| 11 | 10835616 | 10837071 | H_c__274n22_M |
| 11 | 108506148 | 108506284 | H_c__18p13 |
| 11 | 108820202 | 108820307 | H_c140p02 |
| 11 | 109104187 | 109104363 | H_c__7n13 |
| 11 | 109468356 | 109469836 | H_c__161l14_M |
| 11 | 109671651 | 109673103 | H_c__164g24_M |
| 11 | 109700409 | 109701848 | H_c__23e23 |
| 11 | 109891456 | 109891581 | H_c__149g22 |
| 11 | 110026581 | 110026950 | H_c__108a18_M |
| 11 | 110086865 | 110089199 | H_c__120m07_M |
| 11 | 110249838 | 110250187 | H_c__186g13 |
| 11 | 110674413 | 110677129 | H_c__219f17_M |
| 11 | 110887582 | 110889121 | H_c__52j14_M |
| 11 | 110915844 | 110917686 | H_c__241i12_M |
| 11 | 110977743 | 110979276 | H_c__34m20_M |
| 11 | 111142214 | 111142428 | H_c__55c04_M |
| 11 | 111201500 | 111201602 | H_c__62o24 |
| 11 | 111244195 | 111244311 | H_c__206h18 |
| 11 | 111254728 | 111255540 | H_c__48l07_M |
| 11 | 111312772 | 111314368 | H_c__272f01_M |
| 11 | 111352796 | 111354008 | H_c__98l04 |
| 11 | 111401027 | 111402068 | H_c__113h09 |
| 11 | 111585845 | 111585976 | H_c__47m07 |
| 11 | 111602224 | 111602680 | H_c__102p09 |
| 11 | 111665424 | 111666375 | H_c__254h16_M |
| 11 | 111678167 | 111678327 | H_c__246b17 |
| 11 | 111884442 | 111884676 | H_c__218k15 |
| 11 | 112316642 | 112316752 | H_c__31i03 |
| 11 | 112337028 | 112339892 | H_c__26o17_M |
| 11 | 112619159 | 112619903 | H_c__115o16 |
| 11 | 112666648 | 112666819 | H_c__25h07 |
| 11 | 112690192 | 112690815 | H_c__161c03_M |
| 11 | 112849482 | 112852267 | H_c__198i04_M |
| 11 | 112974257 | 112974466 | H_c__31j11 |
| 11 | 113250997 | 113251863 | H_c__223c15_M |
| 11 | 113412004 | 113412375 | H_c__32m12 |
| 11 | 113435250 | 113437626 | H_c__33e20 |
| 11 | 113511690 | 113512129 | H_c__120c21 |
| 11 | 113775899 | 113777070 | H_c__270a13_M |
| 11 | 113815136 | 113815963 | H_c__3m07_M |
| 11 | 114056943 | 114057110 | H_c__160j01 |
| 11 | 114129433 | 114129529 | H_c__57m04 |
| 11 | 114642959 | 114643105 | H_c__186c17 |
| 11 | 114878504 | 114880571 | H_c__8g03_M |
| 11 | 115034825 | 115036002 | H_c__126k02 |
| 11 | 115337236 | 115337358 | H_c__169m13 |
| 11 | 115876637 | 115876842 | H_c__16j15 |
| 11 | 115955725 | 115956606 | H_c__6n19_M |
| 11 | 11598379 | 11599957 | H_c__39d04_M |
| 11 | 116093599 | 116095236 | H_c__91b11 |
| 11 | 116148528 | 116149440 | H_c__162e14 |
| 11 | 116163322 | 116165403 | H_c__95d17_M |
| 11 | 116473535 | 116474777 | H_c__123i07_M |
| 11 | 116554593 | 116554706 | H_c__100l09 |
| 11 | 116607609 | 116609374 | H_c__2c14_M |
| 11 | 116690749 | 116692401 | H_c__215h12_M |
| 11 | 116703620 | 116704367 | H_c__273c17 |
| 11 | 116872763 | 116874748 | H_c__92k08 |
| 11 | 117250731 | 117253087 | H_c__93k08 |
| 11 | 117361941 | 117362516 | H_c__158n18 |
| 11 | 117521182 | 117522412 | H_c__246d02 |
| 11 | 117527802 | 117529999 | H_c__232e22_M |
| 11 | 117906381 | 117908375 | H_c__154j05_M |
| 11 | 118010358 | 118011502 | H_c__200h12 |

TABLE 1-continued

| | | | |
|---|---|---|---|
| 11 | 118165915 | 118168477 | H_c__113n14_M |
| 11 | 11819306 | 11820635 | H_c__224a22_M |
| 11 | 118260566 | 118261589 | H_c__115n03 |
| 11 | 118301021 | 118302608 | H_c__57g01 |
| 11 | 118373909 | 118374872 | H_c__66d01 |
| 11 | 118393654 | 118395289 | H_c__16f14_M |
| 11 | 118405950 | 118406902 | H_c__110p02 |
| 11 | 118432121 | 118433729 | H_c__254i01_M |
| 11 | 118460302 | 118461121 | H_c__28g07 |
| 11 | 118469928 | 118470825 | H_c__62b11_M |
| 11 | 118483236 | 118484390 | H_c__129a08_M |
| 11 | 118497042 | 118498074 | H_c__212o19_M |
| 11 | 118524936 | 118527162 | H_c__239n24_M |
| 11 | 118544266 | 118545341 | H_c__123o17 |
| 11 | 118581740 | 118582739 | H_c__190m05_M |
| 11 | 118696692 | 118697267 | H_c__74d02 |
| 11 | 118732696 | 118732974 | H_c__44l11_M |
| 11 | 118739950 | 118740645 | H_c__163c04_M |
| 11 | 118797550 | 118798446 | H_c__240f11 |
| 11 | 118856829 | 118858351 | H_c__161p15 |
| 11 | 118880875 | 118881088 | H_c__230b17 |
| 11 | 118960594 | 118961816 | H_c__114g24 |
| 11 | 119104106 | 119106282 | H_c__72j04_M |
| 11 | 119341799 | 119341932 | H_c__79k19 |
| 11 | 119415343 | 119415525 | H_c__180m18 |
| 11 | 119544151 | 119545676 | H_c__170m15 |
| 11 | 119586019 | 119586838 | H_c__198h09 |
| 11 | 119586864 | 119589450 | H_c__228d16 |
| 11 | 119615610 | 119618484 | H_c__219p21_M |
| 11 | 119700985 | 119701787 | H_c__87b18_M |
| 11 | 119706953 | 119707239 | H_c__41h08 |
| 11 | 119711544 | 119713615 | H_c__18j04_M |
| 11 | 119817222 | 119817442 | H_c__112g17 |
| 11 | 11985820 | 11988586 | H_c__71e14_M |
| 11 | 119886616 | 119889449 | H_c__22p11_M |
| 11 | 119939907 | 119941146 | H_c__9o14_M |
| 11 | 120072436 | 120074109 | H_c__91f09 |
| 11 | 120308645 | 120308895 | H_c__205l09 |
| 11 | 120361710 | 120362597 | H_c__19h18_M |
| 11 | 120399475 | 120400876 | H_c__38f21_M |
| 11 | 120590285 | 120590466 | H_c__124e11 |
| 11 | 120668432 | 120669166 | H_c__70j11_M |
| 11 | 120748800 | 120749051 | H_c138g11_M |
| 11 | 120769070 | 120769248 | H_c__6l18 |
| 11 | 120808628 | 120808752 | H_c__219d12_M |
| 11 | 120827962 | 120829064 | H_c__183g07_M |
| 11 | 120854407 | 120855529 | H_c__192h09 |
| 11 | 12088115 | 12089333 | H_c__94d05 |
| 11 | 121194827 | 121195094 | H_c__115c14 |
| 11 | 121272296 | 121272558 | H_c__80o17 |
| 11 | 121932465 | 121933626 | H_c133b18 |
| 11 | 12200198 | 12200944 | H_c__69e01 |
| 11 | 122031554 | 122033019 | H_c__40m18 |
| 11 | 122214551 | 122214796 | H_c__6i04 |
| 11 | 122258499 | 122259551 | H_c__245d23_M |
| 11 | 122352691 | 122360639 | H_c__99f17_M_M_M |
| 11 | 122437844 | 122438888 | H_c__240n21_M |
| 11 | 122570428 | 122572979 | H_c__87j11 |
| 11 | 122788228 | 122788307 | H_c__50k13 |
| 11 | 122805791 | 122807534 | H_c__3d23 |
| 11 | 122956279 | 122956875 | H_c__91i09 |
| 11 | 123029260 | 123030951 | H_c__175d15 |
| 11 | 123117048 | 123117744 | H_c__239a23 |
| 11 | 123313328 | 123313522 | H_c__128a13 |
| 11 | 12354884 | 12356364 | H_c__200n10 |
| 11 | 12354894 | 12356478 | H_c__108m12_M |
| 11 | 124048775 | 124048985 | H_c__225j10_M |
| 11 | 124134349 | 124138344 | H_c__183h23_M |
| 11 | 124174534 | 124175857 | H_c132a22 |
| 11 | 124214028 | 124215473 | H_c__54b01_M |
| 11 | 124239825 | 124241460 | H_c__145m23_M |
| 11 | 124243605 | 124246390 | H_c__266l19_M |
| 11 | 124295004 | 124296746 | H_c__205p22 |
| 11 | 124328721 | 124329622 | H_c__28e05 |
| 11 | 124437605 | 124439266 | H_c__118p16_M |
| 11 | 124486775 | 124487286 | H_c__94b15 |
| 11 | 124704606 | 124705609 | H_c__50c05 |
| 11 | 124869830 | 124871501 | H_c__40h11_M |
| 11 | 124944232 | 124945188 | H_c__11d17_M |
| 11 | 125000300 | 125001598 | H_c__238k05_M |
| 11 | 125262747 | 125263444 | H_c__48n19_M |
| 11 | 125279032 | 125279983 | H_c__113p04 |
| 11 | 125436904 | 125438660 | H_c__168e07_M |
| 11 | 125585887 | 125586992 | H_c143g11_M |
| 11 | 125643617 | 125644615 | H_c__71k10_M |
| 11 | 125657861 | 125658956 | H_c__210d15_M |
| 11 | 125678810 | 125679570 | H_c__69b03 |
| 11 | 125791419 | 125792322 | H_c__215g21_M |
| 11 | 125819447 | 125820870 | H_c__258f15 |
| 11 | 126123477 | 126123659 | H_c__38k21 |
| 11 | 126240987 | 126241148 | H_c__124k10 |
| 11 | 126378247 | 126379353 | H_c__52l07_M |
| 11 | 126667855 | 126668059 | H_c__34o23 |
| 11 | 127186346 | 127186416 | H_c__19o14 |
| 11 | 127422636 | 127422716 | H_c__75h12 |
| 11 | 127897165 | 127898473 | H_c__13e08 |
| 11 | 12792780 | 12793142 | H_c__149b21 |
| 11 | 127950520 | 127952198 | H_c__76n22 |
| 11 | 128062148 | 128062446 | H_c__2a21_M |
| 11 | 128067859 | 128070775 | H_c__79l07_M |
| 11 | 128265591 | 128267259 | H_c__72i04_M |
| 11 | 128280140 | 128281003 | H_c__128o18_M |
| 11 | 128654168 | 128655606 | H_c__111h10_M |
| 11 | 128748144 | 128748848 | H_c__76i19_M |
| 11 | 128749204 | 128751417 | H_c__62c07_M |
| 11 | 128929482 | 128929618 | H_c__33p10 |
| 11 | 128992875 | 128993737 | H_c__186c07 |
| 11 | 129270065 | 129271196 | H_c__15o17_M |
| 11 | 129376851 | 129378735 | H_c__71c10_M |
| 11 | 129443002 | 129446162 | H_c__69g15_M |
| 11 | 129689313 | 129690928 | H_c__228l03_M |
| 11 | 129801195 | 129803967 | H_c__79d01 |
| 11 | 129823723 | 129825137 | H_c__19o08_M |
| 11 | 130518425 | 130518508 | H_c__28e19_M |
| 11 | 130578015 | 130578162 | H_c__198a21_M |
| 11 | 130987714 | 130987828 | H_c__202l22 |
| 11 | 131285556 | 131286992 | H_c__243a14 |
| 11 | 1313281 | 1315429 | H_c__175h18 |
| 11 | 132318557 | 132319639 | H_c__49f09_M |
| 11 | 132369214 | 132369389 | H_c__204l22 |
| 11 | 132456802 | 132459028 | H_c__92a16 |
| 11 | 13254860 | 13257422 | H_c137j12_M |
| 11 | 133162754 | 133163234 | H_c140l03_M |
| 11 | 133207430 | 133209127 | H_c__24m04 |
| 11 | 133278580 | 133278660 | H_c__30c15 |
| 11 | 133411911 | 133412829 | H_c__4i20 |
| 11 | 133598655 | 133601127 | H_c131c14_M |
| 11 | 133627816 | 133629228 | H_c136c21_M |
| 11 | 133650944 | 133652502 | H_c__51b05_M |
| 11 | 133706627 | 133707941 | H_c__187m15_M |
| 11 | 133785715 | 133788416 | H_c__109g15_M |
| 11 | 133983153 | 133984109 | H_c__112l14 |
| 11 | 134253918 | 134254183 | H_c__217a23 |
| 11 | 13440728 | 13441849 | H_c__274c17_M |
| 11 | 13645946 | 13647740 | H_c__4n19_M |
| 11 | 13779234 | 13779381 | H_c__145c11 |
| 11 | 13787186 | 13787284 | H_c__12e18 |
| 11 | 14233587 | 14233665 | H_c__197b15 |
| 11 | 14336264 | 14337600 | H_c__111c23_M |
| 11 | 14359010 | 14359709 | H_c__11k14_M |
| 11 | 14404823 | 14405179 | H_c__208h19 |
| 11 | 14497662 | 14498827 | H_c__43e19_M |
| 11 | 14869664 | 14870686 | H_c__34e03 |
| 11 | 14895905 | 14895989 | H_c__29c24 |
| 11 | 14949874 | 14950698 | H_c__38o21_M |
| 11 | 14950881 | 14952278 | H_c__1o16_M |
| 11 | 15049619 | 15052317 | H_c__59m23_M |
| 11 | 15091972 | 15093756 | H_c__111p17_M |
| 11 | 15191285 | 15191440 | H_c__120d06 |
| 11 | 1550313 | 1551398 | H_c__34c12_M |
| 11 | 15627688 | 15628675 | H_c__70e23 |
| 11 | 1605750 | 1607057 | H_c__109n04_M |
| 11 | 16168089 | 16168234 | H_c__215m16 |
| 11 | 16580246 | 16580452 | H_c__70h14 |
| 11 | 16583162 | 16585539 | H_c__33f04_M |
| 11 | 16903400 | 16904563 | H_c__258p07_M |
| 11 | 16990709 | 16992986 | H_c__123c10 |
| 11 | 17185350 | 17186559 | H_c__73j24_M |
| 11 | 17254402 | 17255381 | H_c__205n20_M |
| 11 | 17289472 | 17289650 | H_c__60f21 |

TABLE 1-continued

| | | | |
|---|---|---|---|
| 11 | 17329577 | 17332049 | H_c_85g18_M |
| 11 | 17366901 | 17367906 | H_c_189c08_M |
| 11 | 1741143 | 1742172 | H_c_123m01_M |
| 11 | 17453925 | 17455830 | H_c_190o06_M |
| 11 | 17521565 | 17523558 | H_c_68d15 |
| 11 | 17572206 | 17572697 | H_c_115j15 |
| 11 | 17696154 | 17697728 | H_c_261g19 |
| 11 | 17699730 | 17700502 | H_c_233o08 |
| 11 | 17990340 | 17991862 | H_c_41j20 |
| 11 | 18077239 | 18077409 | H_c135g15 |
| 11 | 18083683 | 18084957 | H_c_30e03_M |
| 11 | 18300091 | 18301077 | H_c_182c02_M |
| 11 | 18447937 | 18447986 | H_c_168m03 |
| 11 | 18566109 | 18567163 | H_c_187l19 |
| 11 | 18676549 | 18677709 | H_c_108d03_M |
| 11 | 18683844 | 18684419 | H_c_74a04_M |
| 11 | 18810028 | 18810191 | H_c_34l23 |
| 11 | 19094962 | 19095895 | H_c_241i07 |
| 11 | 19218937 | 19219701 | H_c_85c18_M |
| 11 | 19219751 | 19221356 | H_c_167k17 |
| 11 | 194920 | 200016 | H_c_209p11_M |
| 11 | 19690605 | 19692284 | H_c_204f11_M |
| 11 | 19755077 | 19755638 | H_c_274k21_M |
| 11 | 20109196 | 20110985 | H_c_27i17 |
| 11 | 20138307 | 20138874 | H_c_259d05_M_M |
| 11 | 20141233 | 20142125 | H_c_69m23_M |
| 11 | 20341561 | 20342462 | H_c_87n24_M |
| 11 | 20365563 | 20366827 | H_c_38a24_M |
| 11 | 20424101 | 20424260 | H_c_246j22 |
| 11 | 20574947 | 20577014 | H_c143g08_M |
| 11 | 20579203 | 20580143 | H_c_15l20_M |
| 11 | 20582158 | 20583413 | H_c_84f20 |
| 11 | 20646898 | 20649178 | H_c_45o01 |
| 11 | 2114304 | 2116470 | H_c_243o04_M |
| 11 | 21197846 | 21197938 | H_c_81f12 |
| 11 | 2121600 | 2122466 | H_c_54j11_M |
| 11 | 21677098 | 21677218 | H_c_161f01 |
| 11 | 21795258 | 21795391 | H_c_229m14 |
| 11 | 21836219 | 21836382 | H_c_187o22 |
| 11 | 21871951 | 21872040 | H_c_15f16 |
| 11 | 22170687 | 22171598 | H_c_209g21 |
| 11 | 22319465 | 22320162 | H_c_53p16 |
| 11 | 2246606 | 2249136 | H_c_4a12_M |
| 11 | 2249192 | 2249335 | H_c_274n06_M |
| 11 | 225735 | 226641 | H_c_14c22 |
| 11 | 226812 | 227403 | H_c_72b23_M |
| 11 | 22733655 | 22733816 | H_c_266k13 |
| 11 | 22807386 | 22808114 | H_c_27f21_M |
| 11 | 23503613 | 23503723 | H_c_206f10 |
| 11 | 2353959 | 2356616 | H_c_103k18 |
| 11 | 2377258 | 2378671 | H_c_237m20_M |
| 11 | 2421856 | 2423838 | H_c_261c09 |
| 11 | 24369628 | 24371406 | H_c_207a06 |
| 11 | 24474823 | 24475806 | H_c_72o18_M |
| 11 | 25173725 | 25173831 | H_c_258o05 |
| 11 | 25346939 | 25347049 | H_c_267k21 |
| 11 | 25429340 | 25429731 | H_c_216m10 |
| 11 | 25442203 | 25442309 | H_c_171k24 |
| 11 | 25918144 | 25918272 | H_c_108p02 |
| 11 | 27340901 | 27341888 | H_c_30c12_M |
| 11 | 27449531 | 27451347 | H_c_31n24 |
| 11 | 2764794 | 2764906 | H_c_215m06 |
| 11 | 27650084 | 27650175 | H_c_223c10 |
| 11 | 27678418 | 27679157 | H_c_22c08_M |
| 11 | 27700618 | 27701365 | H_c_35n04_M |
| 11 | 28086245 | 28086572 | H_c_30m22 |
| 11 | 28141020 | 28141090 | H_c_50i18 |
| 11 | 28324333 | 28324431 | H_c_25f20_M |
| 11 | 2840286 | 2840891 | H_c_115h01_M |
| 11 | 2847110 | 2848644 | H_c_154e07_M |
| 11 | 2861590 | 2865091 | H_c_54k19_M |
| 11 | 2906363 | 2908204 | H_c_167m18 |
| 11 | 2969604 | 2970326 | H_c_226j10_M |
| 11 | 29995064 | 29995986 | H_c_237m15_M |
| 11 | 30339110 | 30339320 | H_c_245n05 |
| 11 | 3034120 | 3035473 | H_c_154f02_M |
| 11 | 30562410 | 30563007 | H_c_92c09 |
| 11 | 30801833 | 30802046 | H_c_89d12 |
| 11 | 30841694 | 30841867 | H_c_42m04 |
| 11 | 31487891 | 31488310 | H_c_184g16 |
| 11 | 31776844 | 31777549 | H_c_48m03_M |
| 11 | 31777676 | 31777982 | H_c138j10 |
| 11 | 31783094 | 31784608 | H_c_9g06_M |
| 11 | 31787588 | 31791451 | H_c_66j01_M |
| 11 | 31794075 | 31798972 | H_c_27j03_M_M |
| 11 | 31803698 | 31804585 | H_c_163c01 |
| 11 | 31964980 | 31966033 | H_c_213k10 |
| 11 | 32068306 | 32070666 | H_c_45n23_M |
| 11 | 32311465 | 32312286 | H_c_97m14 |
| 11 | 32404117 | 32405761 | H_c144a07_M |
| 11 | 32415642 | 32416589 | H_c_122j10 |
| 11 | 32561672 | 32562472 | H_c_73j14_M |
| 11 | 32807771 | 32808603 | H_c_77d18_M |
| 11 | 32870300 | 32872118 | H_c_184g07 |
| 11 | 32993788 | 32994004 | H_c_232h24_M |
| 11 | 33017250 | 33018405 | H_c136a12 |
| 11 | 33224934 | 33225067 | H_c_116i03 |
| 11 | 33235209 | 33237289 | H_c_162h13_M |
| 11 | 33354061 | 33355295 | H_c_59b07_M |
| 11 | 33678420 | 33679810 | H_c_53o09_M |
| 11 | 33713751 | 33714842 | H_c_11b09 |
| 11 | 33751588 | 33753184 | H_c_248g11_M |
| 11 | 33846815 | 33848828 | H_c_241j16_M |
| 11 | 33969618 | 33969777 | H_c_44i10 |
| 11 | 34029266 | 34031304 | H_c_160n19_M |
| 11 | 34083417 | 34083725 | H_c_128a11_M |
| 11 | 34334374 | 34336282 | H_c_76n06_M |
| 11 | 34416657 | 34417705 | H_c141d07_M |
| 11 | 34626081 | 34626301 | H_c_105p16 |
| 11 | 34893803 | 34895366 | H_c_72m08_M |
| 11 | 35117170 | 35118489 | H_c_88g19 |
| 11 | 35282490 | 35282672 | H_c_58o14 |
| 11 | 35284784 | 35285064 | H_c_108o14 |
| 11 | 35397192 | 35397708 | H_c_56i13_M |
| 11 | 35596419 | 35597585 | H_c_225o21 |
| 11 | 35640828 | 35641901 | H_c_187n12_M |
| 11 | 35769503 | 35770134 | H_c_147g09 |
| 11 | 36041264 | 36041388 | H_c_249n12 |
| 11 | 36354243 | 36355006 | H_c_68p16_M |
| 11 | 36355253 | 36356364 | H_c_215a03_M |
| 11 | 36487451 | 36488632 | H_c_56l11_M |
| 11 | 36529548 | 36529709 | H_c_156f07 |
| 11 | 36616694 | 36616798 | H_c_237o08 |
| 11 | 36619776 | 36619957 | H_c_59m22 |
| 11 | 36695050 | 36695205 | H_c_231m23 |
| 11 | 3702308 | 3702450 | H_c_167o15 |
| 11 | 37709828 | 37710066 | H_c_231f01 |
| 11 | 3774735 | 3776592 | H_c_170d17_M |
| 11 | 38130767 | 38130958 | H_c_30f03 |
| 11 | 3817453 | 3819678 | H_c_204c13 |
| 11 | 38200168 | 38200276 | H_c_192l16 |
| 11 | 3832518 | 3834626 | H_c_227k23 |
| 11 | 39249923 | 39250148 | H_c_20j21 |
| 11 | 395388 | 397682 | H_c_108d08_M |
| 11 | 39811462 | 39811693 | H_c_93c06 |
| 11 | 40010519 | 40010605 | H_c142l04 |
| 11 | 40176746 | 40176870 | H_c_47c18 |
| 11 | 40576246 | 40576374 | H_c_123f15 |
| 11 | 4072309 | 4073668 | H_c_228k01_M |
| 11 | 40886173 | 40886320 | H_c_66m22 |
| 11 | 41516775 | 41516963 | H_c_53m07 |
| 11 | 4189927 | 4190137 | H_c_262i02 |
| 11 | 42114578 | 42114657 | H_c_184i13 |
| 11 | 42676249 | 42676552 | H_c139j21 |
| 11 | 42869857 | 42870059 | H_c_160f17 |
| 11 | 43289805 | 43290602 | H_c_270d10_M |
| 11 | 43336785 | 43338208 | H_c_18k03_M |
| 11 | 43336862 | 43338208 | H_c_71a20_M |
| 11 | 43524057 | 43526405 | H_c_15i21_M |
| 11 | 43551989 | 43552245 | H_c_52e02_M |
| 11 | 43557030 | 43557415 | H_c_250f07 |
| 11 | 43558873 | 43559803 | H_c_77h02_M |
| 11 | 43622290 | 43622442 | H_c_122h23 |
| 11 | 43658150 | 43659307 | H_c_230o01_M |
| 11 | 437981 | 439165 | H_c_27d13_M |
| 11 | 439166 | 441291 | H_c_107j15_M |
| 11 | 43919929 | 43921625 | H_c_168h23_M |
| 11 | 44044206 | 44044857 | H_c_1i06_M |
| 11 | 44073662 | 44074961 | H_c_35c19 |
| 11 | 44282960 | 44289037 | H_c_152e14_M_M |

TABLE 1-continued

| | | | |
|---|---|---|---|
| 11 | 44294151 | 44295217 | H_c_219i14_M |
| 11 | 44297120 | 44298772 | H_c_190i01 |
| 11 | 44498307 | 44498522 | H_c_174a10 |
| 11 | 44530523 | 44530638 | H_c_258o13 |
| 11 | 44543003 | 44543510 | H_c_98a15 |
| 11 | 44543514 | 44544152 | H_c_199n07_M |
| 11 | 44926910 | 44929342 | H_c_15c23_M |
| 11 | 45124527 | 45125629 | H_c_80d05 |
| 11 | 45158140 | 45160677 | H_c_179e16_M |
| 11 | 45440808 | 45443155 | H_c_20o18 |
| 11 | 45628376 | 45629296 | H_c_103l10_M |
| 11 | 45642630 | 45644301 | H_c_151e16_M |
| 11 | 45768732 | 45768943 | H_c_186j22 |
| 11 | 45849328 | 45850806 | H_c_125j18 |
| 11 | 45876629 | 45878851 | H_c134h09_M |
| 11 | 45895325 | 45896048 | H_c_117j20 |
| 11 | 46152919 | 46153105 | H_c_147h24 |
| 11 | 46215100 | 46216807 | H_c_86k17_M |
| 11 | 46255711 | 46257533 | H_c_196g09_M |
| 11 | 46367480 | 46371016 | H_c_71m13_M |
| 11 | 46491762 | 46491944 | H_c_62n24 |
| 11 | 46525592 | 46525916 | H_c_212c13 |
| 11 | 46595176 | 46595750 | H_c_87n06_M |
| 11 | 46682135 | 46682300 | H_c_57n18 |
| 11 | 46823807 | 46824663 | H_c_205c01_M |
| 11 | 46842263 | 46842915 | H_c144f06 |
| 11 | 46894969 | 46895192 | H_c133h23_M |
| 11 | 47073154 | 47073322 | H_c_36a22_M |
| 11 | 47145611 | 47145829 | H_c_72p23 |
| 11 | 47154162 | 47155458 | H_c_21i08_M |
| 11 | 47226579 | 47227098 | H_c_173l17 |
| 11 | 47246954 | 47248801 | H_c_191k01_M |
| 11 | 47372106 | 47373317 | H_c_73h19 |
| 11 | 47530502 | 47531887 | H_c_247m08 |
| 11 | 47619944 | 47620811 | H_c_32a11_M |
| 11 | 47744760 | 47746249 | H_c_220j24_M |
| 11 | 47825694 | 47827260 | H_c_4f11_M |
| 11 | 47957967 | 47959768 | H_c_40n18 |
| 11 | 49185873 | 49186808 | H_c132d21 |
| 11 | 4980920 | 4980999 | H_c_198k18 |
| 11 | 4994755 | 4994939 | H_c_29p13 |
| 11 | 50193820 | 50195031 | H_c_52i24_M |
| 11 | 50311354 | 50311525 | H_c_224f15 |
| 11 | 50537727 | 50537896 | H_c_239g09 |
| 11 | 50548167 | 50548264 | H_c_67n17 |
| 11 | 508489 | 513286 | H_c_42i13_M |
| 11 | 51407736 | 51407811 | H_c_56j12 |
| 11 | 5409973 | 5410109 | H_c_232e08_M |
| 11 | 54673331 | 54673418 | H_c_28a12 |
| 11 | 54795603 | 54795677 | H_c144o16 |
| 11 | 550092 | 551507 | H_c_259p14 |
| 11 | 557610 | 560178 | H_c_103i09_M |
| 11 | 55867350 | 55867491 | H_c138a23 |
| 11 | 56011033 | 56011218 | H_c_163i03 |
| 11 | 564260 | 566251 | H_c_28g11_M |
| 11 | 566314 | 567156 | H_c_7l14 |
| 11 | 56834828 | 56835639 | H_c_217o18_M |
| 11 | 56859052 | 56860326 | H_c_27f03_M |
| 11 | 56981851 | 56984415 | H_c_30g09_M |
| 11 | 57037691 | 57040100 | H_c_111b16_M |
| 11 | 57054864 | 57055191 | H_c_248h02_M |
| 11 | 57090393 | 57093156 | H_c_193k06 |
| 11 | 57181257 | 57181854 | H_c_102b20_M |
| 11 | 57191397 | 57192341 | H_c_207b06_M |
| 11 | 57236507 | 57236987 | H_c_129e16 |
| 11 | 57265085 | 57266186 | H_c_227k24_M |
| 11 | 57316300 | 57316620 | H_c_11d23 |
| 11 | 58032185 | 58032321 | H_c_15e18 |
| 11 | 58102471 | 58104222 | H_c_104e15_M |
| 11 | 58666399 | 58669590 | H_c_269h06_M |
| 11 | 59080209 | 59080512 | H_c_101f10 |
| 11 | 59089935 | 59090248 | H_c_19k21_M |
| 11 | 59139034 | 59140543 | H_c_211b07_M |
| 11 | 59192677 | 59194020 | H_c_88e22_M |
| 11 | 59278689 | 59279345 | H_c_125j24 |
| 11 | 59334331 | 59335191 | H_c_27f11 |
| 11 | 59512481 | 59512664 | H_c_34o10 |
| 11 | 59708282 | 59708495 | H_c_154d23 |
| 11 | 59891112 | 59891225 | H_c_272d20 |
| 11 | 60430111 | 60430785 | H_c_243k04_M |
| 11 | 60437811 | 60439019 | H_c_15f23_M |
| 11 | 60474670 | 60477162 | H_c139e04 |
| 11 | 60531371 | 60533153 | H_c_55n01_M |
| 11 | 60685476 | 60685975 | H_c_274n15 |
| 11 | 60856390 | 60857786 | H_c_78n04_M |
| 11 | 60885356 | 60886407 | H_c_258m16_M |
| 11 | 60915316 | 60918086 | H_c_93b23 |
| 11 | 60953085 | 60954390 | H_c_211j03_M |
| 11 | 61091087 | 61092054 | H_c_168f03 |
| 11 | 61203556 | 61205250 | H_c_199m20_M |
| 11 | 61300625 | 61302157 | H_c_212c12_M |
| 11 | 61315902 | 61317506 | H_c_262k22 |
| 11 | 61338661 | 61341400 | H_c_252k17 |
| 11 | 61350558 | 61353439 | H_c_56g24 |
| 11 | 61413922 | 61416613 | H_c_22a15_M |
| 11 | 61439789 | 61441922 | H_c_151b13 |
| 11 | 61478825 | 61480403 | H_c_8m07 |
| 11 | 61491117 | 61492626 | H_c_234h22 |
| 11 | 61500748 | 61502367 | H_c_5l01 |
| 11 | 61606192 | 61606380 | H_c_130c04 |
| 11 | 61647666 | 61648565 | H_c_127c23_M |
| 11 | 61773422 | 61773613 | H_c_100j13 |
| 11 | 61860785 | 61862351 | H_c_8j15_M |
| 11 | 61968251 | 61968904 | H_c_149f07 |
| 11 | 62068890 | 62071079 | H_c_16h12_M |
| 11 | 62097487 | 62098729 | H_c_167g14_M |
| 11 | 6211556 | 6213450 | H_c_127j24 |
| 11 | 62124964 | 62127667 | H_c_100p14_M |
| 11 | 62145570 | 62146688 | H_c_11m23_M |
| 11 | 62170179 | 62171513 | H_c_149d10_M |
| 11 | 62195311 | 62196289 | H_c_152h17_M |
| 11 | 62202269 | 62203541 | H_c_210h21_M |
| 11 | 62229144 | 62231071 | H_c_180f06_M |
| 11 | 62285384 | 62286190 | H_c_84n12 |
| 11 | 62288545 | 62288688 | H_c_210i23 |
| 11 | 62309898 | 62311793 | H_c_25k12_M |
| 11 | 62329073 | 62329604 | H_c_77e05_M |
| 11 | 62354992 | 62357341 | H_c_90g14_M |
| 11 | 6236982 | 6238752 | H_c_128c02 |
| 11 | 62380026 | 62380631 | H_c_258d09 |
| 11 | 62404884 | 62405922 | H_c_57j04_M |
| 11 | 626151 | 628427 | H_c_63f04_M |
| 11 | 629045 | 630678 | H_c_194l02_M |
| 11 | 6297448 | 6299069 | H_c_83l19_M |
| 11 | 63014851 | 63015512 | H_c_14i22_M |
| 11 | 63138251 | 63138745 | H_c_121b20_M |
| 11 | 63194741 | 63195957 | H_c_53g04 |
| 11 | 63205221 | 63206071 | H_c_62i24 |
| 11 | 63292081 | 63292876 | H_c_172c02_M |
| 11 | 63362186 | 63363942 | H_c_89b23 |
| 11 | 63440357 | 63443455 | H_c_24n24_M |
| 11 | 63462482 | 63463221 | H_c_82h18_M |
| 11 | 63498379 | 63499598 | H_c_1i24_M |
| 11 | 63510502 | 63511330 | H_c_187c23_M |
| 11 | 63521732 | 63525049 | H_c_235b21_M |
| 11 | 63552643 | 63554405 | H_c134o15 |
| 11 | 63584207 | 63585725 | H_c131i03_M |
| 11 | 63689300 | 63690865 | H_c_149k01_M |
| 11 | 63709290 | 63711143 | H_c_243c20_M |
| 11 | 63750035 | 63751271 | H_c_81g22_M |
| 11 | 63753786 | 63755164 | H_c_158i23 |
| 11 | 63758401 | 63759836 | H_c_221b23 |
| 11 | 63768898 | 63771955 | H_c132h18_M |
| 11 | 63775296 | 63778021 | H_c_151a03_M |
| 11 | 63791773 | 63793902 | H_c_7p04 |
| 11 | 63793969 | 63795883 | H_c134l04_M |
| 11 | 63815683 | 63817622 | H_c_4k20_M |
| 11 | 63822776 | 63825187 | H_c_228h12_M |
| 11 | 63828692 | 63829002 | H_c_89c20_M |
| 11 | 63841962 | 63843569 | H_c_73m22 |
| 11 | 6396157 | 6397353 | H_c_79j04_M |
| 11 | 64178765 | 64179940 | H_c_122d15 |
| 11 | 64183637 | 64185620 | H_c_87k15 |
| 11 | 6423603 | 6423799 | H_c_5c20 |
| 11 | 64236666 | 64238017 | H_c133g14 |
| 11 | 64246711 | 64248627 | H_c_120f09 |
| 11 | 64267121 | 64269045 | H_c_45c22_M |
| 11 | 64301467 | 64303015 | H_c_202i04 |
| 11 | 64333639 | 64334965 | H_c_39a11_M |
| 11 | 64401707 | 64403573 | H_c133h13_M |

TABLE 1-continued

| | | | |
|---|---|---|---|
| 11 | 64440719 | 64441460 | H_c_252f11_M |
| 11 | 64448633 | 64450512 | H_c_189g16_M |
| 11 | 64494725 | 64496316 | H_c_43l20_M |
| 11 | 64537193 | 64538972 | H_c_217b10_M |
| 11 | 64551044 | 64551716 | H_c_112f08_M |
| 11 | 64565018 | 64565992 | H_c_190p24_M |
| 11 | 64571398 | 64573702 | H_c_5c16_M |
| 11 | 6458344 | 6459829 | H_c_165k13_M |
| 11 | 64607873 | 64608657 | H_c_84m02_M |
| 11 | 64612445 | 64614985 | H_c_161a14 |
| 11 | 64635894 | 64636910 | H_c_160h16_M |
| 11 | 64640472 | 64642521 | H_c_234f24 |
| 11 | 64645234 | 64646524 | H_c_161e02_M |
| 11 | 64657841 | 64658559 | H_c_120p16 |
| 11 | 64704775 | 64705652 | H_c_103f17_M |
| 11 | 64785389 | 64786656 | H_c_206k22_M |
| 11 | 64837385 | 64840209 | H_c_66j14 |
| 11 | 64856823 | 64858698 | H_c_266o12_M |
| 11 | 64910244 | 64911230 | H_c_273i02 |
| 11 | 64946011 | 64946612 | H_c_248f24_M |
| 11 | 64961963 | 64962340 | H_c_192p15 |
| 11 | 64979044 | 64979773 | H_c_36n04 |
| 11 | 65021326 | 65023191 | H_c_42i09_M |
| 11 | 65070259 | 65072467 | H_c_149i05 |
| 11 | 65080956 | 65083993 | H_c_269i22_M |
| 11 | 6508922 | 6509003 | H_c_206n16 |
| 11 | 65093730 | 65099146 | H_c_25f19_M_M |
| 11 | 65139457 | 65140692 | H_c_194e07_M |
| 11 | 65161466 | 65165682 | H_c_157l03_M |
| 11 | 65176069 | 65177768 | H_c_153h07_M |
| 11 | 65186503 | 65187440 | H_c_41j13_M |
| 11 | 65235802 | 65237972 | H_c_215e22 |
| 11 | 65244122 | 65245486 | H_c_61j08 |
| 11 | 65309975 | 65311970 | H_c_56g23_M |
| 11 | 65380964 | 65385230 | H_c_55o13_M_M |
| 11 | 65395152 | 65397996 | H_c_210e18_M |
| 11 | 65412246 | 65415240 | H_c_236m22_M |
| 11 | 65414186 | 65415870 | H_c_240j04_M |
| 11 | 65422851 | 65424901 | H_c_122m23 |
| 11 | 65442889 | 65443394 | H_c_86b05_M |
| 11 | 65443452 | 65445562 | H_c_189j13 |
| 11 | 65485566 | 65486269 | H_c_71n13 |
| 11 | 65526501 | 65527111 | H_c_227n10_M |
| 11 | 65535702 | 65536451 | H_c_117a12_M |
| 11 | 65546439 | 65547577 | H_c_103g01_M |
| 11 | 65571105 | 65573867 | H_c_247p23 |
| 11 | 65593564 | 65595374 | H_c_207o05_M |
| 11 | 65781390 | 65783157 | H_c_33p16_M |
| 11 | 65805889 | 65806791 | H_c_11f20 |
| 11 | 6581115 | 6582601 | H_c_148p03_M |
| 11 | 65811200 | 65817366 | H_c_194o16_M_M |
| 11 | 65871001 | 65872187 | H_c_3f03_M |
| 11 | 65894605 | 65896357 | H_c_55d03 |
| 11 | 65932552 | 65933205 | H_c_28b06_M |
| 11 | 65944518 | 65945918 | H_c_150h09 |
| 11 | 66003237 | 66004678 | H_c_157p11_M |
| 11 | 66069398 | 66070436 | H_c134o19_M |
| 11 | 66116092 | 66117210 | H_c_115a03 |
| 11 | 66140142 | 66141995 | H_c_196g20_M |
| 11 | 66162386 | 66163128 | H_c_56h18_M |
| 11 | 66201419 | 66202237 | H_c_64i22_M |
| 11 | 66268322 | 66270226 | H_c_13f22_M |
| 11 | 6631970 | 6634561 | H_c_45f13 |
| 11 | 66367346 | 66368419 | H_c_207o21_M |
| 11 | 66380045 | 66381575 | H_c_46j13 |
| 11 | 66442286 | 66442408 | H_c_156e04 |
| 11 | 66481084 | 66482996 | H_c_8h13_M |
| 11 | 66641814 | 66644028 | H_c_237b15_M |
| 11 | 66785385 | 66786705 | H_c134g06 |
| 11 | 66798281 | 66800623 | H_c_82f03 |
| 11 | 66840611 | 66842753 | H_c_80k16_M |
| 11 | 66847653 | 66847797 | H_c_266f16 |
| 11 | 66871962 | 66873128 | H_c_100a06 |
| 11 | 66915494 | 66918004 | H_c_233m03 |
| 11 | 66923886 | 66926225 | H_c_125k21 |
| 11 | 66938943 | 66941288 | H_c_269j16_M |
| 11 | 66944529 | 66946178 | H_c_160h13 |
| 11 | 66952032 | 66952808 | H_c134h07 |
| 11 | 66991111 | 66993729 | H_c_84f01 |
| 11 | 67006598 | 67007443 | H_c_108p18_M |
| 11 | 67031676 | 67033167 | H_c_77c04_M |
| 11 | 67130239 | 67131511 | H_c_77c15_M |
| 11 | 67255575 | 67256504 | H_c_112g11 |
| 11 | 67388887 | 67388975 | H_c_27j14 |
| 11 | 67526488 | 67528345 | H_c_101o14_M |
| 11 | 67536049 | 67537671 | H_c_98j11 |
| 11 | 67554371 | 67555943 | H_c_125d11_M |
| 11 | 67562920 | 67564487 | H_c133a20_M |
| 11 | 67651767 | 67652765 | H_c_183i01 |
| 11 | 67737369 | 67740427 | H_c_176o08_M |
| 11 | 67795321 | 67796461 | H_c_8j08_M |
| 11 | 67984464 | 67985392 | H_c_102n13 |
| 11 | 68207771 | 68210437 | H_c_152b21 |
| 11 | 68273899 | 68276670 | H_c_91h05_M |
| 11 | 68363336 | 68367017 | H_c_173h03_M |
| 11 | 68427329 | 68428291 | H_c_38j07 |
| 11 | 68572775 | 68573849 | H_c_29a11_M |
| 11 | 68647173 | 68648585 | H_c_11e04_M |
| 11 | 6876291 | 6876565 | H_c_210l08_M |
| 11 | 6904142 | 6904816 | H_c_44k24_M |
| 11 | 69160524 | 69168311 | H_c_117g18_M_M |
| 11 | 69198787 | 69200028 | H_c_4p14_M |
| 11 | 69209185 | 69211225 | H_c_60c08 |
| 11 | 69227049 | 69229222 | H_c_150n14_M |
| 11 | 69244676 | 69244870 | H_c_36d08 |
| 11 | 69340808 | 69342859 | H_c_199b04_M |
| 11 | 69508986 | 69510322 | H_c_208i07 |
| 11 | 69602050 | 69603854 | H_c_97n23_M |
| 11 | 69793752 | 69795188 | H_c_102o22_M |
| 11 | 69921837 | 69923339 | H_c_4l18_M |
| 11 | 70185542 | 70185949 | H_c_151e20 |
| 11 | 70639861 | 70642037 | H_c_57h16 |
| 11 | 70651534 | 70651656 | H_c_171l08 |
| 11 | 7066682 | 7068211 | H_c_5m16 |
| 11 | 70714384 | 70714735 | H_c_254o20 |
| 11 | 70731666 | 70733309 | H_c_120b15 |
| 11 | 70754166 | 70754259 | H_c_205d18_M |
| 11 | 70836369 | 70838146 | H_c_155c23_M |
| 11 | 70846897 | 70849360 | H_c_239g20 |
| 11 | 71468961 | 71469240 | H_c_88l03_M |
| 11 | 71501230 | 71501609 | H_c_19j02_M |
| 11 | 71611950 | 71612588 | H_c_87k02_M |
| 11 | 71612592 | 71615177 | H_c_199e21 |
| 11 | 71628546 | 71629736 | H_c_257b05 |
| 11 | 71631897 | 71632891 | H_c_25k14_M |
| 11 | 71632797 | 71633205 | H_c_154e06_M |
| 11 | 71849401 | 71849575 | H_c_10e19 |
| 11 | 71865723 | 71865867 | H_c_1d11 |
| 11 | 71971764 | 71973479 | H_c_48j07_M |
| 11 | 72168881 | 72170782 | H_c143f01 |
| 11 | 72180909 | 72183264 | H_c_231i06_M |
| 11 | 72202787 | 72204327 | H_c133h09_M |
| 11 | 7228868 | 7230843 | H_c_269m13_M |
| 11 | 72557023 | 72559162 | H_c_106h24 |
| 11 | 72606461 | 72607663 | H_c_74f10_M |
| 11 | 72675706 | 72677097 | H_c_170a19 |
| 11 | 72695673 | 72698199 | H_c_155b09 |
| 11 | 72717043 | 72717725 | H_c_50g20 |
| 11 | 72774645 | 72776157 | H_c_214m11 |
| 11 | 72986265 | 72987399 | H_c_113g01_M |
| 11 | 73048975 | 73050449 | H_c_36a17_M |
| 11 | 73148714 | 73150267 | H_c_13k13_M |
| 11 | 73371567 | 73372357 | H_c_48b24_M |
| 11 | 73559295 | 73560822 | H_c_84e20_M |
| 11 | 736612 | 738357 | H_c_107p07_M |
| 11 | 73786162 | 73787118 | H_c_223a08_M |
| 11 | 73854984 | 73856641 | H_c_159h05 |
| 11 | 73881774 | 73882484 | H_c_45h12_M |
| 11 | 74071885 | 74072223 | H_c_266g23_M |
| 11 | 74118718 | 74120367 | H_c_56m16_M |
| 11 | 745005 | 746820 | H_c_53b08 |
| 11 | 74816953 | 74820591 | H_c_160g02_M |
| 11 | 7490848 | 7492446 | H_c_196d20_M |
| 11 | 74913624 | 74915307 | H_c_30p20_M |
| 11 | 74950024 | 74951731 | H_c142e09 |
| 11 | 75055453 | 75057424 | H_c_98m18_M |
| 11 | 75156972 | 75158832 | H_c_210a24 |
| 11 | 75418211 | 75418309 | H_c_151g10 |
| 11 | 75540804 | 75541676 | H_c_1m02 |
| 11 | 75595225 | 75595625 | H_c_163g23_M |

TABLE 1-continued

| | | | |
|---|---|---|---|
| 11 | 75832793 | 75834806 | H_c_186f15_M |
| 11 | 76059466 | 76059837 | H_c_189k04_M |
| 11 | 76171556 | 76173544 | H_c_217d21_M |
| 11 | 76187790 | 76188567 | H_c_216l19_M |
| 11 | 76249246 | 76250510 | H_c_57k09_M |
| 11 | 76385933 | 76386159 | H_c_69k05 |
| 11 | 76428124 | 76429616 | H_c_230f08_M |
| 11 | 76455043 | 76456160 | H_c_157l14_M |
| 11 | 7650196 | 7651878 | H_c_153a15_M |
| 11 | 76514174 | 76516281 | H_c_49n11 |
| 11 | 7651922 | 7652388 | H_c_19i07 |
| 11 | 76526618 | 76527711 | H_c_32e16 |
| 11 | 76861520 | 76863261 | H_c_8b10_M |
| 11 | 76977919 | 76979451 | H_c_125b01_M |
| 11 | 77208628 | 77209996 | H_c_21a12 |
| 11 | 77383324 | 77383711 | H_c_18g22 |
| 11 | 77467924 | 77468892 | H_c_87a11_M |
| 11 | 77527966 | 77528426 | H_c_129i19_M |
| 11 | 77538417 | 77538514 | H_c_24e19 |
| 11 | 77564299 | 77564420 | H_c_62o20 |
| 11 | 77575703 | 77577511 | H_c_274a13 |
| 11 | 7770329 | 7770399 | H_c_150m20 |
| 11 | 77746341 | 77746349 | H_c_167b02 |
| 11 | 77805531 | 77806942 | H_c_221i05_M |
| 11 | 77883006 | 77883908 | H_c_200e08 |
| 11 | 77918965 | 77919095 | H_c_226i10 |
| 11 | 77963082 | 77963782 | H_c_81l15 |
| 11 | 78603196 | 78603436 | H_c_126c24 |
| 11 | 78825174 | 78829574 | H_c_186k10_M |
| 11 | 7960893 | 7960973 | H_c_225o20 |
| 11 | 798100 | 799941 | H_c_30j23_M |
| 11 | 79917528 | 79917744 | H_c_156c16 |
| 11 | 80057899 | 80058003 | H_c_159h10 |
| 11 | 8023638 | 8024397 | H_c_273b08 |
| 11 | 80603117 | 80603246 | H_c_5g02_M |
| 11 | 80638672 | 80638793 | H_c_244c06 |
| 11 | 80695532 | 80695748 | H_c_220k14 |
| 11 | 80728256 | 80728422 | H_c_5n17 |
| 11 | 807616 | 809542 | H_c_145g04_M |
| 11 | 80786335 | 80786522 | H_c_267i24 |
| 11 | 809545 | 810169 | H_c_203j06 |
| 11 | 81256273 | 81256483 | H_c_122p24 |
| 11 | 8146684 | 8147605 | H_c_25c05_M |
| 11 | 81598278 | 81598364 | H_c_196m15 |
| 11 | 81812662 | 81812776 | H_c_150b20 |
| 11 | 81860220 | 81860335 | H_c_240i03 |
| 11 | 82121023 | 82122710 | H_c_33k13_M |
| 11 | 82211531 | 82211672 | H_c_38l01 |
| 11 | 82286010 | 82286197 | H_c_206n08 |
| 11 | 8240591 | 8241551 | H_c_274h23_M |
| 11 | 8245775 | 8246948 | H_c_33h09 |
| 11 | 824917 | 825504 | H_c_197a16 |
| 11 | 82545125 | 82546624 | H_c_66c01 |
| 11 | 82581966 | 82583467 | H_c_29m07_M |
| 11 | 82782899 | 82783087 | H_c_233j21 |
| 11 | 83367884 | 83367973 | H_c_165k23_M |
| 11 | 83902391 | 83902514 | H_c_254b04 |
| 11 | 839029 | 841325 | H_c_246e15_M |
| 11 | 84565476 | 84565568 | H_c_183j18 |
| 11 | 84590839 | 84590943 | H_c_214o01 |
| 11 | 85052907 | 85054194 | H_c_152a01_M |
| 11 | 85199551 | 85200279 | H_c_103j24_M |
| 11 | 85243288 | 85244177 | H_c_116f15_M |
| 11 | 85456710 | 85458316 | H_c_48e15 |
| 11 | 85534329 | 85534476 | H_c_13e20 |
| 11 | 85591885 | 85592043 | H_c_212m03 |
| 11 | 8571814 | 8573246 | H_c_24h20_M |
| 11 | 86060121 | 86061506 | H_c_116b14_M |
| 11 | 86188677 | 86189773 | H_c_24k20_M |
| 11 | 86310811 | 86310931 | H_c_205f04 |
| 11 | 86426226 | 86427151 | H_c_50h09 |
| 11 | 8660435 | 8662269 | H_c_93c16_M |
| 11 | 86614804 | 86614957 | H_c_20k22 |
| 11 | 86713143 | 86713341 | H_c_30a13 |
| 11 | 86833138 | 86833318 | H_c_68l24 |
| 11 | 86890448 | 86890539 | H_c_94b07 |
| 11 | 86924867 | 86925266 | H_c_129l10 |
| 11 | 87310416 | 87310581 | H_c_36g17 |
| 11 | 87547910 | 87548351 | H_c_69l10 |
| 11 | 8756664 | 8758399 | H_c_181i20 |
| 11 | 87710146 | 87710826 | H_c_147j15 |
| 11 | 87860481 | 87860755 | H_c_38g06 |
| 11 | 87881286 | 87882494 | H_c_1g04_M |
| 11 | 8848582 | 8849834 | H_c_201o22_M |
| 11 | 8888949 | 8890019 | H_c_56e16_M |
| 11 | 8942058 | 8943001 | H_c_253b18_M |
| 11 | 89689487 | 89689630 | H_c_169m04 |
| 11 | 8981577 | 8983041 | H_c_187d11_M |
| 11 | 899980 | 901599 | H_c_168h15_M |
| 11 | 90292116 | 90292272 | H_c_153k21_M |
| 11 | 90678428 | 90678541 | H_c_188k16 |
| 11 | 9068990 | 9071283 | H_c_117j21 |
| 11 | 91211027 | 91211200 | H_c_213m04 |
| 11 | 91302039 | 91302223 | H_c_234d12 |
| 11 | 91329005 | 91329238 | H_c_45d18 |
| 11 | 91346640 | 91346811 | H_c_240h15 |
| 11 | 91355556 | 91355661 | H_c_156d16 |
| 11 | 913733 | 916566 | H_c_254o18 |
| 11 | 91597158 | 91599944 | H_c_258o06_M |
| 11 | 92037939 | 92038118 | H_c_221h02 |
| 11 | 9242791 | 9244432 | H_c_86h13_M |
| 11 | 92570384 | 92570925 | H_c_171n24_M |
| 11 | 92616535 | 92616656 | H_c_231p13 |
| 11 | 9292219 | 9292969 | H_c_269d23_M |
| 11 | 93113906 | 93114790 | H_c_82p19_M |
| 11 | 93156940 | 93157830 | H_c_239h21_M |
| 11 | 93222511 | 93223516 | H_c_57l10 |
| 11 | 93354419 | 93354621 | H_c_262h01 |
| 11 | 93396074 | 93396222 | H_c_248d03 |
| 11 | 9342110 | 9343021 | H_c_245g06_M |
| 11 | 93501480 | 93503054 | H_c_100f03_M |
| 11 | 9362397 | 9363659 | H_c_66i11_M |
| 11 | 93773087 | 93774716 | H_c_272a11_M |
| 11 | 93798658 | 93798768 | H_c135f16 |
| 11 | 93900925 | 93901106 | H_c_72d20 |
| 11 | 93916507 | 93918678 | H_c_39o16_M |
| 11 | 94112870 | 94114249 | H_c_193a11 |
| 11 | 94140912 | 94142022 | H_c_107i14_M |
| 11 | 94310401 | 94310510 | H_c134f20 |
| 11 | 9438324 | 9439384 | H_c_273k16_M |
| 11 | 94462082 | 94463741 | H_c_204g18 |
| 11 | 94586520 | 94586684 | H_c131f07 |
| 11 | 94592138 | 94592209 | H_c_63p19 |
| 11 | 94718051 | 94718210 | H_c_181n12 |
| 11 | 94724642 | 94724739 | H_c_153c23 |
| 11 | 95161701 | 95163951 | H_c_43a21_M |
| 11 | 9550915 | 9553015 | H_c_94b11_M |
| 11 | 95726899 | 95727049 | H_c_126p14 |
| 11 | 95762142 | 95763180 | H_c_58c23 |
| 11 | 95902527 | 95902604 | H_c_63b16 |
| 11 | 96040254 | 96040341 | H_c_209n01 |
| 11 | 9641677 | 9642996 | H_c_36n24_M |
| 11 | 96765641 | 96765733 | H_c_6f08 |
| 11 | 9735989 | 9737165 | H_c_18p10_M |
| 11 | 98365584 | 98365719 | H_c_45g01 |
| 11 | 98396705 | 98396935 | H_c_215a01_M |
| 11 | 98427938 | 98428093 | H_c_76c15 |
| 11 | 98439747 | 98439973 | H_c_200b22 |
| 11 | 98798863 | 98799135 | H_c_193i01 |
| 11 | 98920615 | 98920830 | H_c_57o07 |
| 11 | 9897321 | 9897496 | H_c_239m22 |
| 11 | 9955194 | 9955258 | H_c_53d13 |
| 12 | 100105091 | 100106513 | H_c_160b20_M |
| 12 | 100178309 | 100178436 | H_c_75f10_M |
| 12 | 100257194 | 100257389 | H_c_81c11 |
| 12 | 100304229 | 100304722 | H_c_14h17 |
| 12 | 100463871 | 100464025 | H_c_76c06 |
| 12 | 100538601 | 100539133 | H_c_28o17 |
| 12 | 100593714 | 100594606 | H_c132a13_M |
| 12 | 100652665 | 100652891 | H_c_116n21 |
| 12 | 100772759 | 100774667 | H_c_69d12 |
| 12 | 101016032 | 101016569 | H_c_210p04_M |
| 12 | 101230698 | 101230873 | H_c_182g19 |
| 12 | 101273450 | 101273557 | H_c_1m22 |
| 12 | 101295296 | 101295474 | H_c_154m24_M |
| 12 | 101314938 | 101315147 | H_c_232l16 |
| 12 | 101415902 | 101416181 | H_c_100h24 |
| 12 | 101538397 | 101538517 | H_c_42d09 |
| 12 | 101852525 | 101855343 | H_c_16k21_M |
| 12 | 101861297 | 101862261 | H_c_5k17 |

TABLE 1-continued

| | | | |
|---|---|---|---|
| 12 | 102391862 | 102392658 | H_c__121b03__M |
| 12 | 102825452 | 102827271 | H_c__128c17__M |
| 12 | 102853249 | 102853569 | H_c141o06__M |
| 12 | 102945841 | 102947379 | H_c__161k24__M |
| 12 | 102960464 | 102961612 | H_c__178f16__M |
| 12 | 103033586 | 103034855 | H_c__153f19__M |
| 12 | 103111695 | 103113073 | H_c__103m10__M |
| 12 | 103352850 | 103355014 | H_c__182n07 |
| 12 | 103361894 | 103362084 | H_c__79d12 |
| 12 | 103853885 | 103855158 | H_c__29j05__M |
| 12 | 103882302 | 103883203 | H_c__200p24__M |
| 12 | 103980501 | 103981591 | H_c__10e03 |
| 12 | 104003732 | 104004803 | H_c__119n15__M |
| 12 | 104131435 | 104132754 | H_c__150d12__M |
| 12 | 104226586 | 104227805 | H_c__87e24__M |
| 12 | 105034415 | 105036455 | H_c__2b13__M |
| 12 | 105143405 | 105145445 | H_c__67o15__M |
| 12 | 105199033 | 105199482 | H_c__155i10 |
| 12 | 105476652 | 105482769 | H_c__85a11__M__M |
| 12 | 105851532 | 105853232 | H_c__61k06__M |
| 12 | 105882868 | 105883691 | H_c__119n12__M |
| 12 | 105989012 | 105990580 | H_c__70a18__M |
| 12 | 106281756 | 106282853 | H_c__207e07 |
| 12 | 10657189 | 10657785 | H_c__146m21 |
| 12 | 106656496 | 106657883 | H_c__239h04__M |
| 12 | 106670851 | 106672073 | H_c__83p15__M |
| 12 | 106739129 | 106741299 | H_c__85n08__M |
| 12 | 106799792 | 106800415 | H_c__176o17 |
| 12 | 106968964 | 106969109 | H_c__106l13 |
| 12 | 107025487 | 107026039 | H_c__54i13__M |
| 12 | 107089781 | 107089886 | H_c__119p21 |
| 12 | 107410998 | 107411935 | H_c__240b05__M |
| 12 | 107456742 | 107459215 | H_c__92d19__M |
| 12 | 10749867 | 10750057 | H_c__68m01 |
| 12 | 107626323 | 107628137 | H_c__12k20__M |
| 12 | 10766445 | 10767580 | H_c__128o23__M |
| 12 | 107751909 | 107754591 | H_c__230f10 |
| 12 | 107827476 | 107827591 | H_c__113n12 |
| 12 | 107997922 | 107999343 | H_c__197c16__M |
| 12 | 108209404 | 108211142 | H_c__4k21__M |
| 12 | 108379191 | 108379344 | H_c__272i02 |
| 12 | 108474170 | 108474673 | H_c__113f06__M |
| 12 | 108611265 | 108616578 | H_c__224a23__M |
| 12 | 108619133 | 108620062 | H_c__80i07 |
| 12 | 108733389 | 108734645 | H_c__35c08 |
| 12 | 108800492 | 108801196 | H_c__55b03 |
| 12 | 108867816 | 108867891 | H_c__99p21 |
| 12 | 108895900 | 108897019 | H_c__65f07__M |
| 12 | 108899191 | 108900431 | H_c__54f13__M |
| 12 | 109024547 | 109025078 | H_c__38o22__M |
| 12 | 109181083 | 109183001 | H_c__51p05__M |
| 12 | 109350212 | 109351716 | H_c__113n22 |
| 12 | 109402652 | 109402959 | H_c__119m13 |
| 12 | 109482453 | 109484089 | H_c__203n18__M |
| 12 | 109514406 | 109515116 | H_c__114b21__M |
| 12 | 109589238 | 109590531 | H_c__229d24__M |
| 12 | 109642579 | 109643836 | H_c__181h17__M |
| 12 | 109934092 | 109935651 | H_c__120d16__M |
| 12 | 110297432 | 110298221 | H_c__227m08 |
| 12 | 110498043 | 110498804 | H_c__218b15__M |
| 12 | 110585882 | 110586687 | H_c__51j08 |
| 12 | 110666909 | 110668301 | H_c__186k18__M |
| 12 | 110742336 | 110743551 | H_c__238k02__M |
| 12 | 110912484 | 110915217 | H_c__118b11__M |
| 12 | 111008293 | 111009357 | H_c__53a21 |
| 12 | 111025758 | 111026658 | H_c__68k24__M |
| 12 | 111229027 | 111229214 | H_c__239e11 |
| 12 | 111281381 | 111283180 | H_c__84i14__M |
| 12 | 111319003 | 111320295 | H_c133c24__M |
| 12 | 111323518 | 111324539 | H_c__54m15 |
| 12 | 111475706 | 111476395 | H_c__211k12__M |
| 12 | 111838625 | 111839252 | H_c__147i21__M |
| 12 | 111956478 | 111957939 | H_c__30b13__M |
| 12 | 112035780 | 112036504 | H_c__121f21__M |
| 12 | 112053565 | 112053875 | H_c141o21__M |
| 12 | 112085429 | 112086588 | H_c__120k24__M |
| 12 | 11214919 | 11215654 | H_c__273m21__M |
| 12 | 112235116 | 112235758 | H_c__244j20__M |
| 12 | 112258974 | 112261843 | H_c__228k09__M |
| 12 | 112363256 | 112369142 | H_c__104h08__M |
| 12 | 112371325 | 112372499 | H_c__81a24 |
| 12 | 112372501 | 112373435 | H_c__35f10__M |
| 12 | 112376321 | 112377326 | H_c__103a14__M |
| 12 | 112538538 | 112538724 | H_c__66c06__M |
| 12 | 112574160 | 112575606 | H_c__64a06 |
| 12 | 112650393 | 112651022 | H_c__234g22 |
| 12 | 112743339 | 112745479 | H_c__216l14 |
| 12 | 113246497 | 113246597 | H_c__25l09 |
| 12 | 113303548 | 113308995 | H_c__56l24__M__M |
| 12 | 113339874 | 113342454 | H_c__158b19__M |
| 12 | 113345167 | 113345360 | H_c__157k17__M |
| 12 | 113347812 | 113349436 | H_c__227p19__M |
| 12 | 113564193 | 113564436 | H_c__186n14 |
| 12 | 113567772 | 113573070 | H_c__240h03__M__M |
| 12 | 113584009 | 113587710 | H_c__68f02__M__M |
| 12 | 113592246 | 113593870 | H_c__178d16__M |
| 12 | 113598602 | 113598825 | H_c__256f12__M |
| 12 | 113635784 | 113636451 | H_c__235f05 |
| 12 | 114352353 | 114353566 | H_c__251f23 |
| 12 | 114601663 | 114601885 | H_c__86j14 |
| 12 | 114866612 | 114866808 | H_c__216m24 |
| 12 | 115172580 | 115172679 | H_c__45d23 |
| 12 | 115177131 | 115177381 | H_c__272a12__M |
| 12 | 115408378 | 115409079 | H_c__98i19__M |
| 12 | 11543441 | 11545499 | H_c__160f15 |
| 12 | 115609388 | 115610578 | H_c__187d05 |
| 12 | 115637449 | 115638667 | H_c__70a07__M |
| 12 | 115718694 | 115720121 | H_c__185c17__M |
| 12 | 115779016 | 115782728 | H_c__183c10__M |
| 12 | 115805829 | 115806021 | H_c__181h18 |
| 12 | 115811210 | 115812365 | H_c__83e22__M |
| 12 | 115998569 | 116000883 | H_c__185m21 |
| 12 | 116090228 | 116091234 | H_c__29b21__M |
| 12 | 116260522 | 116262177 | H_c__3i01__M |
| 12 | 116265810 | 116266097 | H_c__120k16 |
| 12 | 11643543 | 11643619 | H_c__197k15 |
| 12 | 11688212 | 11688352 | H_c__102e03 |
| 12 | 116917011 | 116917790 | H_c__29m22 |
| 12 | 11693032 | 11693360 | H_c131i13__M |
| 12 | 11693113 | 11694220 | H_c__252n23__M |
| 12 | 117003797 | 117005493 | H_c__8j19__M |
| 12 | 117026208 | 117027771 | H_c__52e13 |
| 12 | 117036309 | 117037358 | H_c__274b13 |
| 12 | 117250 | 118968 | H_c__185k22 |
| 12 | 117271845 | 117273904 | H_c__123e10__M |
| 12 | 117276690 | 117278665 | H_c__197c10__M |
| 12 | 11761791 | 11762091 | H_c__21d21 |
| 12 | 117658193 | 117658309 | H_c__156e09 |
| 12 | 117674527 | 117675388 | H_c__207b09 |
| 12 | 11775778 | 11775792 | H_c__26p14 |
| 12 | 117817746 | 117817829 | H_c__236g06 |
| 12 | 117881606 | 117883438 | H_c__188a20 |
| 12 | 118167510 | 118167632 | H_c__268f01__M |
| 12 | 118534989 | 118535189 | H_c__91o05 |
| 12 | 118568112 | 118569059 | H_c__2i07__M |
| 12 | 118888888 | 118891160 | H_c__112e14__M |
| 12 | 118956703 | 118956775 | H_c__30j18 |
| 12 | 118987336 | 118988147 | H_c__87k08__M |
| 12 | 119016549 | 119018280 | H_c__21o21__M |
| 12 | 119094847 | 119095380 | H_c__257d08__M |
| 12 | 119101344 | 119101802 | H_c142e08 |
| 12 | 119128384 | 119129528 | H_c__42f16 |
| 12 | 119346429 | 119347408 | H_c__50n12__M |
| 12 | 119368660 | 119370748 | H_c__232a09__M |
| 12 | 119395955 | 119397281 | H_c__65k13__M |
| 12 | 119434227 | 119435645 | H_c__167h03__M |
| 12 | 119481510 | 119482333 | H_c__114f15__M |
| 12 | 119484811 | 119486288 | H_c__66d04__M |
| 12 | 119549648 | 119550902 | H_c__146h18__M |
| 12 | 119586456 | 119587582 | H_c__204n23 |
| 12 | 119587585 | 119588590 | H_c__94b08__M |
| 12 | 119626180 | 119626877 | H_c__96a12 |
| 12 | 119765534 | 119765717 | H_c__29g08 |
| 12 | 119803599 | 119805820 | H_c__211b19 |
| 12 | 119996222 | 119997225 | H_c__229e04 |
| 12 | 120108996 | 120110916 | H_c__46h20__M |
| 12 | 120141071 | 120141418 | H_c__42l09__M |
| 12 | 120195386 | 120198033 | H_c__199b14__M |
| 12 | 120286586 | 120286737 | H_c__71h15 |
| 12 | 120300095 | 120301213 | H_c__49b23__M |

TABLE 1-continued

| | | | |
|---|---|---|---|
| 12 | 120366839 | 120368749 | H_c__188e22__M |
| 12 | 120437310 | 120439066 | H_c__271k06 |
| 12 | 120478528 | 120481608 | H_c__237j24__M |
| 12 | 120526666 | 120527625 | H_c__8g22__M |
| 12 | 120612873 | 120614050 | H_c__164d11 |
| 12 | 120703879 | 120706134 | H_c__125g03__M |
| 12 | 120712051 | 120712921 | H_c__68m16__M |
| 12 | 120789054 | 120789863 | H_c__6n23__M |
| 12 | 120836377 | 120836866 | H_c__242c13 |
| 12 | 120923401 | 120923736 | H_c__50a04__M |
| 12 | 121234847 | 121236205 | H_c__86g07__M |
| 12 | 121275680 | 121276617 | H_c__18i16__M |
| 12 | 121380975 | 121381263 | H_c__9a20 |
| 12 | 12139204 | 12139636 | H_c__47p16__M |
| 12 | 121431007 | 121432535 | H_c__184o23__M |
| 12 | 121509798 | 121511125 | H_c__79a23 |
| 12 | 121536255 | 121536934 | H_c__168d07__M |
| 12 | 121761997 | 121763384 | H_c__49p11 |
| 12 | 121783506 | 121784212 | H_c__6f02__M |
| 12 | 121844094 | 121845584 | H_c__116f05__M |
| 12 | 121905063 | 121905707 | H_c__51b03__M |
| 12 | 121975485 | 121976235 | H_c__15l17__M |
| 12 | 121984357 | 121985127 | H_c__271a04__M |
| 12 | 121987738 | 121990351 | H_c__16p03__M |
| 12 | 121994645 | 121994828 | H_c__128j06 |
| 12 | 122129612 | 122130399 | H_c__107d18 |
| 12 | 122160879 | 122161098 | H_c__153g03__M |
| 12 | 122242226 | 122243399 | H_c__89g19__M |
| 12 | 122279751 | 122281556 | H_c__198h18 |
| 12 | 122373347 | 122375105 | H_c__160j15__M |
| 12 | 122445392 | 122446597 | H_c__18l18__M |
| 12 | 122593464 | 122594651 | H_c__120k15 |
| 12 | 122610383 | 122611967 | H_c__42n07__M |
| 12 | 122642707 | 122643876 | H_c__23d06__M |
| 12 | 122680310 | 122680805 | H_c__71g18 |
| 12 | 122721310 | 122722452 | H_c__274m12__M |
| 12 | 122771179 | 122772274 | H_c__71k14__M |
| 12 | 122952570 | 122954536 | H_c__22d15 |
| 12 | 122981835 | 122982883 | H_c__197f13__M |
| 12 | 12310548 | 12311786 | H_c136h07 |
| 12 | 123304067 | 123305618 | H_c__75p01 |
| 12 | 123397770 | 123399292 | H_c__108m16__M |
| 12 | 123466631 | 123468038 | H_c__252k20 |
| 12 | 123563567 | 123565227 | H_c__150j24 |
| 12 | 123575219 | 123577175 | H_c__180o19__M |
| 12 | 123655782 | 123657672 | H_c__254a19 |
| 12 | 123784093 | 123784420 | H_c__74j20 |
| 12 | 12378481 | 12378575 | H_c__2i21 |
| 12 | 123871970 | 123874358 | H_c__38b16__M |
| 12 | 123923369 | 123924822 | H_c__92h17__M |
| 12 | 12393786 | 12394736 | H_c__68k18__M |
| 12 | 124002931 | 124004368 | H_c__1f21 |
| 12 | 12401168 | 12401975 | H_c__47l13__M |
| 12 | 124049724 | 124050789 | H_c__69m12 |
| 12 | 124058660 | 124059491 | H_c__85i05 |
| 12 | 124074406 | 124076188 | H_c__17o14__M |
| 12 | 124340374 | 124340786 | H_c__71l10 |
| 12 | 124916934 | 124917705 | H_c__209c16 |
| 12 | 124964536 | 124964697 | H_c134d17 |
| 12 | 125051341 | 125051435 | H_c__187o01 |
| 12 | 125200064 | 125201760 | H_c__123o09__M |
| 12 | 125534869 | 125535103 | H_c__208f22 |
| 12 | 125735733 | 125736677 | H_c__42n17__M |
| 12 | 12605343 | 12607573 | H_c__39c12__M |
| 12 | 126154871 | 126156304 | H_c__55i19__M |
| 12 | 126182167 | 126183059 | H_c__22e21 |
| 12 | 126464633 | 126466665 | H_c__27f10__M |
| 12 | 127096956 | 127097285 | H_c__151j09 |
| 12 | 127275032 | 127277969 | H_c__209k12__M |
| 12 | 12760980 | 12761322 | H_c__119h16__M |
| 12 | 12761327 | 12761467 | H_c__116m15__M |
| 12 | 12767840 | 12770462 | H_c__191k10__M |
| 12 | 127832576 | 127833777 | H_c__31d16__M |
| 12 | 127861917 | 127863667 | H_c__248k11__M |
| 12 | 127885903 | 127886158 | H_c__20k19 |
| 12 | 12830840 | 12832152 | H_c__166j11 |
| 12 | 12857340 | 12857647 | H_c__58p19 |
| 12 | 128810443 | 128811262 | H_c__178k15 |
| 12 | 128900368 | 128900541 | H_c__239h16 |
| 12 | 128913044 | 128914272 | H_c__244c16__M |
| 12 | 129023383 | 129023691 | H_c__187j17__M |
| 12 | 129346632 | 129348970 | H_c__86h21__M |
| 12 | 12934788 | 12935910 | H_c__146k11__M |
| 12 | 129723525 | 129725314 | H_c__190a20 |
| 12 | 129763053 | 129763135 | H_c__214p19 |
| 12 | 129880817 | 129882163 | H_c__159d17 |
| 12 | 130013171 | 130015706 | H_c__238f16 |
| 12 | 130106196 | 130108552 | H_c__58m24 |
| 12 | 130251670 | 130251808 | H_c__48e17 |
| 12 | 13045307 | 13045707 | H_c__8i09__M |
| 12 | 130522696 | 130522965 | H_c__123m16 |
| 12 | 130810307 | 130810384 | H_c138c24 |
| 12 | 130860135 | 130862733 | H_c__110l21__M |
| 12 | 13088334 | 13089288 | H_c__119b21__M |
| 12 | 130978661 | 130979094 | H_c__195n20 |
| 12 | 131046433 | 131047997 | H_c__16j23 |
| 12 | 131080184 | 131081298 | H_c__55l14__M |
| 12 | 131101318 | 131102216 | H_c__233d12 |
| 12 | 131152870 | 131152996 | H_c__47l02__M |
| 12 | 131157265 | 131157484 | H_c__39m04 |
| 12 | 131234689 | 131236133 | H_c__193m15__M |
| 12 | 131247782 | 131247901 | H_c__199e24 |
| 12 | 131294415 | 131295960 | H_c__155h05__M |
| 12 | 131339487 | 131340712 | H_c__124i23__M |
| 12 | 131355922 | 131357117 | H_c__25c02__M |
| 12 | 131435218 | 131436269 | H_c__36g10 |
| 12 | 131711836 | 131712997 | H_c__88h20 |
| 12 | 131785950 | 131786912 | H_c__29h20__M |
| 12 | 131790116 | 131792309 | H_c__161p24__M |
| 12 | 131850731 | 131851669 | H_c__205e21 |
| 12 | 131896967 | 131898425 | H_c__115i24__M |
| 12 | 131948067 | 131949857 | H_c__165k01 |
| 12 | 132014916 | 132015949 | H_c__157b10__M |
| 12 | 132095124 | 132095959 | H_c__66b24__M |
| 12 | 132142352 | 132144912 | H_c__168i05__M |
| 12 | 132153360 | 132155638 | H_c__89e01 |
| 12 | 132172904 | 132173833 | H_c__82d17__M |
| 12 | 132223725 | 132224886 | H_c__234h09__M |
| 12 | 132266969 | 132268307 | H_c142k09 |
| 12 | 132290999 | 132291099 | H_c__258i08 |
| 12 | 132316715 | 132317818 | H_c__250g13__M |
| 12 | 13322472 | 13322649 | H_c__85b05__M |
| 12 | 13666330 | 13666460 | H_c133f17 |
| 12 | 13992145 | 13992273 | H_c__56d15 |
| 12 | 14024924 | 14025378 | H_c137d07__M |
| 12 | 14109886 | 14110022 | H_c__218g20__M |
| 12 | 14179004 | 14179087 | H_c__45h07 |
| 12 | 14409832 | 14410054 | H_c139m10__M |
| 12 | 14611516 | 14612437 | H_c__194d21__M |
| 12 | 14813712 | 14814344 | H_c__131m10__M |
| 12 | 14817664 | 14818948 | H_c__94p07__M |
| 12 | 14847116 | 14848132 | H_c__88f14 |
| 12 | 14972819 | 14972925 | H_c__94a06 |
| 12 | 15366717 | 15367358 | H_c__44m07__M |
| 12 | 1571733 | 1574371 | H_c139p06__M |
| 12 | 15763184 | 15763336 | H_c__39b16 |
| 12 | 15832875 | 15834290 | H_c__107h02__M |
| 12 | 15926178 | 15927002 | H_c__50p10 |
| 12 | 16073203 | 16073337 | H_c__122i23 |
| 12 | 16203197 | 16203268 | H_c__188m08 |
| 12 | 1640647 | 1642843 | H_c__188f02 |
| 12 | 166730 | 169529 | H_c__106n02__M |
| 12 | 16682299 | 16682435 | H_c__191o12 |
| 12 | 1669949 | 1671297 | H_c__13e14 |
| 12 | 16803085 | 16803265 | H_c__204m04 |
| 12 | 17750440 | 17750517 | H_c__157l07 |
| 12 | 1775519 | 1778791 | H_c__67g14__M |
| 12 | 17858255 | 17858552 | H_c__169d06 |
| 12 | 17959021 | 17959172 | H_c__54d04 |
| 12 | 18046210 | 18046394 | H_c__194f12__M |
| 12 | 182775 | 184234 | H_c__187g07__M |
| 12 | 18588927 | 18589116 | H_c__130a04 |
| 12 | 18606650 | 18606763 | H_c__117l15 |
| 12 | 19173676 | 19175449 | H_c__172g12 |
| 12 | 19368155 | 19368323 | H_c__28f14 |
| 12 | 19483353 | 19485015 | H_c__193i14__M |
| 12 | 1983490 | 1984476 | H_c142p22 |
| 12 | 2014114 | 2014708 | H_c__21n05 |
| 12 | 2031735 | 2032873 | H_c__188l17 |
| 12 | 20412555 | 20414333 | H_c__112m20__M |

TABLE 1-continued

| | | | |
|---|---|---|---|
| 12 | 21231074 | 21231157 | H_c_119a01 |
| 12 | 21571503 | 21571870 | H_c_66g15_M |
| 12 | 22090199 | 22090688 | H_c_148p07 |
| 12 | 22314755 | 22314895 | H_c_38g02 |
| 12 | 22379080 | 22379941 | H_c_52i08_M |
| 12 | 22587994 | 22589891 | H_c_151b19_M |
| 12 | 22669093 | 22669902 | H_c_222c17_M |
| 12 | 22831451 | 22831537 | H_c_11l15 |
| 12 | 23230193 | 23230308 | H_c_241c07 |
| 12 | 23382221 | 23382465 | H_c_194c14 |
| 12 | 23511285 | 23511369 | H_c_269a19_M |
| 12 | 23792965 | 23793041 | H_c_77h23 |
| 12 | 24606052 | 24607624 | H_c_101e21_M |
| 12 | 24992931 | 24993746 | H_c_245d16_M |
| 12 | 25074173 | 25074380 | H_c_209j19 |
| 12 | 25430187 | 25430742 | H_c_169g14_M |
| 12 | 25478004 | 25478132 | H_c_230a09 |
| 12 | 2561798 | 2563327 | H_c_100j16_M |
| 12 | 26002133 | 26003684 | H_c_59f08_M |
| 12 | 26158475 | 26159004 | H_c_271b14_M |
| 12 | 26166202 | 26167432 | H_c_174h09_M |
| 12 | 26169795 | 26171001 | H_c_166h01_M |
| 12 | 26239434 | 26240521 | H_c_36b08 |
| 12 | 26271131 | 26271362 | H_c_106d13_M |
| 12 | 2670720 | 2671392 | H_c_210o22_M |
| 12 | 26752123 | 26752202 | H_c_67m19 |
| 12 | 26876573 | 26877975 | H_c_9n06_M |
| 12 | 26981715 | 26983104 | H_c_151d19_M |
| 12 | 27058082 | 27058290 | H_c_66m04 |
| 12 | 2732221 | 2733238 | H_c_7f18 |
| 12 | 27376724 | 27378095 | H_c_181i01 |
| 12 | 27376800 | 27378142 | H_c_201n06 |
| 12 | 27666636 | 27666762 | H_c_148e03 |
| 12 | 2773379 | 2775988 | H_c_271f15_M |
| 12 | 27754836 | 27755453 | H_c_173m23 |
| 12 | 28013119 | 28015005 | H_c_87m20_M |
| 12 | 28018609 | 28019752 | H_c_29m20_M |
| 12 | 28234024 | 28235491 | H_c144f02_M |
| 12 | 2856154 | 2856535 | H_c_75e18 |
| 12 | 2869758 | 2870153 | H_c_59k03_M |
| 12 | 28979614 | 28979746 | H_c_68a04 |
| 12 | 29193097 | 29194406 | H_c140j08_M |
| 12 | 2937865 | 2939795 | H_c_76j07_M |
| 12 | 29696513 | 29696665 | H_c_103b02 |
| 12 | 30344264 | 30344591 | H_c_5a03_M |
| 12 | 3055794 | 3057441 | H_c_191j07_M |
| 12 | 30739435 | 30740342 | H_c_222f22 |
| 12 | 30798477 | 30799771 | H_c_11n08_M |
| 12 | 30839703 | 30840931 | H_c_196n07_M |
| 12 | 30866389 | 30867906 | H_c_69k14_M |
| 12 | 30970662 | 30971704 | H_c_69c23 |
| 12 | 31284126 | 31284231 | H_c_91e13 |
| 12 | 31367723 | 31369019 | H_c_234m03_M |
| 12 | 31369109 | 31370004 | H_c_185j02_M |
| 12 | 31634213 | 31634614 | H_c_65e14_M |
| 12 | 31703342 | 31703596 | H_c_77i03_M |
| 12 | 3179625 | 3180523 | H_c_30d15_M |
| 12 | 32003360 | 32004127 | H_c_211j24_M |
| 12 | 31250211 | 32152567 | H_c_170m01_M |
| 12 | 32201647 | 32201970 | H_c_62n13 |
| 12 | 32443081 | 32444474 | H_c_147l18_M |
| 12 | 32768855 | 32769030 | H_c_7g22 |
| 12 | 32799284 | 32800275 | H_c_120i07_M |
| 12 | 3345238 | 3345777 | H_c_21f01_M |
| 12 | 33483004 | 33484463 | H_c_59l11_M |
| 12 | 34474249 | 34474425 | H_c_21h16 |
| 12 | 34665800 | 34665963 | H_c_122h21 |
| 12 | 34695099 | 34695269 | H_c141e15 |
| 12 | 3407322 | 3470988 | H_c_128b13 |
| 12 | 3470990 | 3473807 | H_c_5m10_M |
| 12 | 36238242 | 36238379 | H_c_265e12 |
| 12 | 368068 | 369143 | H_c_203h22_M |
| 12 | 3731285 | 3732960 | H_c_229h21_M |
| 12 | 37586449 | 37586930 | H_c_187j12_M |
| 12 | 37825157 | 37825750 | H_c_78i06_M |
| 12 | 38122357 | 38124121 | H_c_86h07_M |
| 12 | 38784919 | 38786330 | H_c_118p06 |
| 12 | 38811199 | 38811602 | H_c_241c04_M |
| 12 | 39145862 | 39145962 | H_c_211h07 |
| 12 | 39372049 | 39373189 | H_c_274c08_M |
| 12 | 39644337 | 39644428 | H_c_54f21 |
| 12 | 39770409 | 39770543 | H_c_211d22 |
| 12 | 39868119 | 39869351 | H_c_68p22_M |
| 12 | 39980712 | 39981052 | H_c_186l17 |
| 12 | 4010329 | 4010938 | H_c_45p10_M |
| 12 | 40258926 | 40259769 | H_c_167k21 |
| 12 | 40917432 | 40918897 | H_c_216m08 |
| 12 | 40942632 | 40942706 | H_c_252h10 |
| 12 | 40968337 | 40968403 | H_c_242l20 |
| 12 | 41067233 | 41067382 | H_c_22m13 |
| 12 | 41162810 | 41164486 | H_c_1a05_M |
| 12 | 41268932 | 41270172 | H_c_199h15_M |
| 12 | 4143605 | 4145055 | H_c_274j07_M |
| 12 | 41486029 | 41486236 | H_c135d11 |
| 12 | 41588304 | 41588517 | H_c_171n05 |
| 12 | 42224343 | 42224563 | H_c_39c04 |
| 12 | 42230849 | 42232867 | H_c_211j14_M |
| 12 | 42303290 | 42303520 | H_c_28o05 |
| 12 | 42438887 | 42440761 | H_c140k11_M |
| 12 | 42447247 | 42447371 | H_c138c13 |
| 12 | 4248326 | 4254816 | H_c_97f12_M_M |
| 12 | 42485538 | 42486739 | H_c_36e01_M |
| 12 | 42515410 | 42516675 | H_c_67e16_M |
| 12 | 42875628 | 42875690 | H_c_185j06 |
| 12 | 4299811 | 4301302 | H_c_94a22 |
| 12 | 432490 | 432984 | H_c_53m19_M |
| 12 | 43360912 | 43361027 | H_c_30a01 |
| 12 | 43387628 | 43387734 | H_c_40j07 |
| 12 | 43440191 | 43440290 | H_c_29n04 |
| 12 | 43762433 | 43762532 | H_c_88o20 |
| 12 | 43895888 | 43896890 | H_c_44h23_M |
| 12 | 438981 | 440675 | H_c_170a12_M |
| 12 | 43984432 | 43985379 | H_c_152a04 |
| 12 | 44113758 | 44113979 | H_c_31n03 |
| 12 | 44406937 | 44407182 | H_c_225e13_M |
| 12 | 44409611 | 44410653 | H_c139o17_M |
| 12 | 44480389 | 44480482 | H_c_170l14 |
| 12 | 44669760 | 44671033 | H_c_106k02_M |
| 12 | 44946875 | 44949683 | H_c_45o15_M |
| 12 | 45051141 | 45052223 | H_c131h11_M |
| 12 | 45052266 | 45053163 | H_c_183d06_M |
| 12 | 45062995 | 45064091 | H_c_65o03_M |
| 12 | 4518049 | 4518739 | H_c_11n05 |
| 12 | 45220369 | 45220632 | H_c_218k07 |
| 12 | 45503650 | 45503969 | H_c_66l18 |
| 12 | 45509517 | 45509603 | H_c_27k16 |
| 12 | 45759470 | 45760774 | H_c134l01 |
| 12 | 45963833 | 45964170 | H_c_254l21 |
| 12 | 4628425 | 4628654 | H_c_109p05 |
| 12 | 46361281 | 46361485 | H_c_25m18 |
| 12 | 46385379 | 46386263 | H_c_149f08_M |
| 12 | 46418652 | 46420703 | H_c_215c04 |
| 12 | 46438478 | 46440109 | H_c_241h22_M |
| 12 | 46453011 | 46454279 | H_c_94j18_M |
| 12 | 46492809 | 46493202 | H_c_193m18_M |
| 12 | 46498501 | 46500647 | H_c_3b15 |
| 12 | 46584543 | 46585363 | H_c_127h03_M |
| 12 | 46642726 | 46643881 | H_c_257j16_M |
| 12 | 46785537 | 46786231 | H_c_271p20 |
| 12 | 46836704 | 46838115 | H_c_213b24 |
| 12 | 46863465 | 46865117 | H_c137o12 |
| 12 | 46877816 | 46878660 | H_c_232a01 |
| 12 | 47030151 | 47031608 | H_c_93g12_M |
| 12 | 47286436 | 47286790 | H_c_54o14 |
| 12 | 47307882 | 47309099 | H_c_268h01 |
| 12 | 47361541 | 47363112 | H_c_267b14_M |
| 12 | 47468071 | 47469187 | H_c_78p20_M |
| 12 | 47607710 | 47607798 | H_c_54g13 |
| 12 | 47636994 | 47637791 | H_c_48e19_M |
| 12 | 47649871 | 47654278 | H_c_69m19_M |
| 12 | 47658586 | 47659400 | H_c_99p13 |
| 12 | 47676628 | 47678866 | H_c_16d09_M |
| 12 | 47709924 | 47712112 | H_c_240d22 |
| 12 | 47739459 | 47740850 | H_c_94n24_M |
| 12 | 47769696 | 47770634 | H_c_272d13_M |
| 12 | 47788017 | 47790778 | H_c_54g02 |
| 12 | 47810207 | 47811752 | H_c_161c23_M |
| 12 | 47814122 | 47815846 | H_c132k07 |
| 12 | 47868204 | 47868952 | H_c_273b04_M |
| 12 | 47944448 | 47945358 | H_c_209g20_M |

TABLE 1-continued

| | | | |
|---|---|---|---|
| 12 | 47974883 | 47977758 | H_c141n23_M |
| 12 | 48002574 | 48004392 | H_c_9o11 |
| 12 | 48015758 | 48018618 | H_c_94a11 |
| 12 | 48022000 | 48026847 | H_c_73k14_M_M |
| 12 | 48037362 | 48037586 | H_c131e17 |
| 12 | 48046507 | 48047933 | H_c_96c02_M |
| 12 | 48217480 | 48220825 | H_c_216b20_M |
| 12 | 48247206 | 48248192 | H_c_102g14 |
| 12 | 48303237 | 48304226 | H_c_210p05_M |
| 12 | 48386394 | 48387985 | H_c_124p17_M |
| 12 | 48421533 | 48422646 | H_c_178i20_M |
| 12 | 48523103 | 48523724 | H_c_10c15_M |
| 12 | 4854205 | 4854947 | H_c_227j23 |
| 12 | 48630739 | 48632465 | H_c_224h24 |
| 12 | 48705134 | 48705842 | H_c_224i03 |
| 12 | 48736720 | 48739279 | H_c_51k14 |
| 12 | 48765031 | 48766781 | H_c139l06_M |
| 12 | 48791240 | 48793064 | H_c_253m02_M |
| 12 | 48846698 | 48847979 | H_c_10d24 |
| 12 | 4888744 | 4890031 | H_c_8i07_M |
| 12 | 48963155 | 48963790 | H_c_155g02_M |
| 12 | 49011827 | 49012066 | H_c_222a23_M |
| 12 | 49080620 | 49081758 | H_c_29m01 |
| 12 | 49444203 | 49444774 | H_c_236e03 |
| 12 | 49705809 | 49706924 | H_c_48f14 |
| 12 | 49762868 | 49763839 | H_c_191p20 |
| 12 | 49852254 | 49853327 | H_c_24i19_M |
| 12 | 4989211 | 4990929 | H_c_35d23_M |
| 12 | 49897076 | 49898702 | H_c_89e22_M |
| 12 | 49918457 | 49919295 | H_c134g16_M |
| 12 | 49949122 | 49950985 | H_c_209f14_M |
| 12 | 50003144 | 50005370 | H_c_163b06 |
| 12 | 50014485 | 50015651 | H_c_19a24 |
| 12 | 50070789 | 50072208 | H_c_118p05_M |
| 12 | 50099600 | 50099781 | H_c_217d10 |
| 12 | 50104577 | 50105690 | H_c_197k05_M |
| 12 | 5022074 | 5024232 | H_c_5f12_M |
| 12 | 50270391 | 50271633 | H_c_39b07_M |
| 12 | 50493988 | 50495325 | H_c_203j04_M |
| 12 | 50500230 | 50502658 | H_c142b07_M |
| 12 | 50527607 | 50529795 | H_c_152d13 |
| 12 | 50548849 | 50550288 | H_c134d21_M |
| 12 | 50567885 | 50568999 | H_c_129i04 |
| 12 | 50586270 | 50588838 | H_c_24c05 |
| 12 | 50631107 | 50631564 | H_c_66h21 |
| 12 | 50685865 | 50687523 | H_c_199n05 |
| 12 | 50702694 | 50704384 | H_c_152e18 |
| 12 | 50712978 | 50713487 | H_c_272h22_M |
| 12 | 50728885 | 50731458 | H_c_192h14_M |
| 12 | 50749104 | 50751283 | H_c_166h14_M |
| 12 | 50757923 | 50759163 | H_c_216f16 |
| 12 | 50831305 | 50833946 | H_c_221a10_M |
| 12 | 50929626 | 50930920 | H_c_195n19_M |
| 12 | 50938084 | 50939193 | H_c_33b09_M |
| 12 | 50987941 | 50989931 | H_c_48d10_M |
| 12 | 51176857 | 51177031 | H_c_7j15 |
| 12 | 51280903 | 51281585 | H_c_16k19 |
| 12 | 51371115 | 51371763 | H_c_4h11_M |
| 12 | 51446961 | 51447178 | H_c137d15 |
| 12 | 51470720 | 51470810 | H_c_165o02_M |
| 12 | 51553523 | 51554742 | H_c_5i20_M |
| 12 | 51564349 | 51564706 | H_c_110j17 |
| 12 | 51583199 | 51583807 | H_c_187e16 |
| 12 | 51628477 | 51629965 | H_c_209d16 |
| 12 | 51686105 | 51687147 | H_c144h19_M |
| 12 | 51726249 | 51729079 | H_c_231h15 |
| 12 | 51734408 | 51735277 | H_c_21b01_M |
| 12 | 51758793 | 51759827 | H_c_175c02 |
| 12 | 51860248 | 51863790 | H_c_8j09_M |
| 12 | 51874193 | 51875119 | H_c_53i20 |
| 12 | 51899870 | 51900427 | H_c_120m10_M |
| 12 | 51911830 | 51913928 | H_c_247k05_M |
| 12 | 51948061 | 51948387 | H_c_236j06_M |
| 12 | 51975430 | 51975596 | H_c_84c17_M |
| 12 | 51979817 | 51980142 | H_c_154a01_M |
| 12 | 52004845 | 52006647 | H_c_88c04 |
| 12 | 52024564 | 52025564 | H_c_241p06_M |
| 12 | 52060024 | 52061267 | H_c_54f23_M |
| 12 | 52113935 | 52114095 | H_c_222h06 |
| 12 | 52120763 | 52121930 | H_c_244i18 |
| 12 | 52131711 | 52132922 | H_c_19i14_M |
| 12 | 52172481 | 52173758 | H_c_81h06 |
| 12 | 52179187 | 52181837 | H_c_79l03_M |
| 12 | 52357288 | 52357478 | H_c_55f09_M |
| 12 | 52418039 | 52419822 | H_c_205n05 |
| 12 | 524713 | 526922 | H_c_274k16_M |
| 12 | 52607513 | 52608053 | H_c_230j03 |
| 12 | 52618936 | 52620175 | H_c_254j08_M |
| 12 | 52628806 | 52630558 | H_c_157d05_M |
| 12 | 52632886 | 52636612 | H_c_53l17_M |
| 12 | 52640785 | 52642512 | H_c_185m16_M |
| 12 | 52648151 | 52649086 | H_c_180m06 |
| 12 | 52653298 | 52655737 | H_c_27h11_M |
| 12 | 52665292 | 52666759 | H_c_99c10_M |
| 12 | 52674000 | 52675307 | H_c_25l20 |
| 12 | 52679652 | 52681382 | H_c_53h22_M |
| 12 | 52687988 | 52689722 | H_c_252k12 |
| 12 | 52699044 | 52699767 | H_c_66m21 |
| 12 | 52713309 | 52713870 | H_c_202a19 |
| 12 | 52727220 | 52727584 | H_c_162o01 |
| 12 | 52732161 | 52733932 | H_c_34b09_M |
| 12 | 52961134 | 52961363 | H_c_194n17 |
| 12 | 53048584 | 53049130 | H_c_60j17 |
| 12 | 53228686 | 53230021 | H_c_31k07_M |
| 12 | 53351852 | 53351976 | H_c142c12 |
| 12 | 53767657 | 53767858 | H_c_249f19 |
| 12 | 5410460 | 5413378 | H_c_246d08_M |
| 12 | 54408431 | 54410102 | H_c_185h22_M |
| 12 | 54422283 | 54425054 | H_c_197c05 |
| 12 | 54508967 | 54509814 | H_c_48d12 |
| 12 | 54611471 | 54612841 | H_c_87c14 |
| 12 | 54646551 | 54647721 | H_c_105g23_M |
| 12 | 54653891 | 54654460 | H_c_270l10 |
| 12 | 54721499 | 54722581 | H_c_188e08_M |
| 12 | 54784283 | 54785845 | H_c_191a16 |
| 12 | 54797877 | 54799730 | H_c_29o22_M |
| 12 | 54809203 | 54809781 | H_c_53p11_M |
| 12 | 54832379 | 54832615 | H_c_28b18_M |
| 12 | 549192 | 549444 | H_c_30d01_M |
| 12 | 54937018 | 54939065 | H_c_51d03_M |
| 12 | 54994839 | 54996272 | H_c_270b12_M |
| 12 | 55013609 | 55014948 | H_c133l21 |
| 12 | 55128131 | 55129696 | H_c_29o15_M |
| 12 | 55148468 | 55148851 | H_c_194m02_M |
| 12 | 55167741 | 55168941 | H_c_173j07_M |
| 12 | 55245748 | 55246162 | H_c_225k17 |
| 12 | 55309766 | 55310623 | H_c_179b12 |
| 12 | 55367746 | 55369130 | H_c_130j20_M |
| 12 | 55432311 | 55432649 | H_c_126h16_M |
| 12 | 55491933 | 55492028 | H_c_271f18 |
| 12 | 555483 | 556184 | H_c_102e24 |
| 12 | 5571642 | 5572022 | H_c_34a06 |
| 12 | 55766943 | 55769760 | H_c142o06_M |
| 12 | 55807664 | 55809772 | H_c_7c23_M |
| 12 | 55904502 | 55906145 | H_c_164d13 |
| 12 | 55920191 | 55921788 | H_c_194f04_M |
| 12 | 56022118 | 56022262 | H_c_123l04 |
| 12 | 56110383 | 56111306 | H_c_113f16 |
| 12 | 56139212 | 56142717 | H_c_65n04_M |
| 12 | 56155102 | 56156473 | H_c_8b15_M |
| 12 | 56202648 | 56203580 | H_c_120c04 |
| 12 | 56228927 | 56231267 | H_c_83l09_M |
| 12 | 56270834 | 56272141 | H_c_17i19_M |
| 12 | 56284610 | 56285776 | H_c144a22 |
| 12 | 56290991 | 56292165 | H_c_240i09_M |
| 12 | 56300720 | 56303364 | H_c_106p24_M |
| 12 | 56307745 | 56308507 | H_c_213d11 |
| 12 | 56312531 | 56313081 | H_c_88h17 |
| 12 | 56373943 | 56375055 | H_c_101c15 |
| 12 | 56431430 | 56436098 | H_c_19m14_M |
| 12 | 56446595 | 56447154 | H_c134a18 |
| 12 | 56462453 | 56463469 | H_c_267n13 |
| 12 | 56524908 | 56527243 | H_c_212j19_M |
| 12 | 56531523 | 56533820 | H_c_232b12 |
| 12 | 56545285 | 56545887 | H_c_104c10_M |
| 12 | 56576364 | 56576892 | H_c_70b08_M |
| 12 | 56621097 | 56622262 | H_c_199a23_M |
| 12 | 57089110 | 57089190 | H_c_49m24 |
| 12 | 57599187 | 57600904 | H_c_234k20 |
| 12 | 57768161 | 57768359 | H_c_44m03 |

TABLE 1-continued

| | | | |
|---|---|---|---|
| 12 | 57857276 | 57857413 | H_c_218e16 |
| 12 | 58275548 | 58277240 | H_c_237a13_M |
| 12 | 58534763 | 58534884 | H_c_100l07 |
| 12 | 58834469 | 58834575 | H_c_35b22 |
| 12 | 58901266 | 58901367 | H_c_36h08 |
| 12 | 59050236 | 59050446 | H_c_239c23 |
| 12 | 59189937 | 59190028 | H_c_64e08 |
| 12 | 5924397 | 5925207 | H_c_125e09_M |
| 12 | 59315443 | 59315591 | H_c_128d06 |
| 12 | 59434825 | 59435003 | H_c_2k19_M |
| 12 | 60014682 | 60014805 | H_c_124a12_M |
| 12 | 60229535 | 60229668 | H_c_41f20 |
| 12 | 60267750 | 60267885 | H_c_121p23 |
| 12 | 6035910 | 6036949 | H_c138d06 |
| 12 | 60870914 | 60871821 | H_c_21e16_M |
| 12 | 60921869 | 60921954 | H_c_65n01 |
| 12 | 60939610 | 60941287 | H_c_124g08_M |
| 12 | 61146673 | 61147613 | H_c_79o14_M |
| 12 | 61282433 | 61283972 | H_c139n13_M |
| 12 | 61312199 | 61313936 | H_c_3h04_M |
| 12 | 61613854 | 61615571 | H_c_190g11_M |
| 12 | 6179979 | 6181692 | H_c_32e08_M |
| 12 | 61829763 | 61831488 | H_c_108a10_M |
| 12 | 62078375 | 62079752 | H_c_225a09 |
| 12 | 621968 | 622886 | H_c_66o01 |
| 12 | 62523485 | 62525192 | H_c_274d11_M |
| 12 | 62662512 | 62662976 | H_c_121l06 |
| 12 | 62901754 | 62902883 | H_c_39m15 |
| 12 | 63070070 | 63071074 | H_c_6g20_M |
| 12 | 63084117 | 63085448 | H_c_9j23 |
| 12 | 63131761 | 63132676 | H_c_31g11_M |
| 12 | 63289801 | 63291753 | H_c_48l13 |
| 12 | 63438882 | 63439773 | H_c_66g18 |
| 12 | 63460483 | 63461504 | H_c_199n13_M |
| 12 | 63504203 | 63505778 | H_c_197f20_M |
| 12 | 63801000 | 63802063 | H_c_191i02_M |
| 12 | 63849104 | 63850719 | H_c_166j16_M |
| 12 | 63958017 | 63959584 | H_c_111e15_M |
| 12 | 64067679 | 64067777 | H_c_62c08 |
| 12 | 64319180 | 64319270 | H_c_252j21 |
| 12 | 643361 | 643547 | H_c_179a24 |
| 12 | 64374639 | 64374732 | H_c_45m20 |
| 12 | 64421256 | 64422796 | H_c_198o18_M |
| 12 | 6448906 | 6451452 | H_c_97j21_M |
| 12 | 64503571 | 64506046 | H_c_80e10_M |
| 12 | 64810520 | 64811310 | H_c_169g12 |
| 12 | 64849316 | 64850552 | H_c_157d18_M |
| 12 | 64868422 | 64869915 | H_c_98j16_M |
| 12 | 64914732 | 64915670 | H_c_267d04 |
| 12 | 6512576 | 6515236 | H_c_86i12_M |
| 12 | 6534418 | 6536242 | H_c_4l20_M |
| 12 | 6547647 | 6548319 | H_c_5c07 |
| 12 | 65748701 | 65750135 | H_c_86k10 |
| 12 | 65776809 | 65777054 | H_c_172f10 |
| 12 | 6585151 | 6586834 | H_c140k19_M |
| 12 | 65949291 | 65950388 | H_c_208h05 |
| 12 | 6599364 | 6601044 | H_c_199p08 |
| 12 | 66327178 | 66330152 | H_c_33i07_M |
| 12 | 6667574 | 6669524 | H_c140i05_M |
| 12 | 6679163 | 6680321 | H_c_8d14_M |
| 12 | 67012108 | 67012328 | H_c_194m14 |
| 12 | 6703314 | 6703651 | H_c_55d08_M |
| 12 | 67290583 | 67291780 | H_c_220l10 |
| 12 | 6732138 | 6733329 | H_c_248p02_M |
| 12 | 67366587 | 67367651 | H_c_106c24 |
| 12 | 67390166 | 67390312 | H_c_56m06 |
| 12 | 67426268 | 67427056 | H_c_196f20_M |
| 12 | 6745340 | 6746967 | H_c_190i10_M |
| 12 | 6757122 | 6758941 | H_c_102b07 |
| 12 | 67919337 | 67920467 | H_c_7e16_M |
| 12 | 68039615 | 68040713 | H_c_23k06_M |
| 12 | 6807232 | 6808984 | H_c_151d01_M |
| 12 | 68265287 | 68265764 | H_c_190n10_M |
| 12 | 6831023 | 6832175 | H_c_233e15_M |
| 12 | 68418597 | 68419900 | H_c_27k06_M |
| 12 | 684411 | 684591 | H_c_269a17_M |
| 12 | 6846120 | 6848025 | H_c_273e07_M |
| 12 | 6851516 | 6852979 | H_c_246p24_M |
| 12 | 6870477 | 6871007 | H_c_12b23_M |
| 12 | 68922765 | 68924327 | H_c_7p09_M |
| 12 | 6892577 | 6894795 | H_c_9l22 |
| 12 | 69045660 | 69046087 | H_c131i10_M |
| 12 | 69046120 | 69047344 | H_c_38c11_M |
| 12 | 6925203 | 6926361 | H_c_21g20 |
| 12 | 69289875 | 69290539 | H_c_246a11_M |
| 12 | 69315174 | 69315419 | H_c_56d05 |
| 12 | 6949027 | 6950297 | H_c_59m19_M |
| 12 | 69840280 | 69840500 | H_c_102g22 |
| 12 | 6995992 | 6996567 | H_c_161m22_M |
| 12 | 70119428 | 70121056 | H_c_5j09_M |
| 12 | 7014150 | 7016125 | H_c_55g07 |
| 12 | 70173025 | 70173117 | H_c_91d05 |
| 12 | 70278727 | 70278806 | H_c_112a16 |
| 12 | 70365960 | 70366737 | H_c_20c11_M |
| 12 | 70434479 | 70435301 | H_c_192c20_M |
| 12 | 70519282 | 70520232 | H_c_51j10_M |
| 12 | 70951996 | 70954558 | H_c_8l16_M |
| 12 | 71442060 | 71442159 | H_c_71i15 |
| 12 | 71651616 | 71651706 | H_c_34m17 |
| 12 | 72297746 | 72297842 | H_c138g12 |
| 12 | 7233515 | 7233770 | H_c_274c12_M |
| 12 | 72403611 | 72403778 | H_c_156b24 |
| 12 | 73010048 | 73010215 | H_c_149g09 |
| 12 | 730573 | 734249 | H_c_22j22_M_M |
| 12 | 73117636 | 73117747 | H_c_231d07_M |
| 12 | 73211497 | 73211674 | H_c_193j12 |
| 12 | 73589938 | 73590108 | H_c_69a15 |
| 12 | 7380534 | 7380673 | H_c_202l08 |
| 12 | 73886622 | 73890259 | H_c_168o18_M |
| 12 | 74005397 | 74005471 | H_c_97i09 |
| 12 | 74709873 | 74712489 | H_c_264g16_M |
| 12 | 74763823 | 74765511 | H_c_50d14_M |
| 12 | 7478393 | 7478712 | H_c_121l03 |
| 12 | 7483475 | 7484057 | H_c_25o19 |
| 12 | 75297716 | 75297874 | H_c144f22 |
| 12 | 75659777 | 75660458 | H_c_245k22_M |
| 12 | 75774895 | 75775753 | H_c_148a22_M |
| 12 | 75961224 | 75962344 | H_c_179a20_M |
| 12 | 76221059 | 76221557 | H_c_184a22_M |
| 12 | 76512847 | 76513011 | H_c_177n23 |
| 12 | 76587012 | 76587117 | H_c_196f18 |
| 12 | 76839536 | 76839662 | H_c_35k17 |
| 12 | 76980062 | 76980235 | H_c_101l13 |
| 12 | 77760456 | 77761881 | H_c_39g08 |
| 12 | 77817504 | 77817670 | H_c_236h01_M |
| 12 | 78184914 | 78185017 | H_c_195k06 |
| 12 | 78499382 | 78499667 | H_c_273g18 |
| 12 | 78585616 | 78587672 | H_c_90m02 |
| 12 | 78830045 | 78831862 | H_c_30l13 |
| 12 | 7915942 | 7916816 | H_c_21g19_M |
| 12 | 79604550 | 79605237 | H_c_200n05 |
| 12 | 79833073 | 79834401 | H_c_25o08_M |
| 12 | 79996181 | 79996252 | H_c_75k10 |
| 12 | 80029402 | 80029484 | H_c_58f16 |
| 12 | 8014465 | 8014836 | H_c_181o11_M |
| 12 | 80336401 | 80336603 | H_c_162l09 |
| 12 | 8062475 | 8062697 | H_c_20f23_M |
| 12 | 80654295 | 80655999 | H_c_82b19_M |
| 12 | 8076221 | 8076448 | H_c_99g13_M |
| 12 | 81254275 | 81255017 | H_c_56l23_M |
| 12 | 8126023 | 8126464 | H_c_43f01 |
| 12 | 81582511 | 81583988 | H_c_5g11_M |
| 12 | 81656157 | 81656244 | H_c_168e05 |
| 12 | 81982139 | 81982323 | H_c_63d10 |
| 12 | 82311293 | 82311725 | H_c_172h14 |
| 12 | 82458036 | 82458162 | H_c_86j02 |
| 12 | 82926968 | 82927063 | H_c_244a06_M |
| 12 | 84176357 | 84177246 | H_c_70o19 |
| 12 | 84225319 | 84225401 | H_c_79j12 |
| 12 | 86824057 | 86824222 | H_c_99g08 |
| 12 | 86898712 | 86898844 | H_c_117a07 |
| 12 | 86931618 | 86932478 | H_c_77p06_M |
| 12 | 87037974 | 87039312 | H_c_78l16 |
| 12 | 87475388 | 87477177 | H_c_265k06_M |
| 12 | 87903018 | 87903173 | H_c_226p02 |
| 12 | 88161146 | 88161219 | H_c_166l05 |
| 12 | 88247416 | 88247577 | H_c_81m21 |
| 12 | 88249653 | 88251082 | H_c_216k23 |
| 12 | 88420743 | 88421727 | H_c136d23 |
| 12 | 88488592 | 88488704 | H_c_20d06 |

TABLE 1-continued

| | | | |
|---|---|---|---|
| 12 | 88604191 | 88606478 | H_c_216j05_M |
| 12 | 88891793 | 88891905 | H_c_241k10 |
| 12 | 89553402 | 89553647 | H_c_122k21 |
| 12 | 8957829 | 8959439 | H_c143i09_M |
| 12 | 8993632 | 8994061 | H_c_90f20_M |
| 12 | 90230935 | 90231027 | H_c_194p15 |
| 12 | 90391874 | 90392155 | H_c_180j22 |
| 12 | 90402723 | 90402794 | H_c_107d04 |
| 12 | 90689829 | 90689910 | H_c_164c09 |
| 12 | 91041403 | 91042847 | H_c_61a02 |
| 12 | 9108120 | 9110043 | H_c_4f20_M |
| 12 | 91153757 | 91153842 | H_c_25g12_M |
| 12 | 91172226 | 91172399 | H_c_70f04 |
| 12 | 91447745 | 91447990 | H_c_10c21 |
| 12 | 92274146 | 92274967 | H_c_102d15 |
| 12 | 92337346 | 92338782 | H_c_149e22_M |
| 12 | 92363366 | 92364192 | H_c_120l07_M |
| 12 | 92466606 | 92470134 | H_c_89j21_M |
| 12 | 92519197 | 92519458 | H_c_2a09 |
| 12 | 928701 | 930109 | H_c_203e05 |
| 12 | 93026007 | 93026062 | H_c_83b23 |
| 12 | 93070530 | 93070761 | H_c_271d06 |
| 12 | 93118628 | 93119247 | H_c_47a07 |
| 12 | 93312740 | 93313473 | H_c_106b21 |
| 12 | 93355842 | 93356854 | H_c_3k12_M |
| 12 | 93968960 | 93969304 | H_c_115p02_M |
| 12 | 93969305 | 93970031 | H_c133e01_M |
| 12 | 94113123 | 94114614 | H_c_195n22_M |
| 12 | 94120 | 94356 | H_c_52b07 |
| 12 | 94171045 | 94171286 | H_c_152d09 |
| 12 | 94444371 | 94445454 | H_c_265f12_M |
| 12 | 94686217 | 94687426 | H_c_160d15_M |
| 12 | 94754986 | 94755553 | H_c_73n13_M |
| 12 | 94838475 | 94840075 | H_c_222l01_M |
| 12 | 94930852 | 94931903 | H_c_214l07 |
| 12 | 95090155 | 95091605 | H_c_21p21_M |
| 12 | 95295304 | 95297627 | H_c_252e12 |
| 12 | 95385604 | 95386317 | H_c_44n14_M |
| 12 | 95508824 | 95509049 | H_c_249b23 |
| 12 | 95826110 | 95826282 | H_c_87i22 |
| 12 | 95881801 | 95882047 | H_c_242g17 |
| 12 | 96174465 | 96174584 | H_c_81m23 |
| 12 | 96191213 | 96191398 | H_c_87g15 |
| 12 | 96217523 | 96217651 | H_c_43c15 |
| 12 | 96449860 | 96450075 | H_c_60h01 |
| 12 | 9691474 | 9692329 | H_c_69h11_M |
| 12 | 97411268 | 97412760 | H_c_228l14_M |
| 12 | 97489602 | 97490777 | H_c_119f04_M |
| 12 | 97540502 | 97542357 | H_c_183h14_M |
| 12 | 97971692 | 97971826 | H_c_272o19 |
| 12 | 98881341 | 98881612 | H_c_180f10 |
| 12 | 99038476 | 99039326 | H_c_44h18_M |
| 12 | 99095369 | 99096427 | H_c_19m18 |
| 12 | 99162964 | 99164188 | H_c_148b03 |
| 12 | 99469541 | 99470367 | H_c_129n21_M |
| 12 | 99487820 | 99487885 | H_c_35e22 |
| 12 | 99612263 | 99614095 | H_c_217g02 |
| 12 | 99715534 | 99715620 | H_c_101l24 |
| 13 | 100038592 | 100039574 | H_c_16h18_M |
| 13 | 100124273 | 100125582 | H_c_109g13_M |
| 13 | 100200564 | 100200890 | H_c_118c18 |
| 13 | 100318295 | 100319955 | H_c_42p12 |
| 13 | 100714460 | 100714599 | H_c_129b13 |
| 13 | 100797706 | 100798055 | H_c_222k03 |
| 13 | 100866046 | 100867195 | H_c_192i16_M |
| 13 | 100903901 | 100904567 | H_c_64e14 |
| 13 | 100990411 | 100990549 | H_c_4d05 |
| 13 | 101134617 | 101134724 | H_c_206o12 |
| 13 | 101322834 | 101322906 | H_c_121f15 |
| 13 | 101366090 | 101368140 | H_c_272a13_M |
| 13 | 101577276 | 101577942 | H_c_85i12 |
| 13 | 101844276 | 101845376 | H_c_226n01 |
| 13 | 101850089 | 101851511 | H_c_200n13_M |
| 13 | 101869033 | 101869169 | H_c_58i02 |
| 13 | 102039950 | 102040159 | H_c_2k08 |
| 13 | 102046796 | 102047997 | H_c_15g14_M |
| 13 | 102223518 | 102224447 | H_c_122m14_M |
| 13 | 102248797 | 102251470 | H_c_11e21_M |
| 13 | 102296025 | 102296440 | H_c_169a24_M |
| 13 | 102773012 | 102773121 | H_c_155n16 |
| 13 | 103453423 | 103453566 | H_c_209g07 |
| 13 | 104061572 | 104061827 | H_c_78n12 |
| 13 | 104468843 | 104468942 | H_c_101d14 |
| 13 | 104941218 | 104941361 | H_c_165g11 |
| 13 | 105108865 | 105108947 | H_c_57i10 |
| 13 | 105609286 | 105609474 | H_c144c14 |
| 13 | 106017674 | 106018713 | H_c_223p15 |
| 13 | 106363268 | 106363362 | H_c_2i23 |
| 13 | 106728177 | 106728325 | H_c_34g21 |
| 13 | 107230071 | 107230254 | H_c_173c22 |
| 13 | 107315905 | 107316896 | H_c_149a11 |
| 13 | 107664710 | 107666292 | H_c_84p14 |
| 13 | 107668478 | 107669637 | H_c_17m03_M |
| 13 | 107717132 | 107717413 | H_c_108g19 |
| 13 | 107719943 | 107720291 | H_c_181l14 |
| 13 | 107841277 | 107841479 | H_c_68l06 |
| 13 | 107876788 | 107876920 | H_c_118d04 |
| 13 | 107945549 | 107946973 | H_c_27l16_M |
| 13 | 108152533 | 108152693 | H_c132l08 |
| 13 | 108590257 | 108591866 | H_c139h04_M |
| 13 | 108883493 | 108883614 | H_c_121o14 |
| 13 | 109115056 | 109115311 | H_c_251e03 |
| 13 | 109159242 | 109159379 | H_c_212i15 |
| 13 | 109237336 | 109238414 | H_c_38m04 |
| 13 | 109294859 | 109294936 | H_c_182l09 |
| 13 | 109566387 | 109566865 | H_c_167i11 |
| 13 | 109588475 | 109589368 | H_c_21p19_M |
| 13 | 109757071 | 109758722 | H_c_192n13_M |
| 13 | 110011166 | 110012518 | H_c_269h24_M |
| 13 | 110056273 | 110057610 | H_c_235n22_M |
| 13 | 110065729 | 110066932 | H_c_273k17_M |
| 13 | 110094863 | 110095975 | H_c_180i22 |
| 13 | 110156007 | 110158138 | H_c_58p05 |
| 13 | 110331051 | 110331249 | H_c_124o22 |
| 13 | 110564826 | 110566485 | H_c_163f11_M |
| 13 | 110603483 | 110604895 | H_c133g13_M |
| 13 | 110626594 | 110627283 | H_c_252e16 |
| 13 | 110861652 | 110862602 | H_c_227f15 |
| 13 | 111595500 | 111596959 | H_c_113a09 |
| 13 | 111752721 | 111752985 | H_c_10c10_M |
| 13 | 111755914 | 111760494 | H_c_42g07_M_M |
| 13 | 111763943 | 111765667 | H_c_120l10_M |
| 13 | 111768915 | 111769192 | H_c_205m05 |
| 13 | 111774499 | 111774675 | H_c_61k07_M |
| 13 | 111805062 | 111808473 | H_c_252p20_M |
| 13 | 111897712 | 111899104 | H_c_256g03 |
| 13 | 112289702 | 112290736 | H_c_127n19_M |
| 13 | 112391620 | 112393122 | H_c_183i22_M |
| 13 | 112468285 | 112470944 | H_c_165f08 |
| 13 | 112587001 | 112588561 | H_c_91d10 |
| 13 | 112595896 | 112600034 | H_c_192g19_M |
| 13 | 112645487 | 112647280 | H_c_53o10 |
| 13 | 112811902 | 112813450 | H_c_275o04 |
| 13 | 112910478 | 112912603 | H_c_15l01_M |
| 13 | 112998970 | 113000144 | H_c_14f10_M |
| 13 | 113064995 | 113066437 | H_c_7i09 |
| 13 | 113095152 | 113096796 | H_c_196a12_M |
| 13 | 113191806 | 113193304 | H_c_9k01_M |
| 13 | 113285427 | 113288014 | H_c_198n20 |
| 13 | 113546637 | 113547687 | H_c_59h11 |
| 13 | 113602937 | 113605007 | H_c_56i09 |
| 13 | 113650942 | 113652584 | H_c_30n09_M |
| 13 | 113848671 | 113850955 | H_c_223h13 |
| 13 | 113904953 | 113907766 | H_c_123c16 |
| 13 | 113982043 | 113984685 | H_c_43d15_M |
| 13 | 113994480 | 113995350 | H_c_122i20 |
| 13 | 114018194 | 114019060 | H_c_153m23_M |
| 13 | 114052247 | 114053884 | H_c_59j19_M |
| 13 | 114064837 | 114066088 | H_c_123g02_M |
| 13 | 114097509 | 114098562 | H_c_38f05 |
| 13 | 19105304 | 19105726 | H_c_12n07_M |
| 13 | 19254071 | 19254890 | H_c_154m09_M |
| 13 | 19431141 | 19432222 | H_c_113e20_M |
| 13 | 19589936 | 19591328 | H_c135b16 |
| 13 | 19599588 | 19600939 | H_c_172h22_M |
| 13 | 19608771 | 19609269 | H_c_151n18_M |
| 13 | 19613881 | 19615642 | H_c134j07 |
| 13 | 19632712 | 19634200 | H_c_69e16_M |
| 13 | 19648413 | 19650442 | H_c_58j05 |
| 13 | 19665103 | 19666410 | H_c_75k21_M |

TABLE 1-continued

| | | | |
|---|---|---|---|
| 13 | 19703669 | 19704438 | H_c_90a07_M |
| 13 | 19704486 | 19704970 | H_c_242m08_M |
| 13 | 19840289 | 19840448 | H_c_155g01 |
| 13 | 20038862 | 20039725 | H_c_259l23 |
| 13 | 20127023 | 20127276 | H_c_22l10 |
| 13 | 20175118 | 20177036 | H_c_107n23 |
| 13 | 20245755 | 20245930 | H_c_114h01 |
| 13 | 20374201 | 20375924 | H_c_28l22_M |
| 13 | 20418063 | 20418592 | H_c_77i19_M |
| 13 | 20532142 | 20533969 | H_c_19c05 |
| 13 | 20547607 | 20548400 | H_c135c14 |
| 13 | 20648202 | 20649479 | H_c_220l11 |
| 13 | 20791345 | 20792225 | H_c_107d08 |
| 13 | 20929879 | 20931921 | H_c_70b10_M |
| 13 | 21075770 | 21076746 | H_c_120m05_M |
| 13 | 21141410 | 21143628 | H_c_57k18_M |
| 13 | 21145782 | 21147843 | H_c_27j08_M |
| 13 | 21295075 | 21295225 | H_c_160j04 |
| 13 | 21662810 | 21663015 | H_c_22h16 |
| 13 | 22398209 | 22400516 | H_c_202g20 |
| 13 | 22631640 | 22633094 | H_c_127p05_M |
| 13 | 22846821 | 22848292 | H_c_48a07_M |
| 13 | 22938139 | 22939029 | H_c_222p20 |
| 13 | 23050872 | 23051593 | H_c_205m10 |
| 13 | 23652970 | 23653234 | H_c_274p03 |
| 13 | 23799830 | 23800784 | H_c_272d16_M |
| 13 | 23984338 | 23985127 | H_c135b14_M |
| 13 | 24152676 | 24153869 | H_c_178g20_M |
| 13 | 24376672 | 24376793 | H_c_83o13 |
| 13 | 24394331 | 24395359 | H_c137f12_M |
| 13 | 24518841 | 24519961 | H_c_206j14_M |
| 13 | 24642008 | 24644835 | H_c_87b09_M |
| 13 | 24759047 | 24760110 | H_c_202k13 |
| 13 | 24771480 | 24771717 | H_c_3a08_M |
| 13 | 24773597 | 24774147 | H_c_193a23_M |
| 13 | 24844383 | 24845256 | H_c144c15 |
| 13 | 24940406 | 24941600 | H_c_93k12_M |
| 13 | 25484073 | 25484982 | H_c_73f18_M |
| 13 | 25522568 | 25524867 | H_c_125e08_M |
| 13 | 25619432 | 25619522 | H_c_91j16 |
| 13 | 25658462 | 25659012 | H_c_23j02_M |
| 13 | 25694042 | 25694622 | H_c_109p11_M |
| 13 | 25725767 | 25727216 | H_c_220p06_M |
| 13 | 26029321 | 26030782 | H_c_18i05_M |
| 13 | 26163348 | 26163417 | H_c_70p05 |
| 13 | 26232163 | 26233391 | H_c_42j21_M |
| 13 | 26330890 | 26331114 | H_c_65m16 |
| 13 | 26360583 | 26360763 | H_c_31g06 |
| 13 | 26562434 | 26562580 | H_c_213b17 |
| 13 | 26723246 | 26724003 | H_c_180p18_M |
| 13 | 26742526 | 26743746 | H_c131k12_M |
| 13 | 26896553 | 26897847 | H_c_63e22_M |
| 13 | 26922040 | 26922752 | H_c_120h02_M |
| 13 | 27092175 | 27094363 | H_c_161g23_M |
| 13 | 27261911 | 27262207 | H_c144d08_M |
| 13 | 27264594 | 27266467 | H_c_19i24_M |
| 13 | 27391862 | 27393148 | H_c_195f17_M |
| 13 | 27393154 | 27394964 | H_c_163k08 |
| 13 | 27399543 | 27401718 | H_c_34d05_M |
| 13 | 27432411 | 27433441 | H_c_151b02_M |
| 13 | 27438396 | 27439080 | H_c144g02_M |
| 13 | 27572164 | 27573180 | H_c_101j12_M |
| 13 | 27610140 | 27611716 | H_c_34k07_M |
| 13 | 27777905 | 27778066 | H_c_79a01 |
| 13 | 27966101 | 27968042 | H_c_226p03_M |
| 13 | 28003351 | 28005598 | H_c_152b20_M |
| 13 | 28131037 | 28131947 | H_c_187m13 |
| 13 | 28857123 | 28858206 | H_c_154d05_M |
| 13 | 29066334 | 29068286 | H_c135a10_M |
| 13 | 29322092 | 29322312 | H_c_173k23_M |
| 13 | 29570833 | 29571414 | H_c_193b15 |
| 13 | 29586610 | 29587425 | H_c_265j24_M |
| 13 | 29636363 | 29636788 | H_c_47a06 |
| 13 | 29778854 | 29780129 | H_c_11i21_M |
| 13 | 29879695 | 29881422 | H_c_272g20_M |
| 13 | 29913796 | 29913989 | H_c_234h16 |
| 13 | 29936283 | 29938474 | H_c_120o11_M |
| 13 | 30089246 | 30089749 | H_c_272b18_M |
| 13 | 30377952 | 30379173 | H_c_15j10_M |
| 13 | 30632965 | 30634345 | H_c_122l07_M |
| 13 | 30671695 | 30673121 | H_c_213l09 |
| 13 | 31318406 | 31319403 | H_c_30e02_M |
| 13 | 31502781 | 31504238 | H_c_129g18_M |
| 13 | 31787424 | 31788062 | H_c_194h12_M |
| 13 | 32058247 | 32059581 | H_c_206a23_M |
| 13 | 32128382 | 32128477 | H_c_219l18 |
| 13 | 32883394 | 32883512 | H_c_15o20 |
| 13 | 33014571 | 33014841 | H_c_168n24 |
| 13 | 33014842 | 33015195 | H_c_12j01 |
| 13 | 33744936 | 33745018 | H_c_15k08 |
| 13 | 34149102 | 34149244 | H_c_10j17 |
| 13 | 34413804 | 34415138 | H_c_215n20 |
| 13 | 34437800 | 34437912 | H_c_164e22 |
| 13 | 34943041 | 34943709 | H_c_13j08_M |
| 13 | 35166540 | 35168640 | H_c_104n16 |
| 13 | 35382714 | 35382987 | H_c_19p07_M |
| 13 | 35602998 | 35604103 | H_c_1e22_M |
| 13 | 35769917 | 35770380 | H_c_62m21_M |
| 13 | 35903445 | 35904560 | H_c_217h24 |
| 13 | 35923917 | 35924429 | H_c_221g20 |
| 13 | 36138627 | 36138711 | H_c_203i05 |
| 13 | 36290784 | 36292150 | H_c_242c19_M |
| 13 | 36391713 | 36392909 | H_c_167m06 |
| 13 | 36471191 | 36473016 | H_c_111m11_M |
| 13 | 36531478 | 36532206 | H_c_11e15 |
| 13 | 36964345 | 36964540 | H_c_190e13 |
| 13 | 37821409 | 37822081 | H_c132n24 |
| 13 | 38158944 | 38161271 | H_c_227n16_M |
| 13 | 38509600 | 38510401 | H_c_33f02 |
| 13 | 39074353 | 39075744 | H_c_15b21 |
| 13 | 39127533 | 39128649 | H_c_31c24_M |
| 13 | 39860606 | 39861322 | H_c_114o03 |
| 13 | 39878534 | 39878686 | H_c_52i12 |
| 13 | 40136911 | 40139571 | H_c_228l21_M |
| 13 | 40532209 | 40534332 | H_c_70i23_M |
| 13 | 40783079 | 40783771 | H_c_92i15_M |
| 13 | 40792799 | 40792976 | H_c_53m20 |
| 13 | 40837753 | 40837867 | H_c_42j04 |
| 13 | 40928909 | 40930835 | H_c_94l15_M |
| 13 | 41432662 | 41433614 | H_c_195b21_M |
| 13 | 41519733 | 41521511 | H_c_205n02 |
| 13 | 41744068 | 41744665 | H_c_120a07_M |
| 13 | 42211737 | 42211982 | H_c_193a10 |
| 13 | 42318334 | 42318426 | H_c_170o09 |
| 13 | 42793713 | 42793957 | H_c_21k12_M |
| 13 | 42932484 | 42932641 | H_c_84m21 |
| 13 | 43257668 | 43259975 | H_c_18l02 |
| 13 | 43350942 | 43352517 | H_c_33b17 |
| 13 | 43613982 | 43614357 | H_c_7i14 |
| 13 | 43708283 | 43709843 | H_c_3h09_M |
| 13 | 43757478 | 43757667 | H_c_107j22 |
| 13 | 43762989 | 43763747 | H_c_214g05 |
| 13 | 43848304 | 43848420 | H_c_194h24 |
| 13 | 43907197 | 43907482 | H_c_78a01 |
| 13 | 44410259 | 44410439 | H_c132i11 |
| 13 | 44532298 | 44532384 | H_c_161h15 |
| 13 | 44783138 | 44783690 | H_c_237k04 |
| 13 | 44812531 | 44813688 | H_c_99g22_M |
| 13 | 44889938 | 44891264 | H_c_27l10_M |
| 13 | 44936986 | 44937718 | H_c_83b18_M |
| 13 | 45524407 | 45524801 | H_c_216f23 |
| 13 | 45674698 | 45674849 | H_c_206o02 |
| 13 | 45683845 | 45684911 | H_c_86l11 |
| 13 | 45806482 | 45806553 | H_c_42d10 |
| 13 | 45858570 | 45861129 | H_c_18e21_M |
| 13 | 46024889 | 46026646 | H_c_30i21_M |
| 13 | 46215577 | 46215704 | H_c_92d07 |
| 13 | 46650175 | 46650268 | H_c_225d03 |
| 13 | 47144556 | 47144714 | H_c_273k21_M |
| 13 | 47472790 | 47473533 | H_c_172d04_M |
| 13 | 47484667 | 47484865 | H_c_152f22 |
| 13 | 47509408 | 47510690 | H_c_85g23_M |
| 13 | 47566836 | 47567768 | H_c_88m10_M |
| 13 | 47601872 | 47601981 | H_c_37g03 |
| 13 | 47704896 | 47706109 | H_c_18n05_M |
| 13 | 47754918 | 47755007 | H_c_76n08 |
| 13 | 47775757 | 47777085 | H_c_124c13 |
| 13 | 48004422 | 48005879 | H_c_155g24_M |
| 13 | 48115213 | 48115286 | H_c_117k21 |
| 13 | 48124212 | 48124532 | H_c_113d13 |

TABLE 1-continued

| | | | |
|---|---|---|---|
| 13 | 48447763 | 48448863 | H__c__211p14 |
| 13 | 48691709 | 48693665 | H__c__215h13__M |
| 13 | 48719949 | 48720559 | H__c__64k03 |
| 13 | 48915811 | 48916870 | H__c__217a14__M |
| 13 | 48968062 | 48968868 | H__c__53j14__M |
| 13 | 49056993 | 49058655 | H__c__84f04__M |
| 13 | 49163155 | 49163920 | H__c__198i22__M |
| 13 | 49263610 | 49266209 | H__c__195d19 |
| 13 | 49331711 | 49331891 | H__c__28f19__M |
| 13 | 49407596 | 49408817 | H__c__73l08__M |
| 13 | 49468277 | 49469655 | H__c__42h24__M |
| 13 | 49502118 | 49502204 | H__c__210b18 |
| 13 | 49604234 | 49604407 | H__c__11d24 |
| 13 | 49945125 | 49945274 | H__c__225c22 |
| 13 | 50216404 | 50216509 | H__c142m02__M |
| 13 | 50314958 | 50316519 | H__c__160a04__M |
| 13 | 50381720 | 50382708 | H__c__125m09__M |
| 13 | 50500305 | 50500694 | H__c__208d09 |
| 13 | 50508598 | 50508664 | H__c132h01 |
| 13 | 50530300 | 50530376 | H__c__26k19 |
| 13 | 50693861 | 50695187 | H__c__46f02__M |
| 13 | 51056294 | 51057643 | H__c__70b09__M |
| 13 | 51275755 | 51276637 | H__c__177d04__M |
| 13 | 51483557 | 51484776 | H__c__226m15__M |
| 13 | 51529119 | 51529132 | H__c__21n09 |
| 13 | 51631300 | 51631839 | H__c__55p10__M |
| 13 | 51877995 | 51878570 | H__c__70k16__M |
| 13 | 52072166 | 52072691 | H__c__248n02 |
| 13 | 52210770 | 52212590 | H__c__192d16 |
| 13 | 52316534 | 52317240 | H__c__64k11 |
| 13 | 52363122 | 52363243 | H__c__16j06 |
| 13 | 52672298 | 52674991 | H__c__239a24__M |
| 13 | 53133005 | 53133113 | H__c__226f23 |
| 13 | 53186124 | 53186306 | H__c__78a12 |
| 13 | 53499593 | 53499683 | H__c__124l06 |
| 13 | 54968610 | 54968698 | H__c__17m20 |
| 13 | 55888092 | 55888208 | H__c__152k21 |
| 13 | 56088259 | 56088532 | H__c__8c15 |
| 13 | 56361124 | 56361221 | H__c__100a09 |
| 13 | 56513882 | 56513997 | H__c__165j12 |
| 13 | 57101508 | 57107242 | H__c__232o02__M__M |
| 13 | 57864835 | 57865040 | H__c__119o17__M |
| 13 | 58528748 | 58528834 | H__c__190g17 |
| 13 | 59185774 | 59185855 | H__c__168p08 |
| 13 | 59364191 | 59364271 | H__c__244l05 |
| 13 | 59635516 | 59636226 | H__c__273p12__M |
| 13 | 59648242 | 59648354 | H__c__225n10 |
| 13 | 59868336 | 59870124 | H__c__8f09__M |
| 13 | 60015025 | 60015108 | H__c__88h14 |
| 13 | 60319199 | 60319313 | H__c__162o07 |
| 13 | 60818081 | 60818196 | H__c__10d16 |
| 13 | 60926895 | 60926988 | H__c__18k16 |
| 13 | 61090172 | 61090475 | H__c__24p08 |
| 13 | 61849143 | 61849226 | H__c__174a05 |
| 13 | 62265177 | 62265289 | H__c__161p16 |
| 13 | 62358358 | 62358452 | H__c143h05 |
| 13 | 62624633 | 62624754 | H__c144f16 |
| 13 | 64224184 | 64224280 | H__c__162h03 |
| 13 | 64260502 | 64260601 | H__c__216f20 |
| 13 | 65486233 | 65486440 | H__c__31d21 |
| 13 | 66114073 | 66114166 | H__c__28i03 |
| 13 | 66263615 | 66263888 | H__c__236g15__M |
| 13 | 66686545 | 66686691 | H__c__160g16 |
| 13 | 66702261 | 66703772 | H__c__31g12__M |
| 13 | 67893795 | 67893993 | H__c__266m22 |
| 13 | 67932469 | 67932683 | H__c__119a08 |
| 13 | 69030954 | 69031159 | H__c__204a10 |
| 13 | 69125311 | 69125387 | H__c__34n04 |
| 13 | 69234857 | 69235114 | H__c__12h18 |
| 13 | 70860489 | 70860673 | H__c__151j10 |
| 13 | 70894808 | 70895049 | H__c__113n16 |
| 13 | 71337071 | 71339186 | H__c__145n11__M |
| 13 | 71935693 | 71935797 | H__c__221k22__M |
| 13 | 71987872 | 71988086 | H__c__171i06 |
| 13 | 72064542 | 72064722 | H__c__228k06 |
| 13 | 72199181 | 72200016 | H__c__18p17__M |
| 13 | 72253569 | 72253947 | H__c__124j01__M |
| 13 | 72530671 | 72532068 | H__c__148c21 |
| 13 | 72597388 | 72597526 | H__c__99e08 |
| 13 | 73015713 | 73015858 | H__c__112i21 |
| 13 | 73314254 | 73314432 | H__c__89d03 |
| 13 | 73330580 | 73330811 | H__c__2h13 |
| 13 | 73336504 | 73336779 | H__c__96e21 |
| 13 | 74912239 | 74912437 | H__c__59n18 |
| 13 | 74952929 | 74953319 | H__c__244p14 |
| 13 | 74953318 | 74954856 | H__c__256a07__M |
| 13 | 75009514 | 75010094 | H__c__198f24 |
| 13 | 75021145 | 75022226 | H__c__222e08__M |
| 13 | 75107276 | 75108618 | H__c__26b03__M |
| 13 | 75384887 | 75385068 | H__c__275j11 |
| 13 | 75839090 | 75839223 | H__c__156e18 |
| 13 | 76097124 | 76097312 | H__c__239p20__M |
| 13 | 76356859 | 76359259 | H__c134b23__M |
| 13 | 76463734 | 76464689 | H__c__81a08__M |
| 13 | 76498242 | 76499684 | H__c__66o07__M |
| 13 | 76585326 | 76585464 | H__c__206p20 |
| 13 | 76751315 | 76751469 | H__c__19b14 |
| 13 | 76798029 | 76799544 | H__c__66m17__M |
| 13 | 76924284 | 76924378 | H__c__120c24 |
| 13 | 77094112 | 77094182 | H__c__196a23 |
| 13 | 77933980 | 77934149 | H__c__234f16 |
| 13 | 78068881 | 78069080 | H__c__252j14 |
| 13 | 78073253 | 78076236 | H__c__100k17__M |
| 13 | 78080372 | 78081260 | H__c__11c15__M |
| 13 | 78130850 | 78131004 | H__c__88e02__M |
| 13 | 78877449 | 78878995 | H__c__210f05__M |
| 13 | 78952971 | 78953889 | H__c__84n06__M |
| 13 | 79250636 | 79250748 | H__c__238d02 |
| 13 | 79811937 | 79815271 | H__c__49f02__M |
| 13 | 79976110 | 79976313 | H__c__12l12 |
| 13 | 80116111 | 80116444 | H__c__196c24 |
| 13 | 80204972 | 80205115 | H__c__166n10 |
| 13 | 80484134 | 80484949 | H__c__70h02 |
| 13 | 80591980 | 80592065 | H__c__172a13 |
| 13 | 80639400 | 80639538 | H__c__21d14 |
| 13 | 81857946 | 81858078 | H__c__84d20 |
| 13 | 82550931 | 82551131 | H__c__55m02 |
| 13 | 83055905 | 83055996 | H__c__228f02 |
| 13 | 83118980 | 83119152 | H__c131k10__M |
| 13 | 83135502 | 83135689 | H__c__185c08 |
| 13 | 83309479 | 83309575 | H__c__219l02 |
| 13 | 83417718 | 83417822 | H__c__104m07 |
| 13 | 83565323 | 83565441 | H__c__267n23 |
| 13 | 83772593 | 83772798 | H__c__240g02 |
| 13 | 84735224 | 84735335 | H__c__88b13 |
| 13 | 84866441 | 84867080 | H__c__216a16 |
| 13 | 84931072 | 84931164 | H__c__80h15 |
| 13 | 85357406 | 85357710 | H__c__15j17 |
| 13 | 86039744 | 86039858 | H__c__192f02__M |
| 13 | 86146976 | 86147073 | H__c__261e02 |
| 13 | 86584044 | 86584170 | H__c__116n24 |
| 13 | 87121346 | 87122529 | H__c__23e20__M |
| 13 | 87122528 | 87124030 | H__c__84k23__M |
| 13 | 88069819 | 88069998 | H__c__32j07 |
| 13 | 88606467 | 88606578 | H__c__123j13 |
| 13 | 90797664 | 90799526 | H__c__110f18__M |
| 13 | 90848526 | 90850074 | H__c__231o04__M |
| 13 | 91409789 | 91410166 | H__c__23k15 |
| 13 | 91838112 | 91838196 | H__c__230i16 |
| 13 | 91901795 | 91901953 | H__c__99m17 |
| 13 | 93192653 | 93192746 | H__c__203j14 |
| 13 | 93559138 | 93559279 | H__c__69k09 |
| 13 | 93701047 | 93701125 | H__c__195g06 |
| 13 | 93795006 | 93795128 | H__c__267b16 |
| 13 | 93999142 | 94000521 | H__c__82c14__M |
| 13 | 94046108 | 94046493 | H__c__97o14 |
| 13 | 94051789 | 94052713 | H__c__191h03__M |
| 13 | 94152186 | 94152590 | H__c__203b22 |
| 13 | 94157631 | 94158128 | H__c__252f07__M |
| 13 | 94160557 | 94163529 | H__c__153a17__M |
| 13 | 94353767 | 94353940 | H__c__231p17__M |
| 13 | 94378642 | 94378926 | H__c__91o11 |
| 13 | 94417855 | 94418780 | H__c__267p02 |
| 13 | 94444642 | 94444808 | H__c__15o18 |
| 13 | 94452876 | 94453795 | H__c__166p15 |
| 13 | 95002143 | 95003699 | H__c__238n15__M |
| 13 | 95091458 | 95092672 | H__c__9h01__M |
| 13 | 95094111 | 95095191 | H__c139g06__M |
| 13 | 95126620 | 95128086 | H__c__68l09__M |
| 13 | 95503174 | 95504025 | H__c__4f13__M |

TABLE 1-continued

| | | | |
|---|---|---|---|
| 13 | 95799249 | 95799426 | H_c_169o15 |
| 13 | 95983788 | 95983901 | H_c_36e06 |
| 13 | 96110808 | 96110910 | H_c_88h21 |
| 13 | 96444179 | 96445103 | H_c_98l17_M |
| 13 | 96845250 | 96845361 | H_c_155a04 |
| 13 | 96882981 | 96885316 | H_c_94c18_M |
| 13 | 97593643 | 97594278 | H_c_22c10_M |
| 13 | 97998539 | 97999816 | H_c_28k10 |
| 13 | 98202369 | 98203553 | H_c_162k19_M |
| 13 | 98308467 | 98308570 | H_c_39f03 |
| 13 | 98488393 | 98488497 | H_c_187i18 |
| 13 | 98535729 | 98538270 | H_c_48f12_M |
| 13 | 98650376 | 98651841 | H_c_88e17 |
| 13 | 98948597 | 98949256 | H_c_34c05 |
| 13 | 99056542 | 99057331 | H_c_114a22_M |
| 13 | 99108079 | 99108970 | H_c_270g06 |
| 13 | 99345933 | 99346585 | H_c_82b15_M |
| 13 | 99404744 | 99407402 | H_c_203p24_M |
| 13 | 99409969 | 99410202 | H_c_110k15 |
| 13 | 99419280 | 99420292 | H_c_62o09_M |
| 13 | 99420287 | 99421949 | H_c_124k04_M |
| 13 | 99425345 | 99425472 | H_c_126a09 |
| 13 | 99428799 | 99432008 | H_c_169c17_M_M |
| 13 | 99435041 | 99436026 | H_c_195p02 |
| 13 | 99438575 | 99439555 | H_c_151e17 |
| 13 | 99447258 | 99447874 | H_c_127p13_M |
| 13 | 99538878 | 99539820 | H_c_259k06_M |
| 13 | 99925954 | 99926108 | H_c_97g02 |
| 14 | 100082073 | 100083201 | H_c_205l05_M |
| 14 | 100103537 | 100106255 | H_c_196b18_M |
| 14 | 100122080 | 100124525 | H_c_274k10_M |
| 14 | 100190591 | 100191612 | H_c_65m21 |
| 14 | 100261690 | 100263767 | H_c_250j10 |
| 14 | 100361532 | 100362546 | H_c_51i13_M |
| 14 | 100993273 | 100995747 | H_c_98o01_M |
| 14 | 101100875 | 101101687 | H_c_237o17_M |
| 14 | 101164622 | 101165099 | H_c_265k12 |
| 14 | 101241653 | 101243153 | H_c_89n10_M |
| 14 | 101322582 | 101322842 | H_c_160k12 |
| 14 | 101483903 | 101485406 | H_c_19a12_M |
| 14 | 101500236 | 101501738 | H_c_271o14_M |
| 14 | 101514915 | 101515064 | H_c_253j09 |
| 14 | 101622583 | 101623732 | H_c_207p11 |
| 14 | 101675076 | 101676047 | H_c_246p18 |
| 14 | 101681952 | 101682091 | H_c_70d20 |
| 14 | 101708267 | 101709518 | H_c_58p02 |
| 14 | 101855623 | 101856245 | H_c_272d11_M |
| 14 | 101898829 | 101899560 | H_c_16c23_M |
| 14 | 101941105 | 101941717 | H_c_157f07 |
| 14 | 102045206 | 102047217 | H_c_47g15 |
| 14 | 102052586 | 102054344 | H_c_239e16 |
| 14 | 102077488 | 102081240 | H_c_172e24_M |
| 14 | 102091040 | 102091862 | H_c_78f09_M |
| 14 | 102127495 | 102130191 | H_c_170i12 |
| 14 | 102311852 | 102314629 | H_c_57e02 |
| 14 | 102457982 | 102459486 | H_c_14d19_M |
| 14 | 102459487 | 102460606 | H_c_182g16 |
| 14 | 102526616 | 102526949 | H_c_31j23 |
| 14 | 102592410 | 102594198 | H_c_87k06 |
| 14 | 102611433 | 102613266 | H_c141n22_M |
| 14 | 102627140 | 102627949 | H_c_123d02_M |
| 14 | 102637458 | 102641921 | H_c_3h22_M |
| 14 | 102658920 | 102661445 | H_c_237m19_M |
| 14 | 102743311 | 102744345 | H_c_194e15 |
| 14 | 102808868 | 102810841 | H_c_88p10_M |
| 14 | 102869547 | 102871153 | H_c141l11_M |
| 14 | 102921217 | 102922340 | H_c_157k13_M |
| 14 | 103058951 | 103059510 | H_c_162p15_M |
| 14 | 103063096 | 103063204 | H_c140o17 |
| 14 | 103097846 | 103099363 | H_c_171p03_M |
| 14 | 103164293 | 103166272 | H_c_128c07_M |
| 14 | 103237974 | 103240030 | H_c_147i23 |
| 14 | 103251105 | 103252835 | H_c_181j20_M |
| 14 | 103347405 | 103348814 | H_c_239d05 |
| 14 | 103382850 | 103385187 | H_c_66g08_M |
| 14 | 103407509 | 103408807 | H_c_209k15 |
| 14 | 103651647 | 103653529 | H_c_33p04_M |
| 14 | 103957602 | 103958394 | H_c_189n23 |
| 14 | 103986096 | 103986188 | H_c_47k09 |
| 14 | 103998436 | 103999730 | H_c143h04_M |
| 14 | 104187312 | 104190125 | H_c_213p14 |
| 14 | 104237035 | 104239767 | H_c_178i23 |
| 14 | 104289918 | 104291546 | H_c_45c24_M |
| 14 | 104363672 | 104364501 | H_c_187l08 |
| 14 | 104380059 | 104382097 | H_c_40l17_M |
| 14 | 104402258 | 104403661 | H_c_45i10_M |
| 14 | 104502842 | 104505555 | H_c_154o21_M |
| 14 | 104522748 | 104525367 | H_c_161e12_M |
| 14 | 104557082 | 104559059 | H_c_120c12_M |
| 14 | 104570688 | 104571499 | H_c_35a04 |
| 14 | 104582182 | 104583399 | H_c_69o10 |
| 14 | 104624029 | 104626888 | H_c_195l02_M |
| 14 | 104705339 | 104706259 | H_c_167b24_M |
| 14 | 104706270 | 104707123 | H_c_91e03_M |
| 14 | 104710893 | 104713099 | H_c_160l03 |
| 14 | 104717694 | 104719050 | H_c_61g11_M |
| 14 | 104733149 | 104734711 | H_c_158p09_M |
| 14 | 104901373 | 104902043 | H_c_219l14_M |
| 14 | 104947986 | 104950586 | H_c_196l09 |
| 14 | 104955153 | 104959937 | H_c_237n07_M |
| 14 | 105065076 | 105067425 | H_c_91d11_M |
| 14 | 106029540 | 106029689 | H_c_71m22 |
| 14 | 106323788 | 106324738 | H_c_45c03 |
| 14 | 19637010 | 19638139 | H_c_166k05 |
| 14 | 19749560 | 19751487 | H_c_12h06 |
| 14 | 19843684 | 19843865 | H_c_246a10 |
| 14 | 19880548 | 19881915 | H_c_123j15_M |
| 14 | 19992999 | 19993850 | H_c_84f17_M |
| 14 | 19998774 | 19999962 | H_c_208d12_M |
| 14 | 20006640 | 20008051 | H_c_74l11 |
| 14 | 20147755 | 20148275 | H_c_88j22_M |
| 14 | 20170519 | 20172247 | H_c_98j19_M |
| 14 | 20221611 | 20221749 | H_c136b13 |
| 14 | 20261024 | 20261712 | H_c_22d08 |
| 14 | 20509133 | 20510014 | H_c_56c02 |
| 14 | 20562552 | 20563529 | H_c_121j14 |
| 14 | 20635461 | 20636947 | H_c_273j08 |
| 14 | 20640987 | 20642737 | H_c_5b14_M |
| 14 | 20787754 | 20787826 | H_c_45i17 |
| 14 | 20807184 | 20807955 | H_c_167c21 |
| 14 | 21014415 | 21015786 | H_c_34i04_M |
| 14 | 21913214 | 21913334 | H_c_146n17 |
| 14 | 22095905 | 22096304 | H_c_49p01 |
| 14 | 22242468 | 22242544 | H_c_113m15 |
| 14 | 22410730 | 22411685 | H_c_76i23 |
| 14 | 22467520 | 22468499 | H_c_162a09_M |
| 14 | 22495754 | 22496767 | H_c_244h24_M |
| 14 | 22549120 | 22549470 | H_c_250g24 |
| 14 | 22572925 | 22574015 | H_c_250i15_M |
| 14 | 22597109 | 22597319 | H_c_121m07 |
| 14 | 22633833 | 22634725 | H_c_202g21_M |
| 14 | 22824207 | 22825994 | H_c_61j09_M |
| 14 | 22859405 | 22861193 | H_c_69b17_M |
| 14 | 22890436 | 22892234 | H_c_200k12_M |
| 14 | 22897527 | 22900402 | H_c_107n13_M |
| 14 | 23089118 | 23091008 | H_c_104f02_M |
| 14 | 23114818 | 23117666 | H_c_40l12 |
| 14 | 23590368 | 23591622 | H_c_249f23 |
| 14 | 23619935 | 23621078 | H_c_46b23 |
| 14 | 23633335 | 23633947 | H_c_112i12 |
| 14 | 23674605 | 23675949 | H_c_149j14_M |
| 14 | 23680043 | 23681112 | H_c141f01_M |
| 14 | 23685320 | 23687131 | H_c_201c05_M |
| 14 | 23710547 | 23711449 | H_c_45n05 |
| 14 | 23734071 | 23735405 | H_c_197a12_M |
| 14 | 23751049 | 23752684 | H_c_111o02_M |
| 14 | 23754455 | 23755562 | H_c_199a20 |
| 14 | 23771305 | 23772186 | H_c_17c04 |
| 14 | 23781634 | 23782019 | H_c_235k13_M |
| 14 | 23801430 | 23803705 | H_c_124j23 |
| 14 | 23809660 | 23811142 | H_c_123o16 |
| 14 | 23837946 | 23838960 | H_c_247n16_M |
| 14 | 23849254 | 23850979 | H_c_169e13_M |
| 14 | 23904966 | 23908295 | H_c_220a17_M |
| 14 | 23937930 | 23938925 | H_c_173c10 |
| 14 | 23981039 | 23982149 | H_c_119f18 |
| 14 | 24022100 | 24023085 | H_c_187b22 |
| 14 | 24587645 | 24590070 | H_c_229b21_M |
| 14 | 24602368 | 24602645 | H_c_73l21 |
| 14 | 24890790 | 24890935 | H_c_115n18 |

TABLE 1-continued

| | | | |
|---|---|---|---|
| 14 | 25660332 | 25660526 | H_c_12i20_M |
| 14 | 25722940 | 25723132 | H_c_213d20 |
| 14 | 26059746 | 26059813 | H_c_62o05 |
| 14 | 26136609 | 26137820 | H_c_79c20_M |
| 14 | 26915818 | 26915896 | H_c_196c19 |
| 14 | 26959396 | 26959560 | H_c_27i13_M |
| 14 | 26961409 | 26961619 | H_c_120f17 |
| 14 | 27096970 | 27097101 | H_c_247e13 |
| 14 | 27463577 | 27463666 | H_c_201g03 |
| 14 | 27764949 | 27765169 | H_c_236b21 |
| 14 | 28304557 | 28305691 | H_c_120m04_M |
| 14 | 28324102 | 28324930 | H_c_39f22 |
| 14 | 29213188 | 29213289 | H_c_202c01 |
| 14 | 29356512 | 29356844 | H_c_124o05 |
| 14 | 29635634 | 29635793 | H_c_61m06 |
| 14 | 30097646 | 30098526 | H_c141f08_M |
| 14 | 30112659 | 30112820 | H_c_62p01_M |
| 14 | 30161119 | 30161454 | H_c_86o20 |
| 14 | 30412174 | 30414210 | H_c_205o07_M |
| 14 | 30489413 | 30489669 | H_c_65p15 |
| 14 | 30564269 | 30565470 | H_c_120b24_M |
| 14 | 30565471 | 30565742 | H_c_187c05_M |
| 14 | 30703413 | 30703495 | H_c_123h11 |
| 14 | 30745707 | 30747501 | H_c_77k20_M |
| 14 | 30776940 | 30777031 | H_c_225g06 |
| 14 | 30850374 | 30850545 | H_c_2j07 |
| 14 | 30958653 | 30960007 | H_c_39d21_M |
| 14 | 30996355 | 30996608 | H_c140k15_M |
| 14 | 31100096 | 31100799 | H_c_50p19_M |
| 14 | 31415986 | 31416098 | H_c_209j05 |
| 14 | 31564297 | 31564391 | H_c_221d15 |
| 14 | 31593260 | 31593425 | H_c_155a09 |
| 14 | 31739977 | 31741311 | H_c_9h06 |
| 14 | 31908113 | 31908193 | H_c_208n16 |
| 14 | 32187012 | 32187113 | H_c_145a17 |
| 14 | 32256753 | 32256841 | H_c_113n24 |
| 14 | 32471650 | 32474508 | H_c_80a17_M |
| 14 | 32723958 | 32724276 | H_c140n01 |
| 14 | 32844080 | 32844200 | H_c_161h13 |
| 14 | 33338529 | 33339818 | H_c_49p16_M |
| 14 | 33489246 | 33490333 | H_c_124e10_M |
| 14 | 33598566 | 33599943 | H_c_126h12_M |
| 14 | 34000878 | 34001710 | H_c_26a10_M |
| 14 | 34168195 | 34169237 | H_c_65i10 |
| 14 | 34253174 | 34254165 | H_c_7l12_M |
| 14 | 34412575 | 34414445 | H_c_191b05 |
| 14 | 34521311 | 34522323 | H_c_165l08_M |
| 14 | 34584817 | 34586008 | H_c_187d22_M |
| 14 | 34650426 | 34650534 | H_c_40k16 |
| 14 | 34742945 | 34743027 | H_c_6l01 |
| 14 | 34942033 | 34944514 | H_c_37p15_M |
| 14 | 35072363 | 35075021 | H_c_162l12 |
| 14 | 35133927 | 35134182 | H_c_114i11 |
| 14 | 35144997 | 35145149 | H_c_109h16_M |
| 14 | 35363180 | 35366029 | H_c_198b23_M |
| 14 | 35500716 | 35500796 | H_c_128g13 |
| 14 | 35762803 | 35762971 | H_c_76b20 |
| 14 | 35858874 | 35859884 | H_c_158l19 |
| 14 | 36044320 | 36044669 | H_c_28p12 |
| 14 | 36047127 | 36047821 | H_c_54f11 |
| 14 | 36058649 | 36062555 | H_c_244i14_M |
| 14 | 36063791 | 36064190 | H_c_215d13_M |
| 14 | 36119596 | 36123171 | H_c_25o15_M |
| 14 | 36159823 | 36159901 | H_c_2i22 |
| 14 | 36185611 | 36187651 | H_c_89f22_M |
| 14 | 36196498 | 36197382 | H_c_66a19_M |
| 14 | 36200466 | 36202638 | H_c140i21_M |
| 14 | 36205916 | 36206219 | H_c_74i24 |
| 14 | 36326322 | 36326393 | H_c_15l23 |
| 14 | 36616148 | 36616336 | H_c_201g08 |
| 14 | 36672441 | 36673256 | H_c_92f08 |
| 14 | 36710741 | 36711912 | H_c_163g11 |
| 14 | 36724523 | 36724603 | H_c_122k19 |
| 14 | 36736295 | 36737368 | H_c_223b04 |
| 14 | 36987191 | 36987416 | H_c_35n07 |
| 14 | 37123708 | 37123983 | H_c_9g09_M |
| 14 | 37126652 | 37127577 | H_c_238h02_M |
| 14 | 37133450 | 37138242 | H_c_2l05_M_M |
| 14 | 37161077 | 37162284 | H_c_86c18_M |
| 14 | 37272938 | 37273008 | H_c_172h09 |
| 14 | 37748058 | 37750753 | H_c_154n21_M |
| 14 | 37793840 | 37795612 | H_c_212b18_M |
| 14 | 38480910 | 38481067 | H_c_101p20 |
| 14 | 38641571 | 38642285 | H_c_251i15 |
| 14 | 38708664 | 38709832 | H_c_214i10 |
| 14 | 38713891 | 38714436 | H_c_217o01_M |
| 14 | 38805527 | 38806012 | H_c_151h20_M |
| 14 | 38970306 | 38971641 | H_c_92a02 |
| 14 | 38971811 | 38972106 | H_c_93b08 |
| 14 | 39577398 | 39577489 | H_c_96g11 |
| 14 | 39729061 | 39729201 | H_c_270k11 |
| 14 | 41472491 | 41472563 | H_c_35g24 |
| 14 | 42052205 | 42052485 | H_c_84h09 |
| 14 | 42073703 | 42073850 | H_c_40g17 |
| 14 | 42408230 | 42408319 | H_c_48p17 |
| 14 | 42603993 | 42604234 | H_c_209f02 |
| 14 | 42989769 | 42989879 | H_c_178b14 |
| 14 | 43046804 | 43047130 | H_c_166m03_M |
| 14 | 43158151 | 43158382 | H_c_96h04 |
| 14 | 43940400 | 43940478 | H_c_75l02 |
| 14 | 43947336 | 43947410 | H_c_148a10 |
| 14 | 44435903 | 44437137 | H_c137d09_M |
| 14 | 44450565 | 44452225 | H_c_77f03 |
| 14 | 44791919 | 44793026 | H_c134g05 |
| 14 | 44972868 | 44972952 | H_c_149c17 |
| 14 | 45026991 | 45027153 | H_c_42k22 |
| 14 | 45103371 | 45103474 | H_c_129d03 |
| 14 | 45170647 | 45170786 | H_c_149n08 |
| 14 | 46066545 | 46066638 | H_c_116d11 |
| 14 | 46113171 | 46113449 | H_c_230m06 |
| 14 | 46285171 | 46285466 | H_c_95h13 |
| 14 | 46795621 | 46795694 | H_c_56e12 |
| 14 | 46961556 | 46961666 | H_c_220j22 |
| 14 | 47213166 | 47215499 | H_c_114j16 |
| 14 | 47323808 | 47323921 | H_c_163h22_M |
| 14 | 47933178 | 47933376 | H_c_18d22 |
| 14 | 49134841 | 49136088 | H_c_120p15_M |
| 14 | 49156631 | 49158920 | H_c_270c20_M |
| 14 | 49224487 | 49224769 | H_c_95a01_M |
| 14 | 49229289 | 49229912 | H_c_70l07 |
| 14 | 49303843 | 49305385 | H_c_20c09_M |
| 14 | 49428849 | 49430709 | H_c_30a17_M |
| 14 | 49494092 | 49494266 | H_c_261n22 |
| 14 | 49538964 | 49540212 | H_c_148j14_M |
| 14 | 49642411 | 49642596 | H_c_51l14 |
| 14 | 49767293 | 49768605 | H_c_60h03_M |
| 14 | 49848201 | 49849485 | H_c_80l20_M |
| 14 | 49932988 | 49933813 | H_c_47h23_M |
| 14 | 50040509 | 50040605 | H_c_71j09 |
| 14 | 50068178 | 50069402 | H_c_183d20_M |
| 14 | 50096379 | 50097377 | H_c_188d13 |
| 14 | 50138920 | 50139098 | H_c_121m13 |
| 14 | 50366273 | 50367997 | H_c_8m20_M |
| 14 | 50408408 | 50409246 | H_c140l13_M |
| 14 | 50480288 | 50481447 | H_c_165m24_M |
| 14 | 50630417 | 50632354 | H_c_67k12 |
| 14 | 50776453 | 50777105 | H_c_168e15_M |
| 14 | 51057822 | 51057908 | H_c_30f19 |
| 14 | 51187251 | 51189306 | H_c_13i14 |
| 14 | 51525959 | 51526282 | H_c_59a20_M |
| 14 | 51604276 | 51605678 | H_c_40e23_M |
| 14 | 51803869 | 51805334 | H_c_109m16_M |
| 14 | 51912797 | 51912875 | H_c_194k23 |
| 14 | 52088670 | 52090225 | H_c_66a12_M |
| 14 | 52231233 | 52232530 | H_c_188g03_M |
| 14 | 52266328 | 52267509 | H_c_15a05 |
| 14 | 52327754 | 52328497 | H_c_270f04_M |
| 14 | 52486900 | 52488163 | H_c_202l02_M |
| 14 | 52688425 | 52690065 | H_c_205g15_M |
| 14 | 53483016 | 53483636 | H_c_215p10_M |
| 14 | 53489566 | 53491903 | H_c_239f18_M |
| 14 | 53677647 | 53677740 | H_c_102d09 |
| 14 | 53699815 | 53700019 | H_c_46d24 |
| 14 | 53908861 | 53908937 | H_c_186j23 |
| 14 | 54024802 | 54025439 | H_c142a16 |
| 14 | 54046097 | 54046955 | H_c_249b20_M |
| 14 | 54102539 | 54104425 | H_c_92d20_M |
| 14 | 54437841 | 54439713 | H_c_253i14_M |
| 14 | 54563137 | 54563865 | H_c_12d12_M |
| 14 | 54587719 | 54588749 | H_c_120j05 |

TABLE 1-continued

| | | | |
|---|---|---|---|
| 14 | 54661934 | 54662027 | H_c__273o05 |
| 14 | 54665401 | 54666929 | H_c__251e22_M |
| 14 | 54808475 | 54808771 | H_c__214m15_M |
| 14 | 54947765 | 54948556 | H_c__31f22 |
| 14 | 55187975 | 55188176 | H_c__274g17 |
| 14 | 55416882 | 55417008 | H_c__79f19 |
| 14 | 56116175 | 56116962 | H_c__259k04_M |
| 14 | 56330637 | 56331811 | H_c__1o07_M |
| 14 | 56334225 | 56335424 | H_c__8i24_M |
| 14 | 56345012 | 56348798 | H_c__174i09_M_M |
| 14 | 56804577 | 56805698 | H_c__40a06_M |
| 14 | 56926742 | 56928018 | H_c__52f09_M |
| 14 | 57101252 | 57101357 | H_c__122o03 |
| 14 | 57255311 | 57255437 | H_c__59a12_M |
| 14 | 57687916 | 57688907 | H_c__13g15_M |
| 14 | 57736176 | 57737172 | H_c__95i08_M |
| 14 | 57834082 | 57836584 | H_c__268j20_M |
| 14 | 57900911 | 57901254 | H_c__162n12_M |
| 14 | 57963206 | 57963524 | H_c__63o22 |
| 14 | 58096999 | 58097115 | H_c__234h24 |
| 14 | 58384364 | 58384547 | H_c__35h17 |
| 14 | 58725282 | 58726989 | H_c__23m03_M |
| 14 | 58741340 | 58741497 | H_c__34g20 |
| 14 | 58847558 | 58847756 | H_c__39a12 |
| 14 | 59000164 | 59002247 | H_c__61l04_M |
| 14 | 59020217 | 59021331 | H_c__172i12_M |
| 14 | 59049088 | 59049209 | H_c__65f01 |
| 14 | 59166720 | 59167497 | H_c__49n10_M |
| 14 | 59238092 | 59238273 | H_c__31k03 |
| 14 | 59406608 | 59407590 | H_c__274a11 |
| 14 | 59426363 | 59426561 | H_c__10k17 |
| 14 | 59701380 | 59702103 | H_c__244k15_M |
| 14 | 59784793 | 59786647 | H_c__71j22_M |
| 14 | 60021904 | 60022793 | H_c__30e21_M |
| 14 | 60178263 | 60179801 | H_c__237f19_M |
| 14 | 60184334 | 60186330 | H_c__20m04_M |
| 14 | 60188887 | 60190513 | H_c__60n12 |
| 14 | 60192705 | 60194514 | H_c__201e01_M |
| 14 | 60257598 | 60259069 | H_c__157j07 |
| 14 | 60278728 | 60278857 | H_c134n01 |
| 14 | 60507325 | 60507434 | H_c__234c19_M |
| 14 | 60816252 | 60818177 | H_c__29o09_M |
| 14 | 60857518 | 60859638 | H_c__45c17 |
| 14 | 61231250 | 61232396 | H_c__225n08_M |
| 14 | 61287279 | 61288065 | H_c__213c11 |
| 14 | 61298562 | 61299382 | H_c__110m01 |
| 14 | 62094437 | 62094552 | H_c__191k20_M |
| 14 | 62274794 | 62274893 | H_c__65h07 |
| 14 | 62495834 | 62495985 | H_c__206h22 |
| 14 | 62581201 | 62583210 | H_c__209a05_M |
| 14 | 62795912 | 62796073 | H_c__8i19 |
| 14 | 63035690 | 63035875 | H_c__151f23 |
| 14 | 63078619 | 63080136 | H_c__234k18_M |
| 14 | 63161974 | 63162214 | H_c__274b21_M |
| 14 | 63177794 | 63178566 | H_c__54e15_M |
| 14 | 63263653 | 63264821 | H_c__28d20_M |
| 14 | 63465138 | 63465231 | H_c__270e15 |
| 14 | 63557448 | 63557525 | H_c__205g21 |
| 14 | 63830480 | 63830840 | H_c__106d21 |
| 14 | 64001575 | 64002666 | H_c__84h03_M |
| 14 | 64041376 | 64041902 | H_c__47k06_M |
| 14 | 64076744 | 64078786 | H_c__12f20_M |
| 14 | 64086285 | 64086873 | H_c__92j11_M |
| 14 | 64225865 | 64226103 | H_c132k11 |
| 14 | 64240703 | 64241811 | H_c132a20_M |
| 14 | 64415435 | 64417510 | H_c__116h23_M |
| 14 | 64450573 | 64451795 | H_c__32e10_M |
| 14 | 64498227 | 64498384 | H_c__195g09 |
| 14 | 64507292 | 64509333 | H_c__8e19 |
| 14 | 64523135 | 64523990 | H_c__50i16_M |
| 14 | 64638135 | 64639854 | H_c__259k24 |
| 14 | 64919468 | 64920602 | H_c__59j04 |
| 14 | 64948162 | 64949817 | H_c__244l22_M |
| 14 | 64964548 | 64964655 | H_c__54b05 |
| 14 | 64968147 | 64968316 | H_c__120i11 |
| 14 | 65175751 | 65175847 | H_c__187g09_M |
| 14 | 65352315 | 65352568 | H_c__89o23 |
| 14 | 65833990 | 65834129 | H_c__234b23_M |
| 14 | 65875814 | 65875924 | H_c__184a11_M |
| 14 | 65978488 | 65978642 | H_c__213n16 |
| 14 | 66043902 | 66045964 | H_c143a04_M |
| 14 | 66236107 | 66236351 | H_c__154k11_M |
| 14 | 66500772 | 66500890 | H_c__163a18 |
| 14 | 66729096 | 66729181 | H_c__40i06 |
| 14 | 66777375 | 66778042 | H_c__170e20_M |
| 14 | 66808101 | 66808169 | H_c__70g03 |
| 14 | 66895861 | 66897261 | H_c__152a14_M |
| 14 | 66948213 | 66949058 | H_c139m04_M |
| 14 | 66971898 | 66972038 | H_c__197f24 |
| 14 | 67049609 | 67051982 | H_c__39g17_M |
| 14 | 67069593 | 67070575 | H_c__55b08_M |
| 14 | 67113092 | 67113392 | H_c__42k08_M |
| 14 | 67155765 | 67156943 | H_c__213l21 |
| 14 | 67210511 | 67212144 | H_c__155e17_M |
| 14 | 67799732 | 67799878 | H_c__182o15_M |
| 14 | 67814861 | 67815034 | H_c__56c10 |
| 14 | 68100546 | 68100655 | H_c__48b19_M |
| 14 | 68164802 | 68165859 | H_c__122b20_M |
| 14 | 68246460 | 68246548 | H_c__183j23 |
| 14 | 68325899 | 68327248 | H_c__167k06 |
| 14 | 68329302 | 68332169 | H_c__59d10_M_M |
| 14 | 68352626 | 68353728 | H_c__231e20 |
| 14 | 68514759 | 68517068 | H_c__272k09_M |
| 14 | 68519415 | 68519589 | H_c143k12 |
| 14 | 68687429 | 68690220 | H_c133g23_M |
| 14 | 68727818 | 68728016 | H_c__94j16 |
| 14 | 68900996 | 68901151 | H_c__125l20 |
| 14 | 68934996 | 68935561 | H_c__217e15 |
| 14 | 69020098 | 69022168 | H_c__38p19_M |
| 14 | 69083972 | 69085088 | H_c__6p05_M |
| 14 | 69107794 | 69111280 | H_c__196j15_M |
| 14 | 69147861 | 69148841 | H_c__254e04 |
| 14 | 69200193 | 69201065 | H_c__51n19 |
| 14 | 69263128 | 69263771 | H_c__221o22 |
| 14 | 69303970 | 69304546 | H_c__80i16 |
| 14 | 69415584 | 69416725 | H_c__176o09_M |
| 14 | 69724729 | 69725876 | H_c__272d17_M |
| 14 | 69790958 | 69792004 | H_c__187i11 |
| 14 | 70178193 | 70179821 | H_c__99c18_M |
| 14 | 70344622 | 70346904 | H_c144j08 |
| 14 | 70633954 | 70634098 | H_c__162g16 |
| 14 | 70856570 | 70858091 | H_c__81i09_M |
| 14 | 71468446 | 71469420 | H_c__242o21 |
| 14 | 71523491 | 71523821 | H_c__222h09_M |
| 14 | 71929778 | 71930035 | H_c__155e23 |
| 14 | 72198922 | 72199031 | H_c__211h21 |
| 14 | 72370238 | 72372095 | H_c__84m16 |
| 14 | 72429122 | 72430759 | H_c__49f1_M |
| 14 | 72461975 | 72463764 | H_c__3b11_M |
| 14 | 72562715 | 72563952 | H_c__130d17 |
| 14 | 72594628 | 72595761 | H_c__113h10_M |
| 14 | 72672634 | 72673598 | H_c__254m07_M |
| 14 | 72781869 | 72783226 | H_c__34i10_M |
| 14 | 72805532 | 72806877 | H_c__8o01_M |
| 14 | 72929062 | 72929153 | H_c131k02 |
| 14 | 72993905 | 72995265 | H_c__244d18 |
| 14 | 73027309 | 73029468 | H_c__207d19_M |
| 14 | 73138324 | 73138396 | H_c__24n07 |
| 14 | 73170131 | 73171062 | H_c__233m15_M |
| 14 | 73181277 | 73181691 | H_c__76o19_M |
| 14 | 73250227 | 73251068 | H_c__71h14 |
| 14 | 73295155 | 73296841 | H_c__92g10_M |
| 14 | 73388132 | 73388662 | H_c__117m11 |
| 14 | 73486320 | 73487330 | H_c__163b13_M |
| 14 | 73554938 | 73556173 | H_c__148p04 |
| 14 | 73611604 | 73611696 | H_c__243c11 |
| 14 | 73754134 | 73754912 | H_c__127e09 |
| 14 | 73774984 | 73778855 | H_c__190h05_M |
| 14 | 73787971 | 73788037 | H_c__149i12 |
| 14 | 73792487 | 73794539 | H_c__98b22_M |
| 14 | 73838791 | 73839700 | H_c__227k21 |
| 14 | 74029250 | 74030684 | H_c__236n08_M |
| 14 | 74090111 | 74090231 | H_c__104g24 |
| 14 | 74147662 | 74149678 | H_c__121n16_M |
| 14 | 74220828 | 74221095 | H_c__128b24 |
| 14 | 74299312 | 74300886 | H_c__237n01 |
| 14 | 74358646 | 74358849 | H_c__238c13 |
| 14 | 74457570 | 74459840 | H_c__228o13 |
| 14 | 74539064 | 74540131 | H_c__261p21_M |
| 14 | 74587850 | 74588062 | H_c__86c15_M |

TABLE 1-continued

| | | | |
|---|---|---|---|
| 14 | 74605457 | 74606354 | H_c__66i15__M |
| 14 | 74662860 | 74664332 | H_c__234o10__M |
| 14 | 74682869 | 74683013 | H_c__229m24 |
| 14 | 74813134 | 74816211 | H_c__50h21__M |
| 14 | 74829854 | 74831462 | H_c__86b03__M |
| 14 | 75114221 | 75115015 | H_c__167l13__M |
| 14 | 75196457 | 75197834 | H_c__157d19 |
| 14 | 75518208 | 75519412 | H_c__225p17__M |
| 14 | 75521796 | 75522120 | H_c__234j12__M |
| 14 | 75585544 | 75585626 | H_c__115a23 |
| 14 | 75674932 | 75675181 | H_c__16e24__M |
| 14 | 75687692 | 75689028 | H_c__7c14 |
| 14 | 75888544 | 75889472 | H_c__145o23 |
| 14 | 75895334 | 75895436 | H_c__25n10 |
| 14 | 75912205 | 75913604 | H_c__103c21__M |
| 14 | 76056770 | 76056943 | H_c__238j13 |
| 14 | 76088975 | 76089112 | H_c__63d15 |
| 14 | 76297538 | 76298775 | H_c__196f19__M |
| 14 | 76348398 | 76349152 | H_c__8d17__M |
| 14 | 76403424 | 76404773 | H_c__75p20 |
| 14 | 76416160 | 76417546 | H_c__112o08 |
| 14 | 76563103 | 76565067 | H_c__9b02 |
| 14 | 76595395 | 76595736 | H_c__108g15 |
| 14 | 76633708 | 76635040 | H_c__33k02__M |
| 14 | 76660462 | 76661387 | H_c__201a21__M |
| 14 | 76676731 | 76678405 | H_c133d22__M |
| 14 | 76721009 | 76723144 | H_c__186j21 |
| 14 | 76805951 | 76807329 | H_c__219i16__M |
| 14 | 76856246 | 76857673 | H_c__163h11__M |
| 14 | 76912387 | 76913379 | H_c__32d19__M |
| 14 | 77152150 | 77153089 | H_c__154k03__M |
| 14 | 77177456 | 77178634 | H_c__47e10__M |
| 14 | 77206373 | 77207794 | H_c__48j02 |
| 14 | 77296716 | 77297592 | H_c__209l08__M |
| 14 | 77335966 | 77336879 | H_c__78f02__M |
| 14 | 77374474 | 77376378 | H_c__105g19 |
| 14 | 77516996 | 77518039 | H_c__123b14__M |
| 14 | 78084655 | 78086354 | H_c__206j21 |
| 14 | 78814935 | 78815789 | H_c__151c15__M |
| 14 | 78861051 | 78861280 | H_c__148f07 |
| 14 | 79246790 | 79247003 | H_c__2j10 |
| 14 | 79518071 | 79518185 | H_c__7l02 |
| 14 | 79685863 | 79686005 | H_c__9n23 |
| 14 | 80490971 | 80491378 | H_c__74p03__M |
| 14 | 80620420 | 80620502 | H_c__210i05__M |
| 14 | 80705004 | 80705089 | H_c__182l08 |
| 14 | 80756127 | 80757539 | H_c__55a23__M |
| 14 | 80971704 | 80973119 | H_c__267f22__M |
| 14 | 81604186 | 81604347 | H_c__16b05 |
| 14 | 81640026 | 81640207 | H_c__265l11 |
| 14 | 81765332 | 81765460 | H_c__220g07__M |
| 14 | 82419198 | 82419374 | H_c__7h23 |
| 14 | 82484994 | 82485274 | H_c__9c07 |
| 14 | 82883545 | 82883612 | H_c__192e20 |
| 14 | 83934197 | 83934394 | H_c__231l18 |
| 14 | 84259001 | 84259236 | H_c__128h14 |
| 14 | 84647901 | 84647969 | H_c__123i01 |
| 14 | 85067123 | 85070455 | H_c__247n22__M |
| 14 | 85533446 | 85533752 | H_c__74b10 |
| 14 | 85548228 | 85548366 | H_c__244f17 |
| 14 | 85556499 | 85557138 | H_c__41g08 |
| 14 | 86033876 | 86034033 | H_c__179b22__M |
| 14 | 86046400 | 86046737 | H_c__59f22 |
| 14 | 87108564 | 87108733 | H_c__274f15 |
| 14 | 87528879 | 87529511 | H_c__194e13__M |
| 14 | 87862638 | 87862813 | H_c__163m19 |
| 14 | 87921439 | 87922204 | H_c__79e10__M |
| 14 | 88090493 | 88091244 | H_c__222g06__M |
| 14 | 88098870 | 88099719 | H_c__37i24__M |
| 14 | 88328254 | 88329208 | H_c__24j04__M |
| 14 | 88794801 | 88795323 | H_c__198l23 |
| 14 | 88952160 | 88954431 | H_c__14b08__M |
| 14 | 89043628 | 89043771 | H_c__258j19 |
| 14 | 89155011 | 89155442 | H_c__151m20__M |
| 14 | 89237321 | 89238303 | H_c__152m09__M |
| 14 | 89490552 | 89492429 | H_c__81o03__M |
| 14 | 89919114 | 89920159 | H_c__129l23 |
| 14 | 89932466 | 89934908 | H_c__246c20__M |
| 14 | 90294226 | 90295040 | H_c__42d15__M |
| 14 | 90351773 | 90353584 | H_c__43e20 |
| 14 | 90430791 | 90430962 | H_c__65n24__M |
| 14 | 90595771 | 90597302 | H_c__106f05__M |
| 14 | 90787973 | 90790606 | H_c__15d08__M |
| 14 | 90800141 | 90801765 | H_c__162j11__M |
| 14 | 90865485 | 90865772 | H_c__48f11 |
| 14 | 91109479 | 91111134 | H_c__274o17__M |
| 14 | 91483623 | 91484265 | H_c__269f04__M |
| 14 | 91656965 | 91658527 | H_c__207m03 |
| 14 | 91679800 | 91679942 | H_c__86j01 |
| 14 | 91858853 | 91860518 | H_c__92e15__M |
| 14 | 92048997 | 92050968 | H_c__86a02__M |
| 14 | 92075335 | 92075514 | H_c__64d14 |
| 14 | 92240053 | 92241654 | H_c__200i15 |
| 14 | 92284208 | 92284750 | H_c__167k07__M |
| 14 | 92329845 | 92330592 | H_c__12e02 |
| 14 | 92458600 | 92461097 | H_c__65a16 |
| 14 | 92652065 | 92652994 | H_c__85g21 |
| 14 | 92720361 | 92721405 | H_c__256e23__M |
| 14 | 92742656 | 92743700 | H_c__252p07__M |
| 14 | 92868070 | 92869415 | H_c__69l09__M |
| 14 | 93001524 | 93001680 | H_c__143f23 |
| 14 | 93249471 | 93250639 | H_c__205n24 |
| 14 | 93294557 | 93297079 | H_c__4j14 |
| 14 | 93323343 | 93325269 | H_c__58p18__M |
| 14 | 93475090 | 93478896 | H_c__237b08__M |
| 14 | 93616616 | 93617686 | H_c__81f05 |
| 14 | 94225579 | 94226360 | H_c__169b23 |
| 14 | 94282408 | 94282727 | H_c__11g16 |
| 14 | 94304359 | 94309566 | H_c__38k12__M__M |
| 14 | 94692661 | 94694012 | H_c__186g08__M |
| 14 | 94803142 | 94803231 | H_c134e13 |
| 14 | 94854617 | 94856936 | H_c__117e04__M |
| 14 | 95024624 | 95026109 | H_c__201f13 |
| 14 | 95052479 | 95052988 | H_c__13e10 |
| 14 | 95070911 | 95072604 | H_c__203n01__M |
| 14 | 95411807 | 95413693 | H_c__270c08__M |
| 14 | 95898748 | 95900088 | H_c__194j19__M |
| 14 | 95927752 | 95928592 | H_c__233f10 |
| 14 | 95959498 | 95960803 | H_c__28e13__M |
| 14 | 96037837 | 96039252 | H_c__27d17__M |
| 14 | 96226411 | 96227161 | H_c__219b08 |
| 14 | 96277455 | 96279085 | H_c__179a10 |
| 14 | 96418043 | 96418116 | H_c__205o12 |
| 14 | 96754780 | 96755201 | H_c__100e21 |
| 14 | 97517079 | 97518219 | H_c__126a04__M |
| 14 | 98040596 | 98040832 | H_c__157k19 |
| 14 | 98187760 | 98188119 | H_c__191h05 |
| 14 | 98637432 | 98637542 | H_c__105h09 |
| 14 | 98653659 | 98654535 | H_c__86i16 |
| 14 | 98767146 | 98768458 | H_c__157i22 |
| 14 | 98781390 | 98783354 | H_c__166i10__M |
| 14 | 98805777 | 98807621 | H_c__46l22__M |
| 14 | 98807742 | 98808625 | H_c__2j23__M |
| 14 | 99016102 | 99017803 | H_c__198n01__M |
| 14 | 99140758 | 99141756 | H_c__183e12 |
| 14 | 99181085 | 99182571 | H_c__54m04__M |
| 14 | 99219147 | 99220882 | H_c__2l07__M |
| 14 | 99265985 | 99267571 | H_c__11g21 |
| 14 | 99328714 | 99330051 | H_c__114j07__M |
| 14 | 99507021 | 99509144 | H_c__190a19 |
| 14 | 99694860 | 99697183 | H_c__123p08__M |
| 14 | 99749791 | 99751248 | H_c__20c08__M |
| 14 | 99841527 | 99843939 | H_c__36b18__M |
| 14 | 99911463 | 99912659 | H_c__117m05 |
| 15 | 100009570 | 100010348 | H_c__54a14__M |
| 15 | 100081612 | 100082803 | H_c__44d03__M |
| 15 | 19366148 | 19366310 | H_c__196g18 |
| 15 | 20384068 | 20385474 | H_c__12e14__M |
| 15 | 20388093 | 20388191 | H_c__169b06 |
| 15 | 20443036 | 20445440 | H_c__117o04__M |
| 15 | 20558047 | 20558251 | H_c__218a06__M |
| 15 | 20638126 | 20638397 | H_c__66i01__M |
| 15 | 22255413 | 22255479 | H_c__210p11 |
| 15 | 22347300 | 22347430 | H_c__45j17 |
| 15 | 22569223 | 22569610 | H_c__85j03 |
| 15 | 22750976 | 22752209 | H_c__52e17 |
| 15 | 22944655 | 22944781 | H_c__200m17 |
| 15 | 23233973 | 23235950 | H_c__9i09 |
| 15 | 23658276 | 23659983 | H_c__251g02__M |
| 15 | 23869727 | 23869961 | H_c__41k14 |

TABLE 1-continued

| | | | |
|---|---|---|---|
| 15 | 23878423 | 23879029 | H_c__37e22 |
| 15 | 24568225 | 24570150 | H_c__100g14 |
| 15 | 24615183 | 24615265 | H_c__117n16 |
| 15 | 24795481 | 24796516 | H_c__144n08__M |
| 15 | 24798546 | 24799703 | H_c__4k15 |
| 15 | 25582084 | 25582282 | H_c__67h09 |
| 15 | 25788317 | 25790380 | H_c__269m20__M |
| 15 | 25821456 | 25822467 | H_c__227i08 |
| 15 | 25997631 | 25998923 | H_c__84j21 |
| 15 | 26012349 | 26014163 | H_c__17k13 |
| 15 | 26015438 | 26016304 | H_c__259o09__M |
| 15 | 26026121 | 26026814 | H_c__203i04 |
| 15 | 27182738 | 27184354 | H_c__199m13__M |
| 15 | 27199968 | 27201073 | H_c__264e24 |
| 15 | 27348909 | 27349746 | H_c__101d10__M |
| 15 | 27462967 | 27464606 | H_c__37f01 |
| 15 | 27649312 | 27651096 | H_c__27p06 |
| 15 | 27713151 | 27714267 | H_c__72d15 |
| 15 | 27840615 | 27840787 | H_c__9l13 |
| 15 | 27900916 | 27902243 | H_c142l15__M |
| 15 | 29070528 | 29071863 | H_c__27a02__M |
| 15 | 29293796 | 29296513 | H_c__162d16 |
| 15 | 29405082 | 29407862 | H_c__109d14 |
| 15 | 29470995 | 29473608 | H_c__103e08__M |
| 15 | 29520078 | 29520678 | H_c__53p22__M |
| 15 | 29562479 | 29564448 | H_c136a01 |
| 15 | 29949471 | 29950520 | H_c__108f16__M |
| 15 | 29993314 | 29993557 | H_c__92c12 |
| 15 | 30054616 | 30057189 | H_c__64o31 |
| 15 | 30084769 | 30084879 | H_c__153h10__M |
| 15 | 30109337 | 30110359 | H_c__123a12__M |
| 15 | 30796732 | 30798397 | H_c__148d12__M |
| 15 | 30798490 | 30799026 | H_c__42l21 |
| 15 | 30948046 | 30948233 | H_c__53e09 |
| 15 | 31146001 | 31146163 | H_c__83d08 |
| 15 | 31273313 | 31274834 | H_c__32j03 |
| 15 | 32181091 | 32181517 | H_c__103g23__M |
| 15 | 32218733 | 32218832 | H_c__206m22 |
| 15 | 32288946 | 32289902 | H_c__56l16__M |
| 15 | 32416394 | 32417808 | H_c__195h24__M |
| 15 | 32446482 | 32447512 | H_c133h20__M |
| 15 | 32574011 | 32576767 | H_c137d13__M |
| 15 | 32662208 | 32664530 | H_c__222k13__M |
| 15 | 32834147 | 32834513 | H_c144j23__M |
| 15 | 32834511 | 32834876 | H_c__261l20__M |
| 15 | 32874065 | 32874627 | H_c__216j18 |
| 15 | 32952363 | 32952475 | H_c__170i04 |
| 15 | 33385730 | 33386054 | H_c__39n02 |
| 15 | 33625379 | 33626088 | H_c__39b05__M |
| 15 | 34808482 | 34808561 | H_c__90k23 |
| 15 | 35025060 | 35025181 | H_c__42h18 |
| 15 | 35174584 | 35180991 | H_c__120n13__M_M |
| 15 | 35432808 | 35432909 | H_c__121b14 |
| 15 | 35577345 | 35577462 | H_c__166n03 |
| 15 | 35721001 | 35721091 | H_c__201o19 |
| 15 | 36061385 | 36061729 | H_c__102o18 |
| 15 | 36152309 | 36152959 | H_c__167a19 |
| 15 | 36643141 | 36644500 | H_c__189a10 |
| 15 | 36906263 | 36906468 | H_c__258m10 |
| 15 | 37087426 | 37087582 | H_c__50p16__M |
| 15 | 37143834 | 37143989 | H_c134n22 |
| 15 | 37659769 | 37660005 | H_c__110e04__M |
| 15 | 37660544 | 37660967 | H_c__72n06__M |
| 15 | 37861830 | 37862694 | H_c__37b02 |
| 15 | 37999219 | 38000640 | H_c__254f15 |
| 15 | 38013414 | 38014529 | H_c__124a10 |
| 15 | 38118096 | 38118640 | H_c__6k12 |
| 15 | 38187884 | 38189335 | H_c__66h14__M |
| 15 | 38240291 | 38241095 | H_c__75a06__M |
| 15 | 38331551 | 38332958 | H_c__74k22__M |
| 15 | 38386876 | 38388764 | H_c__273c04 |
| 15 | 38402996 | 38404396 | H_c__26a03__M |
| 15 | 38422506 | 38425263 | H_c__208l13 |
| 15 | 38484891 | 38485849 | H_c__162f03 |
| 15 | 38590396 | 38591462 | H_c__15o13 |
| 15 | 38673378 | 38674272 | H_c__127f19 |
| 15 | 38773854 | 38775202 | H_c__262a14__M |
| 15 | 38843060 | 38844599 | H_c__126m08__M |
| 15 | 38886476 | 38887422 | H_c144l24__M |
| 15 | 38922860 | 38924611 | H_c136i14 |
| 15 | 38951715 | 38954042 | H_c__48j10__M |
| 15 | 38971775 | 38974114 | H_c__123p11 |
| 15 | 39005207 | 39006641 | H_c__91g18__M |
| 15 | 39008562 | 39010228 | H_c141o17__M |
| 15 | 39020669 | 39022029 | H_c__273f02__M |
| 15 | 39032090 | 39033442 | H_c__8h03__M |
| 15 | 39155301 | 39155484 | H_c__27m05 |
| 15 | 39309935 | 39311479 | H_c__55j23__M |
| 15 | 39326394 | 39326551 | H_c__250f21 |
| 15 | 39411268 | 39412736 | H_c__128k09__M |
| 15 | 39496290 | 39497710 | H_c__33l09 |
| 15 | 39572413 | 39574664 | H_c__251o18 |
| 15 | 39590546 | 39593451 | H_c__262i05__M |
| 15 | 39637622 | 39639849 | H_c__190b06__M |
| 15 | 39664596 | 39665160 | H_c__170g19__M |
| 15 | 39700493 | 39701149 | H_c__231c11__M |
| 15 | 39739162 | 39741517 | H_c__84d19__M |
| 15 | 39824053 | 39824139 | H_c132l17 |
| 15 | 39853646 | 39854378 | H_c__18n18 |
| 15 | 39905101 | 39907288 | H_c__245o08 |
| 15 | 39907455 | 39908136 | H_c__72b16 |
| 15 | 39961159 | 39962405 | H_c__34j17 |
| 15 | 40051346 | 40052228 | H_c__59l07 |
| 15 | 40352229 | 40353168 | H_c__91g16 |
| 15 | 40570136 | 40571099 | H_c__64m05 |
| 15 | 40575030 | 40575312 | H_c__66e19__M |
| 15 | 40627861 | 40629249 | H_c__29e20__M |
| 15 | 40654457 | 40655762 | H_c__108l04__M |
| 15 | 40831083 | 40831415 | H_c__74a19 |
| 15 | 40837778 | 40839448 | H_c__49g23 |
| 15 | 40907676 | 40907774 | H_c__227o05 |
| 15 | 41000000 | 41000678 | H_c__115c08__M |
| 15 | 41184893 | 41186238 | H_c__40a05 |
| 15 | 41202638 | 41202863 | H_c__65f02__M |
| 15 | 41212878 | 41214253 | H_c__78g22__M |
| 15 | 41226919 | 41227006 | H_c__204e01 |
| 15 | 41332802 | 41334517 | H_c__180o12 |
| 15 | 41409683 | 41410488 | H_c__262l05__M |
| 15 | 41449753 | 41451467 | H_c__210o13__M |
| 15 | 41855461 | 41857354 | H_c__250k17__M |
| 15 | 41871330 | 41872449 | H_c132n20__M |
| 15 | 41906375 | 41906838 | H_c__154m21__M |
| 15 | 42273100 | 42275304 | H_c__61m03__M |
| 15 | 42506876 | 42507586 | H_c__102a10 |
| 15 | 42615463 | 42617829 | H_c__220k12 |
| 15 | 43193945 | 43197371 | H_c__125j21__M |
| 15 | 43208601 | 43210155 | H_c140p19__M |
| 15 | 43245944 | 43247298 | H_c__99d14__M |
| 15 | 43457108 | 43458347 | H_c__70l18 |
| 15 | 43481641 | 43483294 | H_c__153p17__M |
| 15 | 43509467 | 43510249 | H_c__48c05__M |
| 15 | 43601778 | 43603010 | H_c__127b06__M |
| 15 | 43713365 | 43714689 | H_c__29o13__M |
| 15 | 43864676 | 43864783 | H_c__250e18 |
| 15 | 44447296 | 44447411 | H_c__268a08__M |
| 15 | 44725474 | 44726044 | H_c__77b23 |
| 15 | 45796461 | 45798596 | H_c__217i10__M |
| 15 | 46233897 | 46233976 | H_c__176h12 |
| 15 | 46257570 | 46258146 | H_c__6i17__M |
| 15 | 46410579 | 46412022 | H_c__264f24__M |
| 15 | 46584033 | 46584176 | H_c__178b11 |
| 15 | 46724099 | 46725280 | H_c__145k16__M |
| 15 | 46946005 | 46946102 | H_c__19g14 |
| 15 | 46957389 | 46958229 | H_c__116c20__M |
| 15 | 47054961 | 47056331 | H_c__188i16 |
| 15 | 47234503 | 47235605 | H_c__152j16 |
| 15 | 47640004 | 47640360 | H_c__107n18 |
| 15 | 47700022 | 47700417 | H_c__226h13__M |
| 15 | 47967568 | 47967794 | H_c__119c05 |
| 15 | 48261482 | 48262600 | H_c143k09__M |
| 15 | 48433531 | 48435132 | H_c137c10__M |
| 15 | 48514916 | 48515125 | H_c__207n08__M |
| 15 | 48765413 | 48766546 | H_c__81c14__M |
| 15 | 49173404 | 49174419 | H_c__123l10__M |
| 15 | 49413804 | 49413980 | H_c__159f03__M |
| 15 | 49420039 | 49422006 | H_c__80c17__M |
| 15 | 49485310 | 49485671 | H_c__151d17 |
| 15 | 49657145 | 49657307 | H_c__145k14__M |
| 15 | 49701435 | 49703103 | H_c__81b06__M |
| 15 | 49816138 | 49817337 | H_c__101e03__M |

TABLE 1-continued

| | | | |
|---|---|---|---|
| 15 | 49830500 | 49831769 | H_c__99n18 |
| 15 | 49889602 | 49889757 | H_c__91j04 |
| 15 | 49908841 | 49909835 | H_c__21k13_M |
| 15 | 50098464 | 50099549 | H_c__215n03_M |
| 15 | 50191315 | 50192699 | H_c__71l14_M |
| 15 | 50258843 | 50260289 | H_c__70a16_M |
| 15 | 50374054 | 50375503 | H_c__253c21_M |
| 15 | 50544550 | 50544693 | H_c__162o15 |
| 15 | 50607860 | 50609094 | H_c__15n07_M |
| 15 | 50647678 | 50648985 | H_c__202i08_M |
| 15 | 50733537 | 50733609 | H_c__3c02 |
| 15 | 50757681 | 50759395 | H_c__147b18_M |
| 15 | 50827527 | 50827728 | H_c__189k20 |
| 15 | 50863249 | 50863928 | H_c__44m20_M |
| 15 | 50869724 | 50870383 | H_c__17d01_M |
| 15 | 50885010 | 50885793 | H_c__166m06_M |
| 15 | 51838710 | 51839521 | H_c__57h03 |
| 15 | 51865810 | 51865941 | H_c__191e04 |
| 15 | 52044486 | 52044666 | H_c__195i04 |
| 15 | 52941018 | 52941136 | H_c__219m12 |
| 15 | 53276171 | 53276760 | H_c__102b06 |
| 15 | 53368832 | 53370037 | H_c__28d24_M |
| 15 | 53398472 | 53398676 | H_c__37c24 |
| 15 | 53487303 | 53489358 | H_c__240d15_M |
| 15 | 53821109 | 53823250 | H_c__101l11 |
| 15 | 54072364 | 54072478 | H_c__12o06_M |
| 15 | 54072568 | 54073513 | H_c__106h01_M |
| 15 | 54322318 | 54323623 | H_c__217j16_M |
| 15 | 54544416 | 54544979 | H_c__205d19_M |
| 15 | 54628885 | 54629066 | H_c__189p17 |
| 15 | 54812213 | 54813712 | H_c__67o19_M |
| 15 | 54966289 | 54967148 | H_c__213g12_M |
| 15 | 54996895 | 54998090 | H_c__49g21 |
| 15 | 54998095 | 54999547 | H_c__226j08_M |
| 15 | 55041839 | 55042009 | H_c__41f12 |
| 15 | 55175939 | 55176065 | H_c__78a05 |
| 15 | 55386195 | 55386912 | H_c__253d16 |
| 15 | 55455563 | 55456845 | H_c__30n21_M |
| 15 | 55671287 | 55671885 | H_c__44p05_M |
| 15 | 56144413 | 56146670 | H_c__184k17_M |
| 15 | 56500627 | 56500784 | H_c__181o24 |
| 15 | 56614679 | 56614685 | H_c__50a03 |
| 15 | 56680377 | 56680461 | H_c__166j19 |
| 15 | 56828127 | 56829005 | H_c__6n06 |
| 15 | 56846887 | 56847059 | H_c__90m06 |
| 15 | 56850459 | 56851944 | H_c133f12_M |
| 15 | 57095058 | 57095201 | H_c__147f01 |
| 15 | 57450776 | 57452334 | H_c__70m18_M |
| 15 | 57736603 | 57737162 | H_c131k01_M |
| 15 | 57768166 | 57769790 | H_c__60h16_M |
| 15 | 57844247 | 57844360 | H_c__169m23 |
| 15 | 58076587 | 58077032 | H_c__183k15_M |
| 15 | 58079514 | 58080217 | H_c__14j22_M |
| 15 | 58083077 | 58083740 | H_c__35b16 |
| 15 | 58083797 | 58085242 | H_c__44o19_M |
| 15 | 58459670 | 58459936 | H_c__85m07 |
| 15 | 58593610 | 58593777 | H_c__248m15 |
| 15 | 58887898 | 58888001 | H_c__211e10 |
| 15 | 59035953 | 59036172 | H_c__173b16 |
| 15 | 59201660 | 59201896 | H_c__230f12_M |
| 15 | 59306764 | 59309160 | H_c__18m14_M |
| 15 | 60139234 | 60140707 | H_c__87e11 |
| 15 | 60469318 | 60470387 | H_c__90m24_M |
| 15 | 60701714 | 60701965 | H_c__9c06 |
| 15 | 61121032 | 61123913 | H_c__58p22_M |
| 15 | 61127004 | 61128554 | H_c__128g20 |
| 15 | 61152502 | 61152588 | H_c__110b17 |
| 15 | 61236269 | 61237131 | H_c__76k06_M |
| 15 | 61268499 | 61269387 | H_c__179c15 |
| 15 | 61336075 | 61336169 | H_c143n19 |
| 15 | 61356398 | 61357349 | H_c134n23 |
| 15 | 61583437 | 61584880 | H_c134i16_M |
| 15 | 61656383 | 61656539 | H_c__240b20 |
| 15 | 61680476 | 61681436 | H_c__207l24 |
| 15 | 62172891 | 62173369 | H_c137i07 |
| 15 | 62241781 | 62242937 | H_c__2j18_M |
| 15 | 62337951 | 62338043 | H_c__30l17 |
| 15 | 62434583 | 62435504 | H_c__209e08_M |
| 15 | 62781300 | 62782843 | H_c134l05_M |
| 15 | 62902981 | 62903840 | H_c__60c02_M |
| 15 | 62915010 | 62915379 | H_c__200j20 |
| 15 | 62920190 | 62922128 | H_c__257f22_M |
| 15 | 62990994 | 62992320 | H_c__21i05_M |
| 15 | 63066901 | 63069767 | H_c__225g05_M |
| 15 | 63108201 | 63109211 | H_c__83f12_M |
| 15 | 63155917 | 63157894 | H_c__243c22_M |
| 15 | 63263532 | 63264149 | H_c__181d15_M |
| 15 | 63264152 | 63265125 | H_c__203i11_M |
| 15 | 63365000 | 63366672 | H_c__78j13 |
| 15 | 63416291 | 63416639 | H_c__55i17 |
| 15 | 63434080 | 63435466 | H_c__45h09_M |
| 15 | 63456250 | 63457550 | H_c__154a06_M |
| 15 | 63474877 | 63475670 | H_c__207o16_M |
| 15 | 63596584 | 63597517 | H_c__69l15 |
| 15 | 63609679 | 63610671 | H_c__90p19_M |
| 15 | 63676953 | 63677137 | H_c142f13 |
| 15 | 63690195 | 63691024 | H_c__33c19 |
| 15 | 63870707 | 63872117 | H_c__85a06_M |
| 15 | 63919772 | 63919860 | H_c__31c11 |
| 15 | 63948821 | 63949014 | H_c__129b07_M |
| 15 | 63963823 | 63963931 | H_c__168o24 |
| 15 | 64331653 | 64332092 | H_c__53l15 |
| 15 | 64332289 | 64333657 | H_c__228m23 |
| 15 | 64372633 | 64373835 | H_c139n23 |
| 15 | 64435284 | 64436260 | H_c__226b04 |
| 15 | 64465994 | 64466797 | H_c__263j20 |
| 15 | 64780106 | 64781920 | H_c__164e14_M |
| 15 | 64782207 | 64783686 | H_c__59d11_M |
| 15 | 65112776 | 65113684 | H_c__111c18 |
| 15 | 65600301 | 65601257 | H_c__114p15_M |
| 15 | 65621815 | 65622283 | H_c__9m20_M |
| 15 | 65908227 | 65908844 | H_c__111f22 |
| 15 | 65913930 | 65915763 | H_c__80o12_M |
| 15 | 65919616 | 65920223 | H_c__53j05 |
| 15 | 65963922 | 65964529 | H_c136d20 |
| 15 | 66027238 | 66027475 | H_c__52l16 |
| 15 | 66133531 | 66134750 | H_c__44k13_M |
| 15 | 66247800 | 66247899 | H_c__206e23 |
| 15 | 66279471 | 66280765 | H_c__235o03 |
| 15 | 66038222 | 66309409 | H_c__76k18_M |
| 15 | 66357726 | 66358105 | H_c__157f15_M |
| 15 | 66457665 | 66459251 | H_c__120g07 |
| 15 | 66510171 | 66512130 | H_c__45e01_M |
| 15 | 66656822 | 66658929 | H_c__154k21_M |
| 15 | 66668103 | 66668217 | H_c__46d13 |
| 15 | 66675090 | 66675159 | H_c__239b09 |
| 15 | 66753016 | 66755061 | H_c__147j10 |
| 15 | 66897004 | 66901162 | H_c__72l11_M_M |
| 15 | 66923248 | 66923849 | H_c__43f20 |
| 15 | 66934257 | 66934417 | H_c__46p13 |
| 15 | 67009650 | 67010488 | H_c__170f01 |
| 15 | 67047410 | 67047562 | H_c__45n02 |
| 15 | 67065247 | 67065324 | H_c__14e04 |
| 15 | 67153367 | 67154163 | H_c__55o03 |
| 15 | 67239767 | 67241563 | H_c__168j16_M |
| 15 | 67377190 | 67378817 | H_c__251p03 |
| 15 | 67493535 | 67494583 | H_c__9f24_M |
| 15 | 67532013 | 67532826 | H_c__8i13 |
| 15 | 67765504 | 67765735 | H_c__243m09_M |
| 15 | 68174709 | 68180469 | H_c__232e02_M_M |
| 15 | 68345568 | 68347683 | H_c__220o12_M |
| 15 | 68664195 | 68665417 | H_c__229m13_M |
| 15 | 68842833 | 68843061 | H_c__245c21_M |
| 15 | 68932637 | 68934200 | H_c__204l06_M |
| 15 | 68942674 | 68943585 | H_c__87m16 |
| 15 | 69194023 | 69195767 | H_c__91e20_M |
| 15 | 69283060 | 69283248 | H_c__109f11 |
| 15 | 69294307 | 69295150 | H_c__31a13 |
| 15 | 69646317 | 69646459 | H_c__66n17 |
| 15 | 70067745 | 70067906 | H_c__71p05_M |
| 15 | 70088167 | 70088258 | H_c__93e15 |
| 15 | 70276135 | 70277154 | H_c__31l19_M |
| 15 | 70309306 | 70310820 | H_c__69c03_M |
| 15 | 70351375 | 70352456 | H_c__90o19_M |
| 15 | 70397606 | 70400041 | H_c__33c03 |
| 15 | 70454920 | 70455842 | H_c__55b21 |
| 15 | 70553315 | 70554895 | H_c__123n14 |
| 15 | 70765275 | 70765991 | H_c__13b10 |
| 15 | 70862270 | 70863449 | H_c__84m11_M |
| 15 | 71130800 | 71132563 | H_c__237f15_M |

TABLE 1-continued

| | | | |
|---|---|---|---|
| 15 | 71446798 | 71448375 | H_c_176i11 |
| 15 | 71712044 | 71713511 | H_c_150d08_M |
| 15 | 71760775 | 71760918 | H_c_114g13 |
| 15 | 71763356 | 71764236 | H_c_96h18_M |
| 15 | 71832772 | 71833337 | H_c_214i23_M |
| 15 | 72070442 | 72071922 | H_c_77e23_M |
| 15 | 72127820 | 72128054 | H_c_210c23 |
| 15 | 72206953 | 72207821 | H_c_211c22_M |
| 15 | 72208775 | 72209499 | H_c_217h23 |
| 15 | 72211792 | 72217317 | H_c_204l20_M |
| 15 | 72276682 | 72279307 | H_c_257p03 |
| 15 | 72378688 | 72380026 | H_c_235b04 |
| 15 | 72444515 | 72446025 | H_c_23j11_M |
| 15 | 72450560 | 72450655 | H_c_112l12 |
| 15 | 72452387 | 72454287 | H_c_2g18_M |
| 15 | 72481397 | 72484200 | H_c_22k17 |
| 15 | 72511482 | 72514090 | H_c_69j20_M |
| 15 | 72693508 | 72696357 | H_c_203d21_M |
| 15 | 72803705 | 72806010 | H_c_229g14 |
| 15 | 72840825 | 72841332 | H_c_37k13 |
| 15 | 72905273 | 72906472 | H_c_147k20 |
| 15 | 72922231 | 72923017 | H_c_201d01_M |
| 15 | 72968065 | 72970282 | H_c139b06_M |
| 15 | 72985768 | 72986271 | H_c_75n11_M |
| 15 | 73016761 | 73017734 | H_c_1b05_M |
| 15 | 73035592 | 73037045 | H_c_26e03_M |
| 15 | 73074171 | 73075821 | H_c_226m14_M |
| 15 | 73102549 | 73103332 | H_c_82h08_M |
| 15 | 73257484 | 73258867 | H_c_177j10_M |
| 15 | 73426618 | 73429382 | H_c_232a05_M |
| 15 | 73446620 | 73448382 | H_c_173f20_M |
| 15 | 73480317 | 73480503 | H_c_208p13_M |
| 15 | 73529709 | 73532193 | H_c_94o11_M |
| 15 | 73533579 | 73534794 | H_c_37n24_M |
| 15 | 73657426 | 73659082 | H_c_9p14_M |
| 15 | 73703637 | 73705476 | H_c_227b13_M |
| 15 | 73719549 | 73719687 | H_c137b16_M |
| 15 | 73983024 | 73984050 | H_c134f11_M |
| 15 | 74138565 | 74139690 | H_c_230d04 |
| 15 | 74270715 | 74272517 | H_c_48m12 |
| 15 | 74390307 | 74391651 | H_c_123i15 |
| 15 | 74415733 | 74420896 | H_c_42e08_M_M |
| 15 | 74420926 | 74422451 | H_c_118g16_M |
| 15 | 74425338 | 74426904 | H_c_119k17_M |
| 15 | 74537386 | 74537472 | H_c_73f20 |
| 15 | 74582176 | 74582398 | H_c_160i24 |
| 15 | 74983923 | 74984973 | H_c_45d08 |
| 15 | 75010584 | 75011776 | H_c_89g21_M |
| 15 | 75036107 | 75036249 | H_c_27l20 |
| 15 | 75075647 | 75076971 | H_c_20k14 |
| 15 | 75296056 | 75296165 | H_c_151c10 |
| 15 | 75395882 | 75395969 | H_c_5l03 |
| 15 | 75498641 | 75499844 | H_c_211j10_M |
| 15 | 75683259 | 75685951 | H_c_19f22_M |
| 15 | 75710112 | 75712732 | H_c_39c21 |
| 15 | 75897319 | 75901742 | H_c133h22_M |
| 15 | 76156219 | 76157384 | H_c_33b21_M |
| 15 | 76209744 | 76211426 | H_c_272e12 |
| 15 | 76228509 | 76229805 | H_c_191n21_M |
| 15 | 76343282 | 76344745 | H_c_189h07_M |
| 15 | 76419526 | 76421131 | H_c_23l09_M |
| 15 | 76586141 | 76587527 | H_c_148d22 |
| 15 | 76619515 | 76620323 | H_c_111i22_M |
| 15 | 76644576 | 76645335 | H_c_42l19_M |
| 15 | 76719076 | 76721102 | H_c_224e03 |
| 15 | 76733683 | 76733752 | H_c_149h20 |
| 15 | 76889886 | 76891108 | H_c_186k17_M |
| 15 | 76910262 | 76911653 | H_c_207p18 |
| 15 | 76952027 | 76953345 | H_c_246h11_M |
| 15 | 77168739 | 77170415 | H_c136e24 |
| 15 | 77390042 | 77391268 | H_c_2j11_M |
| 15 | 77430629 | 77430841 | H_c_45m15 |
| 15 | 77510974 | 77512228 | H_c_2i12_M |
| 15 | 77975844 | 77976746 | H_c_249g07 |
| 15 | 78002875 | 78003582 | H_c_45a21_M |
| 15 | 78231768 | 78232658 | H_c_258k12 |
| 15 | 78243219 | 78243369 | H_c_11k24 |
| 15 | 78312673 | 78312789 | H_c_93o23_M |
| 15 | 78330397 | 78331636 | H_c_179f17 |
| 15 | 78387512 | 78389006 | H_c_109b02 |
| 15 | 78483251 | 78485157 | H_c_48d19_M |
| 15 | 78556443 | 78556585 | H_c_153j09_M |
| 15 | 78858292 | 78860013 | H_c_150m03_M |
| 15 | 79068527 | 79069681 | H_c_41h01 |
| 15 | 79079439 | 79082699 | H_c_7a17_M |
| 15 | 79294655 | 79296386 | H_c_225h19 |
| 15 | 79365428 | 79366016 | H_c139k17 |
| 15 | 79403242 | 79403882 | H_c_223b17_M |
| 15 | 79464392 | 79464540 | H_c_63h02 |
| 15 | 79614446 | 79614553 | H_c_94n09 |
| 15 | 79782864 | 79782979 | H_c_69o12 |
| 15 | 79808530 | 79808725 | H_c_22e09 |
| 15 | 80122557 | 80127175 | H_c_246c12_M |
| 15 | 81111952 | 81114076 | H_c_205j11_M |
| 15 | 81174258 | 81176189 | H_c_82o08_M |
| 15 | 81216138 | 81216811 | H_c_1o22_M |
| 15 | 81259610 | 81259765 | H_c_190n05 |
| 15 | 81275062 | 81276601 | H_c_49j16_M |
| 15 | 81411666 | 81412759 | H_c_3b23_M |
| 15 | 81470538 | 81471361 | H_c_145o10_M |
| 15 | 81525737 | 81527286 | H_c_202e16_M |
| 15 | 81566834 | 81567965 | H_c_82d16 |
| 15 | 81638075 | 81638186 | H_c_164a16 |
| 15 | 81671654 | 81671766 | H_c_162j01 |
| 15 | 81743002 | 81745364 | H_c_159g09_M |
| 15 | 81838162 | 81839336 | H_c_235b13 |
| 15 | 81906761 | 81908097 | H_c_70j10_M |
| 15 | 82944552 | 82945860 | H_c_129d20_M |
| 15 | 82997714 | 82998610 | H_c_78c22 |
| 15 | 83002096 | 83003466 | H_c_47d12_M |
| 15 | 83060085 | 83061510 | H_c_17c10_M |
| 15 | 83092302 | 83093699 | H_c_251l07 |
| 15 | 83325065 | 83326909 | H_c_59g13_M |
| 15 | 84138090 | 84139376 | H_c_151a22_M |
| 15 | 84274128 | 84274466 | H_c_179f06 |
| 15 | 84514784 | 84514917 | H_c_155b04 |
| 15 | 85500441 | 85500611 | H_c_25h24_M |
| 15 | 85733703 | 85733807 | H_c_274p19 |
| 15 | 85762493 | 85762666 | H_c139l24 |
| 15 | 85800058 | 85800140 | H_c_149p03 |
| 15 | 86268140 | 86268233 | H_c_29c08 |
| 15 | 86575508 | 86575633 | H_c_193g05 |
| 15 | 86599652 | 86602167 | H_c_212l04_M |
| 15 | 86811307 | 86811752 | H_c_121i21 |
| 15 | 86948182 | 86950421 | H_c_155b10_M |
| 15 | 86965373 | 86966097 | H_c_270h15_M |
| 15 | 87049250 | 87050606 | H_c_61l07_M |
| 15 | 87146961 | 87148343 | H_c140i15_M |
| 15 | 87256176 | 87257878 | H_c_259n03 |
| 15 | 87432001 | 87433264 | H_c_150f13 |
| 15 | 87587900 | 87588489 | H_c_75b03 |
| 15 | 87615387 | 87615532 | H_c_275n04 |
| 15 | 87678278 | 87679357 | H_c_168l05_M |
| 15 | 87702550 | 87703584 | H_c_145i14_M |
| 15 | 87705715 | 87707895 | H_c_119e20 |
| 15 | 87711504 | 87716610 | H_c_252i21_M |
| 15 | 87743882 | 87745833 | H_c_82g01_M |
| 15 | 87755205 | 87756305 | H_c_77l20 |
| 15 | 87774768 | 87775420 | H_c_23m06_M |
| 15 | 87840120 | 87841340 | H_c_70p03 |
| 15 | 88006652 | 88011012 | H_c133o20_M |
| 15 | 88026476 | 88026617 | H_c_88d03 |
| 15 | 88118444 | 88121668 | H_c_274n12_M |
| 15 | 88237979 | 88238740 | H_c_68d12_M |
| 15 | 88256773 | 88257154 | H_c_30p19_M |
| 15 | 88344928 | 88345190 | H_c_29p11_M |
| 15 | 88445952 | 88447017 | H_c_12n04_M |
| 15 | 88528777 | 88529829 | H_c_58c04 |
| 15 | 88545012 | 88546969 | H_c_51o07 |
| 15 | 88577453 | 88578879 | H_c_95c18_M |
| 15 | 88873629 | 88875438 | H_c_10h17_M |
| 15 | 89009165 | 89010207 | H_c_75h09_M |
| 15 | 89061339 | 89062189 | H_c_106j08_M |
| 15 | 89215380 | 89216786 | H_c_40m20_M |
| 15 | 89276539 | 89277588 | H_c_168k07_M |
| 15 | 89300024 | 89301798 | H_c_123f19_M |
| 15 | 89338001 | 89339334 | H_c_80m03_M |
| 15 | 89444313 | 89444838 | H_c_72o05_M |
| 15 | 89834494 | 89834618 | H_c_237o18 |
| 15 | 89921746 | 89921865 | H_c_221o11 |

TABLE 1-continued

| | | | |
|---|---|---|---|
| 15 | 90196748 | 90199093 | H_c_119i24 |
| 15 | 90265179 | 90265306 | H_c_272j07 |
| 15 | 90391025 | 90391211 | H_c_184b07_M |
| 15 | 90563047 | 90563179 | H_c_98f10 |
| 15 | 90999333 | 91000253 | H_c_233m13 |
| 15 | 91058719 | 91060664 | H_c_119j03_M |
| 15 | 91078032 | 91078523 | H_c_24p11_M |
| 15 | 91153290 | 91154023 | H_c_20l09_M |
| 15 | 91164695 | 91165022 | H_c_178i08 |
| 15 | 91226735 | 91227840 | H_c_11e07 |
| 15 | 91248247 | 91248924 | H_c_197n22_M |
| 15 | 91432428 | 91433928 | H_c142b10 |
| 15 | 91906983 | 91907064 | H_c_49j07 |
| 15 | 92088994 | 92089065 | H_c_13d19 |
| 15 | 92575716 | 92576163 | H_c_10e07 |
| 15 | 92690063 | 92690396 | H_c_215d06 |
| 15 | 93188988 | 93189483 | H_c_145p23_M |
| 15 | 94158432 | 94159799 | H_c_209b18_M |
| 15 | 94318571 | 94318659 | H_c_177p12 |
| 15 | 94396997 | 94399082 | H_c_182j06_M |
| 15 | 94554292 | 94554390 | H_c_259j05 |
| 15 | 94666174 | 94666713 | H_c138c15 |
| 15 | 94677308 | 94678276 | H_c_196p24 |
| 15 | 94689873 | 94690665 | H_c_90f19 |
| 15 | 94696020 | 94696613 | H_c_192k10_M |
| 15 | 94701142 | 94705013 | H_c_44j18_M_M |
| 15 | 94707685 | 94707927 | H_c_125m01 |
| 15 | 94712658 | 94713212 | H_c_8g05 |
| 15 | 94753515 | 94754391 | H_c_215h02_M |
| 15 | 94760710 | 94761340 | H_c_67l17_M |
| 15 | 95292118 | 95292526 | H_c_28m05_M |
| 15 | 96273594 | 96273805 | H_c_103l07 |
| 15 | 96304367 | 96306180 | H_c_182i06_M |
| 15 | 96653547 | 96654251 | H_c_17d06 |
| 15 | 96781690 | 96782663 | H_c_123e03_M |
| 15 | 96789127 | 96790074 | H_c_98i10_M |
| 15 | 97007783 | 97009347 | H_c_244g22_M |
| 15 | 97203304 | 97203476 | H_c_76d10 |
| 15 | 97375876 | 97376829 | H_c_86m22_M |
| 15 | 97419518 | 97420689 | H_c_158g11_M |
| 15 | 97458074 | 97458597 | H_c_145m17 |
| 15 | 97462442 | 97463975 | H_c_49f06_M |
| 15 | 97532946 | 97533047 | H_c_205c22 |
| 15 | 97608589 | 97609634 | H_c_16d23_M |
| 15 | 97826323 | 97826408 | H_c_241j12 |
| 15 | 98090260 | 98091741 | H_c_270m03_M |
| 15 | 98174240 | 98174334 | H_c_76f20 |
| 15 | 98283932 | 98286451 | H_c_43f14 |
| 15 | 98901950 | 98902854 | H_c_33p06 |
| 15 | 99236745 | 99238705 | H_c_173h01_M |
| 15 | 99276688 | 99278082 | H_c_122m20_M |
| 15 | 99330291 | 99331943 | H_c_243f11_M |
| 15 | 99608428 | 99610312 | H_c_196i14_M |
| 15 | 99634549 | 99636347 | H_c_188l04_M |
| 15 | 99652643 | 99653470 | H_c_63m18_M |
| 15 | 99847460 | 99848387 | H_c_69m24_M |
| 15 | 99863673 | 99863792 | H_c_3d03 |
| 16 | 10097143 | 10097404 | H_c_59f09 |
| 16 | 10117904 | 10118070 | H_c_190l17 |
| 16 | 1028025 | 1028272 | H_c_51m07 |
| 16 | 10387424 | 10387852 | H_c_101f16 |
| 16 | 10415493 | 10415596 | H_c_16b11 |
| 16 | 10581328 | 10582956 | H_c_64i11 |
| 16 | 10880926 | 10881207 | H_c_26h04 |
| 16 | 10945549 | 10946279 | H_c_107f09 |
| 16 | 11135704 | 11137621 | H_c_24i21 |
| 16 | 11186907 | 11187526 | H_c_18i22 |
| 16 | 11257590 | 11258924 | H_c_27p14_M |
| 16 | 11336505 | 11338108 | H_c_3e13 |
| 16 | 11346598 | 11347487 | H_c_85i21_M |
| 16 | 11587048 | 11589167 | H_c_120j08_M |
| 16 | 11669183 | 11670874 | H_c_69n08 |
| 16 | 11743480 | 11744608 | H_c_157k15_M |
| 16 | 11798380 | 11798856 | H_c_166o11_M |
| 16 | 1184957 | 1186285 | H_c_91b09 |
| 16 | 11852443 | 11853372 | H_c_210l24 |
| 16 | 11916225 | 11917998 | H_c_163j08_M |
| 16 | 11977266 | 11978885 | H_c_219f01_M |
| 16 | 1249205 | 1251091 | H_c_2i17 |
| 16 | 1251094 | 1252164 | H_c_191j11 |
| 16 | 12901797 | 12904846 | H_c_245a01_M |
| 16 | 1290566 | 1293023 | H_c_32n19 |
| 16 | 1299286 | 1300239 | H_c_47n11_M |
| 16 | 1322987 | 1324324 | H_c_38p07 |
| 16 | 1340198 | 1342373 | H_c_52a06_M |
| 16 | 13880917 | 13881115 | H_c_215e15 |
| 16 | 13921097 | 13922402 | H_c_184p04_M |
| 16 | 1398193 | 1399223 | H_c_150j02_M |
| 16 | 1402669 | 1405037 | H_c_15l06 |
| 16 | 14072323 | 14073059 | H_c_183a08_M |
| 16 | 1409770 | 1411361 | H_c_85h19_M |
| 16 | 14187336 | 14187399 | H_c_82b21_M |
| 16 | 14192554 | 14192745 | H_c_273c16 |
| 16 | 14286443 | 14287709 | H_c_254e18_M |
| 16 | 14301855 | 14303759 | H_c_54i11_M |
| 16 | 14303763 | 14304776 | H_c_231f21_M |
| 16 | 14627437 | 14627669 | H_c_154p20_M |
| 16 | 14631029 | 14631897 | H_c_90g22_M |
| 16 | 1464465 | 1466036 | H_c_196i05_M |
| 16 | 1482869 | 1485186 | H_c_265o22_M |
| 16 | 14831429 | 14831498 | H_c_27d09 |
| 16 | 15056553 | 15057990 | H_c_234j09_M |
| 16 | 15435455 | 15436679 | H_c_39f18_M |
| 16 | 15644066 | 15644741 | H_c_212a24_M |
| 16 | 15859019 | 15860030 | H_c_145h12_M |
| 16 | 15950670 | 15951907 | H_c_32d13_M |
| 16 | 1597817 | 1597938 | H_c132c14 |
| 16 | 15980015 | 15980097 | H_c_28i10 |
| 16 | 1600040 | 1603199 | H_c_245c13_M |
| 16 | 163196 | 163596 | H_c_157h20 |
| 16 | 165810 | 166998 | H_c_18i17_M |
| 16 | 1667849 | 1669046 | H_c133e06_M |
| 16 | 167000 | 167362 | H_c_83p07_M |
| 16 | 1695347 | 1697451 | H_c_274f11_M |
| 16 | 169821 | 171509 | H_c_116a14_M |
| 16 | 17087362 | 17087645 | H_c_199j10 |
| 16 | 171536 | 172764 | H_c_60f16 |
| 16 | 17244317 | 17244453 | H_c_104a05 |
| 16 | 17470669 | 17472764 | H_c_266k20_M |
| 16 | 1760310 | 1761562 | H_c_186k24_M |
| 16 | 1772033 | 1773466 | H_c_56o09_M |
| 16 | 17996607 | 17996697 | H_c_176f15 |
| 16 | 18042757 | 18042843 | H_c_105k16 |
| 16 | 1815880 | 1817826 | H_c_93f04_M |
| 16 | 1861143 | 1862982 | H_c_123p06_M |
| 16 | 18708622 | 18709670 | H_c_27f17 |
| 16 | 18719883 | 18721068 | H_c_5k01_M |
| 16 | 18902636 | 18903261 | H_c_272b20_M |
| 16 | 18963326 | 18964727 | H_c_29l17 |
| 16 | 19005114 | 19006194 | H_c_193b09_M |
| 16 | 19032762 | 19034419 | H_c_18l23_M |
| 16 | 1907093 | 1909618 | H_c_82m02_M |
| 16 | 19086770 | 19088751 | H_c_154l20 |
| 16 | 1912791 | 1914171 | H_c_89n02 |
| 16 | 1918566 | 1920920 | H_c_236i14 |
| 16 | 19225601 | 19225741 | H_c_85a04 |
| 16 | 1932058 | 1933986 | H_c_176h13_M |
| 16 | 19440219 | 19441595 | H_c_149c04_M |
| 16 | 1961386 | 1963143 | H_c_41d17 |
| 16 | 19636509 | 19637530 | H_c_6o03_M |
| 16 | 1981768 | 1984028 | H_c_65o20_M |
| 16 | 1998583 | 2000174 | H_c_83g10 |
| 16 | 2008970 | 2010945 | H_c_252o12_M |
| 16 | 2012965 | 2013611 | H_c_32l23_M |
| 16 | 20266891 | 20268127 | H_c_122n15_M |
| 16 | 2036679 | 2038205 | H_c_50b22_M |
| 16 | 20679672 | 20679765 | H_c_88k05 |
| 16 | 20724816 | 20726047 | H_c_121h18_M |
| 16 | 20818627 | 20820190 | H_c_60b03 |
| 16 | 21196782 | 21197415 | H_c_52h03 |
| 16 | 21202276 | 21202959 | H_c139i06 |
| 16 | 21219564 | 21221180 | H_c_18g10_M |
| 16 | 2145325 | 2146458 | H_c_40k03_M |
| 16 | 21582705 | 21583220 | H_c_59j17_M |
| 16 | 218267 | 219754 | H_c_5i18_M |
| 16 | 2185880 | 2188242 | H_c_239e01 |
| 16 | 2194738 | 2195090 | H_c_11i05_M |
| 16 | 2203733 | 2205551 | H_c_28e06 |
| 16 | 22106288 | 22106551 | H_c_33j17 |
| 16 | 22108842 | 22110506 | H_c_245f17_M |

TABLE 1-continued

| | | | |
|---|---|---|---|
| 16 | 22124715 | 22125668 | H_c_167p03_M |
| 16 | 2213456 | 2214820 | H_c_232h18_M |
| 16 | 22215995 | 22217427 | H_c_7o03_M |
| 16 | 22292556 | 22294023 | H_c_123k20_M |
| 16 | 22334717 | 22334818 | H_c142g19 |
| 16 | 2241133 | 2242329 | H_c_119n20_M |
| 16 | 2258389 | 2260048 | H_c_83f16_M |
| 16 | 22731629 | 22732747 | H_c_69g04_M |
| 16 | 22732958 | 22734004 | H_c_195g02_M |
| 16 | 23100838 | 23102645 | H_c_71b08_M |
| 16 | 23163058 | 23163450 | H_c_180g10 |
| 16 | 23217080 | 23217254 | H_c_245a19 |
| 16 | 2329424 | 2331336 | H_c_191n01_M |
| 16 | 23309817 | 23310060 | H_c_36d20 |
| 16 | 23370970 | 23371079 | H_c_20b16 |
| 16 | 23428804 | 23429491 | H_c_46l24 |
| 16 | 23476266 | 23477298 | H_c_111o21 |
| 16 | 23559746 | 23560159 | H_c_30i09 |
| 16 | 23673305 | 23674108 | H_c_101b21_M |
| 16 | 2419686 | 2420091 | H_c_94c05 |
| 16 | 24307001 | 24307212 | H_c_27l12 |
| 16 | 24458026 | 24458376 | H_c_68p18_M |
| 16 | 2449784 | 2451927 | H_c_4b22 |
| 16 | 24933349 | 24934755 | H_c_148h04_M |
| 16 | 24985522 | 24986733 | H_c_170h05 |
| 16 | 25025433 | 25026278 | H_c_121d06_M |
| 16 | 25176101 | 25177794 | H_c_54b03_M |
| 16 | 2521849 | 2523296 | H_c_214n03_M |
| 16 | 25606770 | 25606894 | H_c_130b06 |
| 16 | 2593424 | 2593553 | H_c_112j13 |
| 16 | 262989 | 265985 | H_c_70f08_M |
| 16 | 26345715 | 26345945 | H_c_70c16 |
| 16 | 2672089 | 2672498 | H_c_91g22 |
| 16 | 2689103 | 2690816 | H_c140j22 |
| 16 | 27000796 | 27001010 | H_c_205f22 |
| 16 | 27028472 | 27028942 | H_c_63n19 |
| 16 | 2705160 | 2707335 | H_c_176b09 |
| 16 | 27073382 | 27073973 | H_c_165o12 |
| 16 | 2710717 | 2712247 | H_c_104b08_M |
| 16 | 27122261 | 27123187 | H_c_243e04_M |
| 16 | 27187245 | 27187739 | H_c_125m19_M |
| 16 | 27198288 | 27198458 | H_c_239h05 |
| 16 | 27232206 | 27233595 | H_c_208i13_M |
| 16 | 27305650 | 27305740 | H_c_72n19 |
| 16 | 27366981 | 27369005 | H_c137j07_M |
| 16 | 2741872 | 2743198 | H_c_82b16 |
| 16 | 27468204 | 27469445 | H_c_269n17_M |
| 16 | 2767389 | 2768243 | H_c_193p08_M |
| 16 | 27980907 | 27983599 | H_c_16b24_M |
| 16 | 28129844 | 28131592 | H_c_68a14_M |
| 16 | 28210338 | 28212900 | H_c_66j02_M |
| 16 | 2831820 | 2833175 | H_c_264p24 |
| 16 | 28472634 | 28473327 | H_c_161m15 |
| 16 | 2858210 | 2858712 | H_c_167o23 |
| 16 | 2872945 | 2874011 | H_c_63h03_M |
| 16 | 28741392 | 28741599 | H_c134f19_M |
| 16 | 28755937 | 28756020 | H_c_114b11 |
| 16 | 28764464 | 28766015 | H_c_222l07_M |
| 16 | 28781768 | 28783766 | H_c_150h12_M |
| 16 | 28798613 | 28799168 | H_c_266g11_M |
| 16 | 28843070 | 28844252 | H_c_213l08 |
| 16 | 28869412 | 28870713 | H_c_232c17 |
| 16 | 28876466 | 28876607 | H_c_125c03_M |
| 16 | 28893613 | 28894470 | H_c_153h20_M |
| 16 | 2893760 | 2894741 | H_c_226i15_M |
| 16 | 2894742 | 2896322 | H_c_268e21_M |
| 16 | 29000757 | 29001691 | H_c_117e03 |
| 16 | 2901700 | 2902102 | H_c_38n06_M |
| 16 | 2922566 | 2922708 | H_c_186i14 |
| 16 | 29402305 | 29404579 | H_c_89f16 |
| 16 | 2952670 | 2957700 | H_c_44n17_M_M |
| 16 | 29582407 | 298583750 | H_c_67k13_M |
| 16 | 29664112 | 29665373 | H_c_229m05 |
| 16 | 29708930 | 29710325 | H_c_212o06_M |
| 16 | 29730849 | 29731599 | H_c_110m10 |
| 16 | 29734608 | 2936009 | H_c_78n07_M |
| 16 | 29781414 | 29781995 | H_c_78c24_M |
| 16 | 29795861 | 29796771 | H_c_96j15 |
| 16 | 29880399 | 29881100 | H_c_240f07 |
| 16 | 29891651 | 29894314 | H_c_208f12 |
| 16 | 29912997 | 29914650 | H_c_225h07_M |
| 16 | 29971211 | 29975189 | H_c_45e02_M |
| 16 | 29983103 | 29985157 | H_c_84l08_M |
| 16 | 29994585 | 29995416 | H_c_53f02_M |
| 16 | 30010287 | 30011240 | H_c_232l09_M |
| 16 | 30013433 | 30015784 | H_c_174g01_M |
| 16 | 3010042 | 3014126 | H_c_125o07_M |
| 16 | 30102233 | 30103398 | H_c_193c07 |
| 16 | 3014155 | 3014525 | H_c_160a07_M |
| 16 | 3025748 | 3027117 | H_c_206e17 |
| 16 | 30273717 | 30274394 | H_c_146f08_M |
| 16 | 30287829 | 30289678 | H_c_56g09_M |
| 16 | 30313142 | 30315006 | H_c_168l09_M |
| 16 | 30319056 | 30319411 | H_c_89m22_M |
| 16 | 30336171 | 30337739 | H_c_198p23 |
| 16 | 3035714 | 3035936 | H_c_199j12 |
| 16 | 30363801 | 30364608 | H_c_10b07 |
| 16 | 30445724 | 30446309 | H_c_200h03_M |
| 16 | 30452575 | 30455375 | H_c_41p16_M |
| 16 | 30479446 | 30481056 | H_c_16i16_M |
| 16 | 30527962 | 30530528 | H_c_30l16_M |
| 16 | 30552832 | 30553587 | H_c_38h08_M |
| 16 | 30569268 | 30571289 | H_c_16l15_M |
| 16 | 30576439 | 30579278 | H_c_107a08_M |
| 16 | 30617199 | 30618045 | H_c_117e02 |
| 16 | 30667240 | 30668644 | H_c_171d10 |
| 16 | 30679633 | 30681511 | H_c_56a08_M |
| 16 | 30694117 | 30695531 | H_c_230g23_M |
| 16 | 30724124 | 30726005 | H_c_257b16_M |
| 16 | 30732834 | 30733619 | H_c_173o03 |
| 16 | 30793511 | 30794256 | H_c_40m04 |
| 16 | 30811667 | 30813344 | H_c_52f14 |
| 16 | 30814820 | 30816295 | H_c_113g22 |
| 16 | 30841120 | 30841797 | H_c_72l07_M |
| 16 | 3090097 | 3090591 | H_c_4l22 |
| 16 | 3096350 | 3096914 | H_c_169m02_M |
| 16 | 30973434 | 30975333 | H_c_154f17_M |
| 16 | 30991817 | 30993926 | H_c_179c05_M |
| 16 | 31012837 | 31013858 | H_c_119i18_M |
| 16 | 31036225 | 31037155 | H_c_60i20_M |
| 16 | 31060964 | 31063128 | H_c_145k19_M |
| 16 | 31098804 | 31099659 | H_c137n14_M |
| 16 | 31120075 | 31122206 | H_c_216f04 |
| 16 | 31132291 | 31136748 | H_c_112a05_M |
| 16 | 3113748 | 3114885 | H_c_231l19_M |
| 16 | 31209956 | 31210071 | H_c_58o06 |
| 16 | 3124229 | 3125544 | H_c_181l16 |
| 16 | 31249375 | 31251248 | H_c_114i23_M |
| 16 | 31346370 | 31347272 | H_c_98n22 |
| 16 | 31377277 | 31379389 | H_c_195m18_M |
| 16 | 31389988 | 31391320 | H_c_243c16 |
| 16 | 31395410 | 31397638 | H_c_77j05_M |
| 16 | 3141921 | 3142125 | H_c_153d03_M |
| 16 | 31426089 | 31427560 | H_c_77h12_M |
| 16 | 3147443 | 3149387 | H_c_231m01_M |
| 16 | 31487885 | 31488825 | H_c_10j21 |
| 16 | 3160776 | 3161389 | H_c141k08_M |
| 16 | 31619175 | 31619892 | H_c_11m19 |
| 16 | 3165729 | 3165980 | H_c_72k03 |
| 16 | 31675828 | 31675975 | H_c_37g02 |
| 16 | 3172221 | 3173760 | H_c_106k12_M |
| 16 | 3178498 | 3179617 | H_c_74i22_M |
| 16 | 31831323 | 31831464 | H_c_20c03 |
| 16 | 3224527 | 3225266 | H_c_87j07_M |
| 16 | 323482 | 324957 | H_c_253o12 |
| 16 | 32436427 | 32436596 | H_c_224h06 |
| 16 | 3254057 | 3255617 | H_c_17p22 |
| 16 | 3272718 | 3274329 | H_c_11g13_M |
| 16 | 3294682 | 3296420 | H_c_17a11_M |
| 16 | 33724506 | 33725815 | H_c_30g23 |
| 16 | 33859564 | 33860895 | H_c141d01_M |
| 16 | 33863880 | 33864123 | H_c_128f04 |
| 16 | 3390608 | 3391678 | H_c_113g20_M |
| 16 | 34119695 | 34119889 | H_c_18g01 |
| 16 | 3433374 | 3434555 | H_c_259j09_M |
| 16 | 3447505 | 3448749 | H_c_107b02_M |
| 16 | 34665319 | 34667407 | H_c_215g18 |
| 16 | 34737713 | 34737796 | H_c_47i17 |
| 16 | 3489970 | 3491374 | H_c_84f08_M |
| 16 | 3600699 | 3601826 | H_c_250h18_M |

TABLE 1-continued

| | | | |
|---|---|---|---|
| 16 | 3655166 | 3655400 | H_c_56k11 |
| 16 | 370677 | 372858 | H_c_154k15_M |
| 16 | 3706966 | 3708368 | H_c_262k01 |
| 16 | 3713024 | 3713726 | H_c_73p09 |
| 16 | 3869114 | 3871518 | H_c_55l04_M |
| 16 | 387053 | 388036 | H_c_47o05_M |
| 16 | 390629 | 392451 | H_c_93e18_M |
| 16 | 4047299 | 4048821 | H_c_165b04 |
| 16 | 414971 | 416918 | H_c137f23_M |
| 16 | 4172418 | 4174466 | H_c_61h03_M |
| 16 | 4243426 | 4244584 | H_c_64c05_M |
| 16 | 4261534 | 4264404 | H_c_73a02 |
| 16 | 4297222 | 4298397 | H_c_145k03 |
| 16 | 4303866 | 4304071 | H_c_38j23_M |
| 16 | 43220 | 44199 | H_c_275l20_M |
| 16 | 4361248 | 4362763 | H_c_159o19_M |
| 16 | 4405045 | 4407326 | H_c_231h11_M |
| 16 | 4415609 | 4416495 | H_c_201i07_M |
| 16 | 4466142 | 4467127 | H_c_70l17_M |
| 16 | 45164838 | 45166219 | H_c_93l23 |
| 16 | 45212105 | 45213082 | H_c_115k08 |
| 16 | 4527395 | 4529283 | H_c_206o07 |
| 16 | 45280431 | 45281555 | H_c_202d14_M |
| 16 | 45381159 | 45382356 | H_c_54n16_M |
| 16 | 45421873 | 45423078 | H_c_71l03_M |
| 16 | 45474722 | 45477244 | H_c_70l10_M |
| 16 | 45564134 | 45565338 | H_c_62i10_M |
| 16 | 45628647 | 45629724 | H_c_163e06_M |
| 16 | 45653859 | 45653968 | H_c_33i08 |
| 16 | 45734265 | 45736290 | H_c_89i15_M |
| 16 | 4583583 | 4585324 | H_c_174p04 |
| 16 | 45867257 | 45867339 | H_c_38d06 |
| 16 | 46027070 | 46027233 | H_c_91a09 |
| 16 | 4603711 | 4605842 | H_c_149o04 |
| 16 | 46052108 | 46053099 | H_c_87m05_M |
| 16 | 4606011 | 4606918 | H_c_102c17 |
| 16 | 4614546 | 4616686 | H_c_53o03 |
| 16 | 46197474 | 46197564 | H_c_272m16_M |
| 16 | 46558289 | 46558512 | H_c_259h24 |
| 16 | 466618 | 468034 | H_c_35p08 |
| 16 | 4682997 | 4684842 | H_c_88n12_M |
| 16 | 46835496 | 46836285 | H_c_235j23_M |
| 16 | 46956913 | 46957566 | H_c_81o01 |
| 16 | 46957573 | 46957832 | H_c_150h21 |
| 16 | 47200701 | 47201847 | H_c_94e01 |
| 16 | 4723793 | 4724808 | H_c_57p17_M |
| 16 | 47263762 | 47264475 | H_c_256j04 |
| 16 | 4756235 | 4757434 | H_c_245d14_M |
| 16 | 47580388 | 47580498 | H_c_125n08 |
| 16 | 47587496 | 47589099 | H_c_13c24 |
| 16 | 47612850 | 47613033 | H_c_19g12 |
| 16 | 47754882 | 47755143 | H_c_5e04 |
| 16 | 47866619 | 47866911 | H_c_79p20_M |
| 16 | 47872378 | 47874047 | H_c_38m22_M |
| 16 | 4790653 | 4793244 | H_c_231a06 |
| 16 | 4806763 | 4807298 | H_c_273e18 |
| 16 | 48147359 | 48147573 | H_c_166o01 |
| 16 | 4836537 | 4838323 | H_c_148h09_M |
| 16 | 48429831 | 48431370 | H_c_160f16_M |
| 16 | 48467662 | 48468110 | H_c_7f19 |
| 16 | 48657132 | 48658394 | H_c_274f08_M |
| 16 | 48685485 | 48685645 | H_c_13o22 |
| 16 | 48837054 | 48838387 | H_c_254c15_M |
| 16 | 48894914 | 48897720 | H_c_14a18 |
| 16 | 48959752 | 48960878 | H_c_162k08_M |
| 16 | 49059214 | 49059778 | H_c_40b05_M |
| 16 | 4926084 | 4928052 | H_c_154d22_M |
| 16 | 49333083 | 49334142 | H_c_81c10_M |
| 16 | 49338544 | 49338853 | H_c_207c07 |
| 16 | 49394081 | 49394200 | H_c_56p09_M |
| 16 | 49431870 | 49432213 | H_c_40b08_M |
| 16 | 4947890 | 4949525 | H_c_116e14 |
| 16 | 49602979 | 49603104 | H_c_32a09 |
| 16 | 49630343 | 49630413 | H_c_151f10_M |
| 16 | 49725654 | 49726528 | H_c_129e13_M |
| 16 | 49741069 | 49747629 | H_c_274j24_M_M |
| 16 | 49930180 | 49930385 | H_c_262h05 |
| 16 | 5023190 | 5024046 | H_c_194i07_M |
| 16 | 50316221 | 50316421 | H_c_181g21 |
| 16 | 50381443 | 50381647 | H_c139l09 |
| 16 | 50541156 | 50541342 | H_c_115m18 |
| 16 | 5061331 | 5062241 | H_c_163o11_M |
| 16 | 50870859 | 50870989 | H_c_26i08 |
| 16 | 50965487 | 50965698 | H_c_98g13 |
| 16 | 51136686 | 51139336 | H_c_151a01_M |
| 16 | 51646063 | 51646837 | H_c_178f05 |
| 16 | 51651875 | 51652654 | H_c_83n12 |
| 16 | 51721445 | 51723501 | H_c_108j15_M |
| 16 | 51990363 | 51990524 | H_c_151m10 |
| 16 | 52025759 | 52026530 | H_c_122g13_M |
| 16 | 52094005 | 52095520 | H_c_72p17_M |
| 16 | 52101483 | 52102122 | H_c_115k09 |
| 16 | 52294830 | 52295738 | H_c_261b14_M |
| 16 | 52791117 | 52792767 | H_c_4b19 |
| 16 | 5285708 | 5285798 | H_c_214d16 |
| 16 | 52873212 | 52875059 | H_c_215h09_M |
| 16 | 52881544 | 52882349 | H_c_273j20 |
| 16 | 53235219 | 53235446 | H_c142l14 |
| 16 | 53403760 | 53403908 | H_c_191o22 |
| 16 | 53521302 | 53525157 | H_c_53j22_M |
| 16 | 53527731 | 53528189 | H_c_195h18 |
| 16 | 53529174 | 53530182 | H_c_145p21_M |
| 16 | 53597881 | 53598010 | H_c_203o14 |
| 16 | 53880563 | 53880643 | H_c_186k01 |
| 16 | 53922717 | 53923222 | H_c134n17 |
| 16 | 54070667 | 54071645 | H_c_148g18_M |
| 16 | 54100083 | 54101680 | H_c_224c13_M |
| 16 | 54247021 | 54249481 | H_c_189n02_M |
| 16 | 54789653 | 54789824 | H_c_1m12 |
| 16 | 54860329 | 54860543 | H_c_55a10_M |
| 16 | 55042242 | 55042724 | H_c_190l15_M |
| 16 | 55110412 | 55111722 | H_c_258h16_M |
| 16 | 55199557 | 55200262 | H_c_269p16_M |
| 16 | 55223285 | 55224219 | H_c_251a24 |
| 16 | 55248511 | 55250021 | H_c_21e12 |
| 16 | 55273170 | 55274065 | H_c_181k23_M_M |
| 16 | 55321310 | 55322339 | H_c_239l10_M |
| 16 | 55522769 | 55524962 | H_c_80k13_M |
| 16 | 55557550 | 55557634 | H_c_41n17 |
| 16 | 55579503 | 55581404 | H_c_192o17 |
| 16 | 55645725 | 55645868 | H_c_245a05 |
| 16 | 55683331 | 55684795 | H_c_107f04 |
| 16 | 55776986 | 55778924 | H_c_198g14_M |
| 16 | 55836238 | 55836702 | H_c_27m23_M |
| 16 | 55874648 | 55876712 | H_c138b24_M |
| 16 | 56038238 | 56039467 | H_c_31h01 |
| 16 | 56053965 | 56054786 | H_c_129b24_M |
| 16 | 56125464 | 56127822 | H_c_71a16_M |
| 16 | 56326143 | 56328883 | H_c_237o16_M |
| 16 | 56393210 | 56393932 | H_c_42e01_M |
| 16 | 56561127 | 56562544 | H_c_46j15 |
| 16 | 56575621 | 56576736 | H_c_192g20_M |
| 16 | 56590999 | 56593452 | H_c_9m08 |
| 16 | 56616362 | 56619091 | H_c_273k01_M |
| 16 | 56719882 | 56721220 | H_c_189e04_M |
| 16 | 57053964 | 57055647 | H_c_2d12_M |
| 16 | 57055647 | 57056687 | H_c_149c10_M |
| 16 | 57106393 | 57108492 | H_c_186g10_M |
| 16 | 57220746 | 57221210 | H_c_185d19_M |
| 16 | 57324591 | 57325886 | H_c_220g02_M |
| 16 | 59164229 | 59164374 | H_c_123m05 |
| 16 | 59470173 | 59470258 | H_c_128d19 |
| 16 | 59552352 | 59552585 | H_c_81b02 |
| 16 | 59824165 | 59824242 | H_c_71j07 |
| 16 | 60033161 | 60033345 | H_c_235n20_M |
| 16 | 6008435 | 6011222 | H_c_214c13 |
| 16 | 60504786 | 60504967 | H_c_245o16 |
| 16 | 60626283 | 60628759 | H_c_274n02_M |
| 16 | 60664786 | 60664884 | H_c_189k19 |
| 16 | 60699189 | 60699359 | H_c_226j11 |
| 16 | 60756675 | 60756585 | H_c_258j24 |
| 16 | 60779949 | 60780139 | H_c144f08 |
| 16 | 6215759 | 6215863 | H_c_40k15 |
| 16 | 62208417 | 62210267 | H_c_45c07 |
| 16 | 62629244 | 62629448 | H_c_252e21 |
| 16 | 63185492 | 63185621 | H_c_204g21_M |
| 16 | 631925 | 633340 | H_c_19b12_M |
| 16 | 6346839 | 6347979 | H_c_70o04 |
| 16 | 63712499 | 63715846 | H_c_210m20_M_M |
| 16 | 638747 | 644038 | H_c_63j09_M |

TABLE 1-continued

| | | | |
|---|---|---|---|
| 16 | 6472994 | 6474121 | H_c__190j15 |
| 16 | 64860923 | 64862190 | H_c__272i18 |
| 16 | 65017649 | 65019928 | H_c140o07_M |
| 16 | 65023309 | 65026043 | H_c__121n22 |
| 16 | 65141116 | 65141572 | H_c__268g09_M |
| 16 | 65143779 | 65144530 | H_c__208n13_M |
| 16 | 65169469 | 65171236 | H_c134m13_M |
| 16 | 65195153 | 65198012 | H_c__68b03 |
| 16 | 65287090 | 65288762 | H_c__102c19 |
| 16 | 65342051 | 65343518 | H_c__170f22_M |
| 16 | 65435792 | 65437429 | H_c__20e18_M |
| 16 | 65516968 | 65517656 | H_c__62n12 |
| 16 | 65524740 | 65526357 | H_c__227c21 |
| 16 | 65604621 | 65606644 | H_c__41f03_M |
| 16 | 65619842 | 65621746 | H_c__187e12_M |
| 16 | 65700408 | 65702187 | H_c__194l04 |
| 16 | 65741285 | 65742936 | H_c__144c09_M |
| 16 | 65746733 | 65747831 | H_c140i04_M |
| 16 | 65750478 | 65751767 | H_c__226n06 |
| 16 | 65755593 | 65757881 | H_c__216b12_M |
| 16 | 65765463 | 65767020 | H_c__40g05 |
| 16 | 65775006 | 65775697 | H_c__84p01_M |
| 16 | 65782855 | 65784862 | H_c__192h08_M |
| 16 | 65917031 | 65918601 | H_c__30a10_M |
| 16 | 65983091 | 65987133 | H_c__18j22_M |
| 16 | 66021846 | 66023984 | H_c__204i09_M |
| 16 | 66072465 | 66073322 | H_c__12l06_M |
| 16 | 66077080 | 66077291 | H_c__67b10 |
| 16 | 66153311 | 66155109 | H_c__24j18_M |
| 16 | 66250846 | 66252747 | H_c__208j11 |
| 16 | 66257251 | 66258490 | H_c__242g21 |
| 16 | 66310108 | 66310853 | H_c__74i13_M |
| 16 | 66424341 | 66425330 | H_c__51a12 |
| 16 | 66432951 | 66435013 | H_c__192j23 |
| 16 | 66437866 | 66439225 | H_c__154k20_M |
| 16 | 66463635 | 66465125 | H_c__187o16_M |
| 16 | 66484291 | 66485456 | H_c__27a07_M |
| 16 | 66526398 | 66528917 | H_c__5h05_M |
| 16 | 66612966 | 66615247 | H_c__119e11_M |
| 16 | 66675563 | 66677313 | H_c__51j20_M |
| 16 | 66719558 | 66719729 | H_c__88l13 |
| 16 | 668251 | 670168 | H_c__232c15_M |
| 16 | 66827294 | 66829705 | H_c__252k15_M |
| 16 | 66836749 | 66837255 | H_c__149b02 |
| 16 | 66901652 | 66902937 | H_c134a17_M |
| 16 | 67121163 | 67122508 | H_c__35c15 |
| 16 | 67129722 | 67131804 | H_c__185e18_M |
| 16 | 67233860 | 67237670 | H_c__68b24_M |
| 16 | 67327692 | 67330262 | H_c__192j03_M |
| 16 | 67434956 | 67435616 | H_c__162k09_M |
| 16 | 67506890 | 67507119 | H_c__146h03 |
| 16 | 67564391 | 67565762 | H_c__83i07 |
| 16 | 67656863 | 67657022 | H_c__85c12 |
| 16 | 67697284 | 67699805 | H_c__38e11_M |
| 16 | 67723155 | 67724451 | H_c__87n13_M |
| 16 | 67778144 | 67779502 | H_c__6b14_M |
| 16 | 67902396 | 67903666 | H_c__194f19_M |
| 16 | 67920051 | 67922562 | H_c__125i10_M |
| 16 | 67930460 | 67932032 | H_c__79a04 |
| 16 | 67976745 | 67977943 | H_c__64g18_M |
| 16 | 68015175 | 68016856 | H_c133m24_M |
| 16 | 680192 | 680620 | H_c__28f18_M |
| 16 | 68156883 | 68158635 | H_c__270f24_M |
| 16 | 683498 | 684663 | H_c__72i20_M |
| 16 | 684724 | 686445 | H_c__11m05 |
| 16 | 68841744 | 68843373 | H_c__36o05 |
| 16 | 68880566 | 68881241 | H_c__99e10 |
| 16 | 68938134 | 68938649 | H_c__27h10_M |
| 16 | 68972100 | 68973476 | H_c__7a10_M |
| 16 | 69028712 | 69031287 | H_c__265j02_M |
| 16 | 69045761 | 69046557 | H_c__33l08_M |
| 16 | 69392071 | 69392501 | H_c__11h16_M |
| 16 | 69729458 | 69729620 | H_c__76f22 |
| 16 | 69818283 | 69818450 | H_c__178g02 |
| 16 | 69866803 | 69866926 | H_c__78c05 |
| 16 | 69880130 | 69881214 | H_c__16c24 |
| 16 | 69949658 | 69951391 | H_c__46c12 |
| 16 | 70016018 | 70018336 | H_c__69e18_M |
| 16 | 70031909 | 70034270 | H_c__239m13_M |
| 16 | 70057583 | 70057683 | H_c__125l04 |
| 16 | 70066110 | 70066358 | H_c__37o08_M |
| 16 | 70162347 | 70162417 | H_c__114p14 |
| 16 | 70399721 | 70400300 | H_c__210i12_M |
| 16 | 70436458 | 70438151 | H_c__145e05_M |
| 16 | 70474465 | 70476132 | H_c__64n06_M |
| 16 | 70486401 | 70487263 | H_c__101i04_M |
| 16 | 70599795 | 70600150 | H_c__68h02_M |
| 16 | 70823179 | 70823249 | H_c__55h12 |
| 16 | 70974232 | 70974394 | H_c__118n08_M |
| 16 | 71333392 | 71333579 | H_c__197g18 |
| 16 | 71378532 | 71380242 | H_c__226j04_M |
| 16 | 71638749 | 71639632 | H_c__111b07_M |
| 16 | 71648835 | 71650001 | H_c__81k03_M |
| 16 | 71650009 | 71650487 | H_c__126b11_M |
| 16 | 71654366 | 71654599 | H_c__92b22_M |
| 16 | 71657571 | 71658686 | H_c__191m18_M |
| 16 | 72115261 | 72115505 | H_c__119g07_M |
| 16 | 72170158 | 72170333 | H_c__166o05 |
| 16 | 72268284 | 72268376 | H_c__218f19 |
| 16 | 72297082 | 72297174 | H_c__163g14 |
| 16 | 72307362 | 72307486 | H_c__17e20 |
| 16 | 72645136 | 72645230 | H_c__91d22 |
| 16 | 72888056 | 72889099 | H_c__82f11_M |
| 16 | 7294292 | 7294694 | H_c__7c24 |
| 16 | 7299654 | 7299891 | H_c__252a23 |
| 16 | 730361 | 732059 | H_c__109m18 |
| 16 | 73198541 | 73198718 | H_c__154i13_M |
| 16 | 73291433 | 73292657 | H_c__97h01 |
| 16 | 73316831 | 73319192 | H_c__265n04 |
| 16 | 73365155 | 73366615 | H_c__4e11_M |
| 16 | 73525381 | 73525489 | H_c__122f12 |
| 16 | 73568464 | 73568653 | H_c__66c21 |
| 16 | 73576004 | 73577216 | H_c__160j02 |
| 16 | 73739665 | 73740746 | H_c__92j20 |
| 16 | 73842347 | 73848019 | H_c__65d05_M_M |
| 16 | 73856118 | 73860244 | H_c__238n19_M |
| 16 | 74023950 | 74024981 | H_c__72j20_M |
| 16 | 74054618 | 74056469 | H_c__3b18_M |
| 16 | 74147092 | 74147876 | H_c__62k24_M |
| 16 | 74157193 | 74158818 | H_c__257i21_M |
| 16 | 74214018 | 74214669 | H_c__126p21_M |
| 16 | 74239083 | 74240271 | H_c__200l20_M |
| 16 | 75149134 | 75149251 | H_c__65n13 |
| 16 | 75192651 | 75192780 | H_c139p14 |
| 16 | 75528145 | 75528256 | H_c__32e09 |
| 16 | 75781527 | 75782650 | H_c__6l02_M |
| 16 | 76025823 | 76026692 | H_c__166h21_M |
| 16 | 76102849 | 76103028 | H_c__24d02 |
| 16 | 76313613 | 76314219 | H_c__101l02 |
| 16 | 76379366 | 76380649 | H_c__74g16_M |
| 16 | 76637117 | 76637969 | H_c__247h21_M |
| 16 | 76661635 | 76661719 | H_c__212f15 |
| 16 | 7671043 | 7671164 | H_c__65a10 |
| 16 | 78126562 | 78126703 | H_c__80p07 |
| 16 | 78191237 | 78191834 | H_c131p21 |
| 16 | 78274717 | 78274830 | H_c__211d08 |
| 16 | 78361806 | 78362461 | H_c__168l04_M |
| 16 | 7848102 | 7848221 | H_c__63l15 |
| 16 | 78556491 | 78556618 | H_c__83h14 |
| 16 | 78598350 | 78598507 | H_c__157a21 |
| 16 | 789327 | 792013 | H_c__274d21_M |
| 16 | 79394462 | 79396783 | H_c__82h02 |
| 16 | 79523792 | 79524101 | H_c__152b04_M |
| 16 | 79552416 | 79552681 | H_c__170l04 |
| 16 | 79597307 | 79598827 | H_c__16o01_M |
| 16 | 79626447 | 79627636 | H_c__106j05_M |
| 16 | 79668041 | 79668641 | H_c142h14 |
| 16 | 79686909 | 79688116 | H_c__230c08_M |
| 16 | 797229 | 798279 | H_c__157k10_M |
| 16 | 79905833 | 79907046 | H_c__227m21_M |
| 16 | 80035147 | 80036870 | H_c__77l08_M |
| 16 | 801740 | 804011 | H_c__40b12_M |
| 16 | 80370079 | 80371093 | H_c__16l22_M |
| 16 | 80602251 | 80603009 | H_c__95h14 |
| 16 | 80725087 | 80725614 | H_c__195f21 |
| 16 | 80760802 | 80762373 | H_c__1f14_M |
| 16 | 807620 | 811012 | H_c__185b09_M |
| 16 | 80990398 | 80990543 | H_c__166k01 |
| 16 | 81024219 | 81024873 | H_c__251h21 |
| 16 | 81056996 | 81057159 | H_c__274f17 |

TABLE 1-continued

| | | | |
|---|---|---|---|
| 16 | 81136622 | 81136897 | H_c_71b01 |
| 16 | 81365788 | 81365888 | H_c_3d18 |
| 16 | 81957518 | 81957695 | H_c_78a10 |
| 16 | 82489769 | 82491029 | H_c_209k23_M |
| 16 | 82707495 | 82708644 | H_c_71d14_M |
| 16 | 82735293 | 82736848 | H_c_151j07_M |
| 16 | 82777203 | 82778372 | H_c_114i24 |
| 16 | 82959375 | 82960029 | H_c_190f13 |
| 16 | 83208459 | 83210022 | H_c_108f17_M |
| 16 | 83238455 | 83240974 | H_c_227n07 |
| 16 | 83410336 | 83412697 | H_c_99a19_M |
| 16 | 83602034 | 83603203 | H_c_201c12 |
| 16 | 83618497 | 83620091 | H_c_190f24_M |
| 16 | 83666851 | 83669417 | H_c_15f15 |
| 16 | 84098836 | 84101440 | H_c137e11 |
| 16 | 84144143 | 84146647 | H_c_84g02_M |
| 16 | 84147377 | 84147781 | H_c_86c02_M |
| 16 | 84201648 | 84206877 | H_c_122k06_M_M |
| 16 | 84278665 | 84278801 | H_c_173l22_M |
| 16 | 84389969 | 84391418 | H_c_272f08_M |
| 16 | 84418560 | 84419713 | H_c_234e20_M |
| 16 | 84446271 | 84448103 | H_c_244d12 |
| 16 | 84489560 | 84490511 | H_c_247k12_M |
| 16 | 84513712 | 84513817 | H_c_120c14 |
| 16 | 84538369 | 84539979 | H_c_106n04_M |
| 16 | 8473899 | 8474026 | H_c_268d24_M |
| 16 | 84877385 | 84878789 | H_c_233i10 |
| 16 | 85013331 | 85013502 | H_c_44c22 |
| 16 | 85096266 | 85096937 | H_c_237a08_M |
| 16 | 85099051 | 85107488 | H_c_34b15_M_M |
| 16 | 85154956 | 85155230 | H_c143m23 |
| 16 | 85156514 | 85160019 | H_c_188g18_M |
| 16 | 85469626 | 85470803 | H_c_11o06 |
| 16 | 85653785 | 85654019 | H_c_163b15 |
| 16 | 8571817 | 8572035 | H_c_83a15 |
| 16 | 85802436 | 85802521 | H_c_43f11 |
| 16 | 85908065 | 85908945 | H_c_183m09_M |
| 16 | 85982214 | 85984306 | H_c_82h19_M |
| 16 | 86191239 | 86195835 | H_c_274e24_M |
| 16 | 86367921 | 86371345 | H_c_61h02_M |
| 16 | 86444427 | 86445424 | H_c_31f24 |
| 16 | 86540862 | 86543255 | H_c_29h15_M |
| 16 | 8675657 | 8676689 | H_c_186b11_M |
| 16 | 87024034 | 87025455 | H_c_120f13_M |
| 16 | 87046084 | 87049391 | H_c_72h09_M |
| 16 | 87049393 | 87050049 | H_c_99f24_M |
| 16 | 87126482 | 87129049 | H_c_120m02_M |
| 16 | 87163385 | 87165087 | H_c_215g02_M |
| 16 | 87243218 | 87245261 | H_c_231m14_M |
| 16 | 87255750 | 87257786 | H_c_187o19_M |
| 16 | 87278766 | 87281070 | H_c_30n02_M |
| 16 | 87378409 | 87379889 | H_c_82p03_M |
| 16 | 87397263 | 87398357 | H_c_4p13_M |
| 16 | 87404653 | 87408026 | H_c_12e10_M |
| 16 | 87449579 | 87451480 | H_c_186o07_M |
| 16 | 8753820 | 8753910 | H_c_159n16 |
| 16 | 87559779 | 87561622 | H_c_270n23 |
| 16 | 87687231 | 87688464 | H_c_181e18_M |
| 16 | 87794337 | 87795653 | H_c_267o20_M |
| 16 | 87811202 | 87812304 | H_c131i21_M |
| 16 | 87950143 | 87952031 | H_c_70e07 |
| 16 | 8798283 | 8799529 | H_c_86g24_M |
| 16 | 88083222 | 88085546 | H_c_125f24 |
| 16 | 88101186 | 88102802 | H_c_91k24_M |
| 16 | 88153714 | 88155831 | H_c_124g19 |
| 16 | 88168145 | 88168872 | H_c_214h02_M |
| 16 | 88279235 | 88281297 | H_c_80p19_M |
| 16 | 88363512 | 88365375 | H_c_95a09 |
| 16 | 88393019 | 88393287 | H_c_24o09 |
| 16 | 88421798 | 88423183 | H_c_48h14 |
| 16 | 88466158 | 88468073 | H_c_119b24_M |
| 16 | 88515826 | 88520878 | H_c_29j06_M |
| 16 | 88566301 | 88567182 | H_c_195m17_M |
| 16 | 88612155 | 88613788 | H_c_212c17_M |
| 16 | 8869647 | 8871205 | H_c_124l05_M |
| 16 | 886994 | 888669 | H_c_60c17 |
| 16 | 8964472 | 8965999 | H_c_202l23_M |
| 16 | 9336397 | 9336586 | H_c_32m21 |
| 16 | 969833 | 971743 | H_c_203m19_M |
| 17 | 10041961 | 10043675 | H_c_83o08_M |
| 17 | 1053240 | 1054144 | H_c_121e08_M |
| 17 | 10540997 | 10542091 | H_c_198o19 |
| 17 | 1078744 | 1080239 | H_c_233g07_M |
| 17 | 10898992 | 10900171 | H_c_36p18 |
| 17 | 11104004 | 11104089 | H_c_42j03 |
| 17 | 11238732 | 11238815 | H_c_153j10 |
| 17 | 11442252 | 11442989 | H_c_125j10_M |
| 17 | 11580357 | 11580465 | H_c_179i19 |
| 17 | 11821685 | 11821810 | H_c_78f16 |
| 17 | 11840901 | 11841898 | H_c_173l06_M |
| 17 | 1185710 | 1185847 | H_c_6l17_M |
| 17 | 11864654 | 11865805 | H_c_100a04_M |
| 17 | 12271358 | 12272323 | H_c_165a01 |
| 17 | 12328302 | 12328452 | H_c_158g21 |
| 17 | 12396282 | 12396469 | H_c133k05 |
| 17 | 1249891 | 1250764 | H_c_14i16_M |
| 17 | 12508948 | 12509786 | H_c_62d10 |
| 17 | 12603899 | 12604052 | H_c_37l01 |
| 17 | 12633345 | 12634472 | H_c_233o05 |
| 17 | 12681660 | 12681730 | H_c_24i06 |
| 17 | 12861277 | 12862450 | H_c133f10_M |
| 17 | 1296845 | 1298930 | H_c_201m23 |
| 17 | 13007675 | 13007832 | H_c_83c18 |
| 17 | 1336222 | 1339215 | H_c_14k16_M |
| 17 | 13444280 | 13446783 | H_c_123p18_M |
| 17 | 1366229 | 1367369 | H_c_231d13_M |
| 17 | 13891608 | 13891760 | H_c_196a01 |
| 17 | 13913269 | 13914198 | H_c_217c16_M |
| 17 | 1397417 | 1399627 | H_c_95k07 |
| 17 | 1410850 | 1413131 | H_c_67f15_M |
| 17 | 14144596 | 14146420 | H_c_186e24 |
| 17 | 14153051 | 14154161 | H_c_89o18 |
| 17 | 1454424 | 1456416 | H_c_147i09 |
| 17 | 14699813 | 14699972 | H_c_125e07 |
| 17 | 1498160 | 1500312 | H_c_268h18_M |
| 17 | 15045522 | 15045591 | H_c_84p10 |
| 17 | 15104457 | 15106619 | H_c_80i14_M |
| 17 | 1534371 | 1535273 | H_c_41e24_M |
| 17 | 1559752 | 1561234 | H_c_83p03_M |
| 17 | 15626925 | 15627529 | H_c_101f07 |
| 17 | 1564209 | 1566680 | H_c_129i06_M |
| 17 | 15788524 | 15790218 | H_c_145p14_M |
| 17 | 15843161 | 15844580 | H_c_4n10_M |
| 17 | 15903234 | 15903354 | H_c_159d15 |
| 17 | 16058823 | 16060108 | H_c_252o11_M |
| 17 | 16196903 | 16198014 | H_c_90c16_M |
| 17 | 16283050 | 16283694 | H_c_15a16 |
| 17 | 16308155 | 16309136 | H_c_160i04 |
| 17 | 16334353 | 16336668 | H_c_274o04_M |
| 17 | 16412541 | 16413534 | H_c_1h14_M |
| 17 | 16497522 | 16498274 | H_c_41n06 |
| 17 | 16885990 | 16887619 | H_c_64g04_M |
| 17 | 1696057 | 1696311 | H_c_150c11 |
| 17 | 17048771 | 17051253 | H_c_222d15_M |
| 17 | 17081657 | 17081830 | H_c_187g05_M |
| 17 | 17124142 | 17125485 | H_c_84c24_M |
| 17 | 17146934 | 17148089 | H_c_55b13 |
| 17 | 17196980 | 17198574 | H_c_108o15 |
| 17 | 17276732 | 17276867 | H_c_239g10 |
| 17 | 17284162 | 17285252 | H_c_35a12 |
| 17 | 17302171 | 17302347 | H_c_42k05 |
| 17 | 17339117 | 17341451 | H_c_114i22_M |
| 17 | 17434620 | 17436802 | H_c_224h16 |
| 17 | 17528563 | 17528662 | H_c_251k03 |
| 17 | 17565846 | 17568828 | H_c_242a19_M |
| 17 | 1758205 | 1759130 | H_c_57n13_M |
| 17 | 17592414 | 17592489 | H_c_111g12 |
| 17 | 17625805 | 17627840 | H_c_257e06_M |
| 17 | 17683982 | 17685437 | H_c_158p20 |
| 17 | 1786472 | 1788354 | H_c_148f20_M |
| 17 | 17931568 | 17932707 | H_c_231i02 |
| 17 | 17997762 | 17999860 | H_c_101h08 |
| 17 | 18000484 | 18001672 | H_c_201b10 |
| 17 | 18027495 | 18029209 | H_c_1j22_M |
| 17 | 18102150 | 18107393 | H_c_187b15_M_M |
| 17 | 18159270 | 18159773 | H_c_121n08_M |
| 17 | 18207093 | 18207829 | H_c_8f08_M |
| 17 | 1827773 | 1828218 | H_c_205d23 |
| 17 | 1847805 | 1849756 | H_c143k08_M |
| 17 | 18701772 | 18702673 | H_c_14b10_M |

TABLE 1-continued

| | | | |
|---|---|---|---|
| 17 | 1873840 | 1876390 | H_c_4p16_M |
| 17 | 1880355 | 1880492 | H_c_265m13_M |
| 17 | 18814886 | 18817711 | H_c_208n07 |
| 17 | 18846671 | 18849506 | H_c_270o09_M |
| 17 | 1899043 | 1901455 | H_c_251n13_M |
| 17 | 19206101 | 19206914 | H_c_237h02_M |
| 17 | 19221703 | 19222925 | H_c_100a08_M |
| 17 | 19350857 | 19352184 | H_c_80c18_M |
| 17 | 19376377 | 19378628 | H_c_185c15 |
| 17 | 19423089 | 19424504 | H_c_83b12 |
| 17 | 19491524 | 19493335 | H_c_259j04 |
| 17 | 19507736 | 19508119 | H_c_71d09_M |
| 17 | 19580953 | 19582738 | H_c_167p14 |
| 17 | 19840244 | 19840328 | H_c_62f10 |
| 17 | 19852545 | 19854440 | H_c_28g08_M |
| 17 | 19999542 | 20000769 | H_c_226g22_M |
| 17 | 20432725 | 20433544 | H_c_132h07 |
| 17 | 207254 | 207364 | H_c_5l13 |
| 17 | 20885787 | 20887671 | H_c_186k03 |
| 17 | 20970096 | 20971487 | H_c_2f24_M |
| 17 | 21057380 | 21059135 | H_c_231h09_M |
| 17 | 21094650 | 21097443 | H_c_84a20_M |
| 17 | 21127159 | 21129323 | H_c_129m24_M |
| 17 | 21159118 | 21161295 | H_c_132h05_M |
| 17 | 21221665 | 21223808 | H_c_183j06 |
| 17 | 21394866 | 21395914 | H_c_146k23 |
| 17 | 2153276 | 2154422 | H_c_176o18_M |
| 17 | 21673030 | 21673171 | H_c_118f23 |
| 17 | 22288605 | 22288763 | H_c_122f04 |
| 17 | 22313507 | 22314630 | H_c_54m10 |
| 17 | 2241569 | 2247590 | H_c_271m17_M |
| 17 | 2248773 | 2250488 | H_c_52c12_M |
| 17 | 2250508 | 2252352 | H_c_32g18_M |
| 17 | 22591438 | 22593154 | H_c_115j04 |
| 17 | 22644974 | 22646072 | H_c_253j24_M |
| 17 | 22673431 | 22673637 | H_c_63b06_M |
| 17 | 22700156 | 22701095 | H_c_250b20_M |
| 17 | 22807575 | 22808555 | H_c_274e15_M |
| 17 | 23044658 | 23044766 | H_c_167a18 |
| 17 | 23244131 | 23244935 | H_c_188o01_M |
| 17 | 23392656 | 23393544 | H_c_175b09_M |
| 17 | 23516786 | 23516907 | H_c_203n13 |
| 17 | 2361868 | 2362124 | H_c_36m12_M |
| 17 | 23667714 | 23670744 | H_c_22f08_M |
| 17 | 23698156 | 23698351 | H_c_111g18 |
| 17 | 23708142 | 23709177 | H_c_29n08 |
| 17 | 23731859 | 23733178 | H_c134m18_M |
| 17 | 23756824 | 23757379 | H_c_107a16_M |
| 17 | 23903023 | 23904565 | H_c_128m19 |
| 17 | 23921904 | 23922945 | H_c_60g12_M |
| 17 | 23949568 | 23950784 | H_c_159i06_M |
| 17 | 23995351 | 23996761 | H_c_259m19_M |
| 17 | 24012708 | 24013766 | H_c_183a05_M |
| 17 | 24069903 | 24071015 | H_c_166p01 |
| 17 | 24077665 | 24077978 | H_c_197a08 |
| 17 | 24079621 | 24080518 | H_c_64d23_M |
| 17 | 24094072 | 24095899 | H_c_53a10 |
| 17 | 24103611 | 24105276 | H_c_194i15 |
| 17 | 24193508 | 24194222 | H_c139b21 |
| 17 | 24248199 | 24249181 | H_c_167g08 |
| 17 | 24253499 | 24255142 | H_c_202l21_M |
| 17 | 24300665 | 24303300 | H_c_27d04_M |
| 17 | 24313208 | 24314668 | H_c_110d03 |
| 17 | 24361829 | 24361970 | H_c_79m01 |
| 17 | 2443170 | 2444521 | H_c_212h15_M |
| 17 | 24527505 | 24531934 | H_c_21n06_M |
| 17 | 24740640 | 24741915 | H_c_262o06 |
| 17 | 24875683 | 24875794 | H_c_215k16 |
| 17 | 24917051 | 24919665 | H_c_272g13_M |
| 17 | 24919715 | 24924276 | H_c138e08_M |
| 17 | 24939354 | 24940896 | H_c_210k24_M |
| 17 | 24940916 | 24941378 | H_c131h15_M |
| 17 | 24968998 | 24970403 | H_c_246f06_M |
| 17 | 25112048 | 25112841 | H_c_188a16_M |
| 17 | 25280930 | 25281671 | H_c_12p08_M |
| 17 | 25377713 | 25377892 | H_c_230b03 |
| 17 | 25402038 | 25402216 | H_c_102e09 |
| 17 | 25467699 | 25468081 | H_c_21i19 |
| 17 | 25586448 | 25587483 | H_c_197f02_M |
| 17 | 2560899 | 2561956 | H_c_34o09 |
| 17 | 2561963 | 2562502 | H_c_82p18 |
| 17 | 25642679 | 25643538 | H_c_45e06 |
| 17 | 25729959 | 25731167 | H_c139n22_M |
| 17 | 2598755 | 2600250 | H_c_104a21 |
| 17 | 259998 | 261066 | H_c143a06_M |
| 17 | 26175137 | 26176499 | H_c_28o13_M |
| 17 | 26182912 | 26183794 | H_c_152h14 |
| 17 | 2625696 | 2627735 | H_c_171j08 |
| 17 | 26272944 | 26274166 | H_c_253d08_M |
| 17 | 26320388 | 26320713 | H_c_179i20 |
| 17 | 2639456 | 2641607 | H_c_43e10_M |
| 17 | 26741603 | 26743845 | H_c_197d09_M |
| 17 | 26811395 | 26811583 | H_c_29c02 |
| 17 | 26900276 | 26901874 | H_c_273j16_M |
| 17 | 2702634 | 2705037 | H_c_69c10_M |
| 17 | 27175663 | 27175728 | H_c_268e23 |
| 17 | 27209204 | 27210735 | H_c_167j05 |
| 17 | 27252671 | 27253060 | H_c134i11 |
| 17 | 27267914 | 27269003 | H_c_106a03 |
| 17 | 27493402 | 27494438 | H_c_31e24 |
| 17 | 27616688 | 27618174 | H_c_45c18 |
| 17 | 27700968 | 27702038 | H_c_210f22_M |
| 17 | 27721168 | 27721325 | H_c_12d20_M |
| 17 | 27795308 | 27796486 | H_c_190c08 |
| 17 | 27837185 | 27839717 | H_c_19h13 |
| 17 | 2785657 | 2786004 | H_c_86m03 |
| 17 | 27870254 | 27870970 | H_c_257d06_M |
| 17 | 28173284 | 28173998 | H_c_104d11 |
| 17 | 28278359 | 28279815 | H_c_95e15_M |
| 17 | 2855143 | 2856792 | H_c_28h23 |
| 17 | 2898598 | 2900218 | H_c_233p19 |
| 17 | 29508099 | 29509083 | H_c_191p01_M |
| 17 | 29930465 | 29931645 | H_c_192h16 |
| 17 | 29931648 | 29933258 | H_c_103b13_M |
| 17 | 29976633 | 29978747 | H_c_254g06_M |
| 17 | 30002439 | 30003832 | H_c_36c13 |
| 17 | 30269158 | 30269317 | H_c_186a24 |
| 17 | 30312124 | 30312766 | H_c_265m02 |
| 17 | 30331454 | 30332508 | H_c_200o23_M |
| 17 | 30352354 | 30354250 | H_c_70c09 |
| 17 | 30433397 | 30433486 | H_c_119f11_M |
| 17 | 30439848 | 30441325 | H_c_32f11 |
| 17 | 30470202 | 30471750 | H_c_196h21_M |
| 17 | 30492835 | 30493664 | H_c_35e10_M |
| 17 | 30592780 | 30593469 | H_c_261e11_M |
| 17 | 30725462 | 30725764 | H_c_112f17 |
| 17 | 30733162 | 30733256 | H_c_233c05 |
| 17 | 30811108 | 30812001 | H_c_52g12 |
| 17 | 30937777 | 30937896 | H_c_26e20_M |
| 17 | 31082685 | 31083620 | H_c_53j21 |
| 17 | 31091952 | 31093144 | H_c_148c04_M |
| 17 | 31101170 | 31102110 | H_c_174m21 |
| 17 | 31145917 | 31147330 | H_c_64j05_M |
| 17 | 31160046 | 31161425 | H_c_74e05 |
| 17 | 31911846 | 31913588 | H_c_169l05_M |
| 17 | 31915897 | 31917301 | H_c_23n07_M |
| 17 | 31963879 | 31965635 | H_c_82f20_M |
| 17 | 31974138 | 31976147 | H_c_181f10_M |
| 17 | 32022118 | 32022812 | H_c_1a22 |
| 17 | 32071666 | 32072925 | H_c_98g15 |
| 17 | 32152738 | 32153712 | H_c_81d09 |
| 17 | 32239414 | 32240438 | H_c_125p20_M |
| 17 | 3235867 | 3237001 | H_c_196a03_M |
| 17 | 32365540 | 32370292 | H_c_155c08_M_M |
| 17 | 32380052 | 32381008 | H_c_72f09 |
| 17 | 32789211 | 32790702 | H_c_66k08 |
| 17 | 32923360 | 32924787 | H_c_30h09_M |
| 17 | 32981302 | 32981430 | H_c_45l21 |
| 17 | 33176322 | 33179425 | H_c_125l06_M |
| 17 | 33781652 | 33781739 | H_c_268j24 |
| 17 | 33828060 | 33830365 | H_c_9m23_M |
| 17 | 3385137 | 3387008 | H_c_12j04 |
| 17 | 33862745 | 33864704 | H_c_11g22_M |
| 17 | 33968518 | 33969699 | H_c_78p22_M |
| 17 | 33971212 | 33972744 | H_c142f08_M |
| 17 | 33973157 | 33974456 | H_c_122g16 |
| 17 | 33981927 | 33983039 | H_c_59f10_M |
| 17 | 33988009 | 33989307 | H_c_191c09 |
| 17 | 34015425 | 34016902 | H_c_123m07 |
| 17 | 34082649 | 34085254 | H_c_169d04 |

TABLE 1-continued

| | | | |
|---|---|---|---|
| 17 | 34111744 | 34112951 | H_c_212l24_M |
| 17 | 34139541 | 34141372 | H_c_159h08 |
| 17 | 34157754 | 34159384 | H_c_98m08_M |
| 17 | 34209875 | 34210219 | H_c_75l01 |
| 17 | 34234221 | 34235611 | H_c_78h04 |
| 17 | 34292895 | 34294144 | H_c_117k15 |
| 17 | 34560089 | 34560240 | H_c141h23 |
| 17 | 34607138 | 34607851 | H_c_272f19_M |
| 17 | 34619374 | 34620334 | H_c_85l17 |
| 17 | 34634428 | 34636115 | H_c_190k14_M |
| 17 | 34645608 | 34647370 | H_c_71i21_M |
| 17 | 34810136 | 34812581 | H_c_196m07_M |
| 17 | 3484771 | 3487423 | H_c_89d09_M |
| 17 | 34871281 | 34872960 | H_c_127c13_M |
| 17 | 34983305 | 34984081 | H_c143g02_M |
| 17 | 35014156 | 35014589 | H_c_122j05 |
| 17 | 35027140 | 35027810 | H_c_241n09_M |
| 17 | 35036436 | 35038055 | H_c_57c04_M |
| 17 | 35046180 | 35047271 | H_c_122h09_M |
| 17 | 35109525 | 35110978 | H_c_125a01 |
| 17 | 35139665 | 35140834 | H_c_129p04_M |
| 17 | 3518690 | 3519521 | H_c_181i10 |
| 17 | 35273852 | 35274119 | H_c_33l03_M |
| 17 | 35362646 | 35363079 | H_c_45c14 |
| 17 | 35390117 | 35391247 | H_c_66j24_M |
| 17 | 35419907 | 35421741 | H_c_107b15 |
| 17 | 35425396 | 35426774 | H_c_117d06 |
| 17 | 3544803 | 3546488 | H_c_16l13_M |
| 17 | 35530994 | 35533171 | H_c_69p10_M |
| 17 | 35549757 | 35551054 | H_c_164a12_M |
| 17 | 35600911 | 35601914 | H_c_59n14 |
| 17 | 35628880 | 35629600 | H_c_258p14_M |
| 17 | 35727894 | 35728532 | H_c_234i14 |
| 17 | 3573487 | 3575044 | H_c131f11_M |
| 17 | 35750521 | 35752764 | H_c_29l03_M |
| 17 | 36057080 | 36058421 | H_c_119j22_M |
| 17 | 36228526 | 36229005 | H_c_90p20_M |
| 17 | 36936068 | 36938408 | H_c_120e02_M |
| 17 | 3695504 | 3696729 | H_c_185f21_M |
| 17 | 37075651 | 37077447 | H_c_50c01 |
| 17 | 37098147 | 37099541 | H_c_65f24_M |
| 17 | 37142269 | 37145033 | H_c_63i19_M |
| 17 | 37194775 | 37197224 | H_c_266k02 |
| 17 | 37245295 | 37246656 | H_c_110f24 |
| 17 | 37274148 | 37275225 | H_c_247g05 |
| 17 | 37327713 | 37329221 | H_c_269b19_M |
| 17 | 37372024 | 37374748 | H_c_54n03_M |
| 17 | 37422517 | 37426657 | H_c_208c16_M |
| 17 | 3742929 | 3743870 | H_c136j08 |
| 17 | 37444083 | 37447211 | H_c_50n18_M |
| 17 | 37455399 | 37457012 | H_c_206i02 |
| 17 | 37477927 | 37478994 | H_c_36h01_M |
| 17 | 37502760 | 37505171 | H_c_250g04_M |
| 17 | 37585042 | 37587069 | H_c131g04_M |
| 17 | 37589165 | 37591781 | H_c_76k14_M |
| 17 | 37681525 | 37683841 | H_c_199e10_M |
| 17 | 37693594 | 37695921 | H_c_95b21_M |
| 17 | 37793189 | 37794403 | H_c135i16 |
| 17 | 37828190 | 37829413 | H_c138b06_M |
| 17 | 37864194 | 37864719 | H_c_85b09_M |
| 17 | 37937548 | 37937967 | H_c_44j22_M |
| 17 | 37941416 | 37943571 | H_c_5i09 |
| 17 | 37959464 | 37960579 | H_c_181n06_M |
| 17 | 37972060 | 37973003 | H_c_193o21_M |
| 17 | 37982631 | 37983567 | H_c_146k16_M |
| 17 | 38015128 | 38016338 | H_c_269l23 |
| 17 | 38064275 | 38065337 | H_c_108g08_M |
| 17 | 38149480 | 38151123 | H_c139i04_M |
| 17 | 38182134 | 38182321 | H_c_89l20 |
| 17 | 38185401 | 38187096 | H_c_24f09_M |
| 17 | 38188920 | 38191403 | H_c_39o10_M |
| 17 | 38203928 | 38206014 | H_c_178a07_M |
| 17 | 38228588 | 38230200 | H_c_59a03 |
| 17 | 38238183 | 38239876 | H_c_68f05_M |
| 17 | 38385983 | 38387057 | H_c_59j20_M |
| 17 | 38427152 | 38428007 | H_c_121g14 |
| 17 | 38430204 | 38431855 | H_c_20g05 |
| 17 | 3854654 | 3855477 | H_c_42j12 |
| 17 | 38793669 | 38794265 | H_c_241m19_M |
| 17 | 38820256 | 38822367 | H_c_74k16_M |
| 17 | 38831752 | 38832410 | H_c_72l19_M |
| 17 | 38916540 | 38916755 | H_c_69i23 |
| 17 | 38977470 | 38979805 | H_c_261f02 |
| 17 | 39028856 | 39029038 | H_c_162i06 |
| 17 | 39078646 | 39079551 | H_c_170a22_M |
| 17 | 39085317 | 39085543 | H_c_42c08 |
| 17 | 39146608 | 39147406 | H_c_57c07_M |
| 17 | 39153352 | 39154418 | H_c142h07 |
| 17 | 39187899 | 39188925 | H_c_190m13_M |
| 17 | 39212115 | 39212387 | H_c_74c21 |
| 17 | 39264461 | 39266905 | H_c_25g11_M |
| 17 | 39332546 | 39334232 | H_c_200f22 |
| 17 | 39339767 | 39340457 | H_c_99l17_M |
| 17 | 39416125 | 39417735 | H_c_160d12_M |
| 17 | 39437493 | 39439817 | H_c_262j13 |
| 17 | 39555643 | 39556707 | H_c_153m07_M |
| 17 | 39574804 | 39576248 | H_c_194k10_M |
| 17 | 39619781 | 39620049 | H_c_19k20 |
| 17 | 39651318 | 39655690 | H_c_114f17_M |
| 17 | 39747343 | 39749374 | H_c_93d15_M |
| 17 | 39756849 | 39759785 | H_c_10k11_M |
| 17 | 39786110 | 39788419 | H_c_186b06_M |
| 17 | 39794700 | 39797364 | H_c_264f22 |
| 17 | 39817558 | 39819430 | H_c_273i04_M |
| 17 | 3992435 | 3994421 | H_c_208n04_M |
| 17 | 39935619 | 39936788 | H_c_252a16_M |
| 17 | 39990104 | 39992360 | H_c_65o16_M |
| 17 | 40006326 | 40006474 | H_c_204f19 |
| 17 | 40088691 | 40090086 | H_c_4g15_M |
| 17 | 40141564 | 40141775 | H_c_118f22 |
| 17 | 40206789 | 40209283 | H_c_238e20 |
| 17 | 40262345 | 40263770 | H_c_170i02_M |
| 17 | 40331010 | 40332201 | H_c_16k15 |
| 17 | 40343175 | 40344778 | H_c_126h09_M |
| 17 | 40380340 | 40380944 | H_c_50f03 |
| 17 | 40441428 | 40441610 | H_c_240g15 |
| 17 | 40483869 | 40485233 | H_c_157n01_M |
| 17 | 40548643 | 40548727 | H_c_228b19 |
| 17 | 40552443 | 40554804 | H_c_4h09_M |
| 17 | 40576289 | 40578250 | H_c_53c05 |
| 17 | 40582319 | 40583555 | H_c_204p14_M |
| 17 | 40594036 | 40594762 | H_c_83p06 |
| 17 | 40653761 | 40655646 | H_c_81g02_M |
| 17 | 40680451 | 40682263 | H_c_39e03 |
| 17 | 41018332 | 41020068 | H_c_269k02_M |
| 17 | 4113268 | 4114204 | H_c_242m23_M |
| 17 | 41283714 | 41285651 | H_c_73i15 |
| 17 | 41625825 | 41627468 | H_c_204o08_M |
| 17 | 41699802 | 41700200 | H_c_58g02_M |
| 17 | 4215313 | 4217032 | H_c_7m16_M |
| 17 | 42192503 | 42192650 | H_c_155f06_M |
| 17 | 42204583 | 42204853 | H_c_6j02_M |
| 17 | 42283336 | 42283920 | H_c131j24_M |
| 17 | 42410745 | 42412106 | H_c_191b16_M |
| 17 | 42430556 | 42430765 | H_c137f07_M |
| 17 | 42621038 | 42622013 | H_c_91i15_M |
| 17 | 42755761 | 42756987 | H_c_39c10_M |
| 17 | 42855759 | 42857161 | H_c_246b16_M |
| 17 | 43047992 | 43048083 | H_c_223f21 |
| 17 | 43081656 | 43083338 | H_c_24e08_M |
| 17 | 43125916 | 43127156 | H_c_149e03_M |
| 17 | 43166269 | 43167738 | H_c_204j11 |
| 17 | 43210465 | 43211210 | H_c_214k19 |
| 17 | 43221629 | 43222907 | H_c_109l21 |
| 17 | 43263581 | 43265072 | H_c_188a22 |
| 17 | 43272982 | 43273937 | H_c140n19_M |
| 17 | 43281756 | 43283600 | H_c_80d24_M |
| 17 | 43328495 | 43329090 | H_c_18k08_M |
| 17 | 4335034 | 4336867 | H_c_122n21 |
| 17 | 43417756 | 43419242 | H_c_244f08 |
| 17 | 43454040 | 43456711 | H_c_50l18_M |
| 17 | 43457397 | 43458364 | H_c_63j11_M |
| 17 | 43468758 | 43470971 | H_c_38i21_M |
| 17 | 43479875 | 43480887 | H_c_173b14_M |
| 17 | 43532811 | 43533966 | H_c_100f21_M |
| 17 | 43539486 | 43540337 | H_c_100o19_M |
| 17 | 43862319 | 43863051 | H_c_106d06_M |
| 17 | 43975295 | 43975681 | H_c_121j16_M |
| 17 | 43996116 | 43997310 | H_c_237c24 |
| 17 | 44013600 | 44014848 | H_c_247m19 |

TABLE 1-continued

| | | | |
|---|---|---|---|
| 17 | 44017532 | 44018984 | H_c_239m07_M |
| 17 | 44025304 | 44026063 | H_c_62c05_M |
| 17 | 44026119 | 44026646 | H_c_121k17 |
| 17 | 44029716 | 44030926 | H_c_79o21_M |
| 17 | 44034431 | 44035501 | H_c_254a21 |
| 17 | 44042594 | 44043766 | H_c_109c18 |
| 17 | 44045317 | 44047396 | H_c_41n12_M |
| 17 | 44049739 | 44051953 | H_c_107g07_M |
| 17 | 44057103 | 44059337 | H_c_37a08_M |
| 17 | 44074745 | 44075452 | H_c_185a12 |
| 17 | 44078821 | 44080163 | H_c_224a20_M |
| 17 | 44151546 | 44151999 | H_c_5b21_M |
| 17 | 44155816 | 44156499 | H_c_226k08 |
| 17 | 44165506 | 44167230 | H_c_190i19 |
| 17 | 44182026 | 44182943 | H_c_240j09 |
| 17 | 44187116 | 44188088 | H_c_217e12_M |
| 17 | 44249575 | 44249896 | H_c_85p22_M |
| 17 | 44324073 | 44325340 | H_c_15o07 |
| 17 | 44376960 | 44377568 | H_c_249e19 |
| 17 | 44404155 | 44406445 | H_c_243g08 |
| 17 | 44429041 | 44431246 | H_c_71e20_M |
| 17 | 44436206 | 44436495 | H_c_181p10_M |
| 17 | 44564924 | 44565308 | H_c_153f21_M |
| 17 | 44624319 | 44624874 | H_c_41o22_M |
| 17 | 44792847 | 44795102 | H_c_28b04_M |
| 17 | 44870836 | 44872774 | H_c_114c05 |
| 17 | 44929383 | 44930376 | H_c_204e11_M |
| 17 | 44986870 | 44989409 | H_c_52d07 |
| 17 | 45001112 | 45003711 | H_c_183h10_M |
| 17 | 45007980 | 45009314 | H_c_176p05_M |
| 17 | 45109797 | 45110779 | H_c_257h22_M |
| 17 | 45195655 | 45196976 | H_c_183i05_M |
| 17 | 45283187 | 45283879 | H_c_123e17_M |
| 17 | 45332946 | 45334606 | H_c_119p22 |
| 17 | 45342272 | 45343278 | H_c_91e21_M |
| 17 | 45401712 | 45403317 | H_c_118l19_M |
| 17 | 45424585 | 45429897 | H_c_186h18_M |
| 17 | 45488311 | 45489087 | H_c_18a09 |
| 17 | 45527564 | 45528057 | H_c_228j13 |
| 17 | 4553566 | 4554402 | H_c_262n04_M |
| 17 | 45581983 | 45584147 | H_c_161i16_M |
| 17 | 45592890 | 45594743 | H_c_129g05_M |
| 17 | 45631301 | 45632359 | H_c_103m07_M |
| 17 | 45778012 | 45779337 | H_c_81d03_M |
| 17 | 45805174 | 45805931 | H_c134d03 |
| 17 | 4580948 | 4582031 | H_c135b19 |
| 17 | 45829472 | 45830201 | H_c_58n06 |
| 17 | 45856811 | 45858579 | H_c_19b21_M |
| 17 | 4588219 | 4590270 | H_c_44m13 |
| 17 | 45910862 | 45911648 | H_c_110i02 |
| 17 | 45940288 | 45941465 | H_c_28k08_M |
| 17 | 45990706 | 45994874 | H_c_236f22_M |
| 17 | 46066889 | 46068469 | H_c_179j22 |
| 17 | 46139531 | 46141129 | H_c_196e09_M |
| 17 | 46145564 | 46147321 | H_c_265e07 |
| 17 | 46152126 | 46152479 | H_c_187k19_M |
| 17 | 46185240 | 46185370 | H_c_73o10 |
| 17 | 46213334 | 46213987 | H_c_1h15 |
| 17 | 46297738 | 46299686 | H_c_157d20_M |
| 17 | 46338072 | 46338332 | H_c_229k09 |
| 17 | 46363716 | 46364399 | H_c_239f05_M |
| 17 | 46376403 | 46378262 | H_c_176p12_M |
| 17 | 4638943 | 4640606 | H_c_157j14 |
| 17 | 46490927 | 46491071 | H_c_92h18 |
| 17 | 4656728 | 4659104 | H_c_60n20 |
| 17 | 46585820 | 46586697 | H_c_212f21 |
| 17 | 46598399 | 46599758 | H_c_208f16_M |
| 17 | 46692378 | 46693761 | H_c_8i16_M |
| 17 | 4682641 | 4684616 | H_c_13n06_M |
| 17 | 47391074 | 47391161 | H_c_94d19 |
| 17 | 47409841 | 47410020 | H_c_239g22 |
| 17 | 4742328 | 4745086 | H_c_25o09_M |
| 17 | 47440467 | 47440621 | H_c_103k14 |
| 17 | 4745133 | 4746671 | H_c_259n09 |
| 17 | 47589508 | 47591434 | H_c_129k21_M |
| 17 | 4783585 | 4784501 | H_c_37a02 |
| 17 | 4792956 | 4795796 | H_c_55n16_M |
| 17 | 4811334 | 4811828 | H_c_155d17_M |
| 17 | 4830350 | 4831729 | H_c_42g10 |
| 17 | 48309407 | 48309570 | H_c_167i09 |
| 17 | 4840120 | 4843436 | H_c_10a01_M |
| 17 | 4874547 | 4876046 | H_c_202c08_M |
| 17 | 4922103 | 4922964 | H_c_169g06 |
| 17 | 4940941 | 4942079 | H_c_60e05_M |
| 17 | 4955299 | 4956414 | H_c_89c12_M |
| 17 | 4959491 | 4960820 | H_c_207e21 |
| 17 | 4969535 | 4972349 | H_c_182g24_M |
| 17 | 50300953 | 50301093 | H_c_231p20 |
| 17 | 50332725 | 50334038 | H_c_11o08_M |
| 17 | 5035192 | 5036577 | H_c_42a01 |
| 17 | 50670528 | 50671550 | H_c_232f17_M |
| 17 | 50697038 | 50698174 | H_c_14g22_M |
| 17 | 50853151 | 50854626 | H_c_89h21_M |
| 17 | 51182366 | 51183840 | H_c_256h04_M |
| 17 | 5125830 | 5126905 | H_c_200d14_M |
| 17 | 51328055 | 51328216 | H_c_25d15 |
| 17 | 51577590 | 51577754 | H_c_204p08 |
| 17 | 52024608 | 52026032 | H_c_86i07_M |
| 17 | 52026034 | 52027462 | H_c_264j05_M |
| 17 | 52037303 | 52037467 | H_c_99m03 |
| 17 | 52080063 | 52080163 | H_c_73k16 |
| 17 | 52212390 | 52213009 | H_c_210i01_M |
| 17 | 52265289 | 52266509 | H_c_15k22 |
| 17 | 52266510 | 52267699 | H_c_46a23_M |
| 17 | 52329323 | 52329475 | H_c_83o06 |
| 17 | 52345420 | 52346864 | H_c_270j19 |
| 17 | 52392402 | 52393630 | H_c_122d18 |
| 17 | 52477742 | 52479008 | H_c_8m17_M |
| 17 | 52517113 | 52518867 | H_c_240a18_M |
| 17 | 52688067 | 52689629 | H_c_99d09 |
| 17 | 52719508 | 52721583 | H_c_47n17_M |
| 17 | 53293609 | 53294852 | H_c_69d06_M |
| 17 | 53306116 | 53307570 | H_c_47j11_M |
| 17 | 53348372 | 53348464 | H_c_13e22 |
| 17 | 53420323 | 53421656 | H_c_162o09 |
| 17 | 53438633 | 53439844 | H_c_65i12_M |
| 17 | 53439864 | 53440229 | H_c_231e04 |
| 17 | 5344266 | 5345419 | H_c_266o11 |
| 17 | 53515549 | 53517059 | H_c_9o20 |
| 17 | 53589207 | 53590483 | H_c_20m02 |
| 17 | 53650512 | 53652243 | H_c_165g01_M |
| 17 | 53681272 | 53682661 | H_c_223i02_M |
| 17 | 53756638 | 53757810 | H_c_159c05 |
| 17 | 53784340 | 53785111 | H_c_160o13 |
| 17 | 53919614 | 53921220 | H_c_200b14_M |
| 17 | 53946585 | 53947384 | H_c_22o02_M |
| 17 | 53962935 | 53967531 | H_c_171k21_M |
| 17 | 54008427 | 54008503 | H_c_62o17 |
| 17 | 54124665 | 54125406 | H_c_7a07 |
| 17 | 54187940 | 54188258 | H_c_117g09_M |
| 17 | 54188259 | 54188823 | H_c_39k23 |
| 17 | 54516562 | 54516657 | H_c_46b18 |
| 17 | 54538066 | 54539314 | H_c_160h09_M |
| 17 | 54586479 | 54587342 | H_c_198n24_M |
| 17 | 54641418 | 54642916 | H_c_262i10_M |
| 17 | 54652065 | 54652823 | H_c_274p21_M |
| 17 | 54763380 | 54764846 | H_c_88o08_M |
| 17 | 54997263 | 54998182 | H_c_164b05_M |
| 17 | 55051665 | 55052380 | H_c_83d11_M |
| 17 | 55119339 | 55119416 | H_c_232j19 |
| 17 | 55138781 | 55140449 | H_c_214f21 |
| 17 | 55396354 | 55397128 | H_c_123o05_M |
| 17 | 55581542 | 55583145 | H_c_7f13_M |
| 17 | 55788075 | 55788239 | H_c_16h02 |
| 17 | 55823274 | 55824923 | H_c_182b18 |
| 17 | 55853456 | 55854195 | H_c_99j13_M |
| 17 | 55957852 | 55958759 | H_c_71c13_M |
| 17 | 56032035 | 56033576 | H_c_213o08 |
| 17 | 5615028 | 5616456 | H_c_119g23_M |
| 17 | 564200 | 565657 | H_c_209e04 |
| 17 | 56828610 | 56833273 | H_c_117g14_M_M |
| 17 | 56841362 | 56845404 | H_c_10g02_M |
| 17 | 56882566 | 56889478 | H_c_195a16_M_M |
| 17 | 57359801 | 57360335 | H_c_267k09 |
| 17 | 57496982 | 57497805 | H_c_106p12 |
| 17 | 5798224 | 5798410 | H_c_11c21 |
| 17 | 58057609 | 58059150 | H_c_194e22 |
| 17 | 58083366 | 58084598 | H_c_175e22 |
| 17 | 581841 | 583734 | H_c_186o20 |
| 17 | 58239260 | 58239743 | H_c_15l16 |

TABLE 1-continued

| | | | |
|---|---|---|---|
| 17 | 58288960 | 58289103 | H_c__30h21 |
| 17 | 58380762 | 58380867 | H_c__31h16 |
| 17 | 58763941 | 58764036 | H_c__207o02 |
| 17 | 58865763 | 58867458 | H_c__128a23__M |
| 17 | 58876510 | 58878536 | H_c__150h15 |
| 17 | 58906793 | 58909379 | H_c__182d23 |
| 17 | 58953307 | 58954758 | H_c__19o24__M |
| 17 | 58968889 | 58969924 | H_c__168b14 |
| 17 | 58981406 | 58982078 | H_c__55l18__M |
| 17 | 59031656 | 59032692 | H_c__119i19__M |
| 17 | 59052369 | 59054352 | H_c__81e13__M |
| 17 | 59172695 | 59173823 | H_c133c16__M |
| 17 | 5918234 | 5920670 | H_c__188h09 |
| 17 | 59204258 | 59206227 | H_c__83a11__M |
| 17 | 59257419 | 59259192 | H_c__33f07 |
| 17 | 59272376 | 59274417 | H_c__215k08__M |
| 17 | 59428725 | 59430419 | H_c__80k06 |
| 17 | 59435639 | 59436803 | H_c__173j24 |
| 17 | 59494869 | 59496112 | H_c__81i22 |
| 17 | 59577196 | 59577912 | H_c__104h20__M |
| 17 | 59589755 | 59589955 | H_c__174c19 |
| 17 | 59667830 | 59667903 | H_c__41k08 |
| 17 | 59693700 | 59694518 | H_c__92b13 |
| 17 | 59781167 | 59781371 | H_c__58g16 |
| 17 | 59923616 | 59923911 | H_c__30l01__M |
| 17 | 59931615 | 59934075 | H_c__68j10__M |
| 17 | 601749 | 603587 | H_c__71g05__M |
| 17 | 60345281 | 60347385 | H_c__41c18__M |
| 17 | 60364855 | 60364933 | H_c__174l24 |
| 17 | 60414460 | 60415623 | H_c__122k09 |
| 17 | 60482856 | 60484173 | H_c__213b08__M |
| 17 | 60549608 | 60550218 | H_c__245h12 |
| 17 | 60610588 | 60610780 | H_c__102f13 |
| 17 | 60654338 | 60655576 | H_c__189h14__M |
| 17 | 60678986 | 60679158 | H_c__237n16 |
| 17 | 60833945 | 60834070 | H_c__19g02 |
| 17 | 60985892 | 60988327 | H_c__123m03__M |
| 17 | 61297755 | 61297924 | H_c__226e10 |
| 17 | 61357558 | 61357695 | H_c__247a01__M |
| 17 | 61397322 | 61397559 | H_c__42n21 |
| 17 | 61548257 | 61548405 | H_c__206c08 |
| 17 | 61566981 | 61567708 | H_c__103b06 |
| 17 | 61573236 | 61573336 | H_c__79j16 |
| 17 | 61728392 | 61730284 | H_c__251k12__M |
| 17 | 61728462 | 61730240 | H_c__266n14__M |
| 17 | 62213284 | 62214750 | H_c__116f10 |
| 17 | 62261370 | 62262565 | H_c__259n02__M |
| 17 | 62390835 | 62392853 | H_c__238l21 |
| 17 | 62670860 | 62673148 | H_c__92b02__M |
| 17 | 62720925 | 62722274 | H_c__7b18 |
| 17 | 62792737 | 62793508 | H_c__240f19__M |
| 17 | 62803762 | 62805817 | H_c__104e12__M |
| 17 | 6287520 | 6290224 | H_c__33e10__M |
| 17 | 631918 | 632745 | H_c__57c19 |
| 17 | 63422195 | 63422436 | H_c131e05__M |
| 17 | 63446368 | 63446686 | H_c__259o08 |
| 17 | 63462086 | 63462639 | H_c__145m12__M |
| 17 | 63462642 | 63462874 | H_c__259n07__M |
| 17 | 63798924 | 63800420 | H_c__45j03__M |
| 17 | 6382474 | 6382636 | H_c__154o16__M |
| 17 | 63939006 | 63939318 | H_c__77h20 |
| 17 | 63964347 | 63965765 | H_c__207p13__M |
| 17 | 6399147 | 6401183 | H_c131n24__M |
| 17 | 64018982 | 64021015 | H_c__182k14__M |
| 17 | 64107556 | 64109213 | H_c__199l23__M |
| 17 | 64166287 | 64166436 | H_c__184m14__M |
| 17 | 64396801 | 64397023 | H_c__87d10 |
| 17 | 64603327 | 64603449 | H_c__208a12 |
| 17 | 64834302 | 64835314 | H_c__190i16__M |
| 17 | 6484819 | 6485417 | H_c137k08 |
| 17 | 65089064 | 65089775 | H_c__21c23 |
| 17 | 65328459 | 65330615 | H_c__195i23 |
| 17 | 65443609 | 65443879 | H_c__84o19 |
| 17 | 6547808 | 6550034 | H_c__196m02 |
| 17 | 6556091 | 6558797 | H_c__179o19__M |
| 17 | 65676348 | 65677784 | H_c__268c06__M |
| 17 | 65896183 | 65896357 | H_c__124f01__M |
| 17 | 66022020 | 66022163 | H_c__219o10 |
| 17 | 66954852 | 66955033 | H_c__176i23 |
| 17 | 67287654 | 67287766 | H_c__207e05 |
| 17 | 67624370 | 67626554 | H_c__9n16__M |
| 17 | 67940736 | 67941013 | H_c__87e08 |
| 17 | 68047983 | 68048526 | H_c131h17 |
| 17 | 68099053 | 68101205 | H_c__114f04__M |
| 17 | 6839214 | 6840628 | H_c__38k02__M |
| 17 | 6856178 | 6859329 | H_c__205g14__M |
| 17 | 6865884 | 6868387 | H_c__148e02__M |
| 17 | 68672528 | 68674335 | H_c__252n10__M |
| 17 | 68739381 | 68740317 | H_c__104p03__M |
| 17 | 6879732 | 6881048 | H_c__101j09__M |
| 17 | 68818770 | 68820598 | H_c__44p11__M |
| 17 | 69307173 | 69307376 | H_c__183b17 |
| 17 | 69409282 | 69409738 | H_c134l23 |
| 17 | 69459864 | 69462741 | H_c__54d02 |
| 17 | 6965430 | 6966231 | H_c__26f18 |
| 17 | 69660755 | 69662445 | H_c__202h19 |
| 17 | 69711385 | 69711624 | H_c141n15 |
| 17 | 69719519 | 69722221 | H_c__19o09__M |
| 17 | 69728102 | 69730858 | H_c__182i14 |
| 17 | 69832836 | 69834475 | H_c__169g10__M |
| 17 | 69863529 | 69865831 | H_c__155f11__M |
| 17 | 69953638 | 69955160 | H_c__117b13__M |
| 17 | 69961639 | 69963098 | H_c__258j05 |
| 17 | 70145682 | 70145848 | H_c__191c17 |
| 17 | 70255730 | 70258132 | H_c__199c08 |
| 17 | 70283819 | 70284486 | H_c__27n08__M |
| 17 | 70350112 | 70351969 | H_c133f02__M |
| 17 | 70366928 | 70369779 | H_c__234p06__M |
| 17 | 70379892 | 70380855 | H_c__179b03 |
| 17 | 70443460 | 70444595 | H_c__35g14__M |
| 17 | 70489933 | 70491126 | H_c__246b20__M |
| 17 | 70494980 | 70496977 | H_c__77b07 |
| 17 | 70519421 | 70521123 | H_c__22a24 |
| 17 | 70541197 | 70542757 | H_c__101k11__M |
| 17 | 70554283 | 70557897 | H_c__154k12__M |
| 17 | 7058624 | 7058948 | H_c__192l12__M |
| 17 | 70594614 | 70597064 | H_c__227m05 |
| 17 | 70616687 | 70618824 | H_c__197h10__M |
| 17 | 7063802 | 7064827 | H_c__115j07__M |
| 17 | 70638681 | 70640227 | H_c__227h16__M |
| 17 | 70661748 | 70662627 | H_c__113d08__M |
| 17 | 70689909 | 70691608 | H_c__47j01__M |
| 17 | 70768445 | 70770106 | H_c__155e12__M |
| 17 | 7077487 | 7078587 | H_c__254o02 |
| 17 | 70778251 | 70779600 | H_c__29i05__M |
| 17 | 70796527 | 70797093 | H_c134a20 |
| 17 | 7081687 | 7084208 | H_c__86d23__M |
| 17 | 7085953 | 7087247 | H_c__52i22__M |
| 17 | 70912723 | 70913731 | H_c__43b04__M |
| 17 | 7094964 | 7096478 | H_c__126c19__M |
| 17 | 70963972 | 70965413 | H_c__100h13__M |
| 17 | 71030855 | 71034347 | H_c__224h13__M |
| 17 | 71174750 | 71175351 | H_c__109n20__M |
| 17 | 7125211 | 7126829 | H_c__248g09__M |
| 17 | 71261120 | 71262137 | H_c__181h02__M |
| 17 | 71272361 | 71273786 | H_c__3k19__M |
| 17 | 71363402 | 71364004 | H_c__257e07__M |
| 17 | 7137381 | 7140829 | H_c__72b09__M |
| 17 | 71383799 | 71387194 | H_c136f16__M |
| 17 | 71403471 | 71404652 | H_c144h21__M |
| 17 | 71404658 | 71405247 | H_c__256c17 |
| 17 | 71412056 | 71412962 | H_c__222c15__M |
| 17 | 71448099 | 71448871 | H_c__81m12 |
| 17 | 71486392 | 71487467 | H_c131k05__M |
| 17 | 7151446 | 7152820 | H_c__236g22 |
| 17 | 71579611 | 71580873 | H_c__211o10__M |
| 17 | 71583855 | 71585181 | H_c__235b05__M |
| 17 | 71592426 | 71594612 | H_c__238m15 |
| 17 | 71610576 | 71612812 | H_c__157k09 |
| 17 | 71629221 | 71630777 | H_c__92e03__M |
| 17 | 71648966 | 71649644 | H_c__35i04 |
| 17 | 71691327 | 71691430 | H_c__238f24 |
| 17 | 7173145 | 7174026 | H_c__76i04 |
| 17 | 71747038 | 71748743 | H_c139p11__M |
| 17 | 71772477 | 71774288 | H_c__202e24 |
| 17 | 71860608 | 71861930 | H_c__121k06__M |
| 17 | 71889765 | 71891184 | H_c__11d09__M |
| 17 | 7195499 | 7196176 | H_c__249e22 |
| 17 | 71959846 | 71961182 | H_c__207k17 |
| 17 | 72008712 | 72010524 | H_c__112d14__M |

TABLE 1-continued

| | | | |
|---|---|---|---|
| 17 | 72030702 | 72032998 | H_c_162j15_M |
| 17 | 72065664 | 72065883 | H_c_111d23_M |
| 17 | 72092595 | 72094400 | H_c_100p23 |
| 17 | 72233562 | 72234282 | H_c_11b14_M |
| 17 | 72244173 | 72245733 | H_c_11i23_M |
| 17 | 7224674 | 7225536 | H_c_64m06 |
| 17 | 72347605 | 72349831 | H_c_168k21 |
| 17 | 72361254 | 72361362 | H_c_23c12 |
| 17 | 72476498 | 72477505 | H_c_205n09 |
| 17 | 7248715 | 7250128 | H_c_97c05_M |
| 17 | 72541702 | 72542519 | H_c142h03 |
| 17 | 72788300 | 72789805 | H_c_44p06_M |
| 17 | 72793435 | 72795927 | H_c_238n10 |
| 17 | 72880085 | 72880558 | H_c_47m04_M |
| 17 | 7288957 | 7289691 | H_c_185g24_M |
| 17 | 73036127 | 73037118 | H_c_214a23_M |
| 17 | 7323203 | 7324330 | H_c_159j10_M |
| 17 | 7328216 | 7329179 | H_c_174i24_M |
| 17 | 73465420 | 73467194 | H_c_72l05_M |
| 17 | 73656053 | 73656158 | H_c_57d04 |
| 17 | 73674535 | 73677807 | H_c_48e18_M |
| 17 | 73694752 | 73694974 | H_c_103e11_M |
| 17 | 73739379 | 73739947 | H_c_41f08 |
| 17 | 73761820 | 73762846 | H_c137n06_M |
| 17 | 73821454 | 73822370 | H_c_31c03 |
| 17 | 73886137 | 73886797 | H_c_64h12 |
| 17 | 7392632 | 7394044 | H_c_98k18_M |
| 17 | 7405620 | 7406408 | H_c_71l04 |
| 17 | 7416028 | 7417932 | H_c_209p04_M |
| 17 | 7426539 | 7428228 | H_c_81f13_M |
| 17 | 74289024 | 74291272 | H_c_262m07 |
| 17 | 7432374 | 7433736 | H_c_102n16_M |
| 17 | 74347400 | 74348993 | H_c_99f16_M |
| 17 | 74472622 | 74474721 | H_c_96i15 |
| 17 | 74515649 | 74518093 | H_c_145a03_M |
| 17 | 7458145 | 7459472 | H_c_57f10_M |
| 17 | 74582240 | 74584245 | H_c_212e21 |
| 17 | 74689544 | 74693356 | H_c_225n13_M |
| 17 | 7532258 | 7533787 | H_c_237c03_M |
| 17 | 75329737 | 75330885 | H_c_151b05 |
| 17 | 75335733 | 75337401 | H_c_254h08 |
| 17 | 75365909 | 75367191 | H_c_194b14_M |
| 17 | 75377561 | 75381690 | H_c_53m01_M_M |
| 17 | 75389175 | 75390169 | H_c_97e16 |
| 17 | 75392263 | 75393137 | H_c_77f02_M |
| 17 | 75398317 | 75400660 | H_c_190a23_M |
| 17 | 75420302 | 75420766 | H_c_147e14 |
| 17 | 75431374 | 75433709 | H_c_18e19_M |
| 17 | 7560883 | 7562090 | H_c_207k06 |
| 17 | 75689464 | 75691271 | H_c_254k16_M |
| 17 | 75734436 | 75735472 | H_c_63c18_M |
| 17 | 75735548 | 75736301 | H_c_240g06_M |
| 17 | 75848562 | 75850631 | H_c_117b15_M |
| 17 | 76002983 | 76004333 | H_c_148g02 |
| 17 | 76042875 | 76043614 | H_c_52l06_M |
| 17 | 76063603 | 76068122 | H_c_168k22_M |
| 17 | 76579945 | 76581157 | H_c_245a04_M |
| 17 | 76591555 | 76593075 | H_c_258m01 |
| 17 | 76622372 | 76624413 | H_c_3p07_M |
| 17 | 7677795 | 7681538 | H_c_165h01_M_M |
| 17 | 76810804 | 76812128 | H_c_76f08_M |
| 17 | 76827648 | 76828558 | H_c_29g14_M |
| 17 | 76842862 | 76844939 | H_c_117j01_M |
| 17 | 7688025 | 7688519 | H_c_148e07_M |
| 17 | 76929548 | 76932901 | H_c_30o21_M |
| 17 | 7694681 | 7696302 | H_c_15o15_M |
| 17 | 76973792 | 76976119 | H_c_186l18_M |
| 17 | 76981321 | 76988784 | H_c_104l14_M_M |
| 17 | 77060617 | 77062500 | H_c_165j24_M |
| 17 | 77064502 | 77066858 | H_c_123c14_M |
| 17 | 77094449 | 77097190 | H_c_12n03_M |
| 17 | 77100333 | 77102065 | H_c_128i19 |
| 17 | 77127576 | 77129177 | H_c_151m19 |
| 17 | 77213759 | 77214887 | H_c_189c22_M |
| 17 | 77243594 | 77246235 | H_c_95d19_M |
| 17 | 77260861 | 77262361 | H_c_109h13_M |
| 17 | 77279576 | 77281470 | H_c_72e08_M |
| 17 | 77288780 | 77289652 | H_c_21o11_M |
| 17 | 77289651 | 77290214 | H_c137f18_M |
| 17 | 77410887 | 77413052 | H_c_66b17_M |
| 17 | 77441535 | 77443667 | H_c_82o16_M |
| 17 | 77451408 | 77454038 | H_c_213m07_M |
| 17 | 77461949 | 77463032 | H_c_23g20 |
| 17 | 77468723 | 77469442 | H_c_246i23 |
| 17 | 77473138 | 77474732 | H_c_271n19 |
| 17 | 77477987 | 77480905 | H_c_273a07_M |
| 17 | 77488164 | 77488953 | H_c_109k13 |
| 17 | 77527514 | 77529390 | H_c_251i24 |
| 17 | 77601257 | 77603872 | H_c_256e04_M |
| 17 | 77616286 | 77617536 | H_c_57h12 |
| 17 | 77646660 | 77649422 | H_c_161g10_M |
| 17 | 7766400 | 7768663 | H_c_215a15_M |
| 17 | 7776077 | 7776742 | H_c_42f10 |
| 17 | 77763583 | 77764836 | H_c_9j13_M |
| 17 | 77843522 | 77844857 | H_c_203b20 |
| 17 | 77922903 | 77924692 | H_c_21h05_M |
| 17 | 77969190 | 77970406 | H_c_57e05_M |
| 17 | 78001152 | 78002247 | H_c_226p14_M |
| 17 | 78009007 | 78011105 | H_c_77j11_M |
| 17 | 78070384 | 78071794 | H_c_70j20_M |
| 17 | 78267496 | 78268418 | H_c_100d18 |
| 17 | 7833555 | 7834640 | H_c_42m13 |
| 17 | 78569591 | 78569734 | H_c_15n13 |
| 17 | 78646216 | 78646441 | H_c_83n14 |
| 17 | 7921955 | 7924652 | H_c_24m19 |
| 17 | 7952958 | 7954700 | H_c_201b19_M |
| 17 | 7961383 | 7963230 | H_c_59f01_M |
| 17 | 7966747 | 7971019 | H_c_93d20_M |
| 17 | 7994934 | 7996996 | H_c_152f03_M |
| 17 | 8000855 | 8001264 | H_c_36g18_M |
| 17 | 8006434 | 8007646 | H_c_56i12_M |
| 17 | 8019649 | 8021090 | H_c_165c05_M |
| 17 | 8032408 | 8034249 | H_c_14f18 |
| 17 | 8065197 | 8066240 | H_c_130e23 |
| 17 | 8066241 | 8067843 | H_c_126k16 |
| 17 | 8092304 | 8093096 | H_c_239p03 |
| 17 | 8132797 | 8133191 | H_c_179e13 |
| 17 | 8158743 | 8160293 | H_c_202b09 |
| 17 | 8170509 | 8171736 | H_c_191b01 |
| 17 | 8227051 | 8227740 | H_c_184e20_M |
| 17 | 8279032 | 8280720 | H_c_208f02_M |
| 17 | 846619 | 847859 | H_c_197g06_M |
| 17 | 8473268 | 8475835 | H_c_95d15_M |
| 17 | 8809420 | 8810540 | H_c_183g17_M |
| 17 | 8847103 | 8847773 | H_c136d06_M |
| 17 | 9082735 | 9085564 | H_c_53j04_M |
| 17 | 9178378 | 9178446 | H_c_26a20 |
| 17 | 9419274 | 9420081 | H_c_195a01 |
| 17 | 9488920 | 9490274 | H_c_193c06_M |
| 17 | 9967579 | 9969099 | H_c_67c12 |
| 17 | 999119 | 1001969 | H_c_52d14 |
| 18 | 10021735 | 10023011 | H_c_165i06_M |
| 18 | 10121748 | 10122208 | H_c_21h07_M |
| 18 | 101260 | 102570 | H_c_86i11_M |
| 18 | 10443508 | 10445625 | H_c_254k14_M |
| 18 | 10515712 | 10516812 | H_c_68f18_M |
| 18 | 11069127 | 11069313 | H_c_24f12 |
| 18 | 11138325 | 11139905 | H_c_16c07_M |
| 18 | 11319203 | 11319304 | H_c_274c07 |
| 18 | 11678937 | 11680111 | H_c_71j02_M |
| 18 | 11841206 | 11842208 | H_c_250a11_M |
| 18 | 11877192 | 11877634 | H_c_43a04 |
| 18 | 11898167 | 11899248 | H_c_214g16_M |
| 18 | 11958794 | 11958923 | H_c_172j06 |
| 18 | 11970314 | 11972082 | H_c_148e23 |
| 18 | 12028010 | 12029265 | H_c_77f10_M |
| 18 | 12066345 | 12066868 | H_c_57c20 |
| 18 | 12244001 | 12244330 | H_c_183e06_M |
| 18 | 12297500 | 12299210 | H_c_25l07 |
| 18 | 12366330 | 12368232 | H_c_192j05_M |
| 18 | 12397581 | 12398588 | H_c_107a20_M |
| 18 | 12410212 | 12410887 | H_c131g18_M |
| 18 | 12526265 | 12526350 | H_c_264c17 |
| 18 | 12646640 | 12649040 | H_c_170c14_M |
| 18 | 12692045 | 12693505 | H_c_207c24_M |
| 18 | 12873003 | 12874629 | H_c138j20_M |
| 18 | 12937310 | 12939379 | H_c_15j08_M |
| 18 | 12980729 | 12981652 | H_c_251c02 |
| 18 | 13126505 | 13127694 | H_c_196e23_M |
| 18 | 13207051 | 13209021 | H_c_23i21_M |

TABLE 1-continued

| | | | |
|---|---|---|---|
| 18 | 13600956 | 13602764 | H_c__21i14 |
| 18 | 13631492 | 13633033 | H_c__8l12_M |
| 18 | 13715970 | 13717359 | H_c__160g01_M |
| 18 | 13790834 | 13791551 | H_c__55k01_M |
| 18 | 13814139 | 13814385 | H_c__125o09_M |
| 18 | 16769996 | 16771682 | H_c__275g23 |
| 18 | 16772054 | 16774059 | H_c__247n19_M |
| 18 | 16825767 | 16825900 | H_c__37c17_M |
| 18 | 16944627 | 16946403 | H_c__237d18 |
| 18 | 17075316 | 17077138 | H_c__116h01_M |
| 18 | 17433845 | 17436576 | H_c__172j09 |
| 18 | 17446088 | 17446655 | H_c__71k06_M |
| 18 | 17537932 | 17538997 | H_c__187p20_M |
| 18 | 17544598 | 17544770 | H_c__18p12 |
| 18 | 175886 | 176055 | H_c__50h17 |
| 18 | 17643831 | 17643996 | H_c__239b11 |
| 18 | 17901681 | 17901937 | H_c__69f08 |
| 18 | 17999521 | 18000068 | H_c__68m07_M |
| 18 | 18001050 | 18006717 | H_c__146e20_M_M |
| 18 | 18010573 | 18011410 | H_c__192h15_M |
| 18 | 18014074 | 18014189 | H_c__24n22 |
| 18 | 18182077 | 18182814 | H_c__96j23_M |
| 18 | 18393625 | 18393987 | H_c__81j09 |
| 18 | 18767012 | 18768291 | H_c__28e09_M |
| 18 | 18968355 | 18971219 | H_c__145o12 |
| 18 | 19271458 | 19271982 | H_c__222c19 |
| 18 | 19287176 | 19287871 | H_c135i08_M |
| 18 | 19337396 | 19339826 | H_c__212o14_M |
| 18 | 19419923 | 19421086 | H_c__139k01_M |
| 18 | 19780417 | 19780572 | H_c142g16 |
| 18 | 19847924 | 19849545 | H_c__210p08_M |
| 18 | 19868842 | 19868988 | H_c__265j22 |
| 18 | 19973119 | 19973498 | H_c__94c04 |
| 18 | 20023076 | 20024174 | H_c__161f22 |
| 18 | 20231387 | 20232134 | H_c__239c03 |
| 18 | 20260231 | 20260998 | H_c__222f01_M |
| 18 | 2040096 | 2040463 | H_c__70b24 |
| 18 | 20894955 | 20895671 | H_c__111b22 |
| 18 | 21183013 | 21186470 | H_c__128b14_M |
| 18 | 21557460 | 21557805 | H_c__52k17 |
| 18 | 21923722 | 21925202 | H_c__82c09_M |
| 18 | 219521 | 219600 | H_c__22o05 |
| 18 | 22060281 | 22061364 | H_c__229g11 |
| 18 | 22383085 | 22384307 | H_c__68b01_M |
| 18 | 22384310 | 22385310 | H_c__13f10 |
| 18 | 22455844 | 22456009 | H_c__267f19 |
| 18 | 22490470 | 22491569 | H_c__162n17 |
| 18 | 22611190 | 22612633 | H_c__272g11_M |
| 18 | 22696944 | 22698117 | H_c__274i18_M |
| 18 | 22785659 | 22785777 | H_c__8d13 |
| 18 | 23319000 | 23319205 | H_c__124f14 |
| 18 | 23447345 | 23447432 | H_c__89n09 |
| 18 | 23623965 | 23624055 | H_c__271h09 |
| 18 | 23862148 | 23862298 | H_c__22p19 |
| 18 | 23966805 | 23966934 | H_c__40p08 |
| 18 | 24009055 | 24012717 | H_c__124d14_M |
| 18 | 24456149 | 24456331 | H_c__88c17 |
| 18 | 24524124 | 24524429 | H_c__200h22 |
| 18 | 25141760 | 25141946 | H_c__192k20 |
| 18 | 2560774 | 2561704 | H_c__4c24_M |
| 18 | 25678258 | 25679165 | H_c__223p19 |
| 18 | 257516 | 258473 | H_c__56o18_M |
| 18 | 25978206 | 25978311 | H_c__109g24 |
| 18 | 26072750 | 26072846 | H_c__130f24 |
| 18 | 26149438 | 26149563 | H_c__157m10 |
| 18 | 26265210 | 26265436 | H_c__22k15 |
| 18 | 2645071 | 2646633 | H_c__117f07_M |
| 18 | 26875423 | 26876732 | H_c__58c14_M |
| 18 | 27331242 | 27332657 | H_c__7g17_M |
| 18 | 27611756 | 27611935 | H_c__187j24 |
| 18 | 27776322 | 27777128 | H_c__76b11_M |
| 18 | 27852596 | 27853514 | H_c__68e19_M |
| 18 | 27925608 | 27927489 | H_c__237k14_M |
| 18 | 2836266 | 2838447 | H_c__203c02_M |
| 18 | 28603239 | 28606502 | H_c__188a18_M |
| 18 | 28771708 | 28771973 | H_c__51e03 |
| 18 | 2895938 | 2898113 | H_c__35a19_M |
| 18 | 29274162 | 29275117 | H_c__111g24_M |
| 18 | 29411813 | 29413379 | H_c__204j24_M |
| 18 | 2956690 | 2956759 | H_c__196h10 |
| 18 | 29642616 | 29642742 | H_c__13e17 |
| 18 | 29653424 | 29654760 | H_c__230f23_M |
| 18 | 3002475 | 3003511 | H_c138d17 |
| 18 | 30055749 | 30057840 | H_c__90k06_M |
| 18 | 30327370 | 30328747 | H_c__57f03 |
| 18 | 30875018 | 30875962 | H_c__64g12_M |
| 18 | 31100936 | 31101674 | H_c__40g11 |
| 18 | 3112592 | 3112678 | H_c__91l12_M |
| 18 | 31177572 | 31178585 | H_c__73e21_M |
| 18 | 31199844 | 31200050 | H_c__266b07 |
| 18 | 31210327 | 31211631 | H_c__195e05_M |
| 18 | 31414715 | 31416351 | H_c__92b21_M |
| 18 | 31806133 | 31807028 | H_c__119g03_M |
| 18 | 31868806 | 31868934 | H_c__46b07 |
| 18 | 31929060 | 31929134 | H_c__8h12 |
| 18 | 31962890 | 31964345 | H_c__113e16_M |
| 18 | 32021301 | 32022288 | H_c__192a09_M |
| 18 | 32131294 | 32132588 | H_c__5c15_M |
| 18 | 3237602 | 3238312 | H_c__264m06 |
| 18 | 3251961 | 3252909 | H_c__22g10 |
| 18 | 32639911 | 32640065 | H_c__86f05 |
| 18 | 32661841 | 32663620 | H_c__24e24_M |
| 18 | 33077747 | 33078179 | H_c133n03 |
| 18 | 33086660 | 33089000 | H_c__249a09_M |
| 18 | 33107571 | 33108599 | H_c__200b18 |
| 18 | 33256554 | 33258690 | H_c__12j23 |
| 18 | 33320340 | 33323182 | H_c__251d22 |
| 18 | 33358513 | 33358990 | H_c__9i03_M |
| 18 | 33398794 | 33401690 | H_c__187j16_M |
| 18 | 33524687 | 33524774 | H_c__188d19 |
| 18 | 33881163 | 33881354 | H_c__209l14 |
| 18 | 3401984 | 3402466 | H_c__193b10_M |
| 18 | 34117601 | 34117800 | H_c__207b20 |
| 18 | 3438091 | 3442769 | H_c__15k24_M_M |
| 18 | 3488698 | 3489594 | H_c__17c16_M |
| 18 | 35922808 | 35922896 | H_c__53o14 |
| 18 | 35983589 | 35983684 | H_c__21e18 |
| 18 | 36405040 | 36405179 | H_c__173f11 |
| 18 | 36649514 | 36649613 | H_c__172n23 |
| 18 | 36750245 | 36750465 | H_c__215k10 |
| 18 | 36937625 | 36937698 | H_c__123n04 |
| 18 | 37291367 | 37291555 | H_c__152i21 |
| 18 | 37789039 | 37789316 | H_c__56f17_M |
| 18 | 37883016 | 37883099 | H_c__15h11 |
| 18 | 37886972 | 37887095 | H_c__8g17 |
| 18 | 37960722 | 37960902 | H_c__46j20 |
| 18 | 38241004 | 38241126 | H_c132j16 |
| 18 | 38304266 | 38304468 | H_c__15d23 |
| 18 | 38534838 | 38535100 | H_c__199g22 |
| 18 | 39495107 | 39495207 | H_c__225h16 |
| 18 | 39622840 | 39622924 | H_c__69o06 |
| 18 | 40080052 | 40080125 | H_c__80l17 |
| 18 | 40157370 | 40157475 | H_c__24n06 |
| 18 | 40167973 | 40168106 | H_c__163l12 |
| 18 | 40421575 | 40421657 | H_c__116d23 |
| 18 | 40512969 | 40513807 | H_c__11f19_M |
| 18 | 4068459 | 4068567 | H_c__125k11 |
| 18 | 40775866 | 40775957 | H_c__45m01 |
| 18 | 41321760 | 41321923 | H_c137m24 |
| 18 | 41605794 | 41605970 | H_c__264e16 |
| 18 | 41619944 | 41620060 | H_c__27g10 |
| 18 | 41671102 | 41673273 | H_c__180j07_M |
| 18 | 41800582 | 41801772 | H_c__165p10 |
| 18 | 41861811 | 41862697 | H_c__232f15 |
| 18 | 41884742 | 41885499 | H_c__101f19_M |
| 18 | 41905288 | 41906411 | H_c__249j10 |
| 18 | 41931926 | 41932396 | H_c__16i02 |
| 18 | 42007016 | 42009023 | H_c__266f14 |
| 18 | 42074618 | 42074741 | H_c__211h11 |
| 18 | 42167461 | 42168893 | H_c__117c24 |
| 18 | 4222123 | 4222273 | H_c__160m11 |
| 18 | 42590057 | 42591124 | H_c__211d10_M |
| 18 | 42591128 | 42592350 | H_c__225f08 |
| 18 | 42780693 | 42754578 | H_c__11m10_M_M |
| 18 | 42780751 | 42781030 | H_c__54i07 |
| 18 | 42930415 | 42931185 | H_c137c05_M |
| 18 | 42956182 | 42957205 | H_c__14k20 |
| 18 | 43026897 | 43029701 | H_c__34f17 |
| 18 | 43042782 | 43044210 | H_c__109h10_M |
| 18 | 43529446 | 43529994 | H_c__117i03_M |

TABLE 1-continued

| | | | |
|---|---|---|---|
| 18 | 43562249 | 43562360 | H_c_62p10 |
| 18 | 43643946 | 43644101 | H_c_86c22 |
| 18 | 43711763 | 43712048 | H_c_125b08 |
| 18 | 43787707 | 43789148 | H_c_204l13_M |
| 18 | 43916295 | 43916822 | H_c_69g08_M |
| 18 | 43916952 | 43917523 | H_c_69d02_M |
| 18 | 43940755 | 43940886 | H_c_149o21_M |
| 18 | 4443923 | 4445736 | H_c_273n20_M |
| 18 | 44561229 | 44562324 | H_c_43c07 |
| 18 | 44703375 | 44703483 | H_c_35m20 |
| 18 | 44728815 | 44732947 | H_c_168f09_M_M |
| 18 | 44755704 | 44756935 | H_c_85j20_M |
| 18 | 45101223 | 45101325 | H_c_58k05 |
| 18 | 45146520 | 45146722 | H_c_10i18 |
| 18 | 45240387 | 45241620 | H_c_220d07_M |
| 18 | 45272398 | 45272967 | H_c_151h13 |
| 18 | 45341244 | 45342398 | H_c_66m10_M |
| 18 | 45593288 | 45595020 | H_c_72o02_M |
| 18 | 4584531 | 4584647 | H_c_102h12 |
| 18 | 45974266 | 45975863 | H_c_56f16_M |
| 18 | 46067766 | 46068601 | H_c_208k14_M |
| 18 | 46139780 | 46140672 | H_c_23f02 |
| 18 | 46154754 | 46155844 | H_c_168p22 |
| 18 | 46339401 | 46341078 | H_c_119k01_M |
| 18 | 46509338 | 46510344 | H_c_188e11_M |
| 18 | 46658821 | 46660103 | H_c_11f13_M |
| 18 | 46747973 | 46749093 | H_c_56g17_M |
| 18 | 46809920 | 46813139 | H_c_213j15_M |
| 18 | 46976349 | 46978070 | H_c_104g22_M |
| 18 | 47125295 | 47125408 | H_c_63k24 |
| 18 | 47190231 | 47190431 | H_c_192c13 |
| 18 | 47219716 | 47219859 | H_c_39b04 |
| 18 | 47379254 | 47379496 | H_c_238i08 |
| 18 | 47464865 | 47465096 | H_c_49j19_M |
| 18 | 47553793 | 47553997 | H_c_73n05 |
| 18 | 48323378 | 48323498 | H_c_39a02 |
| 18 | 48478312 | 48478481 | H_c_220j18 |
| 18 | 48737241 | 48737386 | H_c_210k13 |
| 18 | 490209 | 491454 | H_c_70d06 |
| 18 | 50004122 | 50005309 | H_c137i15 |
| 18 | 50009296 | 50009585 | H_c_251c08 |
| 18 | 50049543 | 50050355 | H_c_250f23_M |
| 18 | 50215467 | 50215621 | H_c_173i10 |
| 18 | 50557079 | 50557211 | H_c134o10_M |
| 18 | 50777131 | 50777906 | H_c_86l18_M |
| 18 | 51043344 | 51043544 | H_c_156g24 |
| 18 | 51178194 | 51178400 | H_c_156h16 |
| 18 | 51196780 | 51197015 | H_c_65n09 |
| 18 | 51406026 | 51406449 | H_c_30p17_M |
| 18 | 51598293 | 51599075 | H_c_244e01_M |
| 18 | 51793508 | 51793574 | H_c_195g05 |
| 18 | 5186184 | 5187398 | H_c_96c12_M |
| 18 | 51912000 | 51912151 | H_c_17d02 |
| 18 | 52134275 | 52134508 | H_c_147b16 |
| 18 | 5227694 | 5228680 | H_c_189j12_M |
| 18 | 52760551 | 52760771 | H_c_235j01_M |
| 18 | 5286156 | 5286876 | H_c_234k03_M |
| 18 | 53170649 | 53172170 | H_c_114l18_M |
| 18 | 53194328 | 53194463 | H_c_58g23_M |
| 18 | 53245577 | 53247509 | H_c_166m17_M |
| 18 | 53252938 | 53253097 | H_c_199l08_M |
| 18 | 53256135 | 53259954 | H_c_55g11_M_M |
| 18 | 53265581 | 53266000 | H_c_185k08 |
| 18 | 53404062 | 53405989 | H_c_54m03_M |
| 18 | 53439462 | 53440797 | H_c_151g13 |
| 18 | 53543544 | 53543664 | H_c_104j05 |
| 18 | 53620426 | 53622144 | H_c_88a07_M |
| 18 | 53862055 | 53863662 | H_c_88l06_M |
| 18 | 53922487 | 53922676 | H_c_62g02 |
| 18 | 54110398 | 54110934 | H_c_95f11 |
| 18 | 54681232 | 54683308 | H_c_267n04_M |
| 18 | 55038145 | 55039690 | H_c_104h21 |
| 18 | 55081814 | 55088053 | H_c_15i17_M_M |
| 18 | 55176756 | 55178080 | H_c_169e08_M |
| 18 | 5532697 | 5534465 | H_c_114g20_M |
| 18 | 55717831 | 55718934 | H_c_112k05_M |
| 18 | 55880110 | 55880178 | H_c_48g16 |
| 18 | 56100491 | 56100683 | H_c_24g13 |
| 18 | 56161972 | 56162154 | H_c_121a16 |
| 18 | 5619215 | 5620933 | H_c_66o20_M |
| 18 | 56867907 | 56868053 | H_c_92b14 |
| 18 | 57151487 | 57153052 | H_c_212g14 |
| 18 | 57327539 | 57327865 | H_c_237b14 |
| 18 | 57372248 | 57373069 | H_c_46e10 |
| 18 | 57723297 | 57723495 | H_c_151i24 |
| 18 | 58005131 | 58006348 | H_c_69b21_M |
| 18 | 58143042 | 58144363 | H_c_24m24_M |
| 18 | 58202130 | 58203626 | H_c_173k16 |
| 18 | 58344783 | 58345268 | H_c_241i06_M |
| 18 | 58414124 | 58415787 | H_c_169i09_M |
| 18 | 5880132 | 5882478 | H_c132e22_M |
| 18 | 59066009 | 59066101 | H_c_187d20 |
| 18 | 59137864 | 59139172 | H_c_183c01_M |
| 18 | 59184394 | 59186045 | H_c_211f15_M |
| 18 | 59592836 | 59593423 | H_c_99k24 |
| 18 | 59611412 | 59611440 | H_c_105c18 |
| 18 | 59754342 | 59755483 | H_c_134a16 |
| 18 | 600045 | 600143 | H_c_28a11 |
| 18 | 60029784 | 60030050 | H_c_166m07 |
| 18 | 60845688 | 60845873 | H_c_56m13 |
| 18 | 61568441 | 61569970 | H_c_272d14_M |
| 18 | 61815271 | 61815452 | H_c_83o22 |
| 18 | 62034987 | 62035088 | H_c_66c11 |
| 18 | 62116123 | 62116277 | H_c135g17 |
| 18 | 63301272 | 63301360 | H_c_115b20 |
| 18 | 63334138 | 63335346 | H_c_52e16_M |
| 18 | 63403018 | 63403131 | H_c_70p11 |
| 18 | 63447476 | 63447591 | H_c_190f16 |
| 18 | 6403961 | 6405528 | H_c_106i11 |
| 18 | 64230671 | 64230854 | H_c_3p18 |
| 18 | 6439809 | 6439987 | H_c_32g09 |
| 18 | 64532823 | 64533359 | H_c_155c21_M |
| 18 | 647234 | 648501 | H_c_6l08_M |
| 18 | 65218489 | 65221351 | H_c_4i16_M |
| 18 | 65335842 | 65335958 | H_c_77a06 |
| 18 | 65621503 | 65621607 | H_c_209k19 |
| 18 | 66013954 | 66014120 | H_c_108n06 |
| 18 | 66023465 | 66024453 | H_c144g04_M |
| 18 | 66283098 | 66283277 | H_c_262l23 |
| 18 | 66855332 | 66855513 | H_c_259j13 |
| 18 | 67051151 | 67051302 | H_c_42a13 |
| 18 | 6719009 | 6720236 | H_c_261j07_M |
| 18 | 68359825 | 68362248 | H_c_65i21_M |
| 18 | 68685604 | 68688360 | H_c_271p05_M |
| 18 | 68800367 | 68800521 | H_c_39g13 |
| 18 | 68852776 | 68852888 | H_c_86d03 |
| 18 | 68946054 | 68946160 | H_c143d23 |
| 18 | 69107723 | 69107802 | H_c_9n04 |
| 18 | 69119527 | 69119671 | H_c_51k17 |
| 18 | 69550957 | 69551061 | H_c_204e08 |
| 18 | 69965048 | 69966225 | H_c_224g09_M |
| 18 | 70110341 | 70110485 | H_c_8c06_M |
| 18 | 701751 | 703150 | H_c_60n17_M |
| 18 | 70274733 | 70275767 | H_c_25d17 |
| 18 | 70426167 | 70426279 | H_c_121d21 |
| 18 | 70649669 | 70649824 | H_c_216d24 |
| 18 | 70672257 | 70672340 | H_c_35b10_M |
| 18 | 71007194 | 71007415 | H_c_99h14 |
| 18 | 71045005 | 71046308 | H_c_49k12_M |
| 18 | 71049547 | 71053320 | H_c_35d13_M |
| 18 | 7106648 | 7108324 | H_c_203a09_M |
| 18 | 71296360 | 71297078 | H_c_69h18_M |
| 18 | 71654040 | 71654122 | H_c137f09 |
| 18 | 71756553 | 71758135 | H_c137d05_M |
| 18 | 71892182 | 71892351 | H_c_240d09 |
| 18 | 72063846 | 72063965 | H_c_237d15 |
| 18 | 72239903 | 72240144 | H_c_128g01 |
| 18 | 72331730 | 72334078 | H_c_207l19_M |
| 18 | 72474802 | 72475036 | H_c_201a07 |
| 18 | 72551038 | 72551310 | H_c_54l23_M |
| 18 | 72599313 | 72599629 | H_c_48c21 |
| 18 | 72662928 | 72664994 | H_c_164g02_M |
| 18 | 73134112 | 73134438 | H_c_172a15 |
| 18 | 73219943 | 73220102 | H_c_127l13 |
| 18 | 73348464 | 73349025 | H_c_231o01_M |
| 18 | 73740729 | 73741714 | H_c_244l11 |
| 18 | 74591292 | 74591514 | H_c_182j22 |
| 18 | 74833374 | 74835449 | H_c_84n01_M |
| 18 | 74841935 | 74842372 | H_c139e12_M |
| 18 | 75106457 | 75107866 | H_c_57j15 |

TABLE 1-continued

| | | | |
|---|---|---|---|
| 18 | 75188577 | 75188735 | H_c__181j21_M |
| 18 | 75239038 | 75240430 | H_c__38i03_M |
| 18 | 75254672 | 75260916 | H_c__194i21_M_M |
| 18 | 75260970 | 75264701 | H_c__91k08_M_M |
| 18 | 75367854 | 75369022 | H_c__146j16_M |
| 18 | 75372218 | 75372466 | H_c__261c15 |
| 18 | 75498492 | 75499817 | H_c__122a21 |
| 18 | 75539985 | 75541655 | H_c__163m20 |
| 18 | 7556473 | 7558946 | H_c__209g23 |
| 18 | 75648760 | 75649625 | H_c__30j05_M |
| 18 | 75811038 | 75814253 | H_c__6i08_M |
| 18 | 75824457 | 75827233 | H_c__57m12 |
| 18 | 75849008 | 75850039 | H_c__c142k04_M |
| 18 | 75849090 | 75849959 | H_c__72f04 |
| 18 | 75967528 | 75969037 | H_c__182l24_M |
| 18 | 76018459 | 76019642 | H_c__181j07_M |
| 18 | 7839091 | 7839205 | H_c135a06 |
| 18 | 801597 | 803323 | H_c__205h13_M |
| 18 | 8293127 | 8293541 | H_c__10i06 |
| 18 | 8357174 | 8357843 | H_c__75l12 |
| 18 | 8516197 | 8516680 | H_c__18i24_M |
| 18 | 8597454 | 8600421 | H_c__74o04_M |
| 18 | 8696865 | 8697488 | H_c__30p14 |
| 18 | 8792658 | 8792960 | H_c__77b22 |
| 18 | 894716 | 898288 | H_c__136e11_M |
| 18 | 898387 | 899602 | H_c__113h13 |
| 18 | 9323894 | 9325332 | H_c__193m01_M |
| 18 | 9465016 | 9466277 | H_c__52b21_M |
| 18 | 9569150 | 9569245 | H_c__211j05 |
| 18 | 9603593 | 9605326 | H_c__244k03_M |
| 18 | 9697749 | 9698901 | H_c__c141m20_M |
| 18 | 9733278 | 9733383 | H_c__197a13 |
| 18 | 9737086 | 9737712 | H_c__79b19 |
| 18 | 98166 | 98734 | H_c__191p05_M |
| 18 | 9903411 | 9905421 | H_c__118i22 |
| 19 | 10057302 | 10059308 | H_c__129c16 |
| 19 | 10076432 | 10078438 | H_c__261e09_M |
| 19 | 10165849 | 10167175 | H_c__38c17_M |
| 19 | 1019970 | 1022124 | H_c__39f06_M |
| 19 | 10201396 | 10203427 | H_c__87l09_M |
| 19 | 10223568 | 10224698 | H_c__201c21_M |
| 19 | 10241225 | 10242344 | H_c__266c01_M |
| 19 | 1025511 | 1026841 | H_c__19d19 |
| 19 | 10260532 | 10262587 | H_c__197m03_M |
| 19 | 10262589 | 10265162 | H_c__49l19_M |
| 19 | 10267545 | 10268898 | H_c__40c17 |
| 19 | 1028557 | 1029717 | H_c__12l01 |
| 19 | 10287033 | 10287496 | H_c__213g18 |
| 19 | 10304488 | 10305653 | H_c__17a18_M |
| 19 | 10351841 | 10353123 | H_c__23e02_M |
| 19 | 10376248 | 10377585 | H_c__163f24_M |
| 19 | 10388165 | 10388987 | H_c__72h21 |
| 19 | 10401611 | 10402905 | H_c__229i09 |
| 19 | 10432553 | 10434140 | H_c__206l23 |
| 19 | 1045544 | 1046772 | H_c__69o22_M |
| 19 | 10472858 | 10475242 | H_c__187a23 |
| 19 | 10484438 | 10486928 | H_c__11g05 |
| 19 | 10514871 | 10516468 | H_c__214g08 |
| 19 | 10536451 | 10540972 | H_c__183i15_M |
| 19 | 1056043 | 1056215 | H_c__195h17_M |
| 19 | 10573753 | 10575715 | H_c__195i14_M |
| 19 | 10624968 | 10626981 | H_c__67a16_M |
| 19 | 10666629 | 10667980 | H_c__152d20 |
| 19 | 10672984 | 10673592 | H_c__110k07_M |
| 19 | 10689308 | 10690614 | H_c__92k18 |
| 19 | 10751648 | 10752442 | H_c__148g01 |
| 19 | 1082878 | 1085749 | H_c__272d23 |
| 19 | 10900443 | 10901679 | H_c__252k16_M |
| 19 | 10932086 | 10933370 | H_c__101i06_M |
| 19 | 11061904 | 11062777 | H_c__79g16_M |
| 19 | 11102193 | 11103474 | H_c__168k13 |
| 19 | 11126967 | 11128252 | H_c__229f20 |
| 19 | 11168052 | 11169881 | H_c__187h01 |
| 19 | 11214941 | 11216061 | H_c__217g14 |
| 19 | 11232102 | 11234842 | H_c__10e20_M |
| 19 | 1124893 | 1125619 | H_c__62g15_M |
| 19 | 11265262 | 11265829 | H_c__62j16 |
| 19 | 11317315 | 11318217 | H_c__179j11 |
| 19 | 11352390 | 11353094 | H_c__220o17 |
| 19 | 11392141 | 11395858 | H_c__64j17_M |
| 19 | 11406441 | 11407620 | H_c__124c02_M |
| 19 | 1145014 | 1147465 | H_c__199k01_M |
| 19 | 11476598 | 11478264 | H_c__87b10_M |
| 19 | 11507369 | 11508249 | H_c__125d13_M |
| 19 | 11530688 | 11531540 | H_c__216c09 |
| 19 | 11568328 | 11569776 | H_c__84j05 |
| 19 | 11611347 | 11612763 | H_c__124d20 |
| 19 | 11738049 | 11739348 | H_c__126l17_M |
| 19 | 11785511 | 11786704 | H_c__189c14 |
| 19 | 1190495 | 1191666 | H_c__218h07_M |
| 19 | 11959434 | 11959982 | H_c__274c20 |
| 19 | 1198919 | 1201967 | H_c__102e17_M |
| 19 | 12036314 | 12037046 | H_c__39c06_M |
| 19 | 12063949 | 12064621 | H_c__259h22 |
| 19 | 12127906 | 12128876 | H_c__79h23 |
| 19 | 12134582 | 12136591 | H_c__83b07_M |
| 19 | 12166518 | 12167598 | H_c__185j08 |
| 19 | 1216807 | 1221069 | H_c__257e21_M |
| 19 | 1225033 | 1227073 | H_c__85d10 |
| 19 | 12304528 | 12305952 | H_c__209h20_M |
| 19 | 1245900 | 1247647 | H_c__199c14_M |
| 19 | 12466744 | 12467778 | H_c__181l12_M |
| 19 | 12491255 | 12492954 | H_c__240e02 |
| 19 | 12522559 | 12523544 | H_c__50f08_M |
| 19 | 12582271 | 12583302 | H_c__20g24_M |
| 19 | 12611670 | 12613414 | H_c__20f06 |
| 19 | 12613494 | 12615059 | H_c__252h14 |
| 19 | 12641578 | 12641702 | H_c__24n08 |
| 19 | 12653112 | 12653649 | H_c__245k05 |
| 19 | 12667400 | 12668514 | H_c__47n13_M |
| 19 | 12692456 | 12693286 | H_c__266a10 |
| 19 | 1270172 | 1270266 | H_c__37c16 |
| 19 | 12705784 | 12706987 | H_c__15p11_M |
| 19 | 12728186 | 12730211 | H_c__180k07_M |
| 19 | 12753833 | 12754581 | H_c__72e20_M |
| 19 | 12761107 | 12762695 | H_c137i19_M |
| 19 | 1276356 | 1276480 | H_c__38o06 |
| 19 | 12765130 | 12766339 | H_c__177e12_M |
| 19 | 12772585 | 12774220 | H_c__78e10 |
| 19 | 12804906 | 12806690 | H_c__270c24 |
| 19 | 12809528 | 12813352 | H_c__253m14_M |
| 19 | 12818894 | 12820136 | H_c__192m19_M |
| 19 | 12857011 | 12858289 | H_c__70b17_M |
| 19 | 12862869 | 12864494 | H_c__9d04 |
| 19 | 12889782 | 12891584 | H_c__162i04_M |
| 19 | 12904221 | 12905907 | H_c__273n01 |
| 19 | 12910460 | 12911514 | H_c__32g22_M |
| 19 | 12917407 | 12918259 | H_c__197b17_M |
| 19 | 12985554 | 12985719 | H_c__91e12_M |
| 19 | 13031762 | 13033603 | H_c__28f17_M |
| 19 | 13065997 | 13067799 | H_c__187g23_M |
| 19 | 13070940 | 13071474 | H_c__11d21_M |
| 19 | 13073955 | 13077085 | H_c__82j08_M |
| 19 | 13087646 | 13088667 | H_c__193b21 |
| 19 | 13089730 | 13091073 | H_c__34l04 |
| 19 | 13123816 | 13126035 | H_c__115d21_M |
| 19 | 13134430 | 13135534 | H_c__69e14_M |
| 19 | 1334600 | 1335505 | H_c__48h18_M |
| 19 | 1357994 | 1358224 | H_c__124f18 |
| 19 | 1366975 | 1368418 | H_c__84i07 |
| 19 | 13746168 | 13746964 | H_c__180g15_M |
| 19 | 13767274 | 13767753 | H_c__243f18_M |
| 19 | 13804530 | 13805802 | H_c__41o08_M |
| 19 | 13810473 | 13814756 | H_c__109d24_M |
| 19 | 13821938 | 13822692 | H_c__14e23_M |
| 19 | 13844409 | 13846081 | H_c__207a16 |
| 19 | 13877442 | 13878867 | H_c__64e11_M |
| 19 | 1388993 | 1390189 | H_c__79p16_M |
| 19 | 13949550 | 13951967 | H_c__49f04 |
| 19 | 13978569 | 13979259 | H_c__205g11 |
| 19 | 1400870 | 1401666 | H_c__76j22 |
| 19 | 14027439 | 14029607 | H_c__73l13_M |
| 19 | 14088049 | 14090357 | H_c__33l16_M |
| 19 | 14107847 | 14109623 | H_c__98g07 |
| 19 | 14181155 | 14184038 | H_c__82l11 |
| 19 | 14200663 | 14200753 | H_c__213f04 |
| 19 | 1428839 | 1430308 | H_c__274m10_M |
| 19 | 14389686 | 14392179 | H_c__169i17_M |
| 19 | 14402834 | 14404188 | H_c__112i02 |
| 19 | 14489333 | 14490881 | H_c__151m14_M |

TABLE 1-continued

| | | | |
|---|---|---|---|
| 19 | 14500799 | 14502179 | H_c_166l15_M |
| 19 | 1454057 | 1455661 | H_c_157g22 |
| 19 | 1463381 | 1465604 | H_c_69f06_M |
| 19 | 14646559 | 14646918 | H_c_267k17 |
| 19 | 14661327 | 14662358 | H_c_185j05_M |
| 19 | 14735817 | 14735998 | H_c_225a22 |
| 19 | 14950793 | 14952053 | H_c_234c04 |
| 19 | 14981629 | 14983079 | H_c_28l06_M |
| 19 | 15096018 | 15097355 | H_c_56l01_M |
| 19 | 15148980 | 15151074 | H_c_184d13_M |
| 19 | 15194399 | 15196460 | H_c_270o02_M |
| 19 | 15202610 | 15204734 | H_c_2o13_M |
| 19 | 15350205 | 15352725 | H_c_241l10 |
| 19 | 15390120 | 15391283 | H_c_82b12 |
| 19 | 15403620 | 15404785 | H_c_110l14 |
| 19 | 15420801 | 15421950 | H_c_237c06_M |
| 19 | 1542989 | 1543952 | H_c_2h04_M |
| 19 | 15440939 | 15442283 | H_c_2k20_M |
| 19 | 15522993 | 15523776 | H_c_170o22_M |
| 19 | 1555974 | 1557478 | H_c_5a02_M |
| 19 | 15730067 | 15730210 | H_c_120o04 |
| 19 | 1575102 | 1576015 | H_c_246e14 |
| 19 | 15808162 | 15809143 | H_c_148b06 |
| 19 | 1602505 | 1604581 | H_c_98l11_M |
| 19 | 16047505 | 16050384 | H_c_83m06_M |
| 19 | 16083025 | 16084236 | H_c_9c17_M |
| 19 | 16109140 | 16111243 | H_c_261i21 |
| 19 | 16156757 | 16157690 | H_c_43n22 |
| 19 | 16169131 | 16171155 | H_c_213p08_M |
| 19 | 1622668 | 1623577 | H_c_39j18_M |
| 19 | 1626915 | 1627300 | H_c_113h18 |
| 19 | 16442857 | 16444915 | H_c_219m19 |
| 19 | 16467709 | 16468565 | H_c132f12_M |
| 19 | 1650311 | 1652831 | H_c_186k22 |
| 19 | 16513159 | 16514961 | H_c_148a24_M |
| 19 | 16631774 | 16633855 | H_c_174b02_M |
| 19 | 1676350 | 1677390 | H_c_28c08_M |
| 19 | 16801092 | 16801988 | H_c_246b06 |
| 19 | 16868903 | 16871736 | H_c_209p18 |
| 19 | 1699343 | 1701168 | H_c_75g07_M |
| 19 | 17046781 | 17047953 | H_c_67f14_M |
| 19 | 1707864 | 1709876 | H_c_53i13_M |
| 19 | 17198254 | 17198770 | H_c_38l15_M |
| 19 | 17206772 | 17208832 | H_c_195b08_M |
| 19 | 17253444 | 17256150 | H_c_88l18 |
| 19 | 17263597 | 17264855 | H_c_94m01 |
| 19 | 1727111 | 1728569 | H_c_204e21_M |
| 19 | 17276867 | 17278307 | H_c_202o09_M |
| 19 | 17295121 | 17296371 | H_c_75m19_M |
| 19 | 17362898 | 17363550 | H_c_78c14_M |
| 19 | 17390553 | 17392666 | H_c_19c07_M |
| 19 | 17418667 | 17420692 | H_c_19l15_M |
| 19 | 17427285 | 17428392 | H_c_232h10_M |
| 19 | 17441139 | 17442729 | H_c_4m20_M |
| 19 | 17483142 | 17484479 | H_c_220d06_M |
| 19 | 17510226 | 17512439 | H_c_108j10 |
| 19 | 17527503 | 17528249 | H_c_4l03_M |
| 19 | 17577090 | 17578564 | H_c_200a07 |
| 19 | 17658523 | 17660258 | H_c_98o07_M |
| 19 | 17719312 | 17720174 | H_c_217p02_M |
| 19 | 17819264 | 17820064 | H_c_35d20 |
| 19 | 17831199 | 17832215 | H_c_185g15_M |
| 19 | 17904718 | 17905261 | H_c_275l04 |
| 19 | 17918130 | 17920601 | H_c_185h16_M |
| 19 | 17923611 | 17924820 | H_c132k06_M |
| 19 | 17952558 | 17954331 | H_c_247m04 |
| 19 | 17972404 | 17974608 | H_c_99k10_M |
| 19 | 17978668 | 17981261 | H_c_33c09_M |
| 19 | 1798346 | 1799819 | H_c_79a07 |
| 19 | 18079960 | 18082676 | H_c_97m19_M |
| 19 | 18089587 | 18090463 | H_c_107m20_M |
| 19 | 1810518 | 1815748 | H_c_106m18_M |
| 19 | 18125152 | 18125897 | H_c_123o20_M |
| 19 | 18132919 | 18134492 | H_c_41a20_M |
| 19 | 18174691 | 18176110 | H_c_178a16_M |
| 19 | 18194680 | 18199017 | H_c_163g04_M |
| 19 | 18203889 | 18206084 | H_c_149g17_M |
| 19 | 1826372 | 1827262 | H_c_20m16 |
| 19 | 18293066 | 18295195 | H_c_218b11_M |
| 19 | 18311256 | 18313408 | H_c_196k19_M |
| 19 | 1835466 | 1836750 | H_c_249d08 |
| 19 | 18358951 | 18360884 | H_c_44h17_M |
| 19 | 18389223 | 18392306 | H_c_92i01_M |
| 19 | 18409095 | 18410725 | H_c_16d15_M |
| 19 | 18459345 | 18460543 | H_c_225i23 |
| 19 | 18491836 | 18494573 | H_c_218g07_M |
| 19 | 18514062 | 18515508 | H_c_43i12 |
| 19 | 18529604 | 18530107 | H_c_100g21_M |
| 19 | 1855714 | 1857359 | H_c_154p06_M |
| 19 | 18565072 | 18567929 | H_c_183m03 |
| 19 | 18575351 | 18576649 | H_c_107a04 |
| 19 | 18608031 | 18610683 | H_c_7l07 |
| 19 | 18654710 | 18656897 | H_c_238l20_M |
| 19 | 18672371 | 18673290 | H_c_101e07 |
| 19 | 18759142 | 18759479 | H_c_242k14 |
| 19 | 18803508 | 18805063 | H_c_156d08_M |
| 19 | 18890269 | 18892091 | H_c_106c19 |
| 19 | 18902826 | 18905455 | H_c_243p19_M |
| 19 | 18916506 | 18918042 | H_c_218o21 |
| 19 | 19034988 | 19036012 | H_c_178i05_M |
| 19 | 19052444 | 19052730 | H_c_198c06 |
| 19 | 19081858 | 19083581 | H_c_38g19_M |
| 19 | 19109896 | 19110488 | H_c_118i01 |
| 19 | 19140881 | 19143329 | H_c_203b01 |
| 19 | 19163720 | 19164377 | H_c_103b08 |
| 19 | 19173295 | 19175317 | H_c_115m21 |
| 19 | 19175322 | 19177019 | H_c_160i08 |
| 19 | 19183558 | 19184285 | H_c_12k04 |
| 19 | 19244283 | 19245908 | H_c_273d23 |
| 19 | 19356328 | 19359629 | H_c_212f04_M |
| 19 | 19376783 | 19378381 | H_c_82d19_M |
| 19 | 19485780 | 19487709 | H_c_23h03 |
| 19 | 19509671 | 19511072 | H_c_148l20_M |
| 19 | 19590007 | 19592255 | H_c_116d16_M |
| 19 | 19599801 | 19601625 | H_c_200j08 |
| 19 | 19614110 | 19616097 | H_c_195j05 |
| 19 | 19634926 | 19635971 | H_c_108i10_M |
| 19 | 19704436 | 19705085 | H_c_258b20_M |
| 19 | 1992447 | 1994680 | H_c_11j18_M |
| 19 | 20010765 | 20011556 | H_c_128i13_M |
| 19 | 20106319 | 20106395 | H_c_110n17 |
| 19 | 2030089 | 2031737 | H_c_116m01 |
| 19 | 2042710 | 2043989 | H_c_17d12 |
| 19 | 2046524 | 2050271 | H_c_192m18_M |
| 19 | 2101792 | 2103062 | H_c_15a11 |
| 19 | 2114341 | 2115683 | H_c_266i07 |
| 19 | 2115875 | 2118243 | H_c_123m21_M |
| 19 | 21561105 | 21562089 | H_c_73a13 |
| 19 | 217992 | 218671 | H_c_124a20_M |
| 19 | 2186554 | 2188263 | H_c_184i11_M |
| 19 | 2204495 | 2208106 | H_c_212p05_M |
| 19 | 2220007 | 2222865 | H_c_27o18_M |
| 19 | 22597463 | 22599004 | H_c_204g03 |
| 19 | 2279353 | 2280466 | H_c_170f19_M |
| 19 | 23127319 | 23127452 | H_c_191e08 |
| 19 | 23641816 | 23643974 | H_c_23d24 |
| 19 | 2423260 | 2426106 | H_c_257c12_M |
| 19 | 24338465 | 24338628 | H_c_111h15 |
| 19 | 2439955 | 2441127 | H_c_35b20_M |
| 19 | 2496651 | 2498306 | H_c138k23 |
| 19 | 2573389 | 2574622 | H_c_120o17 |
| 19 | 2584048 | 2586350 | H_c_214a06 |
| 19 | 2652804 | 2655086 | H_c_199g17_M |
| 19 | 2676647 | 2678947 | H_c_273n19 |
| 19 | 2733912 | 2736940 | H_c_119k18_M |
| 19 | 2839924 | 2840308 | H_c_247c06 |
| 19 | 2850696 | 2853533 | H_c_52g01_M |
| 19 | 2895542 | 2896112 | H_c_112c12_M |
| 19 | 2901455 | 2902154 | H_c_208h12 |
| 19 | 2925840 | 2929447 | H_c_19d09_M |
| 19 | 294153 | 296134 | H_c_252d02 |
| 19 | 2977751 | 2980473 | H_c_192e02_M |
| 19 | 2987064 | 2987987 | H_c_123h06_M |
| 19 | 2998263 | 2999191 | H_c_146n07_M |
| 19 | 3012508 | 3014123 | H_c_73g20_M |
| 19 | 3136694 | 3137741 | H_c_196f21_M |
| 19 | 3175340 | 3177791 | H_c_244k18 |
| 19 | 3220964 | 3222016 | H_c_228i24 |
| 19 | 3225329 | 3228179 | H_c_185a10_M |
| 19 | 3236459 | 3237575 | H_c_162h19 |

TABLE 1-continued

| | | | |
|---|---|---|---|
| 19 | 32899430 | 32899730 | H_c_50c18 |
| 19 | 3308122 | 3309688 | H_c_31b17 |
| 19 | 33082065 | 33084135 | H_c_76k20 |
| 19 | 33186335 | 33186485 | H_c_188h10 |
| 19 | 33876091 | 33876280 | H_c_59n10 |
| 19 | 33909834 | 33910924 | H_c_213e12 |
| 19 | 33976036 | 33976867 | H_c_72c09 |
| 19 | 3421628 | 3423948 | H_c_254c11 |
| 19 | 34237075 | 34237169 | H_c_116h10 |
| 19 | 34395232 | 34396232 | H_c_166g16 |
| 19 | 3451439 | 3452014 | H_c134h18 |
| 19 | 34691461 | 34692887 | H_c_186o12 |
| 19 | 34712329 | 34713421 | H_c_268h09_M |
| 19 | 34788572 | 34789112 | H_c_247e11_M |
| 19 | 34847497 | 34849521 | H_c_126g18_M |
| 19 | 34897299 | 34898797 | H_c_196g06_M |
| 19 | 34993950 | 34996253 | H_c_119i21_M |
| 19 | 35027060 | 35028192 | H_c_123k17_M |
| 19 | 35054931 | 35056815 | H_c_254e23_M |
| 19 | 3507956 | 3509063 | H_c_43n15 |
| 19 | 35124744 | 35125708 | H_c_59j11_M |
| 19 | 3523668 | 3525989 | H_c_19j14_M |
| 19 | 35306363 | 35308524 | H_c_250b13 |
| 19 | 3535740 | 3537268 | H_c_169c15_M |
| 19 | 35406116 | 35411903 | H_c_249a01_M_M |
| 19 | 35417732 | 35417913 | H_c_50e20 |
| 19 | 35557265 | 35559562 | H_c_266p15_M |
| 19 | 3557047 | 3558295 | H_c_207i13 |
| 19 | 3577445 | 3578355 | H_c_36e15 |
| 19 | 35901956 | 35902774 | H_c_167g07_M |
| 19 | 359606 | 360504 | H_c_7a05 |
| 19 | 36018018 | 36018162 | H_c_98l18 |
| 19 | 36326156 | 36328095 | H_c_14m18 |
| 19 | 36347446 | 36347583 | H_c_259m05 |
| 19 | 3638498 | 3640007 | H_c_108i13 |
| 19 | 3649834 | 3652564 | H_c_273b01 |
| 19 | 36531206 | 36532570 | H_c_13l04_M |
| 19 | 36532601 | 36534956 | H_c_194i14 |
| 19 | 36539704 | 36540193 | H_c_200m23 |
| 19 | 36811262 | 36811642 | H_c_38h12 |
| 19 | 3682643 | 3683947 | H_c_125p05 |
| 19 | 36955573 | 36955648 | H_c_200b15 |
| 19 | 37406422 | 37407684 | H_c_214m03 |
| 19 | 37587666 | 37589411 | H_c_207a20 |
| 19 | 3772969 | 3773124 | H_c_85b17_M |
| 19 | 37763773 | 37764916 | H_c_116d20 |
| 19 | 37857288 | 37857817 | H_c_33d13 |
| 19 | 37857291 | 37857813 | H_c_154h01_M |
| 19 | 37857820 | 37859902 | H_c_63c20 |
| 19 | 37874373 | 37875522 | H_c_94e03 |
| 19 | 38154405 | 38155285 | H_c_221p24 |
| 19 | 3819053 | 3820228 | H_c_231e06_M |
| 19 | 38246196 | 38248351 | H_c_83p10_M |
| 19 | 38262271 | 38264759 | H_c_93a09_M |
| 19 | 3831662 | 3832460 | H_c_252o01 |
| 19 | 38358983 | 38359819 | H_c_10m14 |
| 19 | 38486189 | 38486796 | H_c_200l13_M |
| 19 | 38555875 | 38557127 | H_c_119c11_M |
| 19 | 38703609 | 38704955 | H_c_186g20_M |
| 19 | 38803723 | 38805999 | H_c_16e15_M |
| 19 | 38938991 | 38940471 | H_c_244j05 |
| 19 | 38960640 | 38961709 | H_c_258d23 |
| 19 | 38977944 | 38978942 | H_c_228g12 |
| 19 | 38981082 | 38981408 | H_c_51g10 |
| 19 | 39002556 | 39004405 | H_c_90f12_M |
| 19 | 39088308 | 39090045 | H_c_103c17_M |
| 19 | 39190142 | 39190774 | H_c_69b14 |
| 19 | 39316958 | 39317329 | H_c_61m12_M |
| 19 | 39354588 | 39356087 | H_c_64i21 |
| 19 | 3935911 | 3936587 | H_c_28p16_M |
| 19 | 39425039 | 39425209 | H_c_202b23_M |
| 19 | 39547438 | 39549709 | H_c_170g10_M |
| 19 | 3957878 | 3959590 | H_c_177n05_M |
| 19 | 39587059 | 39587813 | H_c_29p01_M |
| 19 | 39610886 | 39611854 | H_c_91n19_M |
| 19 | 39662968 | 39665607 | H_c_216g15_M |
| 19 | 39860263 | 39860880 | H_c_118l02 |
| 19 | 40020437 | 40022942 | H_c_258g20 |
| 19 | 40109484 | 40110095 | H_c_111k03 |
| 19 | 4015255 | 4019304 | H_c_155h04_M |
| 19 | 40210721 | 40213518 | H_c_247h18 |
| 19 | 40213522 | 40214128 | H_c_17f17 |
| 19 | 4033399 | 4035454 | H_c_16h15 |
| 19 | 40336130 | 40337011 | H_c_127m16_M |
| 19 | 40449742 | 40450638 | H_c_28a16 |
| 19 | 40450644 | 40452955 | H_c_250b23 |
| 19 | 40478107 | 40478987 | H_c_115n21 |
| 19 | 40535109 | 40536583 | H_c_247l04 |
| 19 | 40608828 | 40609003 | H_c_208p14 |
| 19 | 40645096 | 40645563 | H_c_31i15 |
| 19 | 40727577 | 40728855 | H_c_11n14_M |
| 19 | 40740136 | 40740717 | H_c_249e17_M |
| 19 | 40795217 | 40795901 | H_c_210e14_M |
| 19 | 40884460 | 40885473 | H_c_44l10 |
| 19 | 40899530 | 40901696 | H_c139l17_M |
| 19 | 40922979 | 40924691 | H_c_228n06_M |
| 19 | 40938209 | 40939912 | H_c_2n19 |
| 19 | 40957919 | 40959311 | H_c_74h21_M |
| 19 | 40979400 | 40981117 | H_c_270o11 |
| 19 | 41050750 | 41052853 | H_c_98c15_M |
| 19 | 41082482 | 41082799 | H_c_212b14_M |
| 19 | 41114081 | 41115103 | H_c_216g23_M |
| 19 | 41176959 | 41178423 | H_c_76n16_M |
| 19 | 41191794 | 41193017 | H_c_60h14 |
| 19 | 41196524 | 41198115 | H_c_89g24 |
| 19 | 41237479 | 41238183 | H_c_26d04_M |
| 19 | 41310452 | 41310895 | H_c_243i14_M |
| 19 | 41322651 | 41324049 | H_c_200d06_M |
| 19 | 4132874 | 4134367 | H_c_4l05 |
| 19 | 41356686 | 41357008 | H_c_205o22 |
| 19 | 41396430 | 41397921 | H_c141j10_M |
| 19 | 41428429 | 41429412 | H_c_35l19 |
| 19 | 41600832 | 41601605 | H_c_236d05_M |
| 19 | 41604257 | 41605618 | H_c_253j10 |
| 19 | 41760398 | 41760667 | H_c_57h06 |
| 19 | 41787246 | 41788878 | H_c141e10_M |
| 19 | 41869814 | 41870819 | H_c_185b11_M |
| 19 | 4197842 | 4198981 | H_c_30i05_M |
| 19 | 42062293 | 42062472 | H_c_56a12_M |
| 19 | 42155601 | 42156090 | H_c_169d09 |
| 19 | 42260629 | 42261704 | H_c_91n22_M |
| 19 | 42400555 | 42401421 | H_c_249b09 |
| 19 | 42521918 | 42522020 | H_c_96d01 |
| 19 | 42649862 | 42652666 | H_c_16f04_M |
| 19 | 42732966 | 42734731 | H_c_243m07 |
| 19 | 4279396 | 4280367 | H_c_208d14 |
| 19 | 42837397 | 42839570 | H_c_129j04_M |
| 19 | 42874454 | 42875286 | H_c_69f07 |
| 19 | 4294069 | 4295662 | H_c_196m05_M |
| 19 | 42999880 | 43000712 | H_c_165g18 |
| 19 | 43088718 | 43090348 | H_c_12c02 |
| 19 | 4319773 | 4322442 | H_c_61d07 |
| 19 | 43406205 | 43407332 | H_c_77m23 |
| 19 | 43446625 | 43448132 | H_c_268h08_M |
| 19 | 43486368 | 43487469 | H_c137j22_M |
| 19 | 43501385 | 43502797 | H_c_171o06_M |
| 19 | 4350765 | 4355261 | H_c_67l07_M_M |
| 19 | 43543047 | 43545169 | H_c_195m22_M |
| 19 | 43557090 | 43557769 | H_c_273e14_M |
| 19 | 43575732 | 43579275 | H_c_198k06_M |
| 19 | 43585142 | 43586678 | H_c_151b18_M |
| 19 | 43617028 | 43619195 | H_c_23l07 |
| 19 | 43829048 | 43831026 | H_c_231b19_M |
| 19 | 438882 | 441316 | H_c_65d19_M |
| 19 | 44013475 | 44014578 | H_c_99f07_M |
| 19 | 44031723 | 44033244 | H_c_62o07_M |
| 19 | 44112498 | 44113665 | H_c_268o11_M |
| 19 | 44132107 | 44133133 | H_c_161n21_M |
| 19 | 44157884 | 44158734 | H_c_152e03 |
| 19 | 44255618 | 44255701 | H_c133l09 |
| 19 | 44379420 | 44380952 | H_c_124l15_M |
| 19 | 44501835 | 44504225 | H_c_264o11_M |
| 19 | 44523620 | 44526269 | H_c_18h08_M |
| 19 | 44573028 | 44573785 | H_c_21a08_M |
| 19 | 44584732 | 44586636 | H_c_102f03_M |
| 19 | 44594331 | 44597230 | H_c_7g23_M |
| 19 | 44601926 | 44603020 | H_c_83c16 |
| 19 | 44627445 | 44628816 | H_c_257i12 |
| 19 | 44662658 | 44664144 | H_c_25n19 |
| 19 | 44684918 | 44686062 | H_c_195j09 |

TABLE 1-continued

| | | | |
|---|---|---|---|
| 19 | 44689402 | 44690272 | H_c_169f16_M |
| 19 | 44697500 | 44699483 | H_c_86p13_M |
| 19 | 44721938 | 44722990 | H_c_53k04_M |
| 19 | 44773839 | 44773934 | H_c_88j06_M |
| 19 | 4500805 | 4502177 | H_c_35o23 |
| 19 | 45028157 | 45029338 | H_c_181j03_M |
| 19 | 45112641 | 45113721 | H_c_233n16_M |
| 19 | 45168232 | 45168845 | H_c_71j03_M |
| 19 | 45194516 | 45194846 | H_c_146p13 |
| 19 | 45256554 | 45256676 | H_c_37e08 |
| 19 | 4531405 | 4535706 | H_c_59c11_M |
| 19 | 45388493 | 45390623 | H_c_241n18_M |
| 19 | 45482383 | 45483489 | H_c_235n09_M |
| 19 | 45545588 | 45546721 | H_c_60b10_M |
| 19 | 45617931 | 45619337 | H_c_216e12 |
| 19 | 45623067 | 45624022 | H_c_27l05_M |
| 19 | 45716931 | 45718262 | H_c_130f03 |
| 19 | 45725270 | 45728950 | H_c_254p17_M |
| 19 | 45765239 | 45768516 | H_c_20j19_M |
| 19 | 45794656 | 45795986 | H_c_125j11_M |
| 19 | 45802437 | 45803806 | H_c_10h18_M |
| 19 | 4584014 | 4584548 | H_c_77g09 |
| 19 | 458426 | 460041 | H_c_70m03_M |
| 19 | 45860606 | 45862085 | H_c_20e07_M |
| 19 | 4589969 | 4590715 | H_c_92f13_M |
| 19 | 45912987 | 45916225 | H_c_66g21_M |
| 19 | 45947934 | 45949122 | H_c_164f19_M |
| 19 | 45966551 | 45966714 | H_c_216h22_M |
| 19 | 45975326 | 45976297 | H_c_68l07_M |
| 19 | 4619713 | 4622122 | H_c_249i19_M |
| 19 | 46330999 | 46333802 | H_c_247e12 |
| 19 | 46423562 | 46425160 | H_c_79o24_M |
| 19 | 46461067 | 46462185 | H_c_221j05_M |
| 19 | 46469490 | 46470796 | H_c_185p09 |
| 19 | 46507824 | 46508309 | H_c_39m07 |
| 19 | 46561722 | 46562594 | H_c_246l17 |
| 19 | 46594625 | 46596175 | H_c_65h09 |
| 19 | 4674135 | 4675045 | H_c137k09 |
| 19 | 47055370 | 47057299 | H_c_80i04_M |
| 19 | 47070913 | 47072154 | H_c_222h18 |
| 19 | 47078221 | 47080710 | H_c_164e18_M |
| 19 | 47124077 | 47126005 | H_c_48o03 |
| 19 | 47154127 | 47156455 | H_c_8f04_M |
| 19 | 47271554 | 47271923 | H_c_68o06 |
| 19 | 47328971 | 47330738 | H_c_60c11 |
| 19 | 47412316 | 47414649 | H_c_152e02 |
| 19 | 4742402 | 4743826 | H_c_20l20_M |
| 19 | 47437963 | 47438957 | H_c_152f17_M |
| 19 | 47440658 | 47441043 | H_c_122c12 |
| 19 | 47449737 | 47452001 | H_c_198j10_M |
| 19 | 47463996 | 47465780 | H_c_6l05_M |
| 19 | 47476025 | 47476542 | H_c_124b13_M |
| 19 | 47478628 | 47480975 | H_c_199o10 |
| 19 | 47497663 | 47499342 | H_c_202o12_M |
| 19 | 47597513 | 47598274 | H_c_56g12_M |
| 19 | 47893904 | 47894226 | H_c_229j21 |
| 19 | 4804345 | 4805662 | H_c_37f20 |
| 19 | 4860211 | 4861697 | H_c_249i14_M |
| 19 | 48659027 | 48661852 | H_c_149n13_M |
| 19 | 4866819 | 4868113 | H_c_271g11 |
| 19 | 48671117 | 48671644 | H_c136f18 |
| 19 | 48699534 | 48701236 | H_c_67j15_M |
| 19 | 48723017 | 48723269 | H_c_71p18_M |
| 19 | 48771358 | 48771896 | H_c_51h13 |
| 19 | 48790611 | 48792121 | H_c_45k24_M |
| 19 | 48814787 | 48816400 | H_c_86a10_M |
| 19 | 48820748 | 48821508 | H_c_124k12 |
| 19 | 48863717 | 48866590 | H_c_73e03_M |
| 19 | 48895263 | 48896600 | H_c_228j16 |
| 19 | 48950271 | 48951520 | H_c_231l23_M |
| 19 | 48993551 | 48996077 | H_c_207b15 |
| 19 | 49182183 | 49182302 | H_c_33g17 |
| 19 | 4919178 | 4920420 | H_c_149o20_M |
| 19 | 49220646 | 49221654 | H_c_152b16 |
| 19 | 49268823 | 49269033 | H_c_162h20 |
| 19 | 49293244 | 49293508 | H_c_6g08 |
| 19 | 49329597 | 49329691 | H_c135k19 |
| 19 | 49452785 | 49452957 | H_c_87e03 |
| 19 | 49644038 | 49644846 | H_c_187k24_M |
| 19 | 49695363 | 49696295 | H_c_101k08 |
| 19 | 49838113 | 49840393 | H_c_227g20_M |
| 19 | 49887154 | 49887863 | H_c_220c20 |
| 19 | 49942284 | 49944483 | H_c_208j05 |
| 19 | 50042569 | 50044629 | H_c_215e19 |
| 19 | 50085248 | 50086891 | H_c_151g12 |
| 19 | 50196092 | 50197396 | H_c_15e14_M |
| 19 | 50270201 | 50271738 | H_c_21i10 |
| 19 | 50286594 | 50288870 | H_c_193j23_M |
| 19 | 50347037 | 50349004 | H_c_77h21_M |
| 19 | 50373634 | 50374288 | H_c_249f06 |
| 19 | 50374289 | 50375305 | H_c_84g15_M |
| 19 | 50412455 | 50413813 | H_c_214e11 |
| 19 | 50429216 | 50431057 | H_c_66b10 |
| 19 | 50518831 | 50519797 | H_c_244b05 |
| 19 | 50564867 | 50566434 | H_c_272p20 |
| 19 | 50579324 | 50581615 | H_c_217e07_M |
| 19 | 50592860 | 50594351 | H_c_261b19 |
| 19 | 50601467 | 50602030 | H_c_191m11_M |
| 19 | 50618075 | 50619147 | H_c_55b05 |
| 19 | 50623067 | 50625287 | H_c_17j08_M |
| 19 | 50634539 | 50636353 | H_c_259o24_M |
| 19 | 50645567 | 50647115 | H_c_78e05 |
| 19 | 50662361 | 50663192 | H_c_205j24 |
| 19 | 50674093 | 50674375 | H_c_251m07 |
| 19 | 50693516 | 50694729 | H_c_272m03 |
| 19 | 50723522 | 50724688 | H_c142n22 |
| 19 | 50779783 | 50780098 | H_c_65p17_M |
| 19 | 50834339 | 50834710 | H_c_205h21_M |
| 19 | 50837099 | 50838142 | H_c_121p08_M |
| 19 | 50876599 | 50877293 | H_c_54o05 |
| 19 | 50886631 | 50888192 | H_c_208c10_M |
| 19 | 50902776 | 50904237 | H_c_266o18 |
| 19 | 50925630 | 50926754 | H_c_22n02 |
| 19 | 50986210 | 50987787 | H_c_190g20_M |
| 19 | 50987788 | 50988451 | H_c_265e20 |
| 19 | 51057871 | 51059839 | H_c_79o18_M |
| 19 | 51071222 | 51072531 | H_c_12h10 |
| 19 | 51080656 | 51081321 | H_c_208c24_M |
| 19 | 51096114 | 51098450 | H_c_190l03_M |
| 19 | 51121915 | 51123221 | H_c_261m24 |
| 19 | 51134642 | 51135589 | H_c_192h07 |
| 19 | 51215881 | 51218546 | H_c_21h06 |
| 19 | 51273746 | 51275082 | H_c_150k02_M |
| 19 | 51541618 | 51542849 | H_c_54h14 |
| 19 | 51665936 | 51667027 | H_c_102k13 |
| 19 | 51683098 | 51685516 | H_c_252p06_M |
| 19 | 51796585 | 51796754 | H_c132i22 |
| 19 | 5180023 | 5181319 | H_c_90o20_M |
| 19 | 51828959 | 51829752 | H_c_88b20 |
| 19 | 51855550 | 51857574 | H_c_206j23_M |
| 19 | 51896200 | 51896401 | H_c_175c18 |
| 19 | 51910657 | 51912171 | H_c_145i16_M |
| 19 | 51912176 | 51912434 | H_c_214d02_M |
| 19 | 51940394 | 51942808 | H_c_22e04_M |
| 19 | 51981079 | 51983247 | H_c_33c12_M |
| 19 | 52054811 | 52056742 | H_c_88p11 |
| 19 | 521032 | 524545 | H_c_64i18_M |
| 19 | 52214481 | 52217112 | H_c_210i03_M |
| 19 | 52242958 | 52244001 | H_c_66g02_M |
| 19 | 52306497 | 52308083 | H_c_123n06_M |
| 19 | 52336575 | 52336810 | H_c_242a21 |
| 19 | 52421152 | 52422133 | H_c_196o24_M |
| 19 | 52468912 | 52470898 | H_c_65g11_M |
| 19 | 52544430 | 52545202 | H_c_174e04 |
| 19 | 52624826 | 52626421 | H_c_48k12 |
| 19 | 52642420 | 52643441 | H_c_30c17_M |
| 19 | 52679091 | 52679239 | H_c135i11_M |
| 19 | 52709240 | 52710720 | H_c_161n01_M |
| 19 | 5273429 | 5273535 | H_c_60h02 |
| 19 | 52767599 | 52768759 | H_c_13e15 |
| 19 | 52802782 | 52804267 | H_c_259h21_M |
| 19 | 5290724 | 5292011 | H_c_87o21_M |
| 19 | 52937866 | 52939257 | H_c_257i22_M |
| 19 | 52973002 | 52974430 | H_c_54c05 |
| 19 | 53183131 | 53183244 | H_c_200k16 |
| 19 | 53364433 | 53366534 | H_c_204l07 |
| 19 | 53389560 | 53391718 | H_c_119h06 |
| 19 | 53528918 | 53529912 | H_c_251d01 |
| 19 | 53558095 | 53559579 | H_c_57p09 |
| 19 | 53608793 | 53611607 | H_c_85n11 |

TABLE 1-continued

| | | | |
|---|---|---|---|
| 19 | 53636617 | 53639405 | H_c_6h13_M |
| 19 | 53640760 | 53641312 | H_c_72m13 |
| 19 | 53675351 | 53676355 | H_c_262e18 |
| 19 | 53687646 | 53689389 | H_c_264n06_M |
| 19 | 53813653 | 53814636 | H_c_151a17 |
| 19 | 53819192 | 53820336 | H_c_229g07 |
| 19 | 53830485 | 53832932 | H_c_58k18_M |
| 19 | 53908171 | 53909850 | H_c_74m21 |
| 19 | 53915641 | 53917117 | H_c_5m11 |
| 19 | 53941768 | 53942940 | H_c_237c08_M |
| 19 | 53947198 | 53948511 | H_c_101i01 |
| 19 | 54094821 | 54096234 | H_c_74j12_M |
| 19 | 54128456 | 54128738 | H_c_17l10_M |
| 19 | 54149266 | 54151063 | H_c_202o19_M |
| 19 | 54159269 | 54161093 | H_c_70n06 |
| 19 | 54188175 | 54189828 | H_c_190f10 |
| 19 | 541995 | 543648 | H_c132i10_M |
| 19 | 54280044 | 54281363 | H_c_170m12 |
| 19 | 54308672 | 54310435 | H_c_152i03_M |
| 19 | 54313786 | 54314400 | H_c_71g01_M |
| 19 | 54322665 | 54323300 | H_c_181j24_M |
| 19 | 54327923 | 54329003 | H_c_148j05 |
| 19 | 54557037 | 54557937 | H_c_188i14 |
| 19 | 54617516 | 54619275 | H_c_107e02_M |
| 19 | 54622062 | 54624683 | H_c_236c02 |
| 19 | 54627038 | 54628536 | H_c_1a13_M |
| 19 | 54631254 | 54633625 | H_c_122c10_M |
| 19 | 54638371 | 54639509 | H_c_79n10 |
| 19 | 54646435 | 54647200 | H_c142m03 |
| 19 | 54648356 | 54650801 | H_c_177e17 |
| 19 | 54668730 | 54670930 | H_c141m18 |
| 19 | 54681044 | 54682808 | H_c_74h24_M |
| 19 | 54690166 | 54691367 | H_c_160n17 |
| 19 | 54694017 | 54696423 | H_c_103n08 |
| 19 | 54708282 | 54708670 | H_c_14n24 |
| 19 | 54728460 | 54729779 | H_c_189h21_M |
| 19 | 54761904 | 54763200 | H_c_232k12 |
| 19 | 54784517 | 54788272 | H_c_60i01_M |
| 19 | 54834893 | 54837858 | H_c_187d23_M |
| 19 | 5485865 | 5488021 | H_c_262e15 |
| 19 | 54859121 | 54861369 | H_c_239d20_M |
| 19 | 55005440 | 55008306 | H_c_183m17 |
| 19 | 55012682 | 55013645 | H_c_35h20 |
| 19 | 55027814 | 55029928 | H_c_27d02 |
| 19 | 55045537 | 55047106 | H_c_210k21_M |
| 19 | 55062384 | 55065424 | H_c_117c23_M_M |
| 19 | 55071654 | 55074935 | H_c_14j23_M |
| 19 | 55219861 | 55220831 | H_c_145m01_M |
| 19 | 55342567 | 55343323 | H_c_150l14 |
| 19 | 55387983 | 55389628 | H_c_162d17 |
| 19 | 55398108 | 55399048 | H_c139g07_M |
| 19 | 55520692 | 55524575 | H_c_3l16_M |
| 19 | 55571301 | 55572299 | H_c_114k15 |
| 19 | 55578811 | 55579870 | H_c_102d10_M |
| 19 | 55704787 | 55707067 | H_c_29i02_M |
| 19 | 5572926 | 5575081 | H_c_87n16_M |
| 19 | 55834519 | 55835488 | H_c_104l15_M |
| 19 | 55918595 | 55921156 | H_c_125f18 |
| 19 | 55923396 | 55923788 | H_c_51f20 |
| 19 | 55972633 | 55973408 | H_c_35m07_M |
| 19 | 56030773 | 56031930 | H_c_169i11 |
| 19 | 561754 | 562111 | H_c_171j02 |
| 19 | 56211652 | 56214803 | H_c_182i22_M |
| 19 | 5630087 | 5631692 | H_c142n04_M |
| 19 | 56303811 | 56304091 | H_c_103e19 |
| 19 | 5637054 | 5642198 | H_c139f08_M_M |
| 19 | 56536605 | 56536698 | H_c_17n09 |
| 19 | 56561224 | 56564030 | H_c_81c12 |
| 19 | 5670095 | 5671994 | H_c_211g18 |
| 19 | 56788755 | 56790518 | H_c_245f18_M |
| 19 | 56896786 | 56900615 | H_c_2j16_M |
| 19 | 56913884 | 56915029 | H_c_88k19_M |
| 19 | 57082594 | 57083176 | H_c_4m21_M |
| 19 | 57243790 | 57244033 | H_c_274o06_M |
| 19 | 57334935 | 57335313 | H_c_92a13_M |
| 19 | 57384508 | 57386524 | H_c_8a17_M |
| 19 | 5741463 | 5743764 | H_c_247f02_M |
| 19 | 57531110 | 57531513 | H_c_227g19 |
| 19 | 5754646 | 5757042 | H_c_82m08_M |
| 19 | 57592678 | 57592948 | H_c131c02 |
| 19 | 57796706 | 57796855 | H_c_121m12 |
| 19 | 58157760 | 58158286 | H_c_45f10 |
| 19 | 58354052 | 58354331 | H_c_203n08_M |
| 19 | 58449809 | 58450274 | H_c_116n16 |
| 19 | 5853661 | 5856418 | H_c_53o08 |
| 19 | 58715092 | 58716160 | H_c_139i08 |
| 19 | 58767908 | 58767982 | H_c_241g05 |
| 19 | 58827103 | 58828436 | H_c_189h17 |
| 19 | 589880 | 591281 | H_c_266h22 |
| 19 | 59063603 | 59064668 | H_c_248m02_M |
| 19 | 59077203 | 59079595 | H_c143f22_M |
| 19 | 59101746 | 59104939 | H_c_34c06_M |
| 19 | 59136283 | 59137953 | H_c_80n12 |
| 19 | 59139985 | 59140800 | H_c_64k06 |
| 19 | 5914263 | 5916384 | H_c_76o17 |
| 19 | 59174761 | 59178395 | H_c_199b07_M |
| 19 | 5927958 | 5931367 | H_c140o09_M |
| 19 | 59290095 | 59292429 | H_c_169f07 |
| 19 | 59297434 | 59298472 | H_c_236c22_M |
| 19 | 59331953 | 59332355 | H_c_252o06 |
| 19 | 59351996 | 59359483 | H_c_239j20_M_M |
| 19 | 59396127 | 59397689 | H_c_43p06_M |
| 19 | 59617458 | 59619431 | H_c_65c20_M |
| 19 | 59652130 | 59652914 | H_c_174h11 |
| 19 | 59667890 | 59669524 | H_c_129f23_M |
| 19 | 59674134 | 59674831 | H_c_168p06 |
| 19 | 5971934 | 5974448 | H_c_60b07 |
| 19 | 60265910 | 60267291 | H_c_83f15_M |
| 19 | 60283181 | 60285968 | H_c_9d10_M |
| 19 | 60288902 | 60290939 | H_c_188n24_M |
| 19 | 60320106 | 60321554 | H_c_64a13_M |
| 19 | 60337715 | 60338701 | H_c_128d17_M |
| 19 | 60343324 | 60344867 | H_c_19h20 |
| 19 | 60363336 | 60365373 | H_c_83j23_M |
| 19 | 60368470 | 60370064 | H_c_156e14 |
| 19 | 60376574 | 60377173 | H_c_178a19_M |
| 19 | 60458475 | 60459199 | H_c_127f22 |
| 19 | 60482219 | 60482956 | H_c_152f03 |
| 19 | 60483295 | 60484135 | H_c_105j23 |
| 19 | 60542077 | 60544323 | H_c_32c07 |
| 19 | 60572375 | 60573544 | H_c_226i23 |
| 19 | 60586262 | 60589859 | H_c_209b07_M |
| 19 | 6061007 | 6062019 | H_c_111i08_M |
| 19 | 60610180 | 60611392 | H_c_46p12_M |
| 19 | 60643227 | 60644151 | H_c_267c03 |
| 19 | 60664478 | 60665798 | H_c_212a22_M |
| 19 | 60705253 | 60707777 | H_c_164a13_M |
| 19 | 60719921 | 60720955 | H_c_211f04_M |
| 19 | 60788951 | 60789616 | H_c_3h01 |
| 19 | 60803160 | 60803996 | H_c_75i16_M |
| 19 | 60808547 | 60809500 | H_c_210b17_M |
| 19 | 60838035 | 60838279 | H_c_152j11_M |
| 19 | 60843116 | 60845648 | H_c_213i05_M |
| 19 | 60850994 | 60853291 | H_c_244d07_M |
| 19 | 60856313 | 60857687 | H_c_21p07 |
| 19 | 60857139 | 60857686 | H_c141n08_M |
| 19 | 60857687 | 60858622 | H_c_154l05_M |
| 19 | 60877871 | 60879114 | H_c_109m03 |
| 19 | 613023 | 614937 | H_c_181j04_M |
| 19 | 61343840 | 61345286 | H_c_63m16_M |
| 19 | 61420176 | 61421274 | H_c_54h02 |
| 19 | 6149877 | 6150895 | H_c_113c22_M |
| 19 | 61512509 | 61512616 | H_c_100a15 |
| 19 | 61571171 | 61571828 | H_c_38l06 |
| 19 | 61679816 | 61680860 | H_c_169e22_M |
| 19 | 61680959 | 61682655 | H_c_263j22 |
| 19 | 61710614 | 61711838 | H_c_116p14 |
| 19 | 61741163 | 61742933 | H_c137e15_M |
| 19 | 61797573 | 61799733 | H_c_223e13 |
| 19 | 61845912 | 61846946 | H_c_273m17 |
| 19 | 62015664 | 62015763 | H_c_13p06 |
| 19 | 62043128 | 62044293 | H_c_164b07_M |
| 19 | 62145959 | 62146235 | H_c_210n09 |
| 19 | 6228967 | 6231465 | H_c142d15 |
| 19 | 62309710 | 62310054 | H_c_197d16_M |
| 19 | 62566337 | 62568402 | H_c_22c04 |
| 19 | 626221 | 627097 | H_c_213m22 |
| 19 | 62702281 | 62704038 | H_c_82c03_M |
| 19 | 627096 | 629235 | H_c143h01_M |
| 19 | 62730234 | 62731098 | H_c_274l17_M |

TABLE 1-continued

| | | | |
|---|---|---|---|
| 19 | 62762107 | 62763227 | H_c__79g10_M |
| 19 | 62782239 | 62782313 | H_c__91a20 |
| 19 | 62787070 | 62788591 | H_c__17b23_M |
| 19 | 62802823 | 62804168 | H_c__194b02_M |
| 19 | 62817190 | 62817910 | H_c__49p10_M |
| 19 | 62884925 | 62885475 | H_c__23f14 |
| 19 | 62930274 | 62931359 | H_c__17j17 |
| 19 | 62972701 | 62974628 | H_c__4b12_M |
| 19 | 630037 | 632248 | H_c__106k10 |
| 19 | 6312466 | 6313131 | H_c__259g20_M |
| 19 | 63205358 | 63206386 | H_c__45a14 |
| 19 | 63212410 | 63213505 | H_c__162o13 |
| 19 | 6323566 | 6325194 | H_c__244o16_M |
| 19 | 63261747 | 63262894 | H_c142n20 |
| 19 | 63353208 | 63354136 | H_c__272f11_M |
| 19 | 63357491 | 63358703 | H_c143d21_M |
| 19 | 63386202 | 63387063 | H_c__123e08_M |
| 19 | 63431697 | 63432805 | H_c__2d15_M |
| 19 | 63481372 | 63482424 | H_c__70j21_M |
| 19 | 63505752 | 63506020 | H_c__197h13 |
| 19 | 63529489 | 63531427 | H_c__262n02 |
| 19 | 63550064 | 63551226 | H_c139o03 |
| 19 | 63565034 | 63566354 | H_c__239l23_M |
| 19 | 63583606 | 63584677 | H_c__31i14_M |
| 19 | 63587613 | 63590026 | H_c__131k21_M |
| 19 | 63590112 | 63591485 | H_c__56p01_M |
| 19 | 63603397 | 63604947 | H_c__90l20_M |
| 19 | 63702326 | 63704063 | H_c__82g08_M |
| 19 | 63716389 | 63718203 | H_c__40h08_M |
| 19 | 63721450 | 63723304 | H_c__272p08_M |
| 19 | 6374657 | 6376283 | H_c__191c19 |
| 19 | 63747096 | 63748860 | H_c__202j08_M |
| 19 | 63758285 | 63758908 | H_c__54h03 |
| 19 | 63760926 | 63762366 | H_c__50e06 |
| 19 | 63764658 | 63767364 | H_c__199p11_M |
| 19 | 63776214 | 63782033 | H_c__88m21_M_M |
| 19 | 63784409 | 63784975 | H_c__12b15 |
| 19 | 6409752 | 6411479 | H_c__71m20 |
| 19 | 6452167 | 6454872 | H_c__97h07 |
| 19 | 6541318 | 6542693 | H_c__33n21_M |
| 19 | 659389 | 661816 | H_c__246a19 |
| 19 | 6628578 | 6631174 | H_c__104c21 |
| 19 | 6659874 | 6662247 | H_c__258l04_M |
| 19 | 6672941 | 6673838 | H_c__220e09 |
| 19 | 6688182 | 6692515 | H_c__84i04_M_M |
| 19 | 7049737 | 7050808 | H_c__113j04_M |
| 19 | 7148062 | 7149699 | H_c__100d07_M |
| 19 | 7243749 | 7246347 | H_c__1a18_M |
| 19 | 7365648 | 7366721 | H_c__129b11_M |
| 19 | 746618 | 749886 | H_c__47f21_M |
| 19 | 7471362 | 7473314 | H_c134i08_M |
| 19 | 7486413 | 7487707 | H_c__252n22 |
| 19 | 7505049 | 7505210 | H_c__187g08_M |
| 19 | 7566217 | 7567956 | H_c__42i04 |
| 19 | 7607313 | 7608404 | H_c__99d10_M |
| 19 | 7651267 | 7652019 | H_c__244m16 |
| 19 | 7652524 | 7654850 | H_c__66k14 |
| 19 | 772026 | 774568 | H_c__270e14 |
| 19 | 7770910 | 7771088 | H_c__26i10_M |
| 19 | 7800282 | 7802143 | H_c__195h03 |
| 19 | 7830101 | 7834874 | H_c__93g16_M |
| 19 | 7890746 | 7891796 | H_c__239k22_M |
| 19 | 7895167 | 7897670 | H_c__61n06_M |
| 19 | 7914131 | 7914686 | H_c__12l20_M |
| 19 | 801454 | 802657 | H_c__123i04 |
| 19 | 803081 | 804597 | H_c__22l09 |
| 19 | 811366 | 816736 | H_c__226n13_M |
| 19 | 8119351 | 8120881 | H_c__19d06_M |
| 19 | 8178659 | 8180781 | H_c__226j13_M |
| 19 | 8278819 | 8279499 | H_c__7b02_M |
| 19 | 8303744 | 8305087 | H_c__73a17_M |
| 19 | 8313605 | 8315000 | H_c__82a19 |
| 19 | 8334020 | 8335803 | H_c__192i01_M |
| 19 | 8360875 | 8362013 | H_c__194h06_M |
| 19 | 8383883 | 8384874 | H_c__240a16_M |
| 19 | 8415461 | 8416811 | H_c__268c09_M |
| 19 | 8476584 | 8477998 | H_c__111b06 |
| 19 | 8483048 | 8485359 | H_c__88d05_M |
| 19 | 8580554 | 8582582 | H_c__34d12 |
| 19 | 862839 | 864663 | H_c__60d07_M |
| 19 | 8803537 | 8804978 | H_c__186i10_M |
| 19 | 889890 | 892624 | H_c131g19_M |
| 19 | 9111781 | 9112287 | H_c__37k23 |
| 19 | 9165186 | 9165313 | H_c134f21 |
| 19 | 9315496 | 9315625 | H_c__79p17 |
| 19 | 933289 | 934085 | H_c__35c22 |
| 19 | 935016 | 935866 | H_c__203m10_M |
| 19 | 9357922 | 9358211 | H_c__57l16 |
| 19 | 9406446 | 9408237 | H_c__110g01_M |
| 19 | 945713 | 948177 | H_c__214d05 |
| 19 | 9509647 | 9510267 | H_c__266b06 |
| 19 | 9592410 | 9593468 | H_c131d16 |
| 19 | 9740079 | 9743755 | H_c__9h13_M |
| 19 | 9757095 | 9758077 | H_c__252g13_M |
| 19 | 976608 | 978306 | H_c__207f11_M |
| 19 | 9789424 | 9791529 | H_c__203a13_M |
| 19 | 9799595 | 9800062 | H_c__24j20_M |
| 19 | 9806439 | 9807586 | H_c__158h01_M |
| 19 | 9862550 | 9864386 | H_c__195b23_M |
| 19 | 9884606 | 9886460 | H_c__2b11_M |
| 19 | 9906851 | 9908906 | H_c__22p07_M |
| 20 | 10147281 | 10147448 | H_c__75i13 |
| 20 | 10362149 | 10363025 | H_c__265c17 |
| 20 | 1046978 | 1048623 | H_c__179c02 |
| 20 | 10519813 | 10519900 | H_c__45g14 |
| 20 | 10600799 | 10600985 | H_c__28o22 |
| 20 | 11416337 | 11416777 | H_c__196k09 |
| 20 | 11508912 | 11509076 | H_c__190b12 |
| 20 | 1153951 | 1155490 | H_c133b15 |
| 20 | 11819206 | 11820493 | H_c80m24 |
| 20 | 1194838 | 1195521 | H_c__111h17_M |
| 20 | 1252864 | 1254266 | H_c__111g20 |
| 20 | 13148670 | 13151201 | H_c__219b23 |
| 20 | 1320740 | 1321952 | H_c__48f10_M |
| 20 | 13566832 | 13567868 | H_c140n20_M |
| 20 | 13713108 | 13714426 | H_c__7j23 |
| 20 | 13923487 | 13925267 | H_c__61b04_M |
| 20 | 13943051 | 13943253 | H_c__23o03 |
| 20 | 1394862 | 1395810 | H_c__244c15_M |
| 20 | 14229331 | 14229532 | H_c__187f11 |
| 20 | 14370436 | 14370618 | H_c__49e10 |
| 20 | 14818499 | 14818694 | H_c__266o06 |
| 20 | 16070435 | 16070510 | H_c__71i05 |
| 20 | 16501786 | 16503898 | H_c__231m21_M |
| 20 | 16588992 | 16589119 | H_c__120g13 |
| 20 | 16698118 | 16698219 | H_c__208l10 |
| 20 | 16748190 | 16748293 | H_c__129d24 |
| 20 | 16777043 | 16777127 | H_c__17k18 |
| 20 | 16969797 | 16969917 | H_c__94l10 |
| 20 | 17071324 | 17071683 | H_c__156f17 |
| 20 | 1731742 | 1732783 | H_c__39o02_M |
| 20 | 17382165 | 17382264 | H_c__91b16 |
| 20 | 17395349 | 17395656 | H_c__116o14 |
| 20 | 17459443 | 17460346 | H_c__89c19_M |
| 20 | 17608856 | 17610254 | H_c__44n13 |
| 20 | 17896712 | 17897759 | H_c__12k22_M |
| 20 | 17984712 | 17986486 | H_c__28k21 |
| 20 | 17987081 | 17988263 | H_c__69e05_M |
| 20 | 18216648 | 18218001 | H_c__128n08_M |
| 20 | 1822886 | 1825052 | H_c__198a07_M |
| 20 | 18395215 | 18396650 | H_c__24k24 |
| 20 | 18436057 | 18436964 | H_c136i22 |
| 20 | 18496029 | 18496325 | H_c__53p10_M |
| 20 | 18516273 | 18517156 | H_c138g06 |
| 20 | 18605696 | 18605816 | H_c131o02 |
| 20 | 1875541 | 1876575 | H_c__162i21 |
| 20 | 19139343 | 19142048 | H_c__176n05 |
| 20 | 19685996 | 19687885 | H_c__127j18_M |
| 20 | 19704911 | 19705585 | H_c__14b16_M |
| 20 | 19945622 | 19946614 | H_c__79n19_M |
| 20 | 19980491 | 19981538 | H_c__154k01_M |
| 20 | 20190203 | 20190296 | H_c__173b21 |
| 20 | 20293920 | 20299011 | H_c__246c06_M_M |
| 20 | 2030097 | 2032243 | H_c__129p14_M |
| 20 | 20640802 | 20642188 | H_c__232d18_M |
| 20 | 20937067 | 20937295 | H_c__248k22 |
| 20 | 20947978 | 20949053 | H_c__221n15 |
| 20 | 2100862 | 2101906 | H_c__148n14 |
| 20 | 21028817 | 21030340 | H_c__215g05_M |
| 20 | 21084987 | 21085077 | H_c__92g24 |

TABLE 1-continued

| | | | |
|---|---|---|---|
| 20 | 21231449 | 21232786 | H_c_8j12_M |
| 20 | 21324299 | 21326639 | H_c142g01_M |
| 20 | 2135518 | 2136657 | H_c_223j21_M |
| 20 | 21434205 | 21435242 | H_c_30j16_M |
| 20 | 21439146 | 21442865 | H_c_87i15_M_M |
| 20 | 21449654 | 21451767 | H_c_213o07_M |
| 20 | 21631085 | 21635729 | H_c_2i13_M |
| 20 | 21642525 | 21644326 | H_c_265g18 |
| 20 | 22037321 | 22037511 | H_c_13p22 |
| 20 | 22382173 | 22382319 | H_c_59h06_M |
| 20 | 22403393 | 22403534 | H_c_117d04 |
| 20 | 22496957 | 22497812 | H_c_41j14 |
| 20 | 22506103 | 22507312 | H_c143e22_M |
| 20 | 22510491 | 22512630 | H_c_61g01_M |
| 20 | 22512983 | 22513915 | H_c_66a23_M |
| 20 | 225789 | 227231 | H_c_76j06_M |
| 20 | 22924667 | 22924974 | H_c_87k04 |
| 20 | 22979523 | 22979635 | H_c_77d14 |
| 20 | 23279042 | 23279954 | H_c_39a21 |
| 20 | 23286339 | 23287236 | H_c_101l03_M |
| 20 | 23289846 | 23292410 | H_c_38i23_M |
| 20 | 23348953 | 23350311 | H_c_169p08_M |
| 20 | 23565854 | 23567667 | H_c_266m02 |
| 20 | 23925054 | 23925198 | H_c_223a15 |
| 20 | 24363385 | 24364567 | H_c_242k18 |
| 20 | 24397694 | 24400100 | H_c_66e17_M |
| 20 | 24407699 | 24409054 | H_c_82n02 |
| 20 | 2452984 | 2453856 | H_c132l21_M |
| 20 | 24861917 | 24864164 | H_c_34o11 |
| 20 | 2486934 | 2487852 | H_c_207c06_M |
| 20 | 24985391 | 24986414 | H_c_53l06_M |
| 20 | 24986415 | 24987222 | H_c_241g15_M |
| 20 | 25011546 | 25013595 | H_c_15g19_M |
| 20 | 25108395 | 25108682 | H_c_13n20 |
| 20 | 25123832 | 25126097 | H_c_265l03_M |
| 20 | 25175540 | 25177779 | H_c_78j01_M |
| 20 | 252767 | 256056 | H_c131k07_M |
| 20 | 25318002 | 25319866 | H_c_54d12_M |
| 20 | 25370297 | 25370395 | H_c_63i15 |
| 20 | 25513161 | 25514520 | H_c_9f09_M |
| 20 | 25551999 | 25553383 | H_c_89i09_M |
| 20 | 256058 | 256153 | H_c_180l20_M |
| 20 | 25624613 | 25625817 | H_c_213c17 |
| 20 | 2580633 | 2581792 | H_c_86k18_M |
| 20 | 2592107 | 2593035 | H_c_207k01 |
| 20 | 2679945 | 2681835 | H_c_114f21_M |
| 20 | 2768141 | 2770633 | H_c_100c22_M |
| 20 | 2797111 | 2797341 | H_c_226d05 |
| 20 | 2800388 | 2802747 | H_c_31a06 |
| 20 | 29512170 | 29512296 | H_c_141i07 |
| 20 | 29565582 | 29566912 | H_c_191f24 |
| 20 | 29619107 | 29620985 | H_c_154p13_M |
| 20 | 29624218 | 29625633 | H_c_74h13 |
| 20 | 29638862 | 29639891 | H_c_85e05_M |
| 20 | 29656765 | 29657690 | H_c_65g04_M |
| 20 | 29664176 | 29665023 | H_c_189f19 |
| 20 | 2973715 | 2975610 | H_c_235h19_M |
| 20 | 29774493 | 29775611 | H_c_181m11_M |
| 20 | 29790404 | 29791165 | H_c_80m08_M |
| 20 | 29900905 | 29901559 | H_c_65d20 |
| 20 | 29912617 | 29914640 | H_c_188f23 |
| 20 | 29921268 | 29922723 | H_c_209b04_M |
| 20 | 29931036 | 29931885 | H_c_68h18_M |
| 20 | 3000208 | 3001874 | H_c_17h11 |
| 20 | 30003248 | 30003532 | H_c_92k14_M |
| 20 | 30018348 | 30020485 | H_c_240i07 |
| 20 | 30046301 | 30047262 | H_c_38h20 |
| 20 | 30070086 | 30071186 | H_c_84e16_M |
| 20 | 30082334 | 30083249 | H_c_257c02_M |
| 20 | 30103297 | 30104270 | H_c_35g12_M |
| 20 | 30161144 | 30162481 | H_c_19a07 |
| 20 | 3021341 | 3022597 | H_c_22g13_M |
| 20 | 30240794 | 30242245 | H_c_12l24 |
| 20 | 30257819 | 30260471 | H_c_253o22_M |
| 20 | 3028815 | 3030718 | H_c_67d08 |
| 20 | 30328545 | 30329797 | H_c_81c18_M |
| 20 | 30406490 | 30406726 | H_c_119h22_M |
| 20 | 30409447 | 30411455 | H_c_73h03_M |
| 20 | 30534095 | 30536711 | H_c_75b18_M |
| 20 | 30587634 | 30588150 | H_c_192o16_M |
| 20 | 30630253 | 30632823 | H_c_251n09 |
| 20 | 30813441 | 30814012 | H_c_27p16_M |
| 20 | 30862166 | 30862300 | H_c_102a07 |
| 20 | 30870982 | 30871958 | H_c_86d09 |
| 20 | 309036 | 311598 | H_c_227i12 |
| 20 | 3092263 | 3094721 | H_c_127b05 |
| 20 | 3100982 | 3103128 | H_c_65a15_M |
| 20 | 31232546 | 31234566 | H_c_92g16 |
| 20 | 3137717 | 3138548 | H_c_7c16 |
| 20 | 31452492 | 31453112 | H_c_272e18_M |
| 20 | 3146934 | 3147836 | H_c_57c14_M |
| 20 | 31493976 | 31495645 | H_c_77a20_M |
| 20 | 31541098 | 31541408 | H_c_252h19_M |
| 20 | 3168231 | 3169992 | H_c_26m07_M |
| 20 | 31714409 | 31715331 | H_c_81k14_M |
| 20 | 31736694 | 31739263 | H_c_109p12_M |
| 20 | 3176877 | 3178087 | H_c_227n18 |
| 20 | 31771586 | 31773304 | H_c_93g08_M |
| 20 | 32044549 | 32046223 | H_c_212c15_M |
| 20 | 32163271 | 32164537 | H_c_7i20 |
| 20 | 32319888 | 32320946 | H_c_202p04 |
| 20 | 32414608 | 32415546 | H_c_217f04 |
| 20 | 32566873 | 32568654 | H_c_130f22_M |
| 20 | 32609451 | 32610153 | H_c_27p21_M |
| 20 | 32727978 | 32728873 | H_c_77b08_M |
| 20 | 32755095 | 32757164 | H_c_26g12_M |
| 20 | 32759949 | 32761863 | H_c_6m23_M |
| 20 | 32874314 | 32874507 | H_c_117f11 |
| 20 | 32876045 | 32877523 | H_c_61f05 |
| 20 | 32924017 | 32925065 | H_c_145m08_M |
| 20 | 32927715 | 32928747 | H_c141g06 |
| 20 | 33005673 | 33007304 | H_c_256g18 |
| 20 | 33143435 | 33144593 | H_c_127j14_M |
| 20 | 3314999 | 3315118 | H_c_84o14 |
| 20 | 33197909 | 33198948 | H_c_91c17_M |
| 20 | 33277605 | 33279060 | H_c_230j16_M |
| 20 | 33329170 | 33330156 | H_c_120n17_M |
| 20 | 3335578 | 3336452 | H_c_199b08 |
| 20 | 3336454 | 3336935 | H_c137d19_M |
| 20 | 33580132 | 33581101 | H_c_101l21 |
| 20 | 33592935 | 33594201 | H_c_12h12 |
| 20 | 33643054 | 33643209 | H_c_103p21 |
| 20 | 33652254 | 33653066 | H_c_214i21_M |
| 20 | 33667055 | 33667789 | H_c_212f10_M |
| 20 | 33715229 | 33716555 | H_c_266b16_M |
| 20 | 33749676 | 33751276 | H_c_183k05_M |
| 20 | 33792865 | 33794254 | H_c_42h01_M |
| 20 | 33952935 | 33953005 | H_c_3b20 |
| 20 | 3398817 | 3400542 | H_c_186i03_M |
| 20 | 33996363 | 33996671 | H_c_22m09 |
| 20 | 34287635 | 34288040 | H_c_196d21 |
| 20 | 34522260 | 34524973 | H_c_12k02_M |
| 20 | 34634922 | 34637059 | H_c_213a21 |
| 20 | 34744079 | 34744172 | H_c_4o03 |
| 20 | 34807345 | 34808242 | H_c_24h18_M |
| 20 | 34835088 | 34836003 | H_c_35e17 |
| 20 | 35012645 | 35013887 | H_c_199f15_M |
| 20 | 35157291 | 35158772 | H_c133k09 |
| 20 | 35199251 | 35199390 | H_c_99d04 |
| 20 | 35240766 | 35241719 | H_c_119p24_M |
| 20 | 35351286 | 35352045 | H_c_116o06_M |
| 20 | 35444818 | 35447311 | H_c137d24_M |
| 20 | 35468229 | 35468720 | H_c_146j22_M |
| 20 | 35582003 | 35583528 | H_c_31l08_M |
| 20 | 35588669 | 35590314 | H_c_209n08_M |
| 20 | 35625460 | 35626914 | H_c_251k04_M |
| 20 | 35755320 | 35756496 | H_c_170a02_M |
| 20 | 35763501 | 35763868 | H_c_6a18_M |
| 20 | 3587916 | 3590336 | H_c_74f11_M |
| 20 | 35963910 | 35965858 | H_c_73d03_M |
| 20 | 3601855 | 3603016 | H_c_27m04 |
| 20 | 36094896 | 36096093 | H_c_94d20 |
| 20 | 3609885 | 3611400 | H_c_205m21_M |
| 20 | 36322061 | 36322858 | H_c142c08_M |
| 20 | 36461355 | 36461559 | H_c_78i05 |
| 20 | 36463329 | 36464651 | H_c_156o15 |
| 20 | 36496860 | 36497557 | H_c_253l21 |
| 20 | 3660419 | 3662295 | H_c_250g12_M |
| 20 | 36707424 | 36708648 | H_c_243n16 |
| 20 | 36736164 | 36736849 | H_c_232j20_M |

TABLE 1-continued

| | | | |
|---|---|---|---|
| 20 | 36789433 | 36790805 | H_c_31e16_M |
| 20 | 3680746 | 3681921 | H_c133g15_M |
| 20 | 36809990 | 36810304 | H_c137h08_M |
| 20 | 36931882 | 36931974 | H_c_23k20 |
| 20 | 3695018 | 3697413 | H_c_57p13_M |
| 20 | 36988273 | 36989300 | H_c_247j02 |
| 20 | 37024010 | 37024682 | H_c_101h16_M |
| 20 | 37053105 | 37053302 | H_c_66g12 |
| 20 | 3706173 | 3708582 | H_c_195f05 |
| 20 | 3712830 | 3715690 | H_c_264n19 |
| 20 | 3724503 | 3724692 | H_c_271c01 |
| 20 | 3748620 | 3749554 | H_c_120k03_M |
| 20 | 37525932 | 37526061 | H_c_62i20 |
| 20 | 37626454 | 37626626 | H_c_234c02 |
| 20 | 3817221 | 3818791 | H_c_149o09_M |
| 20 | 38242274 | 38242381 | H_c_47d20 |
| 20 | 38749565 | 38755644 | H_c_229e07_M_M |
| 20 | 390500 | 391669 | H_c_187m23_M |
| 20 | 39090548 | 39091991 | H_c_108h02_M |
| 20 | 39378892 | 39380089 | H_c_159d24 |
| 20 | 39391618 | 39391967 | H_c_197f23 |
| 20 | 39680379 | 39682094 | H_c_58k15 |
| 20 | 39692711 | 39692825 | H_c_56m18 |
| 20 | 40806923 | 40807489 | H_c136b14 |
| 20 | 4100773 | 4101595 | H_c_193d17 |
| 20 | 41249960 | 41252803 | H_c_77o01_M |
| 20 | 4150173 | 4151382 | H_c_212h16_M |
| 20 | 41519572 | 41520979 | H_c_88g16_M |
| 20 | 41652853 | 41653368 | H_c_28k23_M |
| 20 | 41728743 | 41729398 | H_c_44h16 |
| 20 | 4175857 | 4178719 | H_c_29h19_M |
| 20 | 41976350 | 41978660 | H_c_242n02_M |
| 20 | 42176323 | 42178599 | H_c_63m20 |
| 20 | 42272163 | 42274028 | H_c_162n14_M |
| 20 | 42360683 | 42362219 | H_c_63d08 |
| 20 | 42372375 | 42374057 | H_c_187k10_M |
| 20 | 42388631 | 42388694 | H_c_159d12_M |
| 20 | 42537684 | 42538552 | H_c_8a10_M |
| 20 | 42583621 | 42584353 | H_c_88p04_M |
| 20 | 42593293 | 42594277 | H_c_17b22 |
| 20 | 42713784 | 42714167 | H_c_28c14_M |
| 20 | 42807269 | 42808909 | H_c_27l13 |
| 20 | 42811756 | 42813814 | H_c_23j10_M |
| 20 | 42909372 | 42909500 | H_c_231j06 |
| 20 | 42932289 | 42932353 | H_c_56i21 |
| 20 | 42947249 | 42948348 | H_c_3d02_M |
| 20 | 43028064 | 43029023 | H_c_166p23_M |
| 20 | 43159621 | 43160808 | H_c_99a02_M |
| 20 | 43162743 | 43163387 | H_c_37m19 |
| 20 | 43355060 | 43355887 | H_c_253g09_M |
| 20 | 43366050 | 43367346 | H_c_238g06 |
| 20 | 43368363 | 43369654 | H_c_102f18 |
| 20 | 43409329 | 43410888 | H_c_33i09_M |
| 20 | 43425004 | 43425957 | H_c_148p01_M |
| 20 | 43467602 | 43470146 | H_c_53g10 |
| 20 | 43531619 | 43533097 | H_c_114n15_M |
| 20 | 43853651 | 43854293 | H_c_184p03_M |
| 20 | 43874485 | 43875259 | H_c_87l14_M |
| 20 | 43918904 | 43919742 | H_c_104m11 |
| 20 | 43942779 | 43944213 | H_c_72l24 |
| 20 | 43952192 | 43954690 | H_c_91e16_M |
| 20 | 43973064 | 43973550 | H_c_149j04_M |
| 20 | 43996233 | 43997520 | H_c_82d08_M |
| 20 | 44032784 | 44034872 | H_c_118k21 |
| 20 | 44072255 | 44074924 | H_c_196a22_M |
| 20 | 44075134 | 44077088 | H_c_232l08_M |
| 20 | 44119364 | 44120106 | H_c_179b04_M |
| 20 | 44194313 | 44195051 | H_c_80d14 |
| 20 | 44236330 | 44237337 | H_c_15f03_M |
| 20 | 44271920 | 44272941 | H_c_36j23_M |
| 20 | 44312997 | 44313825 | H_c_64a17 |
| 20 | 44354556 | 44354847 | H_c_36f10_M |
| 20 | 44374553 | 44374981 | H_c_56j04_M |
| 20 | 4439808 | 4440090 | H_c_110i06 |
| 20 | 44425557 | 44426906 | H_c_32k17_M |
| 20 | 44468034 | 44468768 | H_c_37d11 |
| 20 | 44574887 | 44575779 | H_c_188m16 |
| 20 | 44626012 | 44626148 | H_c_197o19 |
| 20 | 44722201 | 44722442 | H_c_212e23_M |
| 20 | 44751009 | 44752023 | H_c_173g21 |
| 20 | 44956104 | 44957749 | H_c_31n18_M |
| 20 | 45380161 | 45380259 | H_c_32l21 |
| 20 | 45563811 | 45564135 | H_c_234p08_M |
| 20 | 45784585 | 45786375 | H_c_18h09 |
| 20 | 45847770 | 45848722 | H_c_168l20_M |
| 20 | 45993088 | 45993479 | H_c_248h12 |
| 20 | 4614949 | 4616152 | H_c133b17_M |
| 20 | 46163542 | 46163798 | H_c_170d22 |
| 20 | 46706842 | 46708366 | H_c_171o19 |
| 20 | 46877295 | 46879617 | H_c_9a07 |
| 20 | 4689284 | 4690297 | H_c_157d02 |
| 20 | 46969830 | 46972684 | H_c_248k13 |
| 20 | 47095418 | 47097192 | H_c_172b13 |
| 20 | 47326966 | 47328811 | H_c_194a15_M |
| 20 | 47368002 | 47369146 | H_c_228o20_M |
| 20 | 47463713 | 47464986 | H_c_32n21 |
| 20 | 4750837 | 4753205 | H_c_6k18_M |
| 20 | 47533234 | 47534297 | H_c_157k18 |
| 20 | 47660964 | 47661605 | H_c_141h10_M |
| 20 | 47732331 | 47732565 | H_c_141p09 |
| 20 | 47762573 | 47764840 | H_c_7k10_M |
| 20 | 47964931 | 47966019 | H_c_103c11_M |
| 20 | 47986061 | 47986869 | H_c_211h15_M |
| 20 | 48162720 | 48163460 | H_c_33d10_M |
| 20 | 48202426 | 48204011 | H_c_35l01_M |
| 20 | 48240180 | 48242084 | H_c132d03_M |
| 20 | 48560002 | 48561407 | H_c_99o21 |
| 20 | 48780661 | 48782028 | H_c_211f11_M |
| 20 | 48844709 | 48845557 | H_c_118e14 |
| 20 | 48980072 | 48981942 | H_c_116d19 |
| 20 | 4901533 | 4901652 | H_c_179j23 |
| 20 | 4929395 | 4930567 | H_c_78m06_M |
| 20 | 49612188 | 49613924 | H_c_270h03 |
| 20 | 49817038 | 49819463 | H_c_39d20_M |
| 20 | 49850619 | 49852545 | H_c_167m04_M |
| 20 | 50154383 | 50156292 | H_c_130f04_M |
| 20 | 50217759 | 50217853 | H_c_204i05 |
| 20 | 50241056 | 50242934 | H_c_157e11 |
| 20 | 5041688 | 5041881 | H_c_41l14_M |
| 20 | 5048601 | 5049078 | H_c_160b09_M |
| 20 | 5055274 | 5056517 | H_c_26n04_M |
| 20 | 50893466 | 50893886 | H_c_253n17 |
| 20 | 51021833 | 51022200 | H_c_254o03 |
| 20 | 51110395 | 51110556 | H_c_206n21 |
| 20 | 51642965 | 51644723 | H_c_196e19_M |
| 20 | 51709801 | 51710476 | H_c_117g08 |
| 20 | 52222487 | 52224536 | H_c_83l15_M |
| 20 | 52257837 | 52258933 | H_c_186m03_M |
| 20 | 52439230 | 52439292 | H_c_189j16 |
| 20 | 52525098 | 52526330 | H_c_84m15_M |
| 20 | 538195 | 539605 | H_c_39k19_M |
| 20 | 53942019 | 53942112 | H_c_212p11 |
| 20 | 54011447 | 54014112 | H_c_185e17_M |
| 20 | 54400797 | 54401177 | H_c_30l10_M |
| 20 | 54476724 | 54477372 | H_c_15h21 |
| 20 | 54634557 | 54637967 | H_c_57i07_M |
| 20 | 54637974 | 54640223 | H_c134c01_M |
| 20 | 54666977 | 54667969 | H_c_92g13 |
| 20 | 54909925 | 54910126 | H_c_22i22 |
| 20 | 54933581 | 54934262 | H_c_83h17_M |
| 20 | 55273195 | 55275507 | H_c_50b09 |
| 20 | 55359067 | 55359913 | H_c_15f07_M |
| 20 | 5538719 | 5540387 | H_c_152f18_M |
| 20 | 55397106 | 55398092 | H_c_28l09_M |
| 20 | 55398093 | 55399432 | H_c_72d17 |
| 20 | 55852315 | 55853784 | H_c_274f22 |
| 20 | 55868278 | 55869374 | H_c_104i07 |
| 20 | 55900932 | 55901073 | H_c_31j07 |
| 20 | 55952758 | 55952955 | H_c_258a01 |
| 20 | 56042017 | 56042240 | H_c_49o23_M |
| 20 | 56188070 | 56188340 | H_c_91j13 |
| 20 | 56234698 | 56237376 | H_c_245o14_M |
| 20 | 56245102 | 56245817 | H_c_150m13_M |
| 20 | 56279827 | 56279985 | H_c_252h08 |
| 20 | 56397425 | 56399297 | H_c_257l21_M |
| 20 | 56508462 | 56508657 | H_c_62g14 |
| 20 | 56658309 | 56660484 | H_c_214g09_M |
| 20 | 5676883 | 5677074 | H_c_202d13 |
| 20 | 56848376 | 56850556 | H_c_8j10_M |
| 20 | 56860796 | 56861623 | H_c_158n21 |

TABLE 1-continued

| | | | |
|---|---|---|---|
| 20 | 56989376 | 56990209 | H_c_150f21_M |
| 20 | 57015774 | 57017747 | H_c_186c20 |
| 20 | 57040247 | 57041179 | H_c_267l22_M |
| 20 | 57050351 | 57052073 | H_c132a14_M |
| 20 | 57231046 | 57232234 | H_c_65c17_M |
| 20 | 57307997 | 57310584 | H_c_215p20_M |
| 20 | 57360062 | 57360307 | H_c_232m24 |
| 20 | 57552126 | 57552292 | H_c_165l05 |
| 20 | 57585510 | 57586927 | H_c_79h04_M |
| 20 | 57613364 | 57614369 | H_c_175g13_M |
| 20 | 57685285 | 57685499 | H_c_13b05 |
| 20 | 5792242 | 5792483 | H_c137b09 |
| 20 | 57940784 | 57942744 | H_c_22d19_M |
| 20 | 57947045 | 57949165 | H_c_228g20_M |
| 20 | 57979963 | 57980117 | H_c_185d02 |
| 20 | 58095676 | 58096393 | H_c_76o11_M |
| 20 | 581411 | 581871 | H_c_21f18_M |
| 20 | 581870 | 582312 | H_c_241g21 |
| 20 | 5839680 | 5840710 | H_c_70j24_M |
| 20 | 58544033 | 58544144 | H_c_78f01 |
| 20 | 58737857 | 58738057 | H_c_53p19_M |
| 20 | 5878949 | 5879768 | H_c_38l09_M |
| 20 | 5920673 | 5920827 | H_c_221j11 |
| 20 | 59259156 | 59259470 | H_c_259e07 |
| 20 | 5934355 | 5935513 | H_c_194l24_M |
| 20 | 5980508 | 5982258 | H_c_199b16 |
| 20 | 59809825 | 59814126 | H_c_236a16_M |
| 20 | 59983047 | 59983266 | H_c_188j10 |
| 20 | 60043783 | 60044030 | H_c_234d20_M |
| 20 | 60074483 | 60075060 | H_c_105f05 |
| 20 | 60130210 | 60131857 | H_c_124d04_M |
| 20 | 60190965 | 60191890 | H_c_160g09 |
| 20 | 60246387 | 60247661 | H_c_8f21_M |
| 20 | 602732 | 605319 | H_c_205k01_M |
| 20 | 60394573 | 60396307 | H_c_28b01_M |
| 20 | 60478166 | 60479458 | H_c_238k12 |
| 20 | 6051311 | 6051793 | H_c_246d20 |
| 20 | 60743457 | 60745596 | H_c_3o09 |
| 20 | 60785026 | 60785959 | H_c_87d16_M |
| 20 | 60810026 | 60811984 | H_c_30k15_M |
| 20 | 60828037 | 60830320 | H_c_207k12_M |
| 20 | 60893675 | 60896173 | H_c_139h01_M |
| 20 | 60896176 | 60896559 | H_c_56f20_M |
| 20 | 61027471 | 61028572 | H_c_235g10 |
| 20 | 61039043 | 61040368 | H_c_123c09_M |
| 20 | 61106691 | 61110738 | H_c_232b21_M |
| 20 | 61126526 | 61127518 | H_c_9j06 |
| 20 | 61173278 | 61174679 | H_c_210l19 |
| 20 | 61204104 | 61204817 | H_c_266j21_M |
| 20 | 61234711 | 61235634 | H_c_209f16 |
| 20 | 61276780 | 61281421 | H_c_158o07_M |
| 20 | 61316900 | 61319712 | H_c_240g08 |
| 20 | 61355358 | 61356474 | H_c_52i04_M |
| 20 | 61373874 | 61375339 | H_c_75c04_M |
| 20 | 61620660 | 61624469 | H_c_149b23_M |
| 20 | 61675616 | 61676703 | H_c_60e10_M |
| 20 | 61675735 | 61676693 | H_c_94j21 |
| 20 | 61809385 | 61810942 | H_c_1h09_M |
| 20 | 61931987 | 61932268 | H_c_190b08_M |
| 20 | 61966052 | 61967823 | H_c_249c15 |
| 20 | 61996593 | 61997593 | H_c_56o13_M |
| 20 | 62056748 | 62058950 | H_c_25a14 |
| 20 | 62070787 | 62072191 | H_c_83j12_M |
| 20 | 62140333 | 62141551 | H_c_229k14 |
| 20 | 62144152 | 62144963 | H_c_165p05_M |
| 20 | 62184652 | 62187069 | H_c_247c03_M |
| 20 | 62204567 | 62204823 | H_c_128b19 |
| 20 | 62366428 | 62366647 | H_c_234a21 |
| 20 | 6291537 | 6291613 | H_c_205h09 |
| 20 | 6372676 | 6372781 | H_c_149d21 |
| 20 | 638637 | 638730 | H_c_33k08_M |
| 20 | 656449 | 657319 | H_c_78a20_M |
| 20 | 6695853 | 6697768 | H_c_12j11_M |
| 20 | 7448503 | 7448635 | H_c_203n10 |
| 20 | 769537 | 770761 | H_c_23l24_M |
| 20 | 772925 | 774064 | H_c_229g08_M |
| 20 | 7903714 | 7903863 | H_c_153g01_M |
| 20 | 7947507 | 7948665 | H_c_76o10 |
| 20 | 7997869 | 7997969 | H_c_41a22 |
| 20 | 8060230 | 8062417 | H_c_85d06_M |
| 20 | 8250805 | 8250946 | H_c_229f24 |
| 20 | 8429434 | 8429549 | H_c_261d21 |
| 20 | 8619651 | 8619783 | H_c_239a16 |
| 20 | 8653896 | 8654039 | H_c_149f06 |
| 20 | 8996813 | 8998252 | H_c_215h24_M |
| 20 | 9234320 | 9234422 | H_c_152b07 |
| 20 | 930580 | 931313 | H_c_22k24_M |
| 20 | 9434661 | 9436438 | H_c_29p20_M |
| 20 | 9443922 | 9444849 | H_c_29m10_M |
| 20 | 9766593 | 9767927 | H_c_271l06 |
| 20 | 9963357 | 9964396 | H_c_198j03 |
| 21 | 10090066 | 10090178 | H_c_50e12 |
| 21 | 10104008 | 10104152 | H_c_85e04 |
| 21 | 14596627 | 14596783 | H_c_102f07 |
| 21 | 14676593 | 14678101 | H_c_148p08_M |
| 21 | 15152346 | 15152513 | H_c_45d22 |
| 21 | 15357989 | 15359319 | H_c_36d18_M |
| 21 | 15413243 | 15413426 | H_c_49p15 |
| 21 | 15609713 | 15609814 | H_c_46d16 |
| 21 | 16023625 | 16024898 | H_c_243k10_M |
| 21 | 16285509 | 16285641 | H_c139d01 |
| 21 | 16345916 | 16346063 | H_c_206j02 |
| 21 | 16914784 | 16915018 | H_c_222e16_M |
| 21 | 17263162 | 17263309 | H_c_1f17 |
| 21 | 17512988 | 17513092 | H_c_66p13 |
| 21 | 17786416 | 17786571 | H_c_71l06_M |
| 21 | 17806955 | 17808193 | H_c_182j15_M |
| 21 | 18112894 | 18113895 | H_c_180o18 |
| 21 | 18395791 | 18395975 | H_c_161p20_M |
| 21 | 18505330 | 18505433 | H_c131h10 |
| 21 | 18538947 | 18539666 | H_c_38k01_M |
| 21 | 18631983 | 18632088 | H_c_265e05 |
| 21 | 18680974 | 18681197 | H_c_190k02 |
| 21 | 18708742 | 18708884 | H_c_202o04 |
| 21 | 18731053 | 18731167 | H_c_72i06 |
| 21 | 19365314 | 19365494 | H_c_38i17 |
| 21 | 20110906 | 20111200 | H_c_73g23 |
| 21 | 20326917 | 20327080 | H_c_234f23 |
| 21 | 20362795 | 20362893 | H_c_84f02 |
| 21 | 20645585 | 20645909 | H_c_235f16 |
| 21 | 21157933 | 21158165 | H_c_210o01_M |
| 21 | 21238509 | 21238765 | H_c142b17 |
| 21 | 21291456 | 21292710 | H_c_51c18 |
| 21 | 21319762 | 21320022 | H_c_246b07 |
| 21 | 21324738 | 21324874 | H_c_18g09 |
| 21 | 21393414 | 21393586 | H_c_237l15 |
| 21 | 21717055 | 21717182 | H_c143i20 |
| 21 | 21790245 | 21790361 | H_c_21m05 |
| 21 | 21907547 | 21907800 | H_c_172m24 |
| 21 | 22177700 | 22177834 | H_c_272a20 |
| 21 | 22260240 | 22260608 | H_c_212k22 |
| 21 | 22819763 | 22819854 | H_c_146k05 |
| 21 | 23100325 | 23100768 | H_c_121o10 |
| 21 | 23142463 | 23142686 | H_c_9a03 |
| 21 | 23899999 | 23901320 | H_c_210p14 |
| 21 | 24444351 | 24444443 | H_c_115k13 |
| 21 | 24664661 | 24664890 | H_c_178c08 |
| 21 | 24825240 | 24825566 | H_c_45h17 |
| 21 | 24846407 | 24846486 | H_c_168o10 |
| 21 | 25020018 | 25020168 | H_c_204m21 |
| 21 | 25299889 | 25299975 | H_c_273c14 |
| 21 | 25614621 | 25614814 | H_c131b10 |
| 21 | 25856175 | 25856537 | H_c_116c09 |
| 21 | 25871590 | 25871758 | H_c_87p06 |
| 21 | 25900987 | 25902128 | H_c_36n19_M |
| 21 | 25933254 | 25934320 | H_c139p12_M |
| 21 | 25999589 | 25999792 | H_c_97i03 |
| 21 | 26004109 | 26004356 | H_c_69d21 |
| 21 | 26028654 | 26030143 | H_c_251b24_M |
| 21 | 26463760 | 26465448 | H_c_218f07_M |
| 21 | 26725899 | 26726139 | H_c133m06 |
| 21 | 27138112 | 27141230 | H_c_110p05_M |
| 21 | 27259365 | 27261367 | H_c_241f08_M |
| 21 | 27890526 | 27890730 | H_c_211n20 |
| 21 | 28079078 | 28079213 | H_c_93l05 |
| 21 | 28743844 | 28744040 | H_c_91h12 |
| 21 | 28977633 | 28977865 | H_c_211f17_M |
| 21 | 29179129 | 29179665 | H_c_190e12_M |
| 21 | 29238032 | 29238153 | H_c_11p07 |
| 21 | 29367404 | 29368158 | H_c_269b07_M |

TABLE 1-continued

| | | | |
|---|---|---|---|
| 21 | 29372568 | 29372748 | H_c_24h14 |
| 21 | 29592259 | 29593936 | H_c_78d08_M |
| 21 | 30232914 | 30233704 | H_c_116d12 |
| 21 | 30879067 | 30879706 | H_c_162g13 |
| 21 | 31052134 | 31052229 | H_c_219k09 |
| 21 | 31221885 | 31222073 | H_c_94p20 |
| 21 | 31267760 | 31267965 | H_c_54d18 |
| 21 | 31348207 | 31348462 | H_c_193j02 |
| 21 | 31777665 | 31778666 | H_c_257m18 |
| 21 | 31851613 | 31854491 | H_c_58l11_M |
| 21 | 31952748 | 31954590 | H_c_37l23 |
| 21 | 32025227 | 32026694 | H_c_10g22_M |
| 21 | 32166178 | 32170249 | H_c_90f18_M |
| 21 | 32572750 | 32573534 | H_c_145p01 |
| 21 | 32674949 | 32675505 | H_c_234a14 |
| 21 | 32686422 | 32687957 | H_c_50n11 |
| 21 | 32706143 | 32707293 | H_c_42h04 |
| 21 | 32748821 | 32748934 | H_c_190j09 |
| 21 | 32906639 | 32907923 | H_c_85c07_M |
| 21 | 33021375 | 33023177 | H_c_91a13_M |
| 21 | 33065309 | 33067017 | H_c_193l21_M |
| 21 | 33079375 | 33079456 | H_c_207d10 |
| 21 | 33313532 | 33314672 | H_c_1k01_M |
| 21 | 33316477 | 33318254 | H_c_229k18_M |
| 21 | 33320774 | 33322238 | H_c_92j03 |
| 21 | 33363978 | 33365968 | H_c_258m02_M |
| 21 | 33366219 | 33366415 | H_c_80k14_M |
| 21 | 33523730 | 33525175 | H_c_26j24_M |
| 21 | 33560232 | 33560783 | H_c_13e09 |
| 21 | 33697202 | 33698900 | H_c132h15_M |
| 21 | 33773412 | 33774883 | H_c_3c07_M |
| 21 | 33836185 | 33837586 | H_c_115m22_M |
| 21 | 33881833 | 33883160 | H_c_168f12 |
| 21 | 33935813 | 33937469 | H_c142o14_M |
| 21 | 34209463 | 34210219 | H_c_222h03_M |
| 21 | 34367000 | 34367894 | H_c_44a06_M |
| 21 | 34496142 | 34496774 | H_c_8e04_M |
| 21 | 34562146 | 34563333 | H_c_83h08 |
| 21 | 34669275 | 34670638 | H_c_78k15_M |
| 21 | 34856791 | 34857114 | H_c_81k20 |
| 21 | 34907604 | 34909458 | H_c_194f09_M |
| 21 | 35154014 | 35154236 | H_c_148d21 |
| 21 | 35182200 | 35185540 | H_c_24d22_M_M |
| 21 | 35320772 | 35321104 | H_c_11m02_M |
| 21 | 35387130 | 35388424 | H_c_178g24_M |
| 21 | 35503295 | 35503767 | H_c_266g04 |
| 21 | 36354669 | 36354910 | H_c_145o22_M |
| 21 | 36363518 | 36364805 | H_c_85l05_M |
| 21 | 36429224 | 36430260 | H_c_30d16_M |
| 21 | 36449839 | 36451820 | H_c_41a15 |
| 21 | 36613996 | 36614245 | H_c_127a01 |
| 21 | 36986757 | 36987552 | H_c_216c22 |
| 21 | 36989964 | 36992496 | H_c_78c16_M |
| 21 | 36998530 | 36999724 | H_c_157i11_M |
| 21 | 37041609 | 37042733 | H_c_212d16_M |
| 21 | 37259920 | 37261241 | H_c140j12_M |
| 21 | 37274367 | 37275373 | H_c_247h14_M |
| 21 | 37283814 | 37284789 | H_c_11n12_M |
| 21 | 37288713 | 37289007 | H_c_185b19_M |
| 21 | 37300016 | 37300845 | H_c_27c24_M |
| 21 | 37300845 | 37301470 | H_c_87f12_M |
| 21 | 37552542 | 37552740 | H_c_3f07 |
| 21 | 37560921 | 37562289 | H_c_95g07_M |
| 21 | 37659879 | 37660983 | H_c135l16_M |
| 21 | 37660991 | 37662603 | H_c_148d14_M |
| 21 | 37857286 | 37859577 | H_c_186e22 |
| 21 | 37857288 | 37859574 | H_c_214o04_M |
| 21 | 37857342 | 37859579 | H_c_172c10_M |
| 21 | 37870168 | 37870368 | H_c132a02_M |
| 21 | 37872921 | 37873076 | H_c_166p02 |
| 21 | 37969530 | 37969995 | H_c_88g13 |
| 21 | 38209730 | 38211781 | H_c_154m11_M |
| 21 | 38367129 | 38367286 | H_c_72c20 |
| 21 | 38570408 | 38570516 | H_c_8f11 |
| 21 | 38927937 | 38928255 | H_c_265j05 |
| 21 | 38953773 | 38955601 | H_c_158m05_M |
| 21 | 39098534 | 39100238 | H_c_204c15 |
| 21 | 39188559 | 39188654 | H_c_161f03 |
| 21 | 39476609 | 39478621 | H_c_240k16_M |
| 21 | 39606005 | 39608495 | H_c_15k13_M |
| 21 | 39616896 | 39617042 | H_c_12k06 |
| 21 | 39642031 | 39644082 | H_c_4d10_M |
| 21 | 39673996 | 39674585 | H_c_246b24_M |
| 21 | 39738951 | 39739857 | H_c_180n21_M |
| 21 | 39906403 | 39907020 | H_c_245p19_M |
| 21 | 40971857 | 40972034 | H_c_94a04 |
| 21 | 41055453 | 41055521 | H_c_202b04 |
| 21 | 41140292 | 41141020 | H_c_219l13_M |
| 21 | 41266214 | 41266400 | H_c_30i19 |
| 21 | 41461223 | 41462862 | H_c_116f03_M |
| 21 | 41610301 | 41611655 | H_c_54f15 |
| 21 | 41713870 | 41715053 | H_c_95b22 |
| 21 | 41719405 | 41720878 | H_c140c21 |
| 21 | 41800111 | 41801979 | H_c_88n13_M |
| 21 | 41801985 | 41802185 | H_c_95o08 |
| 21 | 42059369 | 42060489 | H_c_189i19_M |
| 21 | 42171566 | 42173125 | H_c_159d03_M |
| 21 | 42302216 | 42304620 | H_c_228l24 |
| 21 | 42511199 | 42513991 | H_c_38i15_M |
| 21 | 42527421 | 42528553 | H_c_219e04_M |
| 21 | 42789061 | 42790637 | H_c_171h23 |
| 21 | 42806196 | 42808090 | H_c_75k20_M |
| 21 | 42945950 | 42947361 | H_c_69n18_M |
| 21 | 42947364 | 42947951 | H_c_215f16 |
| 21 | 43172058 | 43173428 | H_c_206g20_M |
| 21 | 43186124 | 43187432 | H_c_239c14_M |
| 21 | 43266295 | 43268983 | H_c_207h05_M |
| 21 | 43367377 | 43368106 | H_c_241h16 |
| 21 | 43369458 | 43370100 | H_c_127n05 |
| 21 | 43378008 | 43379667 | H_c_94b20 |
| 21 | 43400114 | 43401246 | H_c_66h08_M |
| 21 | 43672061 | 43672390 | H_c_161n07_M |
| 21 | 43687882 | 43689292 | H_c_115j13 |
| 21 | 43842288 | 43842422 | H_c_54j07_M |
| 21 | 43903308 | 43904196 | H_c_52c19_M |
| 21 | 43943348 | 43943559 | H_c_261e21 |
| 21 | 43962389 | 43964393 | H_c_31o24_M |
| 21 | 43971745 | 43974106 | H_c_29a18_M |
| 21 | 44019902 | 44022189 | H_c_211c08_M |
| 21 | 44033424 | 44034440 | H_c_157h14_M |
| 21 | 44108495 | 44110399 | H_c142e14_M |
| 21 | 44256122 | 44257547 | H_c_36b24_M |
| 21 | 44315805 | 44316020 | H_c_249j09 |
| 21 | 44350854 | 44351887 | H_c_241p09_M |
| 21 | 44377671 | 44378881 | H_c_82k12 |
| 21 | 44409243 | 44412100 | H_c_165o06 |
| 21 | 44484365 | 44487977 | H_c_72o13_M |
| 21 | 44582529 | 44584151 | H_c_227j05 |
| 21 | 44594270 | 44596251 | H_c_18n24_M |
| 21 | 44699098 | 44700664 | H_c_225f06_M |
| 21 | 44950331 | 44952060 | H_c_128l07_M |
| 21 | 44967759 | 44968606 | H_c_113l03_M |
| 21 | 45045661 | 45046987 | H_c_120b11_M |
| 21 | 45116833 | 45118628 | H_c_202n19_M |
| 21 | 45175948 | 45177774 | H_c_24n09_M |
| 21 | 45262334 | 45263953 | H_c_213i13_M |
| 21 | 45458030 | 45458168 | H_c_162j03 |
| 21 | 45462218 | 45462311 | H_c_7j20 |
| 21 | 45530977 | 45533022 | H_c_243p03 |
| 21 | 45608526 | 45611171 | H_c135a16 |
| 21 | 45648178 | 45650778 | H_c_104b02_M |
| 21 | 45680796 | 45685644 | H_c_210g04_M |
| 21 | 45785370 | 45788034 | H_c_253a12 |
| 21 | 45799187 | 45800796 | H_c_206n20_M |
| 21 | 45883347 | 45885174 | H_c_42k17 |
| 21 | 46090037 | 46090218 | H_c_62j06 |
| 21 | 46217542 | 46219911 | H_c_58c01 |
| 21 | 46472259 | 46474078 | H_c_224m03 |
| 21 | 46529957 | 46531049 | H_c_224m07_M |
| 21 | 46565932 | 46568240 | H_c_37c10_M |
| 21 | 46826021 | 46826281 | H_c_174h23 |
| 21 | 46879563 | 46880733 | H_c_43h12 |
| 21 | 46905647 | 46905872 | H_c_253h13 |
| 21 | 46911459 | 46912556 | H_c_184p17 |
| 21 | 9724604 | 9724675 | H_c_101m08 |
| 22 | 15862976 | 15863831 | H_c_100e03 |
| 22 | 15940080 | 15941576 | H_c_2g10_M |
| 22 | 16013800 | 16015163 | H_c137i12_M |
| 22 | 16026585 | 16027640 | H_c_31c07 |
| 22 | 16223790 | 16225581 | H_c_148h11_M |

TABLE 1-continued

| | | | |
|---|---|---|---|
| 22 | 16402132 | 16402304 | H_c_130g21_M |
| 22 | 16485287 | 16486630 | H_c_244f10_M |
| 22 | 16495547 | 16496677 | H_c_108b07_M |
| 22 | 16630604 | 16631992 | H_c_105m24_M |
| 22 | 16857768 | 16859221 | H_c_231a19_M |
| 22 | 16880676 | 16882847 | H_c_150j01 |
| 22 | 16935015 | 16936189 | H_c_37a11 |
| 22 | 16967456 | 16968327 | H_c_20p09_M |
| 22 | 17258505 | 17258623 | H_c_39i17_M |
| 22 | 17266695 | 17268910 | H_c_246g08 |
| 22 | 17297828 | 17298359 | H_c_38l18 |
| 22 | 17448238 | 17449677 | H_c_117c04 |
| 22 | 17483567 | 17484978 | H_c_74j23_M |
| 22 | 17506318 | 17507136 | H_c131a05_M |
| 22 | 17529863 | 17534455 | H_c_81j21_M |
| 22 | 17539584 | 17541386 | H_c_121i03_M |
| 22 | 17653147 | 17654089 | H_c_245f15_M |
| 22 | 17790124 | 17790294 | H_c_13p14 |
| 22 | 17792987 | 17794869 | H_c131a21_M |
| 22 | 17808960 | 17810629 | H_c_128e09_M |
| 22 | 17840617 | 17841389 | H_c_89a22 |
| 22 | 18074970 | 18077470 | H_c_218f21_M |
| 22 | 18119391 | 18122053 | H_c_266h16 |
| 22 | 18168906 | 18171230 | H_c_188e23 |
| 22 | 18212557 | 18218283 | H_c_206e08_M |
| 22 | 18317266 | 18318779 | H_c_268i19_M |
| 22 | 18348629 | 18350102 | H_c_97k11_M |
| 22 | 18377990 | 18379820 | H_c_222e23 |
| 22 | 18441909 | 18442803 | H_c_202e15_M |
| 22 | 18478494 | 18480498 | H_c_67b15_M |
| 22 | 18493246 | 18495246 | H_c_83a09_M |
| 22 | 18606705 | 18608116 | H_c_231p04 |
| 22 | 18658927 | 18661804 | H_c_98e15_M |
| 22 | 18681104 | 18682339 | H_c_213a20 |
| 22 | 19072069 | 19073619 | H_c_200o13_M |
| 22 | 19103908 | 19105476 | H_c_36g24_M |
| 22 | 19175249 | 19175509 | H_c_203p17_M |
| 22 | 19175345 | 19175507 | H_c134f01 |
| 22 | 19185914 | 19187484 | H_c_56d22_M |
| 22 | 19536587 | 19538337 | H_c_215m03_M |
| 22 | 19595689 | 19596988 | H_c_83k04_M |
| 22 | 19635843 | 19637697 | H_c_202b08 |
| 22 | 19643336 | 19645676 | H_c_215j20_M |
| 22 | 19660183 | 19662104 | H_c_60f18 |
| 22 | 19679360 | 19681666 | H_c_168j20_M |
| 22 | 20245912 | 20247576 | H_c_125n02_M |
| 22 | 20320643 | 20323011 | H_c_9d09_M |
| 22 | 20330854 | 20333462 | H_c_212n20_M |
| 22 | 20336216 | 20337605 | H_c_185a21_M |
| 22 | 20344430 | 20345361 | H_c_38n03_M |
| 22 | 20414126 | 20415503 | H_c_67b16_M |
| 22 | 20545876 | 20546709 | H_c_7l13_M |
| 22 | 20661430 | 20661995 | H_c_165n05_M |
| 22 | 20778541 | 20778608 | H_c_234g18 |
| 22 | 21187167 | 21187778 | H_c_61j01 |
| 22 | 21736306 | 21737940 | H_c_36k11_M |
| 22 | 21929333 | 21931859 | H_c_263i13 |
| 22 | 22067447 | 22069808 | H_c_78b21_M |
| 22 | 22196792 | 22199524 | H_c_81g11 |
| 22 | 22253077 | 22254594 | H_c_36f20 |
| 22 | 22383708 | 22385228 | H_c_189o20_M |
| 22 | 22417278 | 22418550 | H_c_13e21_M |
| 22 | 22434360 | 22434919 | H_c_168b04_M |
| 22 | 22453645 | 22454670 | H_c139h11_M |
| 22 | 22482632 | 22485214 | H_c_150c23 |
| 22 | 22504070 | 22505772 | H_c135a09_M |
| 22 | 22523559 | 22524861 | H_c_152g19_M |
| 22 | 22560588 | 22563011 | H_c_187f03 |
| 22 | 22731792 | 22732947 | H_c_24f17 |
| 22 | 22749895 | 22750011 | H_c_122k08 |
| 22 | 22990736 | 22992051 | H_c_262k07_M |
| 22 | 23274645 | 23276908 | H_c_69c04_M |
| 22 | 23312398 | 23314486 | H_c_30c21_M |
| 22 | 23526415 | 23528462 | H_c_81b03_M |
| 22 | 23752222 | 23752413 | H_c_84f09 |
| 22 | 23831303 | 23832478 | H_c_114e18 |
| 22 | 23945065 | 23945973 | H_c_272e04 |
| 22 | 24077730 | 24080237 | H_c_258n01 |
| 22 | 24889788 | 24891626 | H_c_211f05_M |
| 22 | 25149563 | 25150888 | H_c_186f24 |
| 22 | 25203565 | 25204717 | H_c_149f12_M |
| 22 | 25310161 | 25310882 | H_c_217h16 |
| 22 | 25377590 | 25377979 | H_c_31d24_M |
| 22 | 25377980 | 25379831 | H_c_65g20_M |
| 22 | 26334974 | 26335205 | H_c_175f21_M |
| 22 | 26379423 | 26379647 | H_c_206m21 |
| 22 | 26521018 | 26525655 | H_c_188b20_M_M |
| 22 | 26639106 | 26640949 | H_c_82b17_M |
| 22 | 26875714 | 26875866 | H_c_193b01 |
| 22 | 27218774 | 27218914 | H_c_84l01 |
| 22 | 27462261 | 27463282 | H_c_123a07 |
| 22 | 27493053 | 27493756 | H_c_96g19 |
| 22 | 27520612 | 27521347 | H_c_163j13_M |
| 22 | 27793135 | 27795017 | H_c_125i09 |
| 22 | 27925749 | 27927363 | H_c_44p12_M |
| 22 | 27988154 | 27989370 | H_c_149e10_M |
| 22 | 28015867 | 28016095 | H_c_176k13 |
| 22 | 28025888 | 28028058 | H_c_176g01_M |
| 22 | 28033436 | 28037366 | H_c_168c20_M |
| 22 | 28323640 | 28324767 | H_c_231d09_M |
| 22 | 28487242 | 28488210 | H_c_130d13_M |
| 22 | 28747813 | 28747917 | H_c_159e15 |
| 22 | 28800231 | 28801115 | H_c_164a23 |
| 22 | 28956101 | 28956492 | H_c_162p03 |
| 22 | 29009700 | 29011944 | H_c_20a11_M |
| 22 | 29045907 | 29047922 | H_c_86b17 |
| 22 | 29077012 | 29077912 | H_c_210n21_M |
| 22 | 29107076 | 29108995 | H_c_118d17 |
| 22 | 29145907 | 29147239 | H_c_262f21_M |
| 22 | 29209517 | 29211559 | H_c_189b22_M |
| 22 | 29362258 | 29364238 | H_c_123l03 |
| 22 | 29414550 | 29415888 | H_c_86k02_M |
| 22 | 29523123 | 29523713 | H_c_204a19_M |
| 22 | 29542830 | 29543241 | H_c144k06_M |
| 22 | 29688927 | 29689778 | H_c_223e21_M |
| 22 | 29707052 | 29707187 | H_c_243b21 |
| 22 | 29805239 | 29807198 | H_c_237p11_M |
| 22 | 29826832 | 29828421 | H_c_37c18_M |
| 22 | 29932538 | 29933305 | H_c_97k02_M |
| 22 | 30010978 | 30012338 | H_c_180p12_M |
| 22 | 30068123 | 30068307 | H_c_107o08_M |
| 22 | 30119529 | 30120954 | H_c_57d20 |
| 22 | 30209545 | 30210424 | H_c_42o13_M |
| 22 | 30216500 | 30217697 | H_c_169n23_M |
| 22 | 30382125 | 30382802 | H_c_168f01_M |
| 22 | 30456150 | 30456279 | H_c_1b07 |
| 22 | 30664339 | 30666008 | H_c_207g02 |
| 22 | 30896013 | 30897259 | H_c_92o12 |
| 22 | 31069877 | 31070045 | H_c_20f11 |
| 22 | 31194991 | 31196049 | H_c_211f02_M |
| 22 | 31416152 | 31416234 | H_c_129i11 |
| 22 | 31521571 | 31523050 | H_c_148k19_M |
| 22 | 31777832 | 31780079 | H_c_11c17_M |
| 22 | 31924451 | 31924563 | H_c_118p14 |
| 22 | 31957922 | 31957992 | H_c_1d05 |
| 22 | 32728454 | 32728584 | H_c_106l06_M |
| 22 | 33777670 | 33779576 | H_c_73b08 |
| 22 | 33977842 | 33979056 | H_c_194g04_M |
| 22 | 34020207 | 34020838 | H_c_111h02 |
| 22 | 34101374 | 34101934 | H_c_193n21_M |
| 22 | 34115965 | 34116613 | H_c_185m09 |
| 22 | 34120221 | 34121319 | H_c_228c02_M |
| 22 | 34138083 | 34139413 | H_c_22g05 |
| 22 | 34220312 | 34220433 | H_c_107d20 |
| 22 | 34260422 | 34262218 | H_c_57d06_M |
| 22 | 34302532 | 34303724 | H_c135o15 |
| 22 | 34748266 | 34749848 | H_c_66a11_M |
| 22 | 35020539 | 35021882 | H_c_42b11 |
| 22 | 35107971 | 35109037 | H_c_162m05_M |
| 22 | 35174402 | 35176137 | H_c_207f23 |
| 22 | 35226319 | 35227843 | H_c_99f18_M |
| 22 | 35249365 | 35250097 | H_c_52d08_M |
| 22 | 35537135 | 35538796 | H_c_145n03_M |
| 22 | 35771736 | 35774387 | H_c_87j24_M |
| 22 | 36055152 | 36056004 | H_c_3a19 |
| 22 | 36205595 | 36207307 | H_c_13a13_M |
| 22 | 36239017 | 36240767 | H_c_270d14 |
| 22 | 36280576 | 36282114 | H_c_24k17_M |
| 22 | 36328933 | 36329282 | H_c_211o02 |
| 22 | 36359522 | 36361858 | H_c_181l06 |

TABLE 1-continued

| | | | |
|---|---|---|---|
| 22 | 36378947 | 36380450 | H_c_129b10_M |
| 22 | 36465894 | 36468266 | H_c_69g01_M |
| 22 | 36522579 | 36528830 | H_c_38p06_M_M |
| 22 | 36539044 | 36540001 | H_c_92b20_M |
| 22 | 36545145 | 36546279 | H_c144k03 |
| 22 | 36564051 | 36564933 | H_c_84n16_M |
| 22 | 36569084 | 36571013 | H_c_257d05 |
| 22 | 36673896 | 36674779 | H_c_195h01_M |
| 22 | 36800230 | 36803886 | H_c_94d21_M |
| 22 | 36808869 | 36810973 | H_c_209j02_M |
| 22 | 36902156 | 36902462 | H_c_84n14_M |
| 22 | 36922210 | 36924003 | H_c_3e05 |
| 22 | 36993599 | 36993780 | H_c_103c16_M |
| 22 | 37119637 | 37119769 | H_c_65m08 |
| 22 | 37181485 | 37182380 | H_c_166l04_M |
| 22 | 37188197 | 37190320 | H_c_125g11 |
| 22 | 37267066 | 37267252 | H_c_49j09 |
| 22 | 37362426 | 37362557 | H_c_112e08 |
| 22 | 37376515 | 37377646 | H_c_84l09 |
| 22 | 37420749 | 37421920 | H_c_33m07_M |
| 22 | 37426456 | 37427333 | H_c_123l18_M |
| 22 | 37475650 | 37477119 | H_c_59c12_M |
| 22 | 37513930 | 37514823 | H_c_57o21_M |
| 22 | 37592078 | 37593781 | H_c_272d10_M |
| 22 | 37865747 | 37866535 | H_c_245j21_M |
| 22 | 37873424 | 37874246 | H_c_191g22 |
| 22 | 37923133 | 37925150 | H_c_21e02 |
| 22 | 37960709 | 37963222 | H_c142l21_M |
| 22 | 38039841 | 38040515 | H_c_38n10_M |
| 22 | 38041807 | 38041936 | H_c_209n13 |
| 22 | 38108197 | 38109614 | H_c_63h09_M |
| 22 | 38119301 | 38120731 | H_c_17m11 |
| 22 | 38129323 | 38129518 | H_c139l10 |
| 22 | 38239844 | 38241245 | H_c_73h18_M |
| 22 | 38241368 | 38241856 | H_c_227m03 |
| 22 | 38248687 | 38251067 | H_c_78j16 |
| 22 | 38277889 | 38279037 | H_c_19d17_M |
| 22 | 38333644 | 38335078 | H_c_116o01 |
| 22 | 38714860 | 38716353 | H_c_66e15_M |
| 22 | 39066791 | 39067684 | H_c_93o06 |
| 22 | 39090396 | 39091599 | H_c_200o24_M |
| 22 | 39260379 | 39260584 | H_c_36g23_M |
| 22 | 39539416 | 39540108 | H_c_80l13_M |
| 22 | 39576500 | 39578047 | H_c_64e04_M |
| 22 | 39670987 | 39672665 | H_c_204a24_M |
| 22 | 39741980 | 39743379 | H_c_30n20_M |
| 22 | 39917548 | 39918614 | H_c_268g06_M |
| 22 | 40006285 | 40007195 | H_c_166m18 |
| 22 | 40021853 | 40022528 | H_c_75l15_M |
| 22 | 40101459 | 40102376 | H_c_101g05 |
| 22 | 40132930 | 40134847 | H_c_1f03_M |
| 22 | 40166516 | 40168763 | H_c_86f23_M |
| 22 | 40189360 | 40189593 | H_c_99l18 |
| 22 | 40264384 | 40265305 | H_c_3a05_M |
| 22 | 40308945 | 40310672 | H_c_24d06 |
| 22 | 40340623 | 40342454 | H_c_160o23_M |
| 22 | 40402574 | 40403464 | H_c_218b19 |
| 22 | 40409179 | 40409558 | H_c_59b15_M |
| 22 | 40419736 | 40421670 | H_c_118c16 |
| 22 | 40520928 | 40521581 | H_c_104b24 |
| 22 | 40553377 | 40554571 | H_c_123i12 |
| 22 | 40559749 | 40561278 | H_c_8h16_M |
| 22 | 40629909 | 40632239 | H_c_195e09_M |
| 22 | 40666570 | 40667717 | H_c_62n22_M |
| 22 | 40718622 | 40719963 | H_c_79g21_M |
| 22 | 40799915 | 40801162 | H_c_116e09_M |
| 22 | 40899365 | 40899540 | H_c_243h01 |
| 22 | 40989702 | 40991840 | H_c_119l02 |
| 22 | 41002397 | 41004805 | H_c_196l21_M |
| 22 | 41087921 | 41090261 | H_c_240f08 |
| 22 | 41273972 | 41275197 | H_c_84k01_M |
| 22 | 41301985 | 41303610 | H_c_185f20_M |
| 22 | 41334820 | 41335600 | H_c_145d21_M |
| 22 | 41367954 | 41370292 | H_c134f23_M |
| 22 | 41382155 | 41383718 | H_c_57j17 |
| 22 | 41440440 | 41441773 | H_c_85f05_M |
| 22 | 41465958 | 41467370 | H_c_99i18 |
| 22 | 41473628 | 41473718 | H_c_234i09 |
| 22 | 41576723 | 41578489 | H_c_251h03_M |
| 22 | 41809278 | 41810131 | H_c_95i13 |
| 22 | 41830835 | 41832144 | H_c_167g09_M |
| 22 | 41862825 | 41864013 | H_c_32h11_M |
| 22 | 41906922 | 41908448 | H_c_91f24 |
| 22 | 42582249 | 42583727 | H_c_64o22 |
| 22 | 42609743 | 42613144 | H_c_188l19_M |
| 22 | 42618181 | 42619605 | H_c_79g15 |
| 22 | 42644232 | 42646289 | H_c_192e06_M |
| 22 | 42744721 | 42745744 | H_c_55m05 |
| 22 | 43002606 | 43004505 | H_c_271h22 |
| 22 | 43214240 | 43215290 | H_c_228j22_M |
| 22 | 43336804 | 43337005 | H_c_22d16 |
| 22 | 43384560 | 43386529 | H_c_241j20 |
| 22 | 43417481 | 43418692 | H_c_116h22 |
| 22 | 43418695 | 43419464 | H_c_35p22_M |
| 22 | 43468353 | 43469631 | H_c144e02_M |
| 22 | 43538848 | 43538965 | H_c_121p01 |
| 22 | 43656709 | 43656822 | H_c_34j16 |
| 22 | 43723324 | 43726812 | H_c_211j23_M_M |
| 22 | 43849386 | 43849479 | H_c_225b22 |
| 22 | 44000736 | 44002603 | H_c_146h17 |
| 22 | 44025871 | 44027054 | H_c_3l05_M |
| 22 | 44128785 | 44130645 | H_c_120k11_M |
| 22 | 44361811 | 44362421 | H_c_82j07_M |
| 22 | 44387511 | 44389422 | H_c_64b12_M |
| 22 | 44582722 | 44584175 | H_c_48m16_M |
| 22 | 44687521 | 44687707 | H_c_123m13 |
| 22 | 44716509 | 44718107 | H_c_186p13 |
| 22 | 44743543 | 44745546 | H_c_52f12_M |
| 22 | 44752022 | 44753829 | H_c_266p17_M |
| 22 | 44760938 | 44761666 | H_c_114o02 |
| 22 | 44769756 | 44770793 | H_c_104c01 |
| 22 | 44832644 | 44835244 | H_c_158o11 |
| 22 | 44838815 | 44840827 | H_c_114k16 |
| 22 | 44966087 | 44967999 | H_c_7e15_M |
| 22 | 44978824 | 44980345 | H_c_190j16_M |
| 22 | 44983974 | 44985025 | H_c_274c06_M |
| 22 | 45013032 | 45013958 | H_c134i01_M |
| 22 | 45051704 | 45052828 | H_c_109f07_M |
| 22 | 45292782 | 45293452 | H_c_93g07_M |
| 22 | 45478514 | 45480535 | H_c_229d23_M |
| 22 | 45977288 | 45977427 | H_c_161l10 |
| 22 | 46450430 | 46450671 | H_c_35i07 |
| 22 | 46518073 | 46519168 | H_c_118m23 |
| 22 | 46650911 | 46651035 | H_c_213k02 |
| 22 | 46834300 | 46834548 | H_c_229g03 |
| 22 | 47053527 | 47056021 | H_c_172f05 |
| 22 | 47291274 | 47293970 | H_c_154o10_M |
| 22 | 47620639 | 47620790 | H_c_167e22 |
| 22 | 47767840 | 47769414 | H_c_121g24 |
| 22 | 48068680 | 48068893 | H_c_243b04 |
| 22 | 48181505 | 48181646 | H_c_101d13 |
| 22 | 48438892 | 48440495 | H_c_241d18 |
| 22 | 48541022 | 48543409 | H_c_110l10_M |
| 22 | 48567377 | 48568866 | H_c_46b02_M |
| 22 | 48632314 | 48633400 | H_c_7e19_M |
| 22 | 48673215 | 48674903 | H_c_156i12 |
| 22 | 48676217 | 48677121 | H_c_215n07_M |
| 22 | 48754516 | 48757151 | H_c_57j13_M |
| 22 | 48933648 | 48935589 | H_c_88i22 |
| 22 | 48985497 | 48988124 | H_c_151g04 |
| 22 | 49071323 | 49071629 | H_c_264f12_M |
| 22 | 49272434 | 49273061 | H_c_51i21 |
| 22 | 49276516 | 49278664 | H_c_229j11 |
| 22 | 49399885 | 49402406 | H_c_47h22_M |

Table Key
MT  MT_NC_001807
H   Human
c   cpg
M   Merged
Reference sequence: http://www.sanger.ac.uk/HGP/

The invention claimed is:

1. An apparatus for isolating CpG island nucleic acid fragments, said apparatus comprising a peptide capable of binding unmethylated CpG dinucleotide pairs for use in isolating CpG nucleic acid fragments, wherein said peptide is complexed, conjugated, or otherwise bound to an appropriate support.

2. The apparatus according to claim 1 wherein the support is a chromatography medium, affinity label or magnetic support for facilitating separation.

3. The apparatus of claim 1, wherein the support may be selected from the group consisting of agarose, sepharose, polyacrylamide, agarose/polyacrylamide co-polymers, dextran, cellulose, polypropylene, polycarbonate, nitrocellulose, magnetic material and glass paper.

4. The apparatus of claim 1, wherein the peptide capable of binding unmethylated CpG dinucleotide pairs comprises at least a portion of the CpG Binding Domain protein 1 (MBD1) which retains the ability to bind unmethylated CpG dinucleotide pairs.

5. The apparatus of claim 1, wherein the peptide capable of binding unmethylated CpG dinucleotide pairs comprises the MBD1 transcriptional repressor.

6. The apparatus of claim 1, wherein the peptide capable of binding unmethylated CpG dinucleotide pairs comprises the cysteine rich CxxC-3 domain of the MBD1 transcriptional repressor.

7. The apparatus of claim 1, wherein the peptide capable of binding unmethylated CpG dinucleotide pairs is a peptide, or fragment thereof, homologous to the MBD1 transcriptional repressor.

8. The apparatus of claim 1, wherein the peptide capable of binding unmethylated CpG dinucleotide pairs further comprises a binding moiety providing a means of coupling said peptide to the solid support.

9. The apparatus of claim 8, wherein the binding moiety is a peptide or other small chemical moiety, fused, coupled or otherwise bound to the peptide capable of binding CpG dinucleotide pairs.

10. The apparatus of claim 1, wherein the peptide capable of binding unmethylated CpG dinucleotide pairs is chemically cross-linked to the solid support.

* * * * *